US012241053B2

(12) United States Patent
Kuchroo et al.

(10) Patent No.: US 12,241,053 B2
(45) Date of Patent: Mar. 4, 2025

(54) MODULATION OF NOVEL IMMUNE CHECKPOINT TARGETS

(71) Applicants: The Brigham and Women's Hospital, Inc., Boston, MA (US); The Broad Institute, Inc., Cambridge, MA (US); Massachusetts Institute of Technology, Cambridge, MA (US)

(72) Inventors: Vijay K. Kuchroo, Boston, MA (US); Ana C. Anderson, Boston, MA (US); Asaf Madi, Boston, MA (US); Norio Chihara, Boston, MA (US); Aviv Regev, Cambridge, MA (US); Meromit Singer, Cambridge, MA (US)

(73) Assignees: THE BRIGHAM AND WOMEN'S HOSPITAL, INC., Boston, MA (US); THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 1344 days.

(21) Appl. No.: 15/767,074

(22) PCT Filed: Oct. 7, 2016

(86) PCT No.: PCT/US2016/056177

§ 371 (c)(1),
(2) Date: Apr. 9, 2018

(87) PCT Pub. No.: WO2017/069958

PCT Pub. Date: Apr. 27, 2017

(65) Prior Publication Data

US 2019/0255107 A1 Aug. 22, 2019

Related U.S. Application Data

(60) Provisional application No. 62/239,548, filed on Oct. 9, 2015.

(51) Int. Cl.

| | |
|---|---|
| ***A61K 35/17*** | (2015.01) |
| ***A61K 39/00*** | (2006.01) |
| ***A61K 39/39*** | (2006.01) |
| ***A61P 31/04*** | (2006.01) |
| ***A61P 31/12*** | (2006.01) |
| ***A61P 35/00*** | (2006.01) |
| ***C07K 14/705*** | (2006.01) |
| ***C12N 5/0783*** | (2010.01) |
| ***C12N 15/62*** | (2006.01) |
| ***C12Q 1/6827*** | (2018.01) |
| ***C12Q 1/686*** | (2018.01) |
| ***C12Q 1/6881*** | (2018.01) |

(52) U.S. Cl.

CPC ............ *C07K 14/705* (2013.01); *A61K 39/39* (2013.01); *A61K 39/4611* (2023.05); *A61K 39/464492* (2023.05); *A61P 31/04* (2018.01); *A61P 31/12* (2018.01); *A61P 35/00* (2018.01); *C12N 5/0636* (2013.01); *C12N 15/62* (2013.01); *C12Q 1/6827* (2013.01); *C12Q 1/686* (2013.01); *C12Q 1/6881* (2013.01); *A61K 2239/31* (2023.05); *A61K 2239/57* (2023.05); *C12N 2501/2327* (2013.01); *C12N 2510/00* (2013.01)

(58) Field of Classification Search

CPC .......................... C12N 5/0636; C12N 2510/00

See application file for complete search history.

(56) References Cited

FOREIGN PATENT DOCUMENTS

| | | | | |
|---|---|---|---|---|
| WO | WO-2009/092087 A2 | 7/2009 | | |
| WO | WO-2014/059173 A2 | 4/2014 | | |
| WO | WO-2014/070874 A1 | 5/2014 | | |
| WO | WO-2014/134351 A2 | 9/2014 | | |
| WO | WO-2015075175 A1 * | 5/2015 | ............. | A61K 35/17 |
| WO | WO-2015/143343 A2 | 9/2015 | | |
| WO | WO-2015/174439 A1 | 11/2015 | | |

(Continued)

OTHER PUBLICATIONS

Ochoa-Alvarez (2015, Oncotarget, 6(11):9045-9060).*
Oft (Cancer Immunol Res; 2(3) Mar. 2014, 194-199).*
Neumann (J. Exp. Med. 2014 vol. 211 No. 9 1807-1819).*
Nirschi (2013, Clin Cancer Res; 19(18); 4917-24) (Year: 2013).*
Anderson et al., "Lag-3, Tim-3, and TIGIT: Co-inhibitory receptors with specialized functions in immune regulation", Immunity, 2016, vol. 44, No. 5, pp. 989-1004.

(Continued)

*Primary Examiner* — Valarie E Bertoglio
(74) *Attorney, Agent, or Firm* — Wenderoth, Lind & Ponack, L.L.P.

(57) ABSTRACT

Dysfunctional or exhausted T cells arise in chronic diseases including chronic viral infections and cancer, and express high levels of co-inhibitory receptors. Therapeutic blockade of these receptors has clinical efficacy in the treatment of cancer. While co-inhibitory receptors are co-expressed, the triggers that induce them and the transcriptional regulators that drive their co-expression have not been identified. The immunoregulatory cytokine IL-27 induces a gene module in T cells that includes several known co-inhibitory receptors (Tim-3, Lag-3, and TIGIT). The present invention provides a novel immunoregulatory network as well as novel cell surface molecules that have an inhibitory function in the tumor microenvironment. The present invention further provides the novel discovery that the transcription factors Prdm1 and c-Maf cooperatively regulate the expression of the co-inhibitory receptor module. This critical molecular circuit underlies the co-expression of co-inhibitory receptors in dysfunctional T cells and identifies novel regulators of T cell dysfunction.

17 Claims, 56 Drawing Sheets

Specification includes a Sequence Listing.

(56) References Cited

FOREIGN PATENT DOCUMENTS

WO WO-2016/109546 A2 7/2016

OTHER PUBLICATIONS

Peters et al., "Podoplanin negatively regulates CD4 effector T-cell responses", Journal of Clinical Investigation, 2014, vol. 125, pp. 129-140.
Sakuishi et al., "Targeting TIM-3 and PD-1 pathways to reverse T cell exhaustion and restore anti-tumor immunity", Journal of Experimental Medicine, 2010, vol. 207, pp. 2187-2194.
Singer et al., "A distinct gene module for dysfunction uncoupled from activation in tumor-infiltrating T cells", Cell, 2016, vol. 166, No. 6, p. 1500.
Tirosh et al., "Dissecting the multicellular ecosystem of metastatic melanoma by single-cell RNA-seq", Science, 2016, vol. 352, No. 6282, pp. 189-196.
Zhu et al., "An IL-27/NFIL3 signaling axis drives Tim-3 and IL-10 expression and T cell dysfunction", Nature Communications, 2015, vol. 6, 25 pages.
International Search Report issued in International Patent Application No. PCT/US2016/056177, mailed Aug. 8, 2017.
Awasthi, et al., "A dominant function for interleukin 27 in generating interleukin 10-producing anti-inflammatory T cells", Nature Immunology, 2007, vol. 8, No. 12, pp. 1380-1389.
Barber, et al., "Restoring function in exhausted CD8 T cells during chronic viral infection", Nature, 2006, vol. 439, pp. 682-687.
Fitzgerald, et al., "Suppressive Effect of IL-27 on Encephalitogenic Th17 Cells and the Effector Phase of Experimental Autoimmune Encephalomyelitis", The Journal of Immunology, 2007, vol. 179, pp. 3268-3275.
Fourcade, et al., "PD-1 and Tim-3 Regulate the Expansion of Tumor Antigen-Specific CD8? T Cells Induced by Melanoma Vaccines", Cancer Research, 2014, vol. 74, pp. 1045-1055.
Hamid, et al., "Safety and Tumor Responses with Lambrolizumab (Anti-PD-1) in Melanoma", The New England Journal of Medicine, 2013, vol. 369, No. 2, pp. 134-144.
Hirahara, et al., "Interleukin-27 Priming of T Cells Controls IL-17 Production In trans via Induction of the Ligand PD-L1", Immunity, 2012, vol. 36, pp. 1017-1030.
Hodi, et al., "Improved Survival with Ipilimumab in Patients with Metastatic Melanoma", The New England Journal of Medicine, 2010, vol. 363, No. 8, pp. 711-723.
Johnston, et al., "The Immunoreceptor TIGIT Regulates Antitumor and Antiviral CD8+ T Cell Effector Function", Cancer Cell, 2014, vol. 26, pp. 923-937.
Leach, et al., "Enhancement of Antitumor Immunity by CTLA-4 Blockade", Science, 1996, vol. 271, pp. 1734-1736.
Mahoney, et al., "Combination cancer immunotherapy and new immunomodulatory targets", Nature, 2015, vol. 14, pp. 561-584.
Pardoll. "The blockade of immune checkpoints in cancer immunotherapy", Nature, 2012, vol. 12, pp. 252-264.
Robert, et al., "Ipilimumab plus Dacarbazine for Previously Untreated Metastatic Melanoma", The New England Journal of Medicine, 2011, vol. 364, No. 26, pp. 2517-2526.
Topalian, et al., "Safety, Activity, and Immune Correlates of Anti-PD-1 Antibody in Cancer", The New England Journal of Medicine, 2012, vol. 366, No. 26, pp. 2443-2454.
Villarino, et al., "The IL-27R (WSX-1) Is Required to Suppress T Cell Hyperactivity during Infection", Immunity, 2003, vol. 19, pp. 645-655.
Wherry, Kurachi, "Molecular and cellular insights into T cell exhaustion", Nature, 2015, vol. 15, pp. 486-499.
Wherry. "T cell exhaustion", Nature, 2011, vol. 12, No. 6, pp. 492-499.
Wolchok, et al., "Nivolumab plus Ipilimumab in Advanced Melanoma", The New England Journal of Medicine, 2013, vol. 369, No. 2, pp. 122-133.
Woo, et al., "Immune Inhibitory Molecules LAG-3 and PD-1 Synergistically Regulate T-cell Function to Promote Tumoral Immune Escape", Cancer Research, 2012, vol. 72, pp. 917-927.
Yoshida, et al., "The Immunobiology of Interleukin-27", Annual Review of Immunology, 2015, vol. 33, pp. 417-443.

* cited by examiner

FIG. 1C-D
C
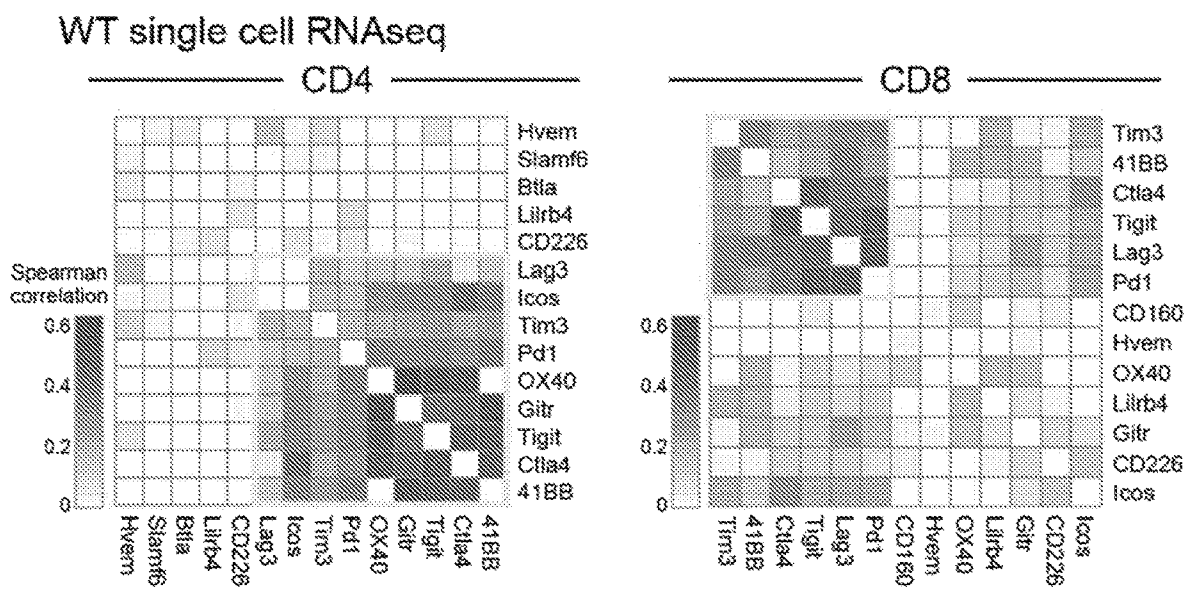
D
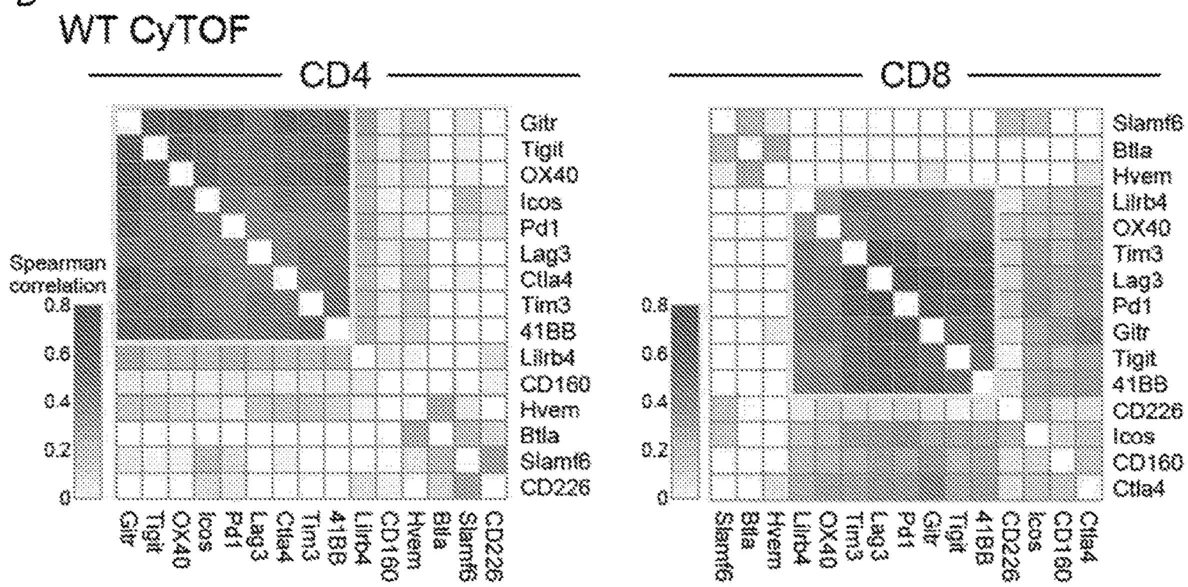

FIG. 1F-G
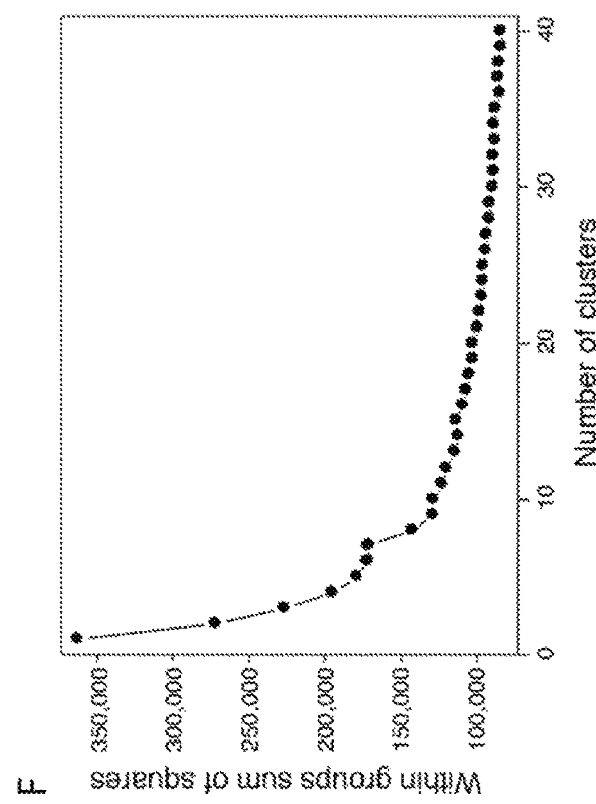
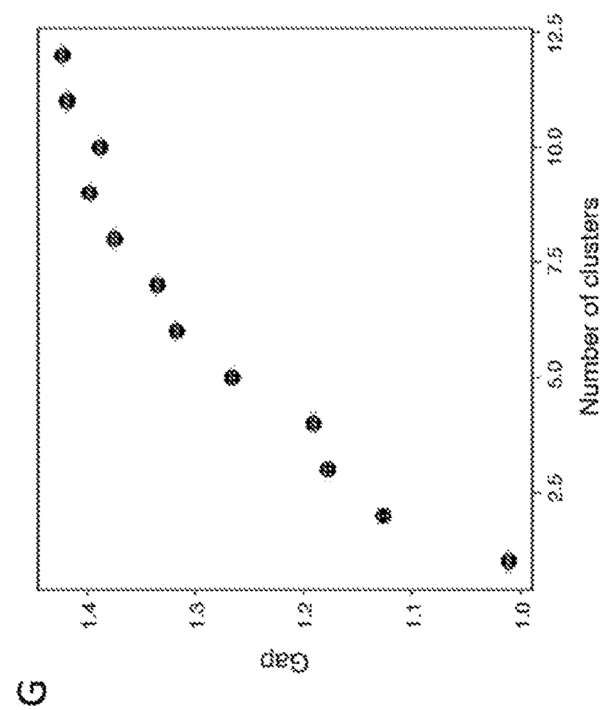

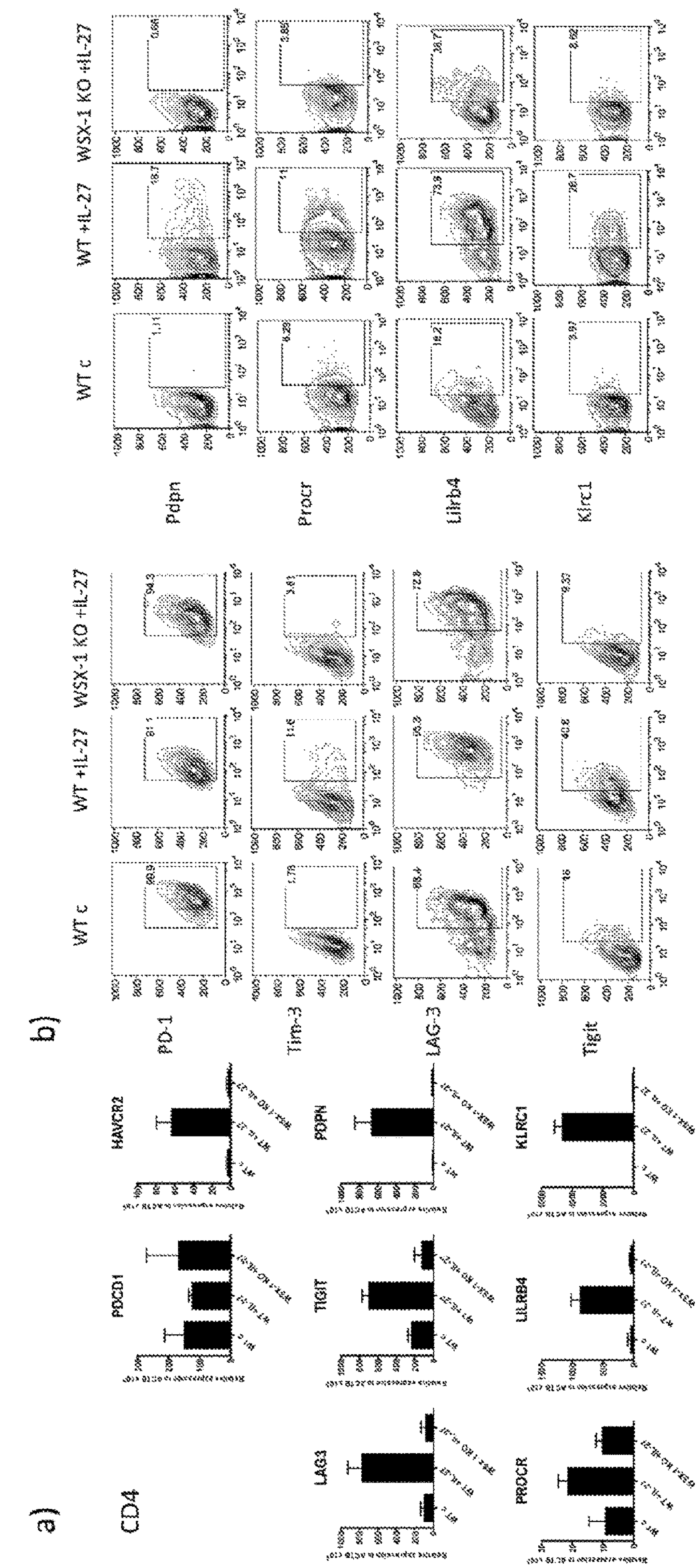
FIG. 2A-B

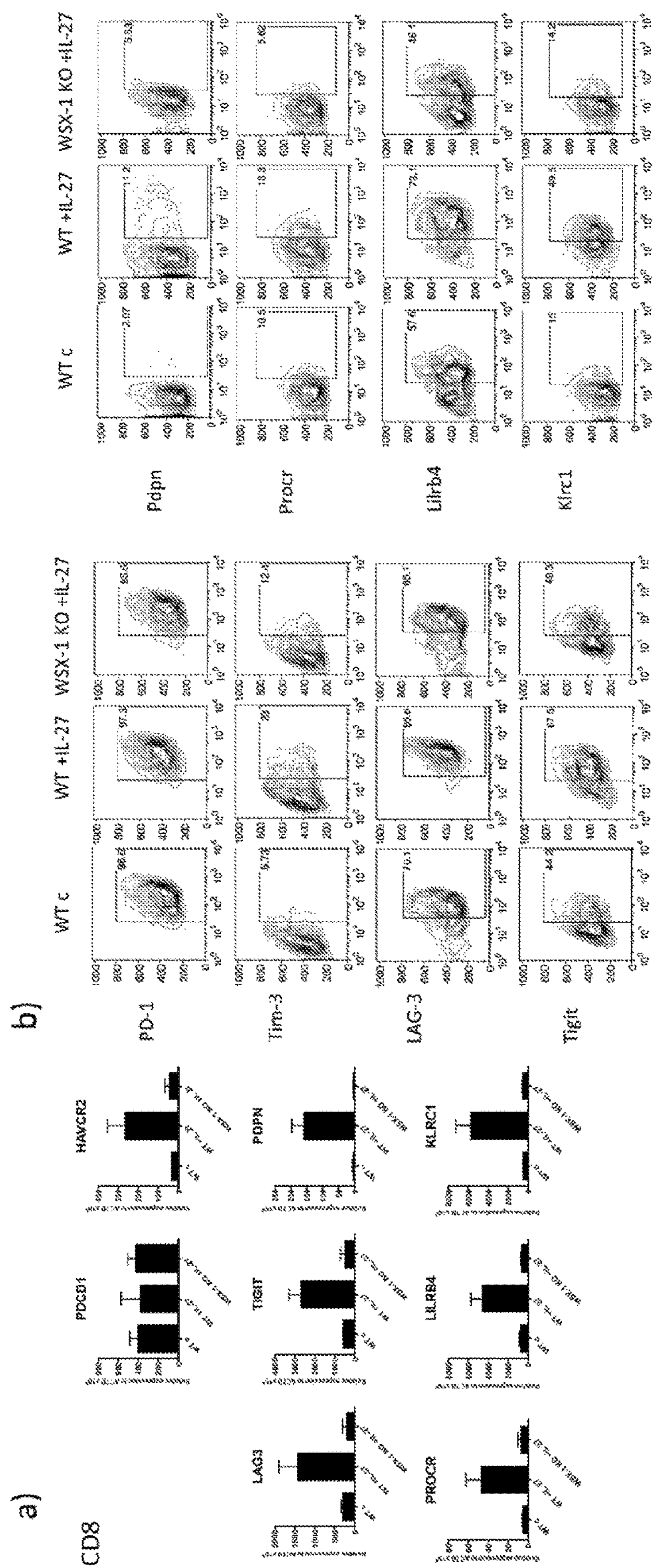
FIG. 3A-B

FIG. 6A-B
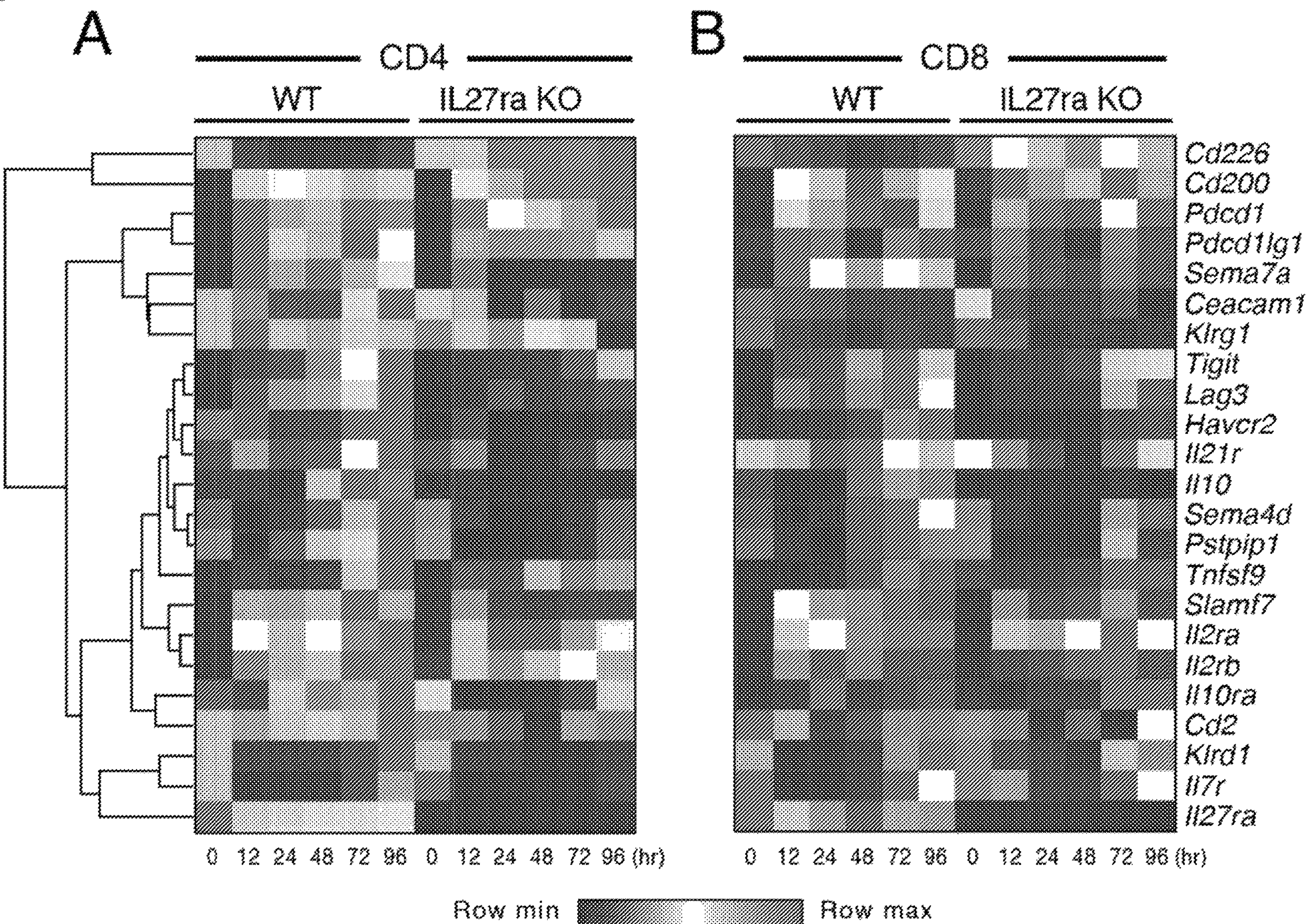

FIG. 6E-F
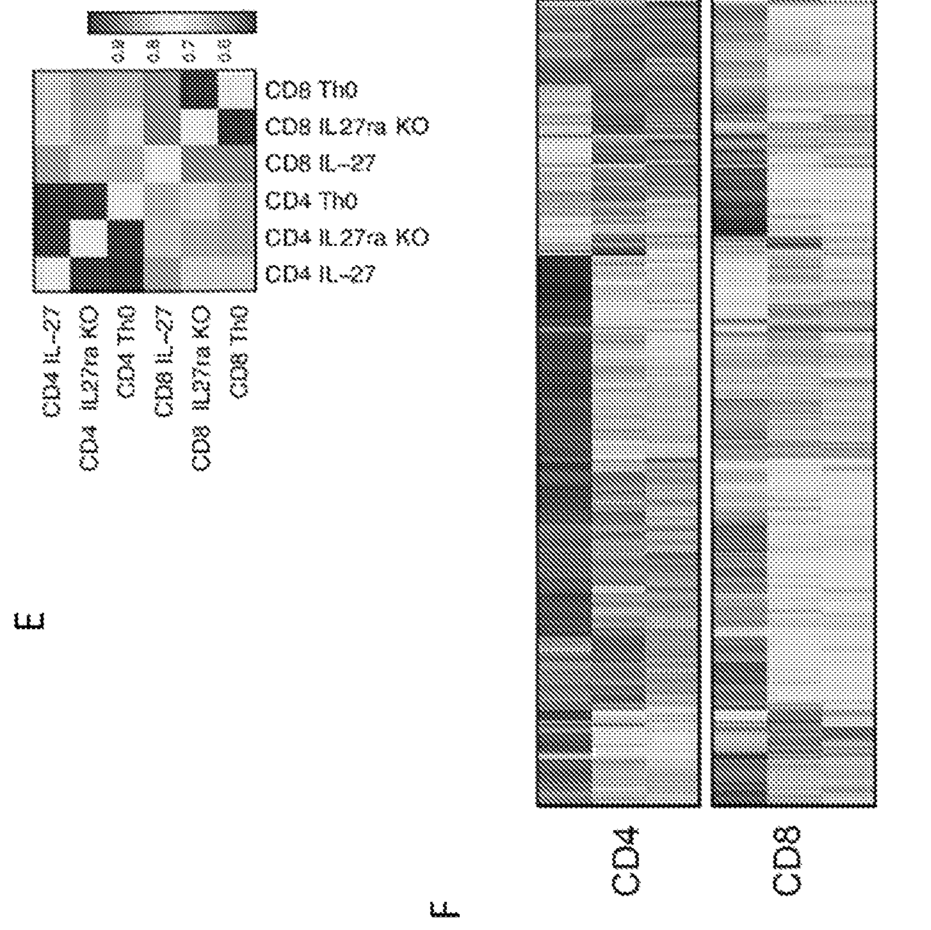

FIG. 6I-J
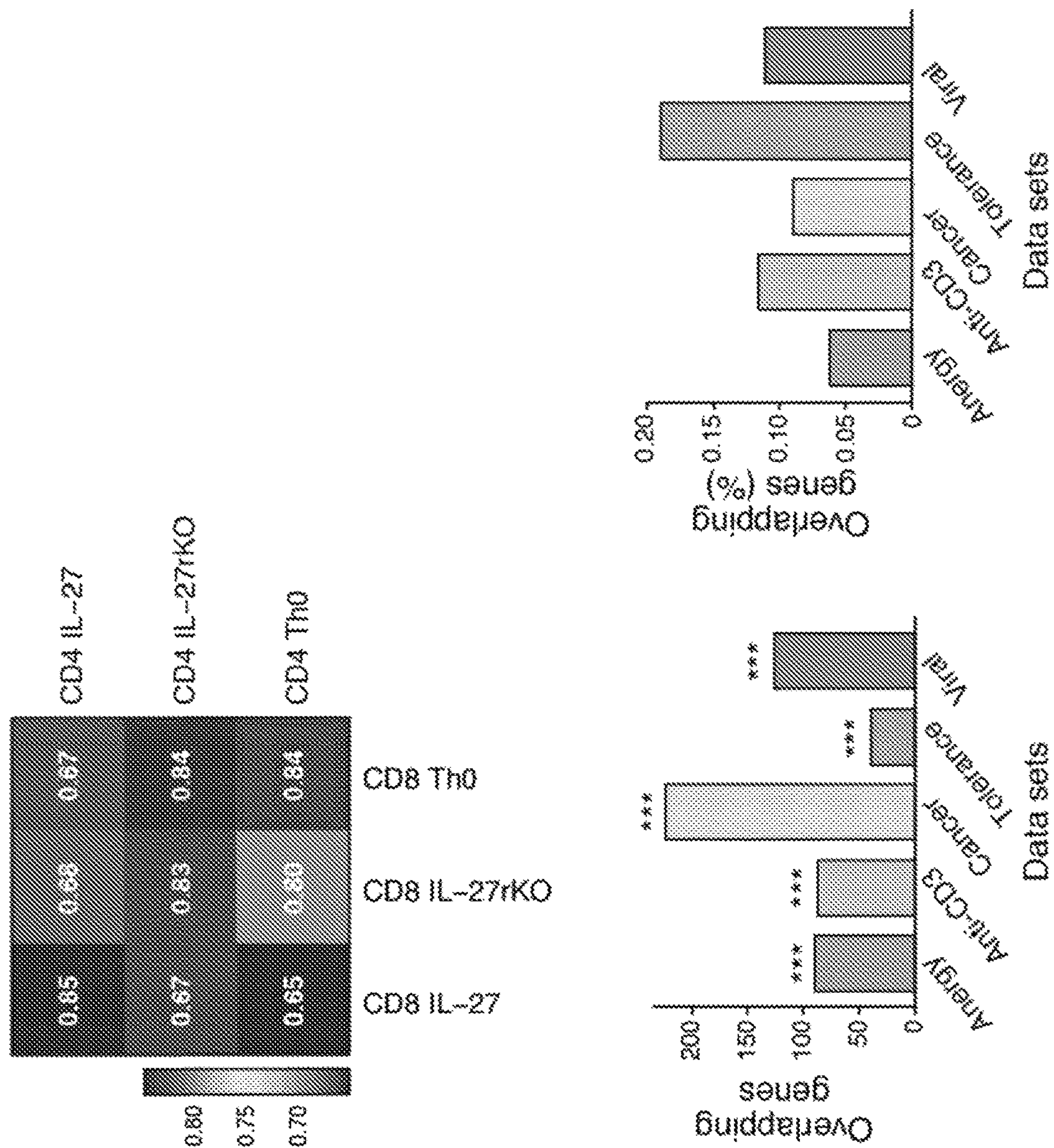

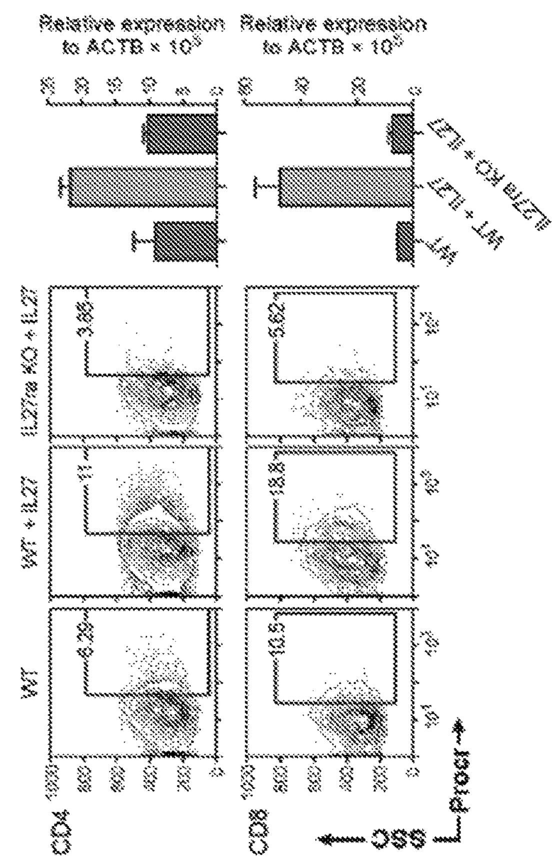
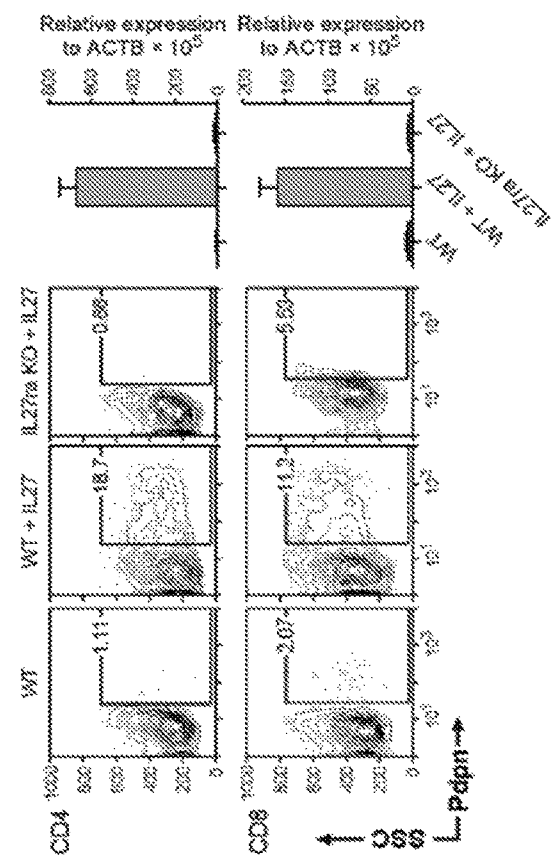
FIG. 6L

I. CD8+ cancer exhaustion signature
II. CD8+ viral exhaustion signature
III. CD4+ nasal anti-CD3 signature
IV. CD4+ tolerance signature
V. CD4+ anergy signature
VI. IL27rKO TILs signature
Signature score
tSNE1
tSNE2
50
25
0
-25
-50

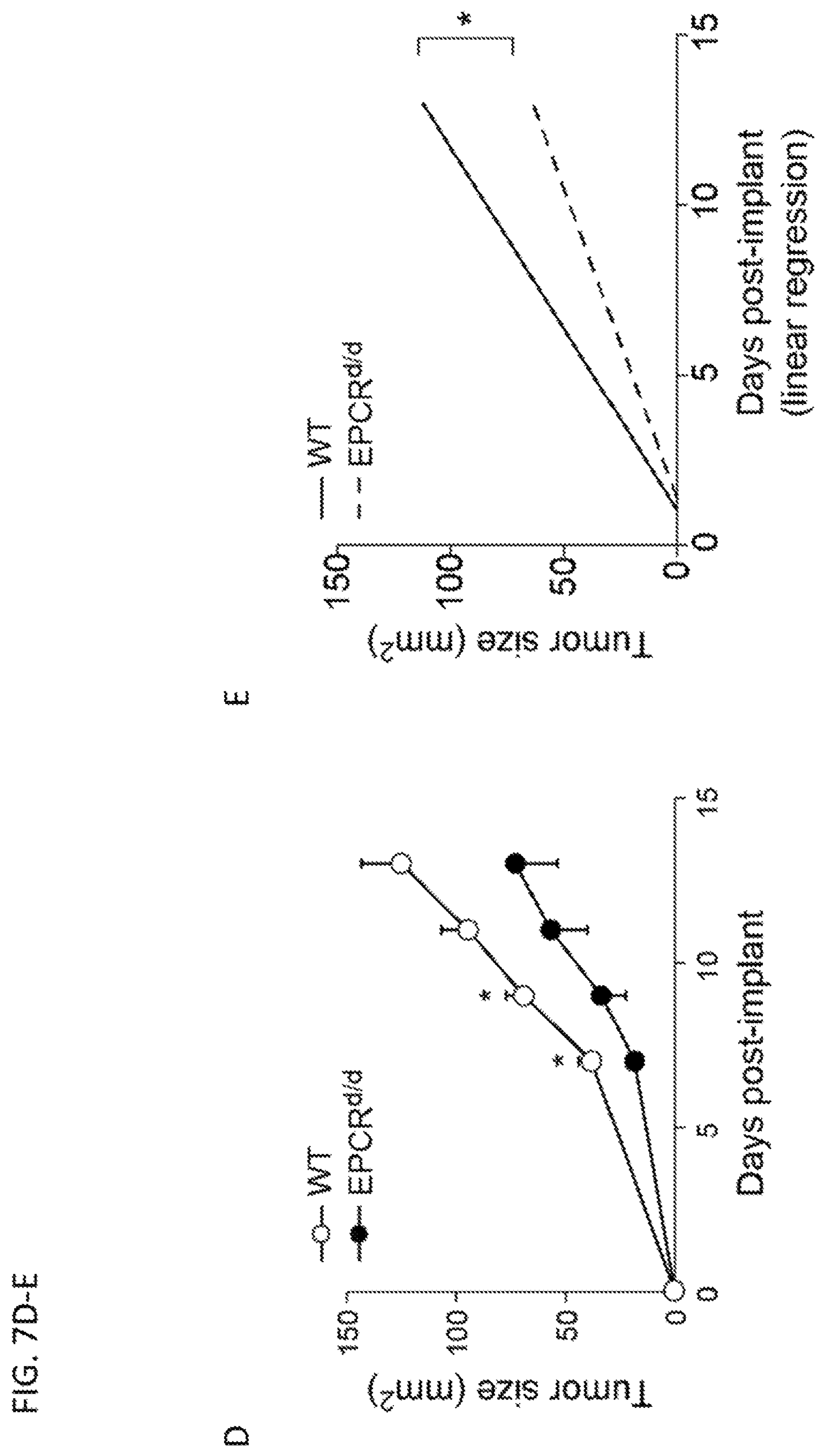
FIG. 7D-E

FIG. 10A-B
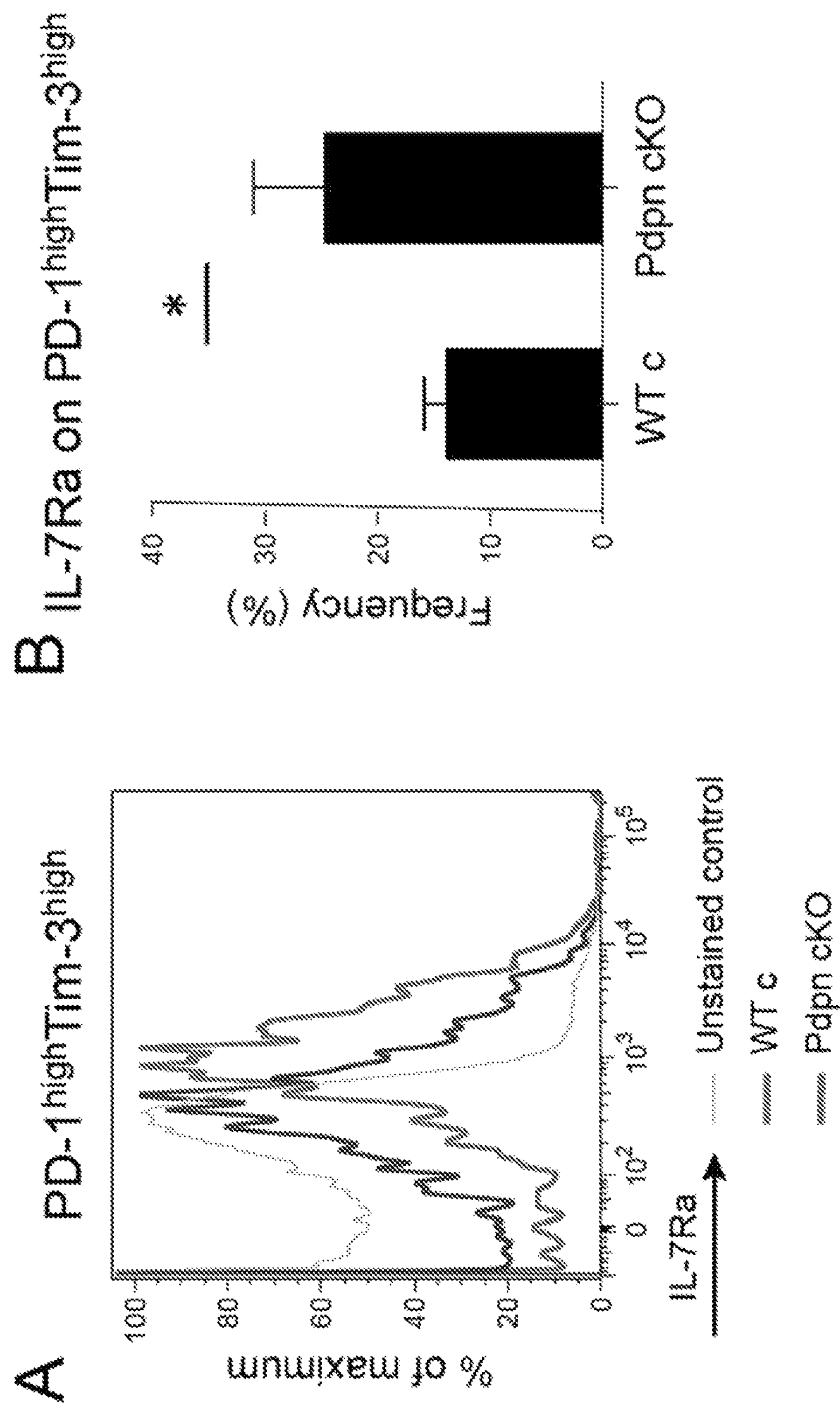

C
WT
Pdpn cKO
46.9
53.1
19
80.7
27.9
21.5
50.7
6.96
16.8
76.6
PD-1
Tim-3
CD8
PD-1 high
PD-1 low
Tim-3 high
Tim-3 low
Frequency (%)
WT
Pdpn cKO
Tim3 mid
%
Pdpnfl/fl
CD4crePdpnfl/fl

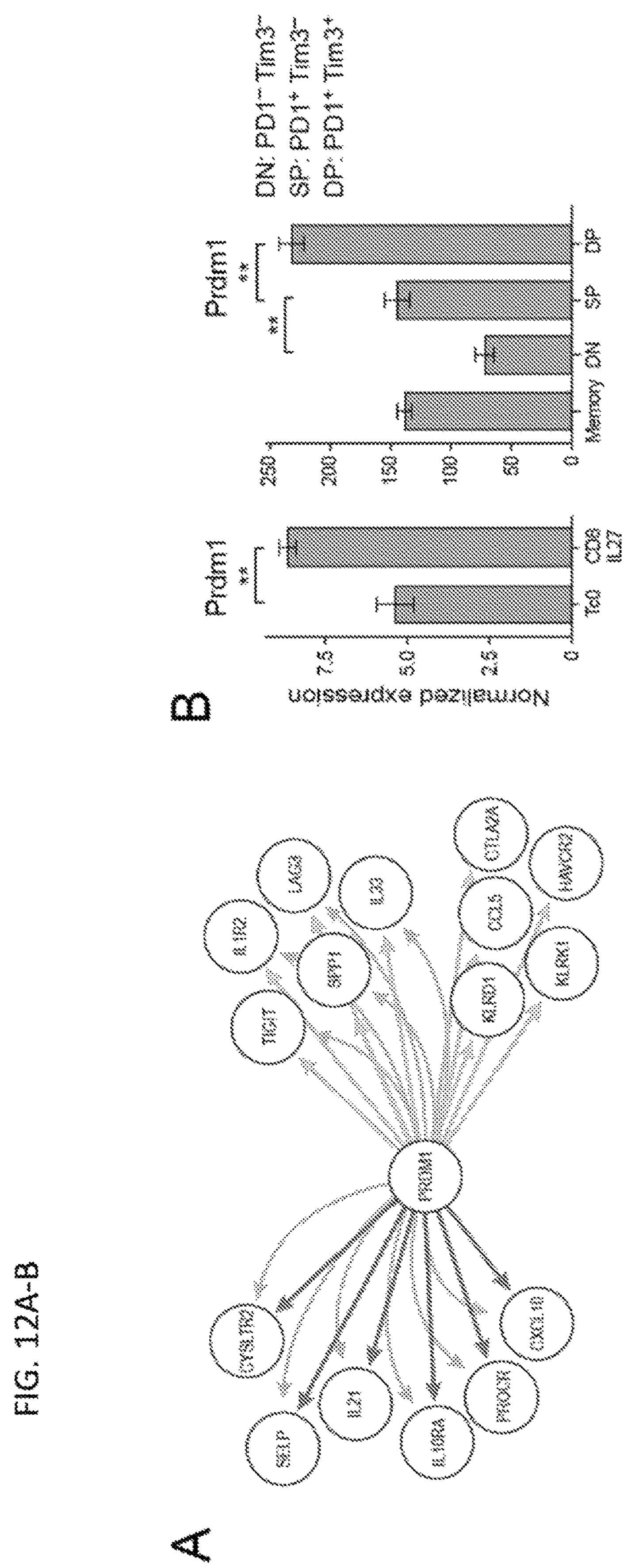
FIG. 12A-B

FIG. 13A
A
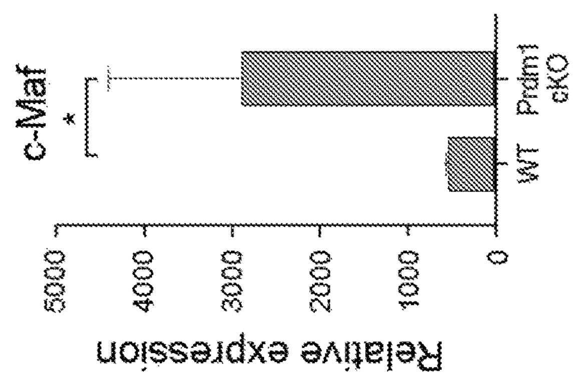
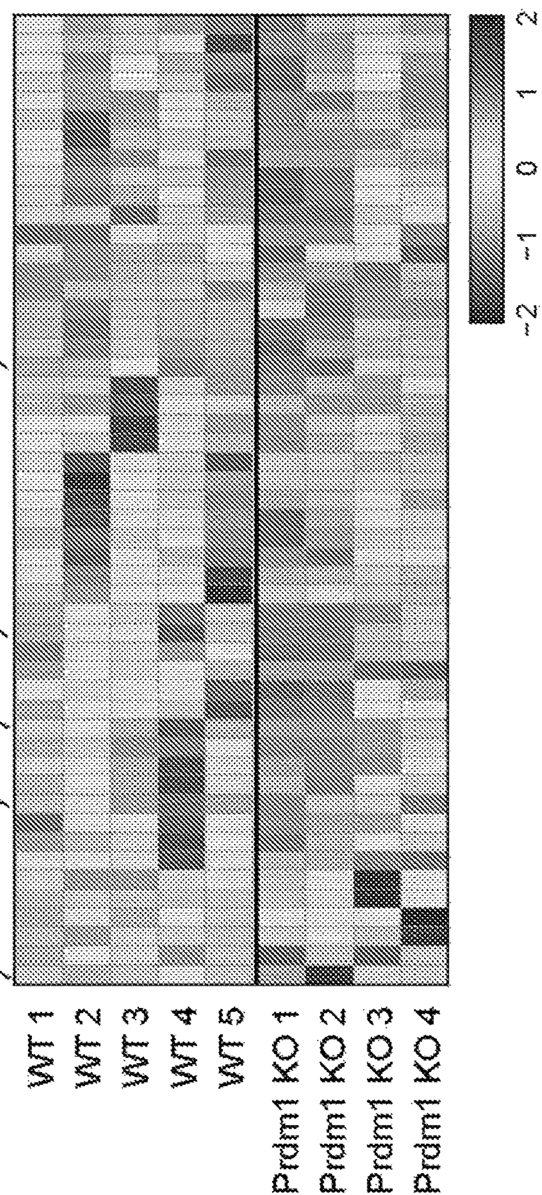

B
WT
Prdm1/
c-Maf
cKDO
Receptor
CD8
Frequency (%)
PD-1
Tim-3
Tigit
Pdpn
Procr
Lag3
47.4
15.9
33.9
10.1
39.8
10.1
21.4
12.6
33.2
12.7
56.8
17.8
WT
c-Maf
cKO
*

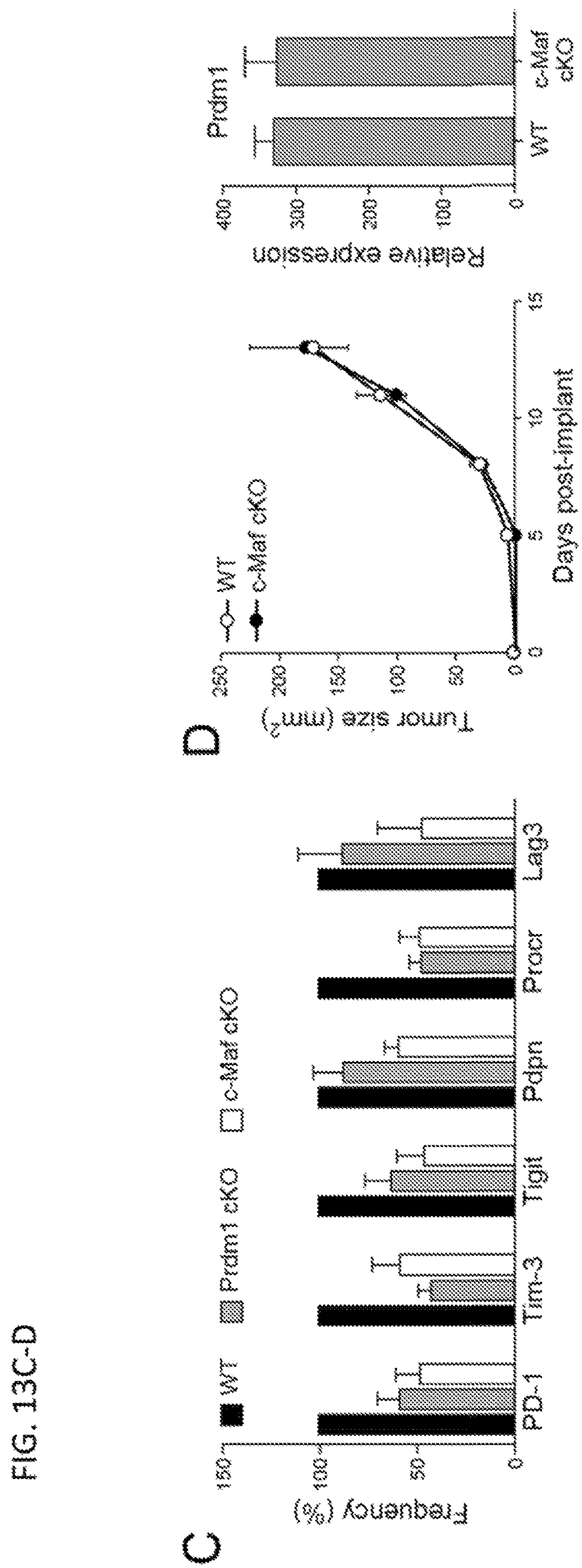
FIG. 13C-D
C
Frequency (%)
150
100
50
0
WT
Prdm1 cKO
c-Maf cKO
PD-1
Tim-3
Tigit
Pdpn
Procr
Lag3
D
Tumor size (mm²)
250
200
150
100
50
0
WT
c-Maf cKO
Days post-implant
0
5
10
15
Relative expression
400
300
200
100
0
Prdm1
WT
c-Maf cKO

A

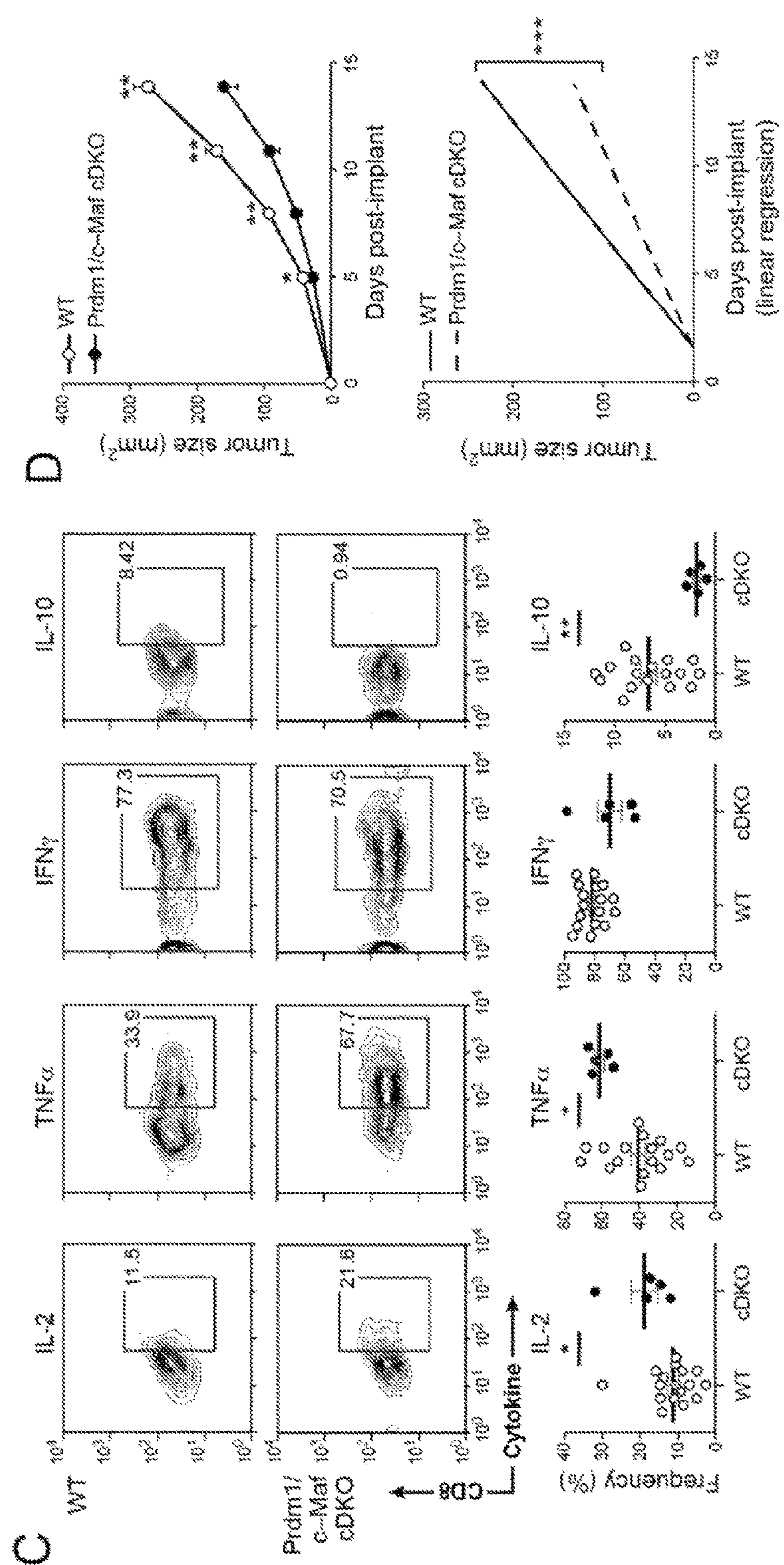
FIG. 14C-D

E

WT
DKO
PD-1+ Tim-3+
PD-1+ Tim-3−
PD-1− Tim-3−
2
0
−2
3
0
−3
Foxo1
Bach2
Sell
Tnfsf8
Lef1
Ccr7
Tcf7
Klf2
Tnfsf4
Tnfrsf9
Entpd1
Havcr2
Cd200
Pdcd1
Tnfrsf4

PD-1
Tim-3
Tigit
Pdpn
Procr
Lag3
WT
cDKO
CD4
TILs
44.5
55
47.8
31.6
23.7
30.8
20.3
11.8
3.93
12.6
4.14
10
Frequency (%)
WT
cDKO
* p < 0.05

FIG. 14G
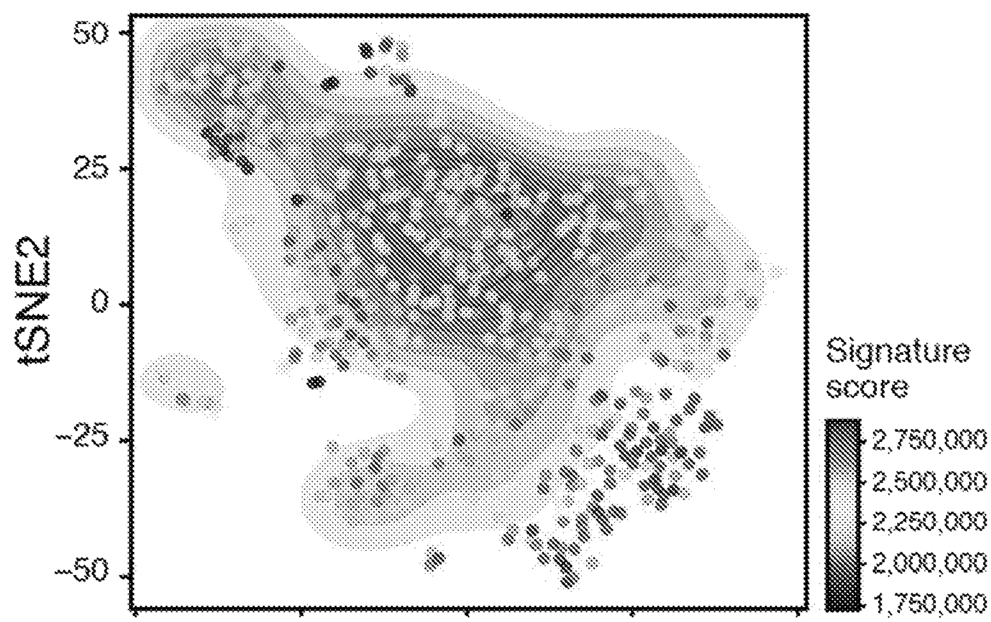
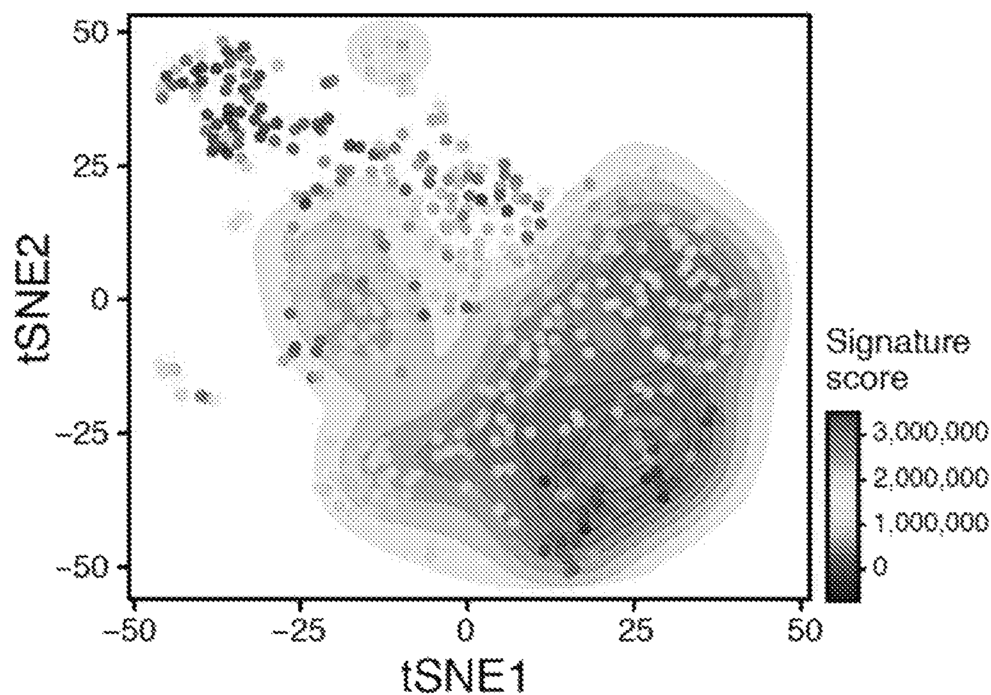

| | One-sample Kolmogorov–Smirnov test | Mean–rank gene set test (Wilcox GST) | Hyper-geometric | Competitive gene set test for inter-gene correlation |
|---|---|---|---|---|
| DP versus DN up-regulated genes | $2.00 \times 10^{-7}$ | $9.76 \times 10^{-5}$ | $1.98 \times 10^{-83}$ | 0.08 |
| DP versus DN down-regulated genes | $2.00 \times 10^{-16}$ | 0.67 | $1.61 \times 10^{-64}$ | 0.046 |
| SP versus DN up-regulated genes | 0.32 | 0.25 | $1.80 \times 10^{-10}$ | 0.26 |
| SP versus DN down-regulated genes | 0.81 | 0.84 | $9.54 \times 10^{-17}$ | 0.067 |
| DP versus memory up-regulated genes | 0.008 | 0.003 | $7.66 \times 10^{-8}$ | 0.14 |
| DP versus memory down-regulated genes | $2.00 \times 10^{-10}$ | 0.99 | $1.82 \times 10^{-15}$ | 0.39 |

C

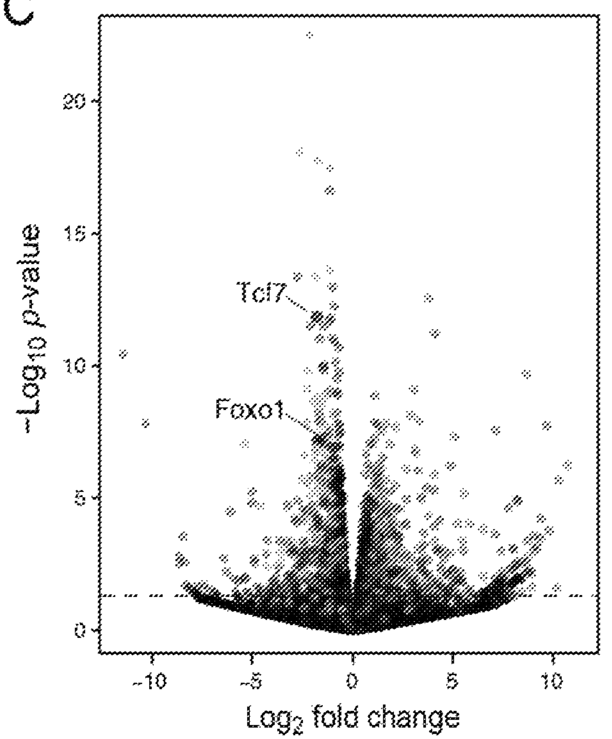

CD8 in TILs
2.2
51.8
33.2
12.8
Tim3
PD-1
Iso vs anti-Lilrb4 (d0,3,6,9)
Tumor size (mm2)
post s.c.
Iso
anti-Lilrb4
P=0.01
62
32
12.8
Lilrb4
CD8
PD1+Tim3+
PD1+Tim3-
PD1-Tim3-

SEQUENCE LISTING

```
<160> NUMBER OF SEQ ID NOS: 165

<210> SEQ ID NO 1
<211> LENGTH: 243
<212> TYPE: PRT
<213> ORGANISM: Homo sapiens

<400> SEQUENCE: 1

Met Gly Gln Thr Ala Gly Asp Leu Gly Trp Arg Leu Ser Leu Leu Leu
1               5                   10                  15

Leu Pro Leu Leu Leu Val Gln Ala Gly Val Trp Gly Phe Pro Arg Pro
            20                  25                  30

Pro Gly Arg Pro Gln Leu Ser Leu Gln Glu Leu Arg Arg Glu Phe Thr
        35                  40                  45

Val Ser Leu His Leu Ala Arg Lys Leu Leu Ser Glu Val Arg Gly Gln
    50                  55                  60

Ala His Arg Phe Ala Glu Ser His Leu Pro Gly Val Asn Leu Tyr Leu
65                  70                  75                  80

Leu Pro Leu Gly Glu Gln Leu Pro Asp Val Ser Leu Thr Phe Gln Ala
                85                  90                  95

Trp Arg Arg Leu Ser Asp Pro Glu Arg Leu Cys Phe Ile Ser Thr Thr
            100                 105                 110

Leu Gln Pro Phe His Ala Leu Leu Gly Gly Leu Gly Thr Gln Gly Arg
        115                 120                 125

Trp Thr Asn Met Glu Arg Met Gln Leu Trp Ala Met Arg Leu Asp Leu
    130                 135                 140

Arg Asp Leu Gln Arg His Leu Arg Phe Gln Val Leu Ala Ala Gly Phe
145                 150                 155                 160

Asn Leu Pro Glu Glu Glu Glu Glu Glu Glu Glu Glu Glu Glu Glu Glu
                165                 170                 175

Arg Lys Gly Leu Leu Pro Gly Ala Leu Gly Ser Ala Leu Gln Gly Pro
            180                 185                 190

Ala Gln Val Ser Trp Pro Gln Leu Leu Ser Thr Tyr Arg Leu Leu His
        195                 200                 205

Ser Leu Glu Leu Val Leu Ser Arg Ala Val Arg Glu Leu Leu Leu Leu
    210                 215                 220

Ser Lys Ala Gly His Ser Val Trp Pro Leu Gly Phe Pro Thr Leu Ser
225                 230                 235                 240

Pro Gln Pro


<210> SEQ ID NO 2
<211> LENGTH: 229
<212> TYPE: PRT
<213> ORGANISM: Homo sapiens

<400> SEQUENCE: 2
```

```
Met Thr Pro Gln Leu Leu Leu Ala Leu Val Leu Trp Ala Ser Cys Pro
1               5                   10                  15

Pro Cys Ser Gly Arg Lys Gly Pro Pro Ala Ala Leu Thr Leu Pro Arg
            20                  25                  30

Val Gln Cys Arg Ala Ser Arg Tyr Pro Ile Ala Val Asp Cys Ser Trp
        35                  40                  45

Thr Leu Pro Pro Ala Pro Asn Ser Thr Ser Pro Val Ser Phe Ile Ala
    50                  55                  60

Thr Tyr Arg Leu Gly Met Ala Ala Arg Gly His Ser Trp Pro Cys Leu
65                  70                  75                  80

Gln Gln Thr Pro Thr Ser Thr Ser Cys Thr Ile Thr Asp Val Gln Leu
                85                  90                  95

Phe Ser Met Ala Pro Tyr Val Leu Asn Val Thr Ala Val His Pro Trp
            100                 105                 110

Gly Ser Ser Ser Ser Phe Val Pro Phe Ile Thr Glu His Ile Ile Lys
        115                 120                 125

Pro Asp Pro Pro Glu Gly Val Arg Leu Ser Pro Leu Ala Glu Arg Gln
    130                 135                 140

Leu Gln Val Gln Trp Glu Pro Pro Gly Ser Trp Pro Phe Pro Glu Ile
145                 150                 155                 160

Phe Ser Leu Lys Tyr Trp Ile Arg Tyr Lys Arg Gln Gly Ala Ala Arg
                165                 170                 175

Phe His Arg Val Gly Pro Ile Glu Ala Thr Ser Phe Ile Leu Arg Ala
            180                 185                 190

Val Arg Pro Arg Ala Arg Tyr Tyr Val Gln Val Ala Ala Gln Asp Leu
        195                 200                 205

Thr Asp Tyr Gly Glu Leu Ser Asp Trp Ser Leu Pro Ala Thr Ala Thr
    210                 215                 220

Met Ser Leu Gly Lys
225


<210> SEQ ID NO 3
<211> LENGTH: 1048
<212> TYPE: DNA
<213> ORGANISM: Homo sapiens

<400> SEQUENCE: 3

ataaaggggt ggcccgtaga agattccagc accctcccct aactccaggc cagactcctt     60

tcagctaaag gggagatctg gatggcatct acttcgtatg actattgcag agtgcccatg    120

gaagacgggg ataagcgctg taagcttctg ctggggatag gaattctggt gctcctgatc    180

atcgtgattc tgggggtgcc cttgattatc ttcaccatca aggccaacag cgaggcctgc    240

cgggacggcc ttcgggcagt gatggagtgt cgcaatgtca cccatctcct gcaacaagag    300

ctgaccgagg cccagaaggg ctttcaggat gtggaggccc aggccgccac ctgcaaccac    360

actgtgatgg ccctaatggc ttccctggat gcagagaagg cccaaggaca aaagaaagtg    420

gaggagcttg agggagagat cactacatta aaccataagc ttcaggacgc gtctgcagag    480

gtggagcgac tgagaagaga aaaccaggtc ttaagcgtga gaatcgcgga caagaagtac    540

taccccagct cccaggactc cagctccgct gcggcgcccc agctgctgat tgtgctgctg    600

ggcctcagcg ctctgctgca gtgagatccc aggaagctgg cacatcttgg aaggtccgtc    660

ctgctcggct tttcgcttga acattccctt gatctcatca gttctgagcg ggtcatgggg    720

caacacggtt agcggggaga gcacggggta gccggagaag ggcctctgga gcaggtctgg    780
```

```
aggggccatg gggaagtcct gggtgtgggg acacagtcgg gttgacccag ggctgtctcc    840

ctccagagcc tccctccgga caatgagtcc cccctcttgt ctcccaccct gagattgggc    900

atggggtgcg gtgtgggggg catgtgctgc ctgttgttat gggttttttt tgcggggggg    960

gttgcttttt tctggggtct ttgagctcca aaaaataaac acttcctttg agggagagca   1020

cacctgaaaa aaaaaaaaaa aaaaaaaa                                      1048
```

```
<210> SEQ ID NO 4
<211> LENGTH: 3072
<212> TYPE: DNA
<213> ORGANISM: Homo sapiens

<400> SEQUENCE: 4

gtctttctgt tcactttttt tcacaaaatc atccaggctc ttcctactct cctctcttac     60

cacctctctc ttcttttttt ttttttttta gttatttcac agatgccact ggggtaggta    120

aactgaccca actctgcagc actcagaaga cgaagcaaag ccttctactt gagcagtttt    180

tccatcactg atatgtgcag gaaatgaaga cattgcctgc catgcttgga actgggaaat    240

tattttgggt cttcttctta atcccatatc tggacatctg gaacatccat gggaaagaat    300

catgtgatgt acagctttat ataaagagac aatctgaaca ctccatctta gcaggagatc    360

cctttgaact agaatgccct gtgaaatact gtgctaacag gcctcatgtg acttggtgca    420

agctcaatgg aacaacatgt gtaaaacttg aagatagaca aacaagttgg aaggaagaga    480

agaacatttc atttttcatt ctacattttg aaccagtgct tcctaatgac aatgggtcat    540

accgctgttc tgcaaatttt cagtctaatc tcattgaaag ccactcaaca actctttatg    600

tgacaggaaa gcaaaatgaa ctctctgaca cagcaggaag ggaaattaac ctggttgatg    660

ctcaccttaa gagtgagcaa acagaagcaa gcaccaggca aaattcccaa gtactgctat    720

cagaaactgg aatttatgat aatgaccctg acctttgttt caggatgcag gaagggtctg    780

aagtttattc taatccatgc ctggaagaaa acaaaccagg cattgtttat gcttccctga    840

accattctgt cattggaccg aactcaagac tggcaagaaa tgtaaaagaa gcaccaacag    900

aatatgcatc catatgtgtg aggagttaag tctgtttctg actccaacag ggaccattga    960

atgatcagca tgttgacatc attgtctggg ctcaacagga tgtcaaataa tatttctcaa   1020

tttgagaatt tttactttag aaatgttcat gttagtgctt gggtcttaag ggtccatagg   1080

ataaatgatt aaaatttctc tcagaaactt atttgggagc tttttatatt atagccttga   1140

ataacaaaat ctctccaaaa ctggttgaca tcatgagtag cagaatagta gaacgtttaa   1200

acttagctac attttaccca atatacaaac tcgatcttgc ctttgaagct attggaaaga   1260

cttgtaggga aaagaggttt gtgttacctg catcagttca ctacacactc ttgaaaacaa   1320

aatgtcccaa tttgactaac caaccataaa tacagtaatg attgtatatt tcaagtcagt   1380

cttccaaaat aagaaatttt tgctgtgtca gtctaagaat ggtgtttctt aaatgcaaag   1440

gagaaatcat tttaggcttg atgtaagaaa atgaaaataa taaatggtgc aataaaaata   1500

tagaatatac caattggata tagggtagat gttccacata cctggcaaac aaatgcttat   1560

atctactctg ttagattgat aagcaaatat aggtattaat ggagcagtca acgtatagca   1620

catttatgag gaaagtagag actcactggg tcacatagac taatggatag gaatgtgaca   1680

taatgctgct gaattaatat acttatgggc atctgaatag tttaaaagtt agtcagaata   1740

ggtatcactg ggcaagtgaa gatagcttaa actgcttcat gcttgacttg atagcaagtt   1800
```

```
aaagtgcaat taatggaatg gaggaaaacc cagaatattt aattggtctg taggggtcaa   1860

tttgctttca ttcaccacat ctgcatcttg ctgttcttct tactaaggaa tcagggcaaa   1920

tcatctgtag tgacatattt tagtttgcta atcatttatt ttaaaatact gaggttgcag   1980

ccacttaaga gtatagcaaa agatggattc agatttttgg actttccaaa gtacttgagt   2040

taaactattt caaaaatagc ctataatttt attcaacagt ttgaggctat tcgaattctc   2100

aggtgctgct actgaataat gtaatagtct tcatacaaag tggatagcaa aggttaaaat   2160

ccatttcaac aaatatgtga gctgagctgc tgcacaaagg aatgtgatgt gtgtgtgtgt   2220

gtgtgtgtgt gtgtgtgtta ggtggggtgg gtgacaacag aaatggtgca cgagaaactg   2280

atcaaattga cattatattt tcagtttgct tatgaagctc aaaatactag agtaaatggg   2340

tcattaaaga aaataatatg tgaaattatg gagtttagaa tacaagtggg gtatatatac   2400

aaaaagacaa aactgaggtt ttgtggtgga gagattttct taagtaacac tggcattaag   2460

ttttagctcc ttagatttgg gggtgcaaat attcttttga gtcactgtta ttttgccaat   2520

tacacctaga atttcaagca accaattcga gataggctgt tttagccagg ctgcatttgt   2580

ggacaactta tgtaagaaag acatgttaga atagctgctt gtggtattct taaaaataga   2640

aacaggaaat atggggagga tacatttagc tgtcctctta tcagatgaac acacgaaatt   2700

gaacagttcc ttcatgattc tctcaaactt aaaagcaaaa tatttctgtc ttatttaaaa   2760

tatccttagt atgtcttata gtaaagataa tgctgataat gatttcatct ctaagatgta   2820

ttaatatatt tgtactgttt gccaaaatca caaatcattt atgtttttat tccttttcaa   2880

aatggtgtca gagacataca tgcattttcc caaatgactc tacttcacta ttatttacat   2940

ggcttatttc attagtttat agagggtttg agaaaaagaa tatgtagata atttaatggt   3000

ttttcacaaa ttttaagctt gtgattgtgc tcaatgagaa ggtaaagtta ttaaaactta   3060

tttgaaatca aa                                                       3072
```

<210> SEQ ID NO 5
<211> LENGTH: 3008
<212> TYPE: DNA
<213> ORGANISM: Mus musculus

<400> SEQUENCE: 5

```
actgcacact gttccctctc ttagaactag catgttgggt gttatgtagt caaaggaggg     60

cattatgagc tgtaccccag ggacttcctg atcctcttac atgtataaat agcaagaccg    120

ggccaggaac agcaagcagt ctgaaggcca gctgggtctg cccactaaga agatgaagcc    180

ttttcatact gccctctcct tcctcattct tacaactgct cttggaatct gggcccagat    240

cacacatgca acagagacaa aagaagtcca gagcagtctg aaggcacagc aagggcttga    300

aattgaaatg tttcacatgg gctttcaaga ctcttcagat tgctgcctgt cctataactc    360

acggattcag tgttcaagat ttataggtta ttttcccacc agtggtgggt gtaccaggcc    420

gggcatcatc tttatcagca agagggggtt ccaggtctgt gccaacccca gtgatcggag    480

agttcagaga tgcattgaaa gattggagca aaactcacaa ccacggacct acaaacaata    540

acatttgctt gaagagaagg gtgtgaactg ccagctactt tctttggtct tccccagtga    600

ccacctaagt ggctctaagt gtttattttt ataggtatat aaacattttt tttttctgtt    660

ccactttaaa gtggcatatc tggctttgtc acagagggga aacttgtctg tgccaacccc    720

agtcatctga aaactcagat gcctggaagg tctgaagctg acctcaatga ctacacataa    780

tatttgattg agataaatgg gcaaggtctg gagagatggc ttggtggtta agagcacctg    840
```

```
ctgctcttcc agaggacctg ggttcaattc ccacttagat ggcagctcaa actatctata    900
attccaattc caaagaaaac tgatgcccta ttttgccctt tagttagtag tatttacagt    960
attctttata aattcacctt gacatgacca tcttgagcta cagccatcct aactgcctca   1020
gaatcactca agttcttcca ctcggtttcc cagcggattt taagtggata aactgtgaga   1080
gtggtctgtg ggactttgga atgtgtctgg ttctgatagt cacttatggc aacccaggta   1140
cattcaacta ggatgaaata aattctgcct tagcccagta gtatgtctgt gtttgtaagg   1200
acccagctga ttttcccacc acccctccat cagtaagcca ctaataaagt gcatctatgc   1260
agccacaggt ctgtctgcct cttttgcttc agtttcctag gactatgggc tgaaattggg   1320
ctgttaggga gaaagcatct cactcgcttt tattgaatct gcagtggaaa agaaacagag   1380
ggagtcaggt aactttgaat attttcttca aaacaaaaga tatcatggta caattttttt   1440
ttaatttttt gtttgtttgt ttttgttttt cgagacaggg tttctctgtg tagccctggc   1500
tgtcctggaa ctcactctgt agaccaggtt ggcctccaac tcagaaatcc gcctgcctct   1560
gcctcccgag tgctgggatt aaaggcgtgc gccaccacca cccggcccat ggtacaattt   1620
ttaaatttcc agaaatatag tttattccaa tgtagacttc atatcaagga tgtattttac   1680
ccactataga gagaatcatt aaagtgatct acaaatcttt ggaagttctc cctgttcgat   1740
aagatcctca attctattcg aggatctcaa cttggtcagc ttgtttttat accagtctca   1800
tgctgttttt ttactgtggc tctgtatgat aatcccttca gcagtgtctc tattgttcag   1860
gggtgtttgg gttacctaag atcttttgtg tttccatatg aattttaaga ttgttatttt   1920
caaaatctgt gaagaattgc attggaattt tgatgggaat tgcaatgaat ctataaattt   1980
tttttgataa gctgaccatt gtcaaaatat taaactagac catgagcata ggtggtcttt   2040
ccatcttctg ggtcttcttt gattgtttta gagttttcat tgtataggcc ttttgcttta   2100
ttcattaggt ttattccaag atattatttt gcaggtattg agagtgggat tttcctccca   2160
atttcttcct cagtatgttt gtcatttgct tataggaaga ctattggttt ttttgtatgt   2220
gcagatcgtg tcctgacact tggctgaaag tgtttatcag ctctacgagt tttctagtgt   2280
agcatttagg gccttttata gagagagaaa gaatgatatc atctgccaat gaatattgct   2340
tgacttcttc ctttcctgtt tgaatccatc ttgtctcctt ctcttgcctt actgctgtag   2400
caaaaacttc aagtactcag ctgaaaagaa gtactgagag aaagtatcca tgtccctttc   2460
ctgattttta gcagaaatgc ttccagtttt tctccggtta gcattccgtt ggctacaggc   2520
ttgttgtata tttcctttat tgtattgaaa tacgttcctt gtatttctgt tgtcttcagg   2580
gctttaataa tgaagagctg ttggttttca ccacaggcat tttctgaatc tactttctgc   2640
tttcttgaat tgagtccatt tatacagtgg atctcattta ctgatttatg tatgttgaac   2700
atccctgcaa gtctggaatg aagctcttta tgatttcaga aaacagattt ttcttagtcc   2760
tcatttgtaa cctctccccc tagcctgaaa cctggctgct caggtttcac tgttagcagg   2820
aagagagcgt ggggtggacc taccgcccta tcgttctgcc actcccactg cggctgcctg   2880
ccacctagct gttcctgagc caacacgtgg tcacctgcaa ctggactcct aggatgattt   2940
ggcgggaatg ggcccctccc ccttttata acccagtgtc tggaatagta aaattgaacc   3000
ttggtcag                                                             3008
```

<210> SEQ ID NO 6
<211> LENGTH: 1657
<212> TYPE: DNA

<213> ORGANISM: Homo sapiens

<400> SEQUENCE: 6
gctcacagga agccacgcac ccttgaaagg caccgggtcc ttcttagcat cgtgcttcct 60
gagcaagcct ggcattgcct cacagacctt cctcagagcc gctttcagaa aagcaagctg 120
cttctggttg ggcccagacc tgccttgagg agcctgtaga gttaaaaaat gaaccccacg 180
gatatagcag acaccaccct cgatgaaagc atatacagca attactatct gtatgaaagt 240
atccccaagc cttgcaccaa agaaggcatc aaggcatttg gggagctctt cctgcccccca 300 ctgtattcct tggtttttgt atttggtctg cttggaaatt ctgtggtggt tctggtcctg 360
ttcaaataca agcggctcag gtccatgact gatgtgtacc tgctcaacct tgccatctcg 420
gatctgctct tcgtgttttc cctccctttt tggggctact atgcagcaga ccagtgggtt 480
tttgggctag gtctgtgcaa gatgatttcc tggatgtact tggtgggctt ttacagtggc 540
atattctttg tcatgctcat gagcattgat agatacctgg caattgtgca cgcggtgttt 600
tccttgaggg caaggacctt gacttatggg gtcatcacca gtttggctac atggtcagtg 660
gctgtgttcg cctcccttcc tggctttctg ttcagcactt gttatactga gcgcaaccat 720
acctactgca aaaccaagta ctctctcaac tccacgacgt ggaaggttct cagctccctg 780
gaaatcaaca ttctcggatt ggtgatcccc ttagggatca tgctgttttg ctactccatg 840
atcatcagga ccttgcagca ttgtaaaaat gagaagaaga acaaggcggt gaagatgatc 900
tttgccgtgg tggtcctctt ccttgggttc tggacacctt acaacatagt gctcttccta 960
gagaccctgg tggagctaga agtccttcag gactgcacct ttgaaagata cttggactat 1020
gccatccagg ccacagaaac tctggctttt gttcactgct gccttaatcc catcatctac 1080
ttttttctgg gggagaaatt tcgcaagtac atcctacagc tcttcaaaac ctgcaggggc 1140
ctttttgtgc tctgccaata ctgtgggctc ctccaaattt actctgctga cacccccagc 1200
tcatcttaca cgcagtccac catggatcat gatctccatg atgctctgta gaaaaatgaa 1260
atggtgaaat gcagagtcaa tgaactttcc acattcagag cttacttaaa attgtatttt 1320
agtaagagat tcctgagcca gtgtcaggag gaaggcttac acccacagtg gaaagacagc 1380
ttctcatcct gcaggcagct tttctctcc cactagacaa gtccagcctg gcaagggttc 1440
acctgggctg aggcatcctt cctcacacca ggcttgcctg caggcatgag tcagtctgat 1500
gagaactctg agcagtgctt gaatgaagtt gtaggtaata ttgcaaggca aagactattc 1560
ccttctaacc tgaactgatg ggtttctcca gagggaattg cagagtactg gctgatggag 1620
taaatcgcta ccttttgctg tggcaaatgg gccctct 1657

<210> SEQ ID NO 7
<211> LENGTH: 1250
<212> TYPE: DNA
<213> ORGANISM: Mus musculus

<400> SEQUENCE: 7
ctttcagtca gcatgataga aacatacagc caaccttccc ccagatccgt ggcaactgga 60
cttccagcga gcatgaagat ttttatgtat ttacttactg ttttccttat cacccaaatg 120
attggatctg tgctttttgc tgtgtatctt catagaagat tggataaggt cgaagaggaa 180
gtaaaccttc atgaagattt tgtattcata aaaaagctaa agagatgcaa caaaggagaa 240
ggatctttat ccttgctgaa ctgtgaggag atgagaaggc aatttgaaga ccttgtcaag 300
gatataacgt taaacaaaga agagaaaaaa gaaaacagct ttgaaatgca aagaggtgat 360

```
gaggatcctc aaattgcagc acacgttgta agcgaagcca acagtaatgc agcatccgtt    420
ctacagtggg ccaagaaagg atattatacc atgaaaagca acttggtaat gcttgaaaat    480
gggaaacagc tgacggttaa aagagaagga ctctattatg tctacactca agtcaccttc    540
tgctctaatc gggagccttc gagtcaacgc ccattcatcg tcggcctctg gctgaagccc    600
agcagtggat ctgagagaat cttactcaag gcggcaaata cccacagttc ctcccagctt    660
tgcgagcagc agtctgttca cttgggcgga gtgtttgaat tacaagctgg tgcttctgtg    720
tttgtcaacg tgactgaagc aagccaagtg atccacagag ttggcttctc atcttttggc    780
ttactcaaac tctgaacagt gcgctgtcct aggctgcagc agggctgatg ctggcagtct    840
tccctataca gcaagtcagt taggacctgc cctgtgttga actgcctatt tataacccta    900
ggatcctcct catggagaac tatttattat gtacccccaa ggcacataga gctggaataa    960
gagaattaca gggcaggcaa aaatcccaag ggaccctgct ccctaagaac ttacaatctg   1020
aaacagcaac cccactgatt cagacaacca gaaaagacaa agccataata cacagatgac   1080
agagctctga tgaaacaaca gataactaat gagcacagtt ttgttgtttt atgggtgtgt   1140
cgttcaatgg acagtgtact tgacttacca gggaagatgc agaagggcaa ctgtgagcct   1200
cagctcacaa tctgttatgg ttgacctggg ctccctgcgg ccctagtagg              1250
```

<210> SEQ ID NO 8
<211> LENGTH: 1912
<212> TYPE: DNA
<213> ORGANISM: Homo sapiens

<400> SEQUENCE: 8

```
tttttttct tccctctagt gggcggggca gaggagttag ccaagatgtg actttgaaac      60
cctcagcgtc tcagtgccct tttgttctaa acaaagaatt ttgtaattgg ttctaccaaa    120
gaaggatata atgaagtcac tatgggaaaa gatggggagg agagttgtag gattctacat    180
taattctctt gtgcccttag cccactactt cagaatttcc tgaagaaagc aagcctgaat    240
tggtttttta aattgcttta aaaatttttt ttaactgggt taatgcttgc tgaattggaa    300
gtgaatgtcc attcctttgc ctcttttgca gatatacact tcagataact acaccgagga    360
aatgggctca ggggactatg actccatgaa ggaaccctgt ttccgtgaag aaaatgctaa    420
tttcaataaa atcttcctgc ccaccatcta ctccatcatc ttcttaactg gcattgtggg    480
caatggattg gtcatcctgg tcatgggtta ccagaagaaa ctgagaagca tgacggacaa    540
gtacaggctg cacctgtcag tggccgacct cctctttgtc atcacgcttc ccttctgggc    600
agttgatgcc gtggcaaact ggtactttgg gaacttccta tgcaaggcag tccatgtcat    660
ctacacagtc aacctctaca gcagtgtcct catcctggcc ttcatcagtc tggaccgcta    720
cctggccatc gtccacgcca ccaacagtca gaggccaagg aagctgttgg ctgaaaaggt    780
ggtctatgtt ggcgtctgga tccctgccct cctgctgact attcccgact tcatctttgc    840
caacgtcagt gaggcagatg acagatatat ctgtgaccgc ttctacccca atgacttgtg    900
ggtggttgtg ttccagtttc agcacatcat ggttggcctt atcctgcctg gtattgtcat    960
cctgtcctgc tattgcatta tcatctccaa gctgtcacac tccaagggcc accagaagcg   1020
caaggccctc aagaccacag tcatcctcat cctggctttc ttcgcctgtt ggctgcctta   1080
ctacattggg atcagcatcg actccttcat cctcctggaa atcatcaagc aagggtgtga   1140
gtttgagaac actgtgcaca agtggatttc catcaccgag gccctagctt tcttccactg   1200
```

ttgtctgaac cccatcctct atgctttcct tggagccaaa tttaaaacct ctgcccagca 1260
cgcactcacc tctgtgagca gagggtccag cctcaagatc ctctccaaag gaaagcgagg 1320
tggacattca tctgtttcca ctgagtctga gtcttcaagt tttcactcca gctaacacag 1380
atgtaaaaga ctttttttta tacgataaat aacttttttt taagttacac atttttcaga 1440
tataaaagac tgaccaatat tgtacagttt ttattgcttg ttggattttt gtcttgtgtt 1500
tctttagttt ttgtgaagtt taattgactt atttatataa attttttttg tttcatattg 1560
atgtgtgtct aggcaggacc tgtggccaag ttcttagttg ctgtatgtct cgtggtagga 1620
ctgtagaaaa gggaactgaa cattccagag cgtgtagtga atcacgtaaa gctagaaatg 1680
atccccagct gtttatgcat agataatctc tccattcccg tggaacgttt ttcctgttct 1740
taagacgtga ttttgctgta gaagatggca cttataacca aagcccaaag tggtatagaa 1800
atgctggttt ttcagttttc aggagtgggt tgatttcagc acctacagtg tacagtcttg 1860
tattaagttg ttaataaaag tacatgttaa acttaaaaaa aaaaaaaaaa aa 1912

<210> SEQ ID NO 9
<211> LENGTH: 4522
<212> TYPE: DNA
<213> ORGANISM: Homo sapiens

<400> SEQUENCE: 9
cctgtcccct cagcagtgtt ggtttctctt cttgacttga tgcaggcaca gatttatcaa 60
gctcctcagt caacaaacac atcaccggaa gaaatatgga aggaaaggaa ttttaaaagg 120
aaataccaat ctctgtgcaa acaaagcctt gtatattcat gtttgcacca atctactgtg 180
agatttatga agaaaaacaa attgcggaca actctctatg tacacttaca aatgcctcag 240
ttgatgcttg tgggctgttt gtcagcgttc tgtgataatg aacacatgga cttctgttta 300
ttaaattcag ttgacccctt tagccaattg ccaggagcct ggatttttac ttccaactgc 360
tgatatctgt gtaaaaattg atctacatcc accctttaaa agcattgatg aattaattag 420
aactttagac aacaaagaaa aattgaaaaa gaattctcag taaaagcgaa ttcgatgttc 480
aaaacaaact acaaagagac aagacttctc tgtttacttt ctaagaacta atataattgc 540
taccttaaaa aggaaaaaat gaacagcaca tgtattgaag aacagcatga cctggatcac 600
tatttgtttc ccattgttta catctttgtg attatagtca gcattccagc caatattgga 660
tctctgtgtg tgtctttcct gcaagcaaag aaggaaagtg aactaggaat ttacctcttc 720
agtttgtcac tatcagattt actctatgca ttaactctcc ctttatggat tgattatacc 780
tggaataaag acaactggac tttctctcct gccttgtgca aagggagtgc ttttctcatg 840
tacatgaatt tttacagcag cacagcattc ctcacctgca ttgccgttga tcggtatttg 900
gctgttgtct accctttgaa gttttttttc ctaaggacaa gaagatttgc actcatggtc 960
agcctgtcca tctggatatt ggaaaccatc ttcaatgctg tcatgttgtg ggaagatgaa 1020
acagttgttg aatattgcga tgccgaaaag tctaatttta ctttatgcta tgacaaatac 1080
cctttagaga aatggcaaat caacctcaac ttgttcagga cgtgtacagg ctatgcaata 1140
cctttggtca ccatcctgat ctgcaaccgg aaagtctacc aagctgtgcg gcacaataaa 1200
gccacggaaa acaaggaaaa gaagagaatc ataaaactac ttgtcagcat cacagttact 1260
tttgtcttat gctttactcc ctttcatgtg atgttgctga ttcgctgcat tttagagcat 1320
gctgtgaact tcgaagacca cagcaattct gggaagcgaa cttacacaat gtatagaatc 1380
acggttgcat taacaagttt aaattgtgtt gctgatccaa ttctgtactg ttttgtaacc 1440

```
gaaacaggaa gatatgatat gtggaatata ttaaaattct gcactgggag gtgtaataca   1500
tcacaaagac aaagaaaacg catactttct gtgtctacaa aagatactat ggaattagag   1560
gtccttgagt agaaccaagg atgttttgaa gggaagggaa gtttaagtta tgcattatta   1620
tatcatcaag attacatttt gaaaaggaaa tctagcatgt gaggggacta agtgttctca   1680
gagtgatgtt ttaatccagt ccaataaaaa tatcttaaaa ctgcattgta cagctccctc   1740
cctgcgtttt attaaatgat gtatattaaa caaagatcaa tattttctta atgactcagg   1800
gtctttattg ttaatgccaa ttgtttttgt atctgtgcta taatccctta gagtcagtaa   1860
agtatgtagg ggactgtttc ttcctttgtg tctgggttta tgatttttct cactctttct   1920
ttggactcca gggtgtcagc catcaggtct cctaatttg tgtaccggtc tccaacaacc   1980
ccagctactg aatactgctt ctaatctcct cattcattaa caaatcttta ttttttttatc   2040
ttgtataaaa taactgcttt attgacacaa aatttacata acttaaaatt caactttgta   2100
ttgtgtacaa ttcagtgatt ttttgtatat tcacagagct gtgcaaccat caccacactc   2160
aaaaaatttt catcacccac caaagaaatc ttatactctt agcagtcgct ccctgctctc   2220
ccgtccatgc cagttattaa tttactttct gtctctaagg attttcatta ctctgaacat   2280
ttcatataaa tagaattata caatatgtgg cctactgtga cgtatttcac ttagtataat   2340
ggtttcaagt tttatccatg tgtagaatgt atcagcactt catttctttt tatggcctga   2400
tagtattctg ttgcatggtt atactccatt ttgtttatct aatcacttgg cttcattaac   2460
aaatatttat tgaatccatt ccataaacta ggttttgagt taagtactgg ggctatgaaa   2520
gaaatggtct catgaagcct cacgaagttt acattagttc aaaagcctag tcaccgagct   2580
tgaaagattt ctatataaag gaaaaggaaa taggctctga gttttatttt gatctctttt   2640
taatttataa ctgggtataa catagctgaa attaccagaa gtttaatgca tagacaaata   2700
aatagttcta ttatatcttt ctttttggac ttagaatgtt agaatatttt gagagttctt   2760
tttttttttt tttttgagtc agagtcttgc tctgtaatcc aggctagagt gtagtggtgc   2820
gatctccact cactgcagcc tccacctccc aggttcaagc gattctcctg cctcagcctc   2880
ccaagtagct gggattacag gcacccacca ccatgcccag ctaatttttg tatttttagt   2940
agagacgggg tttcaccatg ttgcacaggc tggtctcaat cgaactcctg acctcaagtg   3000
atcatcccac ctaggtctcc caaagtgctg agatgacagg cgtgagccac catgcctggc   3060
aaagagagtc ttgatacaac atattctttt gaatcctcat tgtgtaaatt gcctcgttgt   3120
aaatagacac tcagtaaaca ttttcctcac caaaatattt ttaaggattt ttctaccctt   3180
ctccttttct ctttgctttc cttttcttgc ctgttctttc cactcccccc aaaatgatca   3240
gatagcaaat gtcttgataa catgaggtgc cctcacatta aaaaacaaaa tattgagccg   3300
ggcgcggtgg ctcatgcctg taatcccagc actttgggag gctgaggtgg gcagatcgcc   3360
ttaggtcagg agttggagac caggctgacc aatatgatga aactctgtct ctactaaaaa   3420
ttcaaaaatg tgccagacct ggcctggtgg catgtgcctg taatcccagc tacttgggag   3480
gctgagtcat aagcctgcaa tgggaaaatg gatcgaatct ggggtgaggg ggaagtgatg   3540
tgggggttat ggtacctctt ttctcttcca aagatgctgt tcttactgca tcacttgtgg   3600
ctggccagga aaagccatgc aggagttttg tttgtggcca ctaggtgacg atcgtgttct   3660
gtacgggacc tcttattaat agttcaccac tagccgccac tccagaagag cggaggaacc   3720
caggataata ttttgtcaac caagaaacaa gaagtccctc ccaggaactg gaaatgaatg   3780
```

```
gggaaaatgc tgaaatctca tttgcactat tcatttctct tctctctgga aagctcggca   3840
atcatcaggt catttcattt ggcttaaatt ccatgtgtct ttccaaactt ttaaaagctg   3900
gtgaaaattg ttccacccat atgtaaaaga acataggtta agttgtctaa ttcttgcagg   3960
aatgtggata tagcattaaa aatatgtctt tgtatactta tcttacccat gtaagaaaag   4020
agtggccaac tttcatataa atagaaagag aacatttaag ctatatgcag tttgcatttt   4080
tgtctactat tatgaaatta ttatctatga aattcaagct gtaactcaac atatgtataa   4140
ttttaatttc taatttattg ttagatctca gcacttaaaa aattacatct tgtatttgaa   4200
ttgttaaatc tgttccctgc aaagaacagt aatacaatca tgttctaatt tactagcatt   4260
tgcatatttt agaaatataa tggcctgtaa tttacttttc ttttgcctat aattttctga   4320
agctctttat gatgcaccgg tgcattttta tttaaaaaat agattgtgac tcctcaaata   4380
atgttacaat tcgatgttca aaaagcaatc caggtacata gccataaagg gatgagctag   4440
agaggtctcc atattatcat tcaatgtgag aataaaaatt ctatatttta ttctagaata   4500
aaattataaa tttctttatc ta                                             4522
```

<210> SEQ ID NO 10
<211> LENGTH: 2592
<212> TYPE: DNA
<213> ORGANISM: Homo sapiens

<400> SEQUENCE: 10

```
agtctacaga ctcctccgaa cacagagctg cagctcttca gggaagaaat caaaacaaga     60
tcacaagaat actgaaaaat gaagcctaaa atgaagtatt caaccaacaa aatttccaca    120
gcaaagtgga agaacacagc aagcaaagcc ttgtgtttca agctgggaaa atcccaacag    180
aaggccaaag aagtttgccc catgtacttt atgaagctcc gctctggcct tatgataaaa    240
aaggaggcct gttactttag gagagaaacc accaaaaggc cttcactgaa aacaggtaga    300
aagcacaaaa gacatctggt actcgctgcc tgtcaacagc agtctactgt ggagtgcttt    360
gcctttggta tatcaggggt ccagaaatat actagagcac ttcatgattc aagtatcaca    420
gataaggtgt tactgagtta ctatgagtct caacacccct caaatgaatc aggtgacggt    480
gttgatggta agatgttaat ggtaaccctg agtcctacaa aagacttctg gttgcatgcc    540
aacaacaagg aacactctgt ggagctccat aagtgtgaaa aaccactgcc agaccaggcc    600
ttctttgtcc ttcataatat gcactccaac tgtgtttcat ttgaatgcaa gactgatcct    660
ggagtgttta taggtgtaaa ggataatcat cttgctctga ttaaagtaga ctcttctgag    720
aatttgtgta ctgaaaatat cttgtttaag ctctctgaaa cttagttgat ggaaacctgt    780
gagtcttggg ttgagtaccc aaatgctacc actggagaag gaatgagaga taaagaaaga    840
gacaggtgac atctaaggga aatgaagagt gcttagcatg tgtggaatgt tttccatatt    900
atgtataaaa atatttttc taatcctcca gttattcttt tatttccctc tgtataactg     960
catcttcaat acaagtatca gtatattaaa tagggtattg gtaaagaaac ggtcaacatt   1020
ctaaagagat acagtctgac ctttactttt ctctagtttc agtccagaaa gaacttcata   1080
tttagagcta aggccactga ggaaagagcc atagcttaag tctctatgta gacagggatc   1140
cattttaaag agctacttag agaaataatt ttccacagtt ccaaacgata ggctcaaaca   1200
ctagagctgc tagtaaaaag aagaccagat gcttcacaga attatcattt tttcaactgg   1260
aataaaacac caggtttgtt tgtagatgtc ttaggcaaca ctcagagcag atctccctta   1320
ctgtcagggg atatggaact tcaaaggccc acatggcaag ccaggtaaca taaatgtgtg   1380
```

```
aaaaagtaaa gataactaaa aaatttagaa aaataaatcc agtatttgta aagtgaataa   1440

cttcatttct aattgtttaa tttttaaaat tctgattttt atatattgag tttaagcaag   1500

gcattcttac acgaggaagt gaagtaaatt ttagttcaga cataaaattt cacttattag   1560

gaatatgtaa catgctaaaa cttttttttt tttaaagagt actgagtcac aacatgtttt   1620

agagcatcca agtaccatat aatccaacta tcatggtaag gccagaaatc ttctaaccta   1680

ccagagccta gatgagacac cgaattaaca ttaaaatttc agtaactgac tgtccctcat   1740

gtccatggcc taccatccct tctgaccctg gcttccaggg acctatgtct tttaatactc   1800

actgtcacat tgggcaaagt tgcttctaat ccttatttcc catgtgcaca agtctttttg   1860

tattccagct tcctgataac actgcttact gtggaatatt catttgacat ctgtctcttt   1920

tcatttcttt taactaccat gcccttgata tatcttttgc acctgctgaa cttcatttct   1980

gtatcacctg acctctggat gccaaaacgt ttattctgct ttgtctgttg tagaatttta   2040

gataaagcta ttaatggcaa tatttttttg ctaaacgttt ttgtttttta ctgtcactag   2100

ggcaataaaa tttatactca accatataat aacatttttt aactactaaa ggagtagttt   2160

ttattttaaa gtcttagcaa tttctattac aacttttctt agacttaaca cttatgataa   2220

atgactaaca tagtaacaga atctttatga aatatgacct tttctgaaaa tacatacttt   2280

tacatttcta ctttattgag acctattaga tgtaagtgct agtagaatat aagataaaag   2340

aggctgagaa ttaccataca agggtattac aactgtaaaa caatttatct ttgtttcatt   2400

gttctgtcaa taattgttac caaagagata aaaataaaag cagaatgtat atcatcccat   2460

ctgaaaaaca ctaattattg acatgtgcat ctgtacaata aacttaaaat gattattaaa   2520

taatcaaata tatctactac attgtttata ttattgaata aagtatattt tccaaatgta   2580

aaaaaaaaaa aa                                                       2592
```

<210> SEQ ID NO 11
<211> LENGTH: 1223
<212> TYPE: DNA
<213> ORGANISM: Homo sapiens

<400> SEQUENCE: 11

```
tgcagagatg aataaacaaa gaggaacctt ctcagaagtg agtctggccc aggacccaaa     60

gcggcagcaa aggaaaccta aaggcaataa aagctccatt tcaggaaccg aacaggaaat    120

attccaagta gaattaaatc ttcaaaatcc ttccctgaat catcaaggga ttgataaaat    180

atatgactgc caaggtttac tgccacctcc agagaagctc actgccgagg tcctaggaat    240

catttgcatt gtcctgatgg ccactgtgtt aaaaacaata gttcttattc ctttcctgga    300

gcagaacaat ttttccccga atacaagaac gcagaaagca cgtcattgtg gccattgtcc    360

tgaggagtgg attacatatt ccaacagttg ttattacatt ggtaaggaaa gaagaacttg    420

ggaagagagt ttgctggcct gtacttcgaa gaactccagt ctgctttcta tagataatga    480

agaagaaatg aaatttctgg ccagcatttt accttcctca tggattggtg tgtttcgtaa    540

cagcagtcat catccatggg tgacaataaa tggtttggct ttcaaacata agataaaaga    600

ctcagataat gctgaactta actgtgcagt gctacaagta aatcgactta aatcagccca    660

gtgtggatct tcaatgatat atcattgtaa gcataagctt tagaagtaaa gcatttgcgt    720

ttgcagtgca tcagatacat tttatatttc ttaaaataga aatattatga ttgcataaat    780

ctgaaaatga attatgttat ttgctctgat acaaaaattc taaatcaatt attgaaatag    840
```

gatgcacaca attactaaag tacagacatc ctagcatttg tgtcgggctc attttgctca 900
acatggtatt tgtggttttc agcctttcta aaagttgcat gttatgtgag tcagcttata 960
ggaagtacca agaacagtca aacccatgga gacagaaagt agaatagtgg ttgccaatgt 1020
ctcagggagg ttgaaatagg agatgaccac taattgatag aacgtttctt tgtgtcgtga 1080
tgaaaacttt ctaaatttca gtagtggtga tggttgtaac tctgcgaata tactaaacat 1140
cattgatttt taatcatttt aagtgcatga aatgtatgct ttgtacatga cacttcaata 1200
aagctatcca gaaaaaaaaa aaa 1223

<210> SEQ ID NO 12
<211> LENGTH: 3195
<212> TYPE: DNA
<213> ORGANISM: Homo sapiens

<400> SEQUENCE: 12
gctcttgtca cccaggctgg agtgcaatgg tgcgatctca gctcatcaag ttcaagagac 60
tctaatgcct cagcctccca agtagcaggg gttacagatt ctttaatctc cagctcagct 120
tcaacaattc aacgctgttc tttctgaaaa agtacacatc gtgccttctc tacttcgctc 180
ttggaacata atttctcatg gcagtgttta agaccactct gtggaggtta atttctggga 240
ccttagggat aatatgcctt tcgttgatgg ctacgttggg aattttgttg aaaaattctt 300
ttactaaact gagtattgag ccagcattta ctccaggacc caacatagaa ctccagaaag 360
actctgactg ctgttcttgc caagaaaaat gggttgggta ccggtgcaac tgttacttca 420
tttccagtga acagaaaact tggaacgaaa gtcggcatct ctgtgcttct cagaaatcca 480
gcctgcttca gcttcaaaac acagatgaac tggattttat gagctccagt caacaatttt 540
actggattgg actctcttac agtgaggagc acaccgcctg gttgtgggag aatggctctg 600
cactctccca gtatctattt ccatcatttg aaactttttaa tacaaagaac tgcatagcgt 660
ataatccaaa tggaaatgct ttagatgaat cctgtgaaga taaaaatcgt tatatctgta 720
agcaacagct catttaaatg tttcttgggg cagagaaggt ggagagtaaa gacccaacat 780
tactaacaat gatacagttg catgttatat tattactaat tgtctacttc tggagtctat 840
aaaatgtttt taaacagtgt catatacaat tgtcatgtat gtgaaacaat gtgttttaaa 900
attgatgaaa ttcgttcacc tacatttgag aattataaaa ttaacataaa gaattttgta 960
ttttcattta atgtatatat ttaatgttaa attcaatgta gttttattac acatttatgt 1020
aattttattt acattcttgc taattctcag cagaaattta aataagattt aattcacatc 1080
aaataaaatt tagaaaataa aatttaactc acactgccca ggctggagca tagtggcaag 1140
atcatagctc attgcaagct caagtgatcc tcctgactca gcctcccaag tagctaggac 1200
tgcaggcacc atgtcactat gcccgactaa tttttaattt ttaatttttt gtcaagacaa 1260
ggtcttgcta tgttgcccag gctggtcttg aactcctggc ctcaagggat tctcccacct 1320
tggattccca aagtgctggg attataggtg tgaaccacca tccctggccc tcttcacatt 1380
cttgtatgaa gattgatttg ggaaaaatgc atttcaggta actgacaaaa gatataggat 1440
gaaaaataat atctttcaaa tgtttaattt gaactaagag agcttatgca ttgcactttc 1500
tggagatttg taatgttttg gttttgttgt ccatgtgact acaaaataat atatttttta 1560
attaaaaaat ttaaaataat acaggcaagc atgtaatgat tatcaatatt tttttccacc 1620
aactatccta taccccctgac ctcctttcat taggcattat cttctgtttt gattttaaca 1680
cttagagtgg ttttctctgt tatgaatcaa agctgatcta ttttcatcat ttttgtgatg 1740

```
aaaaaattaa ttttgattga cttaggatgg aaggatttgg actgggtgtg gtggtttatg   1800
cctgtaatcg cagcactttg ggaggccaag gcgggtggat cacttgaggt caggagtttg   1860
agaccagcct ggccaacatg gtgaaaccct gtctctacta aaaatacaaa aattggctgg   1920
gtgtggtagt gcacacctgt aatcccagct atttgggagg ctgagtcgag aggatcgctt   1980
gaacctagga ggtggaggtt gcagtgagtc gagattgcac cactgcactc cagcctgggt   2040
gacagagcca gactcctctc caaaaaaaaa aaaaaaaaaa aaagatgaaa ggatttggaa   2100
ccttaattgc atctgaaaaa ctgcctcacc tttgttattt agtgtactcc aaccacggag   2160
taacatccca tcataatccc aaatcctact caaacaaaag gggaagggat tatgcaggtg   2220
tacactaggc cactggtgta ccaattagaa accactttag agttatgcct actgtaccca   2280
cataatccta aaaatatgtt acaactgcta cttcatagtt tatgccactt attttatttt   2340
ttacttttat tatttttttt tctgagacac ggtttcattc ccattgccca ggctgtagtg   2400
caatgatgca atcatggttc actgcagctt caacttccca ggctcaaggg atcctcccac   2460
ctcagccttc tgagtacttg ggactcaggt gcgagccatc atgctcagct aatttttttgt  2520
atcatttgta gaaatggggt tttgtattgt tgcccaggct gatcttgaac tcctggggtc   2580
aaggattctg cccgccttgg cctcctaaag ggctggaatt acaggcataa gccactgtgc   2640
ccggccagtt tatataattt aaacactgcc ttttggttcc ttgattccca tatgctagga   2700
caagtaatta ttattttatt ttattttact ttaagttctg ggttacatgt gcagaacctg   2760
caggtttgtt acataggtat acatgttcca aggtggtttg ctgcacctat tgacccatca   2820
tctaggtttt aagtcccaca tgcattaggt atttgtccta atgctcttcc tccccttgcc   2880
ccccaccccc cgacaggcct tggtctgtga tgttcacctc cctgtgtcca tgtgttctca   2940
ttgttcaact cccacttatt agtaagaaca tgtggtgttt ggttttctgt tcctgtgtta   3000
gtttgctgag aatgatggtt tccagcttca tccatgtcgc tgcaaaggac atgaactcat   3060
tctttttatg gctgcatagt attccatggt gtatatgtgc catattttct ttatccagtc   3120
tatcactgat gggcatttgg gttggttcca agtctttgct atggtaaata gtgctgcaat   3180
aaacatacgt gtgca                                                    3195
```

<210> SEQ ID NO 13
<211> LENGTH: 927
<212> TYPE: DNA
<213> ORGANISM: Mus musculus

<400> SEQUENCE: 13

```
acatatcctg ctccagaccc tgctgattag cacatattaa agttttaaca tctgtgcctg     60
gaattccctc tttgcttcag catttttgtc tttataaaga tggatgaagc acctgtaacc    120
cgttctaccc taaatgtgaa ttcccagcag aagagtaaag caaagaacaa gattaagaat    180
acacttaatt caaatgaatt gtcatccatt gagcagagga aaaaatacca gaaacatctt    240
aagaagcaca aaaacacagc agaagacatc agtggtaaag ggaattgctc acctccatgg    300
aggcttctct cgagtgtgct cggtgccatg tgccttctcc tgatggctgt agccatggtg    360
atgaccactt ttaccacaaa gtcatcttct gaaagatcat cttctactat tcagcaagaa    420
gggctccatc atccctgtcc agagaactgg gtctggttca ggtgcagctg ttatttcttc    480
tccaaggaag agctaatttg gagagacagt cagcgtgcct gcttgtctct taactccagt    540
ctcataagga tgaacaaaga ggaaatgaat ttcttctctt tgaagtcttt cttttgggtt    600
```

```
ggagtttact ataatgaaac tcgcagacag tggctgtggg aagaccattc ggttctaccc    660

tctgggctgt tttctaaact tgaagctaat atgaaaaact tctgtgcatc ttataaatca    720

aaagaagctt atatggaaga aaactgtgcg aacaaactga catatatttg caagaagtag    780

catatttaat tctatgagtt catgaaatat atgaaaatta atctttttta acatttttc     840

ctggagtgct tattttatga agaaaatgtg acaaatattt gcctttgctt aaataaaact    900

gtattcaaat ataaaaaaaa aaaaaaa                                         927
```

<210> SEQ ID NO 14
<211> LENGTH: 3808
<212> TYPE: DNA
<213> ORGANISM: Homo sapiens

<400> SEQUENCE: 14

```
cttcctggac tggggatccc ggctaaatat agctgtttct gtcttacaac acaggctcca     60

gtatataaat caggcaaatt ccccatttga gcatgaacct ctgaaaactg ccggcatctg    120

aggtttcctc caaggccctc tgaagtgcag cccataatga aggtcttggc ggcagtacac    180

agcccagggg gagccgttcc ccaacaacct ggacaagcta tgtggcccca acgtgacgga    240

cttcccgccc ttccacgcca acggcacgga gaaggccaag ctggtggagc tgtaccgcat    300

agtcgtgtac cttggcacct ccctgggcaa catcacccgg gaccagaaga tcctcaaccc    360

cagtgccctc agcctccaca gcaagctcaa cgccaccgcc gacatcctgc gaggcctcct    420

tagcaacgtg ctgtgccgcc tgtgcagcaa gtaccacgtg ggccatgtgg acgtgaccta    480

cggccctgac acctcgggta aggatgtctt ccagaagaag aagctgggct gtcaactcct    540

ggggaagtat aagcagatca tcgccgtgtt ggcccaggcc ttctagcagg aggtcttgaa    600

gtgtgctgtg aaccgaggga tctcaggagt tgggtccaga tgtgggggcc tgtccaaggg    660

tggctggggc ccagggcatc gctaaaccca aatgggggct gctggcagac cccgagggtg    720

cctggccagt ccactccact ctgggctggg ctgtgatgaa gctgagcaga gtggaaactt    780

ccatagggag ggagctagaa gaaggtgccc cttcctctgg gagattgtgg actggggagc    840

gtgggctgga cttctgcctc tacttgtccc tttggcccct tgctcacttt gtgcagtgaa    900

caaactacac aagtcatcta caagagccct gaccacaggg tgagacagca gggcccaggg    960

gagtggacca gcccccagca aattatcacc atctgtgcct ttgctgcccc ttaggttggg   1020

acttaggtgg gccagagggg ctaggatccc aaaggactcc ttgtccccta gaagtttgat   1080

gagtggaaga tagagagggg cctctgggat ggaaggctgt cttcttttga ggatgatcag   1140

agaacttggg cataggaaca atctggcaga agtttccaga aggaggtcac ttggcattca   1200

ggctcttggg gaggcagaga agccaccttc aggcctggga aggaagacac tgggaggagg   1260

agaggcctgg aaagctttgg taggttcttc gttctcttcc ccgtgatctt ccctgcagcc   1320

tgggatggcc agggtctgat ggctggacct gcagcagggg tttgtggagg tgggtagggc   1380

aggggcaggt tgctaagtca ggtgcagagg ttctgaggga cccaggctct tcctctgggt   1440

aaaggtctgt aagaaggggc tggggtagct cagagtagca gctcacatct gaggccctgg   1500

gaggccttgt gaggtcacac agaggtactt gagggggact ggaggccgtc tctggtcccc   1560

agggcaaggg aacagcagaa cttagggtca gggtctcagg gaaccctgag ctccaagcgt   1620

gctgtgcgtc tgacctggca tgatttctat ttattatgat atcctattta tattaactta   1680

ttggtgcttt cagtggccaa gttaattccc ctttccctgg tccctactca acaaaatatg   1740

atgatggctc ccgacacaag cgccagggcc agggcttagc agggcctggt ctggaagtcg   1800
```

```
acaatgttac aagtggaata agccttacgg gtgaagctca gagaagggtc ggatctgaga   1860
gaatggggag gcctgagtgg gagtgggggg ccttgctcca cccccccccca tcccctactg   1920
tgacttgctt tagggtgtca gggtccaggc tgcaggggct gggccaattt gtggagaggc   1980
cgggtgcctt tctgtcttga ttccaggggg ctggttcaca ctgttcttgg gcgccccagc   2040
attgtgttgt gaggcgcact gttcctggca gatattgtgc cccctggagc agtgggcaag   2100
acagtccttg tggcccaccc tgtccttgtt tctgtgtccc catgctgcct ctgaaatagc   2160
gccctggaac aaccctgccc ctgcacccag catgctccga cacagcaggg aagctcctcc   2220
tgtggcccgg acacccatag acggtgcggg gggcctggct gggccagacc ccaggaaggt   2280
ggggtagact ggggggatca gctgcccatt gctcccaaga ggaggagagg gaggctgcag   2340
atgcctggga ctcagaccag gaagctgtgg gccctcctgc tccacccccca tcccactccc   2400
acccatgtct gggctcccag gcagggaacc cgatctcttc ctttgtgctg gggccaggcg   2460
agtggagaaa cgccctccag tctgagagca ggggagggaa ggaggcagca gagttggggc   2520
agctgctcag agcagtgttc tggcttcttc tcaaaccctg agcgggctgc cggcctccaa   2580
gttcctccga caagatgatg gtactaatta tggtactttt cactcacttt gcacctttcc   2640
ctgtcgctct ctaagcactt tacctggatg gcgcgtgggc agtgtgcagg caggtcctga   2700
ggcctggggt tggggtggag ggtgcggccc ggagttgtcc atctgtccat cccaacagca   2760
agacgaggat gtggctgttg agatgtgggc cacactcacc cttgtccagg atgcagggac   2820
tgccttctcc ttcctgcttc atccggctta gcttggggct ggctgcattc ccccaggatg   2880
ggcttcgaga aagacaaact tgtctggaaa ccagagttgc tgattccacc cgggggggccc   2940
ggctgactcg cccatcacct catctccctg tggacttggg agctctgtgc caggcccacc   3000
ttgcggccct ggctctgagt cgctctccca cccagcctgg acttggcccc atggacccca   3060
tcctcagtgc tccctccaga tcccgtccgg cagcttggcg tccaccctgc acagcatcac   3120
tgaatcacag agcctttgcg tgaaacagct ctgccaggcc gggagctggg tttctcttcc   3180
ctttttatct gctggtgtgg accacacctg ggcctggccg gaggaagaga gagtttacca   3240
agagagatgt ctccgggccc ttatttatta tttaaacatt tttttaaaaa gcactgctag   3300
tttacttgtc tctcctcccc atcgtcccca tcgtcctcct tgtccctgac ttggggcact   3360
tccaccctga cccagccagt ccagctctgc cttgccggct ctccagagta gacatagtgt   3420
gtggggttgg agctctggca cccggggagg tagcatttcc ctgcagatgg tacagatgtt   3480
cctgccttag agtcatctct agttccccac ctcaatcccg gcatccagcc ttcagtcccg   3540
cccacgtgct agctccgtgg gcccaccgtg cggccttaga ggtttccctc cttcctttcc   3600
actgaaaagc acatggcctt gggtgacaaa ttcctctttg atgaatgtac cctgtgggga   3660
tgtttcatac tgacagatta tttttattta ttcaatgtca tatttaaaat atttattttt   3720
tataccaaat gaatactttt ttttttaaga aaaaaaagag aaatgaataa agaatctact   3780
cttggctggc aaaaaaaaaa aaaaaaaa                                      3808
```

<210> SEQ ID NO 15
<211> LENGTH: 1738
<212> TYPE: DNA
<213> ORGANISM: Homo sapiens

<400> SEQUENCE: 15

```
aaactttcct ttggctctgg acgcgtcgca ggggtcgctg gagaggaggc gctccgcccg     60
```

```
cccgccgcgt cctccgctgc ttctccgcgc ccggctggag cccggcgccc ggtcgccccg    120
tcgcgctcga ccccgagggc atgcggcagc cgcaggggcc cccgctcccg ggctcggcgg    180
cgcgggtgaa cgtgagcgga tgttcacttc tccacaatga atgagtgtca ctatgacaag    240
cacatggact ttttttataa taggagcaac actgatactg tcgatgactg gacaggaaca    300
aagcttgtga ttgttttgtg tgttgggacg tttttctgcc tgtttatttt tttttctaat    360
tctctggtca tcgcggcagt gatcaaaaac agaaaatttc atttcccctt ctactacctg    420
ttggctaatt tagctgctgc cgatttcttc gctggaattg cctatgtatt cctgatgttt    480
aacacaggcc cagtttcaaa aactttgact gtcaaccgct ggtttctccg tcaggggctt    540
ctggacagta gcttgactgc ttccctcacc aacttgctgg ttatcgccgt ggagaggcac    600
atgtcaatca tgaggatgcg ggtccatagc aacctgacca aaaagagggt gacactgctc    660
attttgcttg tctgggccat cgccattttt atgggggcgg tccccacact gggctggaat    720
tgcctctgca acatctctgc ctgctcttcc ctggccccca tttacagcag gagttacctt    780
gttttctgga cagtgtccaa cctcatggcc ttcctcatca tggttgtggt gtacctgcgg    840
atctacgtgt acgtcaagag gaaaaccaac gtcttgtctc cgcatacaag tgggtccatc    900
agccgccgga ggacacccat gaagctaatg aagacggtga tgactgtctt aggggcgttt    960
gtggtatgct ggaccccggg cctggtggtt ctgctcctcg acggcctgaa ctgcaggcag   1020
tgtggcgtgc agcatgtgaa aaggtggttc ctgctgctgg cgctgctcaa ctccgtcgtg   1080
aaccccatca tctactccta caaggacgag gacatgtatg gcaccatgaa gaagatgatc   1140
tgctgcttct ctcaggagaa cccagagagg cgtccctctc gcatcccctc cacagtcctc   1200
agcaggagtg acacaggcag ccagtacata gaggatagta ttagccaagg tgcagtctgc   1260
aataaaagca cttcctaaac tctggatgcc tctcggccca cccaggcctc ctctgggaaa   1320
agagctgtta agaatgatta cctgtctcta acaaagccca tgtacagtgt tatttgaggt   1380
ctccattaat cactgctaga tttctttaaa aaattttttt tcatagttta aaagcatggg   1440
cagtaaagag aggacctgct gcatttagag aaagcacaga aacgggagag gttcggcggg   1500
tccctgcttg tcctatgaac tgctcagagc tcctgtcagt ccagctgggc cttctgggtt   1560
ctggcaccat ttcgtagcca ttctctttgt attttaaaag gacgttatga aagggcttag   1620
accaaaataa atcataatgt tacttgagcc accttatata gctgcttgga gagtctatgt   1680
agttctttct gcatgcatta aaaatgttta gaaatgcttc aaaaaaaaaa aaaaaaaa     1738
```

<210> SEQ ID NO 16
<211> LENGTH: 2791
<212> TYPE: DNA
<213> ORGANISM: Homo sapiens

<400> SEQUENCE: 16

```
agagccggac ggcgcttccc ggtggcggcg gaggagcccg gagggacgca gccgggcaag     60
gcagggcgca gggcgggcgg cgcgaggcgc agggcgcggc gggcagaggc cacctggcca    120
ccttccctgg cgcccgggga aggcgcggcg atggccgggg cgcgcggggc ggcggcggcg    180
gcgggcgggc ggcggcgggc cgagggggcg cggggacaca gccaggcgcc cctgcccgcc    240
gcggtgcccg ccgcctgaag gccgcctggg cgcgggagcc ggtgccagct cggagcgggc    300
gctggaggca gctcgaggcg cgatgtcggt gccgctgctc aagatcgggg tcgtgctgag    360
caccatggcc atgatcacta actggatgtc ccagacgctg ccctcgctgg tgggcctcaa    420
caccaccaag ctctcggcgg ccggcggcgg gacgctggac cgcagcaccg gcgtgctgcc    480
```

```
caccaaccct gaggagagct ggcaggtgta cagctctgcc caggacagcg agggcaggtg    540
tatctgcaca gtggtcgctc cacagcagac catgtgttca cgggatgccc gcacaaaaca    600
gctgaggcag ctactggaga aggtgcagaa catgtctcaa tccatagagg tcttggacag    660
gcggacccag agagacttgc agtacgtgga gaagatggag aaccaaatga aaggactgga    720
gtccaagttc aaacaggtgg aggagagtca taagcaacac ctggccaggc agtttaaggc    780
gataaaagcg aaaatggatg aacttaggcc tttgatacct gtgttggaag agtacaaggc    840
cgatgccaaa ttggtattgc agtttaaaga ggaggtccag aatctgacgt cagtgcttaa    900
cgagctgcaa gaggaaattg gcgcctatga ctacgatgaa cttcagagca gagtgtccaa    960
tcttgaagaa aggctccgtg catgcatgca aaaactagct tgcgggaagt tgacgggcat   1020
cagtgacccc gtgactgtca agacctccgg ctcgaggttc ggatcctgga tgacagaccc   1080
tctcgcccct gaaggcgata accgggtgtg gtacatggac ggctatcaca acaaccgctt   1140
cgtacgtgag tacaagtcca tggttgactt catgaacacg gacaatttca cctcccaccg   1200
tctcccccac ccctggtcgg gcacggggca ggtggtctac aacggttcta tctacttcaa   1260
caagttccag agccacatca tcatcaggtt tgacctgaag acagagacca tcctcaagac   1320
ccgcagcctg gactatgccg gttacaacaa catgtaccac tacgcctggg gtggccactc   1380
ggacatcgac ctcatggtgg acgagagcgg gctgtgggcc gtgtacgcca ccaaccagaa   1440
cgctggcaac atcgtggtca gtaggctgga ccccgtgtcc ctgcagaccc tgcagacctg   1500
gaacacgagc taccccaagc gcagcgccgg ggaggccttc atcatctgcg gcacgctgta   1560
cgtcaccaac ggctactcag gggtaccaa ggtccactat gcataccaga ccaatgcctc    1620
cacctatgaa tacatcgaca tcccattcca gaacaaatac tcccacatct ccatgctgga   1680
ctacaacccc aaggaccggg ccctgtatgc ctggaacaac ggccaccaga tcctctacaa   1740
cgtgaccctc ttccacgtca tccgctccga cgagttgtag ctccctcctc ctggaagcca   1800
agggcccacg tcctcaccac aaagggactc ctgtgaaact gctgccaaaa agataccaat   1860
aacactaaca ataccgatct tgaaaaatca tcagcagtgc ggattctgac atcgagggat   1920
ggcattacct ccgtgtttct ccctttcgag ccggcgggcc acagacgtcg gaagaaactc   1980
ccgtatttgc agctggaact gcagcccacg gcgccccggt tttcctcccc gccctgtccc   2040
tctctggtca aacaacatac taaagaggcg aggcaatgac tgttggccag ttctcaccgg   2100
ggaaaaaccc actgttagga tggcatgaac atttccttag atcgtggtca gctccgagga   2160
atgtggcgtc caggctcttt gagagccatg ggctgcaccc ggccgtaggc tagtgtaact   2220
cgcatcccat tgcagtgccg tttcttgact gtgttgctgt ctcttagatt aaccgtgctg   2280
aggctccaca tagctcctgg acctgtgtct agtacatact gaagcgatgg tcagagtgtg   2340
tagagtgaag ttgctgtgcc cacattgttt gaactcgcgt accccgtaga tacattgtgc   2400
aacgttcttc tgttattccc ttgaggtggt aacttcgtat gttcagttta tgcgatgatt   2460
gttgtaaatg caatgccgta gtttggatta ataagtggat ggtttttgtt tctaaaaaga   2520
aaaaaaaaat cagtgttcac ccttatagag acatagtcaa gttcatgttg ataataatca   2580
aaggaattac tctcttcttg ttaaattagc taaatcatgt aaccgcagat aggaagggct   2640
cgcctgggga aactctggtt tccgatggga caggaaagtc atacgggcaa cagtatgcgg   2700
aaagtacgtt ttttaagtaa aaaacaaagg caaactttgt actatccagt tatctaagga   2760
acaataaaaa cattaggaga tcttttaaaa a                                  2791
```

<210> SEQ ID NO 17
<211> LENGTH: 2652
<212> TYPE: DNA
<213> ORGANISM: Homo sapiens

<400> SEQUENCE: 17
gacaatgtgc aaatgacacc gttttgtgct caccagggca aagcaaggga gcgccctcac 60
ttcagcatct cagccctgct aaagaaaaag ctgctgggta acatcctttg tttttgccca 120
gggaagcttt agctgtgatt cccttcagcc ggctcctgaa tgtcaaagcc agcacaggcc 180
agccagaaga tgacactgag actacaggtt tggaaggcgg cgttgccatg ccaggtgccg 240
aagatgatgt ggtgactcca ggaaccagcg aagaccgcta taagtctggc ttgacaactc 300
tggtggcaac aagtgtcaac agtgtaacag gcattcgcat cgaggatctg ccaacttcag 360
aaagcacagt ccacgcgcaa gaacaaagtc caagcgccac agcctcaaac gtggccacca 420
gtcactccac ggagaaagtg gatggagaca cacagacaac agttgagaaa gatggtttgt 480
caacagtgac cctggttgga atcatagttg gggtcttact agccatcggc ttcattggtg 540
caatcatcgt tgtggttatg cgaaaaatgt cgggaaggta ctcgccctaa agagctgaag 600
ggttacgccc tgctgccaac gtgcttaaaa aaagaccgtt tctgactctg tgccctgtcc 660
ctgagctcgt gggagaagat gacccgtgga acacttgcct ggcccactca gaatccacgg 720
tgacctctcc gcttgccaaa ataaccgaag gaaagaccgt tcaccagact tggctcctct 780
aaacatttgc tgttcaaaca tgtttttgaa tatacattct ataaaagatt atttgaaaga 840
caaaattcat agaaaatgga gcaaaactgt ataaactgat ttgtaactaa cactggacca 900
ttggatcgat attatatgct gtaaccatgt gtctccgtct gaccattctt gttattgtta 960
aaatgcagag gaatctggaa atatttatat ccacggagtc cttggatcca gtgctacgtc 1020
agtaaatagc accagcattt tgcaattgct gatctgctga aatgtacaca ttctggtcta 1080
gtttggtcta tcttttaaag cctgatctgg tgtgaataat caactaggaa atctaaactt 1140
ggataacacg tggtgaacaa ctgcctttag ctggtccaga ttaatcattt caaagacatc 1200
cattttagat cacaagcagg aagtcgatag tctcaaaggc actttgtttc tcccaagtag 1260
gccaccaggc agcctctaga gttgctttac ccaaatcctt ctccagccat gacttggtga 1320
ctctaagctt gctcccacct gccccctcca cttccctcag atgatgagga gccagggcta 1380
agggggcagc cttctctctt cccagtgatg cacatccttc acattggctg ctttgttctg 1440
gaatatggat atctcagcct ggatgccgag gaagctgctg gatgcttaat ggtgctagag 1500
gctcaagtgt gtttgaaacc aagagccagt tgtcccccat gcagaaagaa atcctgtgtg 1560
agcctctggt atgagaaata aaatctgcca gttttataac attcactttc tgcctctgag 1620
gaaagataca gggaacaaaa atcaatttgt acagtcttaa tattaaaagc agcttgacta 1680
aatacctgat ttaaaaatag aagacatccc cagtcctcat gacataccgc aaatatctgt 1740
ggggtcctgt tgaaaagaac aaaataaagg agcccaaggg gtcattctgt ctcagcacca 1800
tccagcctgg cacttctctt cccatatatc cattggattt tttttttttt ttcctaaaca 1860
aagtttttac actgagcaga tgctctgtca tgatggcggt tgtgcaattc tggtatcctc 1920
taaatttgta agcattcata aaacaggaaa aagtaaacta tcattcggaa gcacagccca 1980
ttcctcccat tttttgcaat gatgtctgga tgttatttta aacagtgtgt ctgtgtgttc 2040
ccaaatccag ctggccccac cagctcagat tccatttttt ttgtgtgtgt gtgtgaaacg 2100
tagtctgcaa ctctgcctcc cggcaattat acatgtgtca ggatgtcaaa aagcaattct 2160

```
cctgcctcag cctcctgagt agctgggact acaggttcct accaccacac ccggccaatt   2220
tttgtatttt tagtagagat ggggtttcac cgtatcggcg aggatgatct ctatctcttg   2280
acctcgtgat ctgcccgcct cggcctccca aagtgctggg attacaggcg tgtgccactg   2340
cgctcggcct cagattccat atttgaacac cagctgattg agagaagggg aatgagaaga   2400
gctggatgag tttaaataac tcattgttca gattcctgaa caggagttgg gataatggcc   2460
atcttttctt tcctatcctt tcttcccccc tcactgtgaa aaataacagt ccaccccaag   2520
tcatacactg gacccagtgc ctgcggggac aggactgtgg gtttcttggt cacacctgtg   2580
ttggtgctca atgcagtgta gacatgtttt caaataaaac aaatgattgt gtacaaaaaa   2640
aaaaaaaaaa aa                                                       2652
```

<210> SEQ ID NO 18
<211> LENGTH: 6599
<212> TYPE: DNA
<213> ORGANISM: Homo sapiens

<400> SEQUENCE: 18

```
atgctcagac ggcggccagg tcgcgccgcg agcgagcttc cgcgccgccc gcacgcgcga     60
cctacctggg cgctccgcgc ccccggatgc tgcaggttat tcagcgatag ttatgacctc    120
ccggttacgt gcgttgggtg gaagaattaa taatatacgc acctcggagt tacccaaaga    180
gaaaactcga tcagaagtca tttgcagcat ccacttttta gatggcgtgg tacagacctt    240
taaagttact aaacaagaca ctggccaggt tcttctggat atggtgcaca accacctggg    300
tgtgactgaa aaggaatatt ttggtttaca gcatgatgac gactccgtgg actctcctag    360
atggctggaa gcaagcaaag ccatcaggaa gcagttaaaa ggaggtttcc cctgtaccct    420
gcattttcga gtaagatttt ttatacctga tcccaacaca ctgcagcaag aacaaaccag    480
gcacttgtat ttcttacaac tgaagatgga tatttgcgaa ggaaggttaa cctgccctct    540
taactcagca gtggttctag cgtcctatgc cgtacaatct cattttggag actataattc    600
ttccatacat catccaggct atctttccga tagtcacttt atacccgatc aaaatgagga    660
ctttttaaca aaagtcgaat ctctgcatga gcagcacagt gggctaaaac aatcagaagc    720
agaatcctgc tatatcaaca tagcgcggac cctcgacttc tatggagtag aactgcacag    780
tggtagggat ctgcacaatt tagacctaat gattggaatt gcttccgcgg gtgttgctgt    840
gtaccgaaaa tacatttgca caagtttcta tccttgggtg aacattctca aaatttcttt    900
caaaaggaaa aagttcttca tacatcagcg acagaaacag gctgaatcca gggaacatat    960
tgtggccttc aacatgctga attaccgatc ttgcaaaaac ttgtggaaat cctgtgttga   1020
gcaccatacg ttctttcagg caaagaagct actacctcag gaaaagaatg ttctgtctca   1080
gtactggact atgggctctc ggaacaccaa aaagcgaagt cctcggctcc ggcacgaaat   1140
ccgaaagcca cgccactctt ctgcagataa ccttgcaaat gaaatgacct acatcacgga   1200
aacggaagat gtattttaca cgtacaaggg ctctctggcc cctcaagaca gcgattctga   1260
agtttctcag aaccgaagcc cgcaccaaga gagtttatcc gagaacaatc cggcacaaag   1320
ctacctgacc cagaagtcat ccagttctgt gtctccatct tcaaatgctc caggctcctg   1380
ctcacctgac ggcgttgatc agcagctctt agatgacttc cacagggtga ccaaaggggg   1440
ctccaccgag gacgccagcc agtactactg tgacaagaat gataatggtg acagctactt   1500
agtcttgatc cgtatcacac cagatgaaga tggaaaattt ggatttaatc ttaagggagg   1560
```

```
agtggatcaa aagatgcctc ttgtggtatc aaggataaac ccagagtcac ctgcggacac   1620
ctgcattcct aagctgaacg aaggggatca aatcgtgtta atcaatggcc gggacatctc   1680
agaacacacg catgaccaag tggtgatgtt catcaaagcc agccgggagt cccactcacg   1740
ggagctggcc ctggtgatca ggaggagagc tgtccgctca tttgctgact tcaagtctga   1800
agatgaactg aaccagcttt tccccgaagc cattttcccc atgtgtccgg agggtgggga   1860
cactttggag ggatccatgg cacagctaaa gaagggcctc gaaagcggga cggtgctgat   1920
ccagtttgag caactctaca gaaaaaagcc aggtttggcc atcacgtttg caaagctgcc   1980
tcaaaatttg gacaaaaacc gatataaaga tgtgctgcct tatgacacca cccgggtatt   2040
attgcaggga aatgaagatt atattaatgc aagttacgtg aacatggaaa ttcctgctgc   2100
taaccttgtg aacaagtaca tcgccactca ggggcccctg ccgcatacct gtgcacagtt   2160
ttggcaggtt gtctgggatc agaagttgtc actcattgtc atgttgacga ctctcacaga   2220
acgagggcgg accaaatgtc accagtactg gccagatccc cccgacgtca tgaaccacgg   2280
cggctttcac atccagtgtc agtcagagga ctgcaccatc gcctatgtgt cccgagaaat   2340
gctggtcaca aacacccaga ccggggaaga acacacagtg acacatctcc agtacgtcgc   2400
atggcctgac cacggtgtgc ccgatgactc ctccgacttt ctggaatttg taaactatgt   2460
gaggtctctg agagtggaca gcgagcccgt cctagttcac tgcagtgctg gaataggtcg   2520
aaccggtgtg ttggtcacta tggaaacagc catgtgccta actgagagga acctgcccat   2580
ttacccactg gatattgtcc gaaaaatgcg agaccagcgc gccatgatgg tgcagacatc   2640
aagccagtac aagtttgtgt gtgaagcgat tcttcgtgtg tatgaagaag gtttagtcca   2700
aatgctggat cctagttaag acaactgtga aaaagttcat tcctctttcc caagggcatc   2760
ctccttgaaa gaggaggaca gacctctctg gaagcagcaa gaggaaccag tagctgtggg   2820
aaaggaatgg gcacctctga acccaggcac tttaaacttc tatagaaaag atatcgtgta   2880
cataggaact ggtgtagata agcatgcaat tatggcatca tttaggcctg tatttctatg   2940
gaaagataca aaaaggatct cagtttgggg cctgtcctaa tgccttcttc cctaacatca   3000
ccacacacac ccctgtcggc atcctggagc aattgagacc ggacacccac agagctgttg   3060
tcctcccagc aacaagatgg tgtggttatc ttgggtcatt tggatgtttt gtttgtttct   3120
gtgtgtcaga ctgtaagggc tgagctttct gtgcttctag gtggagctgg aacaattcag   3180
attcacccgc cctgatgcta aggaaaccct gacgtatgta ctagatggca gggcactggg   3240
ggtcaggctg aaggctgagc aacacctctc tgccctccct ccctttgtcc catctcccag   3300
cgacttccaa tattcatgtt tctgagaatt gtgtccctct tcaggttccc tcttggtgcc   3360
taacctggat tagtaatgtg cattcaggtg aattttcagc tgaggctctg agaactggta   3420
ctctcagtgt gttctggtca tcttgtggct tagttgtaga agcaggtgtg tctcttgcct   3480
ctgcttgcct cctactgcac actcagcacc caggactgga atcaccgact actgaatctc   3540
ctacatgtat tgctgctact tcaagctcct ccacttgaaa ccttatgatt ttcccaaggg   3600
gagatgggac agtgtcatct aaatattccg aatgtttggc cttctgagaa aagagcttct   3660
agtaattgaa ccatgggaaa cccagcttct ggagggttgg ccgtggggct gtgtacatgt   3720
gtgtgcccag gggtgagtgt ttctcaggat tcctaacgat tcaaattacc gttgagtata   3780
tataaagaat gagtctctgt atggaagaac aaatgtgtgc attcaccccc agtcacaatg   3840
gtctccattg catttcaaag gagaggatca gactatctga atataaacac aatctgatgt   3900
taatttattc taagaacacc atcattttga ttgtcctaaa gaattctgcc tttgtgaata   3960
```

```
ccgtgttaaa tttttttaaa tttgtgacag gattgtagca aattattatt taaggaaaat   4020
aaattgtgta aacatttaat gtggtatttt tgaacagcgg tttttatgta ctcagaagag   4080
gaagtaaagc caggttctta atggtattta tagaaaagat gttttcatat tataatgcac   4140
ataaatgaag ccattttgat attcagcaaa ttcggtgcca attgaatagt ttgctggtag   4200
caagacggat gaagacctat atgggagatt ctttatctct agagctagca tatttacttg   4260
catactttgt ttcttttcca catggatatt ttactgctaa atggcagagg tgggagggag   4320
atgtcacaca gtaccataac cccatattga aaacaagaaa ccaccagaaa gtttgcagct   4380
aaggggcagg ggattcagtt cctacgccca ctcagcacta actacttgcg ggcctggttg   4440
cttagaagct ctacctctct ttcattatct gtaaaataga aacaatactt aggactttag   4500
ttggaacatg aggattgaat aagatcacgc tattcatgtg actttttatc ggctagaaca   4560
gcaacagaca ctgctgtggg tgagttactt agaaaagttt agttatcagt gattagccca   4620
aaaacacatc agtcaaaaat agaatccact ggatttttgt ctctcttttt agagacaggg   4680
tctcactgtc gcccaggctg gagtacagtg gcatgatcat tgttcactgc agcctcaaat   4740
tcctgggctc aagcaatcct cgcacctcag cctcctgagt agccgggact ataggcacat   4800
gccacctcac ctggcttgtg tgtgtgtgtg tgtgtgtgtg tgtgtgtgtg tgtgtgtgtg   4860
tgtgtgtgtg tgtgtgtgta gagacaggat cttgatgtgt tgcctaggct ggtctcaaac   4920
tcctggcctc aagtgatctt cccacctcag cctccaaaac tgttgggatt ataggcgtga   4980
gccactgtgc ccagcctaac tgggttttta tgagaggaaa atagaaaatg ctcttctaga   5040
agagagagaa caagagcaca aaataatctg gactcacaaa aattcagcaa gctccaagaa   5100
agggggatgg agggaacgct ggcaaaaatt taaatgccat taggatattt agcaagttat   5160
tactgtttgg taaaaatgca tcatcaccct gtgtgcaaaa tgcttgcaaa gtagtctaaa   5220
tgtctttgga gatgggtgtt ttactgcttt tttccaaaaa caaattgttt attatggttg   5280
cagaaatgca gccattacgg tcacataaat ttctaaaaag cctaccaaag gttgcaagca   5340
gtcttctgcc actgggcagg ccagcagttc agacccagcg aggttgccag gaacaaatcc   5400
aggaaatact gggaagaaca agacaagaga attacctaaa agagcaaaca attcaagtaa   5460
atcctgtagc tattaccact taaaatccgt agctcaagat tcctgtttca ccaccttata   5520
cacttaagca attatactta agcctttttt tagtcctaag tgaagaacta catcagaatc   5580
aggataagta ttttgcctgg gaaatttggc tgcatatgaa tggagaagac atttacatcc   5640
tatgttctgg cactttctga aagatctaat taaacatgtt gatgtgccaa tttaatcaag   5700
atgagagatc cctgctggtg tcaccctcta gaacctgcac ttggtgtttt gactttccag   5760
aagaaaaaaa tgcaactttg gttagggggc agtggttgga tcacacagtt gtctttcgtt   5820
tcctaccaca gtaattcata tttaaatatg cttttagatt agtgtggata ctattgctgc   5880
tgtgttgcta cctgaccttt ttctgggggg ggtacctcag aaatgagcat ttgagggcaa   5940
gcgaaaaagc cctcttcatc ctccagaggc aacaaagagg cagcagaaat ggggaaagat   6000
tgtgagaggc agggcttggg tctagacctg gacttaggca agatatgttg ccctcaaccc   6060
tgagttttct tatatgtaaa aagggaaggt tgggctggac tagatgaggt caagatttgc   6120
cattctggga ggctgatatt ccagagaatc aaaattaatc ctaaaccaaa gctttatggc   6180
tgctacagag acatgtcaca tttctgagac ttgtcaccaa gagtttgtcc ctcagacttt   6240
ggcgctgttg aatgcaaaga caaggatggc caccttctgg ttcttgcctg ttgtcctcag   6300
```

```
ctgagagcag tctcggtaaa ggtggcaaag attctgtgac ctcagaccgg ggaccaaatg   6360

cttgggagtc tgatggccgg gctgggccac cattctcata gctctcattc tgtttggagc   6420

aaccaaagga tttgtgtgaa gttatttgga aaaggacctt aactgagcag taatcttttt   6480

tctgtatatt tggaatgttt ttcattctga cctgttctgt cagtgattct actgaaaaac   6540

aatttaatca atataaaaat gttcaagcta tgcaacactg taaaaaaaaa aaaaaaaaa    6599
```

```
<210> SEQ ID NO 19
<211> LENGTH: 3309
<212> TYPE: DNA
<213> ORGANISM: Homo sapiens

<400> SEQUENCE: 19

ttcagcccct ctcccgggct gcgcctccgc actccgggcc cgggcagaag ggggtgcgcc     60

tcggccccac cacccaggga gcagccgagc tgaaaggccg ggaaccgcgg cttgcgggga    120

ccacagctcc cgaaagcgac gttcggccac cggaggagcg ggagccaagc aggcggagct    180

cggcgggaga ggtgcgggcc gaatccgagc cgagcggaga ggaatccggc agtagagagc    240

ggactccagc cggcggaccc tgcagccctc gcctgggaca gcggcgcgct gggcaggcgc    300

ccaagagagc atcgagcagc ggaacccgcg aagccggccc gcagccgcga cccgcgcagc    360

ctgccgctct cccgccgccg gtccgggcag catgaggcgc gcggcgctct ggctctggct    420

gtgcgcgctg gcgctgagcc tgcagccggc cctgccgcaa attgtggcta ctaatttgcc    480

ccctgaagat caagatggct ctggggatga ctctgacaac ttctccggct caggtgcagg    540

tgctttgcaa gatatcacct tgtcacagca gacccccctcc acttggaagg acacgcagct    600

cctgacggct attcccacgt ctccagaacc caccggcctg gaggctacag ctgcctccac    660

ctccaccctg ccggctggag aggggcccaa ggagggagag gctgtagtcc tgccagaagt    720

ggagcctggc ctcaccgccc gggagcagga ggccaccccc cgacccaggg agaccacaca    780

gctcccgacc actcatcagg cctcaacgac cacagccacc acggcccagg agcccgccac    840

ctcccacccc cacagggaca tgcagcctgg ccaccatgag acctcaaccc ctgcaggacc    900

cagccaagct gaccttcaca ctccccacac agaggatgga ggtccttctg ccaccgagag    960

ggctgctgag gatggagcct ccagtcagct cccagcagca gagggctctg gggagcagga   1020

cttcaccttt gaaacctcgg gggagaatac ggctgtagtg gccgtggagc ctgaccgccg   1080

gaaccagtcc ccagtggatc agggggccac gggggcctca cagggcctcc tggacaggaa   1140

agaggtgctg ggaggggtca ttgccggagg cctcgtgggg ctcatctttg ctgtgtgcct   1200

ggtgggtttc atgctgtacc gcatgaagaa gaaggacgaa ggcagctact ccttggagga   1260

gccgaaacaa gccaacggcg gggcctacca gaagcccacc aaacaggagg aattctatgc   1320

ctgacgcggg agccatgcgc cccctccgcc ctgccactca ctaggccccc acttgcctct   1380

tccttgaaga actgcaggcc ctggcctccc ctgccaccag gccacctccc cagcattcca   1440

gcccctctgg tcgctcctgc ccacggagtc gtggggtgtg ctgggagctc cactctgctt   1500

ctctgacttc tgcctggaga cttagggcac caggggtttc tcgcatagga cctttccacc   1560

acagccagca cctggcatcg caccattctg actcggtttc tccaaactga agcagcctct   1620

ccccaggtcc agctctggag gggagggggga tccgactgct ttggacctaa atggcctcat   1680

gtggctggaa gatcctgcgg gtggggcttg gggctcacac acctgtagca cttactggta   1740

ggaccaagca tcttgggggg gtggccgctg agtggcaggg gacaggagtc cactttgttt   1800

cgtggggagg tctaatctag atatcgactt gtttttgcac atgtttcctc tagttctttg   1860
```

```
ttcatagccc agtagacctt gttacttctg aggtaagtta agtaagttga ttcggtatcc   1920

ccccatcttg cttccctaat ctatggtcgg gagacagcat cagggttaag aagacttttt   1980

tttttttttt ttaaactagg agaaccaaat ctggaagcca aaatgtaggc ttagtttgtg   2040

tgttgtctct tgagtttgtc gctcatgtgt gcaacagggt atggactatc tgtctggtgg   2100

ccccgtttct ggtggtctgt tggcaggctg gccagtccag gctgccgtgg ggccgccgcc   2160

tctttcaagc agtcgtgcct gtgtccatgc gctcagggcc atgctgaggc ctgggccgct   2220

gccacgttgg agaagcccgt gtgagaagtg aatgctggga ctcagccttc agacagagag   2280

gactgtaggg agggcggcag gggcctggag atcctcctgc agaccacgcc cgtcctgcct   2340

gtggcgccgt ctccaggggc tgcttcctcc tggaaattga cgaggggtgt cttgggcaga   2400

gctggctctg agcgcctcca tccaaggcca ggttctccgt tagctcctgt ggccccaccc   2460

tgggccctgg gctggaatca ggaatatttt ccaaagagtg atagtctttt gcttttggca   2520

aaactctact taatccaatg ggtttttccc tgtacagtag attttccaaa tgtaataaac   2580

tttaatataa agtagtcctg tgaatgccac tgccttcgct tcttgcctct gtgctgtgtg   2640

tgacgtgacc ggacttttct gcaaacacca acatgttggg aaacttggct cgaatctctg   2700

tgccttcgtc tttcccatgg ggagggattc tggttccagg gtccctctgt gtatttgctt   2760

ttttgttttg gctgaaattc tcctggaggt cggtaggttc agccaaggtt ttataaggct   2820

gatgtcaatt tctgtgttgc caagctccaa gccccatctt ctaaatggca aaggaaggtg   2880

gatggcccca gcacagcttg acctgaggct gtggtcacag cggaggtgtg gagccgaggc   2940

ctaccccgca gacaccttgg acatcctcct cccacccggc tgcagaggcc agaggccccc   3000

agcccagggc tcctgcactt acttgcttat ttgacaacgt ttcagcgact ccgttggcca   3060

ctccgagagg tgggccagtc tgtggatcag agatgcacca ccaagccaag ggaacctgtg   3120

tccggtattc gatactgcga ctttctgcct ggagtgtatg actgcacatg actcgggggt   3180

ggggaaaggg gtcggctgac catgctcatc tgctggtccg tgggacggtg cccaagccag   3240

aggctgggtt catttgtgta acgacaataa acggtacttg tcatttcggg caaaaaaaaa   3300

aaaaaaaaa                                                            3309
```

<210> SEQ ID NO 20
<211> LENGTH: 3670
<212> TYPE: DNA
<213> ORGANISM: Homo sapiens

<400> SEQUENCE: 20

```
cgcagcaaac acatccgtag aaggcagcgc ggccgccgag aaccgcagcg ccgctcgccc     60

gccgccccccc accccgccgc cccgcccggc gaattgcgcc ccgcgcccct cccctcgcgc   120

ccccgagaca aagaggagag aaagtttgcg cggccgagcg gggcaggtga ggagggtgag   180

ccgcgcggga ggggcccgcc tcggccccgg ctcagccccc gcccgcgccc ccagcccgcc   240

gccgcgagca gcgcccggac cccccagcgg cggcccccgc ccgcccagcc ccccggcccg   300

ccatgggcgc cgcggcccgc accctgcggc tggcgctcgg cctcctgctg ctggcgacgc   360

tgcttcgccc ggccgacgcc tgcagctgct ccccggtgca cccgcaacag gcgttttgca   420

atgcagatgt agtgatcagg gccaaagcgg tcagtgagaa ggaagtggac tctggaaacg   480

acatttatgg caaccctatc aagaggatcc agtatgagat caagcagata aagatgttca   540

aagggcctga gaaggatata gagtttatct acacggcccc ctcctcggca gtgtgtgggg   600
```

-continued

```
tctcgctgga cgttggagga aagaaggaat atctcattgc aggaaaggcc gagggggacg    660
gcaagatgca catcaccctc tgtgacttca tcgtgccctg ggacaccctg agcaccaccc    720
agaagaagag cctgaaccac aggtaccaga tgggctgcga gtgcaagatc acgcgctgcc    780
ccatgatccc gtgctacatc tcctccccgg acgagtgcct ctggatggac tgggtcacag    840
agaagaacat caacgggcac caggccaagt tcttcgcctg catcaagaga agtgacggct    900
cctgtgcgtg gtaccgcggc gcggcgcccc ccaagcagga gtttctcgac atcgaggacc    960
cataagcagg cctccaacgc ccctgtggcc aactgcaaaa aaagcctcca agggtttcga   1020
ctggtccagc tctgacatcc cttcctggaa acagcatgaa taaaacactc atcccatggg   1080
tccaaattaa tatgattctg ctccccccctt ctccttttag acatggttgt gggtctggag   1140
ggagacgtgg gtccaaggtc ctcatcccat cctccctctg ccaggcacta tgtgtctggg   1200
gcttcgatcc ttgggtgcag gcagggctgg gacacgcggc ttccctccca gtccctgcct   1260
tggcaccgtc acagatgcca agcaggcagc acttagggat ctcccagctg ggttagggca   1320
gggcctggaa atgtgcattt tgcagaaact tttgagggtc gttgcaagac tgtgtagcag   1380
gcctaccagg tccctttcat cttgagaggg acatggccct tgttttctgc agcttccacg   1440
cctctgcact ccctgcccct ggcaagtgct cccatcgccc cggtgcccac catgagctcc   1500
cagcacctga ctccccccac atccaagggc agcctggaac cagtggctag ttcttgaagg   1560
agccccatca atcctattaa tcctcagaat tccagtggga gcctccctct gagccttgta   1620
gaaatgggag cgagaaaccc cagctgagct gcgttccagc ctcagctgag tctttttggt   1680
ctgcacccac ccccccaccc cccccccccc gcccacatgc tccccagctt gcaggaggaa   1740
tcggtgaggt cctgtcctga ggctgctgtc cggggccggt ggctgccctc aaggtccctt   1800
ccctagctgc tgcggttgcc attgcttctt gcctgttctg gcatcaggca cctggattga   1860
gttgcacagc tttgctttat ccgggcttgt gtgcagggcc cggctgggct ccccatctgc   1920
acatcctgag gacagaaaaa gctgggtctt gctgtgccct cccaggctta gtgttccctc   1980
cctcaaagac tgacagccat cgttctgcac ggggctttct gcatgtgacg ccagctaagc   2040
atagtaagaa gtccagccta ggaagggaag gattttggag gtaggtggct ttggtgacac   2100
actcacttct ttctcagcct ccaggacact atggcctgtt ttaagagaca tcttattttt   2160
ctaaaggtga attctcagat gataggtgaa cctgagttgc agatatacca acttctgctt   2220
gtatttctta aatgacaaag attacctagc taagaaactt cctagggaac tagggaacct   2280
atgtgttccc tcagtgtggt ttcctgaagc cagtgatatg gggggttagga taggaagaac   2340
tttctcggta atgataagga gaatctcttg tttcctccca cctgtgttgt aaagataaac   2400
tgacgatata caggcacatt atgtaaacat acacacgcaa tgaaaccgaa gcttggcggc   2460
ctgggcgtgg tcttgcaaaa tgcttccaaa gccaccttag cctgttctat tcagcggcaa   2520
ccccaaagca cctgttaaga ctcctgaccc ccaagtggca tgcagccccc atgcccaccg   2580
ggacctggtc agcacagatc ttgatgactt ccctttctag ggcagactgg gagggtatcc   2640
aggaatcggc ccctgcccca cgggcgtttt catgctgtac agtgacctaa agttggtaag   2700
atgtcataat ggaccagtcc atgtgatttc agtatataca actccaccag acccctccaa   2760
cccatataac accccacccc tgttcgcttc ctgtatggtg atatcatatg taacatttac   2820
tcctgtttct gctgattgtt tttttaatgt tttggtttgt ttttgacatc agctgtaatc   2880
attcctgtgc tgtgtttttt attacccttg gtaggtatta gacttgcact tttttaaaaa   2940
aaggtttctg catcgtggaa gcatttgacc cagagtggaa cgcgtggcct atgcaggtgg   3000
```

```
attccttcag gtctttcctt tggttctttg agcatctttg ctttcattcg tctcccgtct   3060

ttggttctcc agttcaaatt attgcaaagt aaaggatctt tgagtaggtt cggtctgaaa   3120

ggtgtggcct ttatatttga tccacacacg ttggtctttt aaccgtgctg agcagaaaac   3180

aaaacaggtt aagaagagcc gggtggcagc tgacagagga agccgctcaa ataccttcac   3240

aataaatagt ggcaatatat atatagttta agaaggctct ccatttggca tcgtttaatt   3300

tatatgttat gttctaagca cagctctctt ctcctatttt catcctgcaa gcaactcaaa   3360

atatttaaaa taaagtttac attgtagtta ttttcaaatc tttgcttgat aagtattaag   3420

aaatattgga cttgctgccg taatttaaag ctctgttgat tttgtttccg tttggatttt   3480

tgggggaggg gagcactgtg tttatgctgg aatatgaagt ctgagacctt ccggtgctgg   3540

gaacacacaa gagttgttga aagttgacaa gcagactgcg catgtctctg atgctttgta   3600

tcattcttga gcaatcgctc ggtccgtgga caataaacag tattatcaaa gagaaaaaaa   3660

aaaaaaaaaa                                                          3670
```

<210> SEQ ID NO 21
<211> LENGTH: 6001
<212> TYPE: DNA
<213> ORGANISM: Homo sapiens

<400> SEQUENCE: 21

```
caaggaggga tcccacagat gtcacagggc tgtcacagag ctgtggtggg aatttcccat     60

gagaccccgc ccctggctga gtcaccgcac tcctgtgttt gacctgaagt cctctcgagc    120

tgcagaagcc tgaagaccaa ggagtggaaa gttctccggc agccctgaga tctcaagagt    180

gacatttgtg agaccagcta atttgattaa aattctcttg gaatcagctt tgctagtatc    240

atacctgtgc cagatttcat catgggaaac agctgttaca acatagtagc cactctgttg    300

ctggtcctca actttgagag gacaagatca ttgcaggatc cttgtagtaa ctgcccagct    360

ggtacattct gtgataataa caggaatcag atttgcagtc cctgtcctcc aaatagtttc    420

tccagcgcag gtggacaaag gacctgtgac atatgcaggc agtgtaaagg tgttttcagg    480

accaggaagg agtgttcctc caccagcaat gcagagtgtg actgcactcc agggtttcac    540

tgcctggggg caggatgcag catgtgtgaa caggattgta aacaaggtca agaactgaca    600

aaaaaaggtt gtaaagactg ttgctttggg acatttaacg atcagaaacg tggcatctgt    660

cgaccctgga caaactgttc tttggatgga aagtctgtgc ttgtgaatgg gacgaaggag    720

agggacgtgg tctgtggacc atctccagcc gacctctctc cgggagcatc ctctgtgacc    780

ccgcctgccc ctgcgagaga gccaggacac tctccgcaga tcatctcctt ctttcttgcg    840

ctgacgtcga ctgcgttgct cttcctgctg ttcttcctca cgctccgttt ctctgttgtt    900

aaacggggca gaaagaaact cctgtatata ttcaaacaac catttatgag accagtacaa    960

actactcaag aggaagatgg ctgtagctgc cgatttccag aagaagaaga aggaggatgt   1020

gaactgtgaa atggaagtca atagggctgt tgggactttc ttgaaaagaa gcaaggaaat   1080

atgagtcatc cgctatcaca gctttcaaaa gcaagaacac catcctacat aatacccagg   1140

attcccccaa cacacgttct tttctaaatg ccaatgagtt ggcctttaaa aatgcaccac   1200

tttttttttt tttttgacag ggtctcactc tgtcacccag gctggagtgc agtggcacca   1260

ccatggctct ctgcagcctt gacctctggg agctcaagtg atcctcctgc ctcagtctcc   1320

tgagtagctg gaactacaag gaagggccac cacacctgac taactttttt gtttttttgtt   1380
```

```
tggtaaagat ggcatttcac catgttgtac aggctggtct caaactccta ggttcacttt   1440
ggcctcccaa agtgctggga ttacagacat gaactgccag gcccggccaa aataatgcac   1500
cacttttaac agaacagaca gatgaggaca gagctggtga taaaaaaaaa aaaaaaaaag   1560
cattttctag ataccactta acaggtttga gctagttttt ttgaaatcca aagaaaatta   1620
tagtttaaat tcaattacat agtccagtgg tccaactata attataatca aaatcaatgc   1680
aggtttgttt tttggtgcta atatgacata tgacaataag ccacgaggtg cagtaagtac   1740
ccgactaaag tttccgtggg ttctgtcatg taacacgaca tgctccaccg tcaggggga    1800
gtatgagcag agtgcctgag tttagggtca aggacaaaaa acctcaggcc tggaggaagt   1860
tttggaaaga gttcaagtgt ctgtatatcc tatggtcttc tccatcctca caccttctgc   1920
ctttgtcctg ctccctttta agccaggtta cattctaaaa attcttaact tttaacataa   1980
tattttatac caaagccaat aaatgaactg catatgatag gtatgaagta cagtgagaaa   2040
attaacacct gtgagctcat tgtcctacca cagcactaga gtgggggccg ccaaactccc   2100
atggccaaac ctggtgcacc atttgccttt gtttgtctgt tggtttgctt gagacagtct   2160
tgctctgttg cccaggctgg aatggagtgg ctattcacag gcacaatcat agcacacttt   2220
agccttaaac tcctgggctc aagtgatcca cccgcctcag tctcccaagt agctgggatt   2280
acaggtgcaa acctggcatg cctgccattg tttggcttat gatctaagga tagcttttta   2340
aattttattc attttatttt tttttgagac agtgtctcac tctgtctccc aggctggagt   2400
acagtggtac aatcttggat caccgcctcc cagtttcaag tgatctccct gcctcagcct   2460
cctaagtagc tgggactaca ggtatgtgcc accacgcctg gctaattttt atatttttag   2520
tagagacggg gtttcaccat gttgtccagg ctggtctcaa actcctgacc tcaggtgatc   2580
tgcccacctc tgcctcccaa agtgctggga ttacaggcat gagccaccat gcctggccat   2640
ttcttacact tttgtatgac atgcctattg caagcttgcg tgcctctgtc ccatgttatt   2700
ttactctggg atttaggtgg agggagcagc ttctatttgg aacattggcc atcgcatggc   2760
aaatgggtat ctgtcacttc tgctcctatt tagttggttc tactataacc tttagagcaa   2820
atcctgcagc caagccaggc atcaataggg cagaaaagta tattctgtaa ataggggtga   2880
ggagaagata tttctgaaca atagtctact gcagtaccaa attgcttttc aaagtggctg   2940
ttctaatgta ctcccgtcag tcatataagt gtcatgtaag tatcccattg atccacatcc   3000
ttgctaccct ctggtactat caggtgccct taattttgcc aagccagtgg gtatagaatg   3060
agatctcact gtggtcttag tttgcatttg cttggttact gatgagcacc ttgtcaaata   3120
tttatatacc atttgtgttt atttttttaa ataaaatgct tgctcatgct tttttgccca   3180
tttgcaaaaa aacttggggc cgggtgcagt ggctcatgcc tgtagtccca gctctttggg   3240
aggccaaggt gggcagatcg cttgagccca ggagttcgag accagccttg gcaacatggc   3300
gaaaccctgt ctttacaaaa aatacaaaaa ttagccgggt gtggtggtgt gcacctgaag   3360
tcccagctac tcagtaggtt cgctttgagc ctgggaggca gaggttgcag tgagctggga   3420
ccgcatcact acacttcagc ctgggcaaca gagaaaaacc ttttctcaga aacaaacaaa   3480
cccaaatgtg gttgtttgtc ctgattccta aaaggtcttt atgtattcta gataataatc   3540
tttggtcagt tatatgtgtt aaaaaaatatc ttctttgtgg ccaggcacgg tagctcacac   3600
ctgtaatccc agcactttgc ggggctgagg tgggtggatc atctgaggtc aagagttcaa   3660
gatcagcctg gccaacacag tgaaaccccca tctctactaa acatgtacaa aacttagctg   3720
ggtatggtgg cgggtgcctg taaccccagc tgctccagag gctgtggcag aagaatcgct   3780
```

```
tgaacccagg aggcagaggt tgcagcgagc caagattgtg ccattgcact ccagactggg   3840
tgacaagagt gaaattctgc ctatctatct atctatctat ctatatctat atatatatat   3900
atatatatcc tttgtaattt atttttccct ttttaaaatt ttttataaaa ttcttttta   3960
tttttatttt tagcagaggt gaggtttctg aggtttcatt atgttgccca ggctggtctt   4020
gaactcctga gctcaagtga tcctcccacc tcagccttcc aaagtgctgg aattgcagac   4080
atgagccacc gcgcccctcc tgtttttctc taattaatgg tgtctttctt tgtctttctg   4140
gtaataagca aaaagttctt catttgattt ggttaaattt ataactgttt tctcatatgg   4200
ttaacatttt ttcttgcctg gctaaagaaa tccttttctg cccaatacta taaagaggtt   4260
tgcccacatt ttattccaaa agttttaagt tttgtctttc atcttgaagt ctaatgtatc   4320
aggaactggc ttttgtgcct gttgggaggt agtgatccaa ttccatgtct tgcatgtagg   4380
taaccactgg tccctgcgcc atgtattcaa tacgtcgtct ttctcctgcg ggtctgcaat   4440
ctcacctacc atccatcaag tttccatagg gccatgggtc tgcttctggg ctccctgttc   4500
tgttccattg tcaatttgtc tatcctgtgc cagtatcaca ctgtgtttat tacaatagct   4560
ttgtaacagc tctcgatatc cggtaggaca tctccctcca ccttcttttt ctacttcaga   4620
agtgtcttag ctaggtcagg cacggtggct cacgcctgta atcccagcac tttgggaggc   4680
cgacgcggat ggatcacctg aggtcaggag ttttgagaca gcctggccaa catggtgaaa   4740
ccccatctct actaaaaaat acaaaaatta gtcaggcatg gtggcatgtg cctgtaatcc   4800
cagctatttg ggaggctgag gccggagaat tgcttgaacc cgggggggcgg aggttgcagt   4860
gagccgagat cgtaccattg cactccagcc tgggtgacag agcgaaactc tgtctcagga   4920
aaaaaaagaa aagagatgtc ttggttattc ttggttcttt attattcaat ataaatttta   4980
gaagctgaat ttgaaaagat ttggattgga atttcattaa atctacaggt caatttaggg   5040
agagttgata attttacaga attgagtcat ctggtgttcc aataagaata agagaacaat   5100
tattggctgt acaattcttg ccaaatagta ggcaaagcaa agcttaggaa gtatactggt   5160
gccatttcag gaacaaagct aggtgcgaat atttttgtct ttctgaatca tgatgctgta   5220
agttctaaag tgatttctcc tcttggcttt ggacacatgg tgtttaatta cctactgctg   5280
actatccaca aacagaaaga gactggtcat gccccacagg gttggggtat ccaagataat   5340
ggagcgaggc tctcatgtgt cctaggttac acaccgaaaa tccacagttt attctgtgaa   5400
gaaaggaggc tatgtttatg atacagactg tgatattttt atcatagcct attctggtat   5460
catgtgcaaa agctataaat gaaaaacaca ggaacttggc atgtgagtca ttgctccccc   5520
taaatgacaa ttaataagga aggaacattg agacagaata aaatgatccc cttctgggtt   5580
taatttagaa agttccataa ttaggtttaa tagaaataaa tgtaaatttc tatgattaaa   5640
aataaattag cacatttagg gatacacaaa ttataaatca ttttctaaat gctaaaaaca   5700
agctcaggtt tttttcagaa gaaagtttta atttttttttc tttagtggaa gatatcactc   5760
tgacggaaag ttttgatgtg aggggcggat gactataaag tgggcatctt cccccacagg   5820
aagatgtttc catctgtggg tgagaggtgc ccaccgcagc tagggcaggt tacatgtgcc   5880
ctgtgtgtgg taggacttgg agagtgatct ttatcaacgt ttttatttaa aagactatct   5940
aataaaacac aaaactatga tgttcacagg aaaaaaagaa taagaaaaaa agaaaaaaaa   6000
a                                                                    6001
```

<210> SEQ ID NO 22

<211> LENGTH: 3562
<212> TYPE: DNA
<213> ORGANISM: Homo sapiens

<400> SEQUENCE: 22

```
ctctccggcc gccgccggtg cgggtgctcc gctaccggct cctctccgtt ctgtgctctc     60
ttctgctctc ggctccccac cccctctccc ttccctcctc tccccttgcc tcccctcctc    120
tgcagcgcct gcattatttt ctgcccgcag gctcggcttg cactgctgct gcagcccggg    180
gaggtggctg ggtgggtggg gaggagactg tgcaagttgt aggggagggg gtgccctctt    240
cttccccgct cccttccccc gccaactcct tcccctcctt ctcccccttt cccctccccg    300
cccccacctt cttcctcctt tcggaaggac tggtaacttg tcgtgcggag cgaacggcgg    360
cggcggcggc ggcggcggca ccatccaggc gggcaccatg ggcacgtccg cgctctgggc    420
gctctggctg ctgctcgcgc tgtgctgggc gccccgggag agcggcgcca ccggaaccgg    480
gagaaaagcc aaatgtgaac cctcccaatt ccagtgcaca aatggtcgct gtattacgct    540
gttgtggaaa tgtgatgggg atgaagactg tgttgacggc agtgatgaaa agaactgtgt    600
aaagaagacg tgtgctgaat ctgacttcgt gtgcaacaat ggccagtgtg ttcccagccg    660
atggaagtgt gatggagatc ctgactgcga agatggttca gatgaaagcc cagaacagtg    720
ccatatgaga acatgccgca tacatgaaat cagctgtggc gcccattcta ctcagtgtat    780
cccagtgtcc tggagatgtg atggtgaaaa tgattgtgac agtggagaag atgaagaaaa    840
ctgtggcaat ataacatgta gtcccgacga gttcacctgc tccagtggcc gctgcatctc    900
caggaacttt gtatgcaatg gccaggatga ctgcagcgat ggcagtgatg agctggactg    960
tgccccgcca acctgtggcg cccatgagtt ccagtgcagc acctcctcct gcatccccat   1020
cagctgggta tgcgacgatg atgcagactg ctccgaccaa tctgatgagt ccctggagca   1080
gtgtggccgt cagccagtca tacacaccaa gtgtccagcc agcgaaatcc agtgcggctc   1140
tggcgagtgc atccataaga agtggcgatg tgatggggac cctgactgca aggatggcag   1200
tgatgaggtc aactgtccct ctcgaacttg ccgacctgac caatttgaat gtgaggatgg   1260
cagctgcatc catggcagca ggcagtgtaa tggtatccga gactgtgtcg atggttccga   1320
tgaagtcaac tgcaaaaatg tcaatcagtg cttgggccct ggaaaattca agtgcagaag   1380
tggagaatgc atagatatca gcaaagtatg taaccaggag caggactgca gggactggag   1440
tgatgagccc ctgaaagagt gtcatataaa cgaatgcttg gtaaataatg gtggatgttc   1500
tcatatctgc aaagacctag ttataggcta cgagtgtgac tgtgcagctg ggtttgaact   1560
gatagatagg aaaacctgtg gagatattga tgaatgccaa aatccaggaa tctgcagtca   1620
aatttgtatc aacttaaaag gcggttacaa gtgtgaatgt agtcgtggct atcaaatgga   1680
tcttgctact ggcgtgtgca aggcagtagg caaagagcca agtctgatct tcactaatcg   1740
aagagacatc aggaagattg gcttagagag gaaagaatat atccaactag ttgaacagct   1800
aagaaacact gtggctctcg atgctgacat tgctgcccag aaactattct gggccgatct   1860
aagccaaaag gctatcttca gtgcctcaat tgatgacaag gttggtagac atgttaaaat   1920
gatcgacaat gtctataatc ctgcagccat tgctgttgat tgggtgtaca agaccatcta   1980
ctggactgat gcggcttcta agactatttc agtagctacc ctagatggaa ccaagaggaa   2040
gttcctgttt aactctgact tgcgagagcc tgcctccata gctgtggacc cactgtctgg   2100
ctttgtttac tggtcagact ggggtgaacc agctaaaata gaaaaagcag gaatgaatgg   2160
attcgataga cgtccactgg tgacagcgga tatccagtgg cctaacggaa ttacacttga   2220
```

```
ccttataaaa agtcgcctct attggcttga ttctaagttg cacatgttat ccagcgtgga   2280

cttgaatggc caagatcgta ggatagtact aaagtctctg gagttcctag ctcatcctct   2340

tgcactaaca atatttgagg atcgtgtcta ctggatagat ggggaaaatg aagcagtcta   2400

tggtgccaat aaattcactg gatcagagct agccactcta gtcaacaacc tgaatgatgc   2460

ccaagacatc attgtctatc atgaacttgt acagccatca ggtaaaaatt ggtgtgaaga   2520

agacatggag aatggaggat gtgaatacct atgcctgcca gcaccacaga ttaatgatca   2580

ctctccaaaa tatacctgtt cctgtcccag tgggtacaat gtagaggaaa atggccgaga   2640

ctgtcaaagg atcaatgtga ccacagcagt atcagaggtc agtgttcccc caaaagggac   2700

ttctgccgca tgggccattc ttcctctctt gctcttagtg atggcagcag taggtggcta   2760

cttgatgtgg cggaattggc aacacaagaa catgaaaagc atgaactttg acaatcctgt   2820

gtacttgaaa accactgaag aggacctctc catagacatt ggtagacaca gtgcttctgt   2880

tggacacacg tacccagcaa tatcagttgt aagcacagat gatgatctag cttgacttct   2940

gtgacaaatg ttgacctttg aggtctaaac aaataatacc cccgtcggaa tggtaaccga   3000

gccagcagct gaagtctctt tttcttcctc tcggctggaa gaacatcaag atacctttgc   3060

gtggatcaag cttgtgtact tgaccgtttt tatattactt ttgtaaatat tcttgtccac   3120

attctacttc agctttggat gtggttaccg agtatctgta acccttgaat ttctagacag   3180

tattgccacc tctggccaaa tatgcacttt ccctagaaag ccatattcca gcagtgaaac   3240

ttgtgctata gtgtatacca cctgtacata cattgtatag gccatctgta aatatcccag   3300

agaacaatca ctattcttaa gcactttgaa aatatttcta tgtaaattat tgtaaacttt   3360

ttcaatggtt gggacaatgg caataggaca aaacgggtta ctaagatgaa attgccaaaa   3420

aaatttataa actaattttg tacgtatgaa tgatatcttt gacctcaatg gaggtttgca   3480

aagactgagt gttcaaacta ctgtacattt tttttcaagt gctaaaaaat taaaccaagc   3540

agcttaacca tgaaaaaaaa aa                                             3562
```

<210> SEQ ID NO 23
<211> LENGTH: 12615
<212> TYPE: DNA
<213> ORGANISM: Homo sapiens

<400> SEQUENCE: 23

```
gtgtacgtgt aaaattatga tcaaataaat ttgtatgcct tttctcctat taacctgcct     60

tttttgtcag cgattgtcag tgaaacttca gagggcaaag gggaagtttt ccttggcccc    120

tccagttttg gtgctgtgaa caggatacca aagctgctct gttcttctgg aagctgcaat    180

gaagggaacc aaggacctga caagccagca gaaggagtct aacgtgaaga cattttgctc    240

caagaatatc ctagccatcc ttggcttctc ctctatcata gctgtgatag ctttgcttgc    300

tgtggggttg acccagaaca aagcattgcc agaaaacgtt aagtatggga ttgtgctgga    360

tgcgggttct tctcacacaa gtttatacat ctataagtgg ccagcagaaa aggagaatga    420

cacaggcgtg gtgcatcaag tagaagaatg cagggttaaa ggtcctggaa tctcaaaatt    480

tgttcagaaa gtaaatgaaa taggcattta cctgactgat tgcatggaaa gagctaggga    540

agtgattcca aggtcccagc accaagagac acccgtttac ctgggagcca cggcaggcat    600

gcggttgctc aggatggaaa gtgaagagtt ggcagacagg gttctggatg tggtggagag    660

gagcctcagc aactacccct ttgacttcca gggtgccagg atcattactg gccaagagga    720
```

```
aggtgcctat ggctggatta ctatcaacta tctgctgggc aaattcagtc agaaaacaag    780
gtggttcagc atagtcccat atgaaaccaa taatcaggaa acctttggag ctttggacct    840
tgggggagcc tctacacaag tcacttttgt accccaaaac cagactatcg agtccccaga    900
taatgctctg caatttcgcc tctatggcaa ggactacaat gtctacacac atagcttctt    960
gtgctatggg aaggatcagg cactctggca gaaactggcc aaggacattc aggttgcaag   1020
taatgaaatt ctcagggacc catgctttca tcctggatat aagaaggtag tgaacgtaag   1080
tgacctttac aagacccct gcaccaagag atttgagatg actcttccat tccagcagtt   1140
tgaaatccag ggtattggaa actatcaaca atgccatcaa agcatcctgg agctcttcaa   1200
caccagttac tgcccttact cccagtgtgc cttcaatggg attttcttgc caccactcca   1260
gggggatttt ggggcatttt cagcttttta ctttgtgatg aagtttttaa acttgacatc   1320
agagaaagtc tctcaggaaa aggtgactga gatgatgaaa aagttctgtg ctcagccttg   1380
ggaggagata aaaacatctt acgctggagt aaaggagaag tacctgagtg aatactgctt   1440
ttctggtacc tacattctct ccctccttct gcaaggctat catttcacag ctgattcctg   1500
ggagcacatc catttcattg gcaagatcca gggcagcgac gccggctgga ctttgggcta   1560
catgctgaac ctgaccaaca tgatcccagc tgagcaacca ttgtccacac ctctctccca   1620
ctccacctat gtcttcctca tggttctatt ctccctggtc cttttcacag tggccatcat   1680
aggcttgctt atctttcaca agccttcata tttctggaaa gatatggtat agcaaaagca   1740
gctgaaatat gctggctgga gtgaggaaaa aaatcgtcca gggagcattt tcctccatcg   1800
cagtgttcaa ggccatcctt ccctgtctgc cagggccagt cttgacgagt gtgaagcttc   1860
cttggctttt actgaagcct ttcttttgga ggtattcaat atcctttgcc tcaaggactt   1920
cggcagatac tgtctctttc atgagttttt cccagctaca cctttctcct ttgtactttg   1980
tgcttgtata ggttttaaag acctgacacc tttcataatc tttgctttat aaaagaacaa   2040
tattgacttt gtctagaaga actgagagtc ttgagtcctg tgataggagg ctgagctggc   2100
tgaaagaaga atctcaggaa ctggttcagt tgtactcttt aagaacccct ttctctctcc   2160
tgtttgccat ccattaagaa agccatatga tgcctttgga gaaggcagac acacattcca   2220
ttcccagcct gctctgtggg taggagaatt ttctacagta ggcaaatatg tgctaaagcc   2280
aaagagtttt ataaggaaat atatgtgctc atgcagtcaa tacagttctc aatcccaccc   2340
aaagcaggta tgtcaataaa tcacatattc ctaggtgata cccaaatgct acagagtgga   2400
acactcagac ctgagatttg caaaaagcag atgtaaatat atgcattcaa acatcagggc   2460
ttactatgag gtaggtggta tatacatgtc acaaataaaa atacagttac aactcagggt   2520
cacaaaaaat gcatcttcca atgcatattt ttattatggt aaaatataca taaatataat   2580
tcaccatttt aacatttaat tcatattaaa tacgtacaaa tcagtgacat ttagtacatt   2640
cacagtgttg tgccaccatc accactattt agttccagaa catttgcatc atcaatacat   2700
tgtctagaga caagactatc ctgggtaggc agaaaccata gatcttttgt gtttacagct   2760
atggaaacca actgtaccat aaagatagtt cactgagttt taaagccaag ccacatctta   2820
tttttccaag gtttaattta gtgagagggc agcattagtg tggagtggca tgcttttgcc   2880
ctatcgtgga atttacacat cagaatgtgc aggatccaag tctgaaagtg ttgccacccg   2940
tcacacaaca tgggctttgt ttgcttattc catgaagcag cagctataga ccttaccatg   3000
gaaacatgaa gagaccctgc accccttcc ttaaggattg ctgcaagagt tacctgttga   3060
gcaggattga ctggtgatgt ttcattctga ccttgtccca agctctccat ctctagatct   3120
```

```
ggggactgac tgttgagctg atggggaaag aaaagctctc acacaaaccg gaagccaaat   3180
gtcccctatc tcttgaatga tcaagtcact tttgacaaca tccaggtgaa tataaaaact   3240
taataaagct gtggaaagga actcttaatc ttcttttctg ctacttaggt taaattcact   3300
agatcttgat taggaatcaa aattcgaatt gggacatgtt caaattcttt cttgtggtag   3360
ttgcctatac tgtcatcgct gctgttggtt gagcatttgt ggtgtaccac gctgtgtgct   3420
caagggtatt acattcatct tctcatttaa tcctcacaac aatctgaaga aggtaggtat   3480
tacaattccc acttcataga aacagaaact gaggttcaga gaggttaagt catttgccca   3540
aatggctgag ccaaagccta ccatgtacct aacctttatt ttctttcccg aacataccag   3600
gctgtctcct cataacttcc aagcatgcac ttaaaactcc acatgaatac aaggttcatg   3660
ggacttggta ttcatagaaa gggaggcaga aagctggtct gttcctgata ggcttgtaat   3720
ttaatatcat tctgttcatg tgctttggat ggaagcacat ctggcatatg atgctaatca   3780
gtggttccca taccccctggc ttcctaattt taatgtttgc tcacagcata gtagattgac   3840
atcaaatagt ggccgatgat gatgaaaata aaggtcaaat aagttgagcc aataacagcc   3900
gctttttttcc ttctgtctgc gtatacaaag cactgtcatg cacacaatct attctgaccc   3960
tcacaacaac ccataagggt gtaaatagta tttccatttt acaaatgagg atcacacaaa   4020
ctactacatg gcagagcaga tactccaact catgtcttct ggttgaagcc tattgctttt   4080
tcttttctaa acactttccc tcagcaagtt ggaattagac ttcacaagtc tccttcagag   4140
aacacaaatc ttttcttatt ccattcctgt ttggttgcct acgtccaatc tccccctccc   4200
cagagatgcc aaaaaaaaaa tcctttaagg tatttgggag ccaaactcaa cttgttaaaa   4260
tctcaaatta tggagacaat cagcagacac aacctaaccc caattatttt ggcaggaagg   4320
ttggtttaga ggcagatcca gcaatctgct ttgggccact ctgggtgggg taggtgaaat   4380
aagattggtc actgttaact aattttaata ttggattggc cattggttat cactgattac   4440
cattctcccc tggattttca cccaggactc aaaacttggt tctgctaacc ctgttccttt   4500
atgaggaacc ttttaaagat tcctttataa ggtgggagtt ttttttctat gaacctatag   4560
gggagaaaaa agatcagcag aagtcattac tttttttttt tttttttttt ttttttgaga   4620
gagagtctca ctccattgcc caggctggag tgcagtggtg ctatctcggc tcactgcaac   4680
ctccgcctcc tgggttcaag caattctcct gcctcagcct cccgagtagc tgggattgca   4740
ggtgcccacc accacacccg gctaattttt gtatttttag taaagacagg gtttcaccat   4800
gttggccagg ctggtctcca actcccaatc tcaggtgatc ctattgcctc gggctcccaa   4860
agtgctggga ttacaggagt gagccaccat gcctggccag aagtggttac ttctgtagac   4920
aaaagaataa tgctacttaa tcaggctttc tgtgtgacaa gaaagagaaa gaaaataaag   4980
aagtttcaat tcatccaatt cttaataaga aatatgtaaa taaaattttt taaaattaca   5040
cttcatttta atgttgtatc agtcaaggtc cctgcaagag atggatggta tggtacactc   5100
aaactgggta acacaggaga gttttcagaa agcaactaaa tccaaaatac tatcaaggaa   5160
tcaatataaa aattgttaat atttttctca tactaaattt tcaaaatatt ttgtgtctat   5220
tacatttaca gcacatctta attaggacta gctgtgtgtt cacctcacat gtggcttgta   5280
gctaccatac tggacagcac atgtccaaaa aaatacacgt aaagttaaag tttaaaagac   5340
acaggaacta agccctcatt gtctttccct tgggaggtag tttaaagagc tatagatgct   5400
gtaacattct tgctattatt tattatatat gacattattc ctaaaaaagc ttttgagatc   5460
```

```
ctaggttgta ttcctcaggt tttgttgcct tcccatgaag atgtgaaggc agggatgcct   5520
gttattcagt ccaagatgca tgacaagaga ccttgggaaa gtttcatctg gatttaaaga   5580
ttaattcttg atgcttacat tccatactca aaatgtaaat ttgaatatta aaataaagat   5640
gatttttttt ttggagctag tcttgctctg ttgcccaggc tggaatgcag tggcatgatc   5700
atggctcact gcagcctcga cctcccaagc tcaagcaagg ctacaggtgt gcacctaagt   5760
agctaggact acaggtgtgc accaccatgt ctagctattt tttttctgt agagacaggg    5820
ttttcctatg ttgtccaggc tggtctcgaa ctcctgccct caagcaatcc tcctgccttg   5880
gcctcccaaa gtgttgagat tacaggcgta agccactgca cctggccaag atgaatattt   5940
taatagctca cagaacaaag tttgccacat aatgataaaa ttactatgaa aatatattcc   6000
ctttattgtc agtttaaaag atgaactgag tttcacccaa actggtctgg cccctctctg   6060
attcaaatac caatagttgc tctgattcaa attccaactg ttagaacatg acagctgctc   6120
ataactagct ttgcttacta accatgtttc tttccatttg tattaggtcc tttacttttt   6180
ataacagcct caaagtttca tgaattgctg cagtaaacat tgattttcat gtttgtgagt   6240
ctgcaagcca gctgggcagc tctacttcag gtggtaaggg tggatcagac ctattccata   6300
tacctcttgt tctccttgtc cagtggtttc tagggatatg ttctcatgat gaaccccgca   6360
gaggctcgtg aaagtgagag gaaactagga tgcctcttaa ggtcttggtc aggatggggt   6420
ctcctgtcac ttctgtcaca ggctattgta agtcatatga gcaagctcaa taaaatataa   6480
acaagtcaga taaacagtgg gaggaatggc aaagtcatat ggccaaggcc atgagtgatt   6540
aattttaaca caggaaaaaa gtaaagcatt aaatgcgatt atttaatata caatgtctta   6600
ttaactgaaa tataaaatgt gtttactgta aaatataatc tgtttatctc accaaagaaa   6660
tattatcttt aaaaaatgtc attacttcta agacatcatc agtctgcaac ttctttccat   6720
agccttaatc aggatgctgt ggcagctccc acattagcct cgcattctaa actggtagat   6780
gtcctaggaa accatacatc tatgtatttt tcttatttta tacgtttagg acaatgtata   6840
gctaattacc caacttttta tttgcataca aatctaatac aactgaacac aatcagtttt   6900
atcacaggta taatggattt ttcaatagtg aggaggtgcc tccatgagcc ttctctttag   6960
aaaagtggca ttcaagactc ttcatttgaa gtgaagattg ctatgtcttt tgcattgctc   7020
tattttacat aaattaagtt ataaattgac actataatca actgacacca tgatcagtga   7080
tgatgatcac cctcatcagc actagagttg acttgttttt ataacccctt tgcatgtatg   7140
ttgaatagca aagttcatca gagaacatgt attagtcaat ggtaagtaag atactctcat   7200
ctaagaaata acatcacctc ttctaatgaa gttctaagaa gagagggaag aaaaagtctt   7260
gggagctagt cagggaatag tgtgtatttg caattaccta aactgaactc taccattact   7320
cctaacccag ttcctcctcc tgtgttttac atgattaatg ccacccctgc ctcaatgaac   7380
caagatcagc tccatcactg ggacctcccc attctgcctg tgcaatattt ttcttttta    7440
tttctccttc taatattact gttattgctc cagtaaagag ctgtaatata ttttacctgg   7500
actgatacca ggaatggtgg tgttgcttcc aatctgttgc tgctagatta atctttgcaa   7560
agcacaggct taatttcatt gctgctcaac taaaaccact ggtggctttc cattgcctac   7620
aaaataaagt caacctcccc atcagacatt caaggctttc aatgatccat ggccgccagc   7680
tctctccagg ctcatatccc actccactcc tctgatgttt cctacactac actacactat   7740
actacactac agccaggtag aatgactgtt cacccaacac cactcaggtt gtcttctcaa   7800
cttggaatac tcttgcacct tcaaagctca tttcaaatgc cccttcattt gtgaagcctt   7860
```

```
ctccaaattt ccaagtcaga atgtctcttc cttgtgctac cacaaccctt taactgagcc   7920
tccattagtg cactgagacc attctgttca gtgtctgggt gaagcttcct ggtgaaaaat   7980
atgttaccta tttctttctg aaaagttgga ttcagggata ttatcacgga cctaaggtaa   8040
tagttctagc caacctccct gtccactgcc aggccgacta caaacccttc tgttgctggc   8100
gagctggtcc gcaccactag ttctgcttca ctctatttat ctcttgatgt aaccatcttc   8160
tttctccagg ttttaagaac cagcccaact cctggttccc tgatgaagct tttattcccc   8220
tagccacatg gaacttttcc tttttggaac atgcctttag tttctgtgta gtttgccatg   8280
cagcacttca ttgtacacat tattaaaaca gaattttaag gattagaatg aaccttaaaa   8340
gatcatgcat ctcaaaattt aatgtacata caaattaccc agggattttg ttgaaataaa   8400
aattatttaa ttttaattaa tataaataat tcagtaggtc tggggtgagg cctgaggttt   8460
tacatttcca acaagctgcc aggtaaagcc aatacatctg tccaggaatc acactttgcg   8520
tatcaaaggt ctagatgaca ttatcattcc aaagagtttc ttttacaggc tctcagatca   8580
gtgttcatcc actacctgac tactgtcatt cacaggcatt ctgttccaca gcaggccagc   8640
taacgtggta tttacaaagc tcactcctct tatacaacaa tccaagtgtt tcttttgtca   8700
gttgtctgtg ccccaggaga tccctctctg ccttgccttg ccctctgcct ttggagacca   8760
gcacctcata ctcagtgaag gcctggagtg cttaagaggg atttcttcca gctctcttgc   8820
cctggtcttc agtgtattag atgtattacc tccatgctct cagtagaggc ccataggaaa   8880
gagtaggtag gttatgccag ctcacacgca tcctttaaaa atggtttaga agtttagctg   8940
gtttcttatt actcctgtct atggatgttt ccttctgtca ctctactagg gatgaaacag   9000
ctaatcatgt tcaatagtta catttagatt ggtttttaaa aactatgatt gtattagttc   9060
gtttccatgc tgctgataaa gacatatctg agactggaaa caaaaagggt ttaattggac   9120
ttacagttcc acatggctgg ggaggcctca aaatcaggtg ggaggcaaaa ggtacttctt   9180
acgtggtggc atcaagagca aaatgaggaa gaagcaaaag cagaaactct tcataaaccc   9240
accagatctt gtgggactta ttatcacgag aatagcacag aaaagactgg cctccatgat   9300
tcaattacct cccactgcgt ccctcccaca acatgtggga attctgggag atacaattca   9360
agttgagatt tgggtgggga cacagccaaa ccatatcatt cctccctggg ctcctccaaa   9420
tttcataatc ctcacatttc aaaaccaatc attccttccc aacagttccc caaagtctta   9480
actcatttca gcattaaccc aaaagtccac agtccaaagt ctcatctgag acaaggcaag   9540
tcccttccac ttacaagcct gtaaaagcaa gctagttacc tcctagatac aatggggggt   9600
acaggtattg ggtaaataca gctgttccaa atgagagaaa ttggccaaaa caaaggggtt   9660
acagggtcca tgcaagtctg aaatccagtg gggcagtcaa attttaaagc tccataatga   9720
tctcctttga ctccatgtct cacattcagg tcatgctgat gcaagagata ggttcccatg   9780
gtcttgtgca gctccgcccc tgtggctttg cagagtacag cctccctcct ggctgctttc   9840
tcaggctgat gttgagtgtc tgtagctttt ccaggcacaa gatgcaagtt ggtggttgat   9900
ctaccattct ggggtctacc attctggggt ctaccgttct gggactgtgg ccttcttctc   9960
acagctccac taggcagtgc cccaacaggg actctgtgtg ggggctctgc cccacatttc  10020
ccttccacac tgccctagga gaggttcccc atgagggctc tgcccctgca gcaaactttt  10080
gcctggacat ccaggtgttt ccatatatat tctgaaatct aggcagaggt tcccaaatct  10140
caattcttga catctctgca cccacaggct caacatcaca tggaagctgc caatgcttgg  10200
```

```
ggcctctacc ctctgaagcc acagcccaag ctctatgttg gctcctttca gccatggctg  10260
gagcagctgg gacacagggc accaagtccc taggctgcac acagcacaga gaccctgggc  10320
ccagcccaca aaaccacttt ttcctcctgg gcctctgggc ctgtgatggg aggggctgcc  10380
atgaaggtct ctgacatgac ctggagacat tttccccatg gtcttgggga ttaacattag  10440
gctccttgct gcttatgcaa atttctgcag ccagcttgaa tttctcctta aaaaaaatgg  10500
gtttttcttt tctactgcat catcaggctg cagattttcc acatttatgc tcttgtttcc  10560
cttttaaaac agaatgtttt taacagcacc caagtcacct tttgaatgct ttgctgctta  10620
gaaatttatt ccaccagata ccctaagtca tctctctcaa gctctaagtt ccacaaatct  10680
ctagggcaag ggtgaaatgc tgccagtctc cttgctaaaa cataacaagg gtcaccttta  10740
cttcagttcc caacaaggtc ttcatctcca tctgagacca cctcagcctg gaccttattg  10800
ttcatatcac tatcagtatt tttgtcaatg ccattcacag tctctaggag gttccaaact  10860
ttcctacatt ttcctatctt cttctgagcc ctccagatta tttcaacacc cagttccaaa  10920
gttgcttcca cattttcggg tatcttttca gcaatgcccc actctactgg tactattagt  10980
ccattttcat gctgctgata aagacatacc tgagactggg aacaaaaaga ggtttaattg  11040
gacttatagt tccacctggc tggggaggcc tcagaatcat ggcaggaggt gaaaggcatt  11100
tcttacacgg cagcagcaag agaaaaatga agaagcagca aaagcagaaa cccctgataa  11160
aaccatcaga tctcgtgaga cttattcact atcacaagaa tagcatggga aagaccagcc  11220
cccttgattc aattacctcc ccctgggtcc tgtgggaatt ctggaaggta caattcaagt  11280
tgagatttgg gtggggacac agccaaacca tatcaatgat tttgtacttt aaccagctga  11340
atggaagtac aatctcttgc tatatgacac aataattatt tgcaaaatga gtaaacatat  11400
cataaggaaa ttatttttac aaggtttgaa acctgaaatg cagtctatta tcatacataa  11460
ctaaaaatag agcctcaata aacagattcc cagttttgaa aatgcaacat ttgtactcca  11520
cattgtcagt tttcttaggt atatttataa atactcctat aaaaatgtaa agaaacacat  11580
aatgtagatt gctaatttta taataacaca agttgatttt gacatccaac ttattaatta  11640
tgaaatgact tttggcctag taacaatgaa aatgggggca aatacagata aatggtaatt  11700
cttagaatga actactcagc accaattcta agtttttctt gatggtaaat cataatgttc  11760
cctttctcct cggttctgca atctataggc ataccataat tgtaatcaat agcttaaaaa  11820
tatgtctctc tgtcctattc tgtatctgta tctcttggat ttttaccttt gcaatagtca  11880
actgaaccat cttcttggag tactcatgaa gatggaagtc tacatggaga atacaggatg  11940
aatccactct gtctcctgca gtgaagtctg tttgaaggat gtatttggct gtcttctgga  12000
caggccattc taataacaga aacaaacaag ttattttaaa acttattgga atattcaaat  12060
attaaccaaa gtagaaaaat ataatacaca tccatgtgcc catcacagaa cttcactgat  12120
tatcatcatt tagccagtct tgaagaagca agtgctaatt acaatcacaa atgaaacaag  12180
attcagactt catgaagagc actgcgctat aataaaagaa gaaatgagca catacattct  12240
tttactgaca gtcaaatggt gaaggtgggc agaatcatta tgtgatgcaa catggcaaaa  12300
gtatacagac agtgcatcca gaggaaggca ccttgctgaa tgactagaat ggaagtagga  12360
gacattttgc aggccccctt catcctgcag ggagaaccag aaccacagca gctctatttg  12420
cctattcctc tttaaattac aaagttaaaa tttgggagta gtagaaaatc aattggttat  12480
cttatagagt ctcctagaat atttcattgg cattgagaag gtggaaaatg caaattatat  12540
actttaaaat gtaatttttg cttttcacat atgcttaaag cctaaaacct cttaataaac  12600
```

```
ttcttctgaa atata                                                    12615

<210> SEQ ID NO 24
<211> LENGTH: 4006
<212> TYPE: DNA
<213> ORGANISM: Homo sapiens

<400> SEQUENCE: 24

tgccaaggct ccagcccggc cgggctccga ggcgagaggc tgcatggagt ggccggcgcg      60

gctctgcggg ctgtgggcgc tgctgctctg cgccggcggc gggggcgggg gcgggggcgc     120

cgcgcctacg gaaactcagc cacctgtgac aaatttgagt gtctctgttg aaaacctctg     180

cacagtaata tggacatgga atccacccga gggagccagc tcaaattgta gtctatggta     240

ttttagtcat tttggcgaca aacaagataa gaaaatagct ccggaaactc gtcgttcaat     300

agaagtaccc ctgaatgaga ggatttgtct gcaagtgggg tcccagtgta gcaccaatga     360

gagtgagaag cctagcattt tggttgaaaa atgcatctca cccccagaag gtgatcctga     420

gtctgctgtg actgagcttc aatgcatttg gcacaacctg agctacatga agtgttcttg     480

gctccctgga aggaatacca gtcccgacac taactatact ctctactatt ggcacagaag     540

cctggaaaaa attcatcaat gtgaaaacat ctttagagaa ggccaatact ttggttgttc     600

ctttgatctg accaaagtga aggattccag ttttgaacaa cacagtgtcc aaataatggt     660

caaggataat gcaggaaaaa ttaaaccatc cttcaatata gtgcctttaa cttcccgtgt     720

gaaacctgat cctccacata ttaaaaacct ctccttccac aatgatgacc tatatgtgca     780

atgggagaat ccacagaatt ttattagcag atgcctattt tatgaagtag aagtcaataa     840

cagccaaact gagacacata atgttttcta cgtccaagag gctaaatgtg agaatccaga     900

atttgagaga aatgtggaga atacatcttg tttcatggtc cctggtgttc ttcctgatac     960

tttgaacaca gtcagaataa gagtcaaaac aaataagtta tgctatgagg atgacaaact    1020

ctggagtaat tggagccaag aaatgagtat aggtaagaag cgcaattcca cactctacat    1080

aaccatgtta ctcattgttc cagtcatcgt cgcaggtgca atcatagtac tcctgcttta    1140

cctaaaaagg ctcaagatta ttatattccc tccaattcct gatcctggca agatttttaa    1200

agaaatgttt ggagaccaga atgatgatac tctgcactgg aagaagtacg acatctatga    1260

gaagcaaacc aaggaggaaa ccgactctgt agtgctgata gaaaacctga agaaagcctc    1320

tcagtgatgg agataattta tttttacctt cactgtgacc ttgagaagat tcttcccatt    1380

ctccatttgt tatctgggaa cttattaaat ggaaactgaa actactgcac catttaaaaa    1440

caggcagctc ataagagcca caggtcttta tgttgagtcg cgcaccgaaa aactaaaaat    1500

aatgggcgct ttggagaaga gtgtggagtc attctcattg aattataaaa gccagcaggc    1560

ttcaaactag gggacaaagc aaaaagtgat gatagtggtg gagttaatct tatcaagagt    1620

tgtgacaact tcctgaggga tctatacttg ctttgtgttc tttgtgtcaa catgaacaaa    1680

ttttatttgt aggggaactc atttggggtg caaatgctaa tgtcaaactt gagtcacaaa    1740

gaacatgtag aaaacaaaat ggataaaatc tgatatgtat tgtttgggat cctattgaac    1800

catgtttgtg gctattaaaa ctcttttaac agtctgggct gggtccggtg gctcacgcct    1860

gtaatcccag caatttggga gtccgaggcg ggcggatcac tcgaggtcag gagttccaga    1920

ccagcctgac caaaatggtg aaacctcctc tctactaaaa ctacaaaaat taactgggtg    1980

tggtggcgcg tgcctgtaat cccagctact cgggaagctg aggcaggtga attgtttgaa    2040
```

```
cctgggaggt ggaggttgca gtgagcagag atcacaccac tgcactctag cctgggtgac   2100

agagcaagac tctgtctaaa aaacaaaaca aaacaaaaca aaacaaaaaa acctcttaat   2160

attctggagt catcattccc ttcgacagca ttttcctctg ctttgaaagc cccagaaatc   2220

agtgttggcc atgatgacaa ctacagaaaa accagaggca gcttctttgc caagaccttt   2280

caaagccatt ttaggctgtt aggggcagtg gaggtagaat gactccttgg gtattagagt   2340

ttcaaccatg aagtctctaa caatgtattt tcttcacctc tgctactcaa gtagcattta   2400

ctgtgtcttt ggtttgtgct aggcccccgg gtgtgaagca cagacccctt ccaggggttt   2460

acagtctatt tgagactcct cagttcttgc cacttttttt tttaatctcc accagtcatt   2520

tttcagacct tttaactcct caattccaac actgatttcc ccttttgcat tctccctcct   2580

tcccttcctt gtagcctttt gactttcatt ggaaattagg atgtaaatct gctcaggaga   2640

cctggaggag cagaggataa ttagcatctc aggttaagtg tgagtaatct gagaaacaat   2700

gactaattct tgcatatttt gtaacttcca tgtgagggtt ttcagcattg atatttgtgc   2760

attttctaaa cagagatgag gtggtatctt cacgtagaac attggtattc gcttgagaaa   2820

aaaagaatag ttgaacctat ttctctttct ttacaagatg ggtccaggat tcctcttttc   2880

tctgccataa atgattaatt aaatagcttt tgtgtcttac attggtagcc agccagccaa   2940

ggctctgttt atgcttttgg ggggcatata ttgggttcca ttctcaccta tccacacaac   3000

atatccgtat atatcccctc tactcttact tcccccaaat ttaaagaagt atgggaaatg   3060

agaggcattt cccccacccc atttctctcc tcacacacag actcatatta ctggtaggaa   3120

cttgagaact ttatttccaa gttgttcaaa catttaccaa tcatattaat acaatgatgc   3180

tatttgcaat tcctgctcct aggggagggg agataagaaa ccctcactct ctacaggttt   3240

gggtacaagt ggcaacctgc ttccatggcc gtgtagaagc atggtgccct ggcttctctg   3300

aggaagctgg ggttcatgac aatggcagat gtaaagttat tcttgaagtc agattgaggc   3360

tgggagacag ccgtagtaga tgttctactt tgttctgctg ttctctagaa agaatatttg   3420

gttttcctgt ataggaatga gattaattcc tttccaggta ttttataatt ctgggaagca   3480

aaacccatgc ctccccctag ccatttttac tgttatccta tttagatggc catgaagagg   3540

atgctgtgaa attcccaaca aacattgatg ctgacagtca tgcagtctgg gagtggggaa   3600

gtgatctttt gttcccatcc tcttctttta gcagtaaaat agctgaggga aaagggaggg   3660

aaaaggaagt tatgggaata cctgtggtgg ttgtgatccc taggtcttgg gagctcttgg   3720

aggtgtctgt atcagtggat ttcccatccc ctgtgggaaa ttagtaggct catttactgt   3780

tttaggtcta gcctatgtgg attttttcct aacataccta agcaaaccca gtgtcaggat   3840

ggtaattctt attctttcgt tcagttaagt ttttcccttc atctgggcac tgaagggata   3900

tgtgaaacaa tgttaacatt tttggtagtc ttcaaccagg gattgtttct gtttaacttc   3960

ttataggaaa gcttgagtaa aataaatatt gtctttttgt atgtca                  4006
```

<210> SEQ ID NO 25
<211> LENGTH: 8888
<212> TYPE: DNA
<213> ORGANISM: Homo sapiens

<400> SEQUENCE: 25

```
actggggtgg cgcgctacct ctgcggagaa ggatctgaca gtgttccgga gccggggcga     60

gcagccaaaa ggcccgcgga gtcgcgctgg gccgccccgg cgcagctgaa ccgggggccg    120

cgcctgccag gccgacgggt ctggcccagc ctggcgccaa ggggttcgtg cgctgtggag    180
```

```
acgcggaggg tcgaggcggc gcggcctgag tgaaacccaa tggaaaaagc atgacattta    240
gaagtagaag acttagcttc aaatccctac tccttcactt actaattttg tgatttggaa    300
atatccgcgc aagatgttga cgttgcagac ttggctagtg caagccttgt ttattttcct    360
caccactgaa tctacaggtg aacttctaga tccatgtggt tatatcagtc ctgaatctcc    420
agttgtacaa cttcattcta atttcactgc agtttgtgtg ctaaaggaaa aatgtatgga    480
ttattttcat gtaaatgcta attacattgt ctggaaaaca aaccatttta ctattcctaa    540
ggagcaatat actatcataa acagaacagc atccagtgtc acctttacag atatagcttc    600
attaaatatt cagctcactt gcaacattct tacattcgga cagcttgaac agaatgttta    660
tggaatcaca ataatttcag gcttgcctcc agaaaaacct aaaaatttga gttgcattgt    720
gaacgagggg aagaaaatga ggtgtgagtg ggatggtgga agggaaacac acttggagac    780
aaacttcact ttaaaatctg aatgggcaac acacaagttt gctgattgca aagcaaaacg    840
tgacaccccc acctcatgca ctgttgatta ttctactgtg tattttgtca acattgaagt    900
ctgggtagaa gcagagaatg cccttgggaa ggttacatca gatcatatca attttgatcc    960
tgtatataaa gtgaagccca atccgccaca taatttatca gtgatcaact cagaggaact   1020
gtctagtatc ttaaaattga catggaccaa cccaagtatt aagagtgtta taatactaaa   1080
atataacatt caatatagga ccaaagatgc ctcaacttgg agccagattc ctcctgaaga   1140
cacagcatcc acccgatctt cattcactgt ccaagacctt aaacctttta cagaatatgt   1200
gtttaggatt cgctgtatga aggaagatgg taagggatac tggagtgact ggagtgaaga   1260
agcaagtggg atcacctatg aagatagacc atctaaagca ccaagtttct ggtataaaat   1320
agatccatcc catactcaag gctacagaac tgtacaactc gtgtggaaga cattgcctcc   1380
ttttgaagcc aatggaaaaa tcttggatta tgaagtgact ctcacaagat ggaaatcaca   1440
tttacaaaat tacacagtta atgccacaaa actgacagta aatctcacaa atgatcgcta   1500
tctagcaacc ctaacagtaa gaaatcttgt tggcaaatca gatgcagctg ttttaactat   1560
ccctgcctgt gactttcaag ggaacttagc agagagcaaa tgctatttga taacagttac   1620
tccagtatat gctgatggac caggaagccc tgaatccata aaggcatacc ttaaacaagc   1680
tccaccttcc aaaggaccta ctgttcggac aaaaaaagta gggaaaaacg aagctgtctt   1740
agagtgggac caacttcctg ttgatgttca gaatggattt atcagaaatt atactatatt   1800
ttatagaacc atcattggaa atgaaactgc tgtgaatgtg gattcttccc acacagaata   1860
tacattgtcc tctttgacta gtgacacatt gtacatggta cgaatggcag catacacaga   1920
tgaaggtggg aaggatggtc cagaattcac ttttactacc ccaaagtttg ctcaaggaga   1980
aattgaagcc atagtcgtgc ctgtttgctt agcattccta ttgacaactc ttctgggagt   2040
gctgttctgc tttaataagc gagacctaat taaaaaacac atctggccta atgttccaga   2100
tccttcaaag agtcatattg cccagtggtc acctcacact cctccaaggc acaattttaa   2160
ttcaaaagat caaatgtatt cagatggcaa tttcactgat gtaagtgttg tggaaataga   2220
agcaaatgac aaaaagcctt ttccagaaga tctgaaatca ttggacctgt tcaaaaagga   2280
aaaaattaat actgaaggac acagcagtgg tattgggggg tcttcatgca tgtcatcttc   2340
taggccaagc atttctagca gtgatgaaaa tgaatcttca caaaacactt cgagcactgt   2400
ccagtattct accgtggtac acagtggcta cagacaccaa gttccgtcag tccaagtctt   2460
ctcaagatcc gagtctaccc agcccttgtt agattcagag gagcggccag aagatctaca   2520
```

```
attagtagat catgtagatg gcggtgatgg tattttgccc aggcaacagt acttcaaaca   2580
gaactgcagt cagcatgaat ccagtccaga tatttcacat tttgaaaggt caaagcaagt   2640
ttcatcagtc aatgaggaag attttgttag acttaaacag cagatttcag atcatatttc   2700
acaatcctgt ggatctgggc aaatgaaaat gtttcaggaa gtttctgcag cagatgcttt   2760
tggtccaggt actgagggac aagtagaaag atttgaaaca gttggcatgg aggctgcgac   2820
tgatgaaggc atgcctaaaa gttacttacc acagactgta cggcaaggcg gctacatgcc   2880
tcagtgaagg actagtagtt cctgctacaa cttcagcagt acctataaag taaagctaaa   2940
atgattttat ctgtgaattc agattttaaa aagtcttcac tctctgaaga tgatcatttg   3000
cccttaagga caaaaatgaa ctgaagtttc acatgagcta tttccattcc agaatatctg   3060
ggattctact ttaagcacta cataaactga ctttatcctc agactagctg aatgattttg   3120
tgctgtttca ggatgtttgc actgaagaaa aacagaaagc ttatctgaaa tttataaaac   3180
tttttgtttt gctacataga aaacagaagg tatttgaata ataagcagtg atatgcttag   3240
tgagcacagc tatactgatt ttgattagaa tagtcatcag agtggcttag ggacagttaa   3300
tataaaagag gagcaaggtg tagaccatca tctacttctg ctaaaataac ttaaaaagag   3360
gtccataggc cataactaca tgagcccagc ttttgtaatc tgacaaaaaa atgaggagca   3420
gcttcgtgta tatcagtgta cacggtattc cttaggtccc ttccattggt agtgatgctg   3480
cgagttatta ctggagaaaa ggaattctag agctttaact tggcagatta aaagtactca   3540
tttttattc atcaataatt agtaatctca ctagttttca aaaatttgca tattattgac   3600
aacctctttg aagatgcatt tcacaaactc aacagagtgc catgataaga gctagggatc   3660
ccccaaacta tctcaagcat ctaaaaaatt gccatttttta aaggcttaaa ttgtagtagt   3720
aaaggggaaa acaggaagta gtagtaaagg ggaaaaaaaa ccaataaagc atctaaaaaa   3780
ttggcatgtt aaaaggctta aattgctaat gtgtgtatat atatatatat atatacacac   3840
acatatcatt gacttttctt aagacttcag agtactgggt agatgaacac tttatacagt   3900
atatatcttc agcttaaatt tgttttgagt atttttttta tttttaaata agtaggcaaa   3960
gatttaaatt tttttatttt tagtaaatgt ttgaggcaca ctaagacaac ttgggcaata   4020
tttgccaaaa caaaacagaa ccccaaaaaa tgtacatctt gttcttagca aatatcatta   4080
ttgtagagac acttaataaa gagatggtat tttaatgtct gcagttctga ggtagggtgg   4140
aacttagttc tacattgtga tttaggaatt tttaaaacct tttttcttca agggagaagt   4200
gacccaggcc tcgagtttag tgctaaagcc gctagtgtac ttatgctgtc ccctaaccac   4260
cacgtgcgat atggaagcag atgctaaata taggggtttt cttagaaagt aagaggaaat   4320
tagcaagcgt tattagtgat tgactactgc tatcaagtga attcaaagga aacaggtttt   4380
tatgccatat ttaagttaca gaaaccaggc atgcttagaa tagtttctag aggttattgg   4440
agaatagaaa gctaagaaaa cttggtatac atttacaatg gaaatataat tacacttttt   4500
actctcagaa tattgttcac attagacttc ctgtttatct tttatattct tgcatttata   4560
taatgcctca tcctttcaaa gttctttcac atattatatg atcttcttta tgaaaaaaat   4620
agatgtttca ttctgatata ttcagtttcc cactttaggc aaaagtagat taatagaatg   4680
acgaattcaa agtagatgag gaaaatcagg cacagagaag taaaggtagg gatagaccca   4740
aatttacaca acaagataat gacatctcca gcttttaagt tgatcatcaa aggctgggct   4800
ggatttgtct tgctgtatgt gtcaggaaat ttatacctat tacattttcc attttctcaa   4860
aatttaagtc acatgactaa tatttagctg caactttcct cataacaaat agtgtcatga   4920
```

```
agaatgttgt agtgtgaagt ttgtacattt cagggtcaga tatacaatat gaactcttaa   4980
tctacaggaa tgagaatgga ggatcattga aggccatgat ataaacaaat ttgcatgttg   5040
aagcctgtat aaaacatggt acagtgagtg aatataccc catccccaag aacactttat    5100
acatattaaa tggatatatg attactgtgc aaaaattcat tctggaaatg aacatatatt   5160
tgagcactaa tatgtaatgt acacctgccc taaggagaaa ataaattata aaacttttta   5220
cattcaaaat tactttccca agcatgtctt agaataatct atgtgttgat gcatgtaaat   5280
tgtactttag gtaggcaaag aaatctggtt atttatgtaa aaactagtct aataaagtta   5340
gttagtggct ttatcacttt aaatctttag tgtccaaaag tggtgtttaa agtaatagca   5400
catcagaaaa ccttgtctgg acaaaactag ttcactcact gcttctgcac ctgcagttgc   5460
tccctttagg gttataaaat aatgacccaa atgttacatg tgttgatatt ataacttgtc   5520
agttactgat gtctgtggta tcctaccctc atctctgaaa gggataatac tgaataatta   5580
ttagaaaact ataaaacttc acactttgta ccattaaaac ctaaaatttt aatcttgtcc   5640
ttttttacta tggatcagtc ggcactcggg aacagcagca aggaaaaaaa gcaaatttca   5700
ttcacatgtt ctgtgttcat acctcttctc tacctaattg ttcatttaaa tttcagcctt   5760
attccttgat aagggatttt accacatgaa gtcatccagt gaccctagct cttattgtga   5820
agttagtgga gtatacttag aaatgttaca actttaaaat gttacaaaac attcattaaa   5880
gctcatattt aaagtagagc atctagtttg agaaatagaa atcaattatt aaagatgtct   5940
tttttctacc catttaacta gttaaaacca tgacatgtaa atgtagaagt agaataatca   6000
tagaattccc taaaatattt ctgtttacta acatatattg accaagtaca tcaagcagga   6060
gagatcttcc ttcattctgt tatagtccac atcattctaa ttttgctcag ttgttattaa   6120
gagcatattc ctaaaccata cacttttgtt tcaataaagt tttattttgt tgagatgaat   6180
aaaataacaa agttataagc tgcataagac aaaagttcaa ttgttcaaaa aaaatttact   6240
gggatagctt tctattacag gtattgttag attatattgt gctgataaga ttactttcta   6300
aaaaatttgt actttctgt aaattaaaag aatatggagt cataaaatgg caagtgtttt    6360
aggattagcc taaaattgga cattgtcatt gatttcaaag aaggtatgaa ctagcagtct   6420
tacagcctaa ttcttctttg gactggtcct tggcagcagt tccttttcag actcgataaa   6480
cagaattcag atgatgtaag tcaaaacaaa actttacaaa gccaagcgta ttatcttttg   6540
cattaaccta tttttttcca tcatacatgc tactagtatg tgcattagca tgatattctc   6600
atatacattg cattaaaaat taaaaggtgg cagctcaggg tgagctcttc tgttgctcat   6660
ttgttcctaa atttttaagg gctttttctc agtcaatagt ttgtacaaac tggttagttt   6720
aacttcatta cccatttcat taaagttgat gggtcgtgtg atgagatgca tttaaggccg   6780
atagtgatag atgttttttt tatttcttga acacaggctt tgtctgaatg atgttctttt   6840
atctcttgaa cacaagcttt gaatgataac tacaggtttt aagtgctgtt acattaatac   6900
cataatgtga tgtgttagaa acaaagggat atttcaaagg tagatatttg aaaattctct   6960
agtctcaata tgtatgtgta ttgaatatac tctaaaaata aatgtgcaat ttgctagtag   7020
gacaatgcag tgactgacta gcattaggta tgtttctttt atatcctagc tatgtcccac   7080
tttcttctaa gtgcaatcct ttcatgttca cttgctgttt taccccatct actctaactt   7140
catttggaag gcttgtctag agtatagcat gtatttttac ctttgcagtg aattgcatgt   7200
gctaattgta accacagcta tttttatgtt gacataactc caaatgttat attaaatgtt   7260
```

```
ctattatata ttagctctaa tcccttaagt aaattttaag aaataaatac ttgttcaaat   7320
tttttttctg tatgtggtta ctatcatctg actatgcata tttgtaacag catttatcat   7380
tagtggtgtt agctaaataa gcatcttagt gtaaatgaga tgcttcgtgt gggttttgtg   7440
acattttaaa tgacataatg gaatgtgatt taaaagaaaa ccagtacact atcttggtct   7500
taataacata gaatggagat ggcaaattta tccactagtt ttccagattt actatttaat   7560
agctgaggtc tgaaatcgta gcatcctccc tcctagtgga cattaaaaaa aaaaaaaaaa   7620
aaaaaaacct acttggttgt caagagccca agtatggagg tgctgcgcca tcttgtggcc   7680
tgtctgtgcc caccctgcac tctgctggag tctccatcct tgttgcagtg agacttgaag   7740
ttcaagattg atacatggca tcctcctgct acttcttgag gttactaagt agtatatgaa   7800
actaatcagt cagcaagtcc acctggaagg aaaagaaaat ctcaactatt aatgtgcctt   7860
cacattgtga ttttgtctaa aaaaatgtag tgagtcaaaa aacccacaag ccagccaaca   7920
gtaactcctt cacatatata ccagagttta tagaaataac atgtcagctt tgggctatgt   7980
gctcctttgt ttaaaatctt ctatttggtt atggcttgta taggctcaag cctgatttct   8040
ttaaggtgtg gtggctcatc ttatcctaat gtgtatgata gatacagtcc atcctgcttt   8100
ggaaaagatt atgtaactcc ttgagagcat actctttctc tagcccaaag gcagtgagag   8160
agttttcttg ttcaggattg cttaactttc catttaagct ttttcttttt aaattaatac   8220
aaacttctac actttcaaaa tacgaaatat attacaactg cgtataggct cttccatact   8280
taagtccagt gcttgggcaa gttaatggag tgaaagacta caagcaaaga ggaactgagg   8340
tagaaaaaga agaatgtgtg aaagcagcag gaagctcagc caactcgaaa gcagggtgaa   8400
cagcttgagt cctgttgctg ctgatcgggg ttggctcttg gacaacttag taagatcatg   8460
gaaaggctgc ttgggttctc catagaaaag ttctgtctcc atcaagggag gaaaatgtac   8520
ctttcaactc aaaattcaat atttgttttt aaatatagct attttcccca accgctaaag   8580
attttcaaca gatacgaagc cagagcttag ttttagaaac ctgtggacat tcaaacctga   8640
ttctttattc cctgtgacta tggttatgtc attttacatg tcaaaaaagt gtatctagaa   8700
ttgtcatttc ttatttttga gctttttttta gtgagaatta tcccctcact taaatggctt   8760
tttatttaaa catctgtgca ttctgtatga aattgtagtc tttctgggat aacatggtga   8820
gctatatggt ggtaatccac acacacaaaa ataaaagcca aaaaaaaacc aaaaaaaaaa   8880
aaaaaaaa                                                            8888
```

<210> SEQ ID NO 26
<211> LENGTH: 2175
<212> TYPE: DNA
<213> ORGANISM: Homo sapiens

<400> SEQUENCE: 26

```
agtacagtat aaaacttcac agtgccaata ccatgaagag gagctcagac agctcttacc     60
acatgataca agagccggct ggtggaagag tggggaccag aaagagaatt tgctgaagag    120
gagaaggaaa aaaaaaacac caaaaaaaaa aataaaaaaa tccacacaca caaaaaaacc    180
tgcgcgtgag gggggaggaa aagcagggcc ttttaaaaag gcaatcacaa caacttttgc    240
tgccaggatg cccttgcttt ggctgagagg atttctgttg gcaagttgct ggattatagt    300
gaggagttcc cccaccccag gatccgaggg gcacagcgcg gcccccgact gtccgtcctg    360
tgcgctggcc gccctcccaa aggatgtacc caactctcag ccagagatgg tggaggccgt    420
caagaagcac attttaaaca tgctgcactt gaagaagaga cccgatgtca cccagccggt    480
```

```
acccaaggcg gcgcttctga acgcgatcag aaagcttcat gtgggcaaag tcggggagaa    540
cgggtatgtg gagatagagg atgacattgg aaggagggca gaaatgaatg aacttatgga    600
gcagacctcg gagatcatca cgtttgccga gtcaggaaca gccaggaaga cgctgcactt    660
cgagatttcc aaggaaggca gtgacctgtc agtggtggag cgtgcagaag tctggctctt    720
cctaaaagtc cccaaggcca acaggaccag gaccaaagtc accatccgcc tcttccagca    780
gcagaagcac ccgcagggca gcttggacac aggggaagag gccgaggaag tgggcttaaa    840
gggggagagg agtgaactgt tgctctctga aaaagtagta gacgctcgga agagcacctg    900
gcatgtcttc cctgtctcca gcagcatcca gcggttgctg gaccagggca agagctccct    960
ggacgttcgg attgcctgtg agcagtgcca ggagagtggc gccagcttgg ttctcctggg   1020
caagaagaag aagaaagaag aggaggggga agggaaaaag aagggcggag gtgaaggtgg   1080
ggcaggagca gatgaggaaa aggagcagtc gcacagacct ttcctcatgc tgcaggcccg   1140
gcagtctgaa gaccaccctc atcgccggcg tcggcggggc ttggagtgtg atggcaaggt   1200
caacatctgc tgtaagaaac agttctttgt cagtttcaag gacatcggct ggaatgactg   1260
gatcattgct ccctctggct atcatgccaa ctactgcgag ggtgagtgcc cgagccatat   1320
agcaggcacg tccgggtcct cactgtcctt ccactcaaca gtcatcaacc actaccgcat   1380
gcggggccat agcccctttg ccaacctcaa atcgtgctgt gtgcccacca agctgagacc   1440
catgtccatg ttgtactatg atgatggtca aaacatcatc aaaaaggaca ttcagaacat   1500
gatcgtggag gagtgtgggt gctcatagag ttgcccagcc caggggggaaa gggagcaaga   1560
gttgtccaga gaagacagtg gcaaaatgaa gaaattttta aggtttctga gttaaccaga   1620
aaaatagaaa ttaaaaacaa aacaaaaaaa aaaacaaaaa aaaacaaaag taaattaaaa   1680
acaaaacctg atgaaacaga tgaaggaaga tgtggaaaaa atccttagcc agggctcaga   1740
gatgaagcag tgaaagagac aggaattggg agggaaaggg agaatggtgt accctttatt   1800
tcttctgaaa tcacactgat gacatcagtt gtttaaacgg ggtattgtcc tttccccccct  1860
tgaggttccc ttgtgagcct tgaatcaacc aatctagtct gcagtagtgt ggactagaac   1920
aacccaaata gcatctagaa agccatgagt ttgaaagggc ccatcacagg cactttccta   1980
cccaattacc caggtcataa ggtatgtctg tgtgacactt atctctgtgt atatcagcat   2040
acacacacac acacacacac acacacacac acacaggcat ttccacacat tacatatata   2100
cacatactgg taaaagaaca atcgtgtgca ggtggtcaca cttccttttt ctgtaccact   2160
tttgcaacaa aacaa                                                    2175
```

```
<210> SEQ ID NO 27
<211> LENGTH: 3767
<212> TYPE: DNA
<213> ORGANISM: Homo sapiens

<400> SEQUENCE: 27

aagaaagagc cccgccccta gtcttatgac tcgcactgaa gcgccgattc ctggcttttg     60
caaggctgtg gtcggtggtc atcagtgctc ttgacccagg tccagcgagc cttttccctg    120
gtgttgcagc tgttgttgta ccgccgccgt cgccgccgtc gccgcctgct ctgcggggtc    180
atggtgtgct tccgcctctt cccggttccg ggctcagggc tcgttctggt ctgcctagtc    240
ctgggagctg tgcggtctta tgcattggaa cttaatttga cagattcaga aaatgccact    300
tgcctttatg caaaatggca gatgaatttc acagtacgct atgaaactac aaataaaact    360
```

```
tataaaactg taaccatttc agaccatggc actgtgacat ataatggaag catttgtggg    420
gatgatcaga atggtcccaa aatagcagtg cagttcggac ctggcttttc ctggattgcg    480
aattttacca aggcagcatc tacttattca attgacagcg tctcattttc ctacaacact    540
ggtgataaca caacatttcc tgatgctgaa gataaaggaa ttcttactgt tgatgaactt    600
ttggccatca gaattccatt gaatgacctt tttagatgca atagtttatc aactttggaa    660
aagaatgatg ttgtccaaca ctactgggat gttcttgtac aagcttttgt ccaaaatggc    720
acagtgagca caaatgagtt cctgtgtgat aaagacaaaa cttcaacagt ggcacccacc    780
atacacacca ctgtgccatc tcctactaca acacctactc caaaggaaaa accagaagct    840
ggaacctatt cagttaataa tggcaatgat acttgtctgc tggctaccat ggggctgcag    900
ctgaacatca ctcaggataa ggttgcttca gttattaaca tcaaccccaa tacaactcac    960
tccacaggca gctgccgttc tcacactgct ctacttagac tcaatagcag caccattaag   1020
tatctagact ttgtctttgc tgtgaaaaat gaaaaccgat tttatctgaa ggaagtgaac   1080
atcagcatgt atttggttaa tggctccgtt ttcagcattg caaataacaa tctcagctac   1140
tgggatgccc ccctgggaag ttcttatatg tgcaacaaag agcagactgt ttcagtgtct   1200
ggagcatttc agataaatac ctttgatcta agggttcagc ctttcaatgt gacacaagga   1260
aagtattcta cagctgaaga atgttctgct gactctgacc tcaactttct tattcctgtt   1320
gcagtgggtg tggccttggg cttccttata attgttgtct ttatctctta tatgattgga   1380
agaaggaaaa gtcgtactgg ttatcagtct gtgtaatcag ttaaatctag tgtttgtttg   1440
tttttttcaa ttagaagtta cgtttccatt ggctaaaagc caggacatgc tgtgcaatag   1500
attgtttaag atatgcagac taacttcagt gagttcctag ctaacttggg catgagtaca   1560
cttatttaag acaaaatata ttaggaccaa tttttttctg ttttttttct tcctttgtta   1620
aagtataatt aaaagaaaaa ttgtggctta gaatttttta agtaaataat gattttaagc   1680
ccctggatcc aattatgaaa gcatttttgc tgatgtgtaa ttttatatgt tacagttact   1740
tatattttac tactttgatg ttatttgcaa aatcaaaggt gttaaagaat ttaacttgct   1800
tcaggaaata aattcaagaa catagtggat tcattttcat tggtggcaga cacgaaattt   1860
ggttcatgat aagacttcct ttccccacct cctgatcagc attatttaaa tctgtatttt   1920
tctgttagtt aagaaagaaa tggcttcatg atattgtatt taatagcaaa agtttggctg   1980
tcttcttcat tactgttaat agctactata ttttaacaag gagatttctt tttttgttgt   2040
tgttgttcta gagtttggaa tatactgatt atctcagact tgacatttat actgaaggat   2100
gaagtaagac ctccagcttt ttttaaaaaa ggtgttgatt tggaacacct gtatgggtta   2160
tggtttatta aggttatggt ttagaaagtt tttttccctc agagccttaa cttgttaaga   2220
aggttcattt atcctgcact gaaaacaaaa actctatata ctttgtttgt gtgcctcctg   2280
cactctccca ttccctatgt gaatatgctc tagttgatat ttttaatata ttgatttctt   2340
ttttctcaca gcaacaagtg cttactctag aggttagtgg gccctgatat gtcatcagtc   2400
agatgcctgc ctagccaaag ctggactaag attattctgt acatttgttg atcttgatat   2460
agacttatat ccctgtaggg actgctaatg gctccggctt ctggagtaag gtactggaga   2520
ccactcatcc ctgtgtctgc ttgattggtt cagctgttga attgcccttt tatttggaag   2580
cagtgttgaa gttgtctagg gttcaaatgg ctgctttgta cacctgtcat tagtataagg   2640
cagatgttta ttttatcaag ctattttatc tctacattta actaaaaaca aaagttccca   2700
aagatctgcc ttcacttcag aaattttttt tggattaaaa aaattaagcc tgaaccttaa   2760
```

```
ataaagtgag ttggttattc attccaagga ttaagtccca atctacctct cagcacaatg   2820
cagaagctca ccactgtatt gctgccatta actcatgcca gaaccctttg ccaataactg   2880
gaattacaaa tttttgttaa agaaaattta tcaagatctt tctttactgc cttctctata   2940
tgtacatctc aaaaacatgt acatctcaaa aactggagta gaaagttaga ttgctcaact   3000
acaactcctc tagaactcta tagctctgac atacagattc acactctcct ctatttgcta   3060
agtatgtaaa gaatgttttc ttttaaaatg ttctcttttg agaacaactg cttatttgtt   3120
ataaaagcat ttggttaaaa tgatgtcatc ataaaaaaca gtggctttgt ttcaatacat   3180
atttttgaga tgattatcta gaagccagat taataaaatc agcttgtgac cttgctaagc   3240
atataaactg gaaattcaga tacattcaaa attatgggtt catttaaaag tgttctacct   3300
tttgggtatg agactaatat cactaattcc tcaatagtta tcatggctct atcttaatta   3360
attagaaaat atgtgtgttt aattctttga gaattaaaat agagaatatt aacagagggt   3420
taaaaactgc ttcaactcca ataagataaa ggaagctcaa aatctatgag ctgagtgttc   3480
aattagcttt gcctactgag ttcaatttta tgtcaataca acagtggatc agacagtacg   3540
actttgaact ggtgaatgta aacaattgtt tttcacctaa gctgctttgg aagaactgat   3600
gcttgctgct aactaaagtt ttggatgtat cgatttagag aaccaattaa tacctgcaaa   3660
ataaagcata ctgtggtact tctgtttgat ctagtatgtg tgattttaga ttgatggatt   3720
aaaaattaat aaagatcata cattccatac caaaaaaaaa aaaaaaa                 3767
```

```
<210> SEQ ID NO 28
<211> LENGTH: 2100
<212> TYPE: DNA
<213> ORGANISM: Homo sapiens

<400> SEQUENCE: 28
```

```
ctgcccatcc gtcccgcccc ctagacgcac gtccgctcgc ccggcgcccg agccagtccg     60
cgcgcacgcc gtctgcgccc cgaaagcccc gccccaaggc gcgcccgccc accgctctcc    120
acgtgctcgc tggagggcgg tgcgaggggc cgagccgaca agatgttctt gctgcctctt    180
ccggctgcgg ggcgagtagt cgtccgacgt ctggccgtga gacgtttcgg gagccggagt    240
ctctccaccg cagacatgac gaagggcctt gttttaggaa tctattccaa agaaaaagaa    300
gatgatgtgc cacagttcac aagtgcagga gagaattttg ataaattgtt agctggaaag    360
ctgagagaga ctttgaacat atctggacca cctctgaagg cagggaagac tcgaaccttt    420
tatggtctgc atcaggactt ccccagcgtg gtgctagttg gcctcggcaa aaaggcagct    480
ggaatcgacg aacaggaaaa ctggcatgaa ggcaaagaaa acatcagagc tgctgttgca    540
gcggggtgca ggcagattca agacctggag ctctcgtctg tggaggtgga tccctgtgga    600
gacgctcagg ctgctgcgga gggagcggtg cttggtctct atgaatacga tgacctaaag    660
caaaaaaaga agatggctgt gtcggcaaag ctctatggaa gtggggatca ggaggcctgg    720
cagaaaggag tcctgtttgc ttctgggcag aacttggcac gccaattgat ggagacgcca    780
gccaatgaga tgacgccaac cagatttgct gaaattattg agaagaatct caaaagtgct    840
agtagtaaaa ccgaggtcca tatcagaccc aagtcttgga ttgaggaaca ggcaatggga    900
tcattcctca gtgtggccaa aggatctgac gagcccccag tcttcttgga aattcactac    960
aaaggcagcc ccaatgcaaa cgaaccaccc ctggtgtttg ttgggaaagg aattaccttt   1020
gacagtggtg gtatctccat caaggcttct gcaaatatgg acctcatgag ggctgacatg   1080
```

-continued

```
ggaggagctg caactatatg ctcagccatc gtgtctgctg caaagcttaa tttgcccatt   1140
aatattatag gtctggcccc tctttgtgaa aatatgccca gcggcaaggc caacaagccg   1200
ggggatgttg ttagagccaa aaacgggaag accatccagg ttgataacac tgatgctgag   1260
gggaggctca tactggctga tgcgctctgt tacgcacaca cgtttaaccc gaaggtcatc   1320
ctcaatgccg ccaccttaac aggtgccatg gatgtagctt tgggatcagg tgccactggg   1380
gtctttacca attcatcctg gctctggaac aaactcttcg aggccagcat tgaaacaggg   1440
gaccgtgtct ggaggatgcc tctcttcgaa cattatacaa gacaggttgt agattgccag   1500
cttgctgatg ttaacaacat tggaaaatac agatctgcag gagcatgtac agctgcagca   1560
ttcctgaaag aattcgtaac tcatcctaag tgggcacatt tagacatagc aggcgtgatg   1620
accaacaaag atgaagttcc ctatctacgg aaaggcatga ctgggaggcc cacaaggact   1680
ctcattgagt tcttacttcg tttcagtcaa gacaatgctt agttcagata ctcaaaaatg   1740
tcttcactct gtcttaaatt ggacagttga acttaaaagg tttttgaata aatggatgaa   1800
aatcttttaa cggagacaaa ggatggtatt taaaaatgta gaacacaatg aaatttgtat   1860
gccttgattt ttttttcatt tcacacaaag atttataaag gtaaagttaa tatcttactt   1920
gataaggatt tttaagatac tctataaatg attaaaattt ttagaacttc ctaatcactt   1980
ttcagagtat atgtttttca ttgagaagca aaattgtaac tcagatttgt gatgctagga   2040
acatgagcaa actgaaaatt actatgcact tgtcagaaac aataaatgca acttgttgtg   2100
```

<210> SEQ ID NO 29
<211> LENGTH: 6936
<212> TYPE: DNA
<213> ORGANISM: Homo sapiens

<400> SEQUENCE: 29

```
aggccgcgct cagcaggcgg ggcgggagcc gcgtgcgccc gaggacccgg ccggaaggct     60
tgcgccagct caggatgagg acaggctggg cgacccctcg ccgcccggcg gggctcctca    120
tgctgctctt ctggttcttc gatctcgcgg agccctctgg ccgcgcagct aatgacccct    180
tcaccatcgt ccatggaaat acgggcaagt gcatcaagcc agtgtatggc tggatagtag    240
cagacgactg tgatgaaact gaggacaagt tatggaagtg ggtgtcccag catcggctct    300
ttcatttgca ctcccaaaag tgccttggcc tcgatattac caaatcggta aatgagctga    360
gaatgttcag ctgtgactcc agtgccatgc tgtggtggaa atgtgagcac cactctctgt    420
acggagctgc ccggtaccgg ctggctctga aggatggaca tggcacagca atctcaaatg    480
catctgatgt ctggaagaaa ggaggctcag aggaaagcct ttgtgaccag ccttatcatg    540
agatctatac cagagatggg aactcttatg ggagaccttg tgaatttcca ttcttaattg    600
atgggacctg gcatcatgat tgcattcttg atgaagatca tagtgggcca tggtgtgcca    660
ccaccttaaa ttatgaatat gaccgaaagt ggggcatctg cttaaagcct gaaaacggtt    720
gtgaagataa ttgggaaaag aacgagcagt ttggaagttg ctaccaattt aatactcaga    780
cggctctttc ttggaaagaa gcttatgttt catgtcagaa tcaaggagct gatttactga    840
gcatcaacag tgctgctgaa ttaacttacc ttaaagaaaa agaaggcatt gctaagattt    900
tctggattgg tttaaatcag ctatactctg ctagaggctg ggaatggtca gaccacaaac    960
cattaaactt tctcaactgg gatccagaca ggcccagtgc acctactata ggtggctcca   1020
gctgtgcaag aatggatgct gagtctggtc tgtggcagag cttttcctgt gaagctcaac   1080
tgccctatgt ctgcaggaaa ccattaaata atacagtgga gttaacagat gtctggacat   1140
```

```
actcagatac ccgctgtgat gcaggctggc tgccaaataa tggattttgc tatctgctgg   1200
taaatgaaag taattcctgg gataaggcac atgcgaaatg caaagccttc agtagtgacc   1260
taatcagcat tcattctcta gcagatgtgg aggtggttgt cacaaaactc cataatgagg   1320
atatcaaaga agaagtgtgg ataggcctta agaacataaa cataccaact ttatttcagt   1380
ggtcagatgg tactgaagtt actctaacat attgggatga gaatgagcca aatgttccct   1440
acaataagac gcccaactgt gtttcctact taggagagct aggtcagtgg aaagtccaat   1500
catgtgagga gaaactaaaa tatgtatgca agagaaaggg agaaaaactg aatgacgcaa   1560
gttctgataa gatgtgtcct ccagatgagg gctggaagag acatggagaa acctgttaca   1620
agatttatga ggatgaggtc ccttttggaa caaactgcaa tctgactatc actagcagat   1680
ttgagcaaga atacctaaat gatttgatga aaaagtatga taaatctcta agaaaatact   1740
tctggactgg cctgagagat gtagattctt gtggagagta taactgggca actgttggtg   1800
gaagaaggcg ggctgtaacc ttttccaact ggaattttct tgagccagct tccccgggcg   1860
gctgcgtggc tatgtctact ggaaagtctg ttggaaagtg ggaggtgaag gactgcagaa   1920
gcttcaaagc actttcaatt tgcaagaaaa tgagtggacc ccttgggcct gaagaagcat   1980
cccctaagcc tgatgacccc tgtcctgaag gctggcagag tttccccgca agtctttctt   2040
gttataaggt attccatgca gaaagaattg taagaaagag gaactgggaa gaagctgaac   2100
gattctgcca agcccttgga gcacaccttt ctagcttcag ccatgtggat gaaataaagg   2160
aatttcttca ctttttaacg gaccagttca gtggccagca ttggctgtgg attggtttga   2220
ataaaaggag cccagattta caaggatcct ggcaatggag tgatcgtaca ccagtgtcta   2280
ctattatcat gccaaatgag tttcagcagg attatgacat cagagactgt gctgctgtca   2340
aggtatttca taggccatgg cgaagaggct ggcatttcta tgatgataga gaatttattt   2400
atttgaggcc ttttgcttgt gatacaaaac ttgaatgggt gtgccaaatt ccaaaaggcc   2460
gtactccaaa aacaccagac tggtacaatc cagaccgtgc tggaattcat ggacctccac   2520
ttataattga aggaagtgaa tattggtttg ttgctgatct tcacctaaac tatgaagaag   2580
ccgtcctgta ctgtgccagc aatcacagct ttcttgcaac tataacatct tttgtgggac   2640
taaaagccat caaaaacaaa atagcaaata tatctggtga tggacagaag tggtggataa   2700
gaattagcga gtggccaata gatgatcatt ttacatactc acgatatcca tggcaccgct   2760
ttcctgtgac atttggagag gaatgcttgt acatgtctgc caagacttgg cttatcgact   2820
taggtaaacc aacagactgt agtaccaagt tgcccttcat ctgtgaaaaa tataatgttt   2880
cttcgttaga gaaatacagc ccagattctg cagctaaagt gcaatgttct gagcaatgga   2940
ttccttttca gaataagtgt tttctaaaga tcaaacccgt gtctctcaca ttttctcaag   3000
caagcgatac ctgtcactcc tatggtggca cccttccttc agtgttgagc cagattgaac   3060
aagactttat tacatccttg cttccggata tggaagctac tttatggatt ggtttgcgct   3120
ggactgccta tgaaaagata aacaaatgga cagataacag agagctgacg tacagtaact   3180
ttcacccatt attggttagt gggaggctga gaataccaga aaattttttt gaggaagagt   3240
ctcgctacca ctgtgcccta atactcaacc tccaaaaatc accgtttact gggacgtgga   3300
attttacatc ctgcagtgaa cgccactttg tgtctctctg tcagaaatat tcagaagtta   3360
aaagcagaca gacgttgcag aatgcttcag aaactgtaaa gtatctaaat aatctgtaca   3420
aaataatccc aaagactctg acttggcaca gtgctaaaag ggagtgtctg aaaagtaaca   3480
```

-continued

```
tgcagctggt gagcatcacg gacccttacc agcaggcatt cctcagtgtg caggcgctcc   3540
ttcacaactc ttccttatgg atcggactct tcagtcaaga tgatgaactc aactttggtt   3600
ggtcagatgg gaaacgtctt cattttagtc gctgggctga aactaatggg caactcgaag   3660
actgtgtagt attagacact gatggattct ggaaaacagt tgattgcaat gacaatcaac   3720
caggtgctat ttgctactat tcaggaaatg agactgaaaa agaggtcaaa ccagttgaca   3780
gtgttaaatg tccatctcct gttctaaata ctccgtggat accatttcag aactgttgct   3840
acaatttcat aataacaaag aataggcata tggcaacaac acaggatgaa gttcatacta   3900
aatgccagaa actgaatcca aaatcacata ttctgagtat tcgagatgaa aaggagaata   3960
actttgttct tgagcaactg ctgtacttca attatatggc ttcatgggtc atgttaggaa   4020
taacttatag aaataagtct cttatgtggt ttgataagac cccactgtca tatacacatt   4080
ggagagcagg aagaccaact ataaaaaatg agaagttttt ggctggttta agtactgacg   4140
gcttctggga tattcaaacc tttaaagtta ttgaagaagc agtttatttt caccagcaca   4200
gcattcttgc ttgtaaaatt gaaatggttg actacaaaga agaatataat actacactgc   4260
cacagtttat gccatatgaa gatggtattt acagtgttat tcaaaaaaag gtaacatggt   4320
atgaagcatt aaacatgtgt tctcaaagtg gaggtcactt ggcaagcgtt cacaaccaaa   4380
atggccagct ctttctggaa gatattgtaa aacgtgatgg atttccacta tgggttgggc   4440
tctcaagtca tgatggaagt gaatcaagtt ttgaatggtc tgatggtagt acatttgact   4500
atatcccatg gaaaggccaa acatctcctg gaaattgtgt tctcttggat ccaaaaggaa   4560
cttggaaaca tgaaaaatgc aactctgtta aggatggtgc tatttgttat aaacctacaa   4620
aatctaaaaa gctgtcccgt cttacatatt catcaagatg tccagcagca aaagagaatg   4680
ggtcacggtg gatccagtac aagggtcact gttacaagtc tgatcaggca ttgcacagtt   4740
tttcagaggc caaaaaattg tgttcaaaac atgatcactc tgcaactatc gtttccataa   4800
aagatgaaga tgagaataaa tttgtgagca gactgatgag ggaaaataat aacattacca   4860
tgagagtttg gcttggatta tctcaacatt ctgttgacca gtcttggagt tggttagatg   4920
gatcagaagt gacatttgtc aaatgggaaa ataaaagtaa gagtggtgtt ggaagatgta   4980
gcatgttgat agcttcaaat gaaacttgga aaaaagttga atgtgaacat ggttttggaa   5040
gagttgtctg caaagtgcct ctgggccctg attacacagc aatagctatc atagttgcca   5100
cactaagtat cttagttctc atgggcggac tgatttggtt cctcttccaa aggcaccgtt   5160
tgcacctggc gggtttctca tcagttcgat atgcacaagg agtgaatgaa gatgagatta   5220
tgcttccttc tttccatgac taaattcttc taaaagtttt ctaatttgca ctaatgtgtt   5280
atgagaaatt agtcacttaa aatgtcccag tgtcagtatt tactctgctc caaagtagaa   5340
ctcttaaata ctttttcagt tgtttagatc ttaggcatgt gctggtatcc acagttaatt   5400
ccctgctaaa tgccatgttt atcaccctaa ttaatagaat ggaggggact ccaaagctgg   5460
aactgaagtc caaattgttt gtacagtaat atgtttaatg ttcattttct ctgtatgaat   5520
gtgattggta actaggatat gtatatttta atagaatttt taacaaaact tcttagaaaa   5580
ttaaaatagg catattacta ggtgacatgt ctacttttta atttttaaga gcatccggcc   5640
aaatgcaaaa ttagtacctc aaagtaaaaa ttgaactgta aactctatca gcattgtttc   5700
aaaatagtca tttttagcac tggggaaaaa taaacaataa gacatgctta ctttttaatt   5760
tttatttttt tgagactgag tctctctctg ttgcccaggc tggagtacaa tggcgtgatc   5820
tcggctcact gcaaatctcc gcctcccagg ttcaagcgat tctcctgcct cagcctcctg   5880
```

```
agtagctggg attacaggca actgccacca tgcccggcta atttttgtat ttttagtaga   5940
gatggggttt caccatgttg gccaggctgg tctcgaactc gtgaccgcag gtgatcctcc   6000
cgcctcggcc tcccaaagtg ctgggattac aggcatgagc caccgcgcct ggcctctgct   6060
tactttttat atagcaaaat gattcctctt ggcaagatgt ttcttatatt attccaaagt   6120
tatttcatac cattattatg taaatatgaa gagttttttt ctgtttataa ttgtttataa   6180
aacaatgact tttaaagatt tagtgcttaa cattttccca agtgtgggaa cattattttt   6240
agattgagta ggtaccttgt agcagtgtgc tttgcatttt ctgatgtatt acatgactgt   6300
ttcttttgta aagagaatca actaggtatt taagactgat aattttacaa tttatatgct   6360
tcacatagca tgtcaacttt tgactaagaa ttttgtttta cttttttaac atgtgttaaa   6420
cagagaaagg gtccatgaag gaaagtgtat gagttgcatt tgtaaaaatg agactttttc   6480
agtggaactc taaaccttgt gatgactact aacaaatgta aaattatgag tgattaagaa   6540
aacattgctt tgtggttatc actttaagtt ttgacaccta gattatagtc ttagtaatag   6600
catccactgg aaaaggtgaa aatgttttat tcggcattta acttacattt gtactttatt   6660
tttgtataaa atccatagat ttattttaca tttagagtat ttacactatg ataaagttgt   6720
aaataatttt ctaagacagt ttttatatag tctacagttg tcctgatttc ttattgaatt   6780
tgttagacta gttctcttgt cctgtgatct gtgtacaatt ttagtcacta agactttcct   6840
ccaagaacta agccaacttg atgtgaaaag cacagctgta tataatggtg atgtcataat   6900
aaagttgttt tatcttttaa gtaaaagtaa aaaaaa                             6936
```

<210> SEQ ID NO 30
<211> LENGTH: 4593
<212> TYPE: DNA
<213> ORGANISM: Homo sapiens

<400> SEQUENCE: 30

```
gctgccgcgc cccgcccttt ctcggccccc ggagggtgac ggggtgaagg cgggggaacc     60
gaggtgggga gtccgccaga gctcccagac tgcgagcacg cgagccgccg cagccgtcac    120
ccgcgccgcg tcacggctcc cgggcccgcc ctcctctgac ccctcccctc tctccgtttc    180
cccctctccc cctcctccgc cgaccgagca gtgacttaag caacggagcg cggtgaagct    240
catttttctc cttcctcgca gccgcgccag ggagctcgcg gcgcgcggcc cctgtcctcc    300
ggcccgagat gaatcctgcg gcagaagccg agttcaacat cctcctggcc accgactcct    360
acaaggttac tcactataaa caatatccac ccaacacaag caaagtttat tcctactttg    420
aatgccgtga aaagaagaca gaaaactcca aattaaggaa ggtgaaatat gaggaaacag    480
tattttatgg gttgcagtac attcttaata agtacttaaa aggtaaagta gtaaccaaag    540
agaaaatcca ggaagccaaa gatgtctaca aagaacattt ccaagatgat gtctttaatg    600
aaaagggatg gaactacatt cttgagaagt atgatgggca tcttccaata gaaataaaag    660
ctgttcctga gggctttgtc attcccagag gaaatgttct cttcacggtg gaaaacacag    720
atccagagtg ttactggctt acaaattgga ttgagactat tcttgttcag tcctggtatc    780
caatcacagt ggccacaaat tctagagagc agaagaaaat attggccaaa tatttgttag    840
aaacttctgg taacttagat ggtctggaat acaagttaca tgattttggc tacagaggag    900
tctcttccca agagactgct ggcataggag catctgctca cttggttaac ttcaaaggaa    960
cagatacagt agcaggactt gctctaatta aaaaatatta tggaacgaaa gatcctgttc   1020
```

```
caggctattc tgttccagca gcagaacaca gtaccataac agcttggggg aaagaccatg   1080
aaaaagatgc ttttgaacat attgtaacac agttttcatc agtgcctgta tctgtggtca   1140
gcgatagcta tgacatttat aatgcgtgtg agaaaatatg gggtgaagat ctaagacatt   1200
taatagtatc aagaagtaca caggcaccac taataatcag acctgattct ggaaaccctc   1260
ttgacactgt gttaaaggtt ttggagattt taggtaagaa gtttcctgtt actgagaact   1320
caaagggtta caagttgctg ccaccttatc ttagagttat tcaaggggat ggagtagata   1380
ttaatacctt acaagagatt gtagaaggca tgaaacaaaa aatgtggagt attgaaaata   1440
ttgccttcgg ttctggtgga ggtttgctac agaagttgac aagagatctc ttgaattgtt   1500
ccttcaagtg tagctatgtt gtaactaatg gccttgggat taacgtcttc aaggacccag   1560
ttgctgatcc caacaaaagg tccaaaaagg gccgattatc tttacatagg acgccagcag   1620
ggaattttgt tacactggag gaaggaaaag gagaccttga ggaatatggt caggatcttc   1680
tccatactgt cttcaagaat ggcaaggtga caaaaagcta ttcatttgat gaaataagaa   1740
aaaatgcaca gctgaatatt gaactggaag cagcacatca ttaggcttta tgactgggtg   1800
tgtgttgtgt gtatgtaata cataatgttt attgtacaga tgtgtggggt ttgtgtttta   1860
tgatacatta cagccaaatt atttgttggt ttatggacat actgcccttt catttttttt   1920
cttttccagt gtttaggtga tctcaaatta ggaaatgcat ttaaccatgt aaaagatgag   1980
tgctaaagta agctttttag ggccctttgc caataggtag tcattcaatc tggtattgat   2040
cttttcacaa ataacagaac tgagaaactt ttatatataa ctgatgatca cataaaacag   2100
atttgcataa aattaccatg attgctttat gtttatattt aacttgtatt tttgtacaaa   2160
caagattgtg taagatatat ttgaagtttc agtgatttaa cagtctttcc aacttttcat   2220
gatttttatg agcacagact ttcaagaaaa tacttgaaaa taaattacat tgccttttgt   2280
ccattaatca gcaaataaaa catggcctta acaaagttgt ttgtgttatt gtacaatttg   2340
aaaattatgt cgggacatac cctatagaat tactaacctt actgcccctt gtagaatatg   2400
tattaatcat tctacattaa agaaaataat ggttcttact ggaatgtcta ggcactgtac   2460
agttattata tatcttggtt gttgtattgt accagtgaaa tgccaaattt gaaaggcctg   2520
tactgcaatt ttatatgtca gagattgcct gtggctctaa tatgcacctc aagattttaa   2580
ggagataatg tttttagaga gaatttctgc ttccactata gaatatatac ataaatgtaa   2640
aatacttaca aaagtggaag tagtgtattt taaagtaatt acacttctga atttattttt   2700
catattctat agttggtatg acttaaatga attactggag tgggtagtga gtgtacttaa   2760
atgtttcaat tctgttatat tttttattaa gtttttaaaa aattaaattg gatattaaat   2820
tgtatggaca tcatttatta attttaaact gaatgccctc aataagtaat actgaagcac   2880
attcttaaat gaagataaat tatctccaat gaaaagcatg acatgtgttt caatagaaga   2940
atcttaagtt ggctaaattc aaagtgcttg acatcaaaat gttctagagt gattagctac   3000
tagattctga atcatacatc acatctgact agagaccagt ttctttcgaa tgattctttt   3060
atgtatgtag atctgttctt ctgaggcagc ggttggccaa ctatagccca aaggccaaat   3120
ttggacttct ttttataaat gcagattgtc tatggctgct ttcccactac tccagcctaa   3180
ggtaaacagc tgcaatagaa gccaaatgag aatcgcaaag cccaaaatgt ttattaacct   3240
gccctttaca caaaattaca caaaaagttt cctgatctct gttctaagaa aaggagtgtg   3300
ccttgcattt aaaaggaaat gttggtttct agggaaggga ggaggctaaa taattgatac   3360
ggaattttcc tcttttgtct tcttttttct cacttaagaa tccgatactg gaagactgat   3420
```

```
ttagaaaagt ttttaacatg acattaaatg tgaaatttta aaaattgaaa agccataaat   3480
catctgtttt aaatagttac atgagaaaat gatcactaga ataacctaat tagaagtgtt   3540
atcttcatta aatgtttttt gtaagtggta ttagaaagaa tatgtttttc agatggttct   3600
ttaaacatgt agtgagaaca ataagcatta ttcactttta gtaagtcttc tgtaatccat   3660
gatataaaat aattttaaaa tgattttttta atgtatttga gtaaagatga gtagtattaa   3720
gaaaaacaca catttcttca caaaatgtgc taaggggcgt gtaaagaatc aaaagaaact   3780
attaccaata atagttttga taatcaccca taattttgtg tttaaacatt gaaattatag   3840
tacagacagt attctctgtg ttctgtgaat ttcagcagct tcagaataga gtttaattta   3900
gaaatttgca gtgaaaaaag ctatctcttt gttcacaacc ataaatcagg agatggagat   3960
taattctatt ggctcttagt cacttggaac tgattaattc tgactttctg tcactaagca   4020
cttggtattt ggccatctcc attctgagca ccaaacggtt aacacgaatg tccactagaa   4080
ctctgctgtg tgtcaccctt aaatcagtct aaatcttcca gacaaaagca aatggcattt   4140
atggatttaa gtcattagat tttcaactga cattaattaa tccctcttga ttgattatat   4200
catcaagtat ttatatctta aataggaggt aggatttctg tgttaagact cttatttgta   4260
ccctataatt aaagtaaaat gttttttatg agtatccctt gttttccctt cttaaattgt   4320
tatcaaacaa tttttataat gaaatctatc ttggaaaatt agaaagaaaa atggcaaggt   4380
atttattgtt ctgtttgcca taatttagaa ctcacactta agtattttgt agttttacat   4440
tcctttttaa cccattcagt ggagaatgtc agcttttctc ccaagttgta tgttaagtct   4500
attctaatat gtactcaaca tcaagttata aacatgtaat aaacatggaa ataaagttta   4560
gctctattag tgaagtgtta aaaaaaaaaa aaa                                4593
```

```
<210> SEQ ID NO 31
<211> LENGTH: 1319
<212> TYPE: DNA
<213> ORGANISM: Homo sapiens

<400> SEQUENCE: 31

gctgcagagg attcctgcag aggatcaaga cagcacgtgg acctcgcaca gcctctccca     60
caggtaccat gaaggtctcc gcggcagccc tcgctgtcat cctcattgct actgccctct    120
gcgctcctgc atctgcctcc ccatattcct cggacaccac accctgctgc tttgcctaca    180
ttgcccgccc actgccccgt gcccacatca aggagtattt ctacaccagt ggcaagtgct    240
ccaacccagc agtcgtccac aggtcaagga tgccaaagag agagggacag caagtctggc    300
aggatttcct gtatgactcc cggctgaaca agggcaagct ttgtcacccg aaagaaccgc    360
caagtgtgtg ccaacccaga gaagaaatgg gttcgggagt acatcaactc tttggagatg    420
agctaggatg gagagtcctt gaacctgaac ttacacaaat ttgcctgttt ctgcttgctc    480
ttgtcctagc ttgggaggct tcccctcact atcctacccc acccgctcct tgaagggccc    540
agattctacc acacagcagc agttacaaaa accttcccca ggctggacgt ggtggctcac    600
gcctgtaatc ccagcacttt gggaggccaa ggtgggtgga tcacttgagg tcaggagttc    660
gagaccagcc tggccaacat gatgaaaccc catctctact aaaaatacaa aaaattagcc    720
gggcgtggta gcgggcgcct gtagtcccag ctactcggga ggctgaggca ggagaatggc    780
gtgaacccgg gaggcggagc ttgcagtgag ccgagatcgc gccactgcac tccagcctgg    840
gcgacagagc gagactccgt ctcaaaaaaa aaaaaaaaaa aaaaaataca aaaattagcc    900
```

```
gggcgtggtg gcccacgcct gtaatcccag ctactcggga ggctaaggca ggaaaattgt    960

ttgaacccag gaggtggagg ctgcagtgag ctgagattgt gccacttcac tccagcctgg   1020

gtgacaaagt gagactccgt cacaacaaca acaacaaaaa gcttccccaa ctaaagccta   1080

gaagagcttc tgaggcgctg ctttgtcaaa aggaagtctc taggttctga gctctggctt   1140

tgccttggct ttgccagggc tctgtgacca ggaaggaagt cagcatgcct ctagaggcaa   1200

ggaggggagg aacactgcac tcttaagctt ccgccgtctc aacccctcac aggagcttac   1260

tggcaaacat gaaaaatcgg cttaccatta aagttctcaa tgcaaccata aaaaaaaaa    1319
```

<210> SEQ ID NO 32
<211> LENGTH: 2475
<212> TYPE: DNA
<213> ORGANISM: Homo sapiens

<400> SEQUENCE: 32

```
gacgggggcg ccccggccta agcgggacta ggagggcgcg ccacccgctt ccgctgcccg     60

ccggggaatc ccccgggctg gcgcgcaggg aagttcccga acgcgcgggc ataaaagggc    120

agccggcgcc cgcgcgccac agctctgcag ctcgtggcag cggcgcagcg ctccagccat    180

gtcgcgcggc ctccagcttc tgctcctgag ctgcgcctac agcctggctc ccgcgacgcc    240

ggaggtgaag gtggcttgct ccgaagatgt ggacttgccc tgcaccgccc cctgggatcc    300

gcaggttccc tacacggtct cctgggtcaa gttattggag ggtggtgaag agaggatgga    360

gacaccccag gaagaccacc tcaggggaca gcactatcat cagaaggggc aaaatggttc    420

tttcgacgcc cccaatgaaa ggccctattc cctgaagatc cgaaacacta ccagctgcaa    480

ctcggggaca tacaggtgca ctctgcagga cccggatggg cagagaaacc taagtggcaa    540

ggtgatcttg agagtgacag gatgccctgc acagcgtaaa gaagagactt ttaagaaata    600

cagagcggag attgtcctgc tgctggctct ggttattttc tacttaacac tcatcatttt    660

cacttgtttt gcacggctac agagtatctt cccagatttt tctaaagctg gcatggaacg    720

agcttttctc ccagttacct ccccaaataa gcatttaggg ctagtgactc ctcacaagac    780

agaactggta tgagcaggat ttctgcaggt tcttcttcct gaagctgagg ctcaggggtg    840

tgcctgtctg ttacactgga ggagagaaga atgagcctac gctgaagatg gcatcctgtg    900

aagtccttca cctcactgaa aacatctgga aggggatccc accccatttt ctgtgggcag    960

gcctcgaaaa ccatcacatg accacatagc atgaggccac tgctgcttct ccatggccac   1020

cttttcagcg atgtatgcag ctatctggtc aacctcctgg acattttttc agtcatataa   1080

aagctatggt gagatgcagc tggaaaaggg tcttgggaaa tatgaatgcc cccagctggc   1140

ccgtgacaga ctcctgagga cagctgtcct cttctgcatc ttggggacat ctctttgaat   1200

tttctgtgtt ttgctgtacc agcccagatg ttttacgtct gggagaaatt gacagatcaa   1260

gctgtgagac agtgggaaat atttagcaaa taatttcctg gtgtgaaggt cctgctatta   1320

ctaaggagta atctgtgtac aaagaaataa caagtcgatg aactattccc cagcagggtc   1380

ttttcatctg ggaaagacat ccataaagaa gcaataaaga agagtgccac atttattttt   1440

atatctatat gtacttgtca aagaaggttt gtgtttttct gcttttgaaa tctgtatctg   1500

tagtgagata gcattgtgaa ctgacaggca gcctggacat agagagggag aagaagtcag   1560

agagggtgac aagatagaga gctatttaat ggccggctgg aaatgctggg ctgacggtgc   1620

agtctgggtg ctcgcccact tgtcccacta tctgggtgca tgatcttgag caagttcctt   1680

ctggtgtctg ctttctccat tgtaaaccac aaggctgttg catgggctaa tgaagatcat   1740
```

```
atacgtgaaa attatttgaa aacatataaa gcactataca gattcgaaac tccattgagt   1800
cattatcctt gctatgatga tggtgttttg gggatgagag ggtgctatcc atttctcatg   1860
ttttccattg tttgaaacaa agaaggttac caagaagcct ttcctgtagc cttctgtagg   1920
aattcttttg gggaagtgag gaagccaggt ccacggtctg ttcttgaagc agtagcctaa   1980
cacactccaa gatatggaca cacgggagcc gctggcagaa gggacttcac gaagtgttgc   2040
atggatgttt tagccattgt tggctttccc ttatcaaact tgggcccttc ccttcttggt   2100
ttccaaaggc attttattgc ttgagttata tgttcactgt cccccctaata ttagggagta   2160
aaacggatac caagttgatt tagtgttttt acctctgtct tggctttcat gttattaaac   2220
gtatgcatgt gaagaaaggg tgtttttctg ttttatattc aactcataag actttgggat   2280
aggaaaaatg agtaatggtt actaggctta atacctgggt gattacataa tctgtacaat   2340
gaaccccccat gatgtaagtt tacctatgta acaaacctgc acttataccc atgaacttaa   2400
aatgaaagtt aaaaataaaa aacatataca aataaaaaaa tcccgacttt gggatgagtg   2460
ctaggatgtt gtaaa                                                   2475
```

<210> SEQ ID NO 33
<211> LENGTH: 1606
<212> TYPE: DNA
<213> ORGANISM: Homo sapiens

<400> SEQUENCE: 33

```
actaagtatc tccactttca attctagatc aggaactgag gacatatcta aattttctag     60
ttttatagaa ggcttttatc cacaagaatc aagatcttcc ctctctgagc aggaatcctt    120
tgtgcattga agactttaga ttcctctctg cggtagacgt gcacttataa gtatttgatg    180
gggtggattc gtggtcggag gtctcgacac agctgggaga tgagtgaatt tcataattat    240
aacttggatc tgaagaagag tgatttttca acacgatggc aaaagcaaag atgtccagta    300
gtcaaaagca aatgtagaga aaatgcatct ccattttttt tctgctgctt catcgctgta    360
gccatgggaa tccgtttcat tattatggta acaatatgga gtgctgtatt cctaaactca    420
ttattcaacc aagaagttca aattcccttg accgaaagtt actgtggccc atgtcctaaa    480
aactggatat gttacaaaaa taactgctac caattttttg atgagagtaa aaactggtat    540
gagagccagg cttcttgtat gtctcaaaat gccagccttc tgaaagtata cagcaaagag    600
gaccaggatt tacttaaact ggtgaagtca tatcattgga tgggactagt acacattcca    660
acaaatggat cttggcagtg ggaagatggc tccattctct cacccaacct actaacaata    720
attgaaatgc agaagggaga ctgtgcactc tatgcctcga gctttaaagg ctatatagaa    780
aactgttcaa ctccaaatac gtacatctgc atgcaaagga ctgtgtaaag atgatcaacc    840
atctcaataa aagccaggaa cagagaagag attacaccag cggtaacact gccaactgag    900
actaaaggaa acaaacaaaa acaggacaaa atgaccaaag actgtcagat ttcttagact    960
ccacaggacc aaaccataga acaatttcac tgcaaacatg catgattctc caagacaaaa   1020
gaagagagat cctaaaggca attcagatat ccccaaggct gcctctccca ccacaagccc   1080
agagtggatg ggctggggga ggggtgctgt tttaatttct aaaggtagga ccaacaccca   1140
ggggatcagt gaaggaagag aaggccagca gatcactgag agtgcaaccc caccctccac   1200
aggaaattgc ctcatgggca gggccacagc agagagacac agcatgggca gtgccttccc   1260
tgcctgtggg ggtcatgctg ccacttttaa tgggtcctcc acccaacggg gtcagggagg   1320
```

tggtgctgcc ccagtgggcc atgattatct taaaggcatt attctccagc cttaagtaag 1380
atcttaggac gtttcctttg ctatgatttg tacttgcttg agtcccatga ctgtttctct 1440
tcctctcttt cttccttttg gaatagtaat atccatccta tgtttgtccc actattgtat 1500
tttggaagca cataacttgt ttggtttcac aggttcacag ttaagaagga attttgcctc 1560
tgaataaata gaatcttgag tctcatgcaa aaaaaaaaaa aaaaaa 1606

<210> SEQ ID NO 34
<211> LENGTH: 3351
<212> TYPE: DNA
<213> ORGANISM: Homo sapiens

<400> SEQUENCE: 34
agtctcggct gattgccgct gtcgctcccg gggccacggg atgacgcctc ctccgcccgg 60
acgtgccgcc cccagcgcac cgcgcgcccg cgtccctggc ccgccggctc ggttggggct 120
tccgctgcgg ctgcggctgc tgctgctgct ctgggcggcc gccgcctccg cccagggcca 180
cctaaggagc ggaccccgca tcttcgccgt ctggaaaggc catgtagggc aggaccgggt 240
ggactttggc cagactgagc cgcacacggt gcttttccac gagccaggca gctcctctgt 300
gtgggtggga ggacgtggca aggtctacct ctttgacttc cccgagggca agaacgcatc 360
tgtgcgcacg gactgcgaga actacatcac tctcctggag aggcggagtg aggggctgct 420
ggcctgtggc accaacgccc ggcaccccag ctgctggaac ctggtgaatg gcactgtggt 480
gccacttggc gagatgagag gctacgcccc cttcagcccg gacgagaact ccctggttct 540
gtttgaaggg gacgaggtgt attccaccat ccggaagcag gaatacaatg ggaagatccc 600
tcggttccgc cgcatccggg gcgagagtga gctgtacacc agtgatactg tcatgcagaa 660
cccacagttc atcaaagcca ccatcgtgca ccaagaccag gcttacgatg acaagatcta 720
ctacttcttc cgagaggaca atcctgacaa gaatcctgag gctcctctca atgtgtcccg 780
tgtggcccag ttgtgcaggg gggaccaggg tggggaaagt tcactgtcag tctccaagtg 840
gaacactttt ctgaaagcca tgctggtatg cagtgatgct gccaccaaca agaacttcaa 900
caggctgcaa gacgtcttcc tgctccctga ccccagcggc cagtggaggg acaccagggt 960
ctatggtgtt ttctccaacc cctggaacta ctcagccgtc tgtgtgtatt ccctcggtga 1020
cattgacaag gtcttccgta cctcctcact caagggctac cactcaagcc ttcccaaccc 1080
gcggcctggc aagtgcctcc cagaccagca gccgataccc acagagacct tccaggtggc 1140
tgaccgtcac ccagaggtgg cgcagagggt ggagcccatg gggcctctga agacgccatt 1200
gttccactct aaataccact accagaaagt ggccgtccac cgcatgcaag ccagccacgg 1260
ggagaccttt catgtgcttt acctaactac agacaggggc actatccaca aggtggtgga 1320
accgggggag caggagcaca gcttcgcctt caacatcatg gagatccagc ccttccgccg 1380
cgcggctgcc atccagacca tgtcgctgga tgctgagcgg aggaagctgt atgtgagctc 1440
ccagtgggag gtgagccagg tgcccctgga cctgtgtgag gtctatggcg ggggctgcca 1500
cggttgcctc atgtcccgag acccctactg cggctgggac caaggccgct gcatctccat 1560
ctacagctcc gaacggtcag tgctgcaatc cattaatcca gccgagccac acaaggagtg 1620
tcccaacccc aaaccagaca aggccccact gcagaaggtt tccctggccc caaactctcg 1680
ctactacctg agctgcccca tggaatcccg ccacgccacc tactcatggc gccacaagga 1740
gaacgtggag cagagctgcg aacctggtca ccagagcccc aactgcatcc tgttcatcga 1800
gaacctcacg gcgcagcagt acggccacta cttctgcgag gcccaggagg gctcctactt 1860

```
ccgcgaggct cagcactggc agctgctgcc cgaggacggc atcatggccg agcacctgct   1920
gggtcatgcc tgtgccctgg ccgcctccct ctggctgggg gtgctgccca cactcactct   1980
tggcttgctg gtccactagg gcctcccgag gctgggcatg cctcaggctt ctgcagccca   2040
gggcactaga acgtctcaca ctcagagccg gctggcccgg gagctccttg cctgccactt   2100
cttccagggg acagaataac ccagtggagg atgccaggcc tggagacgtc cagccgcagg   2160
cggctgctgg gccccaggtg gcgcacggat ggtgaggggc tgagaatgag ggcaccgact   2220
gtgaagctgg ggcatcgatg acccaagact ttatcttctg gaaaatattt ttcagactcc   2280
tcaaacttga ctaaatgcag cgatgctccc agcccaagag cccatgggtc ggggagtggg   2340
tttggatagg agagctggga ctccatctcg accctggggc tgaggcctga gtccttctgg   2400
actcttggta cccacattgc ctccttcccc tccctctctc atggctgggt ggctggtgtt   2460
cctgaagacc cagggctacc ctctgtccag ccctgtcctc tgcagctccc tctctggtcc   2520
tgggtcccac aggacagccg ccttgcatgt ttattgaagg atgtttgctt tccggacgga   2580
aggacggaaa aagctctatt tttatgttag gcttatttca tgtatagcta cttccgactg   2640
catctgtatg aaaataccaa aactacatgc ggggggtgg gtgggaaagg gaggggctgg   2700
gaagggatgg gttggggagc gggggtgatc ccagtctgag gctcccgggg atgagataag   2760
agtctggaga cgggcatggg ttcttggaga gtggcatgag ctggctctgc cctgggagcc   2820
cggtctgagg gggacgttgt tggagcccct agtgttgggg gtggttatgg gagggggtgg   2880
ggtgagggaa acgggagaat gaaggagaaa actgagccct agtttcaccg tgttcatttg   2940
gaaggacgag ccgggtcctc agggggaggt tccaggactc tgcccttggc gttgagggtt   3000
ggggggcggg gggcctcctc ccttcctctc agccccccttc cccaggggct gtgcttccat   3060
gctcctagcc tcccaccttc gctcaggaca tgttataact taggctaaac tgtgaaaatt   3120
ccggtgggga tggcctgggc cgagctctcc aggcaggcgg ccctgccccc agccctgtcc   3180
atccatttca ggggggagct gggcccttct ccggctgtgt ctggccaccc agggcagtgg   3240
ctggggccag tggccttcca gctttggccc ctgcacctct tctcaatgca ctttaataat   3300
gtaacatatt actaataaac aagctattta tttaaaaaaa aaaaaaaaaa a            3351
```

<210> SEQ ID NO 35
<211> LENGTH: 1599
<212> TYPE: DNA
<213> ORGANISM: Homo sapiens

<400> SEQUENCE: 35

```
tctgccccac cctgtcctct ggaacctctg cgagatttag aggaaagaac cagttttcag     60
gcggattgcc tcagatcaca ctatctccac ttgcccagcc ctgtggaaga ttagcggcca    120
tgtattccaa tgtgatagga actgtaacct ctggaaaaag gaaggtttat cttttgtcct    180
tgctgctcat tggcttctgg gactgcgtga cctgtcacgg gagccctgtg gacatctgca    240
cagccaagcc gcgggacatt cccatgaatc ccatgtgcat ttaccgctcc ccggagaaga    300
aggcaactga ggatgagggc tcagaacaga agatcccgga ggccaccaac cggcgtgtct    360
gggaactgtc caaggccaat tcccgctttg ctaccacttt ctatcagcac ctggcagatt    420
ccaagaatga caatgataac attttcctgt caccccctgag tatctccacg gcttttgcta    480
tgaccaagct gggtgcctgt aatgacaccc tccagcaact gatggaggta tttaagtttg    540
acaccatatc tgagaaaaca tctgatcaga tccacttctt ctttgccaaa ctgaactgcc    600
```

```
gactctatcg aaaagccaac aaatcctcca agttagtatc agccaatcgc ctttttggag    660

acaaatccct taccttcaat gagacctacc aggacatcag tgagttggta tatggagcca    720

agctccagcc cctggacttc aaggaaaatg cagagcaatc cagagcggcc atcaacaaat    780

gggtgtccaa taagaccgaa ggccgaatca ccgatgtcat tccctcggaa gccatcaatg    840

agctcactgt tctggtgctg gttaacacca tttacttcaa gggcctgtgg aagtcaaagt    900

tcagccctga gaacacaagg aaggaactgt tctacaaggc tgatggagag tcgtgttcag    960

catctatgat gtaccaggaa ggcaagttcc gttatcggcg cgtggctgaa ggcacccagg   1020

tgcttgagtt gcccttcaaa ggtgatgaca tcaccatggt cctcatcttg cccaagcctg   1080

agaagagcct ggccaaggta gagaaggaac tcaccccaga ggtgctgcaa gagtggctgg   1140

atgaattgga ggagatgatg ctggtggtcc acatgccccg cttccgcatt gaggacggct   1200

tcagtttgaa ggagcagctg caagacatgg gccttgtcga tctgttcagc cctgaaaagt   1260

ccaaactccc aggtattgtt gcagaaggcc gagatgacct ctatgtctca gatgcattcc   1320

ataaggcatt tcttgaggta aatgaagaag gcagtgaagc agctgcaagt accgctgttg   1380

tgattgctgg ccgttcgcta aaccccaaca gggtgacttt caaggccaac aggcctttcc   1440

tggtttttat aagagaagtt cctctgaaca ctattatctt catgggcaga gtagccaacc   1500

cttgtgttaa gtaaaatgtt cttattcttt gcacctcttc ctatttttgg tttgtgaaca   1560

gaagtaaaaa taaatacaaa ctacttccat ctcacatta                          1599
```

```
<210> SEQ ID NO 36
<211> LENGTH: 2689
<212> TYPE: DNA
<213> ORGANISM: Homo sapiens

<400> SEQUENCE: 36

tttattctct ggaacatgaa acattctgtt gtgctcatat catgcaaatt atcactagta     60

ggagagcaga gagtggaaat gttccaggta taaagaccca caagataaag aagctcagag    120

tcgttagaaa caggagcaga tgtacagggt ttgcctgact cacactcaag gttgcataag    180

caagatttca aaattaatcc tattctggag acctcaaccc aatgtacaat gttcctgact    240

ggaaaagaag aactatattt ttctgatttt ttttttcaaa tctttaccat tagttgccct    300

gtatctccgc cttcactttc tgcaggaaac tttatttcct acttctgcat gccaagtttc    360

tacctctaga tctgtttggt tcagttgctg agaagcctga cataccagga ctgcctgaga    420

caagccacaa gctgaacaga gaaagtggat tgaacaagga cgcatttccc cagtacatcc    480

acaacatgct gtccacatct cgttctcggt ttatcagaaa taccaacgag agcggtgaag    540

aagtcaccac ctttttttgat tatgattacg gtgctccctg tcataaattt gacgtgaagc    600

aaattggggc ccaactcctg cctccgctct actcgctggt gttcatcttt ggttttgtgg    660

gcaacatgct ggtcgtcctc atcttaataa actgcaaaaa gctgaagtgc ttgactgaca    720

tttacctgct caacctggcc atctctgatc tgctttttct tattactctc ccattgtggg    780

ctcactctgc tgcaaatgag tgggtctttg ggaatgcaat gtgcaaatta ttcacagggc    840

tgtatcacat cggttatttt ggcggaatct tcttcatcat cctcctgaca atcgatagat    900

acctggctat tgtccatgct gtgtttgctt taaaagccag gacggtcacc tttggggtgg    960

tgacaagtgt gatcacctgg ttggtggctg tgtttgcttc tgtcccagga atcatcttta   1020

ctaaatgcca gaaagaagat tctgtttatg tctgtggccc ttattttcca cgaggatgga   1080

ataatttcca cacaataatg aggaacattt tggggctggt cctgccgctg ctcatcatgg   1140
```

tcatctgcta ctcgggaatc ctgaaaaccc tgcttcggtg tcgaaacgag aagaagaggc 1200
atagggcagt gagagtcatc ttcaccatca tgattgttta ctttctcttc tggactccct 1260
ataatattgt cattctcctg aacaccttcc aggaattctt cggcctgagt aactgtgaaa 1320
gcaccagtca actggaccaa gccacgcagg tgacagagac tcttgggatg actcactgct 1380
gcatcaatcc catcatctat gccttcgttg gggagaagtt cagaagcctt tttcacatag 1440
ctcttggctg taggattgcc ccactccaaa aaccagtgtg tggaggtcca ggagtgagac 1500
caggaaagaa tgtgaaagtg actacacaag gactcctcga tggtcgtgga aaaggaaagt 1560
caattggcag agcccctgaa gccagtcttc aggacaaaga aggagcctag agacagaaat 1620
gacagatctc tgctttggaa atcacacgtc tggcttcaca gatgtgtgat tcacagtgtg 1680
aatcttggtg tctacgttac caggcaggaa ggctgagagg agagagactc cagctgggtt 1740
ggaaaacagt attttccaaa ctaccttcca gttcctcatt tttgaataca ggcatagagt 1800
tcagactttt tttaaatagt aaaaataaaa ttaaagctga aactgcaac ttgtaaatgt 1860 ggtaaagagt tagtttgagt tactatcatg tcaaacgtga aaatgctgta ttagtcacag 1920
agataattct agctttgagc ttaagaattt tgagcaggtg gtatgtttgg gagactgctg 1980
agtcaaccca atagttgttg attggcagga gttggaagtg tgtgatctgt gggcacatta 2040
gcctatgtgc atgcagcatc taagtaatga tgtcgtttga atcacagtat acgctccatc 2100
gctgtcatct cagctggatc tccattctct caggcttgct gccaaaagcc ttttgtgttt 2160
tgttttgtat cattatgaag tcatgcgttt aatcacattc gagtgtttca gtgcttcgca 2220
gatgtccttg atgctcatat tgttccctat tttgccagtg ggaactccta aatcaagttg 2280
gcttctaatc aaagctttta aaccctattg gtaaagaatg gaaggtggag aagctccctg 2340
aagtaagcaa agactttcct cttagtcgag ccaagttaag aatgttctta tgttgcccag 2400
tgtgtttctg atctgatgca agcaagaaac actgggcttc tagaaccagg caacttggga 2460
actagactcc caagctggac tatggctcta ctttcaggcc acatggctaa agaaggtttc 2520
agaaagaagt ggggacagag cagaactttc accttcatat atttgtatga tcctaatgaa 2580
tgcataaaat gttaagttga tggtgatgaa atgtaaatac tgtttttaac aactatgatt 2640
tggaaaataa atcaatgcta taactatgtt gaaaaaaaaa aaaaaaaaa 2689

<210> SEQ ID NO 37
<211> LENGTH: 733
<212> TYPE: DNA
<213> ORGANISM: Homo sapiens

<400> SEQUENCE: 37
aaacagcagg aaatagaaac ttaagagaaa tacacacttc tgagaaactg aaacgacagg 60
ggaaaggagg tctcactgag caccgtccca gcatccggac accacagcgg cccttcgctc 120
cacgcagaaa accacacttc tcaaaccttc actcaacact tccttcccca aagccagaag 180
atgcacaagg aggaacatga ggtggctgtg ctgggggcac cccccagcac catccttcca 240
aggtccaccg tgatcaacat ccacagcgag acctccgtgc ccgaccatgt cgtctggtcc 300
ctgttcaaca ccctcttctt gaactggtgc tgtctgggct tcatagcatt cgcctactcc 360
gtgaagtcta gggacaggaa gatggttggc gacgtgaccg gggcccaggc ctatgcctcc 420
accgccaagt gcctgaacat ctgggccctg attctgggca tcctcatgac cattggattc 480
atcctgttac tggtattcgg ctctgtgaca gtctaccata ttatgttaca gataatacag 540

```
gaaaaacggg gttactagta gccgcccata gcctgcaacc tttgcactcc actgtgcaat    600

gctggccctg cacgctgggg ctgttgcccc tgccccccttg gtcctgcccc tagatacagc    660

agtttatacc cacacacctg tctacagtgt cattcaataa agtgcacgtg cttgtgaaaa    720

aaaaaaaaaa aaa                                                       733
```

```
<210> SEQ ID NO 38
<211> LENGTH: 2787
<212> TYPE: DNA
<213> ORGANISM: Homo sapiens

<400> SEQUENCE: 38

ctctttcact ttgacttgcc ttagggatgg gctgtgacac tttacttttt ttcttttttc     60

tttttttca gtcttttctc cttgctcagc ttcaatgtgt tccggagtgg ggacggggtg    120

gctgaacctc gcaggtggca gagaggctcc cctggggctg tggggctcta cgtggatccg    180

atggagccgc tggtgacctg ggtggtcccc ctcctcttcc tcttcctgct gtccaggcag    240

ggcgctgcct gcagaaccag tgagtgctgt tttcaggacc cgccatatcc ggatgcagac    300

tcaggctcgg cctcgggccc tagggacctg agatgctatc ggatatccag tgatcgttac    360

gagtgctcct ggcagtatga gggtcccaca gctggggtca gccacttcct gcggtgttgc    420

cttagctccg ggcgctgctg ctacttcgcc gccggctcag ccaccaggct gcagttctcc    480

gaccaggctg ggtgtctgt gctgtacact gtcacactct gggtggaatc ctgggccagg    540

aaccagacag agaagtctcc tgaggtgacc ctgcagctct acaactcagt taaatatgag    600

cctcctctgg gagacatcaa ggtgtccaag ttggccgggc agctgcgtat ggagtgggag    660

accccggata accaggttgg tgctgaggtg cagttccggc accggacacc cagcagccca    720

tggaagttgg gcgactgcgg acctcaggat gatgatactg agtcctgcct ctgccccctg    780

gagatgaatg tggcccagga attccagctc cgacgacggc agctggggag ccaaggaagt    840

tcctggagca agtggagcag ccccgtgtgc gttccccctg aaaacccccc acagcctcag    900

gtgagattct cggtggagca gctgggccag gatgggagga ggcggctgac cctgaaagag    960

cagccaaccc agctggagct tccagaaggc tgtcaagggc tggcgcctgg cacggaggtc   1020

acttaccgac tacagctcca catgctgtcc tgcccgtgta aggccaaggc caccaggacc   1080

ctgcacctgg ggaagatgcc ctatctctcg ggtgctgcct acaacgtggc tgtcatctcc   1140

tcgaaccaat ttggtcctgg cctgaaccag acgtggcaca ttcctgccga cacccacaca   1200

gaaccagtgg ctctgaatat cagcgtcgga accaacggga ccaccatgta ttggccagcc   1260

cgggctcaga gcatgacgta ttgcattgaa tggcagcctg tgggccagga cgggggcctt   1320

gccacctgca gcctgactgc gccgcaagac ccggatccgg ctggaatggc aacctacagc   1380

tggagtcgag agtctggggc aatggggcag gaaaagtgtt actacattac catctttgcc   1440

tctgcgcacc ccgagaagct caccttgtgg tctacggtcc tgtccaccta ccactttggg   1500

ggcaatgcct cagcagctgg gacaccgcac cacgtctcgg tgaagaatca tagcttggac   1560

tctgtgtctg tggactgggc accatccctg ctgagcacct gtcccggcgt cctaaaggag   1620

tatgttgtcc gctgccgaga tgaagacagc aaacaggtgt cagagcatcc cgtgcagccc   1680

acagagaccc aagttaccct cagtggcctg cgggctggtg tagcctacac ggtgcaggtg   1740

cgagcagaca cagcgtggct gaggggtgtc tggagccagc cccagcgctt cagcatcgaa   1800

gtgcaggttt ctgattggct catcttcttc gcctccctgg ggagcttcct gagcatcctt   1860

ctcgtgggcg tccttggcta ccttggcctg aacagggccg cacggcacct gtgcccgccg   1920
```

```
ctgcccacac cctgtgccag ctccgccatt gagttccctg gagggaagga gacttggcag   1980
tggatcaacc cagtggactt ccaggaagag gcatccctgc aggaggccct ggtggtagag   2040
atgtcctggg acaaaggcga gaggactgag cctctcgaga agacagagct acctgagggt   2100
gcccctgagc tggccctgga tacagagttg tccttggagg atggagacag atgtgatcgt   2160
tgaggctcag agagggtgag tgactcgccc gaggctacgt agcacacaca ggagtcacat   2220
ttggacccaa ataacccaga gctcctccag gctccagtgc acctgcctcc tctctgcccc   2280
gtgcctgttg ccacccatcc tgcgggggaa ccctagatgc tgccatgaaa tggaagctgc   2340
tgcaccctgc tgggcctggc atccgtgggg caggagcaga ccctgccatt tacctgttct   2400
ggcgtagaat ggactgggaa tgggggcaag gggggctcag atggatccct ggaccctggg   2460
ctgggcatcc acccccagga gcactggatg gggagtctgg actcaagggc tccctgcagc   2520
attgcggggt cttgtagctt ggaggatcca ggcatatagg gaagggggct gtaaactttg   2580
tgggaaaaat gacggtcctc ccatcccacc ccccacccca ccctcacccc cctataaaat   2640
gggggtggtg ataatgacct tacacagctg ttcaaaatca tcgtaaatga gcctcctctt   2700
gggtattttt ttcctgtttg aagcttgaat gtcctgctca aaatctcaaa acacgagcct   2760
tggaattcaa aaaaaaaaaa aaaaaaa                                       2787
```

<210> SEQ ID NO 39
<211> LENGTH: 5170
<212> TYPE: DNA
<213> ORGANISM: Homo sapiens

<400> SEQUENCE: 39

```
gtggccggcg gccggagccg actcggagcg cgcggcgccg gccgggagga gccggagagc     60
ggccgggccg ggcggtgggg gcgccggcct gccccgcgcg ccccagggag cggcaggaat    120
gtgacaatcg cgcgcccgcg caccgaagca ctcctcgctc ggctcctagg gctctcgccc    180
ctctgagctg agccgggttc cgcccggggc tgggatccca tcaccctcca cggccgtccg    240
tccaggtaga cgcaccctct gaagatggtg actccctcct gagaagctgg accccttggt    300
aaaagacaag gccttctcca agaagaatat gaaagtgtta ctcagactta tttgtttcat    360
agctctactg atttcttctc tggaggctga taaatgcaag gaacgtgaag aaaaaataat    420
tttagtgtca tctgcaaatg aaattgatgt tcgtccctgt cctcttaacc caaatgaaca    480
caaaggcact ataacttggt ataaagatga cagcaagaca cctgtatcta cagaacaagc    540
ctccaggatt catcaacaca aagagaaact ttggtttgtt cctgctaagg tggaggattc    600
aggacattac tattgcgtgg taagaaattc atcttactgc ctcagaatta aaataagtgc    660
aaaatttgtg gagaatgagc ctaacttatg ttataatgca caagccatat ttaagcagaa    720
actacccgtt gcaggagacg gaggacttgt gtgcccttat atggagtttt ttaaaaatga    780
aaataatgag ttacctaaat tacagtggta taaggattgc aaacctctac ttcttgacaa    840
tatacacttt agtggagtca aagataggct catcgtgatg aatgtggctg aaaagcatag    900
agggaactat acttgtcatg catcctacac atacttgggc aagcaatatc ctattacccg    960
ggtaatagaa tttattactc tagaggaaaa caaacccaca aggcctgtga ttgtgagccc   1020
agctaatgag acaatggaag tagacttggg atcccagata caattgatct gtaatgtcac   1080
cggccagttg agtgacattg cttactggaa gtggaatggg tcagtaattg atgaagatga   1140
cccagtgcta ggggaagact attacagtgt ggaaaatcct gcaaacaaaa gaaggagtac   1200
```

```
cctcatcaca gtgcttaata tatcggaaat tgaaagtaga ttttataaac atccatttac   1260
ctgttttgcc aagaatacac atggtataga tgcagcatat atccagttaa tatatccagt   1320
cactaatttc cagaagcaca tgattggtat atgtgtcacg ttgacagtca taattgtgtg   1380
ttctgttttc atctataaaa tcttcaagat tgacattgtg ctttggtaca gggattcctg   1440
ctatgatttt ctcccaataa aagcttcaga tggaaagacc tatgacgcat atatactgta   1500
tccaaagact gttggggaag ggtctacctc tgactgtgat atttttgtgt ttaaagtctt   1560
gcctgaggtc ttggaaaaac agtgtggata taagctgttc atttatggaa gggatgacta   1620
cgttggggaa gacattgttg aggtcattaa tgaaaacgta aagaaaagca gaagactgat   1680
tatcatttta gtcagagaaa catcaggctt cagctggctg ggtggttcat ctgaagagca   1740
aatagccatg tataatgctc ttgttcagga tggaattaaa gttgtcctgc ttgagctgga   1800
gaaaatccaa gactatgaga aaatgccaga atcgattaaa ttcattaagc agaaacatgg   1860
ggctatccgc tggtcagggg actttacaca gggaccacag tctgcaaaga caaggttctg   1920
gaagaatgtc aggtaccaca tgccagtcca gcgacggtca ccttcatcta aacaccagtt   1980
actgtcacca gccactaagg agaaactgca aagagaggct cacgtgcctc tcgggtagca   2040
tggagaagtt gccaagagtt ctttaggtgc ctcctgtctt atggcgttgc aggccaggtt   2100
atgcctcatg ctgacttgca gagttcatgg aatgtaacta tatcatcctt tatccctgag   2160
gtcacctgga atcagattat taagggaata agccatgacg tcaatagcag cccagggcac   2220
ttcagagtag agggcttggg aagatctttt aaaaaggcag taggcccggt gtggtggctc   2280
acgcctataa tcccagcact ttgggaggct gaagtgggtg gatcaccaga ggtcaggagt   2340
tcgagaccag cccagccaac atggcaaaac cccatctcta ctaaaaatac aaaaatgagc   2400
taggcatggt ggcacacgcc tgtaatccca gctacacctg aggctgaggc aggagaattg   2460
cttgaaccgg ggagacggag gttgcagtga gccgagtttg ggccactgca ctctagcctg   2520
gcaacagagc aagactccgt ctcaaaaaaa gggcaataaa tgccctctct gaatgtttga   2580
actgccaaga aaaggcatgg agacagcgaa ctagaagaaa gggcaagaag gaaatagcca   2640
ccgtctacag atggcttagt taagtcatcc acagcccaag ggcggggcta tgccttgtct   2700
ggggaccctg tagagtcact gaccctggag cggctctcct gagaggtgct gcaggcaaag   2760
tgagactgac acctcactga ggaagggaga catattcttg gagaactttc catctgcttg   2820
tattttccat acacatcccc agccagaagt tagtgtccga agaccgaatt ttattttaca   2880
gagcttgaaa actcacttca atgaacaaag ggattctcca ggattccaaa gttttgaagt   2940
catcttagct ttccacagga gggagagaac ttaaaaaagc aacagtagca gggaattgat   3000
ccacttctta atgctttcct ccctggcatg accatcctgt cctttgttat tatcctgcat   3060
tttacgtctt tggaggaaca gctccctagt ggcttcctcc gtctgcaatg tcccttgcac   3120
agcccacaca tgaaccatcc ttcccatgat gccgctcttc tgtcatcccg ctcctgctga   3180
aacacctccc aggggctcca cctgttcagg agctgaagcc catgctttcc caccagcatg   3240
tcactcccag accacctccc tgccctgtcc tccagcttcc cctcgctgtc ctgctgtgtg   3300
aattcccagg ttggcctggt ggccatgtcg cctgccccca gcactcctct gtctctgctc   3360
ttgcctgcac ccttcctcct cctttgccta ggaggccttc tcgcattttc tctagctgat   3420
cagaatttta ccaaaattca gaacatcctc caattccaca gtctctggga gactttccct   3480
aagaggcgac ttcctctcca gccttctctc tctggtcagg cccactgcag agatggtggt   3540
gagcacatct gggaggctgg tctccctcca gctggaattg ctgctctctg agggagaggc   3600
```

```
tgtggtggct gtctctgtcc ctcactgcct tccaggagca atttgcacat gtaacataga   3660
tttatgtaat gctttatgtt taaaaacatt ccccaattat cttatttaat ttttgcaatt   3720
attctaattt tatatataga gaaagtgacc tattttttaa aaaaatcaca ctctaagttc   3780
tattgaacct aggacttgag cctccatttc tggcttctag tctggtgttc tgagtacttg   3840
atttcaggtc aataacggtc ccccctcact ccacactggc acgtttgtga gaagaaatga   3900
cattttgcta ggaagtgacc gagtctagga atgcttttat tcaagacacc aaattccaaa   3960
cttctaaatg ttggaatttt caaaaattgt gtttagattt tatgaaaaac tcttctactt   4020
tcatctattc tttccctaga ggcaaacatt tcttaaaatg tttcattttc attaaaaatg   4080
aaagccaaat ttatatgcca ccgattgcag gacacaagca cagttttaag agttgtatga   4140
acatggagag gacttttggt ttttatattt ctcgtattta atatgggtga acaccaactt   4200
ttatttggaa taataatttt cctcctaaac aaaaacacat tgagtttaag tctctgactc   4260
ttgcctttcc acctgctttc tcctgggccc gctttgcctg cttgaaggaa cagtgctgtt   4320
ctggagctgc tgttccaaca gacagggcct agctttcatt tgacacacag actacagcca   4380
gaagcccatg gagcagggat gtcacgtctt gaaaagccta ttagatgttt tacaaattta   4440
attttgcaga ttattttagt ctgtcatcca gaaaatgtgt cagcatgcat agtgctaaga   4500
aagcaagcca atttggaaac ttaggttagt gacaaaattg gccagagagt gggggtgatg   4560
atgaccaaga attacaagta gaatggcagc tggaatttaa ggagggacaa gaatcaatgg   4620
ataagcgtgg gtggaggaag atccaaacag aaaagtgcaa agttattccc catcttccaa   4680
gggttgaatt ctggaggaag aagacacatt cctagttccc cgtgaacttc ctttgactta   4740
ttgtccccac taaaacaaaa caaaaaactt ttaatgcctt ccacattaat tagattttct   4800
tgcagttttt ttatggcatt tttttaaaga tgccctaagt gttgaagaag agtttgcaaa   4860
tgcaacaaaa tatttaatta ccggttgtta aaactggttt agcacaattt atattttccc   4920
tctcttgcct ttcttatttg caataaaagg tattgagcca ttttttaaat gacatttttg   4980
ataaattatg tttgtactag ttgatgaagg agtttttttt aacctgttta tataattttg   5040
cagcagaagc caaatttttt gtatattaaa gcaccaaatt catgtacagc atgcatcacg   5100
gatcaataga ctgtacttat tttccaataa aattttcaaa ctttgtactg ttaaaaaaaa   5160
aaaaaaaaaa                                                          5170
```

<210> SEQ ID NO 40
<211> LENGTH: 2615
<212> TYPE: DNA
<213> ORGANISM: Homo sapiens

<400> SEQUENCE: 40

```
actcgccgca gcctgcgcgc cttctccagt ccgcggtgcc atggccccgg cccgtctgtt     60
cgcgctgctg ctgttcttcg taggcggagt cgccgagtcg atccgagaga ctgaggtcat    120
cgacccccag gacctcctag aaggccgata cttctccgga gccctaccag acgatgagga    180
tgtagtgggg cccgggcagg aatctgatga ctttgagctg tctggctctg gagatctgga    240
tgacttggaa gactccatga tcggccctga agttgtccat cccttggtgc ctctagataa    300
ccatatccct gagagggcag ggtctgggag ccaagtcccc accgaaccca agaaactaga    360
ggagaatgag gttatcccca agagaatctc acccgttgaa gagagtgagg atgtgtccaa    420
caaggtgtca atgtccagca ctgtgcaggg cagcaacatc tttgagagaa cggaggtcct    480
```

```
ggcagctctg attgtgggtg gcatcgtggg catcctcttt gccgtcttcc tgatcctact    540

gctcatgtac cgtatgaaga agaaggatga aggcagctat gacctgggca agaaacccat    600

ctacaagaaa gcccccacca atgagttcta cgcgtgaagc ttgcttgtgg gcactggctt    660

ggactttagc ggggagggaa gccaggggat tttgaagggt ggacattagg gtagggtgag    720

gtcaacctaa tactgacttg tcagtatctc cagctctgat tacctttgaa gtgttcagaa    780

gagacattgt cttctactgt tctgccaggt tcttcttgag ctttgggcct cagttgccct    840

ggcagaaaaa tggattcaac ttggcctttc tgaaggcaag actgggattg gatcacttct    900

taaacttcca gttaagaatc taggtccgcc ctcaagccca tactgaccat gcctcatcca    960

gagctcctct gaagccaggg ggctaacgga tgttgtgtgg agtcctggct ggaggtcctc   1020

ccccagtggc cttcctccct tcctttcaca gccggtctct ctgccaggaa atgggggaag   1080

gaactagaac cacctgcacc ttgagatgtt tctgtaaatg ggtacttgtg atcacactac   1140

gggaatctct gtggtatata cctggggcca ttctaggctc tttcaagtga cttttggaaa   1200

tcaacctttt ttatttgggg gggaggatgg ggaaaagagc tgagagttta tgctgaaatg   1260

gatttataga atatttgtaa atctattttt agtgtttgtt cgttttttta actgttcatt   1320

cctttgtgca gagtgtatat ctctgcctgg gcaagagtgt ggaggtgccg aggtgtcttc   1380

attctctcgc acatttccac agcacctgct aagtttgtat ttaatggttt ttgtttttgt   1440

ttttgtttgt ttcttgaaaa tgagagaaga gccggagaga tgatttttat taattttttt   1500

ttttttttt tttttttact atttatagct ttagataggg cctcccttcc cctcttcttt   1560

ctttgttctc tttcattaaa ccccttcccc agtttttttt ttatacttta aaccccgctc   1620

ctcatggcct tggccctttc tgaagctgct tcctcttata aaatagcttt tgccgaaaca   1680

tagtttttt ttagcagatc ccaaaatata atgaagggga tggtgggata tttgtgtctg   1740

tgttcttata atatattatt attcttcctt ggttctagaa aaatagataa atatattttt   1800

ttcaggaaat agtgtggtgt ttccagtttg atgttgctgg gtggttgagt gagtgaattt   1860

tcatgtggct gggtgggttt ttgccttttt ctcttgccct gttcctggtg ccttctgatg   1920

gggctggaat agttgaggtg gatggttcta ccctttctgc cttctgtttg ggacccagct   1980

ggtgttcttt ggtttgcttt cttcaggctc tagggctgtg ctatccaata cagtaaccac   2040

atgcggctgt ttaaagttaa gccaattaaa atcacataag attaaaaatt ccttcctcag   2100

ttgcactaac cacgtttcta gaggcgtcac tgtatgtagt tcatggctac tgtactgaca   2160

gcgagagcat gtccatctgt tggacagcac tattctagag aactaaactg gcttaacgag   2220

tcacagcctc agctgtgctg ggacgaccct tgtctccctg ggtagggggg ggggaatggg   2280

ggagggctga tgaggcccca gctggggcct gttgtctggg accctccctc tcctgagagg   2340

ggaggcctgg tggcttagcc tgggcaggtc gtgtctcctc ctgaccccag tggctgcggt   2400

gaggggaacc accctccctt gctgcaccag tggccattag ctcccgtcac cactgcaacc   2460

cagggtccca gctggctggg tcctcttctg cccccagtgc ccttcccctt gggctgtgtt   2520

ggagtgagca cctcctctgt aggcacctct cacactgttg tctgttactg attttttttg   2580

ataaaaagat aataaaacct ggtactttct aaaaa                              2615
```

<210> SEQ ID NO 41
<211> LENGTH: 2411
<212> TYPE: DNA
<213> ORGANISM: Homo sapiens

<400> SEQUENCE: 41

```
agctaaaata taaaatggga atataccaaa tgctgatgaa gatggggagc aaatagatct     60
ctcatagatt gctggtggca aggtaaaatg ctctattcac tctgaaaata atttagcaat    120
tactcaatct cacatgtctg cggcgtgacc cctcctgctt ctttaaatat cagctgggga    180
agaggtctga gtaataccta agagggaagt ggcttcattt cagtggctga cttccagaga    240
gcaatatggc tggttcccca acatgcctca ccctcatcta tatcctttgg cagctcacag    300
ggtcagcagc ctctggaccc gtgaaagagc tggtcggttc cgttggtggg gccgtgactt    360
tccccctgaa gtccaaagta aagcaagttg actctattgt ctggaccttc aacacaaccc    420
ctcttgtcac catacagcca gaagggggca ctatcatagt gacccaaaat cgtaataggg    480
agagagtaga cttcccagat ggaggctact ccctgaagct cagcaaactg aagaagaatg    540
actcagggat ctactatgtg ggatatacaa gctcatcact ccagcagccc tccacccagg    600
agtacgtgct gcatgtctac gagaacaatc ctaaaggaag atccagcaaa tacggtttac    660
tccactgtgg aaataccgaa aaagatggaa aatccccact cactgctcac gatgccagac    720
acaccaaggc tatttgccta tgagaatgtt atctagacag cagtgcactc ccctaagtct    780
ctgctcaaaa aaaaaacaat tctcggccca aagaaaacaa tcagaagaat tcactgattt    840
gactagaaac atcaaggaag aatgaagaac gttgactttt ttccaggata aattatctct    900
gatgcttctt tagatttaag agttcataat tccatccact gctgagaaat ctcctcaaac    960
ccagaaggtt taatcacttc atcccaaaaa tgggattgtg aatgtcagca aaccataaaa   1020
aaagtgctta gaagtattcc tataaaaatg taaatgcaag gtcacacata ttaatgacag   1080
cctgttgtat taatgatggc tccaggtcag tgtctggagt ttcattccat cccagggctt   1140
ggatgtcagg attataccaa gagtcttgct accaggaggg caagaagacc aaaacagaca   1200
gacaagtcca gcagaagcag atgcacctga caaaaatgga tgtattaatt ggctctataa   1260
actatgtgcc cagcactatg ctgagcttac actaattggt cagacatgct gtctgccctc   1320
atgaaattgg ctccaaatga atgaactact ttcatgagca gttgtagcag gcctgaccac   1380
agattcccag agggccaggt gtggatccac aggacttgaa ggtcaaagtt cacaaagatg   1440
aagaatcagg gtagctgacc atgtttggca gatactataa tggagacaca gaagtgtgca   1500
tggcccaagg acaaggacct ccagccaggc ttcatttatg cacttgtgct gcaaaagaaa   1560
agtctaggtt ttaaggctgt gccagaaccc atcccaataa agagaccgag tctgaagtca   1620
cattgtaaat ctagtgtagg agacttggag tcaggcagtg agactggtgg ggcacggggg   1680
gcagtgggta cttgtaaacc tttaaagatg gttaattcat tcaatagata tttattaaga   1740
acctatgcgg cccggcatgg tggctcacac ctgtaatccc agcactttgg gaggccaagg   1800
tgggtgggtc atctgaggtc aggagttcaa gaccagcctg gccaacatgg tgaaacccca   1860
tctctactaa agatacaaaa atttgctgag cgtggtggtg tgcacctgta atcccagcta   1920
ctcgagaggc caaggcatga gaatcgcttg aacctgggag gtggaggttg cagtgagctg   1980
agatggcacc actgcactcc ggcctaggca acgagagcaa aactccaata caaacaaaca   2040
aacaaacacc tgtgctaggt cagtctggca cgtaagatga acatccctac caatacagag   2100
ctcaccatct cttatactta agtgaaaaac atggggaagg ggaaagggga atggctgctt   2160
ttgatatgtt ccctgacaca tatcttgaat ggagacctcc ctaccaagtg atgaaagtgt   2220
tgaaaaactt aataacaaat gcttgttggg caagaatggg attgaggatt atcttctctc   2280
agaaaggcat tgtgaaggaa ttgagccaga tctctctccc tactgcaaaa ccctattgta   2340
```

```
gtaaaaaagt cttctttact atcttaataa aacagatatt gtgagattca catacaaaaa   2400

aaaaaaaaaa a                                                        2411


<210> SEQ ID NO 42
<211> LENGTH: 3471
<212> TYPE: DNA
<213> ORGANISM: Homo sapiens

<400> SEQUENCE: 42

aaaatttcag cagagagaaa tagagaaagc agtgtgtgtg catgtgtgtg tgtgtgagag     60

agagagggag aggagcgaga gggagaggga gagggagaga gagaaaggga gggaagcaga    120

gagtcaagtc caagggaatg agcgagagag gcagagacag gggaagaggc gtgcgagaga    180

aggaataaca gctttccgga gcaggcgtgc cgtgaactgg cttctatttt attttatttt    240

tttctccttt ttattttta aagagaagca ggggacagaa gcaatggccg aggcagaaga    300

caagccgagg tgctggtgac cctgggcgtc tgagtggatg attggggctg ctgcgctcag    360

aggcctgcct ccctgccttc caatgcatat aaccccacac cccagccaat gaagacgaga    420

ggcagcgtga acaaagtcat ttagaaagcc cccgaggaag tgtaaacaaa agagaaagca    480

tgaatggagt gcctgagaga caagtgtgtc ctgtactgcc cccaccttta gctgggccag    540

caactgcccg gccctgcttc tccccaccta ctcactggtg atcttttttt ttttactttt    600

ttttcccttt tcttttccat tctcttttct tattttcttt caaggcaagg caaggatttt    660

gattttggga cccagccatg gtccttctgc ttcttcttta aaatacccac tttctcccca    720

tcgccaagcg gcgtttggca atatcagata tccactctat ttatttttac ctaaggaaaa    780

actccagctc ccttcccact cccagctgcc ttgccacccc tcccagccct ctgcttgccc    840

tccacctggc ctgctgggag tcagagccca gcaaaacctg tttagacaca tggacaagaa    900

tcccagcgct acaaggcaca cagtccgctt cttcgtcctc agggttgcca gcgcttcctg    960

gaagtcctga agctctcgca gtgcagtgag ttcatgcacc ttcttgccaa gcctcagtct   1020

ttgggatctg gggaggccgc ctggttttcc tccctccttc tgcacgtctg ctggggtctc   1080

ttcctctcca ggccttgccg tccccctggc ctctcttccc agctcacaca tgaagatgca   1140

cttgcaaagg gctctggtgg tcctggccct gctgaacttt gccacggtca gcctctctct   1200

gtccacttgc accaccttgg acttcggcca catcaagaag aagagggtgg aagccattag   1260

gggacagatc ttgagcaagc tcaggctcac cagcccccct gagccaacgg tgatgaccca   1320

cgtcccctat caggtcctgg ccctttacaa cagcacccgg gagctgctgg aggagatgca   1380

tggggagagg gaggaaggct gcacccagga aaacaccgag tcggaatact atgccaaaga   1440

aatccataaa ttcgacatga tccaggggct ggcggagcac aacgaactgg ctgtctgccc   1500

taaaggaatt acctccaagg ttttccgctt caatgtgtcc tcagtggaga aaaatagaac   1560

caacctattc cgagcagaat tccgggtctt gcgggtgccc aaccccagct ctaagcggaa   1620

tgagcagagg atcgagctct tccagatcct tcggccagat gagcacattg ccaaacagcg   1680

ctatatcggt ggcaagaatc tgcccacacg gggcactgcc gagtggctgt cctttgatgt   1740

cactgacact gtgcgtgagt ggctgttgag aagagagtcc aacttaggtc tagaaatcag   1800

cattcactgt ccatgtcaca cctttcagcc caatggagat atcctggaaa acattcacga   1860

ggtgatggaa atcaaattca aaggcgtgga caatgaggat gaccatggcc gtggagatct   1920

ggggcgcctc aagaagcaga aggatcacca caaccctcat ctaatcctca tgatgattcc   1980

cccacaccgg ctcgacaacc cgggccaggg gggtcagagg aagaagcggg ctttggacac   2040
```

```
caattactgc ttccgcaact tggaggagaa ctgctgtgtg cgccccctct acattgactt   2100

ccgacaggat ctgggctgga agtgggtcca tgaacctaag ggctactatg ccaacttctg   2160

ctcaggccct tgcccatacc tccgcagtgc agacacaacc cacagcacgg tgctgggact   2220

gtacaacact ctgaaccctg aagcatctgc ctcgccttgc tgcgtgcccc aggacctgga   2280

gcccctgacc atcctgtact atgttgggag gacccccaaa gtggagcagc tctccaacat   2340

ggtggtgaag tcttgtaaat gtagctgaga ccccacgtgc gacagagaga ggggagagag   2400

aaccaccact gcctgactgc ccgctcctcg ggaaacacac aagcaacaaa cctcactgag   2460

aggcctggag cccacaacct tcggctccgg gcaaatggct gagatggagg tttccttttg   2520

gaacatttct ttcttgctgg ctctgagaat cacggtggta aagaaagtgt gggtttggtt   2580

agaggaaggc tgaactcttc agaacacaca gactttctgt gacgcagaca gaggggatgg   2640

ggatagagga aagggatggt aagttgagat gttgtgtggc aatgggattt gggctaccct   2700

aaagggagaa ggaagggcag agaatggctg ggtcagggcc agactggaag acacttcaga   2760

tctgaggttg gatttgctca ttgctgtacc acatctgctc tagggaatct ggattatgtt   2820

atacaaggca agcatttttt tttttttttt aaagacaggt tacgaagaca aagtcccaga   2880

attgtatctc atactgtctg ggattaaggg caaatctatt acttttgcaa actgtcctct   2940

acatcaatta acatcgtggg tcactacagg gagaaaatcc aggtcatgca gttcctggcc   3000

catcaactgt attgggcctt ttggatatgc tgaacgcaga agaaagggtg gaaatcaacc   3060

ctctcctgtc tgccctctgg gtccctcctc tcacctctcc ctcgatcata tttccccttg   3120

gacacttggt tagacgcctt ccaggtcagg atgcacattt ctggattgtg gttccatgca   3180

gccttggggc attatgggtt cttcccccac ttcccctcca agaccctgtg ttcatttggt   3240

gttcctggaa gcaggtgcta caacatgtga ggcattcggg gaagctgcac atgtgccaca   3300

cagtgacttg gccccagacg catagactga ggtataaaga caagtatgaa tattactctc   3360

aaaatctttg tataaataaa tatttttggg gcatcctgga tgatttcatc ttctggaata   3420

ttgtttctag aacagtaaaa gccttattct aaggtgtaaa aaaaaaaaaa a            3471
```

<210> SEQ ID NO 43
<211> LENGTH: 4111
<212> TYPE: DNA
<213> ORGANISM: Homo sapiens

<400> SEQUENCE: 43

```
cggcagggtt ggaaaatgat ggaagaggcg gaggtggagg cgaccgagtg ctgagaggaa     60

cctgcggaat cggccgagat ggggtctggc gcgcgctttc cctcggggac ccttcgtgtc    120

cggtggttgc tgttgcttgg cctggtgggc ccagtcctcg gtgcggcgcg gccaggcttt    180

caacagacct cacatctttc ttcttatgaa attataactc cttggagatt aactagagaa    240

agaagagaag cccctaggcc ctattcaaaa caagtatctt atgttattca ggctgaagga    300

aaagagcata ttattcactt ggaaaggaac aaagaccttt tgcctgaaga ttttgtggtt    360

tatacttaca acaaggaagg gactttaatc actgaccatc ccaatataca gaatcattgt    420

cattatcggg gctatgtgga gggagttcat aattcatcca ttgctcttag cgactgtttt    480

ggactcagag gattgctgca tttagagaat gcgagttatg ggattgaacc cctgcagaac    540

agctctcatt ttgagcacat catttatcga atggatgatg tctacaaaga gcctctgaaa    600

tgtggagttt ccaacaagga tatagagaaa gaaactgcaa aggatgaaga ggaagagcct    660
```

```
cccagcatga ctcagctact tcgaagaaga agagctgtct tgccacagac ccggtatgtg    720
gagctgttca ttgtcgtaga caaggaaagg tatgacatga tgggaagaaa tcagactgct    780
gtgagagaag agatgattct cctggcaaac tacttggata gtatgtatat tatgttaaat    840
attcgaattg tgctagttgg actggagatt tggaccaatg gaaacctgat caacatagtt    900
gggggtgctg gtgatgtgct ggggaacttc gtgcagtggc gggaaaagtt tcttatcaca    960
cgtcggagac atgacagtgc acagctagtt ctaaagaaag gttttggtgg aactgcagga   1020
atggcatttg tgggaacagt gtgttcaagg agccacgcag gcgggattaa tgtgtttgga   1080
caaatcactg tggagacatt tgcttccatt gttgctcatg aattgggtca taatcttgga   1140
atgaatcacg atgatgggag agattgttcc tgtggagcaa agagctgcat catgaattca   1200
ggagcatcgg gttccagaaa ctttagcagt tgcagtgcag aggactttga gaagttaact   1260
ttaaataaag gaggaaactg ccttcttaat attccaaagc ctgatgaagc ctatagtgct   1320
ccctcctgtg gtaataagtt ggtggacgct ggggaagagt gtgactgtgg tactccaaag   1380
gaatgtgaat tggacccttg ctgcgaagga agtacctgta agcttaaatc atttgctgag   1440
tgtgcatatg gtgactgttg taaagactgt cggttccttc caggaggtac tttatgccga   1500
ggaaaaacca gtgagtgtga tgttccagag tactgcaatg gttcttctca gttctgtcag   1560
ccagatgttt ttattcagaa tggatatcct tgccagaata acaaagccta ttgctacaac   1620
ggcatgtgcc agtattatga tgctcaatgt caagtcatct ttggctcaaa agccaaggct   1680
gcccccaaag attgtttcat tgaagtgaat tctaaaggtg acagatttgg caattgtggt   1740
ttctctggca atgaatacaa gaagtgtgcc actgggaatg ctttgtgtgg aaagcttcag   1800
tgtgagaatg tacaagagat acctgtattt ggaattgtgc ctgctattat tcaaacgcct   1860
agtcgaggca ccaaatgttg ggtgtggat ttccagctag gatcagatgt tccagatcct    1920
gggatggtta acgaaggcac aaaatgtggt gctggaaaga tctgtagaaa cttccagtgt   1980
gtagatgctt ctgttctgaa ttatgactgt gatgttcaga aaaagtgtca tggacatggg   2040
gtatgtaata gcaataagaa ttgtcactgt gaaaatggct gggctccccc aaattgtgag   2100
actaaaggat acggaggaag tgtggacagt ggacctacat acaatgaaat gaatactgca   2160
ttgagggacg gacttctggt cttcttcttc ctaattgttc cccttattgt ctgtgctatt   2220
tttatcttca tcaagaggga tcaactgtgg agaagctact tcagaaagaa gagatcacaa   2280
acatatgagt cagatggcaa aaatcaagca aacccttcta gacagccggg gagtgttcct   2340
cgacatgttt ctccagtgac acctcccaga gaagttccta tatatgcaaa cagatttgca   2400
gtaccaacct atgcagccaa gcaacctcag cagttcccat caaggccacc tccaccacaa   2460
ccgaaagtat catctcaggg aaacttaatt cctgcccgtc ctgctcctgc acctccttta   2520
tatagttccc tcacttgatt tttttaacct tctttttgca aatgtcttca gggaactgag   2580
ctaatacttt tttttttct tgatgttttc ttgaaaagcc tttctgttgc aactatgaat    2640
gaaaacaaaa caccacaaaa cagacttcac taacacagaa aaacagaaac tgagtgtgag   2700
agttgtgaaa tacaaggaaa tgcagtaaag ccagggaatt tacaataaca tttccgtttc   2760
catcattgaa taagtcttat tcagtcatcg gtgaggttaa tgcactaatc atggattttt   2820
tgaacatgtt attgcagtga ttctcaaatt aactgtattg gtgtaagatt tttgtcatta   2880
agtgtttaag tgttattctg aattttctac cttagttatc attaatgtag ttcctcattg   2940
aacatgtgat aatctaatac ctgtgaaaac tgactaatca gctgccaata atatctaata   3000
tttttcatca tgcacgaatt aataatcatc atactctaga atcttgtctg tcactcacta   3060
```

```
catgaataag caaatattgt cttcaaaaga atgcacaaga accacaatta agatgtcata   3120

ttattttgaa agtacaaaat atactaaaag agtgtgtgtg tattcacgca gttactcgct   3180

tccattttta tgacctttca actataggta ataactctta gagaaattaa tttaatatta   3240

gaatttctat tatgaatcat gtgaaagcat gacattcgtt cacaatagca ctattttaaa   3300

taaattataa gctttaaggt acgaagtatt taatagatct aatcaaatat gttgattcat   3360

ggctataata aagcaggagc aattataaaa tcttcaatca attgaacttt tacaaaacca   3420

cttgagaatt tcatgagcac tttaaaatct gaactttcaa agcttgctat taaatcattt   3480

agaatgttta catttactaa ggtgtgctgg gtcatgtaaa atattagaca ctaatatttt   3540

catagaaatt aggctggaga aagaaggaag aaatggtttt cttaaatacc tacaaaaaag   3600

ttactgtggt atctatgagt tatcatctta gctgtgttaa aaatgaattt ttactatggc   3660

agatatggta tggatcgtaa aattttaagc actaaaaatt ttttcataac ctttcataat   3720

aaagtttaat aataggttta ttaactgaat ttcattagtt ttttaaaagt gtttttggtt   3780

tgtgtatata tacatataca aatacaacat ttacaataaa taaaatactt gaaattctct   3840

tttgtgtctc ctagtagctt cctactcaac tatttataat ctcattaatt aaaaagttat   3900

aattttagat aaaaattcta gtcaaatttt tacagatatt atctcactaa ttttcagact   3960

tttgccaaag tgtgcacaat ggctttttgt taataaagaa cagattagtt ttgaagaagg   4020

caaaaatttc agttttctga agacagcatg ttattttaac aatcaagtat acatattaaa   4080

aattgtgagc aatctcaaaa aaaaaaaaaa a                                  4111
```

<210> SEQ ID NO 44
<211> LENGTH: 6701
<212> TYPE: DNA
<213> ORGANISM: Homo sapiens

<400> SEQUENCE: 44

```
aaagccctca gcctttgtgt ccttctctgc gccggagtgg ctgcagctca cccctcagct     60

ccccttgggg cccagctggg agccgagata gaagctcctg tcgccgctgg gcttctcgcc    120

tcccgcagag ggccacacag agaccgggat ggccacctcc atgggcctgc tgctgctgct    180

gctgctgctc ctgacccagc ccggggcggg gacgggagct gacacggagg cggtggtctg    240

cgtggggacc gcctgctaca cggcccactc gggcaagctg agcgctgccg aggcccagaa    300

ccactgcaac cagaacgggg gcaacctggc cactgtgaag agcaaggagg aggcccagca    360

cgtccagcga gtactggccc agctcctgag gcgggaggca gccctgacgg cgaggatgag    420

caagttctgg attgggctcc agcgagagaa gggcaagtgc ctggacccta gtctgccgct    480

gaagggcttc agctgggtgg gcggggggga ggacacgcct tactctaact ggcacaagga    540

gctccggaac tcgtgcatct ccaagcgctg tgtgtctctg ctgctggacc tgtcccagcc    600

gctccttccc agccgcctcc ccaagtggtc tgagggcccc tgtgggagcc caggctcccc    660

cggaagtaac attgagggct tcgtgtgcaa gttcagcttc aaaggcatgt gccggcctct    720

ggccctgggg ggcccaggtc aggtgaccta caccaccccc ttccagacca ccagttcctc    780

cttggaggct gtgccctttg cctctgcggc caatgtagcc tgtggggaag gtgacaagga    840

cgagactcag agtcattatt tcctgtgcaa ggagaaggcc cccgatgtgt tcgactgggg    900

cagctcgggc cccctctgtg tcagccccaa gtatggctgc aacttcaaca atgggggctg    960

ccaccaggac tgctttgaag ggggggatgg ctccttcctc tgcggctgcc gaccaggatt   1020
```

```
ccggctgctg gatgacctgg tgacctgtgc ctctcgaaac ccttgcagct ccagcccatg   1080
tcgtgggggg gccacgtgcg tcctgggacc ccatgggaaa aactacacgt gccgctgccc   1140
ccaagggtac cagctggact cgagtcagct ggactgtgtg gacgtggatg aatgccagga   1200
ctccccctgt gcccaggagt gtgtcaacac ccctgggggc ttccgctgcg aatgctgggt   1260
tggctatgag ccgggcggtc ctggagaggg ggcctgtcag gatgtggatg agtgtgctct   1320
gggtcgctcg ccttgcgccc agggctgcac caacacagat ggctcatttc actgctcctg   1380
tgaggagggc tacgtcctgg ccggggagga cgggactcag tgccaggacg tggatgagtg   1440
tgtgggcccg gggggccccc tctgcgacag cttgtgcttc aacacacaag ggtccttcca   1500
ctgtggctgc ctgccaggct gggtgctggc cccaaatggg gtctcttgca ccatggggcc   1560
tgtgtctctg ggaccaccat ctgggccccc cgatgaggag gacaaaggag agaaagaagg   1620
gagcaccgtg ccccgtgctg caacagccag tcccacaagg ggccccgagg gcacccccaa   1680
ggctacaccc accacaagta gaccttcgct gtcatctgac gcccccatca catctgcccc   1740
actcaagatg ctggccccca gtgggtcccc aggcgtctgg agggagccca gcatccatca   1800
cgccacagct gcctctggcc cccaggagcc tgcaggtggg gactcctccg tggccacaca   1860
aaacaacgat ggcactgacg ggcaaaagct gcttttattc tacatcctag gcaccgtggt   1920
ggccatccta ctcctgctgg ccctggctct ggggctactg gtctatcgca agcggagagc   1980
gaagagggag gagaagaagg agaagaagcc ccagaatgcg gcagacagtt actcctgggt   2040
tccagagcga gctgagagca gggccatgga gaaccagtac agtccgacac ctgggacaga   2100
ctgctgaaag tgaggtggcc ctagagacac tagagtcacc agccaccatc ctcagagctt   2160
tgaactcccc attccaaagg ggcacccaca tttttttgaa agactggact ggaatcttag   2220
caaacaattg taagtctcct ccttaaaggc cccttggaac atgcaggtat tttctacggg   2280
tgtttgatgt tcctgaagtg gaagctgtgt gttggcgtgc cacggtgggg atttcgtgac   2340
tctataatga ttgttactcc ccctcccttt tcaaattcca atgtgaccaa ttccggatca   2400
gggtgtgagg aggccggggc taaggggctc ccctgaatat cttctctgct cacttccacc   2460
atctaagagg aaaaggtgag ttgctcatgc tgattaggat tgaaatgatt tgtttctctt   2520
cctaggatga aaactaaatc aattaattat tcaattaggt aagaagatct ggttttttgg   2580
tcaaagggaa catgttcgga ctggaaacat ttctttacat ttgcattcct ccatttcgcc   2640
agcacaagtc ttgctaaatg tgatactgtt gacatcctcc agaatggcca gaagtgcaat   2700
taacctctta ggtggcaagg aggcaggaag tgcctcttta gttcttacat ttctaatagc   2760
cttgggttta tttgcaaagg aagcttgaaa aatatgagaa aagttgcttg aagtgcatta   2820
caggtgtttg tgaagtcaca taatctacgg ggctagggcg agagaggcca gggatttgtt   2880
cacagatact tgaattaatt catccaaatg tactgaggtt accacacact tgactacgga   2940
tgtgatcaac actaacaagg aaacaaattc aaggacaacc tgtctttgag ccagggcagg   3000
cctcagacac cctgcctgtg gccccgcctc cacttcatcc tgcccggaat gccagtgctc   3060
cgagctcaga cagaggaagc cctgcagaaa gttccatcag gctgtttcct aaaggatgtg   3120
tgaacgggag atgatgcact gtgttttgaa agttgtcatt ttaaagcatt ttagcacagt   3180
tcatagtcca cagttgatgc agcatcctga gattttaaat cctgaagtgt gggtggcgca   3240
cacaccaagt agggagctag tcaggcagtt tgcttaagga acttttgttc tctgtctctt   3300
ttccttaaaa ttgggggtaa ggagggaagg aagagggaaa gagatgacta actaaaatca   3360
tttttacagc aaaaactgct caaagccatt taaattatat cctcatttta aaagttacat   3420
```

```
ttgcaaatat ttctccctat gataatgtag tcgatagtgt gcactctttc tctctctctc   3480
tctctctcac acacacacac acacacacac acacacacac agagacacgg caccattctg   3540
cctggggcac tggaacacat tcctgggggt caccgatggt cagagtcact agaagttacc   3600
tgagtatctc tgggaggcct catgtctcct gtgggctttt taccaccact gtgcaggaga   3660
acagacagag gaaatgtgtc tccctccaag gccccaaagc ctcagagaaa gggtgtttct   3720
ggttttgcct tagcaatgca tcggtctctg aggtgacact ctggagtggt tgaagggcca   3780
caaggtgcag ggttaatact cttgccagtt ttgaaatata gatgctatgg ttcagattgt   3840
ttttaataga aaactaaagg ggcaggggaa gtgaaaggaa agatggaggt tttgtgcggc   3900
tcgatggggc atttggaact tctttttaaa gtcatctcat ggtctccagt tttcagttgg   3960
aactctggtg tttaacactt aagggagaca aaggctgtgt ccatttggca aaacttcctt   4020
ggccacgaga ctctaggtga tgtgtgaagc tgggcagtct gtggtgtgga gagcagccat   4080
ctgtctggcc attcagagga ttctaaagac atggctggat gcgctgctga ccaacatcag   4140
cacttaaata aatgcaaatg caacatttct ccctctgggc cttgaaaatc cttgccctta   4200
tcatttgggg tgaaggagac atttctgtcc ttggcttccc acagccccaa cgcagtctgt   4260
gtatgattcc tgggatccaa cgagccctcc tattttcaca gtgttctgat tgctctcaca   4320
gcccaggccc atcgtctgtt ctctgaatgc agccctgttc tcaacaacag ggaggtcatg   4380
gaacccctct gtggaaccca caaggggaga aatgggtgat aaagaatcca gttcctcaaa   4440
accttccctg gcaggctggg tccctctcct gctgggtggt gctttctctt gcacaccact   4500
cccaccacgg ggggagagcc agcaacccaa ccagacagct caggttgtgc atctgatgga   4560
aaccactggg ctcaaacacg tgctttattc tcctgtttat ttttgctgtt actttgaagc   4620
atggaaattc ttgtttgggg gatcttgggg ctacagtagt gggtaaacaa atgcccaccg   4680
gccaagaggc cattaacaaa tcgtccttgt cctgaggggc cccagcttgc tcgggcgtgg   4740
cacagtgggg aatccaaggg tcacagtatg gggagaggtg caccctgcca cctgctaact   4800
tctcgctaga cacagtgttt ctgcccaggt gacctgttca gcagcagaac aagccagggc   4860
catggggacg ggggaagttt tcacttggag atggacacca agacaatgaa gatttgttgt   4920
ccaaataggt caataattct gggagactct tggaaaaaac tgaatatatt caggaccaac   4980
tctctccctc ccctcatccc acatctcaaa gcagacaatg taaagagaga acatctcaca   5040
cacccagctc gccatgccta ctcattcctg aatttcaggt gccatcactg ctctttcttt   5100
cttctttgtc atttgagaaa ggatgcagga ggacaattcc cacagataat ctgaggaatg   5160
cagaaaaacc agggcaggac agttatcgac aatgcattag aacttggtga gcatcctctg   5220
tagagggact ccacccctgc tcaacagctt ggcttccagg caagaccaac cacatctggt   5280
ctctgccttc ggtggcccac acacctaagc gtcatcgtca ttgccatagc atcatgatgc   5340
aacacatcta cgtgtagcac tacgacgtta tgtttgggta atgtggggat gaactgcatg   5400
aggctctgat taaggatgtg gggaagtggg ctgcggtcac tgtcggcctt gcaaggccac   5460
ctggaggcct gtctgttagc cagtggtgga ggagcaaggc ttcaggaagg gccagccaca   5520
tgccatcttc cctgcgatca ggcaaaaaag tggaattaaa aagtcaaacc tttatatgca   5580
tgtgttatgt ccattttgca ggatgaactg agtttaaaag aattttttt tctcttcaag   5640
ttgctttgtc ttttccatcc tcatcacaag cccttgtttg agtgtcttat ccctgagcaa   5700
tctttcgatg gatggagatg atcattaggt acttttgttt caacctttat tcctgtaaat   5760
```

```
atttctgtga aaactaggag aacagagatg agatttgaca aaaaaaaatt gaattaaaaa   5820

taacacagtc tttttaaaac taacatagga aagcctttcc tattatttct cttcttagct   5880

tctccattgt ctaaatcagg aaaacaggaa aacacagctt tctagcagct gcaaaatggt   5940

ttaatgcccc ctacatattt ccatcacctt gaacaatagc tttagcttgg gaatctgaga   6000

tatgatccca gaaaacatct gtctctactt cggctgcaaa acccatggtt taaatctata   6060

tggtttgtgc attttctcaa ctaaaaatag agatgataat ccgaattctc catatattca   6120

ctaatcaaag acactatttt catactagat tcctgagaca aatactcact gaagggcttg   6180

tttaaaaata aattgtgttt tggtctgttc ttgtagataa tgcccttcta ttttaggtag   6240

aagctctgga atccctttat tgtgctgttg ctcttatctg caaggtggca agcagttctt   6300

ttcagcagat tttgcccact attcctctga gctgaagttc tttgcataga tttggcttaa   6360

gcttgaatta gatccctgca aaggcttgct ctgtgatgtc agatgtaatt gtaaatgtca   6420

gtaatcactt catgaatgct aaatgagaat gtaagtattt ttaaatgtgt gtatttcaaa   6480

tttgtttgac taattctgga attacaagat ttctatgcag gatttacctt catcctgtgc   6540

atgtttccca aactgtgagg agggaaggct cagagatcga gcttctcctc tgagttctaa   6600

caaaatggtg ctttgagggt cagcctttag gaaggtgcag ctttgttgtc ctttgagctt   6660

tctgttatgt gcctatccta ataaactctt aaacacattg a                      6701
```

<210> SEQ ID NO 45
<211> LENGTH: 2978
<212> TYPE: DNA
<213> ORGANISM: Homo sapiens

<400> SEQUENCE: 45

```
cgtcctatct gcagtcggct actttcagtg gcagaagagg ccacatctgc ttcctgtagg     60

ccctctgggc agaagcatgc gctggtgtct cctcctgatc tgggcccagg ggctgaggca    120

ggctcccctc gcctcaggaa tgatgacagg cacaatagaa acaacgggga acatttctgc    180

agagaaaggt ggctctatca tcttacaatg tcacctctcc tccaccacgg cacaagtgac    240

ccaggtcaac tgggagcagc aggaccagct tctggccatt tgtaatgctg acttggggtg    300

gcacatctcc ccatccttca aggatcgagt ggccccaggt cccggcctgg gcctcaccct    360

ccagtcgctg accgtgaacg atacagggga gtacttctgc atctatcaca cctaccctga    420

tgggacgtac actgggagaa tcttcctgga ggtcctagaa agctcagtgg ctgagcacgg    480

tgccaggttc cagattccat tgcttggagc catggccgcg acgctggtgg tcatctgcac    540

agcagtcatc gtggtggtcg cgttgactag aaagaagaaa gccctcagaa tccattctgt    600

ggaaggtgac ctcaggagaa aatcagctgg acaggaggaa tggagcccca gtgctccctc    660

acccccagga agctgtgtcc aggcagaagc tgcacctgct gggctctgtg gagagcagcg    720

gggagaggac tgtgccgagc tgcatgacta cttcaatgtc ctgagttaca gaagcctggg    780

taactgcagc ttcttcacag agactggtta gcaaccagag gcatcttctg gaagatacac    840

ttttgtcttt gctattatag atgaatatat aagcagctgt actctccatc agtgctgcgt    900

gtgtgtgtgt gtgtgtatgt gtgtgtgtgt tcagttgagt gaataaatgt catcctcttc    960

tccatcttca tttccttggc cttttcgttc tattccattt tgcattatgg caggcctagg   1020

gtgagtaacg tggatcttga tcataaatgc aaaattaaaa aatatcttga cctggtttta   1080

aatctggcag tttgagcaga tcctatgtct ctgagagaca cattcctcat aatggccagc   1140

attttgggct acaaggtttt gtggttgatg atgaggatgg catgactgca gagccatcct   1200
```

```
catctcattt tttcacgtca ttttcagtaa ctttcactca ttcaaaggca ggttataagt   1260

aagtcctggt agcagcctct atggggagat ttgagagtga ctaaatcttg gtatctgccc   1320

tcaagaactt acagttaaat ggggagacaa tgttgtcatg aaaaggtatt atagtaagga   1380

gagaaggaga catacacagg ccttcaggaa gagacgacag tttggggtga ggtagttggc   1440

ataggcttat ctgtgatgaa gtggcctggg agcaccaagg ggatgttgag gctagtctgg   1500

gaggagcagg agttttgtct agggaacttg taggaaattc ttggagctga aagtcccaca   1560

aagaaggccc tggcaccaag ggagtcagca aacttcagat tttattctct gggcaggcat   1620

ttcaagtttc cttttgctgt gacatactca tccattagac agcctgatac aggcctgtag   1680

cctcttccgg ccgtgtgtgc tggggaagcc ccaggaaacg cacatgccca cacagggagc   1740

caagtcgtag catttgggcc ttgatctacc ttttctgcat caatacactc ttgagccttt   1800

gaaaaaagaa cgtttcccac taaaaagaaa atgtggattt ttaaaatagg gactcttcct   1860

aggggaaaaa ggggggctgg gagtgataga gggtttaaaa aataaacacc ttcaaactaa   1920

cttcttcgaa ccctttttatt cactccctga cgactttgtg ctggggttgg ggtaactgaa   1980

ccgcttattt ctgtttaatt gcattcaggc tggatcttag aagactttta tccttccacc   2040

atctctctca gaggaatgag cggggaggtt ggatttactg gtgactgatt ttctttcatg   2100

ggccaaggaa ctgaaagaga atgtgaagca aggttgtgtc ttgcgcatgg ttaaaaataa   2160

agcattgtcc tgcttcctaa gacttagact ggggttgaca attgttttag caacaagaca   2220

attcaactat ttctcctagg atttttatta ttattatttt ttcacttttc taccaaatgg   2280

gttacatagg aagaatgaac tgaaatctgt ccagagctcc aagtcctttg gaagaaagat   2340

tagatgaacg taaaaatgtt gttgtttgct gtggcagttt acagcatttt tcttgcaaaa   2400

ttagtgcaaa tctgttggaa atagaacaca attcacaaat tggaagtgaa ctaaaatgta   2460

atgacgaaaa gggagtagtg ttttgatttg gaggaggtgt atattcggca gaggttggac   2520

tgagagttgg gtgttattta acataattat ggtaattggg aaacatttat aaacactatt   2580

gggatggtga taaaatacaa aagggcctat agatgttaga aatgggtcag gttactgaaa   2640

tgggattcaa tttgaaaaaa attttttttaa atagaactca ctgaactaga ttctcctctg   2700

agaaccagag aagaccattt catagttgga ttcctggaga catgcgctat ccaccacgta   2760

gccactttcc acatgtggcc atcaaccact taagatgggg ttagtttaaa tcaagatgtg   2820

ctgttataat tggtataagc ataaaatcac actagattct ggagatttaa tatgaataat   2880

aagaatacta tttcagtagt tttggtatat tgtgtgtcaa aaatgataat attttggatg   2940

tattgggtga aataaaatat taacattaaa aaaaaaaa                           2978
```

<210> SEQ ID NO 46
<211> LENGTH: 3686
<212> TYPE: DNA
<213> ORGANISM: Homo sapiens

<400> SEQUENCE: 46

```
cttcagatag attatatctg gagtgaagaa tcctgccacc tatgtatctg gcatagtatt     60

ctgtgtagtg ggatgagcag agaacaaaaa caaaataatc cagtgagaaa agcccgtaaa    120

taaaccttca gaccagagat ctattctcta gcttatttta agctcaactt aaaaagaaga    180

actgttctct gattcttttc gccttcaata cacttaatga tttaactcca ccctccttca    240

aaagaaacag catttcctac ttttatactg tctatatgat tgatttgcac agctcatctg    300
```

```
gccagaagag ctgagacatc cgttcccta caagaaactc tccccgggtg gaacaagatg    360
gattatcaag tgtcaagtcc aatctatgac atcaattatt atacatcgga gccctgccaa    420
aaaatcaatg tgaagcaaat cgcagcccgc ctcctgcctc cgctctactc actggtgttc    480
atctttggtt ttgtgggcaa catgctggtc atcctcatcc tgataaactg caaaaggctg    540
aagagcatga ctgacatcta cctgctcaac ctggccatct ctgacctgtt tttccttctt    600
actgtcccct tctgggctca ctatgctgcc gcccagtggg actttggaaa tacaatgtgt    660
caactcttga cagggctcta ttttataggc ttcttctctg gaatcttctt catcatcctc    720
ctgacaatcg ataggtacct ggctgtcgtc catgctgtgt ttgctttaaa agccaggacg    780
gtcacctttg ggggtggtgac aagtgtgatc acttgggtgg tggctgtgtt tgcgtctctc    840
ccaggaatca tctttaccag atctcaaaaa gaaggtcttc attacacctg cagctctcat    900
tttccataca gtcagtatca attctggaag aatttccaga cattaaagat agtcatcttg    960
gggctggtcc tgccgctgct tgtcatggtc atctgctact cgggaatcct aaaaactctg   1020
cttcggtgtc gaaatgagaa gaagaggcac agggctgtga ggcttatctt caccatcatg   1080
attgtttatt ttctcttctg ggctccctac aacattgtcc ttctcctgaa caccttccag   1140
gaattctttg gcctgaataa ttgcagtagc tctaacaggt tggaccaagc tatgcaggtg   1200
acagagactc ttgggatgac gcactgctgc atcaacccca tcatctatgc ctttgtcggg   1260
gagaagttca gaaactacct cttagtcttc ttccaaaagc acattgccaa acgcttctgc   1320
aaatgctgtt ctattttcca gcaagaggct cccgagcgag caagctcagt ttacacccga   1380
tccactgggg agcaggaaat atctgtgggc ttgtgacacg gactcaagtg ggctggtgac   1440
ccagtcagag ttgtgcacat ggcttagttt tcatacacag cctgggctgg gggtggggtg   1500
ggagaggtct tttttaaaag gaagttactg ttatagaggg tctaagattc atccatttat   1560
ttggcatctg tttaaagtag attagatctt ttaagcccat caattataga aagccaaatc   1620
aaaatatgtt gatgaaaaat agcaaccttt ttatctcccc ttcacatgca tcaagttatt   1680
gacaaactct cccttcactc cgaaagttcc ttatgtatat ttaaaagaaa gcctcagaga   1740
attgctgatt cttgagttta gtgatctgaa cagaaatacc aaaattattt cagaaatgta   1800
caacttttta cctagtacaa ggcaacatat aggttgtaaa tgtgtttaaa acaggtcttt   1860
gtcttgctat ggggagaaaa gacatgaata tgattagtaa agaaatgaca cttttcatgt   1920
gtgatttccc ctccaaggta tggttaataa gtttcactga cttagaacca ggcgagagac   1980
ttgtggcctg ggagagctgg ggaagcttct taaatgagaa ggaatttgag ttggatcatc   2040
tattgctggc aaagacagaa gcctcactgc aagcactgca tgggcaagct tggctgtaga   2100
aggagacaga gctggttggg aagacatggg gaggaaggac aaggctagat catgaagaac   2160
cttgacggca ttgctccgtc taagtcatga gctgagcagg gagatcctgg ttggtgttgc   2220
agaaggttta ctctgtggcc aaaggagggt caggaaggat gagcatttag ggcaaggaga   2280
ccaccaacag ccctcaggtc agggtgagga tggcctctgc taagctcaag gcgtgaggat   2340
gggaaggagg gaggtattcg taaggatggg aaggagggag gtattcgtgc agcatatgag   2400
gatgcagagt cagcagaact ggggtggatt tgggttggaa gtgagggtca gagaggagtc   2460
agagagaatc cctagtcttc aagcagattg gagaaaccct tgaaaagaca tcaagcacag   2520
aaggaggagg aggaggttta ggtcaagaag aagatggatt ggtgtaaaag gatgggtctg   2580
gtttgcagag cttgaacaca gtctcaccca gactccaggc tgtctttcac tgaatgcttc   2640
tgacttcata gatttccttc ccatcccagc tgaaatactg aggggtctcc aggaggagac   2700
```

```
tagatttatg aatacacgag gtatgaggtc taggaacata cttcagctca cacatgagat   2760
ctaggtgagg attgattacc tagtagtcat ttcatgggtt gttgggagga ttctatgagg   2820
caaccacagg cagcatttag cacatactac acattcaata agcatcaaac tcttagttac   2880
tcattcaggg atagcactga gcaaagcatt gagcaaaggg gtcccataga ggtgagggaa   2940
gcctgaaaaa ctaagatgct gcctgcccag tgcacacaag tgtaggtatc attttctgca   3000
tttaaccgtc aataggcaaa ggggggaagg gacatattca tttggaaata agctgccttg   3060
agccttaaaa cccacaaaag tacaatttac cagcctccgt atttcagact gaatgggggt   3120
ggggggggcg ccttaggtac ttattccaga tgccttctcc agacaaacca gaagcaacag   3180
aaaaaatcgt ctctccctcc ctttgaaatg aatatacccc ttagtgtttg ggtatattca   3240
tttcaaaggg agagagagag gtttttttct gttctgtctc atatgattgt gcacatactt   3300
gagactgttt tgaatttggg ggatggctaa aaccatcata gtacaggtaa ggtgagggaa   3360
tagtaagtgg tgagaactac tcagggaatg aaggtgtcag aataataaga ggtgctactg   3420
actttctcag cctctgaata tgaacggtga gcattgtggc tgtcagcagg aagcaacgaa   3480
gggaaatgtc tttccttttg ctcttaagtt gtggagagtg caacagtagc ataggaccct   3540
accctctggg ccaagtcaaa gacattctga catcttagta tttgcatatt cttatgtatg   3600
tgaaagttac aaattgcttg aaagaaaata tgcatctaat aaaaaacacc ttctaaaata   3660
aaaaaaaaaa aaaaaaaaaa aaaaaa                                         3686

<210> SEQ ID NO 47
<211> LENGTH: 3316
<212> TYPE: DNA
<213> ORGANISM: Homo sapiens

<400> SEQUENCE: 47

gcggaaaaga gcctcgggcc aggagcgcag gaaccagacc gtgtcccgcg gggctgtcac     60
ctccgcctct gctccccgac ccggccatgc gcggcctcgg gctctggctg ctgggcgcga    120
tgatgctgcc tgcgattgcc cccagccggc cctgggccct catggagcag tatgaggtcg    180
tgttgccgtg gcgtctgcca ggcccccgag tccgccgagc tctgccctcc cacttgggcc    240
tgcacccaga gagggtgagc tacgtccttg gggccacagg gcacaacttc accctccacc    300
tgcggaagaa cagggacctg ctgggctccg gctacacaga gacctatacg gctgccaatg    360
gctccgaggt gacggagcag cctcgcgggc aggaccactg cttctaccag ggccacgtag    420
aggggtaccc ggactcagcc gccagcctca gcacctgtgc cggcctcagg ggtttcttcc    480
aggtggggtc agacctgcac ctgatcgagc ccctggatga aggtggcgag ggcggacggc    540
acgccgtgta ccaggctgag cacctgctgc agacggccgg gacctgcggg gtcagcgacg    600
acagcctggg cagcctcctg ggaccccgga cggcagccgt cttcaggcct cggcccgggg    660
actctctgcc atcccgagag acccgctacg tggagctgta tgtggtcgtg gacaatgcag    720
agttccagat gctggggagc gaagcagccg tgcgtcatcg ggtgctggag gtggtgaatc    780
acgtggacaa gctatatcag aaactcaact tccgtgtggt cctggtgggc ctggagattt    840
ggaatagtca ggacaggttc cacgtcagcc ccgaccccag tgtcacactg gagaacctcc    900
tgacctggca ggcacggcaa cggacacggc ggcacctgca tgacaacgta cagctcatca    960
cgggtgtcga cttcaccggg actaccgtgg ggtttgccag ggtgtccgcc atgtgctccc   1020
acagctcagg ggctgtgaac caggaccaca gcaagaaccc cgtgggcgtg gcctgtacca   1080
```

```
tggcccatga gatgggccac aacctgggca tggaccatga tgagaacgtc cagggctgcc   1140

gctgccagga acgcttcgag gccggccgct gcatcatggc gggcagcatt ggctccagtt   1200

tccccaggat gttcagtgac tgcagccagg cctacctgga gagcttttg gagcggccgc    1260

agtcggtgtg cctcgccaac gcccctgacc tcagccacct ggtgggcggc cccgtgtgtg   1320

ggaacctgtt tgtggagcgt ggggagcagt gcgactgcgg cccccccgag gactgccgga   1380

accgctgctg caactctacc acctgccagc tggctgaggg ggcccagtgt gcgcacggta   1440

cctgctgcca ggagtgcaag gtgaagccgg ctggtgagct gtgccgtccc aagaaggaca   1500

tgtgtgacct cgaggagttc tgtgacggcc ggcaccctga gtgcccggaa gacgccttcc   1560

aggagaacgg cacgccctgc tccgggggct actgctacaa cggggcctgt cccacactgg   1620

cccagcagtg ccaggccttc tgggggccag gtgggcaggc tgccgaggag tcctgcttct   1680

cctatgacat cctaccaggc tgcaaggcca gccggtacag ggctgacatg tgtggcgttc   1740

tgcagtgcaa gggtgggcag cagcccctgg ggcgtgccat ctgcatcgtg gatgtgtgcc   1800

acgcgctcac cacagaggat ggcactgcgt atgaaccagt gcccgagggc acccggtgtg   1860

gaccagagaa ggtttgctgg aaaggacgtt gccaggactt acacgtttac agatccagca   1920

actgctctgc ccagtgccac aaccatgggg tgtgcaacca caagcaggag tgccactgcc   1980

acgcgggctg ggccccgccc cactgcgcga agctgctgac tgaggtgcac gcagcgtccg   2040

ggagcctccc cgtcttcgtg gtggtggttc tggtgctcct ggcagttgtg ctggtcaccc   2100

tggcaggcat catcgtctac cgcaaagccc ggagccgcat cctgagcagg aacgtggctc   2160

ccaagaccac aatggggcgc tccaaccccc tgttccacca ggctgccagc cgcgtgccgg   2220

ccaagggcgg ggctccagcc ccatccaggg gcccccaaga gctggtcccc accacccacc   2280

cgggccagcc cgcccgacac ccggcctcct cggtggctct gaagaggccg ccccctgctc   2340

ctccggtcac tgtgtccagc ccacccttcc cagttcctgt ctacacccgg caggcaccaa   2400

agcaggtcat caagccaacg ttcgcacccc cagtgccccc agtcaaaccc ggggctggtg   2460

cggccaaccc tggtccagct gagggtgctg ttggcccaaa ggttgccctg aagcccccca   2520

tccagaggaa gcaaggagcc ggagctccca cagcacccta gggggcacc tgcgcctgtg    2580

tggaaatttg gagaagttgc ggcagagaag ccatgcgttc cagcattcca cggtccagct   2640

agtgccgctc agccctagac cctgactttg caggctcagc tgctgttcta acctcaggaa   2700

tgcatctacc tgagaggctc ctgctgtcca cgccctcagc caattccttc tccccgcctt   2760

ggccacgtgt agccccagct gtctgcaggc accaggctgg gatgagctgt gtgcttgcgg   2820

gtgcgtgtgt gtgtacgtgt ctccaggtgg ccgctggtct cccgctgtgt tcaggaggcc   2880

acatatacag cccctcccag ccacacctgc ccctgctctg ggcctgctg agccggctgc    2940

cctgggcacc cggttccagg cagcacagac gtggggcatc cccagaaaga ctccatccca   3000

ggaccaggtt cccctgcgtg ctcttcgaga gggtgtcagt gagcagactg caccccaagc   3060

tcccgactcc aggtcccctg atcttggggc ctgtttccca tgggattcaa gagggacagc   3120

cccagctttg tgtgtgttta agcttaggaa tcgcctttat ggaaagggct atgtgggaga   3180

gtcagctatc ttgtctggtt ttcttgagac ctcagatgtg tgttcagcag ggctgaaagc   3240

ttttattctt taataatgag aaatgtatat tttactaata aattattgac cgagttctgt   3300

aaaaaaaaaa aaaaaa                                                   3316
```

<210> SEQ ID NO 48
<211> LENGTH: 1790

```
<212> TYPE: DNA
<213> ORGANISM: Homo sapiens

<400> SEQUENCE: 48

taattacaaa aactaatgac taagagagag gtggctagag ctgaggcccc tgagtcaggc      60
tgtgggtggg atcatctcca gtacaggaag tgagactttc atttcctcct ttccaagaga     120
gggctgaggg agcagggttg agcaactggt gcagacagcc tagctggact ttgggtgagg     180
cggttcagcc atgaggctgg ctgtgctttt ctcgggggcc ctgctggggc tactggcaga     240
gagcactgga acaaccagcc acaggactac caagagccac aaaaccacca ctcacaggac     300
aaccaccaca ggcaccacca gccacggacc cacgactgcc actcacaacc ccaccaccac     360
cagccatgga aacgtcacag ttcatccaac aagcaatagc actgccacca gccagggacc     420
ctcaactgcc actcacagtc ctgccaccac tagtcatgga aatgccacgg ttcatccaac     480
aagcaacagc actgccacca gcccaggatt caccagttct gcccacccag aaccacctcc     540
accctctccg agtcctagcc caacctccaa ggagaccatt ggagactaca cgtggaccaa     600
tggttcccag ccctgtgtcc acctccaagc ccagattcag attcgagtca tgtacacaac     660
ccagggtgga ggagaggcct ggggcatctc tgtactgaac cccaacaaaa ccaaggtcca     720
gggaagctgt gagggtgccc atccccacct gcttctctca ttcccctatg gacacctcag     780
ctttggattc atgcaggacc tccagcagaa ggttgtctac ctgagctaca tggcggtgga     840
gtacaatgtg tccttccccc acgcagcaca gtggacattc tcggctcaga atgcatccct     900
tcgagatctc caagcacccc tggggcagag cttcagttgc agcaactcga gcatcattct     960
ttcaccagct gtccacctcg acctgctctc cctgaggctc caggctgctc agctgcccca    1020
cacaggggtc tttgggcaaa gtttctcctg ccccagtgac cggtccatct tgctgcctct    1080
catcatcggc ctgatccttc ttggcctcct cgccctggtg cttattgctt tctgcatcat    1140
ccggagacgc ccatccgcct accaggccct ctgagcattt gcttcaaacc ccagggcact    1200
gagggggttg gggtgtggtg ggggggtacc cttatttcct cgacacgcaa ctggctcaaa    1260
gacaatgtta ttttccttcc ctttcttgaa gaacaaaaag aaagccgggc atgacggctc    1320
atgcctgtaa tcccagcact ttgggaggct gaggcaggtg gatcactgga ggtcaggagt    1380
ttgagaccag cctggccaac atggtgaaac cctgtctcta ctaaaaatac aattagccag    1440
gtgtggcggc gtaatcccag ctggcctgta atcccagcta cttgggaggc tgaggcagaa    1500
ctgcttgaac ccaggaggtg gaggttgcag tgagccgtca tcgcgccact aagccaagat    1560
cgcgccactg cactccagcc tgggcgacag agccagactg tctcaaataa ataaatatga    1620
gataatgcag tcgggagaag ggagggagag aattttatta aatgtgacga actgcccccc    1680
cccccccccc agcaggagag cagcaaaatt tatgcaaatc tttgacgggg ttttccttgt    1740
cctgccagga ttaaaagcca tgagtttctt gtcaaaaaaa aaaaaaaaaa               1790


<210> SEQ ID NO 49
<211> LENGTH: 1447
<212> TYPE: DNA
<213> ORGANISM: Homo sapiens

<400> SEQUENCE: 49

gcatcccgac attggtttac atttctcttg actgagaatg gtgccacgtg tggtctgtaa      60
gtagcatctc tgagggtccc caaggaacat ggctgggagc cgtgaggtgg tggccatgga     120
ctgcgagatg gtggggctgg ggccccaccg ggagagtggc ctggctcgtt gcagcctcgt     180
```

```
gaacgtccac ggtgctgtgc tgtacgacaa gttcatccgg cctgagggag agatcaccga    240
ttacagaacc cgggtcagcg gggtcacccc tcagcacatg gtgggggcca caccatttgc    300
cgtggccagg ctagagatcc tgcagctcct gaaaggcaag ctggtggtgg gtcatgacct    360
gaagcacgac ttccaggcac tgaaagagga catgagcggc tacacaatct acgacacgtc    420
cactgacagg ctgttgtggc gtgaggccaa gctggaccac tgcaggcgtg tctccctgcg    480
ggtgctgagt gagcgcctcc tacacaagag catccagaac agcctgcttg gacacagctc    540
ggtggaagat gcgagggcaa cgatggagct ctatcaaatc tcccagagaa tccgagcccg    600
ccgagggctg ccccgcctgg ctgtgtcaga ctgaagcccc atccagcccg ttccgcaggg    660
actagaggct ttcggctttt tgggacagca actaccttgc ttttggaaaa tacattttta    720
atagtaaagt ggctctatat tttctctacg ccatcactgg gtcctcttct tattcttctc    780
tccaagctgg gttaacagta gacaggaccc atttctgtgt gatgttagga gggaatgaag    840
tcttatgctg gggaggtggg caagtatcaa tttccttaat atcttgaatc ctgtgggtcc    900
aaaatgtggc ttggaaatct aagtagcatg tggcttaatt actaatccca ccctttgctg    960
ttgcatccca gccctattcc tggtgcattt atgcccagag aggtggcatt atttcctggg   1020
gtggcattca gctcctcttg agttggtgcc acagcatttg tgggctttga agcaaaggta   1080
caggaaatgt caagggtgcc accccggcaa ccttgagcaa gtcacccctc ctatttgtaa   1140
aatgaggaag gaaaggtaac aaactgtgga gtcagagaga agtaggttgg aatcctcttt   1200
gtcatttagt agctgtttga cctaaggtgg tttactgaac ttctcagttt ctccatctgt   1260
aaaatgagaa ttctagcaac tcgtagggta tttgtgagat gttgcaggca aagcccccag   1320
caccatgcct gtcctagctt aagcacccac caggtgtcga taagtaattg ttcttccctg   1380
gactgcctgc acatctaggg caccccagga agagtcaccg cactctgttt cggggctcgg   1440
ctctctg                                                             1447
```

<210> SEQ ID NO 50
<211> LENGTH: 1629
<212> TYPE: DNA
<213> ORGANISM: Homo sapiens

<400> SEQUENCE: 50

```
acacatcagg ggcttgctct tgcaaaacca aaccacaaga cagacttgca aaagaaggca     60
tgcacagctc agcactgctc tgttgcctgg tcctcctgac tggggtgagg gccagcccag    120
gccagggcac ccagtctgag aacagctgca cccacttccc aggcaacctg cctaacatgc    180
ttcgagatct ccgagatgcc ttcagcagag tgaagacttt ctttcaaatg aaggatcagc    240
tggacaactt gttgttaaag gagtccttgc tggaggactt taagggttac ctgggttgcc    300
aagccttgtc tgagatgatc cagttttacc tggaggaggt gatgccccaa gctgagaacc    360
aagacccaga catcaaggcg catgtgaact ccctggggga gaacctgaag accctcaggc    420
tgaggctacg gcgctgtcat cgatttcttc cctgtgaaaa caagagcaag gccgtggagc    480
aggtgaagaa tgcctttaat aagctccaag agaaaggcat ctacaaagcc atgagtgagt    540
ttgacatctt catcaactac atagaagcct acatgacaat gaagatacga aactgagaca    600
tcagggtggc gactctatag actctaggac ataaattaga ggtctccaaa atcggatctg    660
gggctctggg atagctgacc cagccccttg agaaacctta ttgtacctct cttatagaat    720
atttattacc tctgatacct caacccccat ttctatttat ttactgagct tctctgtgaa    780
cgatttagaa agaagcccaa tattataatt tttttcaata tttattattt tcacctgttt    840
```

```
ttaagctgtt tccatagggt gacacactat ggtatttgag tgttttaaga taaattataa    900
gttacataag ggaggaaaaa aaatgttctt tggggagcca acagaagctt ccattccaag    960
cctgaccacg ctttctagct gttgagctgt tttccctgac ctccctctaa tttatcttgt   1020
ctctgggctt ggggcttcct aactgctaca aatactctta ggaagagaaa ccagggagcc   1080
cctttgatga ttaattcacc ttccagtgtc tcggagggat tcccctaacc tcattcccca   1140
accacttcat tcttgaaagc tgtggccagc ttgttattta taacaaccta aatttggttc   1200
taggccgggc gcggtggctc acgcctgtaa tcccagcact ttgggaggct gaggcgggtg   1260
gatcacttga ggtcaggagt tcctaaccag cctggtcaac atggtgaaac cccgtctcta   1320
ctaaaaatac aaaaattagc cgggcatggt ggcgcgcacc tgtaatccca gctacttggg   1380
aggctgaggc aagagaattg cttgaaccca ggagatggaa gttgcagtga gctgatatca   1440
tgcccctgta ctccagcctg ggtgacagag caagactctg tctcaaaaaa taaaaataaa   1500
aataaatttg gttctaatag aactcagttt taactagaat ttattcaatt cctctgggaa   1560
tgttacattg tttgtctgtc ttcatagcag attttaattt tgaataaata aatgtatctt   1620
attcacatc                                                           1629
```

<210> SEQ ID NO 51
<211> LENGTH: 3672
<212> TYPE: DNA
<213> ORGANISM: Homo sapiens

<400> SEQUENCE: 51

```
gtcagtccca gcccaagggt agctggaggc gcgcaggccg gctccgctcc ggccccggac     60
gatgcggcgc gcccaggatg ctgccgtgcc tcgtagtgct gctggcggcg ctcctcagcc    120
tccgtcttgg ctcagacgct catgggacag agctgcccag ccctccgtct gtgtggtttg    180
aagcagaatt tttccaccac atcctccact ggacacccat cccaaatcag tctgaaagta    240
cctgctatga agtggcgctc ctgaggtatg gaatagagtc ctggaactcc atctccaact    300
gtagccagac cctgtcctat gaccttaccg cagtgacctt ggacctgtac cacagcaatg    360
gctaccgggc cagagtgcgg gctgtggacg gcagccggca ctccaactgg accgtcacca    420
acacccgctt ctctgtggat gaagtgactc tgacagttgg cagtgtgaac ctagagatcc    480
acaatggctt catcctcggg aagattcagc tacccaggcc caagatggcc cccgcaaatg    540
acacatatga aagcatcttc agtcacttcc gagagtatga gattgccatt cgcaaggtgc    600
cgggaaactt cacgttcaca cacaagaaag taaaacatga aaacttcagc ctcctaacct    660
ctggagaagt gggagagttc tgtgtccagg tgaaaccatc tgtcgcttcc cgaagtaaca    720
aggggatgtg gtctaaagag gagtgcatct ccctcaccag gcagtatttc accgtgacca    780
acgtcatcat cttctttgcc tttgtcctgc tgctctccgg agccctcgcc tactgcctgg    840
ccctccagct gtatgtgcgg cgccgaaaga agctacccag tgtcctgctc ttcaagaagc    900
ccagcccctt catcttcatc agccagcgtc cctccccaga gacccaagac accatccacc    960
cgcttgatga ggaggccttt ttgaaggtgt ccccagagct gaagaacttg gacctgcacg   1020
gcagcacaga cagtggcttt ggcagcacca agccatccct gcagactgaa gagccccagt   1080
tcctcctccc tgaccctcac ccccaggctg acagaacgct gggaaacagg gagcccctg    1140
tgctggggga cagctgcagt agtggcagca gcaatagcac agacagcggg atctgcctgc   1200
aggagcccag cctgagcccc agcacagggc ccacctggga gcaacaggtg ggagcaaca    1260
```

```
gcaggggcca ggatgacagt ggcattgact tagttcaaaa ctctgagggc cgggctgggg   1320
acacacaggg tggctcggcc ttgggccacc acagtccccc ggagcctgag gtgcctgggg   1380
aagaagaccc agctgctgtg gcattccagg gttacctgag gcagaccaga tgtgctgaag   1440
agaaggcaac caagacaggc tgcctggagg aagaatcgcc cttgacagat ggccttggcc   1500
ccaaattcgg gagatgcctg gttgatgagg caggcttgca tccaccagcc ctggccaagg   1560
gctatttgaa acaggatcct ctagaaatga ctctggcttc ctcaggggcc ccaacgggac   1620
agtggaacca gcccactgag gaatggtcac tcctggcctt gagcagctgc agtgacctgg   1680
gaatatctga ctggagcttt gcccatgacc ttgcccctct aggctgtgtg gcagccccag   1740
gtggtctcct gggcagcttt aactcagacc tggtcaccct gcccctcatc tctagcctgc   1800
agtcaagtga gtgactcggg ctgagaggct gcttttgatt ttagccatgc ctgctcctct   1860
gcctggacca ggaggagggc ccctggggca gaagttaggc acgaggcagt ctgggcactt   1920
ttctgcaagt ccactggggc tggccccagc caggccctgc agggctggtc agggtgtctg   1980
gggcaggagg aggccaactc actgaactag tgcagggtat gtgggtggca ctgacctgtt   2040
ctgttgactg gggccctgca gactctggca gagctgagaa gggcagggac cttctccctc   2100
ctaggaactc tttcctgtat cataaaggat tatttgctca ggggaaccat ggggctttct   2160
ggagttgtgg tgaggccacc aggctgaagt cagctcagac ccagacctcc ctgcttaggc   2220
cactcgagca tcagagcttc cagcaggagg aagggctgta ggaatggaag cttcagggcc   2280
ttgctgctgg ggtcattttt aggggaaaaa ggaggatatg atggtcacat ggggaacctc   2340
ccctcatcgg gcctctgggg caggaagctt gtcactggaa gatcttaagg tatatatttt   2400
ctggacactc aaacacatca taatggattc actgagggga gacaaaggga gccgagaccc   2460
tggatggggc ttccagctca gaacccatcc ctctggtggg tacctctggc acccatctgc   2520
aaatatctcc ctctctccaa caaatggagt agcatccccc tggggcactt gctgaggcca   2580
agccactcac atcctcactt tgctgcccca ccatcttgct gacaacttcc agagaagcca   2640
tggtttttttg tattggtcat aactcagccc tttgggcggc ctctgggctt gggcaccagc   2700
tcatgccagc cccagagggt cagggttgga ggcctgtgct tgtgtttgct gctaatgtcc   2760
agctacagac ccagaggata agccactggg cactgggctg ggtccctgc cttgttggtg   2820
ttcagctgtg tgattttgga ctagccactt gtcagagggc ctcaatctcc catctgtgaa   2880
ataaggactc cacctttagg ggaccctcca tgtttgctgg gtattagcca agctggtcct   2940
gggagaatgc agatactgtc cgtggactac caagctggct tgtttcttat gccagaggct   3000
aacagatcca atgggagtcc atggtgtcat gccaagacag tatcagacac agccccagaa   3060
gggggcatta tgggccctgc ctccccatag gccatttgga ctctgccttc aaacaaaggc   3120
agttcagtcc acaggcatgg aagctgtgag gggacaggcc tgtgcgtgcc atccagagtc   3180
atctcagccc tgcctttctc tggagcattc tgaaaacaga tattctggcc cagggaatcc   3240
agccatgacc cccacccctc tgccaaagta ctcttaggtg ccagtctggt aactgaactc   3300
cctctggagg caggcttgag ggaggattcc tcagggttcc cttgaaagct ttatttattt   3360
attttgttca tttatttatt ggagaggcag cattgcacag tgaaagaatt ctggatatct   3420
caggagcccc gaaattctag ctctgacttt gctgtttcca gtggtatgac cttggagaag   3480
tcacttatcc tcttggagcc tcagtttcct catctgcaga ataatgactg acttgtctaa   3540
ttcgtaggga tgtgaggttc tgctgaggaa atgggtatga atgtgccttg aacacaaagc   3600
tctgtcaata agtgatacat gtttttttatt ccaataaatt gtcaagacca caggaaaaaa   3660
```

aaaaaaaaaa aa 3672

<210> SEQ ID NO 52
<211> LENGTH: 707
<212> TYPE: DNA
<213> ORGANISM: Homo sapiens

<400> SEQUENCE: 52
gctgaagtga aaacgagacc aaggtctagc tctactgttg gtacttatga gatccagtcc 60
tggcaacatg gagaggattg tcatctgtct gatggtcatc ttcttgggga cactggtcca 120
caaatcaagc tcccaaggtc aagatcgcca catgattaga atgcgtcaac ttatagatat 180
tgttgatcag ctgaaaaatt atgtgaatga cttggtccct gaatttctgc cagctccaga 240
agatgtagag acaaactgtg agtggtcagc tttttcctgc tttcagaagg cccaactaaa 300
gtcagcaaat acaggaaaca atgaaaggat aatcaatgta tcaattaaaa agctgaagag 360
gaaaccacct tccacaaatg cagggagaag acagaaacac agactaacat gcccttcatg 420
tgattcttat gagaaaaaac cacccaaaga attcctagaa agattcaaat cacttctcca 480
aaaggtatct accttaagtt tcatttgatt ttctgcttta tctttaccta tccagatttg 540
cttcttagtt actcacggta tactatttcc acagatgatt catcagcatc tgtcctctag 600
aacacacgga agtgaagatt cctgaggatc taacttgcag ttggacacta tgttacatac 660
tctaatatag tagtgaaagt catttctttg tattccaagt ggaggag 707

<210> SEQ ID NO 53
<211> LENGTH: 4050
<212> TYPE: DNA
<213> ORGANISM: Homo sapiens

<400> SEQUENCE: 53
gcagccagag ctcagcaggg ccctggagag atggccacgg tcccagcacc ggggaggact 60
ggagagcgcg cgctgccacc gccccatgtc tcagccaggg cttccttcct cggctccacc 120
ctgtggatgt aatggcggcc cctgctctgt cctggcgtct gcccctcctc atcctcctcc 180
tgcccctggc tacctcttgg gcatctgcag cggtgaatgg cacttcccag ttcacatgct 240
tctacaactc gagagccaac atctcctgtg tctggagcca agatggggct ctgcaggaca 300
cttcctgcca agtccatgcc tggccggaca gacggcggtg gaaccaaacc tgtgagctgc 360
tccccgtgag tcaagcatcc tggcctgca acctgatcct cggagcccca gattctcaga 420
aactgaccac agttgacatc gtcaccctga gggtgctgtg ccgtgagggg gtgcgatgga 480
gggtgatggc catccaggac ttcaagccct ttgagaacct tcgcctgatg gcccccatct 540
ccctccaagt tgtccacgtg gagacccaca gatgcaacat aagctgggaa atctcccaag 600
cctcccacta ctttgaaaga cacctggagt tcgaggcccg gacgctgtcc ccaggccaca 660
cctgggagga ggcccccctg ctgactctca agcagaagca ggaatggatc tgcctggaga 720
cgctcacccc agacacccag tatgagtttc aggtgcgggt caagcctctg caaggcgagt 780
tcacgacctg gagcccctgg agccagcccc tggccttcag gacaaagcct gcagcccttg 840
ggaaggacac cattccgtgg ctcggccacc tcctcgtggg cctcagcggg gcttttggct 900
tcatcatctt agtgtacttg ctgatcaact gcaggaacac cgggccatgg ctgaagaagg 960
tcctgaagtg taacacccca gacccctcga agttcttttc ccagctgagc tcagagcatg 1020
gaggagacgt ccagaagtgg ctctcttcgc ccttcccctc atcgtccttc agccctggcg 1080
gcctggcacc tgagatctcg ccactagaag tgctggagag ggacaaggtg acgcagctgc 1140
tcctgcagca ggacaaggtg cctgagcccg catccttaag cagcaaccac tcgctgacca 1200
gctgcttcac caaccagggt tacttcttct tccacctccc ggatgccttg gagatagagg 1260
cctgccaggt gtactttact tacgacccct actcagagga agaccctgat gagggtgtgg 1320
ccggggcacc cacagggtct tccccccaac ccctgcagcc tctgtcaggg gaggacgacg 1380
cctactgcac cttcccctcc agggatgacc tgctgctctt ctcccccagt ctcctcggtg 1440
gccccagccc cccaagcact gcccctgggg gcagtggggc cggtgaagag aggatgcccc 1500
cttctttgca agaaaagagtc cccagagact gggaccccca gcccctgggg cctcccaccc 1560
caggagtccc agacctggtg gattttcagc caccccctga gctggtgctg cgagaggctg 1620
gggaggaggt ccctgacgct ggccccaggg agggagtcag tttcccctgg tccaggcctc 1680
ctgggcaggg ggagttcagg gcccttaatg ctcgcctgcc cctgaacact gatgcctact 1740
tgtccctcca agaactccag ggtcaggacc caactcactt ggtgtagaca gatggccagg 1800
gtgggaggca ggcagctgcc tgctctgcgc cgagcctcag aaggaccctg ttgagggtcc 1860
tcagtccact gctgaggaca ctcagtgtcc agttgcagct ggacttctcc acccggatgg 1920
cccccaccca gtcctgcaca cttggtccat ccatttccaa acctccactg ctgctcccgg 1980
gtcctgctgc ccgagccagg aactgtgtgt gttgcagggg ggcagtaact ccccaactcc 2040
ctcgttaatc acaggatccc acgaatttag gctcagaagc atcgctcctc tccagccctg 2100
cagctattca ccaatatcag tcctcgcggc tctccagggc tccctgccct gacctcttcc 2160
ctgggttttc tgccccagcc tcctccttcc ctcccctccc cgtccacagg gcagcctgag 2220
cgtgctttcc aaaacccaaa tatggccacg ctccccctcg gttcaaaacc ttgcacaggt 2280
cccactgccc tcagccccac ttctcagcct ggtacttgta cctccggtgt cgtgtgggga 2340
catccccttc tgcaatcctc cctaccgtcc tcctgagcca ctcagagctc cctcacaccc 2400
cctctgttgc acatgctatt ccctggggct gctgtgcgct ccccctcatc taggtgacaa 2460
acttccctga ctcttcaagt gccggttttg cttctcctgg agggaagcac tgcctccctt 2520
aatctgccag aaacttctag cgtcagtgct ggagggagaa gctgtcaggg acccagggcg 2580
cctggagaaa gaggccctgt tactattcct ttgggatctc tgaggcctca gagtgcttgg 2640
ctgctgtatc tttaatgctg gggcccaagt aagggcacag atccccccac aaagtggatg 2700
cctgctgcat cttcccacag tggcttcaca gacccacaag agaagctgat ggggagtaaa 2760
ccctggagtc cgaggcccag gcagcagccc cgcctagtgg tgggccctga tgctgccagg 2820
cctgggacct cccactgccc cctccactgg aggggtctcc tctgcagctc agggactggc 2880
acactggcct ccagaagggc agctccacag ggcagggcct cattattttt cactgcccca 2940
gacacagtgc ccaacacccc gtcgtatacc ctggatgaac gaattaatta cctggcacca 3000
cctcgtctgg gctccctgcg cctgacattc acacagagag gcagagtccc gtgcccatta 3060
ggtctggcat gccccctcct gcaaggggct caacccccta ccccgacccc tccacgtatc 3120
tttcctaggc agatcacgtt gcaatggctc aaacaacatt ccaccccagc aggacagtga 3180
ccccagtccc agctaactct gacctgggag ccctcaggca cctgcactta caggccttgc 3240
tcacagctga ttgggcacct gaccacacgc ccccacaggc tctgaccagc agcctatgag 3300
ggggtttggc accaagctct gtccaatcag gtaggctggg cctgaactag ccaatcagat 3360
caactctgtc ttgggcgttt gaactcaggg agggaggccc ttgggagcag gtgcttgtgg 3420
acaaggctcc acaagcgttg agccttggaa aggtagacaa gcgttgagcc actaagcaga 3480

```
ggaccttggg ttcccaatac aaaaatacct actgctgaga gggctgctga ccatttggtc   3540
aggattcctg ttgcctttat atccaaaata aactcccctt tcttgaggtt gtctgagtct   3600
tgggtctatg ccttgaaaaa agctgaatta ttggacagtc tcacctcctg ccatagggtc   3660
ctgaatgttt cagaccacaa ggggctccac acctttgctg tgtgttctgg ggcaacctac   3720
taatcctctc tgcaagtcgg tctccttatc cccccaaatg gaaattgtat ttgccttctc   3780
cactttggga ggctcccact tcttgggagg gttacatttt ttaagtctta atcatttgtg   3840
acatatgtat ctatacatcc gtatctttta atgatccgtg tgtaccatct ttgtgattat   3900
ttccttaata ttttttcttt aagtcagttc attttcgttg aaatacattt atttaaagaa   3960
aaatctttgt tactctgtaa atgaaaaaac ccattttcgc tataaataaa aggtaactgt   4020
acaaaataag tacaatgcaa caaaaaaaaa                                    4050
```

<210> SEQ ID NO 54
<211> LENGTH: 10515
<212> TYPE: DNA
<213> ORGANISM: Homo sapiens

<400> SEQUENCE: 54

```
ggaggaggga gagcacaggc tttgaccgat agtaacctct gcgctcggtg cagccgaatc     60
tataaaagga actagtcccg gcaaaaaccc cgtaattgcg agcgagagtg agtggggccg    120
ggacccgcag agccgagccg acccttctct cccgggctgc ggcagggcag ggcggggagc    180
tccgcgcacc aacagagccg gttctcaggg cgctttgctc cttgtttttt ccccggttct    240
gttttctccc cttctccgga aggcttgtca aggggtagga gaaagagacg caaacacaaa    300
agtggaaaac agttaatgac cagccacggc gtccctgctg tgagctctgg ccgctgcctt    360
ccagggctcc cgagccacac gctgggggtg ctggctgagg gaacatggct tgttggcctc    420
agctgaggtt gctgctgtgg aagaacctca ctttcagaag aagacaaaca tgtcagctgc    480
tgctggaagt ggcctggcct ctatttatct tcctgatcct gatctctgtt cggctgagct    540
acccacccta tgaacaacat gaatgccatt ttccaaataa agccatgccc tctgcaggaa    600
cacttccttg ggttcagggg attatctgta atgccaacaa cccctgtttc cgttacccga    660
ctcctgggga ggctcccgga gttgttggaa actttaacaa atccattgtg gctcgcctgt    720
tctcagatgc tcggaggctt cttttataca gccagaaaga caccagcatg aaggacatgc    780
gcaaagttct gagaacatta cagcagatca agaaatccag ctcaaacttg aagcttcaag    840
atttcctggt ggacaatgaa accttctctg ggttcctgta tcacaacctc tctctcccaa    900
agtctactgt ggacaagatg ctgagggctg atgtcattct ccacaaggta tttttgcaag    960
gctaccagtt acatttgaca agtctgtgca atggatcaaa atcagaagag atgattcaac   1020
ttggtgacca agaagtttct gagctttgtg gcctaccaag ggagaaactg gctgcagcag   1080
agcgagtact tcgttccaac atggacatcc tgaagccaat cctgagaaca ctaaactcta   1140
catctccctt cccgagcaag gagctggctg aagccacaaa aacattgctg catagtcttg   1200
ggactctggc ccaggagctg ttcagcatga gaagctggag tgacatgcga caggaggtga   1260
tgtttctgac caatgtgaac agctccagct cctccaccca aatctaccag gctgtgtctc   1320
gtattgtctg cgggcatccc gagggagggg ggctgaagat caagtctctc aactggtatg   1380
aggacaacaa ctacaaagcc ctctttggag gcaatggcac tgaggaagat gctgaaacct   1440
tctatgacaa ctctacaact ccttactgca atgatttgat gaagaatttg gagtctagtc   1500
```

```
ctctttcccg cattatctgg aaagctctga agccgctgct cgttgggaag atcctgtata   1560
cacctgacac tccagccaca aggcaggtca tggctgaggt gaacaagacc ttccaggaac   1620
tggctgtgtt ccatgatctg gaaggcatgt gggaggaact cagccccaag atctggacct   1680
tcatggagaa cagccaagaa atggaccttg tccggatgct gttggacagc agggacaatg   1740
accactttg ggaacagcag ttggatggct tagattggac agcccaagac atcgtggcgt   1800
ttttggccaa gcacccagag gatgtccagt ccagtaatgg ttctgtgtac acctggagag   1860
aagctttcaa cgagactaac caggcaatcc ggaccatatc tcgcttcatg gagtgtgtca   1920
acctgaacaa gctagaaccc atagcaacag aagtctggct catcaacaag tccatggagc   1980
tgctggatga gaggaagttc tgggctggta ttgtgttcac tggaattact ccaggcagca   2040
ttgagctgcc ccatcatgtc aagtacaaga tccgaatgga cattgacaat gtggagagga   2100
caaataaaat caaggatggg tactgggacc ctggtcctcg agctgacccc tttgaggaca   2160
tgcggtacgt ctgggggggc ttcgcctact tgcaggatgt ggtggagcag gcaatcatca   2220
gggtgctgac gggcaccgag aagaaaactg gtgtctatat gcaacagatg ccctatccct   2280
gttacgttga tgacatcttt ctgcgggtga tgagccggtc aatgcccctc ttcatgacgc   2340
tggcctggat ttactcagtg gctgtgatca tcaagggcat cgtgtatgag aaggaggcac   2400
ggctgaaaga gaccatgcgg atcatgggcc tggacaacag catcctctgg tttagctggt   2460
tcattagtag cctcattcct cttcttgtga gcgctggcct gctagtggtc atcctgaagt   2520
taggaaacct gctgccctac agtgatccca gcgtggtgtt tgtcttcctg tccgtgtttg   2580
ctgtggtgac aatcctgcag tgcttcctga ttagcacact cttctccaga gccaacctgg   2640
cagcagcctg tgggggcatc atctacttca cgctgtacct gccctacgtc ctgtgtgtgg   2700
catggcagga ctacgtgggc ttcacactca agatcttcgc tagcctgctg tctcctgtgg   2760
cttttgggtt tggctgtgag tactttgccc tttttgagga gcagggcatt ggagtgcagt   2820
gggacaacct gtttgagagt cctgtggagg aagatggctt caatctcacc acttcggtct   2880
ccatgatgct gtttgacacc ttcctctatg gggtgatgac ctggtacatt gaggctgtct   2940
ttccaggcca gtacggaatt cccaggccct ggtattttcc ttgcaccaag tcctactggt   3000
ttggcgagga aagtgatgag aagagccacc ctggttccaa ccagaagaga atatcagaaa   3060
tctgcatgga ggaggaaccc acccacttga agctgggcgt gtccattcag aacctggtaa   3120
aagtctaccg agatgggatg aaggtggctg tcgatggcct ggcactgaat ttttatgagg   3180
gccagatcac ctccttcctg ggccacaatg gagcggggaa gacgaccacc atgtcaatcc   3240
tgaccgggtt gttccccccg acctcgggca ccgcctacat cctgggaaaa gacattcgct   3300
ctgagatgag caccatccgg cagaacctgg gggtctgtcc ccagcataac gtgctgtttg   3360
acatgctgac tgtcgaagaa cacatctggt tctatgcccg cttgaaaggg ctctctgaga   3420
agcacgtgaa ggcggagatg gagcagatgg ccctggatgt tggtttgcca tcaagcaagc   3480
tgaaaagcaa aacaagccag ctgtcaggtg gaatgcagag aaagctatct gtggccttgg   3540
cctttgtcgg gggatctaag gttgtcattc tggatgaacc cacagctggt gtggaccctt   3600
actcccgcag gggaatatgg gagctgctgc tgaaataccg acaaggccgc accattattc   3660
tctctacaca ccacatggat gaagcggacg tcctggggga caggattgcc atcatctccc   3720
atgggaagct gtgctgtgtg ggctcctccc tgtttctgaa gaaccagctg ggaacaggct   3780
actacctgac cttggtcaag aaagatgtgg aatcctccct cagttcctgc agaaacagta   3840
gtagcactgt gtcatacctg aaaaaggagg acagtgtttc tcagagcagt tctgatgctg   3900
```

```
gcctgggcag cgaccatgag agtgacacgc tgaccatcga tgtctctgct atctccaacc   3960
tcatcaggaa gcatgtgtct gaagcccggc tggtggaaga catagggcat gagctgacct   4020
atgtgctgcc atatgaagct gctaaggagg gagcctttgt ggaactcttt catgagattg   4080
atgaccggct ctcagacctg ggcatttcta gttatggcat ctcagagacg accctggaag   4140
aaatattcct caaggtggcc gaagagagtg gggtggatgc tgagacctca gatggtacct   4200
tgccagcaag acgaaacagg cgggccttcg ggacaagca gagctgtctt cgcccgttca    4260
ctgaagatga tgctgctgat ccaaatgatt ctgacataga cccagaatcc agagagacag   4320
acttgctcag tgggatggat ggcaaagggt cctaccaggt gaaaggctgg aaacttacac   4380
agcaacagtt tgtggccctt ttgtggaaga gactgctaat tgccagacgg agtcggaaag   4440
gatttttgc tcagattgtc ttgccagctg tgtttgtctg cattgccctt gtgttcagcc    4500
tgatcgtgcc accctttggc aagtacccca gcctggaact tcagccctgg atgtacaacg   4560
aacagtacac atttgtcagc aatgatgctc ctgaggacac gggaaccctg gaactcttaa   4620
acgccctcac caaagaccct ggcttcggga cccgctgtat ggaaggaaac ccaatcccag   4680
acacgccctg ccaggcaggg gaggaagagt ggaccactgc cccagttccc cagaccatca   4740
tggacctctt ccagaatggg aactggacaa tgcagaaccc ttcacctgca tgccagtgta   4800
gcagcgacaa aatcaagaag atgctgcctg tgtgtccccc aggggcaggg gggctgcctc   4860
ctccacaaag aaaacaaaac actgcagata tccttcagga cctgacagga agaaacattt   4920
cggattatct ggtgaagacg tatgtgcaga tcatagccaa aagcttaaag aacaagatct   4980
gggtgaatga gtttaggtat ggcggctttt ccctgggtgt cagtaatact caagcacttc   5040
ctccgagtca agaagttaat gatgccatca aacaaatgaa gaaacaccta aagctggcca   5100
aggacagttc tgcagatcga tttctcaaca gcttgggaag atttatgaca ggactggaca   5160
ccaaaaataa tgtcaaggtg tggttcaata acaagggctg gcatgcaatc agctctttcc   5220
tgaatgtcat caacaatgcc attctccggg ccaacctgca aaagggagag aaccctagcc   5280
attatggaat tactgctttc aatcatcccc tgaatctcac caagcagcag ctctcagagg   5340
tggctctgat gaccacatca gtggatgtcc ttgtgtccat ctgtgtcatc tttgcaatgt   5400
ccttcgtccc agccagcttt gtcgtattcc tgatccagga gcgggtcagc aaagcaaaac   5460
acctgcagtt catcagtgga gtgaagcctg tcatctactg gctctctaat tttgtctggg   5520
atatgtgcaa ttacgttgtc cctgccacac tggtcattat catcttcatc tgcttccagc   5580
agaagtccta tgtgtcctcc accaatctgc ctgtgctagc ccttctactt ttgctgtatg   5640
ggtggtcaat cacacctctc atgtacccag cctcctttgt gttcaagatc cccagcacag   5700
cctatgtggt gctcaccagc gtgaacctct tcattggcat taatggcagc gtggccacct   5760
ttgtgctgga gctgttcacc gacaataagc tgaataatat caatgatatc ctgaagtccg   5820
tgttcttgat cttcccacat ttttgcctgg gacgagggct catcgacatg gtgaaaaacc   5880
aggcaatggc tgatgccctg gaaaggtttg gggagaatcg ctttgtgtca ccattatctt   5940
gggacttggt gggacgaaac ctcttcgcca tggccgtgga aggggtggtg ttcttcctca   6000
ttactgttct gatccagtac agattcttca tcaggcccag acctgtaaat gcaaagctat   6060
ctcctctgaa tgatgaagat gaagatgtga ggcgggaaag acagagaatt cttgatggtg   6120
gaggccagaa tgacatctta gaaatcaagg agttgacgaa gatatataga aggaagcgga   6180
agcctgctgt tgacaggatt tgcgtgggca ttcctcctgg tgagtgcttt gggctcctgg   6240
```

```
gagttaatgg ggctggaaaa tcatcaactt tcaagatgtt aacaggagat accactgtta   6300
ccagaggaga tgctttcctt aacaaaaata gtatcttatc aaacatccat gaagtacatc   6360
agaacatggg ctactgccct cagtttgatg ccatcacaga gctgttgact gggagagaac   6420
acgtggagtt ctttgccctt ttgagaggag tcccagagaa agaagttggc aaggttggtg   6480
agtgggcgat tcggaaactg ggcctcgtga agtatggaga aaaatatgct ggtaactata   6540
gtggaggcaa caaacgcaag ctctctacag ccatggcttt gatcggcggg cctcctgtgg   6600
tgtttctgga tgaacccacc acaggcatgg atcccaaagc ccggcggttc ttgtggaatt   6660
gtgccctaag tgttgtcaag gaggggagat cagtagtgct tacatctcat agtatggaag   6720
aatgtgaagc tctttgcact aggatggcaa tcatggtcaa tggaaggttc aggtgccttg   6780
gcagtgtcca gcatctaaaa aataggtttg gagatggtta tacaatagtt gtacgaatag   6840
cagggtccaa cccggacctg aagcctgtcc aggatttctt tggacttgca tttcctggaa   6900
gtgttctaaa agagaaacac cggaacatgc tacaatacca gcttccatct tcattatctt   6960
ctctggccag gatattcagc atcctctccc agagcaaaaa gcgactccac atagaagact   7020
actctgtttc tcagacaaca cttgaccaag tatttgtgaa ctttgccaag gaccaaagtg   7080
atgatgacca cttaaaagac ctctcattac acaaaaacca gacagtagtg gacgttgcag   7140
ttctcacatc ttttctacag gatgagaaag tgaaagaaag ctatgtatga agaatcctgt   7200
tcatacgggg tggctgaaag taaagaggaa ctagactttc ctttgcacca tgtgaagtgt   7260
tgtggagaaa agagccagaa gttgatgtgg gaagaagtaa actggatact gtactgatac   7320
tattcaatgc aatgcaattc aatgcaatga aaacaaaatt ccattacagg ggcagtgcct   7380
ttgtagccta tgtcttgtat ggctctcaag tgaaagactt gaatttagtt ttttacctat   7440
acctatgtga aactctatta tggaacccaa tggacatatg ggtttgaact cacacttttt   7500
ttttttttt tgttcctgtg tattctcatt ggggttgcaa caataattca tcaagtaatc   7560
atggccagcg attattgatc aaaatcaaaa ggtaatgcac atcctcattc actaagccat   7620
gccatgccca ggagactggt ttcccggtga cacatccatt gctggcaatg agtgtgccag   7680
agttattagt gccaagtttt tcagaaagtt tgaagcacca tggtgtgtca tgctcacttt   7740
tgtgaaagct gctctgctca gagtctatca acattgaata tcagttgaca gaatggtgcc   7800
atgcgtggct aacatcctgc tttgattccc tctgataagc tgttctggtg gcagtaacat   7860
gcaacaaaaa tgtgggtgtc tccaggcacg ggaaacttgg ttccattgtt atattgtcct   7920
atgcttcgag ccatgggtct acagggtcat ccttatgaga ctcttaaata tacttagatc   7980
ctggtaagag gcaaagaatc aacagccaaa ctgctggggc tgcaagctgc tgaagccagg   8040
gcatgggatt aaagagattg tgcgttcaaa cctagggaag cctgtgccca tttgtcctga   8100
ctgtctgcta acatggtaca ctgcatctca agatgtttat ctgacacaag tgtattattt   8160
ctggcttttt gaattaatct agaaaatgaa aagatggagt tgtattttga caaaaatgtt   8220
tgtacttttt aatgttattt ggaattttaa gttctatcag tgacttctga atccttagaa   8280
tggcctcttt gtagaaccct gtggtataga ggagtatggc cactgcccca ctatttttat   8340
tttcttatgt aagtttgcat atcagtcatg actagtgcct agaaagcaat gtgatggtca   8400
ggatctcatg acattatatt tgagtttctt tcagatcatt taggatactc ttaatctcac   8460
ttcatcaatc aaatattttt tgagtgtatg ctgtagctga aagagtatgt acgtacgtat   8520
aagactagag agatattaag tctcagtaca cttcctgtgc catgttattc agctcactgg   8580
tttacaaata taggttgtct tgtggttgta ggagcccact gtaacaatac tgggcagcct   8640
```

```
ttttttttt ttttttaatt gcaacaatgc aaaagccaag aaagtataag ggtcacaagt   8700
ctaaacaatg aattcttcaa cagggaaaac agctagcttg aaaacttgct gaaaaacaca   8760
acttgtgttt atggcattta gtaccttcaa ataattggct ttgcagatat tggataccc   8820
attaaatctg acagtctcaa atttttcatc tcttcaatca ctagtcaaga aaaatataaa   8880
aacaacaaat acttccatat ggagcatttt tcagagtttt ctaacccagt cttatttttc   8940
tagtcagtaa acatttgtaa aaatactgtt tcactaatac ttactgttaa ctgtcttgag   9000
agaaaagaaa aatatgagag aactattgtt tggggaagtt caagtgatct ttcaatatca   9060
ttactaactt cttccacttt ttccagaatt tgaatattaa cgctaaaggt gtaagacttc   9120
agatttcaaa ttaatctttc tatatttttt aaatttacag aatattatat aacccactgc   9180
tgaaaaagaa aaaaatgatt gttttagaag ttaaagtcaa tattgatttt aaatataagt   9240
aatgaaggca tatttccaat aactagtgat atggcatcgt tgcattttac agtatcttca   9300
aaaatacaga atttatagaa taatttctcc tcatttaata tttttcaaaa tcaaagttat   9360
ggtttcctca ttttactaaa atcgtattct aattcttcat tatagtaaat ctatgagcaa   9420
ctccttactt cggttcctct gatttcaagg ccatatttta aaaaatcaaa aggcactgtg   9480
aactattttg aagaaaacac aacattttaa tacagattga aaggacctct tctgaagcta   9540
gaaacaatct atagttatac atcttcatta atactgtgtt accttttaaa atagtaattt   9600
tttacatttt cctgtgtaaa cctaattgtg gtagaaattt ttaccaactc tatactcaat   9660
caagcaaaat ttctgtatat tccctgtgga atgtacctat gtgagtttca gaaattctca   9720
aaatacgtgt tcaaaaattt ctgcttttgc atctttggga cacctcagaa aacttattaa   9780
caactgtgaa tatgagaaat acagaagaaa ataataagcc ctctatacat aaatgcccag   9840
cacaattcat tgttaaaaaa caaccaaacc tcacactact gtatttcatt atctgtactg   9900
aaagcaaatg ctttgtgact attaaatgtt gcacatcatt cattcactgt atagtaatca   9960
ttgactaaag ccatttgtct gtgttttctt cttgtggttg tatatatcag gtaaaatatt  10020
ttccaaagag ccatgtgtca tgtaatactg aaccactttg atattgagac attaatttgt  10080
acccttgtta ttatctacta gtaataatgt aatactgtag aaatattgct ctaattcttt  10140
tcaaaattgt tgcatccccc ttagaatgtt tctatttcca taaggattta ggtatgctat  10200
tatcccttct tataccctaa gatgaagctg tttttgtgct ctttgttcat cattggccct  10260
cattccaagc actttacgct gtctgtaatg ggatctattt ttgcactgga atatctgaga  10320
attgcaaaac tagacaaaag tttcacaaca gatttctaag ttaaatcatt ttcattaaaa  10380
ggaaaaaaga aaaaaaattt tgtatgtcaa taactttata tgaagtatta aaatgcatat  10440
ttctatgttg taatataatg agtcacaaaa taaagctgtg acagttctgt tggtctacag  10500
aaaaaaaaaa aaaaa                                                    10515
```

<210> SEQ ID NO 55
<211> LENGTH: 4884
<212> TYPE: DNA
<213> ORGANISM: Homo sapiens

<400> SEQUENCE: 55

```
gcacgcggtt ctccctgatc ccggagctgg gctcagggct cggactcagt cctgcagcgc     60
ctctaggctg cggatccgcg cttcaaccac ctgctttgcg ctgcgtccgg ggaagtgggg    120
aggagacggg agggagggag gaggcgggga gaggaggaaa gaggcagctt acacacgcct    180
```

```
tccagtccct ctactcagag cagcccggag accgctgccg ccgctgccgc tgctaccacc    240
gctgccacct gaggagaccc gccgcccccc cgtcgccgcc tcctgcgagt ccttcttagc    300
acctggcgtt tcatgcacat tgccactgcc attattatta tcattccaat acaaggaaaa    360
taaaagaaga taccagcgaa aagaaccgct tacacctttc cgaattactc aagtgtctcc    420
tggaaacaga gggtcgttgt ccccggagga gcagccgaag ggcccgtggg ctggtgttga    480
ccgggaggga ggaggagttg ggggcattgc gtggtggaaa gttgcgtgcg gcagagaacc    540
gaaggtgcag cgccacagcc caggggacgg tgtgtctggg agaagacgct gcccctgcgt    600
cgggacccgc cagcgcgcgg gcaccgcggg gcccgggacg acgccccctc ctgcggcgtg    660
gactccgtca gtggcccacc aagaaggagg aggaatatgg aatccaaggg ggccagttcc    720
tgccgtctgc tcttctgcct cttgatctcc gccaccgtct tcaggccagg ccttggatgg    780
tatactgtaa attcagcata tggagatacc attatcatac cttgccgact tgacgtacct    840
cagaatctca tgtttggcaa atggaaatat gaaaagcccg atggctcccc agtatttatt    900
gccttcagat cctctacaaa gaaaagtgtg cagtacgacg atgtaccaga atacaaagac    960
agattgaacc tctcagaaaa ctacactttg tctatcagta atgcaaggat cagtgatgaa   1020
aagagatttg tgtgcatgct agtaactgag gacaacgtgt ttgaggcacc tacaatagtc   1080
aaggtgttca agcaaccatc taaacctgaa attgtaagca aagcactgtt tctcgaaaca   1140
gagcagctaa aaaagttggg tgactgcatt tcagaagaca gttatccaga tggcaatatc   1200
acatggtaca ggaatggaaa agtgctacat ccccttgaag gagcggtggt cataattttt   1260
aaaaaggaaa tggacccagt gactcagctc tataccatga cttccaccct ggagtacaag   1320
acaaccaagg ctgacataca aatgccattc acctgctcgg tgacatatta tggaccatct   1380
ggccagaaaa caattcattc tgaacaggca gtatttgata tttactatcc tacagagcag   1440
gtgacaatac aagtgctgcc accaaaaaat gccatcaaag aaggggataa catcactctt   1500
aaatgcttag ggaatggcaa ccctccccca gaggaatttt tgttttactt accaggacag   1560
cccgaaggaa taagaagctc aaatacttac acactgacgg atgtgaggcg caatgcaaca   1620
ggagactaca agtgttccct gatagacaaa aaaagcatga ttgcttcaac agccatcaca   1680
gttcactatt tggatttgtc cttaaaccca agtggagaag tgactagaca gattggtgat   1740
gccctacccg tgtcatgcac aatatctgct agcaggaatg caactgtggt atggatgaaa   1800
gataacatca ggcttcgatc tagcccgtca ttttctagtc ttcattatca ggatgctgga   1860
aactatgtct gcgaaactgc tctgcaggag gttgaaggac taaagaaaag agagtcattg   1920
actctcattg tagaaggcaa acctcaaata aaaatgacaa agaaaactga tcccagtgga   1980
ctatctaaaa caataatctg ccatgtggaa ggttttccaa agccagccat tcaatggaca   2040
attactggca gtggaagcgt cataaaccaa acagaggaat ctccttatat taatggcagg   2100
tattatagta aaattatcat ttcccctgaa gagaatgtta cattaacttg cacagcagaa   2160
aaccaactgg agagaacagt aaactccttg aatgtctctg ctaatgaaaa cagagaaaag   2220
gtgaatgacc aggcaaaact aattgtggga atcgttgttg gtctcctcct tgctgccctt   2280
gttgctggtg tcgtctactg gctgtacatg aagaagtcaa agactgcatc aaaacatgta   2340
aacaaggacc tcggtaatat ggaagaaaac aaaaagttag aagaaaacaa tcacaaaact   2400
gaagcctaag agagaaactg tcctagttgt ccagagataa aaatcatata gaccaattga   2460
agcatgaacg tggattgtat ttaagacata aacaaagaca ttgacagcaa ttcatggttc   2520
aagtattaag cagttcattc taccaagctg tcacaggttt tcagagaatt atctcaagta   2580
```

```
aaacaaatga aatttaatta caaacaataa gaacaagttt tggcagccat gataataggt   2640
catatgttgt gtttggttca attttttttc cgtaaatgtc tgcactgagg atttcttttt   2700
ggtttgcctt ttatgtaaat tttttacgta gctattttta tacactgtaa gctttgttct   2760
gggagttgct gttaatctga tgtataatgt aatgttttta tttcaattgt ttatatggat   2820
aatctgagca ggtacatttc tgattctgat tgctatcagc aatgccccaa actttctcat   2880
aagcacctaa aacccaaagg tggcagcttg tgaagattgg ggacactcat attgccctaa   2940
ttaaaaactg tgatttttat cacaagggag gggaggccga gagtcagact gatagacacc   3000
ataggagccg actctttgat atgccaccag cgaactctca gaaataaatc acagatgcat   3060
atagacacac atacataatg gtactcccaa actgacaatt ttacctattc tgaaaaagac   3120
ataaaacaga atttggtagc acttacctct acagacacct gctaataaat tattttctgt   3180
caaaagaaaa aacacaagca tgtgtgagag acagtttgga aaaatcatgg tcaacattcc   3240
cattttcata gatcacaatg taaatcacta taattacaaa ttggtgttaa atcctttggg   3300
ttatccactg ccttaaaatt atacctattt catgtttaaa aagatatcaa tcagaattgg   3360
agtttttaac agtggtcatt atcaaagctg tgttattttc cacagaatat agaatatata   3420
ttttttcgt gtgtgtttt gttaactacc ctacagatat tgaatgcacc ttgagataat   3480
ttagtgtttt taactgatac ataatttatc aagcagtaca tgaaagtgta ataataaaat   3540
gtctatgtat ctttagttac attcaaattt gtaactttat aaacatgttt tatgcttgag   3600
gaaattttta aggtggtagt ataaatggaa actttttgaa gtagaccaga tatgggctac   3660
ttgtgactag acttttaaac tttgctcttt caagcagaag cctggtttct gggagaacac   3720
tgcacagcga tttctttccc aggatttaca caactttaaa gggaagataa atgaacatca   3780
gatttctagg tatagaacta tgttattgaa aggaaaagga aaactggtgt ttgtttctta   3840
gactcatgaa ataaaaaatt atgaaggcaa tgaaaaataa attgaaaatt aaagtcagat   3900
gagaatagga ataatacttt gccacttctg cattatttag aaacatacgt tattgtacat   3960
ttgtaaacca tttactgtct gggcaatagt gactccgttt aataaaagct tccgtagtgc   4020
attggtatgg attaaatgca taaaatattc ttagactcga tgctgtataa aatattatgg   4080
gaaaaaaaga aaatacgtta ttttgcctct aaacttttat tgaagtttta tttggcagga   4140
aaaaaaattg aatcttggtc aacatttaaa ccaaagtaaa aggggaaaaa ccaaagttat   4200
ttgttttgca tggctaagcc attctgttat ctctgtaaat actgtgattt ctttttttatt  4260
ttctctttag aattttgtta aagaaattct aaaattttta aacacctgct ctccacaata   4320
aatcacaaac actaaaataa aattacttcc atataaatat tattttctct tttggtgtgg   4380
gagatcaaag gtttaaagtc taacttctaa gatatatttg cagaaagaag caacatgaca   4440
atagagagag ttatgctaca attatttctt ggtttccact tgcaatggtt aattaagtcc   4500
aaaaacagct gtcagaacct cgagagcaga acatgagaaa ctcagagctc tggaccgaaa   4560
gcagaaagtt tgccgggaaa aaaaaagaca acattattac catcgattca gtgcctggat   4620
aaagaggaaa gcttacttgt ttaatggcag ccacatgcac gaagatgcta agaagaaaaa   4680
gaattccaaa tcctcaactt ttgaggtttc ggctctccaa tttaactctt tggcaacagg   4740
aaacaggttt tgcaagttca aggttcactc cctatatgtg attataggaa ttgtttgtgg   4800
aaatggatta acatacccgt ctatgcctaa aagataataa aactgaaata tgtcttcaca   4860
ggtctcccac aaaaaaaaaa aaaa                                          4884
```

<210> SEQ ID NO 56
<211> LENGTH: 3246
<212> TYPE: DNA
<213> ORGANISM: Homo sapiens

<400> SEQUENCE: 56
aatgacaaaa aaccagtcat tagaggggca gggcaatttt aggtttcttc tttttagaca 60
tagcccctaa ctggaaattt tcacccttct tgagaaggga gcttgcacta acatctacaa 120
tggcttctaa aaagcacaga tgacctgcta cacttcctga cttgcttgct attggttggc 180
actgttcata aatataattt gctctttcac ttttctttga aatgagcaac ctgaattact 240
cggaggagaa aggcaggaga gatagaggca gcagaagcca gggcagctga aagacagaga 300
ccttcagtct gaaccaacaa caagcaaagt taaattatgg atatccaagg gagtctatag 360
aaggtccatg caaggtatgg agagttcctc aacagagaca ttttgactac ttgtctgaac 420
tagatatccc ttgaatgtgc acacaaaaag tgaatgggtc atttgataag agcccaagac 480
caccagaaac cctcctgtaa tggaacaagt tggctttatt actaattgca acaaggcttt 540
tgaaagcctt ctgtcatctt cctggggatc acctcttcag gtgtacagag acagcatagg 600
gaaaactagg ttccaagatg gctgaatagg aagagctcca atctgcagat cccagtgtga 660
gcaacgtgga agacgggtga tttctgcatt tccaactgag catggagaga aaatttatgt 720
ccttgcaacc atccatctcc gtatcagaaa tggaaccaaa tggcaccttc agcaataaca 780
acagcaggaa ctgcacaatt gaaaacttca agagagaatt tttcccaatt gtatatctga 840
taatattttt ctggggagtc ttgggaaatg ggttgtccat atatgttttc ctgcagcctt 900
ataagaagtc cacatctgtg aacgttttca tgctaaatct ggccatttca gatctcctgt 960
tcataagcac gcttcccttc agggctgact attatcttag aggctccaat tggatatttg 1020
gagacctggc ctgcaggatt atgtcttatt ccttgtatgt caacatgtac agcagtattt 1080
atttcctgac cgtgctgagt gttgtgcgtt tcctggcaat ggttcacccc tttcggcttc 1140
tgcatgtcac cagcatcagg agtgcctgga tcctctgtgg gatcatatgg atccttatca 1200
tggcttcctc aataatgctc ctggacagtg gctctgagca gaacggcagt gtcacatcat 1260
gcttagagct gaatctctat aaaattgcta agctgcagac catgaactat attgccttgg 1320
tggtgggctg cctgctgcca tttttcacac tcagcatctg ttatctgctg atcattcggg 1380
ttctgttaaa agtggaggtc ccagaatcgg ggctgcgggt ttctcacagg aaggcactga 1440
ccaccatcat catcaccttg atcatcttct tcttgtgttt cctgccctat cacacactga 1500
ggaccgtcca cttgacgaca tggaaagtgg gtttatgcaa agacagactg cataaagctt 1560
tggttatcac actggccttg gcagcagcca atgcctgctt caatcctctg ctctattact 1620
ttgctgggga gaattttaag gacagactaa agtctgcact cagaaaaggc catccacaga 1680
aggcaaagac aaagtgtgtt ttccctgtta gtgtgtggtt gagaaaggaa acaagagtat 1740
aaggagctct tagatgagac ctgttcttgt atccttgtgt ccatcttcat tcactcatag 1800
tctccaaatg actttgtatt tacatcactc ccaacaaatg ttgattctta atatttagtt 1860
gaccattact tttgttaata agacctactt caaaaatttt attcagtgta ttttcagttg 1920
ttgagtctta atgagggata caggaggaaa aatccctact agagtcctgt gggctgaaat 1980
atcagactgg gaaaaaatgc aaagcacatt ggatcctact tttcttcaga tattgaacca 2040
gatctctggc ccatcaggct ttctaaattc ttcaaaagag ccacaacttc cccagcttct 2100
ccagctcccc tgtcctcttc aatcccttga gatatagcca actaacgacg ctactggaag 2160

```
ccccagagca gaaaagaagc acatcctaag attcagggaa agactaactg tgaaaaggaa   2220
ggctgtccta taacaaagca gcatcaagtc ccaagtaagg acagtgagag aaaaggggga   2280
gaaggattgg agcaaaagag aactggcaat aagtagggga aggaagaatt tcattttgca   2340
ttgggagaga ggttctaaca cactgaaggc aaccctattt ctactgtttc tctcttgcca   2400
gggtattagg aaggacagga aaagtaggag gaggatctgg ggcattgccc taggaaatga   2460
aagaattgtg tatagaatgg aagggggatc atcaaggaca tgtatctcaa attttctttg   2520
agatgcaggt tagttgacct tgctgcagtt ctccttccca ttaattcatt gggatggaag   2580
ccaaaaataa aagaggtgcc tctgaggatt agggttgagc actcaaggga aagatggagt   2640
agagggcaaa tagcaaaagt tgttgcactc ctgaaattct attaacattt ccgcagaaga   2700
tgagtaggga gatgctgcct tcccttttga gatagtgtag aaaaacacta gatagtgtga   2760
gaggttcctt tctgtccact gaaacaaggc taaggatact accaactact atcaccatga   2820
ccattgtact gacaacaatt gaatgcagtc tccctgcagg gcagattatg ccaggcactt   2880
tacatttgtt gatcccattt gacattcaca ccaaagctct gagttccatt ttacagctga   2940
agaaattgaa gcttagagaa attaagaagc ttgtttaagt ttacacagct agtaagagtt   3000
ttaaaaatct ctgtgcagaa gtgttggctg ggtgctctcc ccaccactac ccttgtaaac   3060
ttccaggaag attggttgaa agtctgaata aaagctgtcc tttcctacca atttcctccc   3120
cctcctcact ctcacaagaa aaccaaaagt ttctcttcag agttgttgac tcatagtaca   3180
gtaaagggtg gaggtgatat ggcattctga aagtagggag ggactaagtc agtcatcata   3240
ctaaac                                                              3246
```

<210> SEQ ID NO 57
<211> LENGTH: 5488
<212> TYPE: DNA
<213> ORGANISM: Homo sapiens

<400> SEQUENCE: 57

```
gggcctctgg gggcggcccc ggggcgggcc acgctggtgt gagggctgca ggcgcagctc     60
cggagcgcct agagcgcggc gcggggcggg agcttggtgg agcaggagcg gctgggcatc    120
ctcctgagac tccggggtca gacgcccact ccagatttct ttaaagactc gtgcagcaca    180
tcattatcgc tggatgcccg gacatgtaat acacctgaca gcatgtgaag tgctcagaat    240
ggggcaggat gtcacctgga atcagcacta agtgattcag actttcctta cttttaaatg    300
tgctgctctt catttcaaga tgccgttgca gctctgataa atgcaaactg acaaccttca    360
aggccacgac ggagggaaaa tcattggtgc ttggagcata gaagactgcc cttcacaaag    420
gaaatccctg attattgttt gaaatgctga ggacgttgct gcgaaggaga cttttttctt    480
atcccaccaa atactacttt atggttcttg ttttatccct aatcaccttc tccgttttaa    540
ggattcatca aaagcctgaa tttgtaagtg tcagacactt ggagcttgct ggggagaatc    600
ctagtagtga tattaattgc accaaagttt tacagggtga tgtaaatgaa atccaaaagg    660
taaagcttga gatcctaaca gtgaaattta aaaagcgccc tcggtggaca cctgacgact    720
atataaacat gaccagtgac tgttcttctt tcatcaagag acgcaaatat attgtagaac    780
cccttagtaa agaagaggcg gagtttccaa tagcatattc tatagtggtt catcacaaga    840
ttgaaatgct tgacaggctg ctgagggcca tctatatgcc tcagaatttc tattgcattc    900
atgtggacac aaaatccgag gattcctatt tagctgcagt gatgggcatc gcttcctgtt    960
```

```
ttagtaatgt ctttgtggcc agccgattgg agagtgtggt ttatgcatcg tggagccggg   1020
ttcaggctga cctcaactgc atgaaggatc tctatgcaat gagtgcaaac tggaagtact   1080
tgataaatct ttgtggtatg gattttccca ttaaaaccaa cctagaaatt gtcaggaagc   1140
tcaagttgtt aatgggagaa aacaacctgg aaacggagag gatgccatcc cataaagaag   1200
aaaggtggaa gaagcggtat gaggtcgtta atggaaagct gacaaacaca gggactgtca   1260
aaatgcttcc tccactcgaa acacctctct tttctggcag tgcctacttc gtggtcagta   1320
gggagtatgt ggggtatgta ctacagaatg aaaaaatcca aaagttgatg gagtgggcac   1380
aagacacata cagccctgat gagtatctct gggccaccat ccaaaggatt cctgaagtcc   1440
cgggctcact ccctgccagc cataagtatg atctgtctga catgcaagca gttgccaggt   1500
ttgtcaagtg gcagtacttt gagggtgatg tttccaaggg tgctccctac ccgccctgcg   1560
atggagtcca tgtgcgctca gtgtgcattt tcggagctgg tgacttgaac tggatgctgc   1620
gcaaacacca cttgtttgcc aataagtttg acgtggatgt tgacctcttt gccatccagt   1680
gtttggatga gcatttgaga cacaaagctt tggagacatt aaaacactga ccattacggg   1740
caattttatg aacaagaaga aggatacaca aaacgtaccc ttatctgttt ccccttcctt   1800
gtcagcatcg ggaagatggt atgaagtcct ctttggggca gggactctag tagatcttct   1860
tgtcagagaa gctgcatggt ttctgcagag cacagttagc tagaaaggtg atagcattaa   1920
atgttcatct agagttaata gtgggaggag taaaggtagc cttgaggcca gagcaggtag   1980
caaggcattg tggaaagagg ggaccagggt ggctggggaa gaggccgatg cataaagtca   2040
gcctgttcaa agtgctcagg gacttagcaa aatgagaaga tgtgacctgt gccaaaacta   2100
ttttgagaat tttaaatgtg accatttttc tggtatgaat aaacttacag caacaaataa   2160
tcaaagatac aattaatctg atattatatt tgttgaaata gaaatttgat tgtactataa   2220
atgatttttg taaataattt atattctgct ctaatactgt actgtgtagt gtgtctccgt   2280
atgtcatctc agggagctta aaatgggctt gatttaacat tgtttttgtg ttatttttgc   2340
ttgaaacaac gcacacattt tcaacaacca aaaaatgaca atttctagtt tagttaattt   2400
ctacaaatca tcttatgtta ttagcaaggt taagacatct tttttaaaaa aattatagct   2460
tctaccaaga gaaacactca atttttctag agatttgcct ctatcttcct ttcctcagtc   2520
ttcccagact gctatcaagc tgtgtaaaaa tttactttca ctggacccta aattattgtc   2580
tctgctatct gactgccagt aattagtgca gaaaactaag acaggatgat acaggtttga   2640
ggggctgggg agtgggaggg gggagaaaag gaatgtattt aaacaatttc cgatgcccat   2700
gatgagttta aaaaccagca ttgacaccat ccccaaaatt aaggctgtcg cttattgaat   2760
ccacttgtgt ccaacctccc aggattgttt tatcctaatg tcacctgtat attcatttga   2820
aaggacttgg ccctgttctt gggtcttccc gttacctgcc ccctgggtgg taagtttcct   2880
cctttctcaa ccttccacga ggaggaaaga agtgtgcagt cattccacat ggcctgttgg   2940
aaggcctggg gagggaactt tgggtttggg acagattttt ttttttgttt ttggtatcat   3000
tcacagcata cgatttttac tctctccatc ttcaccataa gacagataat ttggggttgc   3060
tataatgctg tcacacatct caaagtacat tcaaatctta aaaagaaatt ctcgtacttt   3120
tgccatgttg atactgttca gcaaacaagc taccaggaac tgtgaggctt tgtcatttag   3180
cattagactt taaacaagaa ttaaaatcat gtgctgtatt tttaaaatct agccaaatta   3240
aatagtacat gagaaattca gagtattaga cagttttaag gcattcaact gagaaaactt   3300
tatttgtcaa agtcagaaaa cattttcatc ttattgagag atatgttttt aaacttttat   3360
```

```
catcatttgt aaatgtggaa gttggtggat tgctgtgttt ttgcatgatt agcatgggag   3420
tctgttggag caagaggaac atgcttgttt tgaaaactcg agatgatgag ggtggtacat   3480
gcagtgtgtt ctctctttat tggcttctaa accagttttg tcctttaatg catgtcaaat   3540
atttctccca tgcttctctt agcagaaaag tttttaccta taagacaggg caccttttaa   3600
ctctaaaact agtgatactc agtgacatag actttgtctt ataaacattt tttcattttt   3660
tattttgaaa aattgcaaat ctacagcaaa agtaaaacag tagagtgaac accatgtaac   3720
cctcacctgg tgttaacatt gtaccctatt tgctttaagt tgtatgtatt tctgaacttg   3780
gcaaaattgg aaattaaaat ttttaaaaat tacaaatata caaagttatt tatcttagca   3840
catttattat gtgtgactgc atctgattta tatttaaatt ggcaggtttt gagggatttt   3900
tttcttcatc ataaatgtaa acataggatt ttagagtcta tttccccaag cgccacatta   3960
taactgtaaa cttaccatct tctatgtagc tgtgatatct catctttcta aaatggaact   4020
tgttaaaaag tgttcaaaca ctatccctaa tgcctgcggc agaatttata tacgatccat   4080
tcattggggc tcaaagtatc ttttagactt ttaaggacaa tttacagcaa atgaaattta   4140
tgatgctgtg acaagaaatt taaagaatca aaacgatggt ttgaaaagga aacctatgat   4200
acatgcagga gaagcaaaac ccaagtgatt ggtgagaaat atagaaatta tttaaattac   4260
tttatagtaa ttattaaaca ctaatttttg tactgtcatt gaaggtgttt tatagagaaa   4320
tctgagaaat cacattcaca aattagaagt caaacatggc caggcacagt ggctcacacc   4380
tgtaatcttc aggatttcaa gaccagccta gccaacatga cgaaacccca tctctactga   4440
aaatagaaaa aaaaaattag ccaggcttgc acctgtaatc ccagttacct gggaggctga   4500
ggcaggagaa tctcttgagc ccaggaggcg gaggttgcag tgagctgaga tgccaccacc   4560
acaccagcct gggtgacaga gtgaaactcg tatctccaaa caaacaaaca aaaagtcctt   4620
aaacatatgt gaacaaaaat tttgtgatgg aaggattcta gttaatgagt attgcatcaa   4680
gatttacatc tttcttacta aggaaaagag ttaataaaaa ttgttcttta ttttacaggc   4740
agttactgag gctcttccca gatctcagta aacagccact cagccttgaa aatggagtgt   4800
tgttgtttct aaacatatat ttatgtcatt tattaagtac agttcactta aataacataa   4860
gtagattttc tcttgtagtg atttgggtag gaagaggcca tgtttcagtt cgttttctct   4920
gtagggtcga ttgaattgga ccttttcagt tgttcagaaa aataaaaata atttctcata   4980
ttaaatacag acgctcctca acttatgatg tgggtaggtc ccagtaaacc cattataatt   5040
tgaaaatatc acattgaaaa tgcatttaat atctcttacc tgaaatcata acttagccaa   5100
gcctacctta aatgttctca gaacatttag cctgcagttg ggcaaaacca tttaacacaa   5160
agcctatttt ataatgaagt gttgaatagc tcatgttatt tactgaatac tgttgtgaaa   5220
gtgaaaaaca atgattgtat gggtactcaa agtataattt ctactgaatg catatcactt   5280
gtgcactgtt gtaaagctga aaaaccgtta agcctctacg atttttaagt aagttgggga   5340
ccatcagttt aaaataaatg caatactatt tcatgataaa catggtcact gtaagtttta   5400
ctcttttgaa tgagggtgcg acagaatgca gttagaatca gttcatatca ccattaaaat   5460
catccattca gaaaccaaaa aaaaaaaa                                      5488
```

<210> SEQ ID NO 58
<211> LENGTH: 2448
<212> TYPE: DNA
<213> ORGANISM: Homo sapiens

<400> SEQUENCE: 58

```
agaacactta caggatgtgt gtagtgtggc atgacagaga actttggttt cctttaatgt     60
gactgtagac ctggcagtgt tactataaga atcactggca atcagacacc cgggtgtgct    120
gagctagcac tcagtggggg cggctactgc tcatgtgatt gtggagtaga cagttggaag    180
aagtacccag tccatttgga gagttaaaac tgtgcctaac agaggtgtcc tctgactttt    240
cttctgcaag ctccatgttt tcacatcttc cctttgactg tgtcctgctg ctgctgctgc    300
tactacttac aaggtcctca gaagtggaat acagagcgga ggtcggtcag aatgcctatc    360
tgccctgctt ctacacccca gccgccccag ggaacctcgt gcccgtctgc tggggcaaag    420
gagcctgtcc tgtgtttgaa tgtggcaacg tggtgctcag gactgatgaa agggatgtga    480
attattggac atccagatac tggctaaatg gggatttccg caaaggagat gtgtccctga    540
ccatagagaa tgtgactcta gcagacagtg ggatctactg ctgccggatc caaatcccag    600
gcataatgaa tgatgaaaaa tttaacctga agttggtcat caaaccagcc aaggtcaccc    660
ctgcaccgac tcggcagaga gacttcactg cagcctttcc aaggatgctt accaccaggg    720
gacatggccc agcagagaca cagacactgg ggagcctccc tgatataaat ctaacacaaa    780
tatccacatt ggccaatgag ttacgggact ctagattggc caatgactta cgggactctg    840
gagcaaccat cagaataggc atctacatcg gagcagggat ctgtgctggg ctggctctgg    900
ctcttatctt cggcgcttta attttcaaat ggtattctca tagcaaagag aagatacaga    960
atttaagcct catctctttg gccaacctcc ctccctcagg attggcaaat gcagtagcag   1020
agggaattcg ctcagaagaa aacatctata ccattgaaga gaacgtatat gaagtggagg   1080
agcccaatga gtattattgc tatgtcagca gcaggcagca accctcacaa cctttgggtt   1140
gtcgctttgc aatgccatag atccaaccac cttatttttg agcttggtgt tttgtctttt   1200
tcagaaacta tgagctgtgt cacctgactg gttttggagg ttctgtccac tgctatggag   1260
cagagttttc ccattttcag aagataatga ctcacatggg aattgaactg ggacctgcac   1320
tgaacttaaa caggcatgtc attgcctctg tatttaagcc aacagagtta cccaacccag   1380
agactgttaa tcatggatgt tagagctcaa acgggctttt atatacacta ggaattcttg   1440
acgtggggtc tctggagctc caggaaattc gggcacatca tatgtccatg aaacttcaga   1500
taaactaggg aaaactgggt gctgaggtga aagcataact tttttggcac agaaagtcta   1560
aaggggccac tgattttcaa agagatctgt gatccctttt tgttttttgt ttttgagatg   1620
gagtcttgct ctgttgccca ggctggagtg caatggcaca atctcggctc actgcaagct   1680
ccgcctcctg ggttcaagcg attctcctgc ctcagcctcc tgagtggctg ggattacagg   1740
catgcaccac catgcccagc taatttgttg tatttttagt agagacaggg tttcaccatg   1800
ttggccagtg tggtctcaaa ctcctgacct catgatttgc ctgcctcggc ctcccaaagc   1860
actgggatta caggcgtgag ccaccacatc cagccagtga tccttaaaag attaagagat   1920
gactggacca ggtctacctt gatcttgaag attcccttgg aatgttgaga tttaggctta   1980
tttgagcact gcctgcccaa ctgtcagtgc cagtgcatag cccttctttt gtctccctta   2040
tgaagactgc cctgcagggc tgagatgtgg caggagctcc cagggaaaaa cgaagtgcat   2100
ttgattggtg tgtattggcc aagttttgct tgttgtgtgc ttgaaagaaa atatctctga   2160
ccaacttctg tattcgtgga ccaaactgaa gctatatttt tcacagaaga agaagcagtg   2220
acggggacac aaattctgtt gcctggtgga aagaaggcaa aggccttcag caatctatat   2280
taccagcgct ggatcctttg acagagagtg gtccctaaac ttaaatttca agacggtata   2340
```

ggcttgatct gtcttgctta ttgttgcccc ctgcgcctag cacaattctg acacacaatt 2400
ggaacttact aaaaattttt ttttactgtt aaaaaaaaaa aaaaaaaa 2448

<210> SEQ ID NO 59
<211> LENGTH: 1885
<212> TYPE: DNA
<213> ORGANISM: Homo sapiens

<400> SEQUENCE: 59
cagctctagc gaaaagccgc cggtatttct ccatctggct ctcctctacc tccaggcagg 60
ctcacccgag atccccgccc cgaacccccc ctgcacactc ggcccagcgc tgttgccccc 120
ggagcggacg tttctgcagc tattctgagc acaccttgac gtcggctgag ggagcgggac 180
agggtcagcg gcgaaggagg caggccccgc gcggggatct cggaagccct gcggtgcatc 240
atgaagttcc agtacaagga ggaccatccc tttgagtatc ggaaaaagga aggagaaaag 300
atccggaaga aatatccgga cagggtcccc gtgattgtag agaaggctcc aaaagccagg 360
gtgcctgatc tggacaagag gaagtaccta gtgccctctg accttactgt tggccagttc 420
tacttcttaa tccggaagag aatccacctg agacctgagg acgccttatt cttctttgtc 480
aacaacacca tccctcccac cagtgctacc atgggccaac tgtatgagga caatcatgag 540
gaagactatt ttctgtatgt ggcctacagt gatgagagtg tctatgggaa atgagtggtt 600
ggaagcccag cagatgggag cacctggact tgggggtagg ggaggggtgt gtgtgcgcga 660
catggggaaa gagggtggct cccaccgcaa ggagacagaa ggtgaagaca tctagaaaca 720
ttacaccaca cacaccgtca tcacattttc acatgctcaa ttgatatttt ttgctgcttc 780
ctcggcccag ggagaaagca tgtcaggaca gagctgttgg attggctttg atagaggaat 840
ggggatgatg taagtttaca gtattcctgg ggtttaattg ttgtgcagtt tcatagatgg 900
gtcaggaggt ggacaagttg ggccagaga tgatggcagt ccagcagcaa ctccctgtgc 960
tcccttctct ttgggcagag attctatttt tgacatttgc acaagacagg tagggaaagg 1020
ggacttgtgg tagtggacca tacctgggga ccaaaagaga cccactgtaa ttgatgcatt 1080
gtggcccctg atcttccctg tctcacactt cttttctccc atcccggttg caatctcact 1140
cagacatcac agtaccaccc caggggtggc agtagacaac aacccagaaa tttagacagg 1200
gatctcttac ctttggaaaa taggggttag gcatgaaggt ggttgtgatt aagaagatgg 1260
ttttgttatt aaatagcatt aaactggaat tgacaagagt gttgagcatc cctgtctaac 1320
ctgctctttc tctttggtgc cccttatctc acccccttcct tggaatttaa taagtctcag 1380
gcatttccaa ttgtagacta aaaccactct tagcatctcc tctagtattt tccatgtatc 1440
aggacagagg tgtcttatgt agggaggggg caagtatgaa gtaaggtaat tatatactac 1500
tctcattcag gattcttgct cccatgctgc tgtcccttca ggctcacatg cacaggaatg 1560
ctacatgatg gccagctgct tccctccttg gttatcatcc actgcagctg ctagttagaa 1620
aggtttggag ggatgacttt tagtaaatca tggggatttt attgatttat tttcactttt 1680
gggattttgt ggggtgggag tggggagcag gaattgcact cagacatgac atttcaattc 1740
atctctgcta atgaaaaggg ttctttctct tgggggaaat gtgtgtgtca gttctgtcag 1800
ctgcaagttc ttgtataatg aagtcaatgc catcaggcca aggaaataaa ataattgctt 1860
accttaaaaa aaaaaaaaaa aaaaa 1885

<210> SEQ ID NO 60

<211> LENGTH: 3216
<212> TYPE: DNA
<213> ORGANISM: Homo sapiens

<400> SEQUENCE: 60

```
ggcagtttcc tggctgaaca cgccagccca atacttaaag agagcaactc ctgactccga     60
tagagactgg atggacccac aagggtgaca gcccaggcgg accgatcttc ccatccccaca   120
tcctccggcg cgatgccaaa aagaggctga cggcaactgg gccttctgca gagaaagacc    180
tccgcttcac tgccccggct ggtcccaagg gtcaggaaga tggattcata cctgctgatg    240
tggggactgc tcacgttcat catggtgcct ggctgccagg cagagctctg tgacgatgac    300
ccgccagaga tcccacacgc cacattcaaa gccatggcct acaaggaagg aaccatgttg    360
aactgtgaat gcaagagagg tttccgcaga ataaaaagcg ggtcactcta tatgctctgt    420
acaggaaact ctagccactc gtcctgggac aaccaatgtc aatgcacaag ctctgccact    480
cggaacacaa cgaaacaagt gacacctcaa cctgaagaac agaaagaaag gaaaaccaca    540
gaaatgcaaa gtccaatgca gccagtggac caagcgagcc ttccaggtca ctgcagggaa    600
cctccaccat gggaaaatga agccacagag agaatttatc atttcgtggt ggggcagatg    660
gtttattatc agtgcgtcca gggatacagg gctctacaca gaggtcctgc tgagagcgtc    720
tgcaaaatga cccacgggaa gacaaggtgg acccagcccc agctcatatg cacaggtgaa    780
atggagacca gtcagtttcc aggtgaagag aagcctcagg caagccccga aggccgtcct    840
gagagtgaga cttcctgcct cgtcacaaca acagattttc aaatacagac agaaatggct    900
gcaaccatgg agacgtccat atttacaaca gagtaccagg tagcagtggc cggctgtgtt    960
ttcctgctga tcagcgtcct cctcctgagt gggctcacct ggcagcggag acagaggaag   1020
agtagaagaa caatctagaa aaccaaaaga acaagaattt cttggtaaga agccgggaac   1080
agacaacaga agtcatgaag cccaagtgaa atcaaaggtg ctaaatggtc gcccaggaga   1140
catccgttgt gcttgcctgc gttttggaag ctctgaagtc acatcacagg acacggggca   1200
gtggcaacct tgtctctatg ccagctcagt cccatcagag agcgagcgct acccacttct   1260
aaatagcaat ttcgccgttg aagaggaagg gcaaaaccac tagaactctc catcttattt   1320
tcatgtatat gtgttcatta aagcatgaat ggtatggaac tctctccacc ctatatgtag   1380
tataaagaaa agtaggttta cattcatctc attccaactt cccagttcag gagtcccaag   1440
gaaagcccca gcactaacgt aaatacacaa cacacacact ctaccctata caactggaca   1500
ttgtctgcgt ggttcctttc tcagccgctt ctgactgctg attctcccgt tcacgttgcc   1560
taataaacat ccttcaagaa ctctgggctg ctacccagaa atcattttac ccttggctca   1620
atcctctaag ctaacccccct tctactgagc cttcagtctt gaatttctaa aaaacagagg  1680
ccatggcaga ataatctttg ggtaacttca aaacggggca gccaaaccca tgaggcaatg   1740
tcaggaacag aaggatgaat gaggtcccag gcagagaatc atacttagca aagttttacc   1800
tgtgcgttac taattggcct ctttaagagt tagtttcttt gggattgcta tgaatgatac   1860
cctgaatttg gcctgcacta atttgatgtt tacaggtgga cacacaaggt gcaaatcaat   1920
gcgtacgttt cctgagaagt gtctaaaaac accaaaaagg gatccgtaca ttcaatgttt   1980
atgcaaggaa ggaaagaaag aaggaagtga agagggagaa gggatggagg tcacactggt   2040
agaacgtaac cacggaaaag agcgcatcag gcctggcacg gtggctcagg cctataaccc   2100
cagctcccta ggagaccaag gcgggagcat ctcttgaggc caggagtttg agaccagcct   2160
gggcagcata gcaagacaca tccctacaaa aaattagaaa ttggctggat gtggtggcat   2220
```

```
acgcctgtag tcctagccac tcaggaggct gaggcaggag gattgcttga gcccaggagt   2280

tcgaggctgc agtcagtcat gatggcacca ctgcactcca gcctgggcaa cagagcaaga   2340

tcctgtcttt aaggaaaaaa agacaagatg agcataccag cagtccttga acattatcaa   2400

aaagttcagc atattagaat caccgggagg ccttgttaaa agagttcgct gggcccatct   2460

tcagagtctc tgagttgttg gtctggaata gagccaaatg ttttgtgtgt ctaacaattc   2520

ccaggtgctg ttgctgctgc tactattcca ggaacacact ttgagaacca ttgtgttatt   2580

gctctgcacg cccacccact ctcaactccc acgaaaaaaa tcaacttcca gagctaagat   2640

ttcggtggaa gtcctggttc catatctggt gcaagatctc ccctcacgaa tcagttgagt   2700

caacattcta gctcaacaac atcacacgat taacattaac gaaaattatt catttgggaa   2760

actatcagcc agttttcact tctgaagggg caggagagtg ttatgagaaa tcacggcagt   2820

tttcagcagg gtccagattc agattaaata actattttct gtcatttctg tgaccaacca   2880

catacaaaca gactcatctg tgcactctcc ccctccccct tcaggtatat gttttctgag   2940

taaagttgaa aagaatctca gaccagaaaa tatagatata tatttaaatc ttacttgagt   3000

agaactgatt acgacttttg ggtgttgagg ggtctataag atcaaaactt ttccatgata   3060

atactaagat gttatcgacc atttatctgt ccttctctca aaagtgtatg gtggaatttt   3120

ccagaagcta tgtgatacgt gatgatgtca tcactctgct gttaacatat aataaattta   3180

ttgctattgt ttataaaaga ataaatgata tttttt                             3216
```

<210> SEQ ID NO 61
<211> LENGTH: 1616
<212> TYPE: DNA
<213> ORGANISM: Homo sapiens

<400> SEQUENCE: 61

```
ctccctgtgt tggtggagga tgtctgcagc agcatttaaa ttctgggagg gcttggttgt     60

cagcagcagc aggaggaggc agagcacagc atcgtcggga ccagactcgt ctcaggccag    120

ttgcagcctt ctcagccaaa cgccgaccaa ggaaaactca ctaccatgag aattgcagtg    180

atttgctttt gcctcctagg catcacctgt gccataccag ttaaacaggc tgattctgga    240

agttctgagg aaaagcagct ttacaacaaa tacccagatg ctgtggccac atggctaaac    300

cctgacccat ctcagaagca gaatctccta gccccacaga cccttccaag taagtccaac    360

gaaagccatg accacatgga tgatatggat gatgaagatg atgatgacca tgtggacagc    420

caggactcca ttgactcgaa cgactctgat gatgtagatg acactgatga ttctcaccag    480

tctgatgagt ctcaccattc tgatgaatct gatgaactgg tcactgattt tcccacggac    540

ctgccagcaa ccgaagtttt cactccagtt gtccccacag tagacacata tgatggccga    600

ggtgatagtg tggtttatgg actgaggtca aaatctaaga agtttcgcag acctgacatc    660

cagtaccctg atgctacaga cgaggacatc acctcacaca tggaaagcga ggagttgaat    720

ggtgcataca aggccatccc cgttgcccag gacctgaacg cgccttctga ttgggacagc    780

cgtgggaagg acagttatga aacgagtcag ctggatgacc agagtgctga aacccacagc    840

cacaagcagt ccagattata taagcggaaa gccaatgatg agagcaatga gcattccgat    900

gtgattgata gtcaggaact ttccaaagtc agccgtgaat tccacagcca tgaatttcac    960

agccatgaag atatgctggt tgtagacccc aaaagtaagg aagaagataa acacctgaaa   1020

tttcgtattt ctcatgaatt agatagtgca tcttctgagg tcaattaaaa ggagaaaaaa   1080
```

```
tacaatttct cactttgcat ttagtcaaaa gaaaaaatgc tttatagcaa aatgaaagag   1140

aacatgaaat gcttctttct cagtttattg gttgaatgtg tatctatttg agtctggaaa   1200

taactaatgt gtttgataat tagtttagtt tgtggcttca tggaaactcc ctgtaaacta   1260

aaagcttcag ggttatgtct atgttcattc tatagaagaa atgcaaacta tcactgtatt   1320

ttaatatttg ttattctctc atgaatagaa atttatgtag aagcaaacaa aatactttta   1380

cccacttaaa aagagaatat aacattttat gtcactataa tcttttgttt tttaagttag   1440

tgtatatttt gttgtgatta tctttttgtg gtgtgaataa atcttttatc ttgaatgtaa   1500

taagaatttg gtggtgtcaa ttgcttattt gttttcccac ggttgtccag caattaataa   1560

aacataacct tttttactgc ctaaaaaaaa aaaaaaaaaa aaaaaaaaaa aaaaaa       1616
```

<210> SEQ ID NO 62
<211> LENGTH: 1227
<212> TYPE: DNA
<213> ORGANISM: Homo sapiens

<400> SEQUENCE: 62

```
ctttgcagat aaatatggca cactagcccc acgttttctg agacattcct caattgctta     60

gacatattct gagcctacag cagaggaacc tccagtctca gcaccatgaa tcaaactgcc    120

attctgattt gctgccttat ctttctgact ctaagtggca ttcaaggagt acctctctct    180

agaactgtac gctgtacctg catcagcatt agtaatcaac ctgttaatcc aaggtcttta    240

gaaaaacttg aaattattcc tgcaagccaa ttttgtccac gtgttgagat cattgctaca    300

atgaaaaaga agggtgagaa gagatgtctg aatccagaat cgaaggccat caagaattta    360

ctgaaagcag ttagcaagga aaggtctaaa agatctcctt aaaaccagag gggagcaaaa    420

tcgatgcagt gcttccaagg atggaccaca cagaggctgc ctctcccatc acttccctac    480

atggagtata tgtcaagcca taattgttct tagtttgcag ttacactaaa aggtgaccaa    540

tgatggtcac caaatcagct gctactactc ctgtaggaag gttaatgttc atcatcctaa    600

gctattcagt aataactcta ccctggcact ataatgtaag ctctactgag gtgctatgtt    660

cttagtggat gttctgaccc tgcttcaaat atttccctca cctttcccat cttccaaggg    720

tactaaggaa tctttctgct ttggggttta tcagaattct cagaatctca aataactaaa    780

aggtatgcaa tcaaatctgc tttttaaaga atgctcttta cttcatggac ttccactgcc    840

atcctcccaa ggggcccaaa ttctttcagt ggctacctac atacaattcc aaacacatac    900

aggaaggtag aaatatctga aaatgtatgt gtaagtattc ttatttaatg aaagactgta    960

caaagtagaa gtcttagatg tatatatttc ctatattgtt ttcagtgtac atggaataac   1020

atgtaattaa gtactatgta tcaatgagta acaggaaaat tttaaaaata cagatagata   1080

tatgctctgc atgttacata agataaatgt gctgaatggt tttcaaaata aaaatgaggt   1140

actctcctgg aaatattaag aaagactatc taaatgttga aagatcaaaa ggttaataaa   1200

gtaattataa ctaagaaaaa aaaaaaa                                       1227
```

<210> SEQ ID NO 63
<211> LENGTH: 678
<212> TYPE: DNA
<213> ORGANISM: Homo sapiens

<400> SEQUENCE: 63

```
aggaaaagga aactgttgag aaaccgaaac tactggggaa agggagggct cactgagaac     60

catcccagta acccgaccgc cgctggtctt cgctggacac catgaatcac actgtccaaa    120
```

```
ccttcttctc tcctgtcaac agtggccagc cccccaacta tgagatgctc aaggaggagc    180

acgaggtggc tgtgctgggg gcgccccaca accctgctcc cccgacgtcc accgtgatcc    240

acatccgcag cgagacctcc gtgcccgacc atgtcgtctg gtccctgttc aacaccctct    300

tcatgaaccc ctgctgcctg ggcttcatag cattcgccta ctccgtgaag tctagggaca    360

ggaagatggt tggcgacgtg accggggccc aggcctatgc ctccaccgcc aagtgcctga    420

acatctgggc cctgattctg ggcatcctca tgaccattct gctcatcgtc atcccagtgc    480

tgatcttcca ggcctatgga tagatcagga ggcatcactg aggccaggag ctctgcccat    540

gacctgtatc ccacgtactc caacttccat tcctcgccct gcccccggag ccgagtcctg    600

tatcagccct ttatcctcac acgcttttct acaatggcat tcaataaagt gcacgtgttt    660

ctggtgctaa aaaaaaaa                                                  678
```

<210> SEQ ID NO 64
<211> LENGTH: 1204
<212> TYPE: DNA
<213> ORGANISM: Homo sapiens

<400> SEQUENCE: 64

```
cccgtgagga ggaaaaggtg tgtccgctgc cacccagtgt gagcgggtga caccacccgg     60

ttaggaaatc ccagctccca agagggtata aatccctgct ttactgctga gctcctgctg    120

gaggtgaaag tctggcctgg cagccttccc caggtgagca gcaacaaggc cacgtgctgc    180

tgggtctcag tcctccactt cccgtgtcct ctggaagttg tcaggagcaa tgttgcgctt    240

gtacgtgttg gtaatgggag tttctgcctt cacccttcag cctgcggcac acacaggggc    300

tgccagaagc tgccggtttc gtgggaggca ttacaagcgg gagttcaggc tggaagggga    360

gcctgtagcc ctgaggtgcc cccaggtgcc ctactggttg tgggcctctg tcagcccccg    420

catcaacctg acatggcata aaaatgactc tgctaggacg gtcccaggag aagaagagac    480

acggatgtgg gcccaggacg gtgctctgtg gcttctgcca gccttgcagg aggactctgg    540

cacctacgtc tgcactacta gaaatgcttc ttactgtgac aaaatgtcca ttgagctcag    600

agtttttgag aatacagatg ctttcctgcc gttcatctca tacccgcaaa ttttaacctt    660

gtcaacctct ggggtattag tatgccctga cctgagtgaa ttcacccgtg acaaaactga    720

cgtgaagatt caatggtaca aggattctct tcttttggat aaagacaatg agaaatttct    780

aagtgtgagg gggaccactc acttactcgt acacgatgtg gccctggaag atgctggcta    840

ttaccgctgt gtcctgacat ttgcccatga aggccagcaa tacaacatca ctaggagtat    900

tgagctacgc atcaagaaaa aaaaagaaga gaccattcct gtgatcattt ccccccctcaa    960

gaccatatca gcttctctgg ggtcaagact gacaatcccg tgtaaggtgt ttctgggaac   1020

cggcacaccc ttaaccacca tgctgtggtg gacggccaat gacacccaca tagagagcgc   1080

ctacccggga ggccgcgtga ccgaggggcc acgccagtaa gtgggccagg gtcttctgtt   1140

gagaactctg tgggtttcgc tcttcctttt ggagacagtt atcactatga cccacatacc   1200

acat                                                                1204
```

<210> SEQ ID NO 65
<211> LENGTH: 1995
<212> TYPE: DNA
<213> ORGANISM: Homo sapiens

<400> SEQUENCE: 65
acaggggtga aggcccagag accagcagaa cggcatccca gccacgacgg ccactttgct 60
ctgtctgctc tccgccacgg ccctgctctg ttccctggga cacccccgcc cccacctcct 120
caggctgcct gatctgccca gctttccagc tttcctctgg attccggcct ctggtcatcc 180
ctccccaccc tctctccaag gccctctcct ggtctccctt cttctagaac cccttcctcc 240
acctccctct ctgcagaact tctcctttac cccccacccc ccaccactgc cccctttcct 300
tttctgacct ccttttggag ggctcagcgc tgcccagacc ataggagaga tgtgggaggc 360
tcagttcctg ggcttgctgt ttctgcagcc gctttgggtg gctccagtga agcctctcca 420
gccaggggct gaggtcccgg tggtgtgggc ccaggagggg gctcctgccc agctcccctg 480
cagccccaca atcccccctcc aggatctcag ccttctgcga agagcagggg tcacttggca 540
gcatcagcca gacagtggcc cgcccgctgc cgcccccggc catcccctgg cccccggccc 600
tcacccggcg gcgccctcct cctgggggcc caggccccgc cgctacacgg tgctgagcgt 660
gggtcccgga ggcctgcgca gcgggaggct gcccctgcag ccccgcgtcc agctggatga 720
gcgcggccgg cagcgcgggg acttctcgct atggctgcgc ccagcccggc gcgcggacgc 780
cggcgagtac cgcgccgcgg tgcacctcag ggaccgcgcc ctctcctgcc gcctccgtct 840
gcgcctgggc caggcctcga tgactgccag ccccccagga tctctcagag cctccgactg 900
ggtcattttg aactgctcct tcagccgccc tgaccgccca gcctctgtgc attggttccg 960
gaaccggggc cagggccgag tccctgtccg ggagtccccc catcaccact tagcggaaag 1020
cttcctcttc ctgccccaag tcagccccat ggactctggg ccctggggct gcatcctcac 1080
ctacagagat ggcttcaacg tctccatcat gtataacctc actgttctgg gtctggagcc 1140
cccaactccc ttgacagtgt acgctggagc aggttccagg gtggggctgc cctgccgcct 1200
gcctgctggt gtggggaccc ggtctttcct cactgccaag tggactcctc ctgggggagg 1260
ccctgacctc ctggtgactg gagacaatgg cgactttacc cttcgactag aggatgtgag 1320
ccaggcccag gctgggacct acacctgcca tatccatctg caggaacagc agctcaatgc 1380
cactgtcaca ttggcaatca tcacagtgac tcccaaatcc tttgggtcac ctggatccct 1440
ggggaagctg ctttgtgagg tgactccagt atctggacaa gaacgctttg tgtggagctc 1500
tctggacacc ccatcccaga ggagtttctc aggaccttgg ctggaggcac aggaggccca 1560
gctcctttcc cagccttggc aatgccagct gtaccagggg gagaggcttc ttggagcagc 1620
agtgtacttc acagagctgt ctagcccagg tgcccaacgc tctgggagag ccccaggtgc 1680
cctcccagca ggccacctcc tgctgtttct catccttggt gtcctttctc tgctcctttt 1740
ggtgactgga gcctttggct ttcacctttg gagaagacag tggcgaccaa gacgattttc 1800
tgccttagag caagggattc accctccgca ggctcagagc aagatagagg agctggagca 1860
agaaccggag ccggagccgg agccggaacc ggagcccgag cccgagcccg agccggagca 1920
gctctgacct ggagctgagg cagccagcag atctcagcag cccagtccaa ataaactccc 1980
tgtcagcagc aaaaa 1995

<210> SEQ ID NO 66
<211> LENGTH: 972
<212> TYPE: DNA
<213> ORGANISM: Homo sapiens

<400> SEQUENCE: 66
acggcggggc gaagcgccca ggggcctgtg cgtccctccc tgctgagcga gggggcctgt 60
cattgccgtg ggcgtgaccc agaccccaac cacagtgcat cccgccctgg cccagccaga 120

```
gaaggaagct gagtctgggg tctgctgggc cagcaggaag tcccagcagg gtgtgaagca    180
agactttccg ggccactcct ggaatccccc agcagataaa ggcggcccct ccaccgggcg    240
ctcctagcgg tctcccggac cctgccgccc tgccactatg tcccgccgct ctatgctgct    300
tgcctgggct ctccccagcc tccttcgact cggagcggct caggagacag aagacccggc    360
ctgctgcagc cccatagtgc cccggaacga gtggaaggcc ctggcatcag agtgcgccca    420
gcacctgagc ctgcccttac gctatgtggt ggtatcgcac acggcgggca gcagctgcaa    480
cacccccgcc tcgtgccagc agcaggcccg gaatgtgcag cactaccaca tgaagacact    540
gggctggtgc gacgtgggct acaacttcct gattggagaa gacgggctcg tatacgaggg    600
ccgtggctgg aacttcacgg gtgcccactc aggtcactta tggaacccca tgtccattgg    660
catcagcttc atgggcaact acatggatcg ggtgcccaca ccccaggcca tccgggcagc    720
ccagggtcta ctggcctgcg gtgtggctca gggagccctg aggtccaact atgtgctcaa    780
aggacaccgg gatgtgcagc gtacactctc tccaggcaac cagctctacc acctcatcca    840
gaattggcca cactaccgct ccccctgagg ccctgctgat ccgcacccca ttcctcccct    900
cccatggcca aaaaccccac tgtctccttc tccaataaag atgtagctca aaaaaaaaaa    960
aaaaaaaaaa aa                                                        972
```

<210> SEQ ID NO 67
<211> LENGTH: 3902
<212> TYPE: DNA
<213> ORGANISM: Homo sapiens

<400> SEQUENCE: 67

```
agaacctggt gcctgcctca gccctagctc tggggaaatg aaagccaggc tggggttcaa     60
atgagggcag tttcccttcc tgtgggctgc tgatggaaca accccatgac gagaaggacc    120
cagcctccaa gcggccacac cctgtgtgtc tctttgtcct gccggcactg aggactcatc    180
catctgcaca gctggggccc ctgggaggag acgccatgat ccccaccttc acggctctgc    240
tctgcctcgg gctgagtctg ggccccagga cccacatgca ggcagggccc ctccccaaac    300
ccaccctctg ggctgagcca ggctctgtga tcagctgggg gaactctgtg accatctggt    360
gtcaggggac cctggaggct cgggagtacc gtctggataa agaggaaagc ccagcaccct    420
gggacagaca gaacccactg gagcccaaga acaaggccag attctccatc ccatccatga    480
cagaggacta tgcagggaga taccgctgtt actatcgcag ccctgtaggc tggtcacagc    540
ccagtgaccc cctggagctg gtgatgacag gagcctacag taaacccacc ctttcagccc    600
tgccgagtcc tcttgtgacc tcaggaaaga gcgtgaccct gctgtgtcag tcacggagcc    660
caatggacac ttttcttctg atcaaggagc gggcagccca tcccctactg catctgagat    720
cagagcacgg agctcagcag caccaggctg aattccccat gagtcctgtg acctcagtgc    780
acgggggac ctacaggtgc ttcagctcac acggcttctc ccactacctg ctgtcacacc    840
ccagtgaccc cctggagctc atagtctcag gatccttgga gggtcccagg ccctcaccca    900
caaggtccgt ctcaacagct gcaggccctg aggaccagcc cctcatgcct acagggtcag    960
tcccccacag tggtctgaga aggcactggg aggtactgat cggggtcttg gtggtctcca   1020
tcctgcttct ctccctcctc ctcttcctcc tcctccaaca ctggcgtcag ggaaaacaca   1080
ggacattggc ccagagacag gctgatttcc aacgtcctcc aggggctgcc gagccagagc   1140
ccaaggacgg gggcctacag aggaggtcca gcccagctgc tgacgtccag ggagaaaact   1200
```

```
tctgtgctgc cgtgaagaac acacagcctg aggacggggt ggaaatggac actcggcaga   1260
gcccacacga tgaagacccc caggcagtga cgtatgccaa ggtgaaacac tccagaccta   1320
ggagagaaat ggcctctcct ccctccccac tgtctgggga attcctggac acaaaggaca   1380
gacaggcaga agaggacaga cagatggaca ctgaggctgc tgcatctgaa gccccccagg   1440
atgtgaccta cgcccggctg cacagcttta ccctcagaca gaaggcaact gagcctcctc   1500
catcccagga aggggcctct ccagctgagc ccagtgtcta tgccactctg gccatccact   1560
aatccagggg ggacccagac cccacaagcc atggagactc aggaccccag aaggcatgga   1620
agctgcctcc agtagacatc actgaacccc agccagccca gacccctgac acagaccact   1680
agaagattcc gggaacgttg ggagtcacct gattctgcaa agataaataa tatccctgca   1740
ttatcaaaat aaagtagcag acctctcaat tcacaatgag ttaactgata aaacaaaaca   1800
gaagtcagac aatgttttaa attgaatgat catgtaaata ttacacatca aaccaatgac   1860
atgggaaaat gggagcttct aatgaggaca aacaaaaaat agagaaaaat taataaagtc   1920
aaaatgttta ttcttgaaaa cattaatgat acatgaatct tggccacaat gagaaaaata   1980
aaaatgaaaa aagagcaggc atccatttcc atacaggaac aaaataggag gcagcactac   2040
agaccctaca cacagcttta cagaggtgaa agaaaactgt cagcaattct atgctgacat   2100
aacagaaaat gtagatgaga tagatgaaat acgaaaaatt acagtttact taatgaacat   2160
aaggataaat agaaaaactg aatcatcata cataaacata tataaaatgc attgatcctg   2220
taatcaaaaa tgttcccaca aagtaaatgc cacttcagca aggtttgttg gtggtttttt   2280
caaactctta tgcactcatg aaacacacag acacacacac acacaaactt gcataaattt   2340
tccctgagaa tattttgtat atatttacac aaatacattt gatcagacta ggaacaagtt   2400
gataccaaaa cctgaaaagg aaactacaga atgggaaagt catagaagat ctctcacaga   2460
aatataaatc ccttaacaaa tattaacaag taagattcat gtctctataa aatagacagt   2520
atatcatgac cacactggtt ttttgttatc ctttgatttt gtttatgaaa agcaaggata   2580
gcttaatttt caaaaactca atcaatgtaa ttcagtattt taacaaaagg aatgaaaaat   2640
tatcatctca atagacaaag cttttgtctg agcacctttt catatagctg ctgaccattt   2700
gtatgtcttc ttttgagaaa tgcctgttca gctactttgc ccatgtttca agtagttttt   2760
ggtttcttgc tgttgctttg ttttagttcc ttacatattt ttgcatatta accctttatc   2820
aggtatacag cttgcaacta ttttctccca tttctgagtt gtctcttcat tctgtttgca   2880
gaagctgttt agaagccaca ccttttgtct atttttgctt ttgttgcttg tgttttcagg   2940
gccatatcca aaaaaacctt gcccggacca acgtcttgaa gcttttctcc caccccatttt  3000
tgtatatggg ataagggttc aatttcattc ttcttcatat gaatatcccc aggatgtgtc   3060
ctatgcccag ctgcacagct taccctcaaa cagaaaataa tgaagccttc ttcctcccag   3120
gaaaggggac gttcagctga gccgagtgtg tatactgctc tggccatcca ctagcccagg   3180
gaggacccag acctccacac tccatggaga ctcagttctc ctaggaccat ttattcaaaa   3240
ggactgccct ctcttgttct tggaaacttt gttgaggatc aattcaccat aaatatgtgt   3300
gtttccttct ttgctttcat ccctgttgca ctgatcactg tacctgtttc tattccagtt   3360
ccatgatgtc ttcctggctg tagctttgta ggatatttgg ggattccata gtgtgatatc   3420
cccttcttcc ctttgctcaa gattgttttg gctatttggg gtccttttgt agtcccattc   3480
aaattttagg attgtttttc tatttctgtg gaaaacgacc ttggaatttt gttaggaatt   3540
gcattgagtc tgcaggtatg aacttttttt taaagttcca gggcacatgt acaggacctg   3600
```

```
cagctttgtt acataggtag gcttgtgcca tggtggtttg ctgcacctat caacccatta   3660

cctagttatt aagcccagca tgcattagct ctttttcctg atgctctccc tcccttcatc   3720

atccgccctc ccactacaag ccccagtgtg tgttgttccc ctccctgtgt ccatgtgttc   3780

tcattgttat acgaacattt taacaatgtt aattcttgca gaccatgaac ataagctacc   3840

ttcccattta tatgcgtctt gttcaatttc attcatcaat gttataaaga ttttagtgca   3900

ga                                                                  3902
```

<210> SEQ ID NO 68
<211> LENGTH: 1179
<212> TYPE: DNA
<213> ORGANISM: Homo sapiens

<400> SEQUENCE: 68

```
acagttgaga ggagtttgag tggagattca gggccatttt agtatcttct gtaggacaga     60

ggtcagcaag catgccccag aggtacagat gtatatgtct cccaggaagt ctctgtgggt    120

gaaggactga tctcaagttg tggctgacac tagttaaagc caagttagag ggctgtttca    180

gggtctacat tgagactaca gttgatatgc ctacctcctg agacactagt gtgtgagtct    240

cctcctgggc ccctgggcaa atggttttgg cagcatgacc aaggcctaaa tggggctgaa    300

ggcaagcaca ggaggatggg tccctttca ggtctggaga tggaatcact gttgctatag    360

caggcctttt tatgagacta acctggcctc tccactaaag gatgtgtgac tttctgggga    420

cagaagagta cagtccctga catcacacac tgcagagatg gataaccaag gagtaatcta    480

ctcagacctg aatctgcccc caaacccaaa gaggcagcaa cgaaaaccta aaggcaataa    540

aagctccatt ttagcaactg aacaggaaat aacctatgcg gaattaaacc ttcaaaaagc    600

ttctcaggat tttcaaggga atgacaaaac ctatcactgc aaagatttac catcagctcc    660

agagaagctc attgttggga tcctgggaat tatctgtctt atcttaatgg cctctgtggt    720

aacgatagtt gttattccct ctacattaat acagaggcac aacaattctt ccctgaatac    780

aagaactcag aaagcacgtc attgtggcca ttgtcctgag gagtggatta catattccaa    840

cagttgttac tacattggta aggaaagaag aacttgggaa gagagtttgc tggcctgtac    900

ttcgaagaac tccagtctgc tttctataga taatgaagaa gaaatgaaat ttctgtccat    960

catttcacca tcctcatgga ttggtgtgtt tcgtaacagc agtcatcatc catgggtgac   1020

aatgaatggt ttggctttca aacatgagat aaaagactca gataatgctg aacttaactg   1080

tgcagtgcta caagtaaatc gacttaaatc agcccagtgt ggatcttcaa taatatatca   1140

ttaaacttgt taatttaata caatttacaa cacacctgc                          1179
```

<210> SEQ ID NO 69
<211> LENGTH: 1506
<212> TYPE: DNA
<213> ORGANISM: Homo sapiens

<400> SEQUENCE: 69

```
gcaggaggga ggccggcccc ctagtaggaa atgagacaca gtagaaataa cactttataa     60

gcctcttcct cctcccatct cctggcctcc ttccatcctc ctctgcccag actccgcccc    120

tcccagacgg tcctcacttc tcttttccct agactgcagc cagcggagcc cgcagccggc    180

ccgagccagg aacccaggtc cggagcctca acttcaggat gttgacaaca ttgctgccga    240

tactgctgct gtctggctgg gccttttgta gccaagacgc ctcagatggc ctccaaagac    300
```

```
ttcatatgct ccagatctcc tacttccgcg acccctatca cgtgtggtac cagggcaacg    360
cgtcgctggg gggacaccta acgcacgtgc tggaaggccc agacaccaac accacgatca    420
ttcagctgca gcccttgcag gagcccgaga gctgggcgcg cacgcagagt ggcctgcagt    480
cctacctgct ccagttccac ggcctcgtgc gcctggtgca ccaggagcgg accttggcct    540
ttcctctgac catccgctgc ttcctgggct gtgagctgcc tcccgagggc tctagagccc    600
atgtcttctt cgaagtggct gtgaatggga gctcctttgt gagtttccgg ccggagagag    660
ccttgtggca ggcagacacc caggtcacct ccggagtggt caccttcacc ctgcagcagc    720
tcaatgccta caaccgcact cggtatgaac tgcgggaatt cctggaggac acctgtgtgc    780
agtatgtgca gaaacatatt tccgcggaaa acacgaaagg gagccaaaca agccgctcct    840
acacttcgct ggtcctgggc gtcctggtgg gcagtttcat cattgctggt gtggctgtag    900
gcatcttcct gtgcacaggt ggacggcgat gttaattact ctccagcccc ctcagaaggg    960
gctggattga tggaggctgg caagggaaag tttcagctca ctgtgaagcc agactcccca   1020
actgaaacac cagaaggttt ggagtgacag ctcctttctt ctcccacatc tgcccactga   1080
agatttgagg gaggggagat ggagaggaga ggtggacaaa gtacttggtt tgctaagaac   1140
ctaagaacgt gtatgctttg ctgaattagt ctgataagtg aatgtttatc tatctttgtg   1200
gaaaacagat aatggagttg gggcaggaag cctatggccc atcctccaaa gacagacaga   1260
atcacctgag gcgttcaaaa gatataacca aataaacaag tcatccacaa tcaaaataca   1320
acattcaata cttccaggtg tgtcagactt gggatgggac gctgatataa tagggtagaa   1380
agaagtaaca cgaagaagtg gtggaaatgt aaaatccaag tcatatggca gtgatcaatt   1440
attaatcaat taataatatt aataaatttc ttatatttaa ggcaaaaaaa aaaaaaaaaa   1500
aaaaaa                                                              1506
```

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147
<211> LENGTH: 288
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 147

```
Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Pro Ala Pro Ser Pro Ala Phe
    50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
            100                 105                 110

Ala Ala Asp Ala Pro Pro Pro Thr Met Arg Val Ala Val Thr Ala Ala
        115                 120                 125

Arg Pro Pro Arg Ala Lys Pro Ala Pro Arg Arg Arg Ala Ala Gln Pro
    130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175

Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln Asp Met Ile Ala Ala Leu Pro Glu Ala Thr His Glu Ala
```

```
    210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
            260                 265                 270

Glu Ala Val His Ala Trp Arg Asn Ala Leu Thr Gly Ala Pro Leu Asn
        275                 280                 285


<210> SEQ ID NO 148
<211> LENGTH: 183
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
        35                  40                  45

Pro Ala Leu Ile Lys Arg Thr Asn Arg Arg Ile Pro Glu Arg Thr Ser
    50                  55                  60

His Arg Val Ala Asp His Ala Gln Val Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
        115                 120                 125

Arg Trp Asp Arg Ile Leu Gln Ala Ser Gly Met Lys Arg Ala Lys Pro
    130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
            180


<210> SEQ ID NO 149
<211> LENGTH: 7
<212> TYPE: PRT
<213> ORGANISM: Simian virus 40

<400> SEQUENCE: 149

Pro Lys Lys Lys Arg Lys Val
1               5


<210> SEQ ID NO 150
<211> LENGTH: 16
<212> TYPE: PRT
<213> ORGANISM: Unknown
<220> FEATURE:
<223> OTHER INFORMATION: Description of Unknown:
```

Nucleoplasmin bipartite NLS sequence

<400> SEQUENCE: 150

Lys Arg Pro Ala Ala Thr Lys Lys Ala Gly Gln Ala Lys Lys Lys Lys
1 5 10 15

<210> SEQ ID NO 151
<211> LENGTH: 9
<212> TYPE: PRT
<213> ORGANISM: Unknown
<220> FEATURE:
<223> OTHER INFORMATION: Description of Unknown:
C-myc NLS sequence

<400> SEQUENCE: 151

Pro Ala Ala Lys Arg Val Lys Leu Asp
1 5

<210> SEQ ID NO 152
<211> LENGTH: 11
<212> TYPE: PRT
<213> ORGANISM: Unknown
<220> FEATURE:
<223> OTHER INFORMATION: Description of Unknown:
C-myc NLS sequence

<400> SEQUENCE: 152

Arg Gln Arg Arg Asn Glu Leu Lys Arg Ser Pro
1 5 10

<210> SEQ ID NO 153
<211> LENGTH: 38
<212> TYPE: PRT
<213> ORGANISM: Homo sapiens

<400> SEQUENCE: 153

Asn Gln Ser Ser Asn Phe Gly Pro Met Lys Gly Gly Asn Phe Gly Gly
1 5 10 15

Arg Ser Ser Gly Pro Tyr Gly Gly Gly Gly Gln Tyr Phe Ala Lys Pro
20 25 30

Arg Asn Gln Gly Gly Tyr
35

<210> SEQ ID NO 154
<211> LENGTH: 42
<212> TYPE: PRT
<213> ORGANISM: Unknown
<220> FEATURE:
<223> OTHER INFORMATION: Description of Unknown:
IBB domain from importin-alpha sequence

<400> SEQUENCE: 154

Arg Met Arg Ile Glx Phe Lys Asn Lys Gly Lys Asp Thr Ala Glu Leu
1 5 10 15

Arg Arg Arg Arg Val Glu Val Ser Val Glu Leu Arg Lys Ala Lys Lys
20 25 30

Asp Glu Gln Ile Leu Lys Arg Arg Asn Val
35 40

<210> SEQ ID NO 155
<211> LENGTH: 8
<212> TYPE: PRT
<213> ORGANISM: Unknown
<220> FEATURE:
<223> OTHER INFORMATION: Description of Unknown:

Myoma T protein sequence

<400> SEQUENCE: 155

Val Ser Arg Lys Arg Pro Arg Pro
1 5

<210> SEQ ID NO 156
<211> LENGTH: 8
<212> TYPE: PRT
<213> ORGANISM: Unknown
<220> FEATURE:
<223> OTHER INFORMATION: Description of Unknown:
Myoma T protein sequence

<400> SEQUENCE: 156

Pro Pro Lys Lys Ala Arg Glu Asp
1 5

<210> SEQ ID NO 157
<211> LENGTH: 8
<212> TYPE: PRT
<213> ORGANISM: Homo sapiens

<400> SEQUENCE: 157

Pro Gln Pro Lys Lys Lys Pro Leu
1 5

<210> SEQ ID NO 158
<211> LENGTH: 12
<212> TYPE: PRT
<213> ORGANISM: Mus musculus

<400> SEQUENCE: 158

Ser Ala Leu Ile Lys Lys Lys Lys Lys Met Ala Pro
1 5 10

<210> SEQ ID NO 159
<211> LENGTH: 5
<212> TYPE: PRT
<213> ORGANISM: Influenza virus

<400> SEQUENCE: 159

Asp Arg Leu Arg Arg
1 5

<210> SEQ ID NO 160
<211> LENGTH: 7
<212> TYPE: PRT
<213> ORGANISM: Influenza virus

<400> SEQUENCE: 160

Pro Lys Gln Lys Lys Arg Lys
1 5

<210> SEQ ID NO 161
<211> LENGTH: 10
<212> TYPE: PRT
<213> ORGANISM: Hepatitis delta virus

<400> SEQUENCE: 161

Arg Lys Leu Lys Lys Lys Ile Lys Lys Leu
1 5 10

<210> SEQ ID NO 162
<211> LENGTH: 10

```
<212> TYPE: PRT
<213> ORGANISM: Mus musculus

<400> SEQUENCE: 162

Arg Glu Lys Lys Lys Phe Leu Lys Arg Arg
1               5                   10


<210> SEQ ID NO 163
<211> LENGTH: 20
<212> TYPE: PRT
<213> ORGANISM: Homo sapiens

<400> SEQUENCE: 163

Lys Arg Lys Gly Asp Glu Val Asp Gly Val Asp Glu Val Ala Lys Lys
1               5                   10                  15

Lys Ser Lys Lys
            20


<210> SEQ ID NO 164
<211> LENGTH: 17
<212> TYPE: PRT
<213> ORGANISM: Homo sapiens

<400> SEQUENCE: 164

Arg Lys Cys Leu Gln Ala Gly Met Asn Leu Glu Ala Arg Lys Thr Lys
1               5                   10                  15

Lys


<210> SEQ ID NO 165
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aminohexanoyl
<220> FEATURE:
<221> NAME/KEY: MOD_RES
<222> LOCATION: (5)..(5)
<223> OTHER INFORMATION: Aminohexanoyl
<220> FEATURE:
<221> NAME/KEY: MOD_RES
<222> LOCATION: (8)..(8)
<223> OTHER INFORMATION: Aminohexanoyl
<220> FEATURE:
<221> NAME/KEY: MOD_RES
<222> LOCATION: (11)..(11)
<223> OTHER INFORMATION: Aminohexanoyl

<400> SEQUENCE: 165

Arg Xaa Arg Arg Xaa Arg Arg Xaa Arg Arg Xaa Arg
1               5                   10
```

MODULATION OF NOVEL IMMUNE CHECKPOINT TARGETS

CROSS-REFERENCE TO RELATED APPLICATIONS

This application is the National Phase of International Patent Application No. PCT/US2016/056177 filed Oct. 7, 2016 published on Apr. 27, 2017 as WO 2017/069958 A2, which claims priority to U.S. Provisional Application No. 62/239,548, filed Oct. 9, 2015. The contents of these applications are herein incorporated by reference in their entirety.

FEDERAL FUNDING LEGEND

This invention was made with government support under grant numbers NS076410, AI0562999, NS045937, AI039671, AI045757, AI073748, CA187975 and awarded by the National Institutes of Health. The government has certain rights in the invention.

SEQUENCE LISTING

The instant application contains a Sequence Listing which has been submitted in ASCII format via EFS-WEB and is hereby incorporated by reference in its entirety. Said ASCII copy, created on Aug. 28, 2020, is named BROD-5245US.txt and is 300,691 bytes.

RELATED APPLICATIONS AND INCORPORATION BY REFERENCE

Reference is made to U.S. provisional application Ser. No. 62/239,548 filed on Oct. 9, 2015.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present disclosure relates to the modulation of T cell dysfunction.

BACKGROUND OF THE INVENTION

The following discussion is merely provided to aid the reader in understanding the disclosure and is not admitted to describe or constitute prior art thereto.

T cell dysfunction or exhaustion is a state of T cell differentiation that arises in chronic disease settings such as chronic viral infections and cancer. Dysfunctional T cells exhibit diverse deficits in effector functions, including impaired proliferative capacity, cytotoxicity, and production of pro-inflammatory cytokines (Pardoll, D. M. (2012) *Nature reviews. Cancer* 12, 252-264; Wherry and Kurachi, (2015) *Nature reviews Immunology* 15, 486-499). Consequently, dysfunctional T cells are poor mediators of both viral and tumor clearance. Dysfunctional T cells express high levels of co-inhibitory receptors, such as Programmed cell death 1 (PD-1) and cytotoxic T-lymphocyte-associated protein 4 (CTLA-4), and blockade of these receptors is associated with recovery of effector T cell responses in multiple experimental models of chronic viral infection and Consequently, exhausted T cells are poor mediators of viral and/or tumor clearance. Exhausted T cells have been noted to express high levels of co-inhibitory receptors, such as PD-1 and CTLA-4, and blockade of these receptors has been associated with the recovery of effector T cell responses in experimental models of chronic viral infection and cancer (Leach, D. R., et al., (1996) *Science* 271, 1734-1736; Barber, D. L. et al. (2006) *Nature* 439, 682-687; Mahoney et al., (2015) *Nature reviews Drug discovery* 14, 561-584; Wherry and Kurachi, 2015). Indeed, therapeutic blockade of CTLA-4 and PD-1 has been successfully translated to the clinic for the treatment several human cancers (Hodi, F. S. et al., (2010) *The New England journal of medicine* 363, 711-723; Robert, C. et al., (2011) *The New England journal of medicine* 364, 2517-2526, Hamid, O. et al., (2013) *The New England journal of medicine* 369, 134-144; Topalian et al., (2012) *The New England journal of medicine* 366, 2443-2454).

CTLA-4 and PD-1 are not the only co-inhibitory receptors that are expressed by dysfunctional T cells. In fact, as described herein, dysfunctional T cells express multiple co-inhibitory receptors including TIM-3, LAG-3, and TIGIT, indicating shared regulatory mechanisms driving their expression. Importantly, as dysfunctional T cells accumulate expression of co-inhibitory receptors they develop a "deep" state of dysfunction and begin to produce IL-10, which further contributes to local immune suppression (Wherry, E. J. (2011) *Nature immunology* 12, 492-499). Thus, the co-expression of co-inhibitory receptors on dysfunctional T cells has important functional consequences. Indeed, combination therapies that simultaneously target multiple co-inhibitory pathways, such as CTLA-4 together with PD-1, or PD-1 together with TIM-3, LAG-3, or TIGIT, are more potent at restoring anti-tumor immunity than blockade of single co-inhibitory targets in both humans and in experimental mouse tumor models (Wolchok, J. D. et al. (2013) *The New England journal of medicine* 369, 122-133; Woo, S. R. et al. (2012) *Cancer research* 72, 917-927; Johnston, R. J. et al. (2014) *Cancer cell* 26, 923-937; Fourcade, J. et al. (2014) *Cancer research* 74, 1045-1055). Together these observations raise the important issue of understanding how co-inhibitory receptors are induced and co-regulated in exhausted or dysfunctional T cells.

Dysfunctional T cells express multiple co-inhibitory receptors in addition to CTLA-4 and PD-1, including T-cell immunoglobulin and mucin-domain containing-3 (Tim-3), Lymphocyte-activation gene 3 (Lag-3), and T cell immunoreceptor with Ig and ITIM domains (TIGIT); (Anderson et al., (2016) *Immunity* 44, 989-1004; Wherry and Kurachi, 2015). The extent of co-inhibitory receptor co-expression is directly correlated to the severity of dysfunctional phenotype (Wherry and Kurachi, 2015). Thus, combination therapies that simultaneously target multiple co-inhibitory pathways, such as PD-1 together with CTLA-4 are more efficacious at restoring anti-tumor immunity than blockade of single co-inhibitory targets in both mouse tumor models and patients (Fourcade et al., 2014; Johnston et al., 2014; Sakuishi et al., (2010) *The Journal of experimental medicine* 207, 2187-2194; Wolchok et al., 2013; Woo et al., 2012).

Unfortunately, even with combination therapy, a substantial number of patients fail to respond to immune checkpoint blockade, highlighting the importance of identifying additional co-inhibitory receptors that could be targeted for cancer immunotherapy.

The co-expression and co-regulation of co-inhibitory receptors in dysfunctional T cells, suggests that there might be a common trigger that induces them and common regulatory mechanisms that control their expression in dysfunctional T cells. If such common triggers and regulators exist, they may facilitate the development of more efficacious therapies that will simultaneously antagonize multiple co-inhibitory receptors. However, such common mechanisms have not been identified to date.

One compelling candidate for a common trigger is IL-27, a heterodimeric cytokine and a member of the IL-12 family of cytokines that is produced by antigen presenting cells. Although IL-27 was initially shown to promote pro-inflammatory Type 1 immune responses, emerging evidence suggests that this cytokine plays an important role in the resolution of tissue inflammation (Yoshida and Hunter, (2015) *Annual review of immunology* 33, 417-443). IL-27 administration in vivo suppresses the pathogenicity of primed effector T cells and inhibits the development of autoimmunity (Fitzgerald et al., (2007a) *Journal of immunology* 179, 3268-3275). Consistent with a suppressive function for IL-27, IL-27ra (WSX-1) deficient mice exhibit increased inflammation during *Toxoplasma gondii* infection and exacerbated disease in a model of central nervous system autoimmunity (Awasthi et al., (2007) *Nature immunology* 8, 1380-1389; Hirahara et al., (2012) *Immunity* 36, 1017-1030; Villarino et al., (2003) *Immunity* 19, 645-655). Indeed, Applicants (Awasthi et al., 2007) and others (Fitzgerald et al., 2007a; Stumhofer et al., (2007) *Nature immunology* 8, 1363-1371) have shown that exposure of naïve T cells to IL-27 induces IL-10-secreting Type 1 regulatory (Tr1) cells that are immune suppressive. Moreover, Applicants have recently shown that IL-27 induces Tim-3 (Zhu et al., (2015) *Nature communications* 6, 6072), which has been shown to cooperate with PD-1 in promoting a dysfunctional phenotype in T cells (Sakuishi et al., 2010). Taken together, these observations raise the possibility that IL-27 may be one of the triggers that induces multiple co-inhibitory receptors, which in turn promote T cell dysfunction in effector T cells.

Citation or identification of any document in this application is not an admission that such document is available as prior art to the present invention.

SUMMARY OF THE INVENTION

Here, Applicants used a systems biology approach, to find that IL-27 signaling drives the expression of a gene module that includes not only Tim-3, but also Lag-3, TIGIT, and IL-10, all molecules that are associated with T cell dysfunction. The IL-27-induced transcriptional module significantly overlaps with the gene signatures that define dysfunctional T cells in chronic viral infection and cancer, as well as with gene signatures associated with other suppressed or tolerant T cell states. Applicants further identify a number of novel molecules within the IL-27-induced gene module that mediate T cell dysfunction and can be modulated to improve anti-tumor T cell responses in vivo. Finally, using network-based approaches Applicants identify Prdm1 and c-Maf as key transcriptional regulators that cooperatively drive the inhibitory gene module. Our study defines a new role for IL-27 signaling in immune regulation and uncovers the downstream regulatory network that drives the expression of an inhibitory gene module that sets the stage for the development of dysfunctional phenotype in effector T cells.

Accordingly, the methods and compositions described herein are based, in part, on the discovery of target gene(s) that are involved in T cell dysfunction, including but not limited to, T cell exhaustion and T cell non-responsiveness. Accordingly, provided herein are methods and compositions for modulating T cell dysfunction by modulating the expression, activity and/or function of at least one target gene or gene product, for example, the target genes listed herein in Table 1, Table 10, Table 11, Table 12, Table 13 or the pairs of target genes listed herein in Table 2, or any combination thereof.

In one aspect, provided herein is a method of modulating T-cell dysfunction, the method comprising contacting a dysfunctional T-cell with a modulating agent or agents that modulate the expression, activity and/or function of one or more target genes or gene products thereof selected from the target genes listed in Table 1, Table 2, Table 10, Table 11, Table 12, Table 13 or any combination thereof.

In one embodiment of this aspect and all other aspects provided herein, the T-cell dysfunction is T-cell exhaustion.

In another embodiment of this aspect and all other aspects provided herein, the modulation of T-cell exhaustion comprises a decrease in the exhausted T-cell phenotype, such that functional T-cell activity is increased.

In another embodiment of this aspect and all other aspects provided herein, the modulation of T-cell exhaustion comprises an increase in the exhausted T-cell phenotype, such that functional T-cell activity is decreased.

In another embodiment of this aspect and all other aspects provided herein, the selected target gene or gene product or a combination thereof is/are identified as participating in the inhibition of functional T-cell activity.

In another embodiment of this aspect and all other aspects provided herein, the modulating agent inhibits the expression, activity and/or function of the selected target gene or gene product or combination thereof.

In another embodiment of this aspect and all other aspects provided herein, the selected target gene or combination of target genes is/are identified as participating in the promotion of functional T-cell activity.

In another embodiment of this aspect and all other aspects provided herein, the modulating agent promotes or activates the expression, activity and/or function of the selected target gene or gene product or combination thereof.

In another embodiment of this aspect and all other aspects provided herein, the method further comprises contacting the dysfunctional T-cell with modulating agents that modulate the expression, activity and/or function of at least two target genes or gene products selected from the target genes listed in Table 1, Table 2, or any combination thereof.

In another embodiment of this aspect and all other aspects provided herein, the modulating agent comprises a peptide agent, polypeptide agent, a soluble variant of a membrane-associated polypeptide, antibody or antigen-binding fragment thereof agent, a nucleic acid agent, a nucleic acid ligand, or a small molecule agent.

In another embodiment of this aspect and all other aspects provided herein, the methods can further comprise contacting the dysfunctional T-cell with an agent or treatment selected from the group consisting of a PD-1 inhibitor, CTLA4 inhibitor, chemotherapy, radiation therapy, a Braf inhibitor, a MEK inhibitor, a Sting agonist, a TLR agonist, an IDO inhibitor, and an activator or agonist for OX-40, 4-1BB, GITR, CD226, KLRC2, KLRE1, KLRK1, IL12RB1, IL1R1, and/or SLAMF7.

Another aspect provided herein relates to a method of treating a condition involving or characterized by the presence of T cells exhibiting an exhausted or dysfunctional phenotype, the method comprising administering an amount of a modulating agent effective to modulate the expression, activity and/or function of one or more target genes or gene products thereof selected from the target genes listed in Table 1, Table 2, or any combination thereof.

In one embodiment of this aspect and all other aspects provided herein, the condition is cancer or a persistent infection.

In another embodiment of this aspect and all other aspects provided herein, the selected target gene or combination of target genes is/are identified as participating in the inhibition of T cell activation.

In another embodiment of this aspect and all other aspects provided herein, the modulating agent inhibits the expression, activity and/or function of the target gene or gene product or combination thereof.

In another embodiment of this aspect and all other aspects provided herein, a selected target gene or combination of target genes is/are identified as participating in the promotion of T cell activation.

In another embodiment of this aspect and all other aspects provided herein, the modulating agent promotes or activates the expression, activity and/or function of the target gene or gene product or combination thereof.

In another embodiment of this aspect and all other aspects provided herein, the modulating agent comprises a peptide agent, polypeptide agent, a soluble variant of a membrane-associated polypeptide, antibody or antigen-binding fragment agent, a nucleic acid agent, a nucleic acid ligand, or a small molecule agent.

Provided herein in another aspect is a pharmaceutical composition for modulating T cell dysfunction, the composition comprising a first modulating agent and a second modulating agent that modulate the expression, activity and/or function of two or more target genes or gene products thereof selected from the target genes listed in Table 1, Table 2, Table 10, Table 11, Table 12, Table 13 or any combination thereof.

Another aspect provided herein relates to a pharmaceutical composition for modulating T cell dysfunction, the composition comprising a first modulating agent that inhibits the expression, activity and/or function of one or more target genes or gene products thereof selected from the target genes listed in Table 1, Table 2, Table 10, Table 11, Table 12, Table 13 or any combination thereof and a second modulating agent that promotes the expression, activity and/or function of one or more target genes or gene products thereof selected from the target genes listed in Table 1, Table 2, Table 10, Table 11, Table 12, Table 13 or any combination thereof.

Also provided herein, in another aspect, is a pharmaceutical composition for modulating T cell dysfunction, the composition comprising a modulating agent that modulates the expression, activity and/or function of one or more target genes or gene products thereof selected from the target genes listed in Table 1, Table 2, Table 10, Table 11, Table 12, Table 13 or any combination thereof and an agent selected from the group consisting of a PD-1 inhibitor, a CTLA4 inhibitor, chemotherapy, a Braf inhibitor, a MEK inhibitor, a Sting agonist, a TLR agonist, an IDO inhibitor, and an agonist for OX-40, 4-1BB, GITR, CD226, KLRC2, KLRE1, KLRK1, IL12RB1, IL1R, and SLAMF7.

Also provided herein, in another aspect, are pharmaceutical compositions for modulating T cell dysfunction, the composition comprising at least one modulating agent that modulates the expression, activity and/or function of one or more target genes or gene products thereof selected from the target genes listed in Table 1, Table 2, Table 10, Table 11, Table 12, Table 13 or any combination thereof. In another aspect, the pharmaceutical compositions comprise at least two modulating agents that modulate the expression, activity and/or function of one or more target genes or gene products thereof selected from the target genes listed in Table 1, Table 2, Table 10, Table 11, Table 12, Table 13 or any combination thereof.

Also provided herein, in another aspect, are pharmaceutical compositions for modulating T cell dysfunction, the composition comprising at least one modulating agent that modulates the expression, activity and/or function of one or more target genes or gene products thereof selected from the target genes listed in Table 5, Table 6, Table 7, Table 8, Table 9 or any combination thereof. In another aspect, the pharmaceutical compositions comprise at least two modulating agents that modulate the expression, activity and/or function of one or more target genes or gene products thereof selected from the target genes listed in Table 5, Table 6, Table 7, Table 8, Table 9 or any combination thereof.

In one embodiment of this aspect and all other aspects provided herein, the T cell dysfunction comprises T cell exhaustion.

In another embodiment of this aspect and all other aspects provided herein, the T cell exhaustion occurs in an individual with cancer or a persistent infection.

Another aspect provided herein relates to a pharmaceutical composition for modulating T cell dysfunction, the composition comprising an inhibitor of the expression and/or activity of PDPN, an inhibitor of the expression and/or activity of PROCR, or a combination thereof.

Also provided herein in another aspect is a pharmaceutical composition for modulating T cell dysfunction comprising: (a) an inhibitor of the expression and/or activity of PDPN and an inhibitor of the expression and/or activity of PROCR; and (b) an inhibitor of the expression and/or activity of at least one of the molecules selected from the group consisting of TIGIT, LAG3, LILRB4, and KLRC1; and/or an activator of the expression and/or activity of at least one of the molecules selected from the group consisting of CD226, OX-40, GITR, TNFSF9 (4-1BB), KLRC2, KLRE1, KLRK1, IL12RB1, IL1R, and SLAMF7.

Provided herein in another aspect is a pharmaceutical composition for modulating an IL-27-regulated co-inhibitory module comprising: (a) an inhibitor of the expression and/or activity of at least one of the molecules selected from the group consisting of PDPN, PROCR, TIGIT, LAG3, LILRB4, ALCAM, and KLRC1; and (b) an activator of the expression and/or activity of at least one of the molecules selected from the group consisting of CD226, OX-40, GITR, TNFSF9 (4-1BB), KLRC2, KLRE1, KLRK1, IL12RB1, IL1R1, and SLAMF7.

In one embodiment of this aspect and all other aspects provided herein, the composition further comprises an inhibitor of the expression and/or activity of TIM-3.

In another embodiment of this aspect and all other aspects provided herein, the composition further comprises an inhibitor of the expression and/or activity of PD-1.

In another embodiment of this aspect and all other aspects provided herein, the composition further comprises an inhibitor of the expression and/or activity of CTLA4.

In another embodiment of this aspect and all other aspects provided herein, the composition further comprises an inhibitor of the expression and/or activity of TIM-3 and an inhibitor of the expression and/or activity of PD-1. In another embodiment of this aspect and all other aspects provided herein, the composition further comprises an inhibitor of the expression and/or activity of TIM-3 and an inhibitor of the expression and/or activity of CTLA4. In another embodiment of this aspect and all other aspects provided herein, the composition further comprises an inhibitor of the expression and/or activity of CTLA4 and an inhibitor of the expression and/or activity of PD-1. In another embodiment of this aspect and all other aspects provided herein, the composition further comprises an inhibitor of the expression and/or activity of CTLA4, and an inhibitor of the expression and/or activity of PD-1 and an inhibitor of the expression and/or activity of TIM-3.

In another embodiment of this aspect and all other aspects provided herein, the inhibitors and activators are selected from an antibody or antigen binding fragment thereof, a small molecule compound, a protein or peptide molecule, a DNA or RNA aptamer, an antisense or siRNA molecule, and a structural analog.

In another embodiment of this aspect and all other aspects provided herein, the antibody or antigen binding fragment thereof, a small molecule compound, a protein or peptide molecule, a DNA or RNA aptamer, an antisense or siRNA molecule, and a structural analog is selected from: an anti-CTLA4 antibody, an anti-PD-1 antibody, or aPDL-1 antagonist. In certain embodiments, the antibody or antigen binding fragment thereof is selected from the group consisting of: nivolumab, pembrolizumab, lambrolizumab, ipilimumab, and atezolizumab.

Another aspect provided herein relates to a method of modulating an IL-27-regulated co-inhibitory module in a subject in need thereof, the method comprising administering a pharmaceutical composition comprising an inhibitor of the expression and/or activity of PDPN, an inhibitor of the expression and/or activity of PROCR, or a combination thereof.

An additional aspect provided herein relates to a method of modulating an IL-27-regulated co-inhibitory module in a subject in need thereof, the method comprising: (a) administering a pharmaceutical composition comprising an inhibitor of the expression and/or activity of PDPN, and an inhibitor of the expression and/or activity of PROCR; and (b) administering a pharmaceutical composition comprising an inhibitor of the expression and/or activity of at least one of the molecules selected from the group consisting of an inhibitor of the expression and/or activity of TIGIT, LAG3, LILRB4, and KLRC1; and/or an activator of the expression and/or activity of at least one of the molecules selected from the group consisting of CD226, OX-40, GITR, TNFSF9 (4-1BB), KLRC2, KLRE1, KLRK1, IL12RB1, IL1R1, and SLAMF7.

Also provided herein in another aspect is a method of modulating an IL-27-regulated co-inhibitory module in a subject in need thereof, the method comprising: (a) administering a pharmaceutical composition comprising an inhibitor of the expression and/or activity of at least one of the molecules selected from the group consisting of PDPN, PROCR, TIGIT, LAG3, LILRB4, ALCAM and KLRC1; and (b) administering a pharmaceutical composition comprising an activator the expression and/or activity of at least one of the molecules selected from the group consisting of CD226, OX-40, GITR, TNFSF9 (4-1BB), KLRC2, KLRE1, KLRK1, IL12RB1, IL1R1, and SLAMF7.

In one embodiment of this aspect and all other aspects provided herein, the method further comprises administering an inhibitor of the expression and/or activity of TIM-3.

In another embodiment of this aspect and all other aspects provided herein, the method further comprises administering an inhibitor of the expression and/or activity of PD-1.

In another embodiment of this aspect and all other aspects provided herein, the method further comprises administering an inhibitor of the expression and/or activity of CTLA-4.

In another embodiment of this aspect and all other aspects provided herein, the method further comprises administering an inhibitor of the expression and/or activity of TIM-3 and an inhibitor of the expression and/or activity of PD-1.

In another embodiment of this aspect and all other aspects provided herein, the inhibitors and activators are selected from an antibody or antigen binding fragment thereof, a small molecule compound, a protein or peptide molecule, a DNA or RNA aptamer, an antisense or siRNA molecule, and a structural analog.

In another embodiment of this aspect and all other aspects provided herein, the antibody or antigen binding fragment thereof, a small molecule compound, a protein or peptide molecule, a DNA or RNA aptamer, an antisense or siRNA molecule, and a structural analog is selected from the group consisting of: an anti-CTLA4 antibody, an anti-PD-1 antibody, or aPDL-1 antagonist. In certain embodiments, the antibody or antigen binding fragment thereof is selected from the group consisting of: nivolumab, pembrolizumab, lambrolizumab, ipilimumab, and atezolizumab.

In another embodiment of this aspect and all other aspects provided herein, the subject in need thereof has a disease or disorder characterized by T-cell exhaustion.

In another embodiment of this aspect and all other aspects provided herein, the subject in need thereof is diagnosed as having a cancer or tumor.

In another embodiment of this aspect and all other aspects provided herein, the subject in need thereof is diagnosed as having a chronic or persistent infection.

Also provided herein in another aspect is a method of modulating T cell dysfunction, the method comprising contacting a dysfunctional T cell with a modulating agent or agents that modulate the expression, activity and/or function of one or more target genes or gene products thereof selected from the group consisting of: the subset of genes listed in Table 5, the subset of genes listed in Table 6, the subset of genes listed in Table 7, the subset of genes listed in Table 8, and the subset of genes listed in Table 9.

In one embodiment of this aspect and all other aspects provided herein, the T cell dysfunction is T cell exhaustion.

In another embodiment of this aspect and all other aspects provided herein, the modulation of T cell exhaustion comprises a decrease in the exhausted T cell phenotype, such that T cell activation is increased.

In another embodiment of this aspect and all other aspects provided herein, the modulation of T cell exhaustion comprises an increase in the exhausted T cell phenotype, such that T cell activation is decreased.

In another embodiment of this aspect and all other aspects provided herein, the selected target gene or combination of target genes is/are identified as participating in the inhibition of T cell activation.

In another embodiment of this aspect and all other aspects provided herein, the modulating agent inhibits the expression, activity and/or function of the target gene or gene product or combination thereof.

In another embodiment of this aspect and all other aspects provided herein, the selected target gene or combination of target genes is/are identified as participating in the promotion of T cell activation.

In another embodiment of this aspect and all other aspects provided herein, the modulating agent promotes or activates the expression, activity and/or function of the target gene or gene product or combination thereof.

In another embodiment of this aspect and all other aspects provided herein, the modulating agent comprises a peptide agent, polypeptide agent, a soluble variant of a membrane-associated polypeptide, antibody agent, a nucleic acid agent, a nucleic acid ligand, or a small molecule agent.

Also provided herein in another aspect is a method of treating a condition involving or characterized by the presence of T cells exhibiting an exhausted phenotype, the method comprising administering an amount of a modulating agent effective to modulate the expression, activity and/or function of one or more target genes or gene products thereof selected from the group consisting of: the subset of genes listed in Table 5, the subset of genes listed in Table 6, the subset of genes listed in Table 7, the subset of genes listed in Table 8, and the subset of genes listed in Table 9.

In one embodiment of this aspect and all other aspects provided herein, the condition is cancer or a persistent infection.

In another embodiment of this aspect and all other aspects provided herein, the selected target gene or combination of target genes is/are identified as participating in the inhibition of T cell activation.

In another embodiment of this aspect and all other aspects provided herein, the modulating agent inhibits the expression, activity and/or function of the target gene or gene product or combination thereof.

In another embodiment of this aspect and all other aspects provided herein, the selected target gene or combination of target genes is/are identified as participating in the promotion of T cell activation.

In another embodiment of this aspect and all other aspects provided herein, the modulating agent promotes or activates the expression, activity and/or function of the target gene or gene product or combination thereof.

In another embodiment of this aspect and all other aspects provided herein, the agent comprises a peptide agent, polypeptide agent, a soluble variant of a membrane-associated polypeptide, antibody agent, a nucleic acid agent, a nucleic acid ligand, or a small molecule agent.

Another aspect provided herein relates to a method of determining the presence of T cells exhibiting an exhausted phenotype, the method comprising detecting, in a sample comprising T cells, a level of expression, activity and/or function of one or more genes or expression products thereof selected from the target genes listed in Table 1, Table 2 or any combination thereof, and comparing the detected level to a reference, wherein a difference in the detected level relative to the reference indicates the presence of T cells exhibiting an exhausted phenotype.

In one embodiment of this aspect and all other aspects provided herein, the sample is from an individual with cancer or a persistent infection.

In some aspects, provided herein are methods of treating a disease or disorder characterized by aberrant or unwanted T-cell functional activity in a subject in need thereof, the method comprising administering a therapeutically effective amount of a modulating agent effective to modulate the expression, activity and/or function of one or more target genes or gene products thereof selected from the target genes listed in Table 1, Table 2, or any combination thereof.

In one embodiment of this aspect and all other aspects provided herein, the disease or disorder is an autoimmune disease or graft vs. host disease.

In one embodiment of this aspect and all other aspects provided herein, the selected target gene or combination of target genes is/are identified as participating in the inhibition of T cell activation and the modulating agent promotes or activates the expression, activity and/or function of the target gene or gene product or combination thereof.

In another embodiment of this aspect and all other aspects provided herein, the selected target gene(s) is/are identified as participating in the promotion of T cell activation and the modulating agent inhibits the expression, activity and/or function of the target gene or gene product or combination thereof.

In one embodiment of this aspect and all other aspects provided herein, the modulating agent promotes or activates the expression, activity and/or function of the target gene or gene product or combination thereof.

In one embodiment of this aspect and all other aspects provided herein, the modulating agent comprises a peptide agent, polypeptide agent, a soluble variant of a membrane-associated polypeptide, antibody agent, a nucleic acid agent, a nucleic acid ligand, or a small molecule agent.

In some aspects, provided herein are methods of modulating T-cell dysfunction, the method comprising contacting a dysfunctional T-cell with a modulating agent or agents that modulate the expression, activity and/or function of one or more target genes or gene products thereof selected from the target genes listed in Table 5. In one embodiment of this aspect and all other aspects provided herein, two or more target genes or gene products thereof selected from the target genes listed in Table 5 are modulated.

In some aspects, provided herein are methods of modulating T-cell dysfunction, the method comprising contacting a dysfunctional T-cell with a modulating agent or agents that modulate the expression, activity and/or function of one or more target genes or gene products thereof selected from the target genes listed in Table 6. In one embodiment of this aspect and all other aspects provided herein, two or more target genes or gene products thereof selected from the target genes listed in Table 6 are modulated.

In some aspects, provided herein are methods of modulating T-cell dysfunction, the method comprising contacting a dysfunctional T-cell with a modulating agent or agents that modulate the expression, activity and/or function of one or more target genes or gene products thereof selected from the target genes listed in Table 7. In one embodiment of this aspect and all other aspects provided herein, two or more target genes or gene products thereof selected from the target genes listed in Table 7 are modulated.

In some aspects, provided herein are methods of modulating T-cell dysfunction, the method comprising contacting a dysfunctional T-cell with a modulating agent or agents that modulate the expression, activity and/or function of one or more target genes or gene products thereof selected from the target genes listed in Table 8. In one embodiment of this aspect and all other aspects provided herein, two or more target genes or gene products thereof selected from the target genes listed in Table 8 are modulated.

In some aspects, provided herein are methods of modulating T-cell dysfunction, the method comprising contacting a dysfunctional T-cell with a modulating agent or agents that modulate the expression, activity and/or function of one or more target genes or gene products thereof selected from the target genes listed in Table 9. In one embodiment of this aspect and all other aspects provided herein, two or more target genes or gene products thereof selected from the target genes listed in Table 9 are modulated.

In one embodiment of this aspect and all other aspects provided herein, the T-cell dysfunction is T-cell exhaustion.

In one embodiment of this aspect and all other aspects provided herein, the modulation of T-cell exhaustion comprises a decrease in the exhausted T-cell phenotype, such that functional T-cell activity is increased.

In another embodiment of this aspect and all other aspects provided herein, the modulation of T cell exhaustion comprises an increase in the exhausted T cell phenotype, such that T cell activation is decreased.

In one embodiment of this aspect and all other aspects provided herein, the selected target gene or gene product or a combination thereof is/are identified as participating in the inhibition of functional T-cell activity.

In one embodiment of this aspect and all other aspects provided herein, the modulating agent inhibits the expression, activity and/or function of the selected target gene or gene product or combination thereof.

In one embodiment of this aspect and all other aspects provided herein, the selected target gene or combination of target genes is/are identified as participating in the promotion of functional T-cell activity.

In one embodiment of this aspect and all other aspects provided herein, the modulating agent promotes or activates the expression, activity and/or function of the selected target gene or gene product or combination thereof.

In one embodiment of this aspect and all other aspects provided herein, the modulating agent comprises a peptide agent, polypeptide agent, a soluble variant of a membrane-associated polypeptide, antibody agent, a nucleic acid agent, a nucleic acid ligand, or a small molecule agent.

In one embodiment of this aspect and all other aspects provided herein, the method further comprises contacting the dysfunctional T-cell with an agent or treatment selected from the group consisting of a PD-1 inhibitor, a CTLA4 inhibitor, chemotherapy, radiation therapy, a Braf inhibitor, a MEK inhibitor, a Sting agonist, a TLR agonist, an IDO inhibitor, and an agonist for CD226, OX-40, GITR, TNFSF9 (4-1BB), KLRC2, KLRE1, KLRK1, IL12RB1, IL1R1, and/or SLAMF7.

Also provided herein in another aspect is method of treating a condition involving or characterized by the presence of T cells exhibiting a dysfunctional or exhausted phenotype, the method comprising administering an amount of a modulating agent effective to modulate the expression, activity and/or function of one or more target genes or gene products thereof selected from the target genes listed in Table 5, Table 6, Table 7, Table 8, or Table 9.

In one embodiment of this aspect and all other aspects provided herein, the condition is cancer or a persistent infection.

In one embodiment of this aspect and all other aspects provided herein, the selected target gene or combination of target genes is/are identified as participating in the inhibition of T cell activation.

In one embodiment of this aspect and all other aspects provided herein, the modulating agent inhibits the expression, activity and/or function of the target gene or gene product or combination thereof.

In one embodiment of this aspect and all other aspects provided herein, the selected target gene or combination of target genes is/are identified as participating in the promotion of T cell activation.

In one embodiment of this aspect and all other aspects provided herein, the modulating agent promotes or activates the expression, activity and/or function of the target gene or gene product or combination thereof.

In one embodiment of this aspect and all other aspects provided herein, the modulating agent comprises a peptide agent, polypeptide agent, a soluble variant of a membrane-associated polypeptide, antibody agent, a nucleic acid agent, a nucleic acid ligand, or a small molecule agent.

In some aspects, provided herein are pharmaceutical compositions for modulating T cell dysfunction, the composition comprising a first modulating agent and a second modulating agent that modulate the expression, activity and/or function of two or more target genes or gene products thereof selected from the target genes listed in Table 5, Table 6, Table 7, Table 8, or Table 9.

In some aspects, provided herein are pharmaceutical compositions for modulating T cell dysfunction, the composition comprising a first modulating agent that inhibits the expression, activity and/or function of one or more target genes or gene products thereof selected from the target genes listed in Table 5, Table 6, Table 7, Table 8, or Table 9 and a second modulating agent that promotes the expression, activity and/or function of one or more target genes or gene products thereof selected from the target genes listed in Table 5, Table 6, Table 7, Table 8, or Table 9.

In another aspect, the present invention provides for an isolated immune cell modified to comprise an altered expression or activity of at least one gene listed in Table 1 or Table 2. The immune cell may be a T cell, preferably a CD8+ T cell. In preferred embodiments, the immune cell is a CD8+ T cell. The immune cell may display tumor specificity. The immune cell may have been isolated from a tumor of a subject, preferably the immune cell is a tumor infiltrating lymphocyte. The immune cell may comprise a tumor-specific T cell receptor or a tumor-specific chimeric antigen receptor (CAR). Not being bound by a theory, modulation of expression or activity results in a more activated or less dysfunctional T cell. Not being bound by a theory, dysfunctional autologous T cells may be used for generating a CAR T cell. Alternatively, non-dysfunctional T cells may be used to generate CAR T cells that are modified to prevent them from becoming dysfunctional. The isolated immune cell may be modified to comprise downregulated or abolished expression or activity of at least one gene listed in Table 1 or Table 2. An endogenous gene may be modified, whereby the cell comprises downregulated or abolished expression or activity of at least one gene listed in Table 1 or Table 2. The endogenous gene may be modified using a nuclease. The nuclease may comprise (i) a DNA-binding portion configured to specifically bind to the endogenous sequence of at least one gene listed in Table 1 or Table 2 and (ii) a DNA cleavage portion. The DNA-binding portion may comprise a zinc finger protein or DNA-binding domain thereof, a transcription activator-like effector (TALE) protein or DNA-binding domain thereof, or an RNA-guided protein or DNA-binding domain thereof. The DNA-binding portion may comprise (i) a Cas protein modified to eliminate its nuclease activity, or (ii) DNA-binding domain of a Cas protein. The DNA cleavage portion may comprise FokI or variant thereof or DNA cleavage domain of FokI or variant thereof. The nuclease may be an RNA-guided nuclease, such as a Cas protein. The cell may comprise a protein comprising a DNA-binding portion configured to specifically bind to at least one gene listed in Table 1 or Table 2. The protein may be a heterologous repressor protein capable of repressing the transcription of at least one gene listed in Table 1 or Table 2. The heterologous repressor protein may comprise at least a DNA-binding portion configured to specifically bind to at least one gene listed in Table 1 or Table 2, preferably to the endogenous promoter of the gene. The heterologous repressor protein may comprise (i) a DNA-binding portion configured to specifically bind to at least one gene listed in Table 1 or Table 2, preferably to the endogenous promoter of the gene, and (ii) a transcription repression portion. The DNA-binding portion may comprise a zinc finger protein or DNA-binding domain thereof, TALE protein or DNA-binding domain thereof, or RNA-guided nuclease protein or DNA-binding domain thereof. The DNA-binding portion may comprise (i) a Cas protein modified to eliminate its nuclease activity, or (ii) DNA-binding domain of a Cas protein.

In another aspect, the present invention provides for an isolated immune cell modified to comprise an agent capable of inducibly altering expression or activity of at least one gene listed in Table 1 or Table 2. The agent may comprise: a nuclease capable of modifying at least one gene listed in Table 1 or Table 2, such as to downregulate or abolish expression of the gene, such as the nuclease as defined in any embodiment herein; or a heterologous repressor protein capable of repressing the transcription of the gene, such as the heterologous repressor protein as defined in any embodiment herein.

In another aspect, the present invention provides for an isolated immune cell modified to comprise an altered expression or activity of PDPN. The immune cell may be a T cell, preferably a CD8+ T cell. In preferred embodiments, the immune cell is a CD8+ T cell. The immune cell may display tumor specificity. The immune cell may have been isolated from a tumor of a subject, preferably the immune cell is a tumor infiltrating lymphocyte. The immune cell may comprise a tumor-specific T cell receptor or a tumor-specific chimeric antigen receptor (CAR). Not being bound by a theory, modulation of expression or activity results in a more activated or less dysfunctional T cell. Not being bound by a theory, dysfunctional autologous T cells may be used for generating a CAR T cell. Alternatively, non-dysfunctional T cells may be used to generate CAR T cells that are modified to prevent them from becoming dysfunctional. The isolated immune cell may be modified to comprise downregulated or abolished expression or activity of PDPN. The endogenous PDPN gene may be modified, whereby the cell comprises downregulated or abolished expression or activity of PDPN. The endogenous PDPN gene may be modified using a nuclease. The nuclease may comprise (i) a DNA-binding portion configured to specifically bind to the endogenous PDPN gene and (ii) a DNA cleavage portion. The DNA-binding portion may comprise a zinc finger protein or DNA-binding domain thereof, a transcription activator-like effector (TALE) protein or DNA-binding domain thereof, or an RNA-guided protein or DNA-binding domain thereof. The DNA-binding portion may comprise (i) a Cas protein modified to eliminate its nuclease activity, or (ii) DNA-binding domain of a Cas protein. The DNA cleavage portion may comprise FokI or variant thereof or DNA cleavage domain of FokI or variant thereof. The nuclease may be an RNA-guided nuclease, such as a Cas protein. The cell may comprise a protein comprising a DNA-binding portion configured to specifically bind to the endogenous PDPN gene. The protein may be a heterologous repressor protein capable of repressing the transcription of the endogenous PDPN gene. The heterologous repressor protein may comprise at least a DNA-binding portion configured to specifically bind to the endogenous PDPN gene, preferably to the endogenous PDPN gene promoter. The heterologous repressor protein may comprise (i) a DNA-binding portion configured to specifically bind to the endogenous PDPN gene, preferably to the endogenous PDPN gene promoter, and (ii) a transcription repression portion. The DNA-binding portion may comprise a zinc finger protein or DNA-binding domain thereof, TALE protein or DNA-binding domain thereof, or RNA-guided nuclease protein or DNA-binding domain thereof. The DNA-binding portion may comprise (i) a Cas protein modified to eliminate its nuclease activity, or (ii) DNA-binding domain of a Cas protein.

In another aspect, the present invention provides for an isolated immune cell modified to comprise an agent capable of inducibly altering expression or activity of PDPN. The agent may comprise: a nuclease capable of modifying the endogenous PDPN gene, such as to downregulate or abolish expression of PDPN, such as the nuclease as defined in any embodiment herein; or a heterologous repressor protein capable of repressing the transcription of the endogenous PDPN gene, such as the heterologous repressor protein as defined in any embodiment herein.

In another aspect, the present invention provides for an isolated immune cell modified to comprise an altered expression or activity of PRDM1 and/or c-MAF. The immune cell may be a T cell, preferably a CD8+ T cell. In preferred embodiments, the immune cell is a CD8+ T cell. The immune cell may display tumor specificity. The immune cell may have been isolated from a tumor of a subject, preferably the immune cell is a tumor infiltrating lymphocyte. The immune cell may comprise a tumor-specific chimeric antigen receptor (CAR). Not being bound by a theory, modulation of expression or activity results in a more activated or less dysfunctional T cell. Not being bound by a theory, dysfunctional autologous T cells may be used for generating a CAR T cell. Alternatively, non-dysfunctional T cells may be used to generate CAR T cells that are modified to prevent them from becoming dysfunctional. The isolated immune cell may be modified to comprise downregulated or abolished expression or activity of PRDM1 and/or c-MAF. The endogenous PRDM1 and c-MAF gene may be modified, whereby the cell comprises downregulated or abolished expression or activity of PRDM1 and/or c-MAF. Preferably, the cell comprises downregulated or abolished expression or activity of PRDM1 and c-MAF.

Alternatively, the endogenous PRDM1 and c-MAF genes may be modified, whereby the cell comprises upregulated expression or activity of PRDM1 and/or c-MAF. Alternatively, expression or activity may be modified by introducing a transgene. Not being bound by a theory, providing an immune cell with abolished expression or activity of both PRDM1 and c-MAF results in decreasing a dysfunctional phenotype of the immune cell or renders the immune cell more resistant to becoming dysfunctional, whereas a dysfunctional phenotype is not affected when only one of PRDM1 or c-MAF has abolished expression or activity. Not being bound by a theory, providing an immune cell with increased expression or activity of either one of or both of PRDM1 and/or c-MAF results in increasing a dysfunctional phenotype of the immune cell.

The endogenous PRDM1 and c-MAF genes may be modified using a nuclease. The nuclease may comprise (i) a DNA-binding portion configured to specifically bind to the endogenous PRDM1 and/or c-MAF gene and (ii) a DNA cleavage portion. The DNA-binding portion may comprise a zinc finger protein or DNA-binding domain thereof, a transcription activator-like effector (TALE) protein or DNA-binding domain thereof, or an RNA-guided protein or DNA-binding domain thereof. The DNA-binding portion may comprise (i) a Cas protein modified to eliminate its nuclease activity, or (ii) DNA-binding domain of a Cas protein. The DNA cleavage portion may comprise FokI or variant thereof or DNA cleavage domain of FokI or variant thereof. The nuclease may be an RNA-guided nuclease, such as a Cas protein. More than one guide RNA may be used to target PRDM1 and/or c-MAF. In certain embodiments, multiple guides target each gene. The cell may comprise a protein comprising a DNA-binding portion configured to specifically bind to the endogenous PRDM1 and/or c-MAF gene. The protein may be a heterologous repressor protein capable of repressing the transcription of the endogenous PRDM1 and/or c-MAF gene. The heterologous repressor protein may comprise at least a DNA-binding portion configured to specifically bind to the endogenous PRDM1 and/or c-MAF gene, preferably to the endogenous PRDM1 and/or c-MAF gene promoter. The heterologous repressor protein may comprise (i) a DNA-binding portion configured to specifically bind to the endogenous PRDM1 and/or c-MAF gene, preferably to the endogenous PRDM1 and/or c-MAF gene promoter, and (ii) a transcription repression portion. The DNA-binding portion may comprise a zinc finger protein or DNA-binding domain thereof, TALE protein or DNA-binding domain thereof, or RNA-guided nuclease protein or DNA-binding domain thereof. The DNA-binding portion may comprise (i) a Cas protein modified to eliminate its nuclease activity, or (ii) DNA-binding domain of a Cas protein.

In another aspect, the present invention provides for an isolated immune cell modified to comprise an agent capable of inducibly altering expression or activity of PRDM1 and/or c-MAF. The agent may comprise: a nuclease capable of modifying the endogenous PRDM1 and/or c-MAF gene, such as to downregulate or abolish expression of PRDM1 and c-MAF, such as the nuclease as defined in any embodiment herein; or a heterologous repressor protein capable of repressing the transcription of the endogenous PRDM1 and c-MAF gene, such as the heterologous repressor protein as defined in any embodiment herein. The agent may comprise more than one nuclease. In certain embodiments, the agent comprises more than one TALE or zinc finger protein, whereby one TALE or Zinc finger targets PRDM1 and one targets c-MAF. In other embodiments, the agent comprises more than two nucleases, capable of targeting multiple genes. In certain embodiments, a CRISPR-Cas system is used and multiple guide RNAs are used to target the CRISPR enzyme to multiple gene targets.

In another aspect, the present invention provides for an isolated immune cell modified to comprise an altered expression or activity of PROCR. The immune cell may be a T cell, preferably a CD8+ T cell. In preferred embodiments, the immune cell is a CD8+ T cell. The immune cell may display tumor specificity. The immune cell may have been isolated from a tumor of a subject, preferably the immune cell is a tumor infiltrating lymphocyte. The immune cell may comprise a tumor-specific chimeric antigen receptor (CAR). Not being bound by a theory, modulation of expression or activity results in a more activated or less dysfunctional T cell. Not being bound by a theory, dysfunctional autologous T cells may be used for generating a CAR T cell. Alternatively, non-dysfunctional T cells may be used to generate CAR T cells that are modified to prevent them from becoming dysfunctional. The isolated immune cell may be modified to comprise downregulated or abolished expression or activity of PROCR. The endogenous PROCR gene may be modified, whereby the cell comprises downregulated or abolished expression or activity of PROCR. The endogenous PROCR gene may be modified using a nuclease. The nuclease may comprise (i) a DNA-binding portion configured to specifically bind to the endogenous PROCR gene and (ii) a DNA cleavage portion. The DNA-binding portion may comprise a zinc finger protein or DNA-binding domain thereof, a transcription activator-like effector (TALE) protein or DNA-binding domain thereof, or an RNA-guided protein or DNA-binding domain thereof. The DNA-binding portion may comprise (i) a Cas protein modified to eliminate its nuclease activity, or (ii) DNA-binding domain of a Cas protein. The DNA cleavage portion may comprise FokI or variant thereof or DNA cleavage domain of FokI or variant thereof. The nuclease may be an RNA-guided nuclease, such as a Cas protein. The cell may comprise a protein comprising a DNA-binding portion configured to specifically bind to the endogenous PROCR gene. The protein may be a heterologous repressor protein capable of repressing the transcription of the endogenous PROCR gene. The heterologous repressor protein may comprise at least a DNA-binding portion configured to specifically bind to the endogenous PROCR gene, preferably to the endogenous PROCR gene promoter. The heterologous repressor protein may comprise (i) a DNA-binding portion configured to specifically bind to the endogenous PROCR gene, preferably to the endogenous PROCR gene promoter, and (ii) a transcription repression portion. The DNA-binding portion may comprise a zinc finger protein or DNA-binding domain thereof, TALE protein or DNA-binding domain thereof, or RNA-guided nuclease protein or DNA-binding domain thereof. The DNA-binding portion may comprise (i) a Cas protein modified to eliminate its nuclease activity, or (ii) DNA-binding domain of a Cas protein.

In another aspect, the present invention provides for an isolated immune cell modified to comprise an agent capable of inducibly altering expression or activity of PROCR. The agent may comprise: a nuclease capable of modifying the endogenous PROCR gene, such as to downregulate or abolish expression of PROCR, such as the nuclease as defined in any embodiment herein; or a heterologous repressor protein capable of repressing the transcription of the endogenous PROCR gene, such as the heterologous repressor protein as defined in any embodiment herein.

The isolated immune cell according to any embodiment described herein, may be further modified to comprise: an altered expression or activity of PDPN; an altered expression or activity of PRDM1 and/or c-MAF; an altered expression or activity of PROCR; an altered expression or activity of any one or more of PD1, CTLA4, TIGIT, TIM3, LAG3, or PDL1; an altered expression or activity of any one or more of TIGIT, LAG3, LILRB4, or KLRC1; an altered expression or activity of any one or more of CD226, OX-40, GITR, TNFSF9 (4-1BB), KLRC2, KLRE1, KLRK1, IL12RB1, IL1R1, or SLAMF7; an altered expression or activity of any one or more of PDPN, PROCR, TIGIT, LAG3, LILRB4, ALCAM or KLRC1; an altered expression or activity of any one or more of BTLA, TIGIT, HAVCR2 (TIM-3), LAG3, PDPN, IL1ORA, IL1R2, PROCR, LILRB4, KLRC1, KLRC2, KLRE1, TNFSF9 (4-1BB), KLRK1, IL12RB1, IL1R1, or SLAMF7; an agent capable of inducibly altering expression or activity of PDPN; an agent capable of inducibly altering expression or activity of PRDM1 and c-MAF; an agent capable of inducibly altering expression or activity of PROCR; an agent capable of inducibly altering expression or activity of any one or more of PD1, CTLA4, TIGIT, TIM3, LAG3, or PDL1; an agent capable of inducibly altering expression or activity of any one or more of TIGIT, LAG3, LILRB4, or KLRC1; an agent capable of inducibly altering expression or activity of any one or more of CD226, OX-40, GITR, TNFSF9 (4-1BB), KLRC2, KLRE1, KLRK1, IL12RB1, IL1R1, or SLAMF7; an agent capable of inducibly altering expression or activity of any one or more of PDPN, PROCR, TIGIT, LAG3, LILRB4, ALCAM or KLRC1; or an agent capable of inducibly altering expression or activity of any one or more of BTLA, TIGIT, HAVCR2 (TIM-3), LAG3, PDPN, IL1ORA, IL1R2, PROCR, LILRB4, KLRC1, KLRC2, KLRE1, TNFSF9 (4-1in), KLRK1, IL12RB1, IL1R1, or SLAMF7. The agent may comprise more than one nuclease. In certain embodiments, the agent comprises more than one TALE or zinc finger protein, whereby one TALE or Zinc finger targets one gene and one targets another gene. In other embodiments, the agent comprises more than two nucleases, capable of targeting multiple genes. In certain embodiments, a CRISPR-Cas system is used and multiple guide RNAs are used to target the CRISPR enzyme to multiple gene targets.

In another aspect, the present invention provides for a cell population of immune cells as defined in any embodiment herein.

In another aspect, the present invention provides for a method for generating the modified immune cell of any embodiment described herein, the method comprising (i) providing an isolated immune cell, and (ii) modifying said isolated immune cell such as to comprise an altered expression or activity of PDPN, PROCR, or PRDM1 and/or c-MAF, preferably PRDM1 and c-MAF.

In another aspect, the present invention provides for a method for generating the modified immune cell of any embodiment described herein, the method comprising (i) providing an isolated immune cell, and (ii) modifying said isolated immune cell such as to comprise an agent capable of inducibly altering expression or activity of PDPN, PROCR, or PRDM1 and c-MAF.

In certain embodiments, the step of providing the isolated immune cell comprises providing the immune cell isolated from a subject, or isolating the immune cell from a subject. The immune cell isolated from the subject preferably expresses PDPN, PROCR, and/or PRDM1 and c-MAF. The immune cell isolated from the subject may be dysfunctional or may be not dysfunctional. Not being bound by a theory, a dysfunctional cell may be modulated to have an activation phenotype and a nondysfunctional cell may be modulated to have an enhanced activation phenotype. The immune cell isolated from the subject may expresses a signature of dysfunction as defined herein. The method may further comprise the step of expanding the isolated immune cell prior to and/or subsequent to the modification.

In another aspect, the present invention provides for a pharmaceutical composition comprising the isolated immune cell or the cell population according to any embodiment described herein. The isolated immune cell or the cell population may be for use in therapy. The isolated immune cell or the cell population may be for use in immunotherapy or adoptive immunotherapy, preferably immunotherapy or adoptive immunotherapy of a proliferative disease, such as a tumor or cancer, or a chronic infection, such as a chronic viral infection. The isolated immune cell or cell population may be for use according in a subject, wherein the subject has been determined to comprise immune cells which: express PDPN, PROCR and/or PRDM1 and/or c-MAF, preferably PRDM1 and c-MAF; are dysfunctional, or are not dysfunctional; or express a signature of dysfunction as defined herein.

In another aspect, the present invention provides for a method of treating a subject in need thereof, preferably a subject in need of immunotherapy or adoptive immunotherapy, more preferably immunotherapy or adoptive immunotherapy of a proliferative disease, such as a tumor or cancer, or a chronic or persistent infection, such as a chronic viral infection, comprising administering to said subject the isolated immune cell or the cell population of any embodiment described herein. The method may further comprise administering to said subject one or more other active pharmaceutical ingredient, preferably wherein said one or more other active pharmaceutical ingredient is useful in immunotherapy or adoptive immunotherapy, or wherein said one or more other active pharmaceutical ingredient is useful in the treatment of a proliferative disease, such as a tumor or cancer, or a chronic infection, such as a chronic viral infection. The one or more other active pharmaceutical ingredient may be: an agonist of a cell molecule, such as a cell surface molecule, which when activated is capable of upregulating immune response, such as one or more of an agonist of 4-1BB, an agonist of OX40, an agonist of GITR, an agonist of STING, an agonist of TLR, or an agonist of BTLA; and/or an inhibitor of a cell molecule, such as a cell surface molecule, which when not inhibited is capable of downregulating immune response, such as a checkpoint inhibitor, or such as one or more of an antagonist of PD1, an antagonist of CTLA4, an antagonist of BTLA, an antagonist of TIGIT, an antagonist of TIM3, an antagonist of LAG3, an antagonist of VISTA, an antagonist of LILRB4, an antagonist of CD160, an antagonist of CD274, or an antagonist of IDO. The subject may comprise immune cells which: express PDPN, PROCR, PRDM1 and/or c-MAF; are dysfunctional, or are not dysfunctional; or express a signature of dysfunction as defined herein. Non-limiting examples on immuntherapeutics that may be used in the claimed methods or in conjunction with the claimed compositions include IMP321, BMS-986016, LAG525, TSR022, MTIG7192A, TRX518, INCAGN01876, GWN323, MEDI1873, MEDI9447, PF-05082566 (utomilumab), BMS-663513 (urelumab), MOXR0916, MEDI6469, MEDI6383, PF04518600, KHK4083, and combinations of two or more thereof.

In another aspect, the present invention provides for a method of treating a subject in need thereof, preferably a subject in need of immunotherapy or adoptive immunotherapy, more preferably immunotherapy or adoptive immunotherapy of a proliferative disease, such as a tumor or cancer, or a chronic infection, such as a chronic viral infection, comprising: providing an isolated immune cell from the subject, or isolating an immune cell from a subject; modifying said isolated immune cell such as to comprise an altered expression or activity of PDPN, PROCR, and/or PRDM1 and/or c-MAF, or modifying said isolated immune cell such as to comprise an agent capable of inducibly altering expression or activity of PDPN, PROCR, and/or PRDM1 and c-MAF; and reintroducing the modified isolated immune cell to the subject. The immune cell isolated from the subject: may express PDPN, PROCR, and/or PRDM1 and c-MAF; may be dysfunctional or is not dysfunctional; or may expresse a signature of dysfunction as defined herein. The method may further comprise the step of expanding the isolated immune cell prior to and/or subsequent to the modification, and before reintroduction to the subject. The subject may additionally be treated with known immunotherapies, including but not limited to, IMP321, BMS-986016, LAG525, TSR022, MTIG7192A, TRX518, INCAGN01876, GWN323, MEDI1873, MEDI9447, PF-05082566 (utomilumab), BMS-663513 (urelumab), MOXR0916, MEDI6469, MEDI6383, PF04518600, KHK4083, and combinations of two or more thereof.

In another aspect, the present invention provides for a method of detecting dysfunctional immune cells comprising detection of a gene expression signature comprising one or more markers selected from the group consisting of Abca1, Adam8, Adam9, A1cam, Ccl5, Ccl9, Ccl9, Ccl9, Ccr2, Ccr5, Cd68, Cd93, Cxcl10, Cysltr2, Ddr1, Entpd1, Entpd1, Epcam, Gabarapl1, Gcnt1, Gpr65, Havcr2, Ifitm1, Ifitm3, Il10, Il10ra, Il12rb1, Il13ra1, Il1r1, Il1r2, Il21, Il2ra, Il2rb, Il33, Il6st, Inhba, Isg20, Klrc2, Klrc2, Klrc2, Klrc2, Klrc2, Klrc2, Klrd1, Klrk1, Lag3, Lamp2, Lpar3, Ly75, Ly75, Nampt, Olfm1, Pdpn, Pglyrp1, Procr, Pstpip1, Ptpn3, Sdc1, Sdc4, Selp, Sema7a, Slamf7, Spp1, Tgfb3, Tigit, Tnfrsf8, Tnfsf9, Vldlr, Bst2, Btla, Ccl1, Ccr4, Cd226, Cd401g, Cd83, Cd8a, Csf2, Cxcl13, Cxcr4, Ifitm3, Isg20, Lap3, Lif, Serpinc1, Timp2, Tnfsf11, Acvr11, Ada, Are, Bmp2, Bmprla, ccl22, Ccr6, Ccr8, Cdl60, Cd200r4, Cd24a, Cd70, Cd74, Cmtm7, Csf1, Ctla2a, Ctla2b, Ctsd, Cts1, Dlk1, Enpep, Enpp1, Eps8, F2r, Fgf2, Flt31, H2-Ab1, Hspb1, Ifngr1, Il12rb2, Il18, Il18r1, Il18rap, Il2, Il24, Il27ra, Il4, Il4ra, Il7r, Itga4, Itga7, Itga9, Klrc1, Klre1, Lpar2, Lta, Ly6a, Ly6e, Nlgn2, Nrp1, Flt31, H2-Ab2, Hspb2, Ifngr2, I2rb3, Il19, Il18r2, Il18rap, Il46, Il68, Il27ra, Il5, Smpd1, Tgdb3, Tirap, Tnfrsf13c, Tnfrsf23, Tnfsf10, Tnfsf4, Trem12, Trpc1, Trpm4, Tspan32, and Xcl1; or selected from the group consisting of ABCA1, ADAM8, ADAM9, ALCAM, CCL5, CCL15, CCL23, CCL15-CCL14, CCR2, CCR2, CD68, CD93, CXCL10, CYSLTR2, DDR1, ENTPD1, EPCAM, GABARAPL1, GCNT1, GPR65, HAVCR2, IFITM1, IFITM1, IL1O, IL1ORA, IL12RB1, IL13RA1, IL1R1, IL1R2, IL21, IL2RA, IL2RB, IL33, IL6ST, INHBA, ISG20, KLRC4-KLRK1, KLRC4, KLRC1, KLRC3, KLRC2, KLRD1, KLRK1, LAG3, LAMP2, LPAR3, LY75-CD302, LY75, NAMPT, OLFM1, PDPN, PGLYRP1, PROCR, PSTPIP1, PTPN3, SDC1, SDC4, SELP, SEMA7A, SLAMF7, SPP1, TGFB3, TIGIT, TNFRSF8, TNFSF9, VLDLR, BST2, BTLA, CCL1, CCR4, CD226, CD40LG, CD83, CD8A, CSF2, CXCL13, CXCR4, IFITM1, ISG20, LAP3, LIF, SERPINC1, TIMP2, TNFSF11, ACVRL1, ADA, BMPR1A, CCR5, CD160, CD24, CMTM7, CSF1, CTSD, CTSL1, CYSLTR2, ENPP1, EPS8, F2R, FLT3LG, HSPB1, IFNGR1, IL18, IL18R1, IL18RAP, IL24, IL24, IL27RA, IL27RA, IL4R, IL7R, ITGA4, ITGA7, LY6E, NLGN2, NRP1, OSM, PDE4B, PEAR1, PLXNC1, PRNP, PRNP, PRNP, PTPRJ, S1PR1, SDC1, SELL, SEMA4D, SERPINE2, SERPINE2, SMPD1, TIRAP, TNFSF10, TRPC1, TRPM4, and XCL1.

In another aspect, the present invention provides for a method of detecting dysfunctional immune cells comprising detection of a gene expression signature comprising one or more markers selected from the group consisting of ABCA1, ADAM8, ADAM9, ALCAM, CCL5, CCL9, CCR2, CCR5, CD68, CD93, CTLA2A, CXCL10, CYSLTR2, ENTPD1, EPCAM, GABARAPL1, GCNT1, GPR65, HAVCR2, IFITM1, IFITM3, IL1OIL1ORA, IL12RB1, IL13RA1, IL1R1, IL1R2, IL21, IL2RA, IL2RB, IL33, IL6ST, INHBA, ISG20, KLRC2, KLRD1, KLRE1, KLRK1, LAG3, LAMP2, LILRB4, LPAR3, LY75, NAMPT, OLFM1, PDPN, PGLYRP1, PROCR, PSTPIP1, PTPN3, SDC1, SDC4, SELP, SEMA7A, SLAMF7, SPP1, TGFB3, TIGIT, TNFRSF8, TNFSF9, and VLDLR.

In another aspect, the present invention provides for a method of detecting dysfunctional immune cells comprising detection of a gene expression signature comprising one or more markers selected from the group consisting of IL33, KLRC2, KLRD1, KLRE1, OLFM1, PDPN, PTPN3, SDC1, TNFSF9, VLDLR, PROCR, GABARAPL1, SPP1, ADAM8, LPAR3, CCL9, CXCL10, CCR2, IL1ORA, IL2RB, CD68, KLRK1, IL12RB2, IL6ST, IL7R, INHBA, ISG20, LAMP2, LY75, NAMPT, SlPRl, IL21, IL13RA1, TIGIT, CCR5, ALCAM, HAVCR2, LAG3, IL1R2, CYSLTR2, ENTPD1, GCNT1, IFITM3, IL2RA, PGLYRP1, CD93, ADAM9, LILRB4, IL-10, CTLA2A, and GPR65.

Any of the signatures described herein may comprise at least two markers, or at least three markers, or at least four markers, or at least five markers, or six or more markers, such as wherein the signature consists of two markers, three markers, four markers, or five markers. Any of the signatures described herein may comprise two or more markers, and wherein: one of said two or more markers is PDPN; one of said two or more markers is PROCR; or two of said two or more markers are PDPN and PROCR.

In another aspect, the present invention provides for a method of isolating a dysfunctional immune cell comprising binding of an affinity ligand to a signature gene as defined in any embodiment herein, wherein the signature gene is expressed on the surface of the immune cell.

In another aspect, the present invention provides for a kit of parts comprising means for detection of the signature of dysfunction as defined in any embodiment herein.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1A-M. illustrates that IL-27 induces multiple co-inhibitory receptors on CD4$^+$ and CD8$^+$ T cells. CD4$^+$ and CD8$^+$ tumor-infiltrating lymphocytes (TILs) harvested from WT mice bearing B16F10 melanoma tumors. A) Naïve T cells from either wild type (WT) or IL-27ra deficient mice (IL27ra KO) were stimulated with anti-CD3/CD28 in the presence or absence of IL-27 as indicated. Expression of the indicated co-inhibitory molecules was examined by real-time PCR at 96 hr (CD4) and 72 hr (CD8), n≥3, error bars indicate s.e.m. B) Surface expression of co-inhibitory receptors on T cells stimulated as in (A) was determined by flow cytometry. Representative data are shown. C) Co-expression analysis of co-inhibitory and co-stimulatory receptor mRNA expression as determined by single cell RNAseq (316 and 516 for CD4$^+$ and CD8$^+$ respectively). For visualization purposes negative correlation values were set to zero. D) Protein expression by CyTOF for 23,656 CD4$^+$ and 36,486 CD8$^+$ TILs. Co-expression was analyzed using Spearman correlation. For visualization purposes negative correlation values were set to zero. E) TILs were harvested from WT and IL27ra KO mice bearing B16F10 melanoma and analyzed using CyTOF. CyTOF data were analyzed using vi-SNE. Polygons indicating clusters 1, 2 (in CD8$^+$ T cells), 3 and 4 (in CD4$^+$ T cells) are shown. F) The within groups sum of squared error (SSE) plot. The location of the elbow or a bend in the resulting plot suggests a suitable number of clusters for the k-means algorithm, which in this case is somewhere between 7 and 11 clusters. G) Gap statistics for estimating the optimal number of clusters using k-means from 1 up to 12 clusters using bootstrapping and first SE max method. This method suggested 9 clusters as optimal. H) Applying k-means clustering with (k=9) on our CyTOF data resulted in clear distinction between clusters 1, 2, 3 and 4. Visualization of cluster distribution using two-dimensional non-linear embedding of the protein expression profiles by t-SNE. I) CyTOF expression analysis of co-inhibitory and co-stimulatory receptors in TILs harvested from B16F10 melanoma tumor-bearing WT and IL17Ra KO mice from FIGS. 1A and 1J using t-SNE. J) vi-SNE plot highlighting the distribution of CD8$^+$ TILs from WT (red) and IL27ra KO (blue) mice in clusters 1 and 2 and CD4$^+$ TILs from WT (red) and IL27ra KO (blue) mice in clusters 3 and 4. Pie charts show the distribution of WT or IL27ra KO CD8$^+$ and CD4$^+$ TILs in each cluster. Bar graphs show the mean of signal intensity for PD-1, Tim-3, Lag-3, and TIGIT from WT and IL27ra KO TILs. Error bars are the standard error and p-values for significance are calculated using standard t-test (**p<0.01). K) Expression of PD-1, Tim-3, Lag-3, TIGIT, and IL-10 on CD8$^+$ TILs obtained from WT and IL27ra KO mice bearing B16F10 melanoma was determined by flow cytometry. Thy1.1-IL-10 reporter mice crossed with WT and IL27ra KO mice were used for IL-10 expression analysis. L, M) Impact of IL-27 signaling on co-inhibitory receptor expression in TILs. Pie charts show the distribution of CD8$^+$ and CD4$^+$ TILs from WT and IL27ra KO mice bearing B16F10 melanoma between clusters 1 and 2 for CD8$^+$ and between clusters 3 and 4 for CD4$^+$ TILs as determined by k-means clustering of CyTOF protein expression data. Data are from independent WT and IL27ra KO TILs samples from that shown in FIG. 1J.

FIG. 2A-2B. IL-27 inducing inhibitory molecules. FIG. 2A. Naïve T cells from either wild type or IL-27ra deficient were stimulated in the presence or absence of IL-27 as indicated. Expression of known co-inhibitory molecules was examined by real-time PCR at 96 hr. N≥3, error bars indicate SD FIG. 2B. Surface expression of co-inhibitory receptors on T cells stimulated as in was examined by flow cytometry. Representative data are shown.

FIG. 3A-3B. IL-27 inducing inhibitory molecules. FIG. 3A. Naïve T cells from either wild type or IL-27ra deficient were stimulated in the presence or absence of IL-27 as indicated. Expression of known co-inhibitory molecules was examined by real-time PCR at 72 hr. N≥3, error bars indicate SD. FIG. 3B. Surface expression of co-inhibitory receptors on T cells stimulated as in was examined by flow cytometry. Representative data are shown.

FIG. 7A-E. Role of Procr in T cell dysfunction and anti-tumor immunity. A) Lack of Procr signaling (EPCRdd) suppresses tumor growth (B16 melanoma). WT (n=8) and $Procr^{d/d}$ (n=8) mice were implanted with B16F10 melanoma and the change of tumor size were plotted. Left panel, mean tumor size ±s.e.m. p<0.01; *p<0.001, t-test. Right panel, linear regression, p<0.001. Data are from two experiments and are representative of a total of 4 independent experiments. B) Top panels, representative flow cytometry data showing cytokine production of $CD8^+$ TILs from WT and $Procr^{d/d}$ mice bearing B16F10 melanoma. Bottom panels, summary data. *p<0.05, t-test. C) Left panels, representative flow cytometry data showing Tim-3 and PD-1 expression on $CD8^+$ TILs from WT and $Procr^{d/d}$ mice bearing B16F10 melanoma. Right panels, summary data. p<0.01; *p<0.001, t-test. D-E) T cell intrinsic effects of Procr. $5\times10^5$ $CD8^+$ T cells from wild type or $Procr^{dd}$ mice were transferred along with $1\times10^6$ wild type $CD4^+$ T cells to $Rag1^{-/-}$ mice. On day 2, $5\times10^5$ B16F10 cells were implanted. D), mean tumor size ±s.e.m, *p<0.05, t-test. E), linear regression, *p<0.05.

FIG. 10A-C. IL-7R expression on PD-$1^{high}$Tim-$3^{high}$ $CD8^+$ TILs from wild type and Pdpn cKO mice. TILs were obtained from WT and Pdpn cKO mice bearing B16F10 melanoma and stained for the expression of IL-7R. A) Representative flow cytometry data. B) Summary data, error bars are the standard error and p-values for significance are calculated using standard t-test (*p<0.05). C) Pdpn deficient CD8 T cells maintain IL-7R on PD-$1^+$ $Tim3^+$ cells. IL-7R expression on PD-$1^+$ Tim-$3^+$ CD8 TILs is increased in CD4CrePdpnfl/fl mice compared to Pdpnfl/fl mice. TILs were obtained from Pdpnfl/fl and CD4CrePdpnfl/fl mice bearing B16F10 melanoma and stained for the expression of IL-7R and IL-2Ra. Representative data is shown as flow-cytometric schemes and the data from multiple experiments are combined and shown as plots. The t-test provided the statistical p values (*p<0.05). The bars represent the SD.

FIG. 12A-D. Prdm1 regulate multiple co-inhibitory molecules on T cells in cancer. A) Network model based on gene expression data of naïve $CD8^+$ T cells from $Prdm1^{fl/fl}$ (WT) or $CD4erePrdm1^{fl/fl}$ (Prdm1 cKO) mice stimulated in the presence of IL-27 and ChIPseq data for Prdm1. Green arrows designate genes up-regulated by Prdm1 and red arrows designate genes down-regulated by Prdm1. Gray arrows designate potential Prdm1 binding sites on each gene promoter. B) Prdm1 expression in naïve $CD8^+$ T cell stimulated in the presence of IL-27 and in PD-$1^+$ Tim-$3^+$ $CD8^+$ (DP) compared to PD-$1^-$Tim-$3^-$ $CD8^+$ (DN) TILs as determined by global gene expression profiling. *p<0.05 C) Representative flow cytometry data showing PD-1, Tim-3, Tigit, Lag3, Procr, and Pdpn expression on $CD8^+$ TILs from WT and Pdrm1 cKO mice bearing B16F10 melanoma. *p<0.05, ***p<0.001. D) WT (n=5) and Prdm1 cKO (n=5) mice were implanted with B16F10 melanoma. Mean tumor size ±s.e.m is shown. Data are representative of 3 independent experiments.

FIG. 13A-D. c-Maf regulates multiple co-inhibitory molecules on T cells in cancer. A) Left panel, gene expression in $CD8^+$ TILs from WT and Prdm1 cKO mice bearing B16F10 melanoma was analyzed by n-counter code-set of 397 genes. Differentially expressed genes are shown as a heatmap. Red designates up-regulated genes and blue designates down-regulated genes. Right panel, expression of c-Maf in $CD8^+$ TILs from WT and Prdm1 cKO mice as determined by qPCR. *p<0.05, t-test. B) Expression shown as representative contour plots for PD-1, Tim-3, Tigit, Lag3, Procr, and Pdpn expression on $CD8^+$ TTLs from Prdm1 KO and $CD4^{cre}$c-$Maf^{fl/fl}$ (c-Maf cKO) as determined by flow cytometry and summarized below *p<0.05, t-test. C) Frequency of co-inhibitory receptor expression of prdm1 cKO (gray bar) and c-Maf cKO (open bar) $CD8^+$ TILs relative to WT (filled bar). D) Left panel, c-$Ma^{fl/fl}$ (WT, n=5) and c-Maf cKO (n=5) mice were implanted with B16F10 melanoma. Mean tumor size ±s.e.m is shown. Data are representative of 3 independent experiments. Right panel, expression of Prdm1 in $CD8^+$ TILs from WT and c-Maf cKO mice as determined by qPCR.

FIG. 14A-G. Prdm1 and c-Maf together regulate a co-inhibitory gene module that determines anti-tumor immunity. A) Network model based on coupling gene expression data of naïve $CD8^+$ T cells from Prdm1 cKO or c-Maf cKO mice stimulated in the presence of IL-27 and ChIP data for Prdm1 and c-Maf. Green arrows indicate up-regulated genes and red arrows indicate down-regulated genes. Gray arrows indicate potential binding on each promoter region by either Prdm1 or c-Maf. B) Top panels, representative flow cytometry data shown as contour plots for PD-1, Tim-3, Tigit, Lag3, Procr, and Pdpn expression on $CD8^+$ TILs from WT and $CD4^{cre}Prdm1^{fl/fl}c\text{-}Maf^{fl/fl}$ (cDKO) bearing B16F10 melanoma. Bottom panels, summary of expression data by flowcytometry. $^{}p<0.01$; $^{*}p<0.001$, t-test. C) Top panels, representative flow cytometry data showing cytokine production from $CD8^+$ TILs WT and $Prdm1^{fl/fl}c\text{-}Maf^{fl/fl}$cDKO bearing B16F10 melanoma. Bottom panels, summary data $^{*}p<0.05$, t-test. $^{**}p<0.01$ D) Top panel, WT (n=14) and $CD4^{cre}Prdm1^{fl/fl}$ $c\text{-}Maf^{fl/fl}$ cDKO (n=8) mice were implanted with B16F10 melanoma. Mean tumor size ±s.e.m is shown. $^{*}p<0.05$, $^{}p<0.01$, t-test. Bottom panel, Linear regression $^{*}p<0.001$. Data shown are pooled from 3 independent experiments. E) 940 differentially expressed genes between $CD8^+$ TTLs from wild type control (WT) and $CD4^{cre}Prdm1^{fl/fl}c\text{-}Maf^{fl/fl}$ (cDKO) bearing B16F10 melanoma. (adj. P. value<0.05, likelihood ratio test and FDR correction) (top panel) and their corresponding expression pattern in $PD\text{-}1^+$ $Tim\text{-}3^+$ $CD8^+$ (DP), $PD\text{-}1^+$ $Tim\text{-}3^-$ $CD8^+$ (SP) and $PD\text{-}1^+$ $Tim\text{-}3^-$ $CD8^+$ (DN) TTLs (bottom panel). F) Co-inhibitory receptor expression in $CD4^+$ TTLs from Prdm1/c-Maf cDKO mice. Top panels, representative flow cytometry data for TTLs from WT and Prdm1/c-Maf cDKO stained for PD-1, Tim-3, TIGIT, Pdpn, and Procr expression. Bottom panels show summary data. $^{*}p<0.05$, t-test. G) A tSNE plot of the 516 $CD8^+$ single-cell tumor-infiltrating lymphocytes (TILs) harvested from WT mice bearing B16F10 melanoma tumors, colored by the relative signature score for co-inhibitory module and the cDKO signature (shown in (E)). The contour plot marks the region of highly scored cells by taking into account only those cells that have a signature score above the mean.

FIG. 15A-C. Comparison of gene expression between Prdm1/c-Maf cDKO TILs and $CD8^+$ TILs populations from wild type mice. A) Barcode enrichment plot displaying two gene sets in a ranked gene list. The ranked gene list was defined as fold change in gene expression between Prdm1/c-Maf cDKO and WT $CD8^+$ TILs. The three gene sets consist of differentially expressed genes between: $PD\text{-}1^+$ $Tim\text{-}3^+$ $CD8^+$ (DP) and $PD\text{-}1^-$ $Tim\text{-}3^-$ $CD8^+$ (DN) TILs, $PD\text{-}1^+$ $Tim\text{-}3^+$ $CD8^+$ (DP) TILs and Memory $CD8^+$, and $PD\text{-}1^+$ $Tim\text{-}3^-$ $CD8^+$ (SP) and $PD\text{-}1^-Tim\text{-}3^-$ $CD8^+$ (DN) TILs. B) This analysis was followed by four statistical tests (one-sample Kolmogorov-Smirnov test, mean-rank gene set test (wilcoxGST), hypergeometric and competitive gene set test accounting for inter-gene correlation) for enrichment of these signatures in the DKO expression profile. C) WT versus DKO volcano plot, in green are all the genes that were up-regulated in the $PD\text{-}1^-Tim\text{-}3^-$ $CD8^+$ (DN) TILs and in red are all the genes that were up-regulated in the $PD\text{-}1^+$ $Tim\text{-}3^+$ $CD8^+$ (DP) TILs.

DETAILED DESCRIPTION OF THE INVENTION

Definitions

Figure 1A:
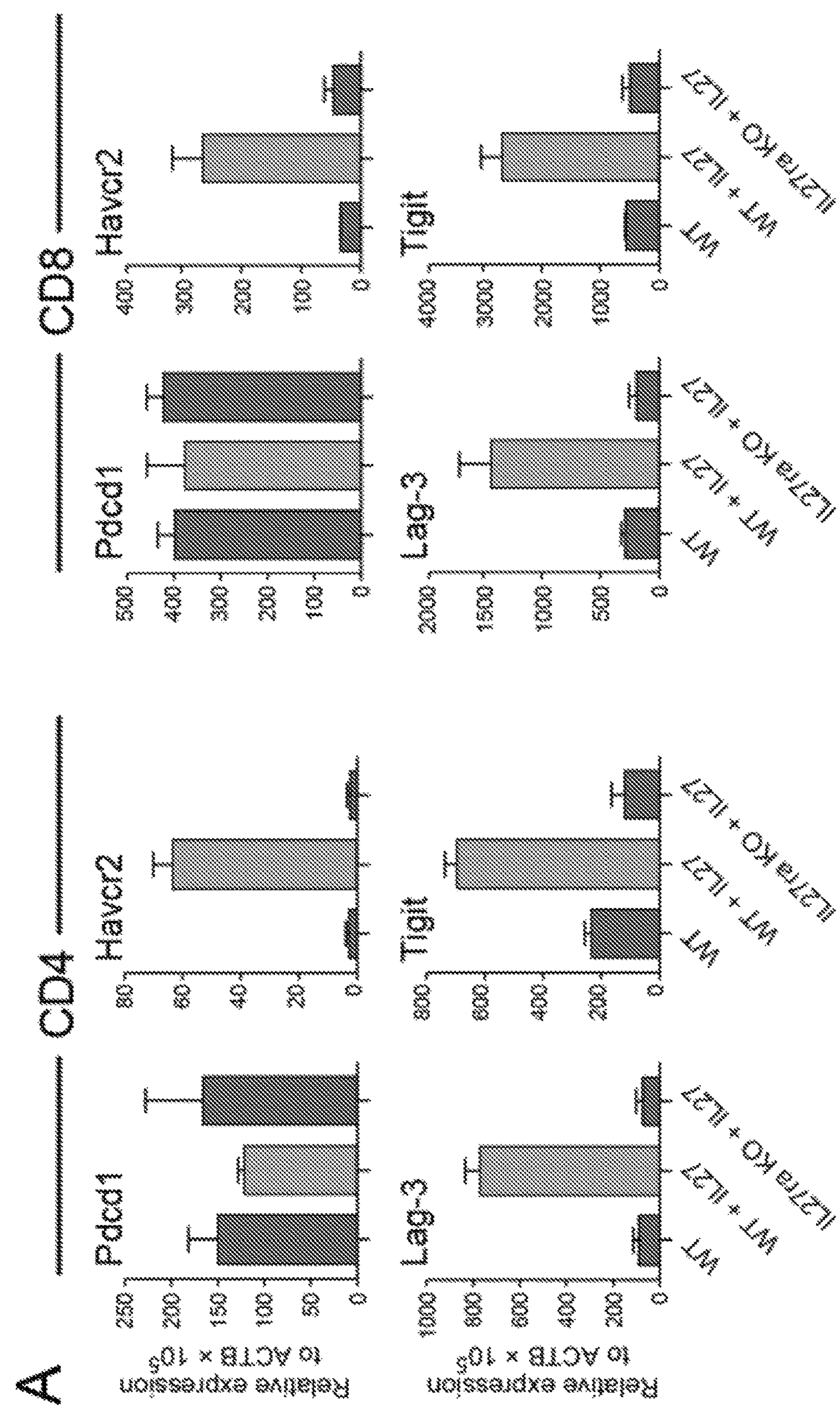
Figure 1B:
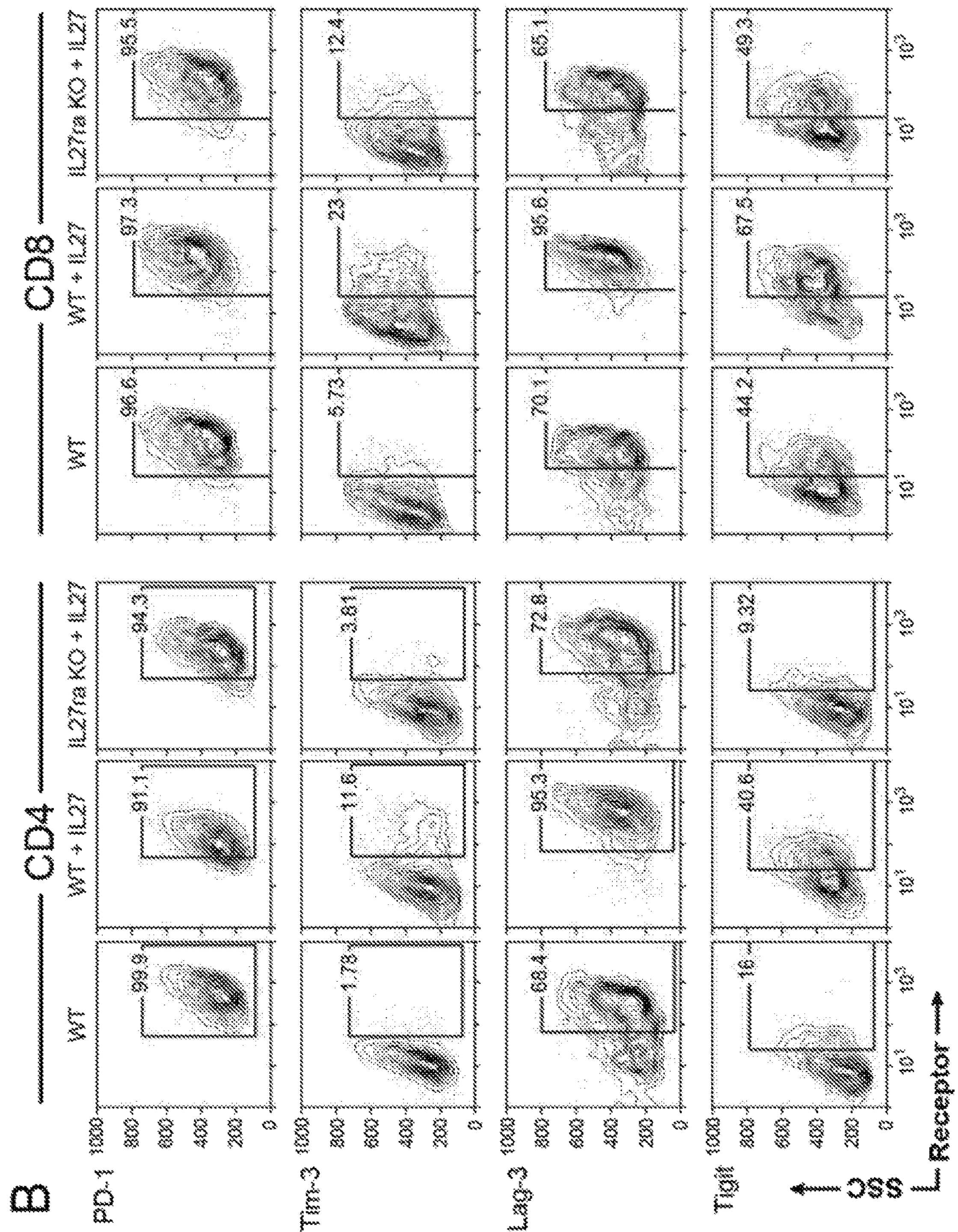

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the invention. When specific terms are defined in connection with a particular aspect of the invention or a particular embodiment of the invention, such connotation is meant to apply throughout this specification, i.e., also in the context of other aspects or embodiments of the invention, unless otherwise defined.

As used herein, the term “unresponsiveness” includes refractivity to activating receptor-mediated stimulation. Such refractivity is generally antigen-specific and persists after exposure to the antigen has ceased. Unresponsive immune cells can have a reduction of at least 10%, at least 20%, at least at least 30%, at least 40%, at least 50%, at least 60%, at least 70%, at least 80%, at least 90%, at least 95%, or even 100% in cytotoxic activity, cytokine production, proliferation, trafficking, phagocytotic activity, or any combination thereof, relative to a corresponding control immune cell of the same type.

As described herein, the terms “modulating” or “to modulate” generally means either reducing or inhibiting the activity or expression of, or alternatively increasing the activity or expression of, a given entity or effect. As non-limiting examples, one can modulate the activity or expression of a target or antigen, such as at least one of the target genes listed in Table 1 (e.g., PROCR and/or PDPN), as measured using a suitable in vitro, cellular or in vivo assay, such as those described herein in the Examples. As another non-limiting example, one can modulate a T cell phenotype, including e.g., exhaustion or responsiveness to stimulation. As another non-limiting example, one can modulate a disease phenotype, e.g, an autoimmune or other immune disease phenotype. In particular, “modulating” or “to modulate” can mean either reducing or inhibiting the activity or expression of, or alternatively increasing a (relevant or intended) biological activity or expression of, a target or antigen, or a phenotype, as measured using a suitable in vitro, cellular or in vivo assay (which will usually depend on the target or antigen involved), by at least 5%, at least 10%, at least 25%, at least 50%, at least 60%, at least 70%, at least 80%, or 90% or more, compared to activity of the target or antigen in the same assay under the same conditions but without the presence of the inhibitor/antagonist agents or activator/agonist agents described herein.

As will be clear to the skilled person, "modulating" can also involve effecting a change (which can either be an increase or a decrease) in affinity, avidity, specificity and/or selectivity of a target or antigen for one or more of its ligands, binding partners, partners for association into a homomultimeric or heteromultimeric form, or substrates; and/or effecting a change (which can either be an increase or a decrease) in the sensitivity of the target or antigen for one or more conditions in the medium or surroundings in which the target or antigen is present (such as pH, ion strength, the presence of co-factors, etc.), compared to the same conditions but without the presence of a modulating agent. Again, this can be determined in any suitable manner and/or using any suitable assay known per se, depending on the target or antigen involved. In particular, an action as an inhibitor/antagonist or activator/agonist can be such that an intended biological or physiological activity is increased or decreased, respectively, by at least 5%, at least 10%, at least 25%, at least 50%, at least 60%, at least 70%, at least 80%, or 90% or more, compared to the biological or physiological activity in the same assay under the same conditions but without the presence of the inhibitor/antagonist agent or activator/agonist agent. Modulating can, for example, also involve allosteric modulation of the target or antigen; and/or reducing or inhibiting the binding of the target or antigen to one of its substrates or ligands and/or competing with a natural ligand, substrate for binding to the target or antigen. Modulating can also involve activating the target or antigen or the mechanism or pathway in which it is involved. Modulating can for example also involve effecting a change in respect of the folding or conformation of the target or antigen, or in respect of the ability of the target or antigen to fold, to change its conformation (for example, upon binding of a ligand), to associate with other (sub)units, or to disassociate. Such a change will have a functional effect.

The terms "decrease", "reduced", "reduction", or "inhibit" are all used herein to mean a decrease or lessening of a property, level, or other parameter by a statistically significant amount. In some embodiments, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased","increase" or "enhance" or "activate" are all used herein to generally mean an increase of a property, level, or other parameter by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 1-fold, at least about a 1.5-fold, at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

A "pharmaceutical composition" refers to a composition that usually contains an excipient, such as a pharmaceutically acceptable carrier that is conventional in the art and that is suitable for administration to cells or to a subject. In addition, compositions for topical (e.g., oral mucosa, respiratory mucosa) and/or oral administration can be in the form of solutions, suspensions, tablets, pills, capsules, sustained-release formulations, oral rinses, or powders, as known in the art and described herein. The compositions also can include stabilizers and preservatives. For examples of carriers, stabilizers and adjuvants, University of the Sciences in Philadelphia (2005) Remington: The Science and Practice of Pharmacy with Facts and Comparisons, 21 st Ed.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable carrier" can include any material or substance that, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. The term "pharmaceutically acceptable carriers" excludes tissue culture media.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Further, unless otherwise required by context, singular terms shall include pluralities and plural terms shall include the singular. As used herein, the singular forms "a", "an", and "the" include both singular and plural referents unless the context clearly dictates otherwise.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more members or at least one member of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members. In another example, "one or more" or "at least one" may refer to 1, 2, 3, 4, 5, 6, 7 or more.

The term "optional" or "optionally" means that the subsequent described event, circumstance or substituent may or may not occur, and that the description includes instances where the event or circumstance occurs and instances where it does not.

It should be understood that this invention is not limited to the particular methodologies, protocols, and reagents, etc., described herein and as such can vary therefrom. The terminology used herein is for the purpose of describing particular embodiments only, and is not intended to limit the scope of the present invention, which is defined solely by the claims.

IL-27 and IL-27 Signaling Pathways

IL-27 is a heterodimeric cytokine of the IL-6 and IL-12 family composed of the IL-27p28 and EBI3 subunits. IL-27p28 and EBI3 are produced primarily by antigen-presenting cells after stimulation by microbial products or inflammatory mediators. The IL-27 receptor is composed of WSX-1 (also known as T cell cytokine receptor), a type I cytokine receptor, and glycoprotein 130 (gp130), a receptor subunit utilized by several other IL-6 and IL-12 family members. Although gp130 expression is ubiquitous, WSX-1 expression is largely restricted to leukocytes, including T cells, natural killer (NK) cells, human monocytes, and human mast cells. IL-27 binds specifically to WSX-1, and EBI3 is required for signal transduction (E. D. Tait Wojno and C. A. Hunter, Trends Immunol. 2012 February; 33(2): 91-7).

Accordingly, the term "IL-27," as used herein, refers to the heterodimer composed of: the mature form of the precursor IL-27p28 polypeptide having the amino acid sequence of:

MGQTAGDLGWRLSLLLLPLLLVQAGVWGF-PRPPGRPQLSLQELRREFTVSLHLARK LLSEVRGQAHRFAESHLPGVN-LYLLPLGEQLPDVSLTFQAWRRLSDPERLCFIST-TLQ PFHALLGGLGTQGRWTNMERMQL-WAMRLDLRDLQRHLRFQVLAAGFNLPEEEEEE EEEEEEERKGLLPGALGSALQGPAQVSWPQLL-STYRLLHSLELVLSRAVRELLLLSKA GHSVWPLGFPTLSPQP (SEQ ID NO: 1), as described by, e.g., NP_663634.2, together with any naturally occurring allelic, splice variants, and processed forms (e.g., the mature form IL-27p28(29-243)) thereof, and the mature form of the precursor EBI3 or IL-27B polypeptide having the amino acid sequence of:

MTPQLLLALVLWASCPPCSGRKGPPAALTL-PRVQCRASRYPIAVDCSWTLPPAPNST SPVSFIA-TYRLGMAARGHSWPCLQQTPTSTSC-TITDVQLFSMAPYVLNVTAVHPWGS SSSFVPFITEHIIKPDPPEGVRLSPLAER-QLQVQWEPPGSWPFPEIFSLKYWIRYKRQGA ARFHRVGPIEATSFILRAVR-PRARYYVQVAAQDLTDYGELSDWSLPA-TATMSLGK (SEQ ID NO: 2), as described by, e.g., NP_005746.2, together with any naturally occurring allelic, splice variants, and processed forms (e.g., the mature form IL-27B(21-229)) thereof. Typically, IL-27 refers to human IL-27. Specific residues of IL-27 can be referred to as, for example, "IL-27(62)."

IL-27 was initially described as a proinflammatory cytokine that promoted T helper (Th)1 responses. Subsequent studies in multiple models of infectious and autoimmune disease demonstrated an anti-inflammatory role for IL-27 in Th1, Th2 and Th17 responses, and recent work has shown that IL-27 can induce T cells to produce the anti-inflammatory cytokine IL-10. The consequences of IL-27 signaling appear to depend, in part, on the immunological context, the temporal regulation of IL-27 production, and tissue- and cell-specific expression of components of the IL-27 receptor (E.D. Tait Wojno and C. A. Hunter, Trends Immunol. 2012 February; 33(2):91-7).

IL-27 has been shown to promote the generation of Tr-1 cells that produce IL-10 by inducing expression of the activator protein-1 family transcription factor c-Maf. c-Maf directly transactivates the I110 promoter to upregulate IL-10, and binds to the promoter of the common γ chain cytokine Il21 to elicit IL-21 production that maintains IL-10 producers. Moreover, IL-27 signaling upregulates expression of the aryl hydrocarbon receptor (AhR), which partners with c-Maf to optimize interactions with the I110 and 1121 promoters, further supporting Tr-1 development. IL-27-mediated IL-10 production also depends on STAT1 and STAT3 signaling, and the inducible co-stimulator (ICOS). IL-27 signaling is also believed to elicit Tfh responses by inducing c-Maf and IL-21 that promote Tfh activity. However, IL-27 alone does not cause $CD4^+$ T cells to differentiate into functional Tfhs, and IL-27 signaling is not required for the generation of antibody responses in models of infection, allergy and autoimmunity. IL-27 also has direct effects on B cells. IL-27 has also been shown to regulate regulatory T cell (Treg) populations and acts as an antagonist of inducible Treg differentiation (E.D. Tait Wojno and C. A. Hunter, Trends Immunol. 2012 February; 33(2):91-7). Recently, it was also demonstrated that IL-27 priming of naïve CD4 and CD8 T cells upregulates expression of PD-L1 in a STAT1-dependent manner and such IL-27 primed cells can limit in trans the effect of pathogenic IL-17-producing Th17 cells in vitro and in vivo (Hirahara K. et al., Immunity. 2012 Jun. 29; 36(6):1017-30).

As demonstrated herein, IL-27 plays a critical role in the development of T cell exhaustion, and drives an IL-27 inhibitory gene module in which the expression and activity of a variety of co-inhibitory and co-stimulatory molecules are induced.

T Cell Dysfunction

As used herein, the term "T cell dysfunction" refers to a state in which a T cell or population of T cells fail to respond with effector function when stimulated with antigen and/or stimulatory cytokines sufficient to elicit an effector response in non-dysfunctional T cells. The term encompasses T cell tolerance, a normal state required to avoid self-reactivity, as well as T cell ignorance, T cell exhaustion, and T cell anergy.

As used herein, in regard to T cell tolerance, thymocytes that express a T cell receptor with affinity for self antigen/MHC complexes are actively deleted (referred to herein as central tolerance, involving negative selection). As used herein, in regard to peripheral tolerance, self-reactive T cells that escape negative selection are inactivated in the periphery by deletion, suppression by regulatory T cells and/or induction of an imprinted cell-intrinsic program resulting in a state of functional unresponsiveness. Self-tolerant T cells have been exposed to self antigen.

As used herein, in regard to T cell ignorance, self-reactive peripheral T cells are "unaware of" self-antigen, e.g., due to physical sequestration of the antigen from immune surveillance, or because the level of self-antigen and/or its presentation is too low to elicit a response.

As used herein, T cell anergy, originally referred to the absence of delayed skin test hypersensitivity responses to recall antigens in cancer patients, now commonly also refers to the dysfunctional state of T cells stimulated in vitro in the absence of co-stimulatory signals. Anergic T cells induced in vitro fail to produce IL-2 or to proliferate in response to later antigen stimulation under optimal conditions. An in vivo state referred to as T cell anergy or adaptive tolerance involves unresponsiveness as a result of suboptimal stimulation.

T cell exhaustion is a state of functional hyporesponsiveness to stimuli that tends to occur with chronic exposure to antigen, e.g., in chronic infection or in cancer. Exhausted T cells fail to induce effector function following stimulation with CD28 and TCR/CD3 cross-linking, and express one or more of eomesodermin (Eomes), and the transcription factor (s) Blimp-1, T-bet, BATF, and NFAT. Exhausted T cells also generally express PD-1 and TIM-3. In one embodiment, T cell exhaustion can be assessed by an in vitro assay comprising contacting a T cell with a CD28 stimulus and measuring the degree of response. An exhausted T cell will fail to respond to stimulation with CD28. Other methods for measuring T cell exhaustion include proliferation assays or cytotoxic assays and/or are known in the art (see e.g., Yi et al. (2010) *Immunol* 129(4):474-481).

T cell dysfunction and the similarities and differences between the various types of dysfunction are discussed by Schietinger and Greenberg, Trends in Immunol. 35: 51-60, 2014, "Tolerance and exhaustion: defining mechanisms of T cell dysfunction," the contents of which are incorporated herein by reference.

As used herein, the terms "functional exhaustion" or "unresponsiveness" refer to a state of a cell where the cell does not perform its usual function or activity in response to normal input signals, and includes refractivity of immune cells to stimulation, such as stimulation via an activating receptor or a cytokine. Such a usual function or activity includes, but is not limited to, proliferation or cell division, entrance into the cell cycle, cytokine production, cytotoxicity, trafficking, phagocytotic activity, or any combination thereof. Normal input signals can include, but are not limited to, stimulation via a receptor (e.g., T cell receptor, B cell receptor, co-stimulatory receptor). Unresponsive immune cells can have a reduction of at least 10%, at least 20%, at least 30%, at least 40%, at least 50%, at least 60%, at least 70%, at least 80%, at least 90%, at least 95%, or even 100% in one or more effector functions, such as cytotoxic activity, cytokine production, proliferation, trafficking, phagocytotic activity, or any combination thereof, relative to a corresponding control immune cell of the same type. In some particular embodiments of the aspects described herein, a cell that is functionally exhausted is a CD4 or helper T lymphocyte that expresses the CD4 cell surface marker. Such CD4 cells normally proliferate, and/or produce cytokines, such as IL-2, TNFα, IFNγ, IL-4, IL-5, IL-17, or a combination thereof, in response to T cell receptor and/or co-stimulatory receptor stimulation. Thus, a functionally exhausted or unresponsive CD4 T cell is one which has a reduction in proliferation, and/or cytokine production, such as IL-2, TNFα, IFNγ, in response to normal input signals. The cytokines produced by CD4 T cells act, in part, to activate and/or otherwise modulate, i.e., "provide help," to other immune cells such as B cells and $CD8^+$ cells. In some particular embodiments of the aspects described herein, a cell that is functionally exhausted is a CD8 or cytotoxic T lymphocyte that expresses the CD8cell surface marker. Such CD8 cells normally proliferate, engage in cytotoxic or cytolytic activity, and/or produce cytokines, such as IL-2 and IFNγ, or a combination thereof, in response to T cell receptor and/or co-stimulatory receptor stimulation. Thus, a functionally exhausted or unresponsive CD8 T cell is one which has a reduction in proliferation, cytotoxic activity, and/or cytokine production, such as IL-2, TNFα, IFNγ, in response to normal input signals.

As used herein, the term "reduces T cell tolerance" means that a given treatment or set of conditions leads to reduced T cell tolerance as evidenced by an increase in one or more T cell effector functions, e.g., greater T cell proliferation, cytokine production, responsiveness, and/or ability or receptiveness with regards to activation. Methods of measuring T cell activity are known in the art. By way of non-limiting example, T cell tolerance can be induced by contacting T cells with recall antigen, anti-CD3 in the absence of costimulation, and/or ionomycin. Levels of, e.g., LDH-A, RAB10, and/or ZAP70 (both intracellular or secreted) can be monitored, for example, to determine the extent of T cell tolerogenesis (with levels of IL-2, interferon-γ and TNF correlating with increased T cell tolerance). The response of cells pre-treated with, e.g. ionomycin, to an antigen can also be measured in order to determine the extent of T cell tolerance in a cell or population of cells, e.g. by monitoring the level of secreted and/or intracellular IL-2 and/or TNF-α (see, e.g., Macian et al. Cell 2002 109:719-731; which is incorporated by reference herein in its entirety). Other characteristics of T cells having undergone adaptive tolerance is that they have increased levels of Fyn and ZAP-70/Syk, Cb1-b, GRAIL, Ikaros, CREM (cAMP response element modulator), B lymphocyte-induced maturation protein-1 (Blimp-1), PD1, CD5, and SHP2; increased phosphorylation of ZAP-70/Syk, LAT, PLγ½, ERK, PKC-O/IKBA; increased activation of intracellular calcium levels; decreased histone acetylation or hypoacetylation and/or increased CpG methylation at the IL-2 locus. Thus, in some embodiments, modulation of one or more of any of these parameters can be assayed to determine whether one or more modulating agents modulates an immune response in vivo or modulates immune tolerance.

Modulation of T cell tolerance can also be measured by determining the proliferation of T cells in the presence of a relevant antigen assayed, e.g., by a $^3$H-thymidine incorporation assay, flow cytometry based assay, such as CFSE or other fluorochrome-based proliferation assay, or cell number. Markers of T cell activation after exposure to the relevant antigen can also be assayed, e.g. flow cytometry analysis of cell surface markers indicative of T cell activation (e.g. CD69, CD30, CD25, and HLA-DR). Reduced T cell activation in response to antigen-challenge is indicative of tolerance induction. Conversely, increased T cell activation in response to antigen-challenge is indicative of reduced tolerance.

Modulation of T cell tolerance can also be measured, in some embodiments, by determining the degree to which the modulating agent inhibits or increase the activity of its target. For example, the SEB model can be used to measure T cell tolerance and modulation thereof. In normal mice, neonatal injection of staphylococcal enterotoxin B(SEB) induces tolerance in T cells that express reactive T cell receptor (TCR) V beta regions. If, in the presence of an IL-27 or NFIL-3 modulating, T cells expressing reactive TCR V beta regions (e.g., Vbeta8) display a statistically significant reduction or increase in T cell activity than T cells not contacted with the modulating agent, the modulating agent is one that modulates T cell tolerance.

Other in vivo models of peripheral tolerance that can be used in some aspects and embodiments to measure modulation in T cell tolerance using the modulating agents described herein include, for example, models for peripheral tolerance in which homogeneous populations of T cells from TCR transgenic and double transgenic mice are transferred into hosts that constitutively express the antigen recognized by the transferred T cells, e.g., the H-Y antigen TCR transgenic; pigeon cytochrome C antigen TCR transgenic; or hemagglutinin (HA) TCR transgenic. In such models, T cells expressing the TCR specific for the antigen constitutively or inducibly expressed by the recipient mice typically undergo an immediate expansion and proliferative phase, followed by a period of unresponsiveness, which is reversed when the antigen is removed and/or antigen expression is inhibited. Accordingly, if, in the presence of one or more modulating agents, for example, in such models if the T cells proliferate or expand, show cytokine activity, etc. significantly more than T cells in the absence of the inhibitory agent, than that agent is one that reduces T cell tolerance. Such measurements of proliferation can occur in vivo using T cells labeled with BrDU, CFSE or another intravital dye that allows tracking of proliferation prior to transferring to a recipient animal expressing the antigen, or cytokine reporter T cells, or using ex vivo methods to analyze cellular proliferation and/or cytokine production, such as thymidine proliferation assays, ELISA, cytokine bead assays, and the like.

Modulation of T cell tolerance can also be assessed by examination of tumor infiltrating lymphocytes or T lymphocytes within lymph nodes that drain from an established tumor. Such T cells exhibit features of "exhaustion" through expression of cell surface molecules, such as TIM-3, for example, and decreased secretion of cytokines such as interferon-γ. Accordingly, if, in the presence of an inhibitory agent, increased quantities of T cells with, for example, 1) antigen specificity for tumor associated antigens are observed (e.g. as determined by major histocompatibility complex class I or class II tetramers which contain tumor associated peptides) and/or 2) that are capable of secreting high levels of interferon-γ and cytolytic effector molecules such as granzyme-B, relative to that observed in the absence of the inhibitory agent, this would be evidence that T cell tolerance had been reduced.

Target Genes/Gene Products that Modulate T Cell Function/Dysfunction

Provided herein are target genes, gene products, and combinations thereof that are useful in modulating T cell dysfunction, particularly T cell exhaustion. Any of the target genes/gene products can be targeted alone or in any combination thereof. Also provided herein are novel gene signatures for detecting and isolating T cells having a particular phenotype, particularly dysfunctional T cells.

TABLE 1

| Genes that modulate T cell function/dysfunction | | |
|---|---|---|
| Bst2 | NM_004335.3 | SEQ ID NO: 3. |
| Btla | NM_001085357.1 | SEQ ID NO: 4. |

TABLE 1-continued

| Genes that modulate T cell function/dysfunction | | |
|---|---|---|
| Ccl9 | NM_011338.2 (*Mus Musculus*) | SEQ ID NO: 5. |
| Ccr4 | NM_005508.4 | SEQ ID NO: 6. |
| Cd40lg | NM_011616.2 (*Mus Musculus*) | SEQ ID NO: 7. |
| Cxcr4 | NM_001008540.1 | SEQ ID NO: 8. |
| Gpr65 | NM_003608.3 | SEQ ID NO: 9. |
| Il33 | NM_001199640.1 | SEQ ID NO: 10. |
| Klrc2 | NM_002260.3 | SEQ ID NO: 11. |
| Klrd1 | NM_001114396.1 | SEQ ID NO: 12. |
| Klre1 | NM_153590.3 (*Mus Musculus*) | SEQ ID NO: 13. |
| Lif | NM_001257135.1 | SEQ ID NO: 14. |
| Lpar3 | NM_012152.2 | SEQ ID NO: 15. |
| Olfm1 | NM_001282611.1 | SEQ ID NO: 16. |
| Pdpn | NM_001006624.1 | SEQ ID NO: 17. |
| Ptpn3 | NM_001145368.1 | SEQ ID NO: 18. |
| Sdc1 | NM_001006946.1 | SEQ ID NO: 19. |
| Timp2 | NM_003255.4 | SEQ ID NO: 20. |
| Tnfsf9 (4-1BB) | NM_001561.5 | SEQ ID NO: 21. |
| Vldlr | NM_001018056.1 | SEQ ID NO: 22. |
| Entpd1 | NM_001098175.1 | SEQ ID NO: 23. |
| Il13ra1 | NM_001560.2 | SEQ ID NO: 24. |
| Il6st | NM_001190981.1 | SEQ ID NO: 25. |
| Inhba | NM_002192.2 | SEQ ID NO: 26. |
| Lamp2 | NM_001122606.1 | SEQ ID NO: 27. |
| Lap3 | NM_015907.2 | SEQ ID NO: 28. |
| Ly75 | NM_002349.3 | SEQ ID NO: 29. |
| Nampt | NM_005746.2 | SEQ ID NO: 30. |
| Ccl5 | NM_001278736.1 | SEQ ID NO: 31. |
| Cd83 | NM_001040280.1 | SEQ ID NO: 32. |
| Klrk1 | NM_007360.3 | SEQ ID NO: 33. |
| Sema7a | NM_001146029.1 | SEQ ID NO: 34. |
| Serpinc1 | NM_000488.3 | SEQ ID NO: 35. |
| Ccr2 | NM_001123041.2 | SEQ ID NO: 36. |
| Ifitm1 | NM_003641.3 | SEQ ID NO: 37. |
| Il12rb1 | NM_001290023.1 | SEQ ID NO: 38. |
| Il1r1 | NM_000877.3 | SEQ ID NO: 39. |
| Sdc4 | NM_002999.3 | SEQ ID NO: 40. |
| Slamf7 | NM_001282588.1 | SEQ ID NO: 41. |
| Tgfb3 | NM_003239.3 | SEQ ID NO: 42. |
| Adam9 | NM_003816.2 | SEQ ID NO: 43. |
| Cd93 | NM_012072.3 | SEQ ID NO: 44. |
| Tigit | NM_173799.3 | SEQ ID NO: 45. |
| Ccr5 | NM_000579.3 | SEQ ID NO: 46. |
| Adam8 | NM_001109.4 | SEQ ID NO: 47. |
| Cd68 | NM_001040059.1 | SEQ ID NO: 48. |
| Isg20 | NM_001303233.1 | SEQ ID NO: 49. |
| Il10 | NM_000572.2 | SEQ ID NO: 50. |
| Il10ra | NM_001558.3 | SEQ ID NO: 51. |
| Il21 | NM_001207006.2 | SEQ ID NO: 52. |
| Il2rb | NM_000878.3 | SEQ ID NO: 53. |
| Abca1 | NM_005502.3 | SEQ ID NO: 54. |
| Alcam | NM_001243280.1 | SEQ ID NO: 55. |
| Cysltr2 | NM_001308465.1 | SEQ ID NO: 56. |
| Gcnt1 | NM_001097633.1 | SEQ ID NO: 57. |
| Havcr2(Tim-3) | NM_032782.4 | SEQ ID NO: 58. |
| Gabarapl1 | NM_031412.2 | SEQ ID NO: 59. |
| Il2ra | NM_000417.2 | SEQ ID NO: 60. |
| Spp1 | NM_000582.2 | SEQ ID NO: 61. |
| Cxcl10 | NM_001565.3 | SEQ ID NO: 62. |
| Ifitm3 | NM_021034.2 | SEQ ID NO: 63. |
| Il1r2 | NM_001261419.1 | SEQ ID NO: 64. |
| Lag3 | NM_002286.5 | SEQ ID NO: 65. |
| Pglyrp1 | NM_005091.2 | SEQ ID NO: 66. |
| Lilrb4 | NM_001278426.3 | SEQ ID NO: 67. |
| Klrc1 | NM_001304448.1 | SEQ ID NO: 68. |
| Procr | NM_006404.4 | SEQ ID NO: 69. |

TABLE 2

| Pairs of Target Genes | | | | | | | | | | | | | | |
|---|---|---|---|---|---|---|---|---|---|---|---|---|---|---|
| | Bst2 | Btla | Cc19 | Ccr4 | Cd401g | Cxcr4 | Gpr65 | Il33 | Klrc2 | Klrd1 | Klre1 | Lif | Lpar3 | Olfm1 |
| Bst2 | X | • | • | • | • | • | • | • | • | • | • | • | • | • |
| Btla | • | X | • | • | • | • | • | • | • | • | • | • | • | • |
| Cc19 | • | • | X | • | • | • | • | • | • | • | • | • | • | • |

TABLE 2-continued

Pairs of Target Genes

| | | | | | | | | | | | | | | |
|---|---|---|---|---|---|---|---|---|---|---|---|---|---|---|
| Ccr4 | • | • | • | X | • | • | • | • | • | • | • | • | • | • |
| Cd401g | • | • | • | • | X | • | • | • | • | • | • | • | • | • |
| Cxcr4 | • | • | • | • | • | X | • | • | • | • | • | • | • | • |
| Gpr65 | • | • | • | • | • | • | X | • | • | • | • | • | • | • |
| Il33 | • | • | • | • | • | • | • | X | • | • | • | • | • | • |
| Klrc2 | • | • | • | • | • | • | • | • | X | • | • | • | • | • |
| Klrd1 | • | • | • | • | • | • | • | • | • | X | • | • | • | • |
| Klre1 | • | • | • | • | • | • | • | • | • | • | X | • | • | • |
| Lif | • | • | • | • | • | • | • | • | • | • | • | X | • | • |
| Lpar3 | • | • | • | • | • | • | • | • | • | • | • | • | X | • |
| Olfm1 | • | • | • | • | • | • | • | • | • | • | • | • | • | X |
| Pdpn | • | • | • | • | • | • | • | • | • | • | • | • | • | • |
| Ptpn3 | • | • | • | • | • | • | • | • | • | • | • | • | • | • |
| Sdc1 | • | • | • | • | • | • | • | • | • | • | • | • | • | • |
| Timp2 | • | • | • | • | • | • | • | • | • | • | • | • | • | • |
| Tnfsf9 (4-1BB) | • | • | • | • | • | • | • | • | • | • | • | • | • | • |
| Vldlr | • | • | • | • | • | • | • | • | • | • | • | • | • | • |
| Entpd1 | • | • | • | • | • | • | • | • | • | • | • | • | • | • |
| Il13ra1 | • | • | • | • | • | • | • | • | • | • | • | • | • | • |
| Il6st | • | • | • | • | • | • | • | • | • | • | • | • | • | • |
| Inhba | • | • | • | • | • | • | • | • | • | • | • | • | • | • |
| Lamp2 | • | • | • | • | • | • | • | • | • | • | • | • | • | • |
| Lap3 | • | • | • | • | • | • | • | • | • | • | • | • | • | • |
| Ly75 | • | • | • | • | • | • | • | • | • | • | • | • | • | • |
| Nampt | • | • | • | • | • | • | • | • | • | • | • | • | • | • |
| Ccl5 | • | • | • | • | • | • | • | • | • | • | • | • | • | • |
| Cd83 | • | • | • | • | • | • | • | • | • | • | • | • | • | • |
| Klrk1 | • | • | • | • | • | • | • | • | • | • | • | • | • | • |
| Sema7a | • | • | • | • | • | • | • | • | • | • | • | • | • | • |
| Serpinc1 | • | • | • | • | • | • | • | • | • | • | • | • | • | • |
| Ccr2 | • | • | • | • | • | • | • | • | • | • | • | • | • | • |
| Ifitm1 | • | • | • | • | • | • | • | • | • | • | • | • | • | • |
| Il12rb1 | • | • | • | • | • | • | • | • | • | • | • | • | • | • |
| Il1r1 | • | • | • | • | • | • | • | • | • | • | • | • | • | • |
| Sdc4 | • | • | • | • | • | • | • | • | • | • | • | • | • | • |
| Slamf7 | • | • | • | • | • | • | • | • | • | • | • | • | • | • |
| Tgfb3 | • | • | • | • | • | • | • | • | • | • | • | • | • | • |
| Adam9 | • | • | • | • | • | • | • | • | • | • | • | • | • | • |
| Cd93 | • | • | • | • | • | • | • | • | • | • | • | • | • | • |
| Tigit | • | • | • | • | • | • | • | • | • | • | • | • | • | • |
| Ccr5 | • | • | • | • | • | • | • | • | • | • | • | • | • | • |
| Adam8 | • | • | • | • | • | • | • | • | • | • | • | • | • | • |
| Cd68 | • | • | • | • | • | • | • | • | • | • | • | • | • | • |
| Isg20 | • | • | • | • | • | • | • | • | • | • | • | • | • | • |
| Il10 | • | • | • | • | • | • | • | • | • | • | • | • | • | • |
| Il10ra | • | • | • | • | • | • | • | • | • | • | • | • | • | • |
| Il21 | • | • | • | • | • | • | • | • | • | • | • | • | • | • |
| Il2rb | • | • | • | • | • | • | • | • | • | • | • | • | • | • |
| Abca1 | • | • | • | • | • | • | • | • | • | • | • | • | • | • |
| Alcam | • | • | • | • | • | • | • | • | • | • | • | • | • | • |
| Cysltr2 | • | • | • | • | • | • | • | • | • | • | • | • | • | • |

| | Pdpn | Ptpn3 | Sdc1 | Timp2 | Tnfsf9 (4-1BB) | Vldlr | Entpd1 | Il13ra1 | Il6st | Inhba | Lamp2 | Lap3 | Ly75 | Nampt |
|---|---|---|---|---|---|---|---|---|---|---|---|---|---|---|
| Bst2 | • | • | • | • | • | • | • | • | • | • | • | • | • | • |
| Btla | • | • | • | • | • | • | • | • | • | • | • | • | • | • |
| Cc19 | • | • | • | • | • | • | • | • | • | • | • | • | • | • |
| Ccr4 | • | • | • | • | • | • | • | • | • | • | • | • | • | • |
| Cd401g | • | • | • | • | • | • | • | • | • | • | • | • | • | • |
| Cxcr4 | • | • | • | • | • | • | • | • | • | • | • | • | • | • |
| Gpr65 | • | • | • | • | • | • | • | • | • | • | • | • | • | • |
| Il33 | • | • | • | • | • | • | • | • | • | • | • | • | • | • |
| Klrc2 | • | • | • | • | • | • | • | • | • | • | • | • | • | • |
| Klrd1 | • | • | • | • | • | • | • | • | • | • | • | • | • | • |
| Klre1 | • | • | • | • | • | • | • | • | • | • | • | • | • | • |
| Lif | • | • | • | • | • | • | • | • | • | • | • | • | • | • |
| Lpar3 | • | • | • | • | • | • | • | • | • | • | • | • | • | • |
| Olfm1 | • | • | • | • | • | • | • | • | • | • | • | • | • | • |
| Pdpn | X | • | • | • | • | • | • | • | • | • | • | • | • | • |
| Ptpn3 | • | X | • | • | • | • | • | • | • | • | • | • | • | • |
| Sdc1 | • | • | X | • | • | • | • | • | • | • | • | • | • | • |
| Timp2 | • | • | • | X | • | • | • | • | • | • | • | • | • | • |
| Tnfsf9 | • | • | • | • | X | • | • | • | • | • | • | • | • | • |
| Vldlr | • | • | • | • | • | X | • | • | • | • | • | • | • | • |
| Entpd1 | • | • | • | • | • | • | X | • | • | • | • | • | • | • |
| Il13ra1 | • | • | • | • | • | • | • | X | • | • | • | • | • | • |

TABLE 2-continued

| Pairs of Target Genes | | | | | | | | | | | | | | |
|---|---|---|---|---|---|---|---|---|---|---|---|---|---|---|
| Il6st | • | • | • | • | • | • | • | • | X | • | • | • | • | • |
| Inhba | • | • | • | • | • | • | • | • | • | X | • | • | • | • |
| Lamp2 | • | • | • | • | • | • | • | • | • | • | X | • | • | • |
| Lap3 | • | • | • | • | • | • | • | • | • | • | • | X | • | • |
| Ly75 | • | • | • | • | • | • | • | • | • | • | • | • | X | • |
| Nampt | • | • | • | • | • | • | • | • | • | • | • | • | • | X |
| Cc15 | • | • | • | • | • | • | • | • | • | • | • | • | • | • |
| Cd83 | • | • | • | • | • | • | • | • | • | • | • | • | • | • |
| Klrk1 | • | • | • | • | • | • | • | • | • | • | • | • | • | • |
| Sema7a | • | • | • | • | • | • | • | • | • | • | • | • | • | • |
| Serpinc1 | • | • | • | • | • | • | • | • | • | • | • | • | • | • |
| Ccr2 | • | • | • | • | • | • | • | • | • | • | • | • | • | • |
| Ifitm1 | • | • | • | • | • | • | • | • | • | • | • | • | • | • |
| Il12rb1 | • | • | • | • | • | • | • | • | • | • | • | • | • | • |
| Il1r1 | • | • | • | • | • | • | • | • | • | • | • | • | • | • |
| Sdc4 | • | • | • | • | • | • | • | • | • | • | • | • | • | • |
| Slamf7 | • | • | • | • | • | • | • | • | • | • | • | • | • | • |
| Tgfb3 | • | • | • | • | • | • | • | • | • | • | • | • | • | • |
| Adam9 | • | • | • | • | • | • | • | • | • | • | • | • | • | • |
| cd93 | • | • | • | • | • | • | • | • | • | • | • | • | • | • |
| Tigit | • | • | • | • | • | • | • | • | • | • | • | • | • | • |
| Ccr5 | • | • | • | • | • | • | • | • | • | • | • | • | • | • |
| Adam8 | • | • | • | • | • | • | • | • | • | • | • | • | • | • |
| Cd68 | • | • | • | • | • | • | • | • | • | • | • | • | • | • |
| Isg20 | • | • | • | • | • | • | • | • | • | • | • | • | • | • |
| Il10 | • | • | • | • | • | • | • | • | • | • | • | • | • | • |
| Il10ra | • | • | • | • | • | • | • | • | • | • | • | • | • | • |
| Il21 | • | • | • | • | • | • | • | • | • | • | • | • | • | • |
| Il2rb | • | • | • | • | • | • | • | • | • | • | • | • | • | • |
| Abca1 | • | • | • | • | • | • | • | • | • | • | • | • | • | • |
| Alcam | • | • | • | • | • | • | • | • | • | • | • | • | • | • |
| Cysltr2 | • | • | • | • | • | • | • | • | • | • | • | • | • | • |

| | Cc15 | Cd83 | Klrk1 | Sema7a | Serpinc1 | Ccr2 | Ifitm1 | Il12rb1 | Il1r1 | Sdc4 | Slamf7 | Tgfb3 | Adam9 |
|---|---|---|---|---|---|---|---|---|---|---|---|---|---|
| Bst2 | • | • | • | • | • | • | • | • | • | • | • | • | • |
| Btla | • | • | • | • | • | • | • | • | • | • | • | • | • |
| Cc19 | • | • | • | • | • | • | • | • | • | • | • | • | • |
| Ccr4 | • | • | • | • | • | • | • | • | • | • | • | • | • |
| Cd401g | • | • | • | • | • | • | • | • | • | • | • | • | • |
| Cxcr4 | • | • | • | • | • | • | • | • | • | • | • | • | • |
| Gpr65 | • | • | • | • | • | • | • | • | • | • | • | • | • |
| Il33 | • | • | • | • | • | • | • | • | • | • | • | • | • |
| Klrc2 | • | • | • | • | • | • | • | • | • | • | • | • | • |
| Klrd1 | • | • | • | • | • | • | • | • | • | • | • | • | • |
| Klre1 | • | • | • | • | • | • | • | • | • | • | • | • | • |
| Lif | • | • | • | • | • | • | • | • | • | • | • | • | • |
| Lpar3 | • | • | • | • | • | • | • | • | • | • | • | • | • |
| Olfm1 | • | • | • | • | • | • | • | • | • | • | • | • | • |
| Pdpn | • | • | • | • | • | • | • | • | • | • | • | • | • |
| Ptpn3 | • | • | • | • | • | • | • | • | • | • | • | • | • |
| Sdc1 | • | • | • | • | • | • | • | • | • | • | • | • | • |
| Timp2 | • | • | • | • | • | • | • | • | • | • | • | • | • |
| Tnfsf9 | • | • | • | • | • | • | • | • | • | • | • | • | • |
| Vldlr | • | • | • | • | • | • | • | • | • | • | • | • | • |
| Entpd1 | • | • | • | • | • | • | • | • | • | • | • | • | • |
| Il13ra1 | • | • | • | • | • | • | • | • | • | • | • | • | • |
| Il6st | • | • | • | • | • | • | • | • | • | • | • | • | • |
| Inhba | • | • | • | • | • | • | • | • | • | • | • | • | • |
| Lamp2 | • | • | • | • | • | • | • | • | • | • | • | • | • |
| Lap3 | • | • | • | • | • | • | • | • | • | • | • | • | • |
| Ly75 | • | • | • | • | • | • | • | • | • | • | • | • | • |
| Nampt | • | • | • | • | • | • | • | • | • | • | • | • | • |
| Cc15 | X | • | • | • | • | • | • | • | • | • | • | • | • |
| Cd83 | • | X | • | • | • | • | • | • | • | • | • | • | • |
| Klrk1 | • | • | X | • | • | • | • | • | • | • | • | • | • |
| Sema7a | • | • | • | X | • | • | • | • | • | • | • | • | • |
| Serpinc1 | • | • | • | • | X | • | • | • | • | • | • | • | • |
| Ccr2 | • | • | • | • | • | X | • | • | • | • | • | • | • |
| Ifitm1 | • | • | • | • | • | • | X | • | • | • | • | • | • |
| Il12rb1 | • | • | • | • | • | • | • | X | • | • | • | • | • |
| Il1r1 | • | • | • | • | • | • | • | • | X | • | • | • | • |
| Sdc4 | • | • | • | • | • | • | • | • | • | X | • | • | • |
| Slamf7 | • | • | • | • | • | • | • | • | • | • | X | • | • |
| Tgfb3 | • | • | • | • | • | • | • | • | • | • | • | X | • |
| Adam9 | • | • | • | • | • | • | • | • | • | • | • | • | X |
| Cd93 | • | • | • | • | • | • | • | • | • | • | • | • | • |
| Tigit | • | • | • | • | • | • | • | • | • | • | • | • | • |

TABLE 2-continued

| Pairs of Target Genes | | | | | | | | | | | | | |
|---|---|---|---|---|---|---|---|---|---|---|---|---|---|
| Ccr5 | • | • | • | • | • | • | • | • | • | • | • | • | • |
| Adam8 | • | • | • | • | • | • | • | • | • | • | • | • | • |
| Cd68 | • | • | • | • | • | • | • | • | • | • | • | • | • |
| Isg20 | • | • | • | • | • | • | • | • | • | • | • | • | • |
| Il10 | • | • | • | • | • | • | • | • | • | • | • | • | • |
| Il10ra | • | • | • | • | • | • | • | • | • | • | • | • | • |
| Il21 | • | • | • | • | • | • | • | • | • | • | • | • | • |
| Il2rb | • | • | • | • | • | • | • | • | • | • | • | • | • |
| Abca1 | • | • | • | • | • | • | • | • | • | • | • | • | • |
| Alcam | • | • | • | • | • | • | • | • | • | • | • | • | • |
| Cysltr2 | • | • | • | • | • | • | • | • | • | • | • | • | • |

| | Cd93 | Tigit | Ccr5 | Adam8 | Cd68 | Isg20 | Il10 | Il10ra | Il21 | Il2rb | Abca1 | Alcam | Cysltr2 |
|---|---|---|---|---|---|---|---|---|---|---|---|---|---|
| Bst2 | • | • | • | • | • | • | • | • | • | • | • | • | • |
| Btla | • | • | • | • | • | • | • | • | • | • | • | • | • |
| Cc19 | • | • | • | • | • | • | • | • | • | • | • | • | • |
| Ccr4 | • | • | • | • | • | • | • | • | • | • | • | • | • |
| Cd401g | • | • | • | • | • | • | • | • | • | • | • | • | • |
| Cxcr4 | • | • | • | • | • | • | • | • | • | • | • | • | • |
| Gpr65 | • | • | • | • | • | • | • | • | • | • | • | • | • |
| Il33 | • | • | • | • | • | • | • | • | • | • | • | • | • |
| Klrc2 | • | • | • | • | • | • | • | • | • | • | • | • | • |
| Klrd1 | • | • | • | • | • | • | • | • | • | • | • | • | • |
| Klre1 | • | • | • | • | • | • | • | • | • | • | • | • | • |
| Lif | • | • | • | • | • | • | • | • | • | • | • | • | • |
| Lpar3 | • | • | • | • | • | • | • | • | • | • | • | • | • |
| Olfm1 | • | • | • | • | • | • | • | • | • | • | • | • | • |
| Pdpn | • | • | • | • | • | • | • | • | • | • | • | • | • |
| Ptpn3 | • | • | • | • | • | • | • | • | • | • | • | • | • |
| Sdc1 | • | • | • | • | • | • | • | • | • | • | • | • | • |
| Timp2 | • | • | • | • | • | • | • | • | • | • | • | • | • |
| Tnfsf9 | • | • | • | • | • | • | • | • | • | • | • | • | • |
| Vldlr | • | • | • | • | • | • | • | • | • | • | • | • | • |
| Entpd1 | • | • | • | • | • | • | • | • | • | • | • | • | • |
| Il13ra1 | • | • | • | • | • | • | • | • | • | • | • | • | • |
| Il6st | • | • | • | • | • | • | • | • | • | • | • | • | • |
| Inhba | • | • | • | • | • | • | • | • | • | • | • | • | • |
| Lamp2 | • | • | • | • | • | • | • | • | • | • | • | • | • |
| Lap3 | • | • | • | • | • | • | • | • | • | • | • | • | • |
| Ly75 | • | • | • | • | • | • | • | • | • | • | • | • | • |
| Nampt | • | • | • | • | • | • | • | • | • | • | • | • | • |
| Ccl5 | • | • | • | • | • | • | • | • | • | • | • | • | • |
| Cd83 | • | • | • | • | • | • | • | • | • | • | • | • | • |
| Klrk1 | • | • | • | • | • | • | • | • | • | • | • | • | • |
| Sema7a | • | • | • | • | • | • | • | • | • | • | • | • | • |
| Serpinc1 | • | • | • | • | • | • | • | • | • | • | • | • | • |
| Ccr2 | • | • | • | • | • | • | • | • | • | • | • | • | • |
| Ifitm1 | • | • | • | • | • | • | • | • | • | • | • | • | • |
| Il12rb1 | • | • | • | • | • | • | • | • | • | • | • | • | • |
| Il1r1 | • | • | • | • | • | • | • | • | • | • | • | • | • |
| Sdc4 | • | • | • | • | • | • | • | • | • | • | • | • | • |
| Slamf7 | • | • | • | • | • | • | • | • | • | • | • | • | • |
| Tgfb3 | • | • | • | • | • | • | • | • | • | • | • | • | • |
| Adam9 | • | • | • | • | • | • | • | • | • | • | • | • | • |
| Cd93 | X | • | • | • | • | • | • | • | • | • | • | • | • |
| Tigit | • | X | • | • | • | • | • | • | • | • | • | • | • |
| Ccr5 | • | • | X | • | • | • | • | • | • | • | • | • | • |
| Adam8 | • | • | • | X | • | • | • | • | • | • | • | • | • |
| Cd68 | • | • | • | • | X | • | • | • | • | • | • | • | • |
| Isg20 | • | • | • | • | • | X | • | • | • | • | • | • | • |
| Il10 | • | • | • | • | • | • | X | • | • | • | • | • | • |
| Il10ra | • | • | • | • | • | • | • | X | • | • | • | • | • |
| Il21 | • | • | • | • | • | • | • | • | X | • | • | • | • |
| Il2rb | • | • | • | • | • | • | • | • | • | X | • | • | • |
| Abca1 | • | • | • | • | • | • | • | • | • | • | X | • | • |
| Alcam | • | • | • | • | • | • | • | • | • | • | • | X | • |
| Cysltr2 | • | • | • | • | • | • | • | • | • | • | • | • | X |

| | Gent1 | Haver2 (Tim-3) | Gabarapl | Il2ra | Spp1 | Cxc110 | Ifitm3 | Il1r2 | Lag3 | Pglyrp1 | Lilrb4 | Klrc1 | Procr |
|---|---|---|---|---|---|---|---|---|---|---|---|---|---|
| Bst2 | • | • | • | • | • | • | • | • | • | • | • | • | • |
| Btla | • | • | • | • | • | • | • | • | • | • | • | • | • |
| Cc19 | • | • | • | • | • | • | • | • | • | • | • | • | • |
| Ccr4 | • | • | • | • | • | • | • | • | • | • | • | • | • |
| Cd401g | • | • | • | • | • | • | • | • | • | • | • | • | • |
| Cxcr4 | • | • | • | • | • | • | • | • | • | • | • | • | • |

TABLE 2-continued

Pairs of Target Genes

| | | | | | | | | | | | | | |
|---|---|---|---|---|---|---|---|---|---|---|---|---|---|
| Gpr65 | • | • | • | • | • | • | • | • | • | • | • | • | • |
| Il33 | • | • | • | • | • | • | • | • | • | • | • | • | • |
| Klrc2 | • | • | • | • | • | • | • | • | • | • | • | • | • |
| Klrd1 | • | • | • | • | • | • | • | • | • | • | • | • | • |
| Klre1 | • | • | • | • | • | • | • | • | • | • | • | • | • |
| Lif | • | • | • | • | • | • | • | • | • | • | • | • | • |
| Lpar3 | • | • | • | • | • | • | • | • | • | • | • | • | • |
| Olfm1 | • | • | • | • | • | • | • | • | • | • | • | • | • |
| Pdpn | • | • | • | • | • | • | • | • | • | • | • | • | • |
| Ptpn3 | • | • | • | • | • | • | • | • | • | • | • | • | • |
| Sdc1 | • | • | • | • | • | • | • | • | • | • | • | • | • |
| Timp2 | • | • | • | • | • | • | • | • | • | • | • | • | • |
| Tnfsf9 | • | • | • | • | • | • | • | • | • | • | • | • | • |
| Vldlr | • | • | • | • | • | • | • | • | • | • | • | • | • |
| Entpd1 | • | • | • | • | • | • | • | • | • | • | • | • | • |
| Il13ra1 | • | • | • | • | • | • | • | • | • | • | • | • | • |
| Il6st | • | • | • | • | • | • | • | • | • | • | • | • | • |
| Inhba | • | • | • | • | • | • | • | • | • | • | • | • | • |
| Lamp2 | • | • | • | • | • | • | • | • | • | • | • | • | • |
| Lap3 | • | • | • | • | • | • | • | • | • | • | • | • | • |
| Ly75 | • | • | • | • | • | • | • | • | • | • | • | • | • |
| Nampt | • | • | • | • | • | • | • | • | • | • | • | • | • |
| Ccl5 | • | • | • | • | • | • | • | • | • | • | • | • | • |
| Cd83 | • | • | • | • | • | • | • | • | • | • | • | • | • |
| Klrk1 | • | • | • | • | • | • | • | • | • | • | • | • | • |
| Sema7a | • | • | • | • | • | • | • | • | • | • | • | • | • |
| Serpinc1 | • | • | • | • | • | • | • | • | • | • | • | • | • |
| Ccr2 | • | • | • | • | • | • | • | • | • | • | • | • | • |
| Ifitm1 | • | • | • | • | • | • | • | • | • | • | • | • | • |
| Il12rb1 | • | • | • | • | • | • | • | • | • | • | • | • | • |
| Il1r1 | • | • | • | • | • | • | • | • | • | • | • | • | • |
| Sdc4 | • | • | • | • | • | • | • | • | • | • | • | • | • |
| Slamf7 | • | • | • | • | • | • | • | • | • | • | • | • | • |
| Tgfb3 | • | • | • | • | • | • | • | • | • | • | • | • | • |
| Adam9 | • | • | • | • | • | • | • | • | • | • | • | • | • |
| Cd93 | • | • | • | • | • | • | • | • | • | • | • | • | • |
| Tigit | • | • | • | • | • | • | • | • | • | • | • | • | • |
| Ccr5 | • | • | • | • | • | • | • | • | • | • | • | • | • |
| Adam8 | • | • | • | • | • | • | • | • | • | • | • | • | • |
| Cd68 | • | • | • | • | • | • | • | • | • | • | • | • | • |
| Isg20 | • | • | • | • | • | • | • | • | • | • | • | • | • |
| Il10 | • | • | • | • | • | • | • | • | • | • | • | • | • |
| Il10ra | • | • | • | • | • | • | • | • | • | • | • | • | • |
| Il21 | • | • | • | • | • | • | • | • | • | • | • | • | • |
| Il2rb | • | • | • | • | • | • | • | • | • | • | • | • | • |
| Abca1 | • | • | • | • | • | • | • | • | • | • | • | • | • |
| Alcam | • | • | • | • | • | • | • | • | • | • | • | • | • |
| Cysltr2 | • | • | • | • | • | • | • | • | • | • | • | • | • |

| | Bst2 | Btla | Cc19 | Ccr4 | Cd401g | Cxcr4 | Gpr65 | Il33 | Klrc2 | Klrd1 | Klre1 | Lif | Lpar3 | Olfm1 |
|---|---|---|---|---|---|---|---|---|---|---|---|---|---|---|
| Gent1 | • | • | • | • | • | • | • | • | • | • | • | • | • | • |
| Havcr2 (Tim-3) | • | • | • | • | • | • | • | • | • | • | • | • | • | • |
| Gabarapl | • | • | • | • | • | • | • | • | • | • | • | • | • | • |
| Il2ra | • | • | • | • | • | • | • | • | • | • | • | • | • | • |
| Spp1 | • | • | • | • | • | • | • | • | • | • | • | • | • | • |
| Cxcl10 | • | • | • | • | • | • | • | • | • | • | • | • | • | • |
| Ifitm3 | • | • | • | • | • | • | • | • | • | • | • | • | • | • |
| Il1r2 | • | • | • | • | • | • | • | • | • | • | • | • | • | • |
| Lag3 | • | • | • | • | • | • | • | • | • | • | • | • | • | • |
| Pglyrp1 | • | • | • | • | • | • | • | • | • | • | • | • | • | • |
| Lilrb4 | • | • | • | • | • | • | • | • | • | • | • | • | • | • |
| Klrc1 | • | • | • | • | • | • | • | • | • | • | • | • | • | • |
| Procr | • | • | • | • | • | • | • | • | • | • | • | • | • | • |

| | Pdpn | Ptpn3 | Sdc1 | Timp2 | Tnfsf9 (4-1BB) | Vldlr | Entpd1 | Il13ra1 | Il6st | Inhba | Lamp2 | Lap3 | Ly75 | Nampt |
|---|---|---|---|---|---|---|---|---|---|---|---|---|---|---|
| Gent1 | • | • | • | • | • | • | • | • | • | • | • | • | • | • |
| Haver2 (Tim-3) | • | • | • | • | • | • | • | • | • | • | • | • | • | • |
| Gabarapl | • | • | • | • | • | • | • | • | • | • | • | • | • | • |
| Il2ra | • | • | • | • | • | • | • | • | • | • | • | • | • | • |
| Spp1 | • | • | • | • | • | • | • | • | • | • | • | • | • | • |
| Cxcl10 | • | • | • | • | • | • | • | • | • | • | • | • | • | • |
| Ifitm3 | • | • | • | • | • | • | • | • | • | • | • | • | • | • |
| Il1r2 | • | • | • | • | • | • | • | • | • | • | • | • | • | • |

TABLE 2-continued

| Pairs of Target Genes | | | | | | | | | | | | | | |
|---|---|---|---|---|---|---|---|---|---|---|---|---|---|---|
| Lag3 | • | • | • | • | • | • | • | • | • | • | • | • | • | • |
| Pglyrp1 | • | • | • | • | • | • | • | • | • | • | • | • | • | • |
| Lilrb4 | • | • | • | • | • | • | • | • | • | • | • | • | • | • |
| Klrc1 | • | • | • | • | • | • | • | • | • | • | • | • | • | • |
| Procr | • | • | • | • | • | • | • | • | • | • | • | • | • | • |

| | Ccl5 | Cd83 | Klrk1 | Sema7a | Serpinc1 | Ccr2 | Ifitm1 | Il12rb1 | Il1r1 | Sdc4 | Slamf7 | Tgfb3 | Adam9 |
|---|---|---|---|---|---|---|---|---|---|---|---|---|---|
| Gent1 | • | • | • | • | • | • | • | • | • | • | • | • | • |
| Havcr2 (Tim-3) | • | • | • | • | • | • | • | • | • | • | • | • | • |
| Gabarapl | • | • | • | • | • | • | • | • | • | • | • | • | • |
| Il2ra | • | • | • | • | • | • | • | • | • | • | • | • | • |
| Spp1 | • | • | • | • | • | • | • | • | • | • | • | • | • |
| Cxcl10 | • | • | • | • | • | • | • | • | • | • | • | • | • |
| Ifitm3 | • | • | • | • | • | • | • | • | • | • | • | • | • |
| Il1r2 | • | • | • | • | • | • | • | • | • | • | • | • | • |
| Lag3 | • | • | • | • | • | • | • | • | • | • | • | • | • |
| Pglyrp1 | • | • | • | • | • | • | • | • | • | • | • | • | • |
| Lilrb4 | • | • | • | • | • | • | • | • | • | • | • | • | • |
| Klrc1 | • | • | • | • | • | • | • | • | • | • | • | • | • |
| Procr | • | • | • | • | • | • | • | • | • | • | • | • | • |

| | Cd93 | Tigit | Ccr5 | Adam8 | Cd68 | Isg20 | Il10 | Il10ra | Il21 | Il2rb | Abca1 | Alcam | Cysltr2 | Gent1 |
|---|---|---|---|---|---|---|---|---|---|---|---|---|---|---|
| Gent1 | • | • | • | • | • | • | • | • | • | • | • | • | • | X |
| Haver2 (Tim-3) | • | • | • | • | • | • | • | • | • | • | • | • | • | • |
| Gabarapl | • | • | • | • | • | • | • | • | • | • | • | • | • | • |
| Il2ra | • | • | • | • | • | • | • | • | • | • | • | • | • | • |
| Spp1 | • | • | • | • | • | • | • | • | • | • | • | • | • | • |
| Cxcl10 | • | • | • | • | • | • | • | • | • | • | • | • | • | • |
| Ifitm3 | • | • | • | • | • | • | • | • | • | • | • | • | • | • |
| Il1r2 | • | • | • | • | • | • | • | • | • | • | • | • | • | • |
| Lag3 | • | • | • | • | • | • | • | • | • | • | • | • | • | • |
| Pglyrp1 | • | • | • | • | • | • | • | • | • | • | • | • | • | • |
| Lilrb4 | • | • | • | • | • | • | • | • | • | • | • | • | • | • |
| Klrc1 | • | • | • | • | • | • | • | • | • | • | • | • | • | • |
| Procr | • | • | • | • | • | • | • | • | • | • | • | • | • | • |

| | Haver2 (Tim-3) | Gabarapl | Il2ra | Spp1 | Cxcl10 | Ifitm3 | Il1r2 | Lag3 | Pglyrp1 | Lilrb4 | Klrc1 | Procr |
|---|---|---|---|---|---|---|---|---|---|---|---|---|
| Gent1 | • | • | • | • | • | • | • | • | • | • | • | • |
| Haver2 (Tim-3) | X | • | • | • | • | • | • | • | • | • | • | • |
| Gabarapl | • | X | • | • | • | • | • | • | • | • | • | • |
| Il2ra | • | • | X | • | • | • | • | • | • | • | • | • |
| Spp1 | • | • | • | X | • | • | • | • | • | • | • | • |
| Cxcl10 | • | • | • | • | X | • | • | • | • | • | • | • |
| Ifitm3 | • | • | • | • | • | X | • | • | • | • | • | • |
| Il1r2 | • | • | • | • | • | • | X | • | • | • | • | • |
| Lag3 | • | • | • | • | • | • | • | X | • | • | • | • |
| Pglyrp1 | • | • | • | • | • | • | • | • | X | • | • | • |
| Lilrb4 | • | • | • | • | • | • | • | • | • | X | • | • |
| Klrc1 | • | • | • | • | • | • | • | • | • | • | X | • |
| Procr | • | • | • | • | • | • | • | • | • | • | • | X |

In one embodiment, at least two target genes are modulated using a combination of inhibitors and/or activators as described herein. In one embodiment, the at least two target genes are selected from the gene pairs listed in Table 2. In one embodiment, one or more target genes to be modulated are positive regulators of T cell function as listed in Table 3. In another embodiment, the one or more target genes to be modulated are negative regulators of T cell function as listed in Table 4.

TABLE 3

| Positive Regulators of T cell function | | | |
|---|---|---|---|
| Klrc2 | Klre1 | Tnfsf9 (4-1BB) | Klrk1 |
| Il12rb1 | Il1r1 | Slamf7 | |

TABLE 4

| Negative Regulators of T cell function | | | |
|---|---|---|---|
| Btla | Tigit | Havcr2(Tim-3) | Lag3 |
| Pdpn | Il10ra | Il1r2 | Procr |
| Lilrb4 | Klrc1 | | |

In some embodiments, two or more target genes are modulated using two or more modulating agents as described herein. In some embodiments, at least three target genes are modulated; in other embodiments at least 4, at least 5, at least 6, at least 7, at least 8, at least 9, at least 10 or more target genes are modulated in the methods and/or compositions provided herein.

In some embodiments, at least one pair of target genes as listed in Table 2 is modulated in combination with at least one additional target gene as listed in Tables 1, 3, or 4.

In some embodiments, two or more target genes selected from Table 4 are modulated using two or more modulating agents as described herein.

Figure 6C:
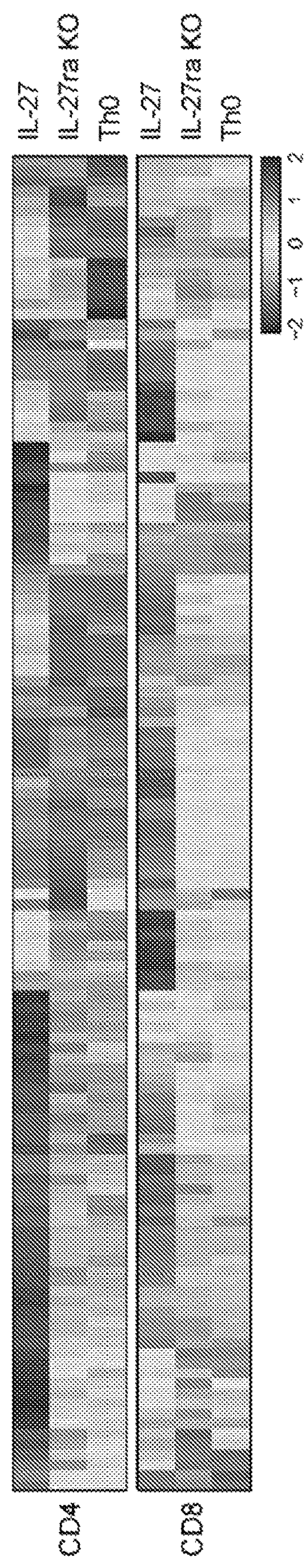
FIG. 6A-O. The IL-27-driven gene signature overlaps with multiple signatures of T cell dysfunction and tolerance and includes cytokines and cell-surface molecules. Temporal analysis of gene expression during the differentiation of A) CD4$^+$ and B) CD8$^+$ T cells from WT and IL27ra KO mice upon IL-27 stimulation over different time points. Data were obtained using a custom nanostring code-set containing probes (Table 16) for regulatory genes on T cells. Data shown are representative of 3 different experiments. Naïve CD4$^+$ and CD8$^+$ T cells from either WT or IL-27ra KO mice were stimulated with anti-CD3/CD28 in the presence or absence of IL-27 and harvested at 96 hr (CD4) and 72 hr (CD8) for global gene expression analysis. C) Naïve CD4$^+$ and CD8$^+$ T cells from either wild type or IL-27ra KO mice were stimulated with anti-CD3/CD28 in the presence or absence of IL-27 and harvested at 96 hr (CD4) and 72 hr (CD8) for global gene expression analysis. Expression level of 118 genes encoding cell surface receptors and cytokines are shown as a heatmap. D) Naïve CD4$^+$ and CD8$^+$ T cells from either WT or IL-27ra KO mice were stimulated with anti-CD3/CD28 in the presence or absence of IL-27 and harvested at 96 hr (CD4) and 72 hr (CD8) for global gene expression analysis. 118 genes encoding cell surface receptors and cytokines are shown as in FIG. 6C. E) Pearson correlation between the samples described in (D) for all 1,392 genes that were differentially expressed between WT CD4$^+$ T cells stimulated in the presence or absence of IL-27 (Fold change>2 and FDR<0.2). F) Corresponding gene expression heatmap for all 1,392 genes in (E). G) Graphical representation of the overlap of IL-27-signature up-regulated genes with genes expressed in several different dysfunctional or tolerant T cell states. The width of the gray bars reflects the extent of overlap across groups. H) IL-27 driven surface molecules overlapped with regulatory signatures. Five different T cells from regulatory state: CD8 TILs from cancer environment, virus-antigen specific CD8 T cells from chronic virus infection, anergic CD4 T cells, over stimulated CD4 T cells by anti-CD3 antibody, tolerated CD4 T cells. All the molecules shown were differentially expressed by IL-27 stimulation and appeared on Venn figures overlapped with each regulatory T cell state. Highlighted molecules were further biologically validated. I) Pearson correlation between WT CD4$^+$ and CD8$^+$ T cells for the 1,392 genes that were differentially expressed between WT CD4$^+$ T cells stimulated in the presence or absence of IL-27 (Fold change>2 and FDR<0.2). J) IL-27 signature genes were compared to T cell signatures obtained from five states of T cell impairment/tolerance/dysfunction. Number (left panel) and frequency (right panel) of overlapping genes between the IL-27 signature and each signature is depicted. P values were determined by hypergeometric test: Anergy—3.2e-05, Nasal anti-CD3-4.7e-21, Cancer—1.2e-33, Specific tolerance—4e-14 and Viral exhaustion—1.7e-26. K) Graphical representation of IL-27-driven soluble and cell surface molecules that overlap between dysfunctional $CD8^+$ T cell signatures from cancer and chronic viral infection. All of the molecules depicted were induced by IL-27 stimulation. The shaded background reflects the ranking based on the extent of overlap with the T cell states depicted in G. L) Pdpn and Procr protein and mRNA expression was determined in T cells from WT and IL27Ra KO stimulated with anti-CD3/CD28 in the presence or absence of IL-27. $CD4^+$ cells were analyzed at 96 hr (CD4) and $CD8^+$ cells at 72 hr (CD8). Representative flow cytometry and qPCR data are shown. M) Pdpn and Procr expression on $CD8^+$ TILs. Representative flow cytometry data showing Pdpn and Procr expressions with PD-1 and Tim-3 on $CD8^+$ TILs obtained from WT and IL27ra KO mice bearing B16F10 melanoma. N) TILs from WT mice bearing B16F10 melanoma were stimulated with PMA and Ionomycin. Cytokine production in $Procr^+$ or Procr $CD8^+$ TILs is shown. Thy1.1-IL-10 reporter mice were used for IL-10 expression analysis. Statistical significance was determined by paired-t-test (*p<0.05; **p<0.01). O) panels I-VI, tSNE plots of the 516 $CD8^+$ single-cell TILs (dots) harvested from WT mice bearing B16F10 melanoma tumor. Cells are colored in each panel by the relative average expression of the genes in the overlap of the IL-27 gene signature with the signatures for each of the indicated states of T cell non-responsiveness. The contour plot marks the region of highly scored cells by taking into account only those cells that have a signature score above the mean.
Figure 6D:
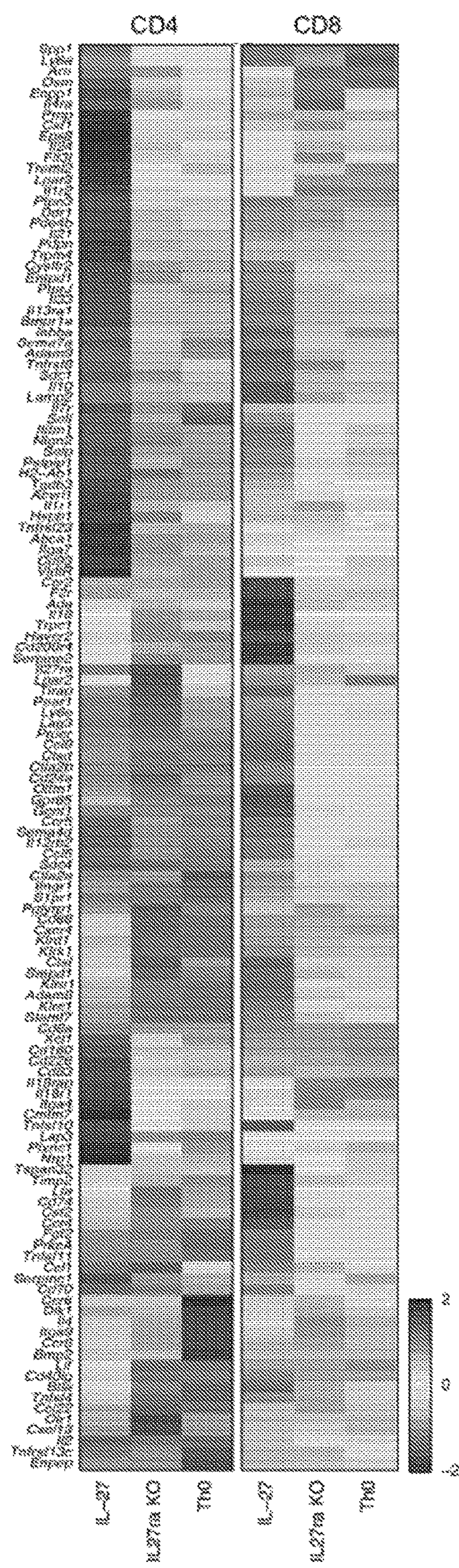
Figure 6G:
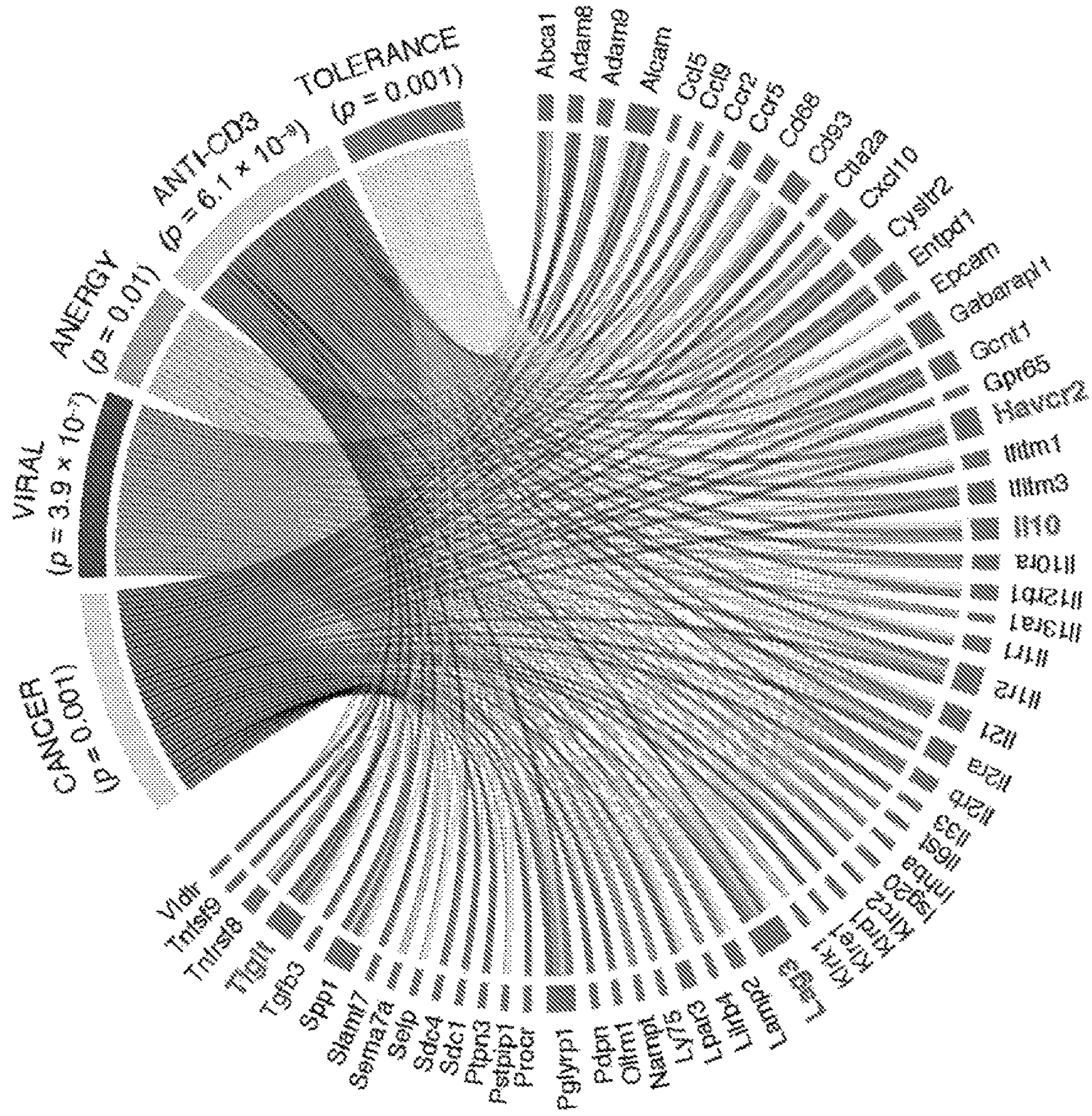
Figure 6H:
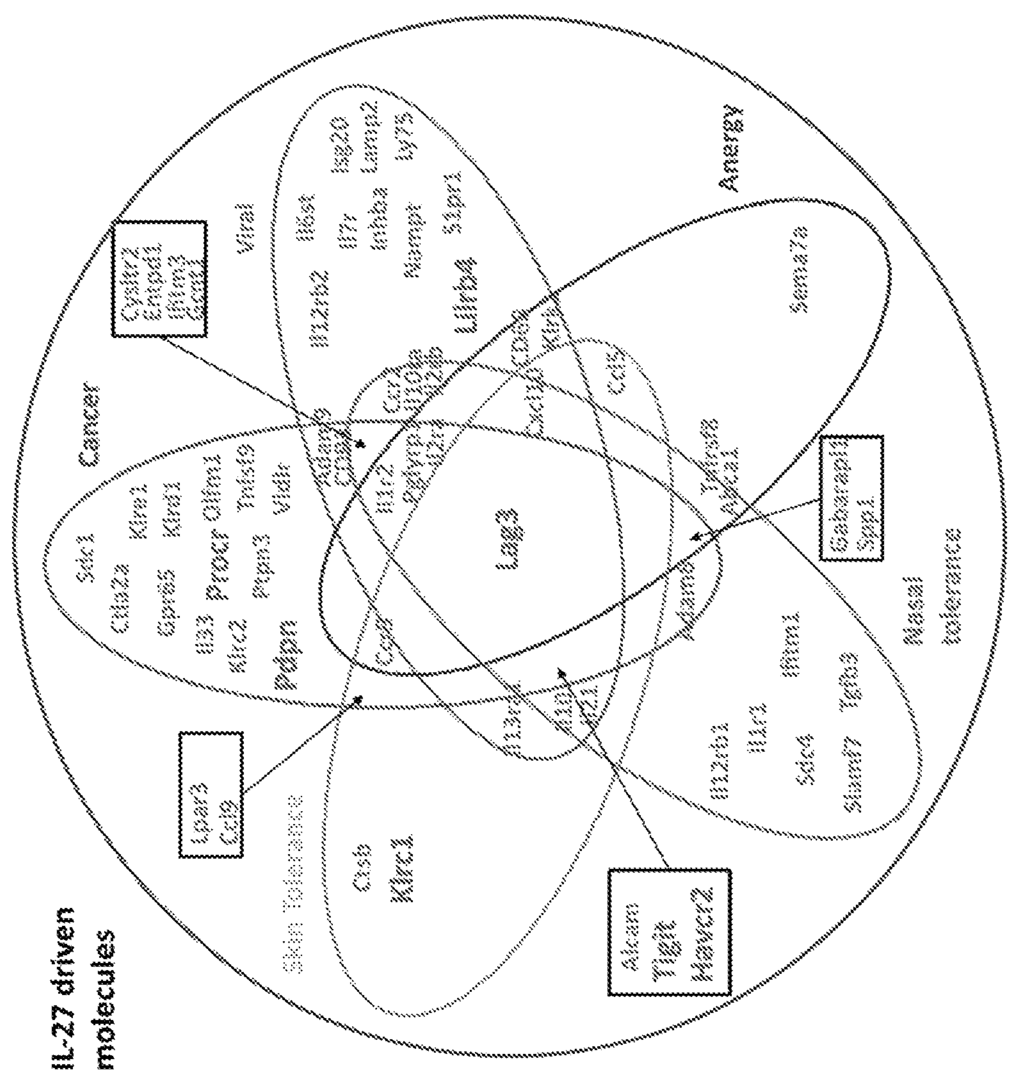

As described herein, T cells isolated from a cancer environment express an IL-27 inhibitory gene module in which the expression and activity of a subset of co-inhibitory and co-stimulatory molecules are induced, as described in FIG. 6H and listed in Table 5.

Accordingly, in some embodiments, one or more target genes selected from Table 5 are modulated using one or more modulating agents as described herein, for the treatment of certain disorders, such as cancer. In some embodiments, two or more target genes selected from Table 5 are modulated using two or more modulating agents as described herein, for the treatment of certain disorders such as cancer.

TABLE 5

| Cancer Associated IL-27 driven molecules | | | |
|---|---|---|---|
| LAG3 | PDPN | PROCR | SDC1 |
| CTLA2A | KLRE1 | GPR65 | KLRD1 |
| IL33 | OLFM1 | KLRC2 | PTPN3 |
| TNFSF9 | VLDLR | CCR5 | ADAM9 |
| CYSLTR2 | CCL9 | LPAR3 | CD93 |
| ENTPD1 | IFITM3 | ADAM8 | GABARAPL1 |
| SPP1 | IL1R2 | PGLYRP1 | IL2RA |
| GCNT1 | ALCAM | TIGIT | HAVCR2 |

As described herein, T cells isolated under conditions of a chronic viral infection express an IL-27 inhibitory gene module in which the expression and activity of a subset of co-inhibitory and co-stimulatory molecules are induced, as described in FIG. 6H and listed in Table 6.

Accordingly, in some embodiments, one or more target genes selected from Table 6 are modulated using one or more modulating agents as described herein, for the treatment of certain disorders, such as chronic infections. In some embodiments, two or more target genes selected from Table 6 are modulated using two or more modulating agents as described herein, for the treatment of certain disorders, such as chronic infections.

TABLE 6

| Chronic Infection Associated IL-27 driven molecules | | | |
|---|---|---|---|
| LAG3 | ADAM9 | CD93 | CYSLTR2 |
| IL1R2 | PGLYRP1 | IL2RA | ENTPD1 |
| IFITM3 | GCNT1 | ALCAM | TIGIT |
| HAVCR2 | IL13RA1 | IL10 | IL21 |
| CCR2 | IL10RB | IL10RA | CXCL10 |
| CD68 | KLKR1 | LILRB4 | IL12RB2 |
| IL6ST | IL7R | LNHBA | NAMPT |
| S1PR1 | LSG20 | LAMP2 | LY75 |

As described herein, T cells isolated under anergic conditions express an IL-27 inhibitory gene module in which the expression and activity of a subset of co-inhibitory and co-stimulatory molecules are induced, as described in FIG. 6H and listed in Table 7.

Accordingly, in some embodiments, one or more target genes selected from Table 7 are modulated using one or more modulating agents as described herein, for the treatment of certain disorders, such as conditions involving anergy. In some embodiments, two or more target genes selected from Table 7 are modulated using two or more modulating agents as described herein, for the treatment of certain disorders, such as conditions involving anergy.

TABLE 7

| Anergy Associated IL-27 driven molecules | | | |
|---|---|---|---|
| LAG3 | IL1R2 | PGLYRP1 | IL2RA |
| CXCL10 | CD68 | KLKR1 | CCL5 |
| GABARAPL1 | SPP1 | TNFRSF8 | ABCA1 |
| SEMA7A | CCR5 | | |

As described herein, T cells isolated under conditions of nasal tolerance express an IL-27 inhibitory gene module in which the expression and activity of a subset of co-inhibitory and co-stimulatory molecules are induced, as described in FIG. 6H and listed in Table 8.

Accordingly, in some embodiments, one or more target genes selected from Table 8 are modulated using one or more modulating agents as described herein, for the treatment of certain disorders, such as conditions in which tolerance is to be induced (e.g., autoimmunity). In some embodiments, two or more target genes selected from Table 8 are modulated using two or more modulating agents as described herein, for the treatment of certain disorders, such as conditions in which tolerance is to be induced (e.g., autoimmunity).

TABLE 8

| Nasal Tolerance Associated IL-27 driven molecules | | | |
|---|---|---|---|
| LAG3 | ADAM8 | GABARAPL1 | CYSLTR2 |
| IL1R2 | PGLYRP1 | IL2RA | ENTPD1 |
| IFITM3 | GCNT1 | ALCAM | TIGIT |
| HAVCR2 | SPP1 | IL10 | IL21 |
| CCR2 | IL10RB | IL10RA | CXCL10 |
| TNFRSF8 | ABCA1 | IL12RB1 | IL1R1 |
| SDC4 | IFITM1 | SLAMF7 | TGFB3 |

As described herein, T cells isolated under conditions of skin tolerance express an IL-27 inhibitory gene module in which the expression and activity of a subset of co-inhibitory and co-stimulatory molecules are induced, as described in FIG. 6H and listed in Table 9.

Accordingly, in some embodiments, one or more target genes selected from Table 9 are modulated using one or more modulating agents as described herein, for the treatment of certain disorders, such as conditions in which tolerance is to be induced (e.g., autoimmunity). In some embodiments, two or more target genes selected from Table 9 are modulated using two or more modulating agents as described herein, for the treatment of certain disorders, such as conditions in which tolerance is to be induced (e.g., autoimmunity).

TABLE 9

| Skin Tolerance Associated IL-27 driven molecules | | | |
|---|---|---|---|
| LAG3 | ALCAM | TIGIT | HAVCR2 |
| IL10 | IL21 | IL13RA1 | CCR5 |
| CXCL10 | CCL5 | CTSB | KLRC1 |
| LPAR3 | CCL9 | | |

In some embodiments, one or more target genes selected from Tables 8 and 9 are modulated using one or more modulating agents as described herein, for the treatment of certain disorders, such as conditions in which tolerance is to be induced (e.g., autoimmunity). In some embodiments, two or more target genes selected from Tables 8 and 9 are modulated using two or more modulating agents as described herein, for the treatment of certain disorders, such as conditions in which tolerance is to be induced (e.g., autoimmunity).

As described further herein, 1,392 genes were identified that were differentially expressed between WT CD4$^+$ T cells stimulated in the presence or absence of IL-27. In certain embodiments differential expression of these genes may be used as a gene signature to identify or detect T cells with a dysfunctional phenotype. In other embodiments, differentially expressed genes may be modulated or targeted with an agent capable of modulating expression or activity of a gene. In certain preferred embodiments, genes that encode cell surface receptors or cytokines are targeted for modulation. Not being bound by a theory, cell surface receptors or cytokines facilitate targeting by a therapeutic agent. Not being bound by a theory, cell surface receptors or cytokines facilitate detection or isolation of cells without destroying the cell, such as by cell sorting, particularly FACS or magnetic sorting. Cell surface receptors or cytokines found to be differentially expressed between WT CD4$^+$ T cells stimulated in the presence or absence of IL-27 are described in Table 10, FIGS. 6C and 6D. Table 10 lists the mouse and human gene names. The present invention may use the corresponding genes in any mammal, preferably human. Accordingly, in some embodiments, one or more target genes selected from Table 10 are modulated using one or more modulating agents as described herein for the treatment of certain disorders, such as cancer. In some embodiments, two or more target genes selected from Table 10 are modulated using two or more modulating agents as described herein, for the treatment of certain disorders, such as cancer.

TABLE 10

Table 10a: Mouse genes encoding cell surface receptors and cytokines differentially expressed between WT CD4+ T cells stimulated in the presence or absence of IL-27

| Up-regulated | | | Down-Regulated |
|---|---|---|---|
| Abcal | Ifitm3 | Lamp2 | Bst2 |
| Adam8 | Il10 | Lpar3 | Btla |
| Adam9 | Il10ra | Ly75 | Ccl1 |
| Alcam | Il12rb1 | Ly75 | Ccr4 |
| Cc15 | Il13ral | Nampt | Cd226 |
| Cc19 | Il1rl | Olfm1 | Cd401g |
| Ccl9 | Il1r2 | Pdpn | Cd83 |
| Ccl9 | Il21 | Pglyrp1 | Cd8a |
| Ccr2 | Il2ra | Procr | Csf2 |
| Ccr5 | Il2rb | Pstpip1 | Cxcl13 |
| Cd68 | Il33 | Ptpn3 | Cxcr4 |
| Cd93 | Il6st | Sdc1 | Ifitm3 |
| Cxc110 | Inhba | Sdc4 | Isg20 |
| Cysltr2 | Isg20 | Selp | Lap3 |
| Ddr1 | Klrc2 | Sema7a | Lif |
| Entpd1 | Klrc2 | Slamf7 | Serpinc1 |
| Entpd1 | Klrc2 | Spp 1 | Timp2 |
| Epcam | Klrc2 | Tgfb3 | Tnfsf11 |
| Gabarapl1 | Klrc2 | Tigit | |
| Gent1 | Klrc2 | Tnfrsf8 | |
| Gpr65 | Klrd1 | Tnfsf9 | |
| Havcr2 | Klrk1 | Vldlr | |
| Ifitm1 | Lag3 | | |

Table 10b: Human genes encoding cell surface receptors and cytokines differentially expressed between WT CD4+ T cells stimulated in the presence or absence of IL-27

| Up-regulated | | | Down-regulated |
|---|---|---|---|
| ABCA1 | IFITM1 | LAMP2 | BST2 |
| ADAM8 | IL10 | LPAR3 | BTLA |
| ADAM9 | IL10RA | LY75-CD302 | CCL1 |
| ALCAM | IL12RB1 | LY75 | CCR4 |
| CCL5 | IL13RA1 | NAMPT | CD226 |
| CCL15 | IL1R1 | OLFM1 | CD40LG |
| CCL23 | IL1R2 | PDPN | CD83 |
| CCL15-CCL14 | IL21 | PGLYRP1 | CD8A |
| CCR2 | IL2RA | PROCR | CSF2 |
| CCR2 | IL2RB | PSTPIP1 | CXCL13 |
| CD68 | IL33 | PTPN3 | CXCR4 |
| CD93 | IL6ST | SDC1 | IFITM1 |
| CXCL10 | INHBA | SDC4 | ISG20 |
| CYSLTR2 | ISG20 | SELP | LAP3 |
| DDR1 | KLRC4-KLRK1 | SEMA7A | LIF |
| ENTPD1 | KLRC4 | SLAMF7 | SERPINC1 |
| EPCAM | KLRC1 | SPP1 | TIMP2 |
| GABARAPLI | KLRC3 | TGFB3 | TNFSF11 |
| GCNT1 | KLRC2 | TIGIT | |
| GPR65 | KLRD1 | TNFRSF8 | |
| HAVCR2 | KLRK1 | TNFSF9 | |
| IFITM1 | LAG3 | VLDLR | |

*The up- and down-regulated genes were determined over a 96 h time-course. Therefore the same gene can be both up-regulated and down-regulated at different time points along the differentiation.

As described herein, IL-27-signatures of up-regulated and down-regulated genes with overlapping expression in several different dysfunctional or tolerant T cell states were identified (Table 11, FIGS. 6G and 6H). Not being bound by a theory, T cells become exhausted after having cancer or chronic infection or become tolerant after prolonged exposure to antigens. Thus, in certain embodiments the identified genes may be used as a gene signature to identify or detect T cells with a dysfunctional phenotype. In other embodiments, the overlapping genes may be modulated or targeted with an agent capable of modulating expression or activity of a gene for the treatment of certain disorders, such as cancer. Accordingly, in some embodiments, one or more target genes selected from Table 11 are modulated using one or more modulating agents as described herein. In some embodiments, two or more target genes selected from Table 11 are modulated using two or more modulating agents as described herein, for the treatment of certain disorders, such as cancer. In some embodiments, genes that are up-regulated in Table 11 are modulated by down-regulation of expression or activity. In some embodiments, genes that are down-regulated in Table 11 are modulated by up-regulation of expression or activity.

TABLE 11

Table 11a:
IL-27-signature of up-regulated mouse genes
expressed in several different dysfunctional or tolerant T cell states.

| | | | | | | | |
|---|---|---|---|---|---|---|---|
| 1700012B09Rik | Cdh17 | Ets1 | Havcr2 | Klrc2 | Nfia | Rab31 | Sqrdl |
| AA467197 | Cdk6 | Etv6 | Hhat | Klrc2 | Nfil3 | Ramp3 | Srgap3 |
| Abca1 | Cdkn2d | F2rl1 | Hhex | Klrd1 | Nkg7 | Rbp1 | Stat1 |
| Abcb9 | Cds2 | Fam129b | Hif1a | Klre1 | Oas2 | Rfk | Stat3 |
| Acadl | Cebpd | Fam20a | Hlx | Klrk1 | Ociad2 | Rgs1 | Stom |
| Adam19 | Cela1 | Fbxw7 | Hopx | Ksr1 | Oit3 | Rhoc | Styk1 |
| Adam8 | Cercam | Ffar2 | Hpse | Lag3 | Olfm1 | Rhoq | Syt11 |
| Adam9 | Chac1 | Fgl2 | Id2 | Lama5 | Ormdl3 | Ripk3 | Tbx21 |
| Agpat3 | Chit1 | Fhit | Ier3 | Lamp2 | Osr2 | Rnf125 | Tcp11l2 |
| Ahnak | Chm | Filip1 | Ifih1 | Lat2 | Ovol2 | Rnh1 | Tgfb3 |
| Ahr | Chst11 | Flot1 | Ifitm1 | Lgals3 | Padi2 | Rorc | Tigit |
| Ahr | Chst2 | Fndc3a | Ifitm3 | Lgals3bp | Parp14 | Runx2 | Timp1 |
| Ak1 | Clip3 | Frmd4b | Igf2bp2 | Lilrb4 | Pdpn | S100a4 | Tmcc3 |
| Akr1b8 | Clybl | Gabarapl1 | Il10 | Litaf | Pfkp | S100a6 | Tnfrsf8 |
| Akr1b8 | Cnih2 | Galc | Il10ra | Lpar3 | Pglyrp1 | Sccpdh | Tnfsf9 |
| Akt2 | Copz2 | Gatm | Il12rb1 | Lpxn | Phactr2 | Sdc1 | Tor2a |
| Alcam | Creb312 | Gbe1 | Il13ra1 | Lrrk1 | Pik3ap1 | Sdc4 | Tpbg |
| Aldoc | Ctla2a | Gbp3 | Il1r1 | Ltbp3 | Piwil2 | Sdcbp2 | Tpd52 |
| Anxa2 | Cxcl10 | Gbp3 | Il1r2 | Ly75 | Pkp2 | Sec24d | Trib3 |
| Anxa3 | Cysltr1 | Gbp6 | Il21 | Ly75 | Plac8 | Selenbp1 | Tspan4 |
| Aplp1 | Cysltr2 | Gcnt1 | Il2ra | Maf | Plekhf1 | Selm | Tspan5 |
| Aqp9 | Dapk2 | Gem | Il2rb | Map3k5 | Plekho2 | Selp | Ttc39b |
| Arfgap3 | Dclk1 | Gemin8 | Il33 | Med12l | Plekho2 | Sema7a | Ttc39c |
| Arhgap18 | Ddr1 | Gfra1 | Il6st | Mettl7a1 | Plod2 | Serpinb1a | Tubb6 |
| Arl5a | Dhx58 | Gimap7 | Impa2 | Mmp15 | Ppme1 | Serpinb6b | Tulp4 |
| Armcx3 | Dock9 | Gja1 | Inhba | Ms4a6d | Ppp1r3b | Serpinb9 | Ubac2 |
| Asb2 | Dst | Glg1 | Irf1 | Ms4a6d | Pqlc3 | Serpinf1 | Upp1 |
| Atf6 | E330009J07Rik | Glrx | Irf4 | Mt1 | Prdm1 | Sigirr | Usp18 |
| Atp6v0d2 | Eaf2 | Gmfg | Irf8 | Mt1 | Prex1 | Skap2 | Usp18 |
| Auh | Ecm1 | Gmppa | Irf9 | Mt1 | Prf1 | Slamf7 | Vldlr |
| Bcl2l15 | Egln3 | Gnb5 | Isg15 | Mt1 | Procr | Slc2a3 | Wdr54 |
| Bnip3 | Elmo2 | Gnpda2 | Isg20 | Mt1 | Prss2 | Slc2a3 | Wdr81 |
| C3 | Emilin2 | Golga7 | Jun | Mt1 | Prss2 | Slc39a14 | Zbp1 |
| Ccl5 | Emp1 | Gpm6b | Junb | Mt2 | Prss2 | Slc41a2 | Zeb2 |
| Ccl9 | Enpp2 | Gpr65 | Kctd11 | Mxd1 | Psmb9 | Slc4a11 | Zfp36 |
| Ccl9 | Entpd1 | Gpt2 | Klf10 | Mxi1 | Pstpip1 | Slc7a3 | |
| Ccl9 | Entpd1 | Gsn | Klhl24 | Nampt | Ptpn1 | Sord | |
| Ccr2 | Epcam | Gsn | Klrc2 | Ndrg1 | Ptpn3 | Sox5 | |
| Ccr5 | Ern1 | Gsn | Klrc2 | Neb | Pygl | Spats2 | |
| Cd68 | Ero1l | Gzmb | Klrc2 | Nedd4 | Rab11fip5 | Spp1 | |
| Cd93 | Errfi1 | Gzmc | Klrc2 | Nek6 | Rab27a | Sqrdl | |

Table 11b:
IL-27-signature of down-regulated mouse genes
expressed in several different dysfunctional or tolerant T cell states.

| | | | | | | | |
|---|---|---|---|---|---|---|---|
| Aatf | Cd40lg | Dph5 | Gucy1b3 | Lrig1 | Phb | Rrs1 | Taf1d |
| Adi1 | Cd83 | Dus4l | Hells | Marcksl1 | Phlda1 | Rtp4 | Timm9 |
| Agpat5 | Cd8a | Egr3 | Hist2h3c1 | Mettl1 | Pkp4 | Sema4b | Timp2 |
| Akr1c18 | Cdk5r1 | Eomes | Id3 | Mmachc | Pmepa1 | Sema4c | Tm4sf5 |
| Akr1c18 | Chd9 | Fam26f | Idi2 | Mpeg1 | Prkcdbp | Serpinb6b | Tmem97 |
| Akr1c18 | Cnksr3 | Fhit | Ifih1 | Mtap | Prmt1 | Serpinb9 | Tnfaip8 |
| Akr1c18 | Cnn3 | Ftsj3 | Ifitm3 | Myb | Prmt3 | Serpinc1 | Tnfsf11 |
| Atp2a3 | Cpd | Galnt6 | Ipcef1 | Ndufa4 | Pter | Sh3bp5 | Top1mt |
| Bst2 | Crtam | Gch1 | Irf6 | Ndufaf4 | Ptger4 | Shmt1 | Trat1 |
| Btla | Cse1l | Gemin4 | Irgm1 | Nhp2 | Pus71 | Slamf6 | Trip13 |
| Cacna1a | Csf2 | Gfi1 | Isg20 | Noc4l | Rcl1 | Slamf9 | Trpm1 |
| Cadm1 | Cxcl13 | Gnaq | Kbtbd8 | Nolc1 | Rcsd1 | Slc19a1 | Tsr2 |
| Camkk2 | Cxcr4 | Gnl3 | Klf10 | Nop16 | Rfc4 | Snhg7 | Ttc27 |
| Capn3 | D930015E06Rik | Gpatch4 | Kti12 | Nop2 | Rnmtl1 | Snhg7 | Umps |
| Ccdc86 | Dapl1 | Gpd1l | Lad1 | Nop56 | Rpp14 | Snhg7 | Utp20 |
| Ccl1 | Ddit4 | Gramd1b | Lap3 | Nr4a3 | Rpp40 | St6gal1 | Wdr77 |
| Ccr4 | Ddx18 | Grwd1 | Lgals3bp | Pde7a | Rragd | St8sia4 | Zbtb10 |
| Cd226 | Dennd5a | Gucy1a3 | Lif | Pde8a | Rrp15 | Stc2 | Zfp608 |

Table 11c:
IL-27-signature of up-regulated human genes
expressed in several different dysfunctional or tolerant T cell states.

| | | | | | | | |
|---|---|---|---|---|---|---|---|
| ABCA1 | CD93 | ETS1 | HAVCR2 | KLRC2 | NEDD4 | PYGL | SPATS2 |
| ABCB9 | CDH17 | ETV6 | HHAT | KLRC3 | NEK6 | RAB11FIP5 | SPP1 |
| ACADL | CDK6 | F2RL1 | HHEX | KLRC4 | NFIA | RAB27A | SQRDL |
| ADAM19 | CDKN2D | FAM129B | HIF1A | KLRC4-KLRK1 | NFIL3 | RAB31 | SRGAP3 |
| ADAM8 | CDS2 | FAM20A | HLX | KLRD1 | NKG7 | RAMP3 | STAT1 |
| ADAM9 | CEBPD | FBXW7 | HOPX | KLRK1 | OAS2 | RBP1 | STAT3 |
| AGPAT3 | CELA1 | FFAR2 | HPSE | KSR1 | OCIAD2 | RFK | STOM |

TABLE 11-continued

| | | | | | | | |
|---|---|---|---|---|---|---|---|
| AHNAK | CERCAM | FGL2 | ID2 | LAG3 | OIT3 | RGS1 | STYK1 |
| AHR | CHAC1 | FHIT | IER3 | LAMA5 | OLFM1 | RHOQ | SYT11 |
| AK1 | CHIT1 | FILIP1 | IFIH1 | LAMP2 | ORMDL3 | RIPK3 | TBX21 |
| AKR1B10 | CHM | FLOT1 | IFITM1 | LAT2 | OSR2 | RNF125 | TCP11L2 |
| AKR1B15 | CHST11 | FNDC3A | IFITM1 | LGALS3 | OVOL2 | RNH1 | TGFB3 |
| AKT2 | CHST2 | FRMD4B | IGF2BP2 | LGALS3BP | PADI2 | RORC | TIGIT |
| ALCAM | CLIP3 | GABARAPL1 | IL10 | LITAF | PARP14 | RUNX2 | TIMP1 |
| ALDOC | CLYBL | GALC | IL10RA | LPAR3 | PDPN | S100A4 | TMCC3 |
| ANXA2 | CNIH2 | GATM | IL12RB1 | LPXN | PFKP | S100A6 | TNFRSF8 |
| ANXA3 | COPZ2 | GBE1 | IL13RA1 | LRRK1 | PGLYRP1 | SCCPDH | TNFSF9 |
| APLP1 | CREB3L2 | GBP4 | IL1R1 | LTBP3 | PHACTR2 | SDC1 | TOR2A |
| AQP9 | CXCL10 | GBP6 | IL1R2 | LY75 | PIK3AP1 | SDC4 | TPBG |
| ARFGAP3 | CYSLTR1 | GBP7 | IL21 | LY75-CD302 | PIWIL2 | SDCBP2 | TPD52 |
| ARHGAP18 | CYSLTR2 | GCNT1 | IL2RA | MAF | PKP2 | SEC24D | TRIB3 |
| ARL5A | DAPK2 | GEM | IL2RB | MAP3K5 | PLAC8 | SELENBP1 | TSPAN4 |
| ARMCX3 | DCLK1 | GEMIN8 | IL33 | MED12L | PLEKHF1 | SELP | TSPAN5 |
| ASB2 | DDR1 | GFRA1 | IL6ST | METTL7A | PLEKHO2 | SEMA7A | TTC39B |
| ATF6 | DHX58 | GIMAP7 | IMPA2 | MMP15 | PLOD2 | SERPINB1 | TTC39C |
| ATP6V0D2 | DOCK9 | GJA1 | INHBA | MS4A6A | PPME1 | SERPINB6 | TUBB6 |
| AUH | DST | GLG1 | IRF1 | MS4A6E | PPP1R3B | SERPINB9 | TULP4 |
| BCL2L15 | EAF2 | GLRX | IRF4 | MT1B | PQLC3 | SERPINF1 | UBAC2 |
| BNIP3 | ECM1 | GMFG | IRF8 | MT1E | PRDM1 | SIGIRR | UPP1 |
| C11orf97 | EGLN3 | GMPPA | IRF9 | MT1F | PREX1 | SKAP2 | USP18 |
| C15orf48 | ELMO2 | GNB5 | ISG15 | MT1G | PRF1 | SLAMF7 | USP41 |
| C3 | EMILIN2 | GNPDA2 | ISG20 | MT1M | PROCR | SLC2A14 | VLDLR |
| CCL15 | EMP1 | GOLGA7 | JUN | MT1X | PRSS1 | SLC2A3 | WDR54 |
| CCL15-CCL14 | ENPP2 | GPM6B | JUNB | MT2A | PRSS2 | SLC39A14 | WDR81 |
| CCL23 | ENTPD1 | GPR65 | KCTD11 | MXD1 | PRSS3 | SLC41A2 | ZBP1 |
| CCL5 | EPCAM | GPT2 | KIAA1147 | MXI1 | PSMB9 | SLC4A11 | ZEB2 |
| CCR2 | ERN1 | GSN | KLF10 | NAMPT | PSTPIP1 | SLC7A3 | ZFP36 |
| CCR2 | ERO1A | GZMB | KLHL24 | NDRG1 | PTPN1 | SORD | |
| CD68 | ERRFI1 | GZMB | KLRC1 | NEB | PTPN3 | SOX5 | |

Table 11d:
IL-27-signature of down-regulated human genes
expressed in several different dysfunctional or tolerant T cell states.

| | | | | | | | |
|---|---|---|---|---|---|---|---|
| AATF | CD40LG | EGR3 | HIST2H3C | LRIG1 | PDE8A | RRS1 | TIMP2 |
| ADI1 | CD83 | EOMES | ID3 | MARCKSL1 | PHB | RTP4 | TM4SF5 |
| AGPAT5 | CD8A | FAM26F | IDI2 | METTL1 | PHLDA1 | SEMA4B | TMEM97 |
| AKR1C1 | CDK5R1 | FHIT | IFIH1 | MMACHC | PKP4 | SEMA4C | TNFAIP8 |
| AKR1C2 | CHD9 | FTSJ3 | IFITM1 | MPEG1 | PMEPA1 | SERPINB6 | TNFSF11 |
| AKR1C3 | CNN3 | GALNT6 | IPCEF1 | MRM3 | PRKCDBP | SERPINB9 | TOP1MT |
| AKR1C4 | CPD | GCH1 | IPCEF1 | MTAP | PRMT1 | SERPINC1 | TRAT1 |
| ATP2A3 | CRTAM | GEMIN4 | IRF6 | MYB | PRMT3 | SH3BP5 | TRIP13 |
| BST2 | CSE1L | GFI1 | IRGM | NDUFA4 | PTER | SHMT1 | TRPM1 |
| BTLA | CSF2 | GNAQ | ISG20 | NDUFAF4 | PTGER4 | SLAMF6 | TSR2 |
| CACNA1A | CXCL13 | GNL3 | KBTBD8 | NHP2 | PUS7L | SLAMF9 | TTC27 |
| CADM1 | CXCR4 | GPATCH4 | KIAA0922 | NOC4L | RCL1 | SLC19A1 | UMPS |
| CAMKK2 | DAPL1 | GPD1L | KLF10 | NOLC1 | RCSD1 | SNORA17B | UTP20 |
| CAPN3 | DDIT4 | GRAMD1B | KTI12 | NOP16 | RFC4 | ST6GAL1 | WDR77 |
| CCDC86 | DDX18 | GRWD1 | LAD1 | NOP2 | RPP14 | ST8SIA4 | ZBTB10 |
| CCL1 | DENND5A | GUCY1A3 | LAP3 | NOP56 | RPP40 | STC2 | ZNF608 |
| CCR4 | DPH5 | GUCY1B3 | LGALS3BP | NR4A3 | RRAGD | TAF1D | |
| CD226 | DUS4L | HELLS | LIF | PDE7A | RRP15 | TIMM9 | |

Figure 6K:
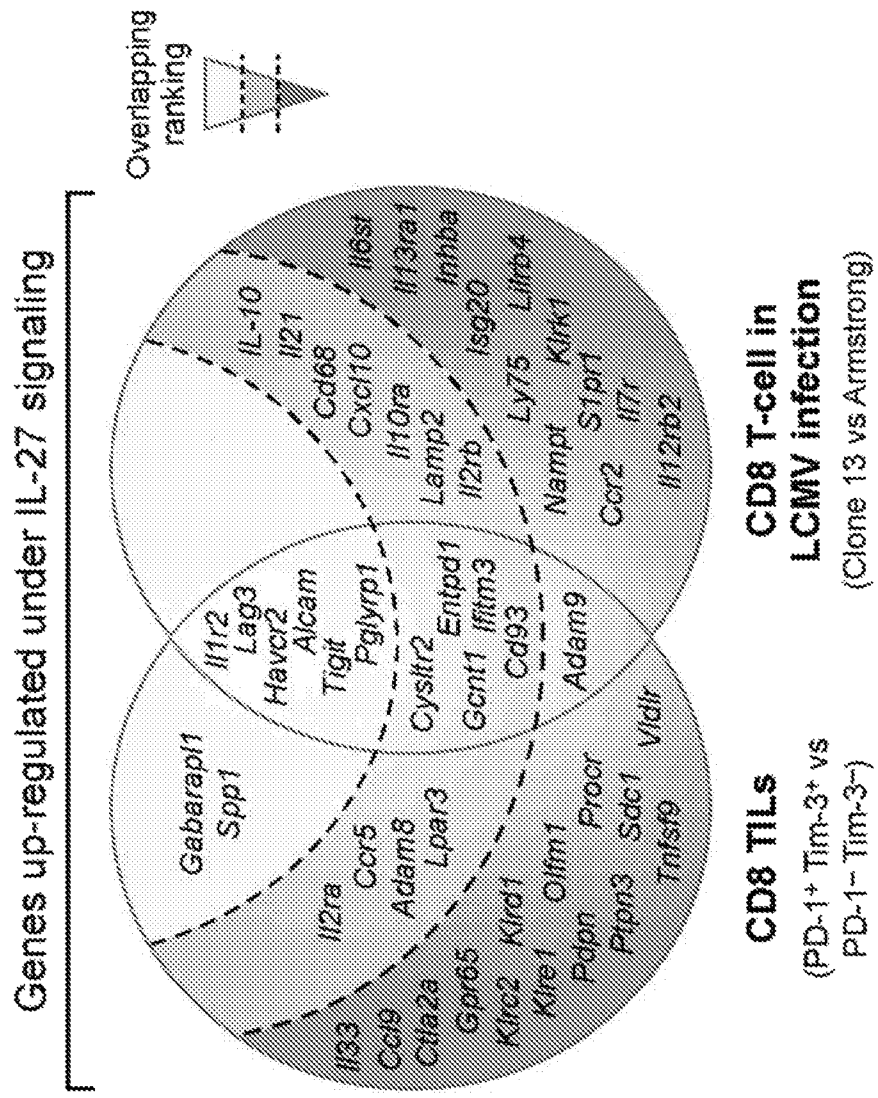

As described herein, genes were identified that were up-regulated in response to IL-27 signaling and overlap with dysfunctional CD8$^+$ T cell signatures from cancer and chronic viral infection (Table 12, FIG. 6K). Not being bound by a theory, these genes may be negative regulators of T cell function or be regulators of the T cell dysfunctional program and are targets for modulation. Down-regulation of the genes that are up-regulated in response to IL-27 signaling may result in an enhanced immune response and reactivation of exhausted T cells. Thus, in certain embodiments the identified genes may be used as a gene signature to identify or detect T cells with a dysfunctional phenotype. In other embodiments, the overlapping genes may be modulated or targeted with an agent capable of modulating expression or activity of a gene for the treatment of certain disorders, such as cancer. Accordingly, in some embodiments, one or more target genes selected from Table 12 are modulated using one or more modulating agents as described herein. In some embodiments, two or more target genes selected from Table 12 are modulated using two or more modulating agents as described herein, for the treatment of certain disorders, such as cancer. In preferred embodiments, genes selected from Table 12 are modulated by downregulation of expression or activity.

TABLE 12

Genes up-regulated under IL-27 signaling
that overlap between dysfunctional CD8+ T cell
signatures from cancer and chronic viral infection.

| | | | |
|---|---|---|---|
| Il33 | Adam8 | Isg20 | Cysltr2 |
| Klrc2 | Lpar3 | Lamp2 | Entpd1 |
| Klrd1 | Ccl9 | Ly75 | Gcnt1 |
| Klre1 | Cxcl10 | Nampt | Ifitm3 |
| Olfm1 | Ccr2 | S1pr1 | Il2ra |
| Pdpn | Il10ra | Il21 | Pglyrp1 |
| Ptpn3 | Il2rb | Il13ra1 | Cd93 |

TABLE 12-continued

| Genes up-regulated under IL-27 signaling that overlap between dysfunctional CD8+ T cell signatures from cancer and chronic viral infection. | | | |
|---|---|---|---|
| Sdc1 | Cd68 | Tigit | Adam9 |
| Tnfsf9 | Klrk1 | Ccr5 | Lilrb4 |
| Vldlr | Ill12rb2 | Alcam | IL-10 |
| Procr | Il6st | Havcr2 | Ctla2a |
| Gabarapl1 | Il7r | Lag3 | Gpr65 |
| Spp1 | Inhba | Il1r2 | |

As described herein, genes were identified that are enriched in a population of dysfunctional CD8$^+$ T cells that had high scores for the disclosed signature associated with IL-27 signaling (i.e. the gene expression signature shown in Table 11). Not being bound by a theory, these genes may be negative regulators of CD8$^+$ T cell function or be regulators of the T cell dysfunctional program and are targets for modulation. Down-regulation of the genes that are up-regulated in CD8$^+$ T cells bearing an IL-27 signaling signature may result in an enhanced immune response and reactivation of exhausted T cells. Thus, described herein are genes that were identified as up-regulated or down-regulated in CD8$^+$ TILs which exhibited expression signatures similar to those associated with IL-27 signaling (Table 13). Not being bound by a theory, up-regulation of the genes that are down-regulated in CD8$^+$ T cells bearing an IL-27 signaling signature may result in an enhanced immune response and reactivation of exhausted T cells. Thus, in certain embodiments the enriched genes may be used as a gene signature to identify or detect CD8$^+$ T cells with a dysfunctional phenotype. In other embodiments, the enriched genes may be modulated or targeted with an agent capable of modulating expression or activity of a gene for the treatment of certain disorders, such as cancer. Accordingly, in some embodiments, one or more target genes selected from Table 13 are modulated using one or more modulating agents as described herein. In some embodiments, two or more target genes selected from Table 13 are modulated using two or more modulating agents as described herein, for the treatment of certain disorders, such as cancer. In preferred embodiments, up-regulated genes selected from Table 13a are modulated by down-regulation of expression or activity. In preferred embodiments, down-regulated genes selected from Table 13b are modulated by up-regulation of expression or activity.

TABLE 13

| Table 13a: Up-regulated mouse genes that were in enriched in CD8+ TILs with high score for the IL-27 signature | | | | | | | |
|---|---|---|---|---|---|---|---|
| 5-Mar | Ccdc127 | Evi2b | H2-Q2 | Lrrc58 | Pdxdc1 | Sh2d2a | Tsc22d4 |
| 1600014C10Rik | Ccdc82 | Fam102a | H2-Q4 | Lrrn4cl | Phc3 | Sh3glb1 | Ttc39b |
| 1700017B05Rik | Ccdc88c | Fam149b | H2-Q4 | Luc712 | Phf1 | Sipa1l1 | Tyr |
| 2810474O19Rik | Ccl5 | Fam189b | H2-Q4 | Luc712 | Phf2011 | Skil | Uba7 |
| 4932438A13Rik | Ccni | Fam65b | H2-Q4 | Macf1 | Pigv | Sla2 | Ube2h |
| A230046K03Rik | Ccr5 | Fam65b | H2-Q4 | Maoa | Pik3cg | Slc35e2 | Ubr4 |
| Aak1 | Cd244 | Fcho1 | H2-Q4 | Map3k1 | Pik3r1 | Slc35e2 | Ulk3 |
| Abcb1a | Cd300a | Fgl2 | H2-T10 | Mbd4 | Pitpnc1 | Slc7a14 | Unkl |
| Abcg1 | Cd300a | Fli1 | H2-T10 | Mcmdc2 | Plcg1 | Slc9a9 | Usp48 |
| Abr | Cd38 | Fmnl1 | H2-T10 | Mfap1a | Pnpla7 | Slfn5 | Usp9x |
| Abt1 | Cdc14b | Foxn3 | H2-T10 | Mfsd11 | Pot1b | Slfn8 | Utp23 |
| Acad9 | Cdkn1b | Fryl | H2-T10 | Mgea5 | Ppm1k | Slfn8 | Utrn |
| Acsbg1 | Celf2 | Fut8 | H2-T10 | Mier1 | Ppp1r12a | Soat2 | Vasp |
| Adam19 | Chrna1 | Fyco1 | Hdac4 | Miip | Ppp1r12b | Son | Vps13a |
| Adar | Cic | Gabpb2 | Herc1 | Milr1 | Ppp1r16b | Sorl1 | Vps37b |
| Adcy7 | Cnppd1 | Gak | Hip1 | Mplkip | Ppp1r18 | Spata13 | Vps54 |
| Ahnak | Colec12 | Galnt2 | Hipk1 | Mpv17 | Ppp3cc | Spata13 | Wasf2 |
| Akap13 | Cpne8 | Gbp7 | Hmha1 | Mpv17l | Prex1 | Spn | Wbp2 |
| Akna | Crebbp | Gbp7 | Hnrnpd | Mpv17l | Prrc2b | Srrm2 | Wdr34 |
| Alox8 | Csnk1g1 | Gbp9 | Hnrnpl | Mtfmt | Prrc2c | Stim1 | Wdr92 |
| Ankrd11 | Ctcfl | Ggnbp2 | Ifnar1 | Mtmr1 | Ptpn22 | Stk10 | Whsc1l1 |
| Ankrd12 | Ctsa | Ghdc | Ifngr1 | Myh9 | Purb | Stxbp2 | Wipf1 |
| Ankrd13a | Ctsd | Gimap3 | Igf2r | Myo1f | Pxmp4 | Suv420h1 | Wnk1 |
| Ankrd44 | Ctsd | Gimap3 | Ikbip | Mysm1 | Rab33b | Syne1 | Wtap |
| Ankrd44 | Cxcr2 | Gimap4 | Il16 | Nabp1 | Rapgef6 | Synj2bp | Xaf1 |
| Aplf | Cxcr6 | Gimap6 | Intu | Nbeal2 | Rapgef6 | Sytl2 | Xiap |
| Arhgef1 | Cybrd1 | Gimap8 | Irak1 | Nbr1 | Rassf2 | Tab2 | Xiap |
| Arid1a | Cyld | Gjc3 | Irak2 | Ncoa3 | Rbm41 | Tacc1 | Xpo7 |
| Arid4a | Cytip | Gje1 | Irf2bpl | Ncor1 | Rbm5 | Tbc1d14 | Yipf4 |
| Arid4b | Dcaf10 | Glrx2 | Itga4 | Neu3 | Rdh1 | Tbc1d24 | Ypel5 |
| Arid5a | Dclre1c | Gm11127 | Itgal | Neurl3 | Rgs1 | Tecpr1 | Zbtb44 |
| Arl4c | Ddx58 | Gm11127 | Itgav | Nktr | Rgs3 | Tet2 | Zc3h12a |
| Arsb | Decr2 | Gm11127 | Kansl1 | Nlrc5 | Ripply3 | Tigit | Zc3hav1 |
| Ash1l | Dennd1c | Gm11127 | Kdm5a | Nlrp1a | Rmi2 | Tmem127 | Zcchc11 |
| Asxl2 | Dennd4a | Gm11127 | Kif21b | Nmrk1 | Rnf139 | Tmem63a | Zcchc6 |
| Atf7 | Dgat1 | Gm11127 | Klf13 | Notch1 | Rnf166 | Tmem69 | Zfp113 |
| Atp2b1 | Dgka | Gm7102 | Klf6 | Npc2 | Rnf167 | Tmem88b | Zfp202 |
| Atp2b4 | Dnajc14 | Gmeb1 | Klrc2 | Nsd1 | Rnf168 | Tmf1 | Zfp277 |
| Atxn1 | Dock10 | Gng2 | Klrc2 | Nsl1 | Rock1 | Tnfrsf10b | Zfp316 |
| Azi2 | Dock2 | Gpsm3 | Klrc2 | Nup210 | Rprd2 | Tnfrsf10b | Zfp3612 |
| B4galnt2 | Dtx31 | Grap2 | Klrc2 | Oas3 | Rsbn1l | Tnfrsf10b | Zfp488 |
| Baiap3 | Dusp11 | Grina | Klrc2 | Olfr1033 | Runx2 | Tnfrsf10b | Zfp605 |
| Bcl11b | Dusp5 | Grk4 | Klrc2 | Omd | Runx3 | Tnfsf10 | Zfp781 |
| Birc6 | E030030106Rik | Grk6 | Lbh | Osbpl3 | S1pr4 | Tnrc6a | Zfp9 |
| Bnip31 | Eif2ak2 | Gsk3b | Ldb1 | P2ry10 | Samhd1 | Tnrc6b | Zmym5 |
| Brip1 | Elf1 | Gtdc1 | Leng8 | Padi2 | Sap18 | Tor4a | Zmynd8 |

TABLE 13-continued

| | | | | | | | |
|---|---|---|---|---|---|---|---|
| Btbd16 | Entpd1 | Gzmk | Lime1 | Pak2 | Sec62 | Tprkb | Zscan26 |
| Camk4 | Entpd1 | H2-Q2 | Lime1 | Pan3 | Selplg | Trappc9 | Zyg11b |
| Car5b | Ep300 | H2-Q2 | Lipi | Pced1b | Serinc3 | Trim12c | |
| Casc4 | Ep400 | H2-Q2 | Lnpep | Pcnt | Serpina3i | Trim65 | |
| Cbfa2t2 | Epsti1 | H2-Q2 | Loxl2 | Pdcd4 | Serpina3i | Trp53i11 | |
| Cblb | Ets1 | H2-Q2 | Lpp | Pde3b | Sfi1 | Trp53inp1 | |

Table 13b:
Up-regulated mouse cell surface and cytokine genes that were in enriched in CD8+ TILs with high score for the IL-27 signature

| | | | | | | | |
|---|---|---|---|---|---|---|---|
| Cast | Cd200r1 | Csf1 | Flot2 | Il12rb2 | Klrc1 | Ncor2 | Smpd1 |
| Ccl3 | Cd200r1 | Ctla4 | Gpi1 | Il18rap | Klrc1 | Nrp1 | Spn |
| Ccl3 | Cd200r4 | Ctsb | Gpr160 | Irak2 | Klrc1 | Pdcd1 | Tnfrsf9 |
| Ccl3 | Cd200r4 | Cx3cr1 | Hcst | Itga4 | Klrc1 | Pear1 | Trpv2 |
| Ccl4 | Cd244 | Cxcr6 | Icos | Itgal | Klrc1 | Selplg | |
| Ccrl2 | Cd38 | Erp44 | Ifng | Itgav | Klrc1 | Sema4d | |
| Cd164 | Cd3g | Fasl | Ifngr1 | Itgb2 | Lgals1 | Serpine2 | |
| Cast | Cd200r1 | Csf1 | Flot2 | Il12rb2 | Klrc1 | Ncor2 | |

Table 13c:
Up-regulated human genes that were in enriched in CD8+ TILs with high score for the IL-27 signature

| | | | | | | | |
|---|---|---|---|---|---|---|---|
| 5-Mar | CCDC127 | FAM149B1 | HLA-C | LRRN4CL | PDXDC1 | SH3GLB1 | UBA7 |
| AAK1 | CCDC82 | FAM189B | HLA-C | LUC7L2 | PHC3 | SIPA1L1 | UBE2H |
| ABCB1 | CCDC88C | FAM65B | HLA-E | MACF1 | PHF1 | SKIL | UBR4 |
| ABCG1 | CCL5 | FCHO1 | HLA-E | MAOA | PHF20L1 | SLA2 | ULK3 |
| ABR | CCNI | FGL2 | HLA-E | MAP3K1 | PIGV | SLC35E2 | UNKL |
| ABT1 | CCR2 | FLI1 | HLA-E | MBD4 | PIK3CG | SLC35E2B | USP48 |
| ACAD9 | CD244 | FMNL1 | HLA-F | MCMDC2 | PIK3R1 | SLC7A14 | USP9X |
| ACSBG1 | CD300A | FOXN3 | HLA-F | MFAP1 | PITPNC1 | SLC9A9 | UTP23 |
| ADAM19 | CD300C | FRYL | HLA-F | MFSD11 | PLCG1 | SLFN11 | UTRN |
| ADAR | CD38 | FUT8 | HLA-F | MGEA5 | PNPLA7 | SLFN13 | VASP |
| ADCY7 | CDC14B | FYCO1 | HLA-G | MIER1 | POT1 | SLFN5 | VPS13A |
| AHNAK | CDK6 | GABPB2 | HLA-G | MIIP | PPM1K | SOAT2 | VPS37B |
| AKAP13 | CDKN1B | GAK | HLA-G | MILR1 | PPP1R12A | SON | VPS54 |
| AKNA | CELF2 | GALNT2 | HLA-G | MPLKIP | PPP1R12B | SORL1 | WASF2 |
| ALOX15B | CHRNA1 | GBP4 | HNRNPD | MPLKIP | PPP1R16B | SPATA13 | WBP2 |
| ANKRD11 | CIC | GBP6 | HNRNPL | MPV17 | PPP1R18 | SPN | WDR34 |
| ANKRD12 | CNPPD1 | GBP7 | IFNAR1 | MPV17L | PPP3CC | SRRM2 | WDR92 |
| ANKRD13A | COLEC12 | GGNBP2 | IFNGR1 | MTFMT | PREX1 | STIM1 | WHSC1L1 |
| ANKRD44 | CPNE8 | GHDC | IGF2R | MTMR1 | PRRC2B | STK10 | WIPF1 |
| APLF | CREBBP | GIMAP1-GIMAP5 | IKBIP | MYH9 | PRRC2C | STXBP2 | WNK1 |
| ARHGAP45 | CSNK1G1 | GIMAP4 | IL16 | MYO1F | PTPN22 | SYNE1 | WTAP |
| ARHGEF1 | CTCFL | GIMAP5 | INTU | MYSM1 | PURB | SYNJ2BP | XAF1 |
| ARID1A | CTSA | GIMAP6 | IRAK1 | NABP1 | PXMP4 | SYTL2 | XIAP |
| ARID4A | CTSD | GIMAP8 | IRAK2 | NBEAL2 | RAB33B | TAB2 | XPO7 |
| ARID4B | CXCR2 | GJC3 | IRF2BPL | NBR1 | RAPGEF6 | TACC1 | YIPF4 |
| ARID5A | CXCR6 | GJE1 | ITGA4 | NCOA3 | RASSF2 | TBC1D14 | YPEL5 |
| ARL4C | CYBRD1 | GLRX2 | ITGAL | NCOR1 | RBM41 | TECPR1 | ZBTB44 |
| ARSB | CYLD | GMEB1 | ITGAV | NEU3 | RBM5 | TET2 | ZC3H12A |
| ASH1L | CYTIP | GNG2 | KANSL1 | NEURL3 | RDH16 | TIGIT | ZC3HAV1 |
| ASXL2 | DCAF10 | GPSM3 | KDM5A | NKTR | RGS1 | TMEM127 | ZCCHC11 |
| ATF7 | DCLRE1C | GRAP2 | KIAA1033 | NLRC5 | RGS3 | TMEM63A | ZCCHC6 |
| ATP2B1 | DDX58 | GRINA | KIAA1109 | NLRP1 | RIPPLY3 | TMEM69 | ZFP36L2 |
| ATP2B4 | DECR2 | GRK4 | KIAA1551 | NMRK1 | RMI2 | TMEM88B | ZMYM5 |
| ATXN1 | DENND1C | GRK6 | KIF21B | NOTCH1 | RNF139 | TMF1 | ZMYND8 |
| AZI2 | DENND4A | GSK3B | KLF13 | NPC2 | RNF166 | TNFRSF10A | ZNF202 |
| B4GALNT2 | DGAT1 | GTDC1 | KLF6 | NSD1 | RNF167 | TNFRSF10B | ZNF25 |
| BAIAP3 | DGKA | GZMK | KLRC1 | NSL1 | RNF168 | TNFRSF10C | ZNF277 |
| BCL11B | DOCK10 | HDAC4 | KLRC2 | NTN3 | ROCK1 | TNFRSF10D | ZNF3 |
| BIRC6 | DOCK2 | HERC1 | KLRC3 | NUP210 | RPRD2 | TNFSF10 | ZNF316 |
| BIRC8 | DTX3L | HIP1 | KLRC4 | OAS3 | RSBN1L | TNRC6A | ZNF488 |
| BNIP3L | DUSP11 | HIPK1 | KLRC4-KLRK1 | OMD | RUNX2 | TNRC6B | ZNF605 |
| BRIP1 | DUSP5 | HLA-A | KMT5B | OR5M3 | RUNX3 | TOR4A | ZNF781 |
| BTBD16 | EIF2AK2 | HLA-A | LBH | OSBPL3 | S1PR4 | TP53111 | ZSCAN26 |
| C15orf39 | ELF1 | HLA-A | LDB1 | P2RY10 | SAMHD1 | TP53INP1 | ZYG11B |
| C19orf12 | ENTPD1 | HLA-A | LENG8 | PADI2 | SAP18 | TPRKB | |
| C7orf55-LUC7L2 | EP300 | HLA-B | LIME1 | PAK2 | SEC62 | TRAPPC9 | |
| CA5B | EP400 | HLA-B | LIPI | PAN3 | SELPLG | TRIM5 | |
| CAMK4 | EPSTI1 | HLA-B | LNPEP | PCED1B | SERINC3 | TRIM65 | |
| CASC4 | ETS1 | HLA-B | LOXL2 | PCNT | SERPINA3 | TSC22D4 | |
| CBFA2T2 | EVI2B | HLA-C | LPP | PDCD4 | SFI1 | TTC39B | |
| CBLB | FAM102A | HLA-C | LRRC58 | PDE3B | SH2D2A | TYR | |

TABLE 13-continued

Table 13d:
Up-regulated human cell surface and cytokine genes that
were in enriched in CD8+ TILs with high score for the IL-27 signature

| | | | | | | | |
|---|---|---|---|---|---|---|---|
| CAST | CD200R1 | CSF1 | FLOT2 | IL12RB2 | KLRC1 | NRP1 | SPN |
| CCL18 | CD200R1 | CTLA4 | GPI | IL18RAP | KLRC2 | PDCD1 | TNFRSF9 |
| CCL3 | CD200R1L | CTSB | GPR160 | IRAK2 | KLRC3 | PEAR1 | TRPV2 |
| CCL3L3 | CD200R1L | CX3CR1 | HCST | ITGA4 | KLRC4 | SELPLG | |
| CCL4 | CD244 | CXCR6 | ICOS | ITGAL | KLRC4-KLRK1 | SEMA4D | |
| CCRL2 | CD38 | ERP44 | IFNG | ITGAV | LGALS1 | SERPINE2 | |
| CD164 | CD3G | FASLG | IFNGR1 | ITGB2 | NCOR2 | SMPD1 | |

Table 13e:
Down-regulated mouse genes that were in
enriched in CD8+ TILs with high score for the IL-27 signature

| | | | | | | | |
|---|---|---|---|---|---|---|---|
| 1810022K09Rik | Cdk4 | Eif5a | Iars | Ndufa4 | Polr2h | Rpn1 | Tcp1 |
| 2810004N23Rik | Cebpz | Eif5a | Idh3a | Ndufab1 | Polr2j | Rpn2 | Tex30 |
| Aatf | Chchd1 | Eif6 | Il2ra | Ndufaf2 | Ppa1 | Rps19bp1 | Tfdp1 |
| Abce1 | Chchd2 | Eif6 | Imp4 | Ndufb4 | Ppan | Rps27l | Tfrc |
| Abcf2 | Chchd4 | Emc2 | Impdh2 | Ndufb6 | Ppan | Rrp1 | Thoc5 |
| Adpgk | Cinp | Emc6 | Ipo4 | Ndufc2 | Ppat | Rrp15 | Thumpd3 |
| Adrm1 | Cirh1a | Eno3 | Ipo5 | Ndufc2 | Ppib | Rrp9 | Thyn1 |
| Aen | Cisd1 | Enoph1 | Jtb | Ndufs3 | Ppid | Rrs1 | Timm10 |
| Aga | Cks1b | Erh | Kars | Ndufs8 | Ppie | Rsl1d1 | Timm13 |
| Ahcy | Clns1a | Exosc1 | Kpna2 | Ndufv1 | Ppif | Rsl24d1 | Timm17a |
| Aifm1 | Cluh | Exosc5 | Kti12 | Ndufv2 | Ppp5c | Ruvbl1 | Timm23 |
| Akr7a5 | Cops3 | Exosc7 | Lad1 | Nfkbia | Prdx1 | Ruvbl2 | Timm23 |
| Aldh18a1 | Cops6 | Fam136a | Lap3 | Nfkbib | Prdx4 | Samm50 | Timm50 |
| Aldh9a1 | Cox6b1 | Fam162a | Ldha | Nhp2 | Prelid1 | Sarnp | Timm8a1 |
| Alg8 | Cox7c | Fam96a | Letm1 | Nhp2l1 | Prmt1 | Sdf2l1 | Tkt |
| Anapc15 | Crtam | Fbl | Llph | Nme1 | Prmt5 | Sdhaf1 | Tma16 |
| Anapc5 | Cse1l | Fdps | Lsm2 | Nme2 | Prmt7 | Sec13 | Tma7 |
| Anp32e | Ctps | Fdx1l | Lsm7 | Nob1 | Prps1 | Sec61b | Tmed2 |
| Apex1 | Ctsz | Fdx1l | Lta | Noc4l | Psat1 | Serbp1 | Tmem14c |
| Api5 | Cyc1 | Fkbp1a | Lyar | Nolc1 | Psma2 | Set | Tmem14c |
| Aprt | Cycs | Fkbp2 | M6pr | Nop10 | Psma2 | Set | Tmem97 |
| Arf1 | Dad1 | Fkbp4 | Magoh | Nop16 | Psma3 | Sf3b5 | Tnfrsf9 |
| Atad3a | Dapl1 | Ftsj3 | Manf | Nop2 | Psmb5 | Sfxn1 | Tomm22 |
| Atad3a | Dars | G3bp1 | Mat2a | Nop56 | Psmb6 | Shmt1 | Tomm40 |
| Atad3a | Dbi | Gadd45b | Mcm2 | Nop58 | Psmc5 | Shmt2 | Tomm5 |
| Atp5a1 | Dctpp1 | Gars | Mcm3 | Nsun2 | Psmd11 | Siva1 | Tpi1 |
| Atp5b | Ddb1 | Gart | Mcm5 | Ntmt1 | Psmd3 | Skp1a | Trp53 |
| Atp5e | Ddx1 | Gcsh | Mcm7 | Nudc | Psmd6 | Skp1a | Tsr1 |
| Atp5e | Ddx18 | Gfer | Med11 | Nudt19 | Psmd7 | Slc19a1 | Tuba1b |
| Atp5g1 | Ddx21 | Gins2 | Mettl1 | Nudt21 | Psmg1 | Slc1a5 | Tubg1 |
| Atp5g2 | Ddx27 | Gnl3 | Mif | Nudt5 | Psmg2 | Slc25a39 | Tufm |
| Atp5g3 | Ddx39 | Gpatch4 | Mphosph6 | Nup54 | Ptbp1 | Smyd2 | Txn1 |
| Atp5j | Dkc1 | Gps1 | Mrpl12 | Nup62 | Ptges3 | Smyd5 | Txn2 |
| Atp5j2 | Dnajb11 | Gpx1 | Mrpl20 | Nutf2-ps1 | Ptpn6 | Snrpa1 | Txnl4a |
| Atp5k | Dnajc19 | Gramd1b | Mrpl23 | Ost4 | Pus1 | Snrpd1 | U2af1 |
| Atpif1 | Dohh | Grwd1 | Mrpl23 | Ostc | Pusl1 | Snrpd3 | U2af1 |
| Banf1 | Dpagt1 | Gtf2f2 | Mrpl28 | P4hb | Pwp2 | Snrpe | Uchl3 |
| Bcap29 | Dpy30 | Gtf2h1 | Mrpl3 | Pa2g4 | Pwp2 | Snrpf | Uchl5 |
| Bccip | Drg2 | Gtpbp4 | Mrpl30 | Pa2g4 | Pycrl | Snrpg | Uck2 |
| Bola2 | Dtymk | Gypc | Mrpl30 | Paics | Rabggtb | Spcs3 | Uhrf1 |
| Bola2 | Dusp14 | Hars | Mrpl30 | Parp1 | Rad51 | Spr | Umps |
| Bop1 | Dut | Haus7 | Mrpl38 | Pbdc1 | Rae1 | Srm | Ung |
| Brix1 | Ebna1bp2 | Hax1 | Mrpl42 | Pcbp1 | Ran | Srsf10 | Uqcr10 |
| Bsg | Eef1d | Hint1 | Mrpl52 | Pdcd2l | Ranbp1 | Srsf3 | Uqcrb |
| Bud31 | Eef1e1 | Hivep3 | Mrps18b | Pdia6 | Rars | Srsf6 | Uqcrc1 |
| Bzw2 | Eftud2 | Hmbs | Mrps26 | Pebp1 | Rbbp7 | Srsf7 | Uqcrq |
| C1qbp | Eif2b1 | Hn1l | Mrps28 | Pes1 | Rbfa | Ssb | Usmg5 |
| Cacybp | Eif2b3 | Hnrnpa1 | Mrps36 | Pfdn2 | Rbm38 | Ssr2 | Usp10 |
| Cad | Eif2s1 | Hnrnpa1 | Mrps5 | Pgk1 | Rcc1 | Sssca1 | Vars |
| Calr | Eif2s2 | Hnrnpc | Mrps6 | Phb | Rcc2 | Stat5a | Vcp |
| Canx | Eif2s3x | Hnrnpc | Mrto4 | Phb2 | Rcl1 | Stip1 | Wdr12 |
| Ccdc86 | Eif2s3x | Hnrnpc | Ms4a4c | Phf5a | Rel | Stmn1 | Wdr18 |
| Ccl1 | Eif3a | Hnrnpc | Ms4a4c | Phgdh | Rexo2 | Stoml2 | Wdr4 |
| Ccne1 | Eif3c | Hnrnpc | Mtap | Pigu | Rfc3 | Strap | Wdr43 |
| Ccr7 | Eif3c | Hnrnpm | Mtap | Plrg1 | Rfc4 | Stt3a | Wdr46 |
| Cct2 | Eif3d | Hsp90ab1 | Mtch2 | Pmf1 | Rgcc | Suclg1 | Wdr61 |
| Cct3 | Eif3e | Hsp90b1 | Mthfd1 | Pmpcb | Rnmtl1 | Syncrip | Wdr74 |
| Cct4 | Eif3g | Hspa4 | Mthfd2 | Pno1 | Rnps1 | Syngr2 | Wdr75 |
| Cct5 | Eif3i | Hspa5 | Mybbp1a | Pola2 | Rpf2 | Taf1d | Wdr77 |
| Cct7 | Eif3l | Hspa9 | Naa20 | Pold2 | Rpl22l1 | Taf6 | Xcl1 |
| Cct8 | Eif3m | Hspbp1 | Naa25 | Poldip2 | Rpl26 | Tagln2 | Xcl1 |
| Cd83 | Eif4a1 | Hspd1 | Nasp | Polr1e | Rpl30 | Tbcb | Ywhae |

TABLE 13-continued

| | | | | | | | |
|---|---|---|---|---|---|---|---|
| Cdca7 | Eif4a3 | Hspe1 | Ncl | Polr2c | Rpl35 | Tbrg4 | Ywhaq |
| Cdk2 | Eif4e | Hsph1 | Ndufa12 | Polr2f | Rpl36al | Tceb2 | Zfp593 |

Table 13f:
Down-regulated mouse cell surface and cytokine genes that were in enriched in

| | | | |
|---|---|---|---|
| C1qbp | Hnrnpu | Itgb7 | Wnt4 |
| Ccnd2 | Hsp90aa1 | S1pr1 | Xcl1 |
| Ccr7 | Hspa9 | Sell | Xcl1 |
| Cd69 | Il7r | Tnfsf14 | |

Table 13g:
Down-regulated human genes that were in
enriched in CD8+ TILs with high score for the IL-27 signature

| | | | | | | | |
|---|---|---|---|---|---|---|---|
| AATF | CDK2 | EIF5A | IDH3A | NDUFB6 | PPIB | RSL24D1 | TIMM13 |
| ABCE1 | CDK4 | EIF5AL1 | IL2RA | NDUFC2 | PPID | RUVBL1 | TIMM17A |
| ABCF2 | CEBPZ | EIF6 | IMP4 | NDUFC2-KCTD14 | PPIE | RUVBL2 | TIMM23 |
| ADPGK | CHCHD1 | EMC2 | IMPDH2 | NDUFS3 | PPIF | SAMM50 | TIMM23B |
| ADRM1 | CHCHD2 | EMC6 | IPO4 | NDUFS8 | PPP5C | SARNP | TIMM50 |
| AEN | CHCHD4 | ENO3 | IPO5 | NDUFV1 | PRDX1 | SDF2L1 | TIMM8A |
| AGA | CINP | ENOPH1 | JTB | NDUFV2 | PRDX4 | SDHAF1 | TKT |
| AHCY | CISD1 | ERH | KARS | NFKBIA | PRELID1 | SEC13 | TMA16 |
| AIFM1 | CKS1B | EXOSC1 | KPNA2 | NFKBIB | PRMT1 | SEC61B | TMA7 |
| AKR7A2 | CLNS1A | EXOSC5 | KTI12 | NHP2 | PRMT5 | SERBP1 | TMED2 |
| ALDH18A1 | CLUH | EXOSC7 | LAD1 | NME1 | PRMT7 | SET | TMEM14B |
| ALDH9A1 | COPS3 | FAM136A | LAP3 | NME2 | PRPS1 | SETSIP | TMEM14C |
| ALG8 | COPS6 | FAM162A | LDHA | NOB1 | PSAT1 | SF3B5 | TMEM97 |
| ANAPC15 | COX6B1 | FAM96A | LETM1 | NOC4L | PSMA2 | SFXN1 | TNFRSF9 |
| ANAPC5 | COX7C | FBL | LLPH | NOLC1 | PSMA3 | SHMT1 | TOMM22 |
| ANP32E | CRTAM | FDPS | LSM2 | NOP10 | PSMB5 | SHMT2 | TOMM40 |
| APEX1 | CSE1L | FDX2 | LSM7 | NOP16 | PSMB6 | SIVA1 | TOMM5 |
| API5 | CTPS1 | FKBP1A | LTA | NOP2 | PSMC5 | SKP1 | TP53 |
| APRT | CTSZ | FKBP2 | LYAR | NOP56 | PSMD11 | SLC19A1 | TPI1 |
| ARF1 | CYC1 | FKBP4 | M6PR | NOP58 | PSMD3 | SLC1A5 | TSR1 |
| ATAD3A | CYCS | FTSJ3 | MAGOH | NSUN2 | PSMD6 | SLC25A39 | TUBA1B |
| ATAD3B | DAD1 | G3BP1 | MANF | NTMT1 | PSMD7 | SMYD2 | TUBG1 |
| ATAD3C | DAPL1 | GADD45B | MAT2A | NUDC | PSMG1 | SMYD5 | TUFM |
| ATP5A1 | DARS | GARS | MCM2 | NUDT19 | PSMG2 | SNRPA1 | TXN |
| ATP5B | DBI | GART | MCM3 | NUDT21 | PTBP1 | SNRPD1 | TXN2 |
| ATP5E | DCTPP1 | GCSH | MCM5 | NUDT5 | PTGES3 | SNRPD3 | TXNL4A |
| ATP5EP2 | DDB1 | GFER | MCM7 | NUP54 | PTPN6 | SNRPE | U2AF1 |
| ATP5G1 | DDX1 | GINS2 | MED11 | NUP62 | PUS1 | SNRPF | U2AF1L5 |
| ATP5G2 | DDX18 | GNL3 | METTL1 | NUTF2 | PUSL1 | SNRPG | UCHL3 |
| ATP5G3 | DDX21 | GPATCH4 | MIF | OST4 | PWP2 | SNU13 | UCHL5 |
| ATP51 | DDX27 | GPS1 | MPHOSPH6 | OSTC | PYCRL | SPCS3 | UCK2 |
| ATP5J | DDX39A | GPX1 | MRM3 | P4HB | RABGGTB | SPR | UHRF1 |
| ATP5J2 | DKC1 | GRAMD1B | MRPL12 | PA2G4 | RAD51 | SRM | UMPS |
| ATPIF1 | DNAJB11 | GRWD1 | MRPL20 | PAICS | RAE1 | SRSF10 | UNG |
| BANF1 | DNAJC19 | GTF2F2 | MRPL23 | PARP1 | RAN | SRSF3 | UQCR10 |
| BCAP29 | DOHH | GTF2H1 | MRPL28 | PBDC1 | RANBP1 | SRSF6 | UQCRB |
| BCCIP | DPAGT1 | GTPBP4 | MRPL3 | PCBP1 | RARS | SRSF7 | UQCRC1 |
| BOLA2 | DPY30 | GYPC | MRPL30 | PDCD2L | RBBP7 | SSB | UQCRQ |
| BOLA2B | DRG2 | HARS | MRPL38 | PDIA6 | RBFA | SSR2 | USMG5 |
| BOP1 | DTYMK | HAUS7 | MRPL42 | PEBP1 | RBM38 | SSSCA1 | USP10 |
| BRIX1 | DUSP14 | HAX1 | MRPL52 | PES1 | RCC1 | STAT5A | UTP4 |
| BSG | DUT | HINT1 | MRPS18B | PFDN2 | RCC2 | STIP1 | VARS |
| BUD31 | EBNA1BP2 | HIVEP3 | MRPS26 | PGK1 | RCL1 | STMN1 | VCP |
| BZW2 | EEF1D | HMBS | MRPS28 | PHB | REL | STOML2 | WDR12 |
| C1orf131 | EEF1E1-BLOC1S5 | HN1L | MRPS36 | PHB2 | REXO2 | STRAP | WDR18 |
| C1QBP | EFTUD2 | HNRNPA1 | MRPS5 | PHF5A | RFC3 | STT3A | WDR4 |
| C8orf59 | EIF2B1 | HNRNPA1L2 | MRPS6 | PHGDH | RFC4 | SUCLG1 | WDR43 |
| CACYBP | EIF2B3 | HNRNPC | MRTO4 | PIGU | RGCC | SYNCRIP | WDR46 |
| CAD | EIF2S1 | HNRNPCL1 | MS4A4A | PLRG1 | RNPS1 | SYNGR2 | WDR61 |
| CALR | EIF2S2 | HNRNPCL2 | MS4A4E | PMF1 | RPF2 | TAF1D | WDR74 |
| CANX | EIF2S3 | HNRNPCL3 | MTAP | PMPCB | RPL22L1 | TAF6 | WDR75 |
| CCDC86 | EIF3A | HNRNPCL4 | MTCH2 | PNO1 | RPL26 | TAGLN2 | WDR77 |
| CCL1 | EIF3C | HNRNPM | MTHFD1 | POLA2 | RPL30 | TBCB | XCL1 |
| CCNE1 | EIF3CL | HSP90AB1 | MTHFD2 | POLD2 | RPL35 | TBRG4 | XCL2 |
| CCR7 | EIF3D | HSP90B1 | MYBBP1A | POLDIP2 | RPL36A | TCEB2 | YWHAE |
| CCT2 | EIF3E | HSPA4 | NAA20 | POLR1E | RPN1 | TCP1 | YWHAQ |
| CCT3 | EIF3G | HSPA5 | NAA25 | POLR2C | RPN2 | TEX30 | ZNF593 |
| CCT4 | EIF31 | HSPA9 | NASP | POLR2F | RPS19BP1 | TFDP1 | |
| CCT5 | EIF3L | HSPBP1 | NCL | POLR2H | RPS27L | TFRC | |
| CCT7 | EIF3M | HSPD1 | NDUFA12 | POLR2J | RRP1 | THOC5 | |
| CCT8 | EIF4A1 | HSPE1 | NDUFA4 | PPA1 | RRP15 | THUMPD3 | |
| CD83 | EIF4A3 | HSPH1 | NDUFAB1 | PPAN | RRP9 | THYN1 | |
| CDCA7 | EIF4E | IARS | NDUFAF2 | PPAN-P2RY11 | RRS1 | TIMM10 | |

TABLE 13-continued

Table 13h:
Down-regulated human cell surface and cytokine genes
that were in enriched in CD8+ TILs with high score for the IL-27 signature

| | | | |
|---|---|---|---|
| C1QBP | HNRNPU | ITGB7 | WNT4 |
| CCND2 | HSP90AA1 | S1PR1 | XCL1 |
| CCR7 | HSPA9 | SELL | XCL2 |
| CD69 | IL7R | TNFSF14 | |

As described herein, Prdm1 and c-Maf together regulate a co-inhibitory gene module that determines anti-tumor immunity. Applicants describe that anti-tumor immunity can be modulated upon modulating both genes (e.g., see FIGS. 12-14). Accordingly, in some embodiments, anti-tumor immunity is modulated using two or more modulating agents as described herein for the treatment of certain disorders, such as cancer. In preferred embodiments, Prdm1 and c-Maf are modulated by downregulation of expression or activity. In other embodiments, Prdm1 and c-Maf are modulated by upregulation of expression or activity.

Because Prdm1 and c-Maf each regulate numerous co-inhibitory receptors, it may be advantageous to modulate express of only one of Prdm1 or c-Maf at a time. Thus, in some embodiments, Prdm1 or c-Maf are modulated by downregulation of expression or activity. In other embodiments, Prdm1 or c-Maf are modulated by upregulation of expression or activity. In preferred embodiments, Prdm1 and c-Maf are modulated by downregulation of expression or activity. In preferred embodiments, Prdm1 and c-Maf are modulated by upregulation of expression or activity.

In one embodiment, at least one target gene selected from the list in Table 1, Table 10, Table 11, or Table 12 or the combination of Prdm1 and/or c-Maf is modulated in combination with a treatment selected from the group consisting of: an immune checkpoint inhibitor, a CTLA-4 inhibitor, a PD-1 inhibitor, chemotherapy, a Braf inhibitor, a MEK inhibitor, a Sting agonist, a TLR agonist, an IDO inhibitor, and an agonist for OX-40, 4-1BB and/or GITR. In some embodiments, the combination of modulation of at least one target gene selected from the list in Table 1, Table 10, Table 11, or Table 12 or the combination of Prdm1 and/or c-Maf in combination with a treatment selected from the group consisting of: an immune checkpoint inhibitor, a CTLA-4 inhibitor, a PD-1 inhibitor, chemotherapy, a Braf inhibitor, a MEK inhibitor, a Sting agonist, a TLR agonist, an IDO inhibitor, and an agonist for OX-40, 4-1BB and/or GITR produces a synergistic effect (e.g., the effect of the agents used in combination is greater than the sum of the effect of each agent alone).

In one embodiment, the methods, compositions and uses described herein comprise modulation of PDPN expression, activity and/or function, PROCR expression, activity, and/or function, or modulation of the combination of Prdm1 and c-Maf expression, activity and/or function, and at least one additional target gene/gene product or combination selected from the group consisting of those listed in Table 1, Table 10, Table 11, or Table 12 or the combination of Prdm1 and c-Maf. In another embodiment, the methods, compositions and uses described herein comprise modulation of PDPN expression, activity and/or function, PROCR expression, activity, and/or function, or modulation of the combination of Prdm1 and c-Maf expression, activity and/or function, and at least one additional target gene/gene product selected from the group consisting of TIGIT, LAG3, LILRB4, and KLRC1. In another embodiment, the methods, compositions and uses described herein comprise inhibition of PDPN expression, activity and/or function, PROCR expression, activity, and/or function, or modulation of the combination of Prdm1 and c-Maf expression, activity and/or function, and inhibition of at least one additional target gene/gene product selected from the group consisting of TIGIT, LAG3, LILRB4, and KLRC1. In another embodiment, the methods, compositions, and uses describe herein comprise inhibition of PDPN, PROCR, at least one additional target gene/gene product selected from the group consisting of TIGIT, LAG3, LILRB4, and KLRC1, and activation of expression, activity, and/or function of at least one of the target genes/gene products selected from the group consisting of: CD226, OX-40, GITR, TNFSF9 (4-1BB), KLRC2, KLRE1, KLRK1, IL12RB1, IL1R1, and SLAMF7. In another embodiment, the methods, compositions, and uses described herein comprise inhibition of the combination of Prdm1 and c-Maf, at least one additional target gene/gene product selected from the group consisting of TIGIT, LAG3, LILRB4, and KLRC1, and activation of expression, activity, and/or function of at least one of the target genes/gene products selected from the group consisting of: CD226, OX-40, GITR, TNFSF9 (4-1BB), KLRC2, KLRE1, KLRK1, IL12RB1, IL1R1, and SLAMF7. In one embodiment, a combination therapy comprising (i) a treatment selected from the group consisting of: an immune checkpoint inhibitor, a CTLA-4 inhibitor, a PD-1 inhibitor, chemotherapy, a Braf inhibitor, a MEK inhibitor, a Sting agonist, a TLR agonist, an IDO inhibitor, and an agonist for OX-40, 4-1BB and/or GITR, (ii) modulation of PDPN, PROCR or the combination of Prdm1 and c-Maf (iii) optionally modulating at least one additional target gene/gene product selected from the group consisting of TIGIT, LAG3, LILRB4, and KLRC1 and (iv) optionally inducing activation of expression, activity, and/or function of at least one of the target genes/gene products selected from the group consisting of: CD226, OX-40, GITR, TNFSF9 (4-1BB), KLRC2, KLRE1, KLRK1, IL12RB1, IL1R1, and SLAMF7 is used in the methods and compositions described herein.

In one embodiment, at least one target gene selected from the list in Table 1, Table 10, Table 11, or Table 12 or the combination of Prdm1 and/or c-Maf is modulated in an immune cell. In certain embodiments, the immune cell is a CD8+ T cell. In other embodiments, the immune cell is modulated ex vivo and is used in an adoptive cell transfer therapy. In certain embodiments, autologous T cells are used in a personalized therapy. In other embodiments, a cell is provided with at least one gene modulated selected from the list in Table 1, Table 10, Table 11, or Table 12 or the combination of Prdm1 and/or c-Maf. In preferred embodiments, the cell is a CD8+ T cell. The CD8+ T cell may be a chimeric antigen receptor (CAR) T cell, described further herein.

In one embodiment, at least one target gene selected from the list in Table 1, Table, 5, Table 6, Table 7, Table 8, Table 9, Table 10, Table 11, Table 12, or Table 13 is used as part of a gene signature or biomarker signature to detect and/or isolate an immune cell, preferably a T cell with a specific immune state. In some embodiments, the biomarker or gene signature may comprise, consist essentially of, or consist of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 59, or 50 or more genes disclosed in Table 1, Table, 5, Table 6, Table 7, Table 8, Table 9, Table 10, Table 11, Table 12, or Table 13. For example, disclosed herein, a gene signature for dysfunctional T cell associated with chronic infection can comprise any combination of the genes disclosed in Table 6.

In some embodiments, the gene signature may comprise, consist essentially of, or consist of all types of genes, for instance genes that encode transcription factors, cell signaling molecule, cell surface receptors, or cytokines. In some embodiments, the gene signature may comprise, consist essentially of, or consist of genes that encode transcription factorscell surface receptors, and cytokines. In some embodiments, the gene signature may comprise, consist essentially of, or consist of genes that encode cell surface receptors and cytokines. Not being bound by a theory, cell surface receptors or cytokines facilitate detection or isolation of cells without destroying the cell, such as by cell sorting, particularly FACS or magnetic sorting. In preferred embodiments, dysfunctional T cells are detected.

Detection may be part of a diagnostic assay or may be used as a method of determining whether a patient is suitable for administering an immunotherapy or another type of therapy. For example, detection of the disclosed gene or biomarker signatures may be performed in or to determine whether a patient is responding to a given treatment or, if the patient is not responding, if this may be due to T cell dysfunction. Such detection is informative regarding the types of therapy the patient is best suited to receive. For example, whether the patient should receive immunotherapy. Non-limiting examples on immunotherapeutics (exemplary embodiments also shown in Table 14) that may be used in the claimed methods or in conjunction with the claimed compositions include IMP321, BMS-986016, LAG525, TSR022, MTIG7192A, TRX518, INCAGN01876, GWN323, MEDI1873, MEDI9447, PF-05082566 (utomilumab), BMS-663513 (urelumab), MOXR0916, MEDI6469, MEDI6383, PF04518600, KHK4083, and combinations of two or more thereof. In preferred embodiments the immunotherapy may comprise administering at least one check point inhibitor.

TABLE 14

| Target | Active agents investigated in clinical trials |
|---|---|
| Lag-3 | IMP321, BMS-986016, LAG525 |
| Tim-3 | TSR022 |
| Tigit | MTIG7192A |
| Gitr (CD357) | TRX518, INCAGN01876, GWN323, MEDI1873 |
| CD73 | MEDI9447, |
| 4-1BB (CD137, TNFRSF9) | PF-05082566 (utomilumab), BMS-663513 (urelumab) |
| OX40 (CD134) | MOXR0916, MEDI6469, MEDI6383, PF04518600, KHK4083 |

In some embodiments, a patient that is not responding to ACT may benefit from use of the detection methods to determine whether the adoptive cells are dysfunctional, and if so, what course of treatment could correct the dysfunction.

In some embodiments, the disclosed gene signature can be detected using methods disclosed herein or methods know in the art. For example, the disclosed gene signatures immunofluorescence, mass cytometry (CyTOF), FACS, drop-seq, RNA-seq, single cell qPCR, MERFISH (multiplex (in situ) RNA FISH), microarray and/or by in situ hybridization. Other methods including absorbance assays and colorimetric assays are known in the art and may be used herein. In some aspects, measuring expression of signature genes comprises measuring protein expression levels. Protein expression levels may be measured, for example, by performing a Western blot, an ELISA or binding to an antibody array. In another aspect, measuring expression of said genes comprises measuring RNA expression levels. RNA expression levels may be measured by performing RT-PCR, Northern blot, an array hybridization, or RNA sequencing methods.

Signature Genes

As used herein a signature may encompass any gene or genes, or protein or proteins, whose expression profile or whose occurrence is associated with a specific cell type, subtype, or cell state of a specific cell type or subtype within a population of cells. Increased or decreased expression or activity or prevalence may be compared between different cells in order to characterize or identify for instance specific cell (sub)populations. A gene signature as used herein, may thus refer to any set of up- and down-regulated genes between different cells or cell (sub)populations derived from a gene-expression profile. For example, a gene signature may comprise a list of genes differentially expressed in a distinction of interest. It is to be understood that also when referring to proteins (e.g. differentially expressed proteins), such may fall within the definition of "gene" signature.

The signatures as defined herein (being it a gene signature, protein signature or other genetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. blood samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type. In one embodiment, the novel signatures are used to detect multiple cell states or hierarchies that occur in subpopulations of immune cells that are linked to particular pathological condition (e.g. cancer), or linked to a particular outcome or progression of the disease, or linked to a particular response to treatment of the disease.

The signature according to certain embodiments of the present invention may comprise or consist of one or more genes and/or proteins, such as for instance 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 59, or 50 or more. In certain embodiments, the signature may comprise or consist of two or more genes and/or proteins, such as for instance 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 59, or 50 or more. In certain embodiments, the signature may comprise or consist of three or more genes and/or proteins, such as for instance 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 59, or 50 or more. In certain embodiments, the signature may comprise or consist of four or more genes and/or proteins, such as for instance 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 59, or 50 or more. In certain embodiments, the signature may comprise or consist of five or more genes and/or proteins, such as for instance 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 59, or 50 or more. In certain embodiments, the signature may comprise or consist of six or more genes and/or proteins, such as for instance 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 59, or 50 or more. In certain embodiments, the signature may comprise or consist of seven or more genes and/or proteins, such as for instance 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 59, or 50 or more. In certain embodiments, the signature may comprise or consist of eight or more genes and/or proteins, such as for instance 8, 9, 10 or more. In certain embodiments, the signature may comprise or consist of nine or more genes and/or proteins, such as for instance 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 59, or 50 or more. In certain embodiments, the signature may comprise or consist of ten or more genes and/or proteins, such as for instance 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 59, or 50 or more. For example, a signature for use in the disclosed detection methods can include a combination of genes either Table 1, Table 2, Table 5, Table 6, Table 7, Table 8, Table 9, Table 10, Table 11, Table 12, or Table 13. It is to be understood that a signature according to the invention may for instance also include a combination of genes or proteins.

It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins may be differentially expressed on a single cell level, or may be differentially expressed on a cell population level. Preferably, the differentially expressed genes/proteins as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferable is meant induction or alternatively suppression (or upregulation or downregulation) of at least one gene/protein of the signature, such as for instance at least to, at least three, at least four, at least five, at least six, or all genes/proteins of the signature.

Signatures may be functionally validated as being uniquely associated with a particular immune phenotype. Induction or suppression of a particular signature may consequentially be associated with or causally drive a particular immune phenotype.

Various aspects and embodiments of the invention may involve analyzing gene signatures, protein signature, and/or other genetic signature based on single cell analyses (e.g. single cell RNA sequencing) or alternatively based on cell population analyses, as is defined herein elsewhere.

In further aspects, the invention relates to gene signatures, protein signature, and/or other genetic signature of particular immune cell subpopulations, as defined herein. The invention hereto also further relates to particular immune cell subpopulations, which may be identified based on the methods according to the invention as discussed herein; as well as methods to obtain such cell (sub)populations and screening methods to identify agents capable of inducing or suppressing particular immune cell (sub)populations.

The invention further relates to various uses of the gene signatures, protein signature, and/or other genetic signature as defined herein, as well as various uses of the immune cells or immune cell (sub)populations as defined herein. Particular advantageous uses include methods for identifying agents capable of inducing or suppressing particular immune cell (sub)populations based on the gene signatures, protein signature, and/or other genetic as defined herein. The invention further relates to agents capable of inducing or suppressing particular immune cell (sub)populations based on the gene signatures, protein signature, and/or other genetic signature as defined herein, as well as their use for modulating, such as inducing or repressing, a particular gene signature, protein signature, and/or other genetic signature. In related aspects, modulating, such as inducing or repressing, a particular gene signature, protein signature, and/or other genetic signature may modify overall immune cell composition, such as activated or dysfunctional immune cell composition, or distribution, or functionality.

As used herein the term "signature gene" means any gene or genes whose expression profile is associated with a specific cell type, subtype, or cell state of a specific cell type or subtype within a population of cells. The signature gene can be used to indicate the presence of a cell type, a subtype of the cell type, the state of the microenvironment of a population of cells, and/or the overall status of the entire cell population. Furthermore, the signature genes may be indicative of cells within a population of cells in vivo. Not being bound by a theory, the signature genes can be used to deconvolute the cells present in a tumor based on comparing them to data from bulk analysis of a tumor sample. The signature gene may indicate the presence of one particular cell type. In one embodiment, the signature genes may indicate that dysfunctional or activated tumor infiltrating T-cells are present. The presence of cell types within a tumor may indicate that the tumor will be resistant to a treatment. In one embodiment the signature genes of the present invention are applied to bulk sequencing data from a tumor sample to transform the data into information relating to disease outcome and personalized treatments. In one embodiment, the novel signature genes are used to detect multiple cell states that occur in a subpopulation of tumor cells that are linked to resistance to targeted therapies and progressive tumor growth. In preferred embodiments, immune cell states of tumor infiltrating lymphocytes are detected.

In one embodiment, the signature genes are detected by immunofluorescence, mass cytometry (CyTOF), FACS, drop-seq, RNA-seq, single cell qPCR, MERFISH (multiplex (in situ) RNA FISH), microarray and/or by in situ hybridization. Other methods including absorbance assays and colorimetric assays are known in the art and may be used herein. In some aspects, measuring expression of signature genes comprises measuring protein expression levels. Protein expression levels may be measured, for example, by performing a Western blot, an ELISA or binding to an antibody array. In another aspect, measuring expression of said genes comprises measuring RNA expression levels. RNA expression levels may be measured by performing RT-PCR, Northern blot, an array hybridization, or RNA sequencing methods.

Modulating Agents

Provided herein are methods and compositions comprising one or more modulating agents that modulate the expression, activity and/or function of one or more target genes in Table 1, Table 10, Table 11, Table 12, or Table 13 or that modulate the expression, activity and/or function of the combination of Prdm1 and c-Maf and/or Prdm1 and c-Maf, individually, or pairs of target genes as shown in Table 2, or combinations thereof as described herein in any of Tables 3-9. In one embodiment, one or a combination of modulating agents is used to modulate T cell exhaustion. In some embodiments, the combination of modulating agents has a synergistic effect compared to the effect of each agent alone.

In some embodiments, the modulating agent is an activator of the expression, activity and/or function of one or more target genes. In some embodiments, where the desired effect is to increase non-responsiveness of a T-cell (e.g., in autoimmune disease and/or transplants), an agent that induces an increase in the expression, activity and/or function of a negative regulator of T cell function from the list of target genes, such as in Table 4, will induce an increase in T cell non-responsiveness or exhaustion. Where the desired effect is to decrease T-cell exhaustion, an activating agent that increases the expression, activity and/or function of a positive regulator of T cell function from the list of target genes, such as in Table 3, can be used.

In some embodiments, the modulating agent is an inhibitor of the expression, activity, and/or function of one or more target genes listed in Table 1, Table 10, Table 11, or Table 12 or the combination of Prdm1 and c-Maf and/or Prdm1 and c-Maf, individually, or the pairs of target genes as shown in Table 2, or other combinations thereof as described herein. Where the desired effect of the inhibiting agent is to reduce T-cell exhaustion, an agent that inhibits the expression, activity and/or function of a negative regulator of T-cell function (see e.g., Table 4) will induce a reduction in T-cell exhaustion. Where the desired effect of the inhibiting agent is to increase T-cell non-responsiveness (e.g., autoimmune disease and/or transplant), an agent that inhibits the expression, activity and/or function of a positive regulator of T-cell function (e.g., those listed in Table 4 and/or Tables 8-9), will induce T-cell non-responsiveness.

In some embodiments, one or more modulating agents are used in combination with the methods and compositions described herein. In some embodiments, two or more modulating agents are used in combination with the methods and compositions described herein. One of skill in the art will appreciate that, depending on the identities of the selected target genes or proteins, one can employ both inhibiting agents and activating agents in the same method and/or composition provided that the agents are employed with a common goal (i.e., to produce a similar biological effect such as reduction of T-cell exhaustion) such that the agents work together additively, or preferably synergistically, towards the desired overall biological effect. In some embodiments, at least 3, at least 4, at least 5, at least 6, at least 7, at least 8, at least 9, at least 10 or more agents are formulated or administered in combination.

Inhibitors: As used herein, the terms "inhibitor," "antagonist," and "silencing agent," refer to a molecule or agent that significantly blocks, inhibits, reduces, or interferes with one or more target genes listed in Table 1, Table 10, Table 11, or Table 12 or the combination of Prdm1 and c-Maf or Prdm1 and c-Maf, individually, their biological activity in vitro, in situ, and/or in vivo, including activity of downstream pathways mediated by gene signaling. In some embodiments, the inhibitor or antagonist will modulate markers of T-cell exhaustion, such as, for example, lack of/reduction in proliferation, lack of/reduction in cytokine production, lack of/reduction in cytotoxic activity, lack of/reduction in trafficking or migration, transcription factor induction, IL-10 induction, and/or elicitation of a cellular response to IL-27. Exemplary inhibitors contemplated for use in the various aspects and embodiments described herein include, but are not limited to, antibodies or antigen-binding fragments thereof that specifically bind to one or more target genes listed in Table 1, Table 10, Table 11, or Table 12, or gene products thereof, or one or more subunits of the target gene(s)/product(s); anti-sense molecules directed to a nucleic acid encoding the target protein or subunits thereof; short interfering RNA ("siRNA") molecules directed to a nucleic acid encoding the target protein or subunits thereof; RNA or DNA aptamers that bind to the target gene or gene product or a subunit thereof, gene product structural analog; soluble variant proteins or fusion polypeptides thereof; DNA targeting agents, such as CRISPR systems, Zinc finger binding proteins, TALES or TALENS; and small molecule agents that target or bind to the target gene or subunit(s) thereof. In some embodiments of the compositions, methods, and uses described herein, the inhibitor inhibits some or all of IL-27 mediated signal transduction. Exemplary assays to measure inhibition or reduction of downstream IL-27 signaling pathway activities are known to those of ordinary skill in the art and/or are provided herein.

As used herein, an inhibitor or antagonist has the ability to reduce the activity and/or expression of the target gene in a cell (e.g., T cells, such as CD8+ or CD4+ T cells) by at least 5%, at least 10%, at least 20%, at least 30%, at least 40%, at least 50%, at least 60%, at least 70%, at least 80%, at least 90%, at least 95%, at least 98%, at least 99%, or more, relative to the activity or expression level in the absence of the antagonist.

In some embodiments of the compositions, methods, and uses described herein, an inhibitor or antagonist is a monoclonal antibody.

In some embodiments of the compositions, methods, and uses described herein, an inhibitor or antagonist is an antibody fragment or antigen-binding fragment. The terms "antibody fragment," "antigen binding fragment," and "antibody derivative" as used herein, refer to a protein fragment that comprises only a portion of an intact antibody, generally including an antigen binding site of the intact antibody and thus retaining the ability to bind antigen.

In some embodiments of the compositions, methods, and uses described herein, an inhibitor or antagonist is a chimeric antibody derivative of an antagonist antibody or antigen-binding fragment thereof.

The inhibitor or antagonist antibodies and antigen-binding fragments thereof described herein can also be, in some embodiments, a humanized antibody derivative.

In some embodiments, the inhibitor or antagonist antibodies and antigen-binding fragments thereof described herein, i.e., antibodies that are useful for decreasing T cell exhaustion, include derivatives that are modified, i.e., by the covalent attachment of any type of molecule to the antibody, provided that the covalent attachment does not prevent the antibody from binding to the target antigen, e.g., one or more target gene products from Table 1, Table 10, Table 11, or Table 12.

In some embodiments of the compositions, methods, and uses described herein, fully human antibodies are used, which are particularly desirable for the therapeutic treatment of human patients.

In some embodiments of the compositions, methods, and uses described herein, an inhibitor or antagonist is a small molecule inhibitor or antagonist, including, but is not limited to, small peptides or peptide-like molecules, soluble peptides, and synthetic non-peptidyl organic or inorganic compounds. A small molecule inhibitor or antagonist can have a molecular weight of any of about 100 to about 20,000 daltons (Da), about 500 to about 15,000 Da, about 1000 to about 10,000 Da. In some embodiments of the compositions, methods, and uses described herein, an inhibitor or antagonist comprises a small molecule that binds the target gene product selected from the genes listed in Table 1, Table 2, Table 10, Table 11, or Table 12 or the combination of Prdm1 and c-Maf or Prdm1 and c-Maf, individually.

In some embodiments of the compositions, methods, and uses described herein, an inhibitor or antagonist is an RNA or DNA aptamer that binds or physically interacts with a target gene/gene product, and blocks interactions between the gene product and a binding partner.

In some embodiments of the compositions, methods, and uses described herein, an inhibitor or antagonist comprises at least one structural analog of a target gene/gene product as listed in Table 1, Table 10, Table 11, or Table 12 or the combination of Prdm1 and c-Maf, or Prdm1 and c-Maf, individually. The term "structural analogs" as used herein, refers to compounds that have a similar three dimensional structure as the target gene or portion thereof, under physiological conditions in vitro or in vivo, wherein the binding of the analog in the signaling pathway reduces a desired biological activity. Suitable structural analogs can be designed and synthesized through molecular modeling of protein binding. The structural analogs and receptor structural analogs can be monomers, dimers, or higher order multimers in any desired combination of the same or different structures to obtain improved affinities and biological effects.

In some embodiments of the compositions, methods, and uses described herein, an inhibitor or antagonist comprises at least one soluble peptide, or portion of the target gene product, or fusion polypeptide thereof. In some such embodiments, the soluble peptide is fused to an immunoglobulin constant domain, such as an Fc domain, or to another polypeptide that modifies its in vivo half-life, e.g., albumin.

In some embodiments of the compositions, methods, and uses described herein, an inhibitor or antagonist comprises at least one antisense molecule capable of blocking or decreasing the expression of a desired target gene by targeting nucleic acids encoding the gene or subunit thereof. Methods are known to those of ordinary skill in the art for the preparation of antisense oligonucleotide molecules that will specifically bind one or more target gene(s) without cross-reacting with other polynucleotides. Exemplary sites of targeting include, but are not limited to, the initiation codon, the 5' regulatory regions, including promoters or enhancers, the coding sequence, including any conserved consensus regions, and the 3' untranslated region. In some embodiment of these aspects and all such aspects described herein, the antisense oligonucleotides are about 10 to about 100 nucleotides in length, about 15 to about 50 nucleotides in length, about 18 to about 25 nucleotides in length, or more. In certain embodiments, the oligonucleotides further comprise chemical modifications to increase nuclease resistance and the like, such as, for example, phosphorothioate linkages and 2'-O-sugar modifications known to those of ordinary skill in the art.

In some embodiments of the compositions, methods, and uses described herein, an inhibitor or antagonist comprises at least one siRNA molecule capable of blocking or decreasing the expression of a target gene product or a subunit thereof. Generally, one would prepare siRNA molecules that will specifically target one or more mRNAs without cross-reacting with other polynucleotides. siRNA molecules for use in the compositions, methods, and uses described herein can be generated by methods known in the art, such as by typical solid phase oligonucleotide synthesis, and often will incorporate chemical modifications to increase half-life and/or efficacy of the siRNA agent, and/or to allow for a more robust delivery formulation. Alternatively, siRNA molecules are delivered using a vector encoding an expression cassette for intracellular transcription of siRNA.

Inhibitors or antagonists for use in the compositions, methods, and uses described herein can be identified or characterized using methods known in the art, such as protein-protein binding assays, biochemical screening assays, immunoassays, and cell-based assays, which are well known in the art.

Activators: Also provided herein, in other aspects, are compositions comprising activators or agonists for use in the methods and compositions described herein.

As used herein, the terms "activator," "agonist," or "activating agent," refer to a molecule or agent that mimics or up-regulates (e.g., increases, potentiates or supplements) the expression and/or biological activity of a target gene/gene product in vitro, in situ, and/or in vivo, including downstream pathways mediated by gene signaling. In some embodiments, an activator or agonist as described herein can modulate markers of T-cell exhaustion, such as, for example, transcription factor induction (e.g., NFIL3 or T-bet induction), IL-10 induction, histone acetylation at the TIM-3 locus, TIM-3 mRNA or protein upregulation, and/or elicitation of a cellular response to IL-27. An "activator" of a given polypeptide can include the polypeptide itself, in that supplying the polypeptide itself will increase the level of the function provided by the polypeptide. An activator or agonist can be a protein or derivative thereof having at least one bioactivity of the wild-type target gene/gene product. An activator or agonist can also be a compound that upregulates expression of the desired target gene product or its subunits. An activator or agonist can also be a compound which increases the interaction of the target gene with its receptor, for example. Exemplary activators or agonists contemplated for use in the various aspects and embodiments described herein include, but are not limited to, antibodies or antigen-binding fragments thereof that specifically bind to a target gene/gene product or subunits thereof; RNA or DNA aptamers that bind to the target gene/gene product; structural analogs or soluble mimics or fusion polypeptides thereof, DNA targeting agents, such as CRISPR systems, Zinc finger binding proteins, and TALES; and small molecule agents that target or bind to a target gene product binding partner and act as functional mimics.

As used herein, an agonist has the ability to increase or enhance the activity and/or expression of a target gene/gene product in a cell (e.g., T cells, such as CD8+ or CD4+ T cells) by at least 5%, at least 10%, at least 20%, at least 30%, at least 40%, at least 50%, at least 60%, at least 70%, at least 80%, at least 90%, at least 95%, at least 98%, at least 99%, at least 100%, at least 1.5-fold, at least 2-fold, at least 5-fold, at least 10-fold, at least 25-fold, at least 50-fold, at least 100-fold, at least 1000-fold, or more relative to the activity or expression level in the absence of the activator or agonist.

In some embodiments of the compositions, methods, and uses described herein, the activator or agonist increases or enhances signal transduction mediated by the target gene/gene product. In some embodiments of the compositions and methods described herein, the activator or agonist increases or enhances transcription factor induction or activation.

In some embodiments of the compositions, methods, and uses described herein, the binding sites of the activators or agonists, such as an antibody or antigen-binding fragment thereof, are directed against an interaction site between the target gene product and one or more of its binding partners. By binding to an interaction site, an activator or agonist described herein can mimic or recapitulate the binding of the target gene product to its partner and increase the activity or expression of the target gene product, and downstream signaling consequences.

In some embodiments of the compositions, methods, and uses described herein, an activator or agonist is a monoclonal antibody. In some embodiments of the compositions, methods, and uses described herein, an activator or agonist is an antibody fragment or antigen-binding fragment.

In some embodiments of the compositions, methods, and uses described herein, an activator or agonist is a chimeric antibody derivative of the agonist antibodies and antigen-binding fragments thereof.

In some embodiments of the compositions, methods, and uses described herein, an activator or agonist is a humanized antibody derivative.

In some embodiments, the activator or agonist antibodies and antigen-binding fragments thereof described herein, i.e., antibodies that are useful for increasing T cell exhaustion, include derivatives that are modified, i.e., by the covalent attachment of any type of molecule to the antibody, provided that covalent attachment does not prevent the antibody from binding to the target antigen.

The activator or agonist antibodies and antigen-binding fragments thereof described herein can be generated by any suitable method known in the art.

In some embodiments, the activator or agonist antibodies and antigen-binding fragments thereof described herein are fully human antibodies or antigen-binding fragments thereof, which are particularly desirable for the therapeutic treatment of human patients. Human antibodies can be made by a variety of methods known in the art, and as described in more detail elsewhere herein.

In some embodiments of the compositions, methods, and uses described herein, an activator or agonist is a small molecule activator or agonist, including, but not limited to, small peptides or peptide-like molecules, soluble peptides, and synthetic non-peptidyl organic or inorganic compounds. A small molecule activator or agonist can have a molecular weight of any of about 100 to about 20,000 daltons (Da), about 500 to about 15,000 Da, or about 1000 to about 10,000 Da.

In some embodiments of the compositions, methods, and uses described herein, an activator or agonist is an RNA or DNA aptamer that binds or physically interacts with a target gene product and one or more of its binding partners, and enhances or promotes protein-protein interactions.

In some embodiments of the compositions, methods, and uses described herein, an activator or agonist comprises at least one structural analog of a target gene or gene product as listed in Table 1, Table 10, Table 11, or Table 12 or the combination of Prdm1 and c-Maf, or Prdm1 and c-Maf, individually. The term "structural analog," as used herein, refers to compounds that have a similar three dimensional structure as all or a portion of the desired target gene product under physiological conditions in vitro or in vivo, wherein the binding at least partially mimics or increases a biological activity mediated by the target gene product. Suitable structural analogs can be designed and synthesized through molecular modeling of binding of a target gene product and its binding partner(s). The structural analogs can be monomers, dimers, or higher order multimers in any desired combination of the same or different structures to obtain improved affinities and biological effects.

Activators or agonists for use in the compositions, methods, and uses described herein can be identified or characterized using methods known in the art, such as protein-protein binding assays, biochemical screening assays, immunoassays, and cell-based assays, which are well known in the art.

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-

0234972 A1 (U.S. application Ser. No. 14/183,471), US 2014-0227787 A1 (U.S. application Ser. No. 14/256,912), US 2014-0189896 A1 (U.S. application Ser. No. 14/105, 035), US 2014-0186958 (U.S. application Ser. No. 14/105, 017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), WO2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814, 263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013.

Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014 6/10/14; PCT/US2014/041808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055,484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to US provisional patent application U.S. Ser. No. 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, Dec. 12, 2014, PROTECTED GUIDE RNAS (PGRNAS); U.S. application 62/096,708, Dec. 24, 2014, PROTECTED GUIDE RNAS (PGRNAS); U.S. application 62/091,462, Dec. 12, 2014, DEAD GUIDES FOR CRISPR TRANSCRIPTION FACTORS; U.S. application 62/096,324, Dec. 23, 2014, DEAD GUIDES FOR CRISPR TRANSCRIPTION FACTORS; U.S. application 62/091,456, Dec. 12, 2014, ESCORTED AND FUNCTIONALIZED GUIDES FOR CRISPR-CAS SYSTEMS; U.S. application 62/091,461, Dec. 12, 2014, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, Dec. 19, 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, Dec. 24, 2014, ENGINEERING OF SYSTEMS, METHODS AND OPTIMIZED ENZYME AND GUIDE SCAFFOLDS FOR SEQUENCE MANIPULATION; U.S. application 62/098,059, Dec. 30, 2014, RNA-TARGETING SYSTEM; U.S. application 62/096,656, Dec. 24, 2014, CRISPR HAVING OR ASSOCIATED WITH DESTABILIZATION DOMAINS; U.S. application 62/096,697, Dec. 24, 2014, CRISPR HAVING OR ASSOCIATED WITH AAV; U.S. application 62/098,158, Dec. 30, 2014, ENGINEERED CRISPR COMPLEX INSERTIONAL TARGETING SYSTEMS; U.S. application 62/151,052, Apr. 22, 2015, CELLULAR TARGETING FOR EXTRACELLULAR EXOSOMAL REPORTING; U.S. application 62/054,490, Sep. 24, 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, Sep. 25, 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, Dec. 4, 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, Sep. 24, 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, Oct. 23, 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, Sep. 24, 2014, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, Sep. 24, 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, Sep. 24, 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, Sep. 24, 2014, MULTIFUNCTIONAL-CRISPR COMPLEXES AND/OR OPTIMIZED ENZYME LINKED FUNCTIONAL-CRISPR COMPLEXES; U.S. application 62/087,475, Dec. 4, 2014, FUNCTIONAL SCREENING WITH OPTIMIZED FUNCTIONAL CRISPR-CAS SYSTEMS; U.S. application 62/055,487, Sep. 25, 2014, FUNCTIONAL SCREENING WITH OPTIMIZED FUNCTIONAL CRISPR-CAS SYSTEMS; U.S. application 62/087,546, Dec. 4, 2014, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 30, 2014, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR Cas9 for Enhanced Genome Editing Specificity. Ran, FA., Hsu, PD., Lin, CY., Gootenberg, J S., Konermann, S., Trevino, AE., Scott, DA., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, FA., Konermann, S., Agarwala, V., Li, Y., Fine, E., Wu, X., Shalem, O., Cradick, TJ., Marraffini, LA., Bao, G., & Zhang, F. Nat Biotechnol doi:10.1038/nbt.2647 (2013);

Genome engineering using the CRISPR-Cas9 system. Ran, FA., Hsu, PD., Wright, J., Agarwala, V., Scott, DA., Zhang, F. Nature Protocols November; 8(11):2281-308 (2013-B);

Genome-Scale CRISPR-Cas9 Knockout Screening in Human Cells. Shalem, O., Sanjana, NE., Hartenian, E., Shi, X., Scott, DA., Mikkelson, T., Heckl, D., Ebert, BL., Root, DE., Doench, JG., Zhang, F. Science Dec. 12. (2013). [Epub ahead of print];

Crystal structure of cas9 in complex with guide RNA and target DNA. Nishimasu, H., Ran, FA., Hsu, PD., Konermann, S., Shehata, SI., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure™, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR/Cas9 cleavage of viral DNA efficiently suppresses hepatitis B virus,"Scientific Reports 5:10833. doi: 10.1038/srep10833 (Jun. 2, 2015);

Nishimasu et al., Crystal Structure of *Staphylococcus aureus* Cas9," Cell 162, 1113-1126 (Aug. 27, 2015);

Zetsche et al., "Cpf1 Is a Single RNA-Guided Endonuclease of a Class 2 CRISPR-Cas System," Cell 163, 1-13 (Oct. 22, 2015);

Shmakov et al., "Discovery and Functional Characterization of Diverse Class 2 CRISPR-Cas Systems," Molecular Cell 60, 1-13 (Available online Oct. 22, 2015);

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA: Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Zetsche et al. (2015) reported the characterization of Cpf1, a putative class 2 CRISPR effector. It was demonstrated that Cpf1 mediates robust DNA interference with features distinct from Cas9. Identifying this mechanism of interference broadens our understanding of CRISPR-Cas systems and advances their genome editing applications.

Shmakov et al. (2015) reported the characterization of three distinct Class 2 CRISPR-Cas systems. The effectors of two of the identified systems, C2c1 and C2c3, contain RuvC like endonuclease domains distantly related to Cpf1. The third system, C2c2, contains an effector with two predicted HEPN RNase domains.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

In addition, mention is made of PCT application PCT/US14/70057, entitiled "DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS (claiming priority from one or more or all of US provisional patent applications: 62/054,490, filed Sep. 24, 2014; 62/010,441, filed Jun. 10, 2014; and 61/915,118, 61/915,215 and 61/915,148, each filed on Dec. 12, 2013) ("the Particle Delivery PCT"), incorporated herein by reference, with respect to a method of preparing an sgRNA-and-Cas9 protein containing particle comprising admixing a mixture comprising an sgRNA and Cas9 protein (and optionally HDR template) with a mixture comprising or consisting essentially of or consisting of surfactant, phospholipid, biodegradable polymer, lipoprotein and alcohol; and particles from such a process. For example, wherein Cas9 protein and sgRNA were mixed together at a suitable, e.g., 3:1 to 1:3 or 2:1 to 1:2 or 1:1 molar ratio, at a suitable temperature, e.g., 15-30C, e.g., 20-25C, e.g., room temperature, for a suitable time, e.g., 15-45, such as 30 minutes, advantageously in sterile, nuclease free buffer, e.g., 1× PBS. Separately, particle components such as or comprising: a surfactant, e.g., cationic lipid, e.g., 1,2-dioleoyl-3-trimethylammonium-propane (DOTAP); phospholipid, e.g., dimyristoylphosphatidylcholine (DMPC); biodegradable polymer, such as an ethylene-glycol polymer or PEG, and a lipoprotein, such as a low-density lipoprotein, e.g., cholesterol were dissolved in an alcohol, advantageously a C1-6 alkyl alcohol, such as methanol, ethanol, isopropanol, e.g., 100% ethanol. The two solutions were mixed together to form particles containing the Cas9-sgRNA complexes. Accordingly, sgRNA may be pre-complexed with the Cas9 protein, before formulating the entire complex in a particle. Formulations may be made with a different molar ratio of different components known to promote delivery of nucleic acids into cells (e.g. 1,2-dioleoyl-3-trimethylammonium-propane (DOTAP), 1,2-ditetradecanoyl-sn-glycero-3-phosphocholine (DMPC), polyethylene glycol (PEG), and cholesterol) For example DOTAP: DMPC: PEG: Cholesterol Molar Ratios may be DOTAP 100, DMPC 0, PEG 0, Cholesterol 0; or DOTAP 90, DMPC 0, PEG 10, Cholesterol 0; or DOTAP 90, DMPC 0, PEG 5, Cholesterol 5. DOTAP 100, DMPC 0, PEG 0, Cholesterol 0. That application accordingly comprehends admixing sgRNA, Cas9 protein and components that form a particle; as well as particles from such admixing. Aspects of the instant invention can involve particles; for example, particles using a process analogous to that of the Particle Delivery PCT, e.g., by admixing a mixture comprising sgRNA and/or Cas9 as in the instant invention and components that form a particle, e.g., as in the Particle Delivery PCT, to form a particle and particles from such admixing (or, of course, other particles involving sgRNA and/or Cas9 as in the instant invention).

In general, the CRISPR-Cas or CRISPR system is as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, a tracr (transactivating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell. In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA, i.e. RNA capable of guiding Cas to a target genomic locus, are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10 30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In a classic CRISPR-Cas systems, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and advantageously tracr RNA is 30 or 50 nucleotides in length. However, an aspect of the invention is to reduce off-target interactions, e.g., reduce the guide interacting with a target sequence having low complementarity. Indeed, in the examples, it is shown that the invention involves mutations that result in the CRISPR-Cas system being able to distinguish between target and off-target sequences that have greater than 80% to about 95% complementarity, e.g., 83%-84% or 88-89% or 94-95% complementarity (for instance, distinguishing between a target having 18 nucleotides from an off-target of 18 nucleotides having 1, 2 or 3 mismatches). Accordingly, in the context of the present invention the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In particularly preferred embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e. an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence.

The methods according to the invention as described herein comprehend inducing one or more mutations in a eukaryotic cell (in vitro, i.e. in an isolated eukaryotic cell) as herein discussed comprising delivering to cell a vector as herein discussed. The mutation(s) can include the introduction, deletion, or substitution of one or more nucleotides at each target sequence of cell(s) via the guide(s) RNA(s) or sgRNA(s). The mutations can include the introduction, deletion, or substitution of 1-75 nucleotides at each target sequence of said cell(s) via the guide(s) RNA(s) or sgRNA (s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 40, 45, 50, 75, 100, 200, 300, 400 or 500 nucleotides at each target sequence of said cell(s) via the guide(s) RNA(s) or sgRNA(s).

For minimization of toxicity and off-target effect, it will be important to control the concentration of Cas mRNA and guide RNA delivered. Optimal concentrations of Cas mRNA and guide RNA can be determined by testing different concentrations in a cellular or non-human eukaryote animal model and using deep sequencing the analyze the extent of modification at potential off-target genomic loci. Alternatively, to minimize the level of toxicity and off-target effect, Cas nickase mRNA (for example *S. pyogenes* Cas9 with the D10A mutation) can be delivered with a pair of guide RNAs targeting a site of interest. Guide sequences and strategies to minimize toxicity and off-target effects can be as in WO 2014/093622 (PCT/US2013/074667); or, via mutation as herein.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

The nucleic acid molecule encoding a Cas is advantageously codon optimized Cas. An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a Cas is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way how the Cas transgene is introduced in the cell is may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox(LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus, such as for instance one or more oncogenic mutations, as for instance and without limitation described in Platt et al. (2014), Chen et al., (2014) or Kumar et al., (2009).

In some embodiments, the Cas sequence is fused to one or more nuclear localization sequences (NLSs), such as about or more than about 1, 2, 3, 4, 5, 6, 7, 8, 9, 10, or more NLSs. In some embodiments, the Cas comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the Cas comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV(SEQ ID NO: 149); the NLS from nucleoplasmin (e.g. the nucleoplasmin bipartite NLS with the sequence KRPAATKKAGQAKKKK) (SEQ ID NO: 150); the c-myc NLS having the amino acid sequence PAAKRVKLD (SEQ ID NO: 151) or RQRRNELKRSP(SEQ ID NO: 152); the hRNPA1 M9 NLS having the sequence NQSSNFGPMKGGNFGGRSSGPYGGGGQYFAKPRNQGGY(SEQ ID NO: 153); the sequence RMRIZFKNKGKDTAELRRRRVEVSVELRKAKKDEQILKRRNV (SEQ ID NO: 154) of the IBB domain from importin-alpha; the sequences VSRKRPRP (SEQ ID NO: 155) and PPKKARED (SEQ ID NO: 156) of the myoma T protein; the sequence PQPKKKPL (SEQ ID NO: 157) of human p53; the sequence SALIKKKKKMAP (SEQ ID NO: 158) of mouse c-abl IV; the sequences DRLRR (SEQ ID NO: 159) and PKQKKRK (SEQ ID NO: 160) of the influenza virus NS1; the sequence RKLKKKIKKL (SEQ ID NO: 161) of the Hepatitis virus delta antigen; the sequence REKKKFLKRR (SEQ ID NO: 162) of the mouse Mx1 protein; the sequence KRKGDEVDGVDEVAKKKSKK (SEQ ID NO: 163) of the human poly(ADP-ribose) polymerase; and the sequence RKCLQAGMNLEARKTKK (SEQ ID NO: 164) of the steroid hormone receptors (human) glucocorticoid. In general, the one or more NLSs are of sufficient strength to drive accumulation of the Cas in a detectable amount in the nucleus of a eukaryotic cell. In general, strength of nuclear localization activity may derive from the number of NLSs in the Cas, the particular NLS(s) used, or a combination of these factors. Detection of accumulation in the nucleus may be performed by any suitable technique. For example, a detectable marker may be fused to the Cas, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or Cas enzyme activity), as compared to a control no exposed to the Cas or complex, or exposed to a Cas lacking the one or more NLSs.

In certain embodiments, the DNA-targeting agent may comprise a transcription activator-like effector (TALE) protein or DNA-binding domain thereof. Hence, certain embodiments may make use of isolated, non-naturally occurring, recombinant or engineered DNA binding proteins that comprise TALE monomers or TALE monomers or half monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", "TALE monomers" or "monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is X1-11-(X12X13)-X14-33 or 34 or 35, where the subscript indicates the amino acid position and X represents any amino acid. X12X13 indicate the RVDs. In some polypeptide monomers, the variable amino acid at position 13 is missing or absent and in such monomers, the RVD consists of a single amino acid. In such cases the RVD may be alternatively represented as X*, where X represents X12 and (*) indicates that X13 is absent. The DNA binding domain comprises several repeats of TALE monomers and this may be represented as (X1-11-(X12X13)-X14-33 or 34 or 35)z, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), monomers with an RVD of NG preferentially bind to thymine (T), monomers with an RVD of HD preferentially bind to cytosine (C) and monomers with an RVD of NN preferentially bind to both adenine (A) and guanine (G). In yet another embodiment of the invention, monomers with an RVD of IG preferentially bind to T. Thus, the number and order of the polypeptide monomer repeats in the nucleic acid binding domain of a TALE determines its nucleic acid target specificity. In still further embodiments of the invention, monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The polypeptides used in methods of certain embodiments of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the polypeptides of the invention will bind. As used herein the monomers and at least one or more half monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases this region may be referred to as repeat 0. In animal genomes, TALE binding sites do not necessarily have to begin with a thymine (T) and polypeptides of the invention may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer. Therefore, it follows that the length of the nucleic acid or DNA being targeted is equal to the number of full monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

(SEQ ID NO: 147)
```
M D P I R S R T P S P A R E L L S G P Q P D G V Q

P T A D R G V S P P A G G P L D G L P A R R T M S

R T R L P S P P A P S P A F S A D S F S D L L R Q

F D P S L F N T S L F D S L P P F G A H H T E A A

T G E W D E V Q S G L R A A D A P P P T M R V A V

T A A R P P R A K P A P R R R A A Q P S D A S P A

A Q V D L R T L G Y S Q Q Q Q E K I K P K V R S T

V A Q H H E A L V G H G F T H A H I V A L S Q H P

A A L G T V A V K Y Q D M I A A L P E A T H E A I

V G V G K Q W S G A R A L E A L L T V A G E L R G

P P L Q L D T G Q L L K I A K R G G V T A V E A V

H A W R N A L T G A P L N
```

An exemplary amino acid sequence of a C-terminal capping region is:

(SEQ ID NO: 148)
```
R P A L E S I V A Q L S R P D P A L A A L T N D H

L V A L A C L G G R P A L D A V K K G L P H A P A

L I K R T N R R I P E R T S H R V A D H A Q V V R

V L G F F Q C H S H P A Q A F D D A M T Q F G M S

R H G L L Q L F R R V G V T E L E A R S G T L P P

A S Q R W D R I L Q A S G M K R A K P S P T S T Q

T P D Q A S L H A F A D S L E R D L D A P S P M H

E G D Q T R A S
```

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In certain embodiments, the DNA-targeting agent may comprise a zinc finger protein or DNA-binding domain thereof. Artificial zinc-finger (ZF) technology allows to provide programmable DNA-binding domains, and involves arrays of ZF modules to target new DNA-binding sites in the genome. Each finger module in a ZF array targets three DNA bases. A customized array of individual zinc finger domains is assembled into a ZF protein (ZFP). ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to FokI cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79).

In certain embodiments, the protein comprising the DNA-targeting agent may further comprise one or more suitable effector portions or domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments, the activity mediated by the effector domain is a biological activity. For example, in some embodiments the effector domain may be a transcriptional inhibitor (i.e., a repressor domain), such as an mSin interaction domain (SID). SID4× domain or a Kruppel-associated box (KRAB) or fragments of the KRAB domain. In some embodiments the effector domain may be an enhancer of transcription (i.e. an activation domain), such as the VP16, VP64 or p65 activation domain. In some embodiments, the nucleic acid binding portion may be linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal. In some embodiments, the effector domain may be a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

Adoptive Cell Transfer (ACT)

The immune cells of the present invention may be used for adoptive cell transfer. Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57.) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma and colorectal carcinoma, as well as patients with CD19-expressing hematologic malignancies (Kalos et al., (2011) Science Translational Medicine 3 (95): 95ra73).

Aspects of the invention involve the adoptive transfer of immune system cells, such as T cells, specific for selected antigens, such as tumor associated antigens (see Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144). Various strategies may for example be employed to genetically modify T cells by altering the specificity of the T cell receptor (TCR) for example by introducing new TCR a and R chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fc domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane-bound or transmembrane protein. Transmembrane regions of particular use in this disclosure may be derived from CD8, CD28, CD3, CD45, CD4, CD5, CDS, CD9, CD16, CD22, CD33, CD37, CD64, CD80, CD86, CD134, CD137, CD154, TCR. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a $V_L$ linked to a $V_H$ of a specific antibody, linked by a flexible linker, for example by a CD8a hinge domain and a CD8a transmembrane domain, to the transmembrane and intracellular signaling domains of either CD3δ or FcRγ (scFv-CD3δ or scFv-FcRγ; see U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3(; see U.S. Pat. Nos. 8,911,993; 8,916,381; 8,975,071; 9,101,584; 9,102,760; 9,102,761). Third-generation CARs include a combination of costimulatory endodomains, such a CD3δ-chain, CD97, GDI 1a-CD18, CD2, ICOS, CD27, CD154, CDS, OX40, 4-1BB, CD2, CD7, LIGHT, LFA-1, NKG2C, B7-H3, CD30, CD40, PD-1, or CD28 signaling domains (for example scFv-CD28-4-1BB-CD3δ or scFv-CD28-OX40-CD3(; see U.S. Pat. Nos. 8,906,682; 8,399,645; 5,686,281; PCT Publication No. WO2014134165; PCT Publication No. WO2012079000). Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects.

Alternatively, T-cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T-cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015), in order to elicit a T-cell response. Some CARs may also comprise a "suicide switch" to induce cell death of the CAR T-cells following treatment (Buddee et al., PLoS One, 2013) or to downregulate expression of the CAR following binding to the target antigen (WO 2016/011210).

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3δ and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to treat tumor xenografts.

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoreponsive cell, thereby treating or preventing the disease (such as a neoplasia, a pathogen infection, an autoimmune disorder, or an allogeneic transplant reaction).

Additionally, the disclosed biomarker signature (e.g., the genes displayed in Tables 5-13 or a selection of genes therefrom) may be used to identify CAR T cells or other cells used in ACT that are dysfunctional or exhausted. Using the disclosed biomarkers as a diagnostic platform allows clinicians to identify whether a patient's response to the ACT is due to cell dysfunction, and if it is, the levels of up-regulation and down-regulation across the biomarker signature will allow problems to be addressed. For example, if a patient receiving ACT is non-responsive, the cells administered as part of the ACT may be assayed by an assay disclosed herein to determine the relative level of expression of a disclosed biomarker signature (e.g., Tables 5-13 or a selection of genes therefrom). If a particular inhibitory receptor or molecule is up-regulated in the ACT cells, the patient may be treated with an inhibitor of that receptor or molecule. If a particular stimulatory receptor or molecule is down-regulated in the ACT cells, the patient may be treated with an agonist of that receptor or molecule.

In one embodiment, the treatment can be administrated into patients undergoing an immunosuppressive treatment. The cells or population of cells, may be made resistant to at least one immunosuppressive agent due to the inactivation of a gene encoding a receptor for such immunosuppressive agent. Not being bound by a theory, the immunosuppressive treatment should help the selection and expansion of the immunoresponsive or T cells according to the invention within the patient.

The administration of the cells or population of cells according to the present invention may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853). Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed to eliminate potential alloreactive T-cell receptors (TCR), disrupt the target of a chemotherapeutic agent, block an immune checkpoint, activate a T cell, and/or increase the differentiation and/or proliferation of functionally exhausted or dysfunctional CD8+ T-cells (see PCT Patent Publications: WO2013176915, WO2014059173, WO2014172606, WO2014184744, and WO2014191128). Editing may result in inactivation of a gene.

By inactivating a gene it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art.

T cell receptors (TCR) are cell surface receptors that participate in the activation of T cells in response to the presentation of antigen. The TCR is generally made from two chains, a and p, which assemble to form a heterodimer and associates with the CD3-transducing subunits to form the T cell receptor complex present on the cell surface. Each a and p chain of the TCR consists of an immunoglobulin-like N-terminal variable (V) and constant (C) region, a hydrophobic transmembrane domain, and a short cytoplasmic region. As for immunoglobulin molecules, the variable region of the a and p chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRα or TCRβ can result in the elimination of the TCR from the surface of T cells preventing recognition of alloantigen and thus GVHD. However, TCR disruption generally results in the elimination of the CD3 signaling component and alters the means of further T cell expansion.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy?Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT1 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS(CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL1ORA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1 or TIM-3. In preferred embodiments, the gene locus involved in the expression of PD-1 or CTLA-4 genes is targeted. In other preferred embodiments, combinations of genes are targeted, such as but not limited to PD-1 and TIGIT. In preferred embodiments, the novel genes or gene combinations described herein are targeted or modulated.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC1O and TCRα, SIGLEC10 and TCRβ, 2B4 and TCRα, 2B4 and TCRβ.

Whether prior to or after genetic modification of the T cells, the T cells can be activated and expanded generally using methods as described, for example, in U.S. Pat. Nos.

6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

Immune cells may be obtained using any method known in the art. In one embodiment T cells that have infiltrated a tumor are isolated. T cells may be removed during surgery. T cells may be isolated after removal of tumor tissue by biopsy. T cells may be isolated by any means known in the art. In one embodiment the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Lagomorpha, such as rabbits; the order Carnivora, including Felines (cats) and Canines (dogs); the order Artiodactyla, including Bovines (cows) and Swines (pigs); or of the order Perissodactyla, including Equines (horses). The mammals may be non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells, bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD10b, CD16, HLA-DR, and CD8.

Further, monocyte populations (i.e., $CD14^+$ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may also be antigen-specific T cells. For example, tumor-specific T cells can be used. In certain embodiments, antigen-specific T cells can be isolated from a patient of interest, such as a patient afflicted with a cancer or an infectious disease. In one embodiment neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation And Isolation of Antigen-Specific T Cells, or in U.S. Pat. Nos. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHIC tetramers (Altman, et al., Science. 1996 Oct. 4; 274(5284):94-6). In another embodiment the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHIC tetramers can be generated using techniques known in the art and can be made with any MHIC molecule of interest and any antigen of interest as described herein. Specific epitopes to be used in this context can be identified using numerous assays known in the art. For example, the ability of a polypeptide to bind to MHIC class I may be evaluated indirectly by monitoring the ability to promote incorporation of $^{125}$I labeled β2-microglobulin (β2m) into MHIC class I/β2m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one T cells are isolated by contacting the T cell specific antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™ BD™ LSR II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

Treatment of Chronic Immune Conditions

A "cancer" or "tumor" as used herein refers to an uncontrolled growth of cells which interferes with the normal functioning of the bodily organs and systems. A subject that has a cancer or a tumor is a subject having objectively measurable cancer cells present in the subject's body. Included in this definition are benign and malignant cancers, as well as dormant tumors or micrometastases. Cancers which migrate from their original location and seed vital organs can eventually lead to the death of the subject through the functional deterioration of the affected organs. Hemopoietic cancers, such as leukemia, are able to outcompete the normal hemopoietic compartments in a subject, thereby leading to hemopoietic failure (in the form of anemia, thrombocytopenia and neutropenia) ultimately causing death.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Examples of cancer include but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

In some embodiments of these methods and all such methods described herein, the methods further comprise administering a tumor or cancer antigen to a subject being administered the one or more agents described herein.

A number of tumor antigens have been identified that are associated with specific cancers. As used herein, the terms "tumor antigen" and "cancer antigen" are used interchangeably to refer to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), and fusion proteins resulting from internal deletions or chromosomal translocations. Still other cancer antigens can be encoded by viral genes such as those carried on RNA and DNA tumor viruses. Many tumor antigens have been defined in terms of multiple solid tumors: MAGE 1, 2, & 3, defined by immunity; MART-1/Melan-A, gp100, carcinoembryonic antigen (CEA), HER-2, mucins (i.e., MUC-1), prostate-specific antigen (PSA), and prostatic acid phosphatase (PAP). In addition, viral proteins such as hepatitis B (HBV), Epstein-Barr (EBV), and human papilloma (HPV) have been shown to be important in the development of hepatocellular carcinoma, lymphoma, and cervical cancer, respectively. However, due to the immunosuppression of patients diagnosed with cancer (including T cell exhaustion), the immune systems of these patients often fail to respond to the tumor antigens.

Additionally, neoantigens have been described that are subject specific. Neoantigens specific for a subject result from abundant intra-tumor and inter-tumor heterogeneity. In one instance, Ott et al., (Hematol. Oncol. Clin. N. Am. 28 (2014) 559-569) discusses the advantages of neoantigens in the context of melanoma. Ott et al., discusses the "NeoVax" approach and shows how tumor neoantigens provide optimal immunogenicity and tumor specificity compared to native antigens such as overexpressed or selectively expressed antigens commonly used in cancer vaccines (see, e.g., FIG. 2 on page 565). Van Rooij et al. (Journal of Clinical Oncology 31(32):e439-e442) shows the critical role of neoantigens in antitumor immune responses. Gubin et al. (2014) (Nature 515:577-581), identified tumor-specific mutant antigens (i.e. neoantigens) by sequencing and found that peptide vaccines incorporating these mutant epitopes induced tumor rejection comparably to checkpoint inhibitor therapies (e.g. targeting CTLA-4 or PD-1). Rajasagi et al. (2014), (Blood 124(3):453-62) used whole-exome sequencing to identify neoantigenic peptides in patients with chronic lymphocytic leukemia. Significantly, CLL patients showing long-term remission had long-lived cytotoxic T cell responses against neoantigenic mutations. Rizvi et al. (2014) (Science Express 10.1126/science.aaa1348) discloses that in non-small cell lung cancer, whole exome sequencing revealed that a higher neoantigen burden correlated with progression-free survival and efficacy of anti-PD-1 therapy. Neoantigen-specific T cell responses also paralleled tumor regression.

In some embodiments of these methods and all such methods described herein, the methods further comprise administering one or more anti-cancer therapies or agents to a subject in addition to the one or more agents described herein.

The term "anti-cancer therapy" refers to a therapy useful in treating cancer. Examples of anti-cancer therapeutic agents include, but are not limited to, e.g., surgery, chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., HERCEPTIN®), anti-CD20 antibodies, an epidermal growth factor receptor (EGFR) antagonist (e.g., a tyrosine kinase inhibitor), HER1/EGFR inhibitor (e.g., erlotinib (TARCEVA®)), platelet derived growth factor inhibitors (e.g., GLEEVEC™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also specifically contemplated for the methods described herein.

The term "cytotoxic agent" as used herein refers to a substance that inhibits or prevents the function of cells and/or causes destruction of cells. The term is intended to include radioactive isotopes (e.g. $At^{211}$, $V^{131}$, $I^{125}$, $Y^{90}$, $Re^{186}$, $Re^{188}$, $Sm^{153}$, $Bi^{212}$, $p^{32}$ and radioactive isotopes of Lu), chemotherapeutic agents, and toxins such as small molecule toxins or enzymatically active toxins of bacterial, fungal, plant or animal origin, including active fragments and/or variants thereof.

In some embodiments of these methods and all such methods described herein, the methods further comprise administering a chemotherapeutic agent to the subject being administered the one or more agents or combination thereof described herein.

Non-limiting examples of chemotherapeutic agents can include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolmelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimustine; antibiotics such as the enediyne antibiotics (e.g., calicheamicin, especially calicheamicin gammaII and calicheamicin omegaI1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomycin, actinomycin, anthramycin, azaserine, bleomycins, cactinomycin, carabicin, caminomycin, carzinophilin, chromomycin, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozotocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatrexate; defofamine; demecolcine; diaziquone; eflornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verrucarin A, roridin A and anguidine); urethan; vindesine;

dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, I11.), and TAXOTERE® docetaxel (Rhone-Poulenc Rorer, Antony, France); chlorambucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE, vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DFMO); retinoids such as retinoic acid; capecitabine; combretastatin; leucovorin (LV); oxaliplatin, including the oxaliplatin treatment regimen (FOLFOX); lapatinib (TYKERB.); inhibitors of PKC-alpha, Raf, H-Ras, EGFR (e.g., erlotinib (TARCEVA®)) and VEGF-A that reduce cell proliferation and pharmaceutically acceptable salts, acids or derivatives of any of the above. In addition, the methods of treatment can further include the use of radiation or radiation therapy.

In certain embodiments, the one or more additional agents are synergistic in that they increase immunogenicity after treatment. In one embodiment the additional agent allows for lower toxicity and/or lower discomfort due to lower doses of the additional therapeutic agents or any components of the therapy described herein. In another embodiment the additional agent results in longer lifespan due to increased effectiveness of the therapy described herein. Chemotherapeutic treatments that enhance the immunological response in a patient have been reviewed (Zitvogel et al., Immunological aspects of cancer chemotherapy. Nat Rev Immunol. 2008 January; 8(1):59-73). Additionally, chemotherapeutic agents can be administered safely with immunotherapy without inhibiting vaccine specific T-cell responses (Perez et al., A new era in anticancer peptide vaccines. Cancer May 2010). In one embodiment the additional agent is administered to increase the efficacy of the therapy described herein. In one embodiment the additional agent is a chemotherapy treatment. In one embodiment low doses of chemotherapy potentiate delayed-type hypersensitivity (DTH) responses. In one embodiment the chemotherapy agent targets regulatory T-cells. In one embodiment cyclophosphamide is the therapeutic agent. In one embodiment cyclophosphamide is administered prior to treatment with a target gene or gene product modulator. In one embodiment cyclophosphamide is administered as a single dose before treatment (Walter et al., Multipeptide immune response to cancer vaccine IMA901 after single-dose cyclophosphamide associates with longer patient survival. Nature Medicine; 18:8 2012). In another embodiment, cyclophosphamide is administered according to a metronomic program, where a daily dose is administered for one month (Ghiringhelli et al., Metronomic cyclophosphamide regimen selectively depletes CD4+CD25+ regulatory T cells and restores T and NK effector functions in end stage cancer patients. Cancer Immunol Immunother 2007 56:641-648). In another embodiment taxanes are administered before treatment to enhance T-cell and NK-cell functions (Zitvogel et al., 2008). In another embodiment a low dose of a chemotherapeutic agent is administered with the therapy described herein. In one embodiment the chemotherapeutic agent is estramustine. In one embodiment the cancer is hormone resistant prostate cancer. A ≥50% decrease in serum prostate specific antigen (PSA) was seen in 8.7% of advanced hormone refractory prostate cancer patients by personalized vaccination alone, whereas such a decrease was seen in 54% of patients when the personalized vaccination was combined with a low dose of estramustine (Itoh et al., Personalized peptide vaccines: A new therapeutic modality for cancer. Cancer Sci 2006; 97: 970-976). In another embodiment glucocorticoids are not administered with or before the therapy described herein (Zitvogel et al., 2008). In another embodiment glucocorticoids are administered after the therapy described herein. In another embodiment Gemcitabine is administered before, simultaneously, or after the therapy described herein to enhance the frequency of tumor specific CTL precursors (Zitvogel et al., 2008). In another embodiment 5-fluorouracil is administered with the therapy described herein as synergistic immune effects were seen with a peptide based vaccine (Zitvogel et al., 2008). In another embodiment an inhibitor of Braf, such as Vemurafenib, is used as an additional agent. Braf inhibition has been shown to be associated with an increase in melanoma antigen expression and T-cell infiltrate and a decrease in immunosuppressive cytokines in tumors of treated patients (Frederick et al., BRAF inhibition is associated with enhanced melanoma antigen expression and a more favorable tumor microenvironment in patients with metastatic melanoma. Clin Cancer Res. 2013; 19:1225-1231). In another embodiment, an inhibitor of tyrosine kinases is used as an additional agent. In one embodiment the tyrosine kinase inhibitor is used before treatment with the therapy described herein. In one embodiment the tyrosine kinase inhibitor is used simultaneously with the therapy described herein. In another embodiment the tyrosine kinase inhibitor is used to create a more immune permissive environment. In another embodiment the tyrosine kinase inhibitor is sunitinib or imatinib mesylate. It has previously been shown that favorable outcomes could be achieved with sequential administration of continuous daily dosing of sunitinib and recombinant vaccine (Farsaci et al., Consequence of dose scheduling of sunitinib on host immune response elements and vaccine combination therapy. Int J Cancer; 130: 1948-1959). Sunitinib has also been shown to reverse type-1 immune suppression using a daily dose of 50 mg/day (Finke et al., Sunitinib Reverses Type-1 Immune Suppression and Decreases T-Regulatory Cells in Renal Cell Carcinoma Patients. Clin Cancer Res 2008; 14(20)). In another embodiment additional targeted therapies are administered in combination with the therapy described herein. Doses of targeted therapies has been described previously (Alvarez, Present and future evolution of advanced breast cancer therapy. Breast Cancer Research 2010, 12(Suppl 2):S1). In another embodiment temozolomide is administered with the therapy described herein. In one embodiment temozolomide is administered at 200 mg/day for 5 days every fourth week of the therapy described herein. Results of a similar strategy have been shown to have low toxicity (Kyte et al., Telomerase Peptide Vaccination Combined with Temozolomide: A Clinical Trial in Stage IV Melanoma Patients. Clin Cancer Res; 17(13) 2011). In another embodiment the target gene or gene product modulator therapy is administered with an additional therapeutic agent that results in lymphopenia. In one embodiment the additional agent is temozolomide. An immune response can still be induced under these conditions (Sampson et al., Greater chemotherapy-induced lymphopenia enhances tumor-specific immune responses that eliminate EGFRvIII-expressing tumor cells in patients with glioblastoma. Neuro-Oncology 13(3):324-333, 2011).

In one embodiment the method may comprise administering the target gene or gene product modulator therapy within a standard of care for a particular cancer. In another embodiment the target gene or gene product modulator therapy is administered within a standard of care where addition of the therapy is synergistic with the steps in the standard of care.

In another aspect, the combination therapy described herein provides selecting the appropriate point to administer the target gene or gene product modulator therapy in relation to and within the standard of care for the cancer being treated for a patient in need thereof. The therapy can be effectively administered even within the standard of care that includes surgery, radiation, or chemotherapy. The standards of care for the most common cancers can be found on the website of National Cancer Institute (www.cancer.gov/cancertopics). The standard of care is the current treatment that is accepted by medical experts as a proper treatment for a certain type of disease and that is widely used by healthcare professionals. Standard or care is also called best practice, standard medical care, and standard therapy. Standards of Care for cancer generally include surgery, lymph node removal, radiation, chemotherapy, targeted therapies, antibodies targeting the tumor, and immunotherapy. Immunotherapy can include checkpoint blockers (CBP), chimeric antigen receptors (CARs), and adoptive T-cell therapy. The therapy described herein can be incorporated within the standard of care. The therapy described herein may also be administered where the standard of care has changed due to advances in medicine.

Incorporation of the target gene or gene product modulator therapy described herein may depend on a treatment step in the standard of care that can lead to activation of the immune system. Treatment steps that can activate and function synergistically with the therapy have been described herein. The therapy can be advantageously administered simultaneously or after a treatment that activates the immune system.

Incorporation of the therapy described herein may depend on a treatment step in the standard of care that causes the immune system to be suppressed. Such treatment steps may include irradiation, high doses of alkylating agents and/or methotrexate, steroids such as glucosteroids, surgery, such as to remove the lymph nodes, imatinib mesylate, high doses of TNF, and taxanes (Zitvogel et al., 2008). The target gene or gene product modulator therapy may be administered before such steps or may be administered after. Advantageously, the treatment is administered as part of adoptive T-cell therapy.

In one embodiment the therapy may be administered after bone marrow transplants and peripheral blood stem cell transplantation. Bone marrow transplantation and peripheral blood stem cell transplantation are procedures that restore stem cells that were destroyed by high doses of chemotherapy and/or radiation therapy. After being treated with high-dose anticancer drugs and/or radiation, the patient receives harvested stem cells, which travel to the bone marrow and begin to produce new blood cells. A "mini-transplant" uses lower, less toxic doses of chemotherapy and/or radiation to prepare the patient for transplant. A "tandem transplant" involves two sequential courses of high-dose chemotherapy and stem cell transplant. In autologous transplants, patients receive their own stem cells. In syngeneic transplants, patients receive stem cells from their identical twin. In allogeneic transplants, patients receive stem cells from their brother, sister, or parent. A person who is not related to the patient (an unrelated donor) also may be used. In some types of leukemia, the graft-versus-tumor (GVT) effect that occurs after allogeneic BMT and PBSCT is crucial to the effectiveness of the treatment. GVT occurs when white blood cells from the donor (the graft) identify the cancer cells that remain in the patient's body after the chemotherapy and/or radiation therapy (the tumor) as foreign and attack them. Immunotherapy with the therapy described herein can take advantage of this by increasing immunity after a transplant.

In one embodiment the therapy is administered to a patient in need thereof with a cancer that requires surgery. In one embodiment the combination therapy described herein is administered to a patient in need thereof in a cancer where the standard of care is primarily surgery followed by treatment to remove possible micro-metastases, such as breast cancer. Breast cancer is commonly treated by various combinations of surgery, radiation therapy, chemotherapy, and hormone therapy based on the stage and grade of the cancer. Adjuvant therapy for breast cancer is any treatment given after primary therapy to increase the chance of long-term survival. Neoadjuvant therapy is treatment given before primary therapy. Adjuvant therapy for breast cancer is any treatment given after primary therapy to increase the chance of long-term disease-free survival. Primary therapy is the main treatment used to reduce or eliminate the cancer. Primary therapy for breast cancer usually includes surgery, a mastectomy (removal of the breast) or a lumpectomy (surgery to remove the tumor and a small amount of normal tissue around it; a type of breast-conserving surgery). During either type of surgery, one or more nearby lymph nodes are also removed to see if cancer cells have spread to the lymphatic system. When a woman has breast-conserving surgery, primary therapy almost always includes radiation therapy. Even in early-stage breast cancer, cells may break away from the primary tumor and spread to other parts of the body (metastasize). Therefore, doctors give adjuvant therapy to kill any cancer cells that may have spread, even if they cannot be detected by imaging or laboratory tests.

In one embodiment the target gene or gene product modulator therapy is administered consistent with the standard of care for Ductal carcinoma in situ (DCIS). The standard of care for this breast cancer type is:

1. Breast-conserving surgery and radiation therapy with or without tamoxifen.
2. Total mastectomy with or without tamoxifen.
3. Breast-conserving surgery without radiation therapy.

The therapy may be administered before breast conserving surgery or total mastectomy to shrink the tumor before surgery. In another embodiment the therapy can be administered as an adjuvant therapy to remove any remaining cancer cells.

In another embodiment patients diagnosed with stage I, II, IIIA, and Operable IIIC breast cancer are treated with the therapy as described herein. The standard of care for this breast cancer type is:

1. Local-regional treatment:

Breast-conserving therapy (lumpectomy, breast radiation, and surgical staging of the axilla).

Modified radical mastectomy (removal of the entire breast with level I-II axillary dissection) with or without breast reconstruction.

Sentinel node biopsy.

2. Adjuvant radiation therapy postmastectomy in axillary node-positive tumors:

For one to three nodes: unclear role for regional radiation (infra/supraclavicular nodes, internal mammary nodes, axillary nodes, and chest wall).

For more than four nodes or extranodal involvement: regional radiation is advised.

3. Adjuvant systemic therapy

In one embodiment the therapy is administered as a neoadjuvant therapy to shrink the tumor. In another embodiment the therapy is administered as an adjuvant systemic therapy.

In another embodiment patients diagnosed with inoperable stage IIIB or IIIC or inflammatory breast cancer are treated with the therapy as described herein. The standard of care for this breast cancer type is:

1. Multimodality therapy delivered with curative intent is the standard of care for patients with clinical stage IIIB disease.
2. Initial surgery is generally limited to biopsy to permit the determination of histology, estrogen-receptor (ER) and progesterone-receptor (PR) levels, and human epidermal growth factor receptor 2 (HER2/neu) overexpression. Initial treatment with anthracycline-based chemotherapy and/or taxane-based therapy is standard. For patients who respond to neoadjuvant chemotherapy, local therapy may consist of total mastectomy with axillary lymph node dissection followed by postoperative radiation therapy to the chest wall and regional lymphatics. Breast-conserving therapy can be considered in patients with a good partial or complete response to neoadjuvant chemotherapy. Subsequent systemic therapy may consist of further chemotherapy. Hormone therapy should be administered to patients whose tumors are ER-positive or unknown. All patients should be considered candidates for clinical trials to evaluate the most appropriate fashion in which to administer the various components of multimodality regimens.

In one embodiment the therapy is administered as part of the various components of multimodality regimens. In another embodiment the therapy is administered before, simultaneously with, or after the multimodality regimens. In another embodiment the therapy is administered based on synergism between the modalities. In another embodiment the therapy is administered after treatment with anthracycline-based chemotherapy and/or taxane-based therapy (Zitvogel et al., 2008). The therapy may also be administered after radiation.

In another embodiment the therapy described herein is used in the treatment in a cancer where the standard of care is primarily not surgery and is primarily based on systemic treatments, such as Chronic Lymphocytic Leukemia (CLL).

In another embodiment patients diagnosed with stage I, II, III, and IV Chronic Lymphocytic Leukemia are treated with the therapy as described herein. The standard of care for this cancer type is:

1. Observation in asymptomatic or minimally affected patients
2. Rituximab
3. Ofatumumab
4. Oral alkylating agents with or without corticosteroids
5. Fludarabine, 2-chlorodeoxyadenosine, or pentostatin
6. Bendamustine
7. Lenalidomide
8. Combination chemotherapy.
   Combination chemotherapy regimens include the following:
   - Fludarabine plus cyclophosphamide plus rituximab.
   - Fludarabine plus rituximab as seen in the CLB-9712 and CLB-9011 trials.
   - Fludarabine plus cyclophosphamide versus fludarabine plus cyclophosphamide plus rituximab.
   - Pentostatin plus cyclophosphamide plus rituximab as seen in the MAYO-MC0183 trial, for example.
   - Ofatumumab plus fludarabine plus cyclophosphamide.
   - CVP: cyclophosphamide plus vincristine plus prednisone.
   - CHOP: cyclophosphamide plus doxorubicin plus vincristine plus prednisone.
   - Fludarabine plus cyclophosphamide versus fludarabine as seen in the E2997 trial [NCT00003764] and the LRF-CLL4 trial, for example.
   - Fludarabine plus chlorambucil as seen in the CLB-9011 trial, for example.
9. Involved-field radiation therapy.
10. Alemtuzumab
11. Bone marrow and peripheral stem cell transplantations are under clinical evaluation.
12. Ibrutinib In one embodiment the therapy is administered before, simultaneously with or after treatment with Rituximab or Ofatumumab. As these are monoclonal antibodies that target B-cells, treatment with the combination therapy may be synergistic. In another embodiment the therapy is administered after treatment with oral alkylating agents with or without corticosteroids, and Fludarabine, 2-chlorodeoxyadenosine, or pentostatin, as these treatments may negatively affect the immune system if administered before. In one embodiment bendamustine is administered with the therapy in low doses based on the results for prostate cancer described herein. In one embodiment the therapy is administered after treatment with bendamustine.

As used herein, the terms "chemotherapy" or "chemotherapeutic agent" refer to any chemical agent with therapeutic usefulness in the treatment of diseases characterized by abnormal cell growth. Such diseases include tumors, neoplasms and cancer as well as diseases characterized by hyperplastic growth. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most if not all of these agents are directly toxic to cancer cells and do not require immune stimulation. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2.sup.nd ed., 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993).

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

By "reduce" or "inhibit" in terms of the cancer treatment methods described herein is meant the ability to cause an overall decrease preferably of 20% or greater, 30% or greater, 40% or greater, 45% or greater, more preferably of 50% or greater, of 55% or greater, of 60% or greater, of 65% or greater, of 70% or greater, and most preferably of 75% or greater, 80% or greater, 85% or greater, 90% or greater, or 95% or greater, for a given parameter or symptom. Reduce or inhibit can refer to, for example, the symptoms of the disorder being treated, the presence or size of metastases or micrometastases, the size of the primary tumor, or the presence or the size of a dormant tumor.

In other embodiments of the methods of treating chronic immune conditions by decreasing T cell exhaustion described herein, the subject being administered the one or more agents has or has been diagnosed as having a persistent infection with a bacterium, virus, fungus, or parasite.

"Persistent infections" refer to those infections that, in contrast to acute infections, are not effectively cleared by the induction of a host immune response. During such persistent infections, the infectious agent and the immune response reach equilibrium such that the infected subject remains infectious over a long period of time without necessarily expressing symptoms. Persistent infections often involve stages of both silent and productive infection without rapidly killing or even producing excessive damage of the host cells. Persistent infections include for example, latent, chronic and slow infections. Persistent infection occurs with viruses including, but not limited to, human T-Cell leukemia viruses, Epstein-Barr virus, cytomegalovirus, herpes viruses, varicella-zoster virus, measles, papovaviruses, prions, hepatitis viruses, adenoviruses, parvoviruses and papillomaviruses.

In a "chronic infection," the infectious agent can be detected in the subject at all times. However, the signs and symptoms of the disease can be present or absent for an extended period of time. Non-limiting examples of chronic infection include hepatitis B (caused by hepatitis B virus (HBV)) and hepatitis C (caused by hepatitis C virus (HCV)) adenovirus, cytomegalovirus, Epstein-Barr virus, herpes simplex virus 1, herpes simplex virus 2, human herpesvirus 6, varicella-zoster virus, hepatitis D virus, papilloma virus, parvovirus B19, polyomavirus BK, polyomavirus JC, measles virus, rubella virus, human immunodeficiency virus (HIV), human T cell leukemia virus I, and human T cell leukemia virus II. Parasitic persistent infections can arise as a result of infection by, for example, *Leishmania, Toxoplasma, Trypanosoma, Plasmodium, Schistosoma*, and Encephalitozoon.

In a "latent infection," the infectious agent (such as a virus) is seemingly inactive and dormant such that the subject does not always exhibit signs or symptoms. In a latent viral infection, the virus remains in equilibrium with the host for long periods of time before symptoms again appear; however, the actual viruses cannot typically be detected until reactivation of the disease occurs. Non-limiting examples of latent infections include infections caused by herpes simplex virus (HSV)-1 (fever blisters), HSV-2 (genital herpes), and varicella zoster virus (VZV) (chickenpox-shingles).

In a "slow infection," the infectious agents gradually increase in number over a very long period of time during which no significant signs or symptoms are observed. Non-limiting examples of slow infections include AIDS (caused by HIV-1 and HIV-2), lentiviruses that cause tumors in animals, and prions.

In addition, persistent infections that can be treated using the methods described herein include those infections that often arise as late complications of acute infections. For example, subacute sclerosing panencephalitis (SSPE) can occur following an acute measles infection or regressive encephalitis can occur as a result of a rubella infection.

The mechanisms by which persistent infections are maintained can involve modulation of virus and cellular gene expression and modification of the host immune response. Reactivation of a latent infection can be triggered by various stimuli, including changes in cell physiology, superinfection by another virus, and physical stress or trauma. Host immunosuppression is often associated with reactivation of a number of persistent virus infections.

Additional examples of infectious viruses include: Retroviridae; Picornaviridae (for example, polio viruses, hepatitis A virus; enteroviruses, human coxsackie viruses, rhinoviruses, echoviruses); Caliciviridae (such as strains that cause gastroenteritis); Togaviridae (for example, equine encephalitis viruses, rubella viruses); Flaviviridae (for example, dengue viruses, encephalitis viruses, yellow fever viruses); Coronaviridae (for example, coronaviruses); Rhabdoviridae (for example, vesicular stomatitis viruses, rabies viruses); Filoviridae (for example, ebola viruses); Paramyxoviridae (for example, parainfluenza viruses, mumps virus, measles virus, respiratory syncytial virus); Orthomyxoviridae (for example, influenza viruses); Bunyaviridae (for example, Hantaan viruses, bunga viruses, phleboviruses and Nairo viruses); Arenaviridae (hemorrhagic fever viruses); Reoviridae (e.g., reoviruses, orbiviruses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and HSV-2, varicella zoster virus, cytomegalovirus (CMV), herpes viruses); Poxviridae (variola viruses, vaccinia viruses, pox viruses); and Iridoviridae (such as African swine fever virus); and unclassified viruses (for example, the etiological agents of Spongiform encephalopathies), the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses). The compositions, methods, and uses described herein are contemplated for use in treating infections with these viral agents.

Examples of fungal infections include but are not limited to: aspergillosis; thrush (caused by *Candida albicans*); cryptococcosis (caused by *Cryptococcus*); and histoplasmosis. Thus, examples of infectious fungi include, but are not limited to, *Cryptococcus neoformans, Histoplasma capsulatum, Coccidioides immitis, Blastomyces dermatitidis, Chlamydia trachomatis, Candida albicans*. The compositions, methods, and uses described herein are contemplated for use in treating infections with these fungal agents.

Examples of infectious bacteria include: *Helicobacterpylori, Borrelia burgdorferi, Legionella pneumophilia, Mycobacteria* sps (such as *M. tuberculosis, M avium, M. intracellulare, M. kansasii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Strep-*

*tococcus pneumoniae*, pathogenic *Campylobacter* sp., *Enterococcus* sp., *Haemophilus influenzae, Bacillus anthracis, Corynebacterium diphtheriae, corynebacterium* sp., Erysipelothrix rhusiopathiae, *Clostridium perfringens, Clostridium tetani, Enterobacter aerogenes, Klebsiella pneumoniae, Pasteurella multocida, Bacteroides* sp., *Fusobacterium nucleatum, Streptobacillus monilformis, Treponema pallidum, Treponema pertenue, Leptospira*, and *Actinomyces israelii*. The compositions, methods, and uses described herein are contemplated for use in treating infections with these bacterial agents. Other infectious organisms (such as protists) include: *Plasmodium falciparum* and *Toxoplasma gondii*. The compositions, methods, and uses described herein are contemplated for use in treating infections with these agents.

In some embodiments, the methods described herein comprise administering an effective amount of the one or more modulators (i.e., inhibitor or activator) described herein to a subject or immune cell, preferably a T cell, in order to alleviate a symptom of persistent infection. As used herein, "alleviating a symptom of a persistent infection" is ameliorating any condition or symptom associated with the persistent infection. Alternatively, alleviating a symptom of a persistent infection can involve reducing the infectious microbial (such as viral, bacterial, fungal or parasitic) load in the subject relative to such load in an untreated control. As compared with an equivalent untreated control, such reduction or degree of prevention is at least 5%, 10%, 20%, 40%, 50%, 60%, 80%, 90%, 95%, or more as measured by any standard technique. Desirably, the persistent infection is cleared, or pathogen replication has been suppressed, as detected by any standard method known in the art, in which case the persistent infection is considered to have been treated. A patient who is being treated for a persistent infection is one who a medical practitioner has diagnosed as having such a condition. Diagnosis can be by any suitable means. Diagnosis and monitoring can involve, for example, detecting the level of microbial load in a biological sample (for example, a tissue biopsy, blood test, or urine test), detecting the level of a surrogate marker of the microbial infection in a biological sample, detecting symptoms associated with persistent infections, or detecting immune cells involved in the immune response typical of persistent infections (for example, detection of antigen specific T cells that are anergic and/or functionally impaired).

Autoimmune Disease

As used herein, an "autoimmune disease" refers to a class of diseases in which a subject's own antibodies react with host tissue or in which immune effector T cells are autoreactive to endogenous self-peptides and cause destruction of tissue. Thus an immune response is mounted against a subject's own antigens, referred to as self-antigens. A "self-antigen" as used herein refers to an antigen of a normal host tissue. Normal host tissue does not include cancer cells.

Modulation of T cell dysfunction as described herein can promote tolerance or dampen an inappropriate, unwanted, or undesirable immune response, thereby permitting treatment of autoimmune disease and/or conditions associated with transplants (e.g., graft vs. host disease).

Accordingly, in some embodiments of these methods and all such methods described herein, the autoimmune diseases to be treated or prevented using the methods described herein, include, but are not limited to: rheumatoid arthritis, Crohn's disease or colitis, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjogren's syndrome, insulin resistance, and autoimmune diabetes mellitus (type 1 diabetes mellitus; insulin-dependent diabetes mellitus), gastritis, autoimmune hepatitis, hemolytic anemia, autoimmune hemophilia, autoimmune lymphoproliferative syndrome (ALPS), autoimmune uveoretinitis, glomerulonephritis, Guillain-Barre syndrome, and psoriasis. Autoimmune disease has been recognized also to encompass atherosclerosis and Alzheimer's disease.

In some embodiments of the methods of promoting T cell tolerance, the subject being administered the one or more agents as described herein has or has been diagnosed with host versus graft disease (HVGD). In a further such embodiment, the subject being treated with the methods described herein is an organ or tissue transplant recipient. In other embodiments of the methods of promoting T cell tolerance by increasing T cell exhaustion described herein, the methods are used for increasing transplantation tolerance in a subject. In some such embodiments, the subject is a recipient of an allogenic transplant. The transplant can be any organ or tissue transplant, including but not limited to heart, kidney, liver, skin, pancreas, bone marrow, skin or cartilage. "Transplantation tolerance," as used herein, refers to a lack of rejection of the donor organ by the recipient's immune system.

Dosage, Administration and Efficacy

The terms "subject" and "individual" as used in regard to any of the methods described herein are used interchangeably herein, and refer to an animal, for example a human, recipient of the bispecific or multispecific polypeptide agents described herein. For treatment of disease states which are specific for a specific animal such as a human subject, the term "subject" refers to that specific animal. The terms "non-human animals" and "non-human mammals" are used interchangeably herein, and include mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like. Production mammal, e.g. cow, sheep, pig, and the like are also encompassed in the term subject.

As used herein, in regard to any of the compositions, methods, and uses comprising one or more modulating agents (i.e., inhibitors or activators) or combinations thereof described herein, or adoptive cell transfer, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with a chronic immune condition, such as, but not limited to, a chronic infection or a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

The term "effective amount" as used herein refers to the amount of one or more modulating agents (i.e., inhibitor or activator), or combinations thereof described herein, needed to alleviate at least one or more symptom of the disease or disorder being treated, and relates to a sufficient amount of pharmacological composition to provide the desired effect, i.e., reverse the functional exhaustion of antigen-specific T cells in a subject having a chronic immune condition, such as cancer or hepatitis C. The term "therapeutically effective amount" therefore refers to an amount of the one or more modulating agents (i.e., one or more inhibitor(s) and/or activator(s)), or combinations thereof described herein, using the methods as disclosed herein, that is sufficient to provide a particular effect when administered to a typical subject. An effective amount as used herein would also include an amount sufficient to delay the development of a symptom of the disease, alter the course of a symptom of the disease (for example but not limited to, slow the progression of a symptom of the disease), or reverse a symptom of the disease. Thus, it is not possible to specify the exact "effective amount". However, for any given case, an appropriate "effective amount" can be determined by one of ordinary skill in the art using only routine experimentation. Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions, methods, and uses that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the one or more modulators (i.e., inhibitor and/or activator)), or combinations thereof described herein, which achieves a half-maximal inhibition of measured function or activity as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment. For example, increased production of one or more cytokines, such as IL-2 or TNFa or IFNg, decreased production of cytokines such as IL-10, increased expression of granzyme B or CD107a, increased ability to proliferate, or increased cytotoxicity are effector functions that can be used to determine whether a treatment is efficacious in a subject.

Modes of Administration

The one or more modulating agents (i.e., inhibitors and/or activators), or combinations thereof described herein, described herein can be administered to a subject in need thereof or a cell ex vivo by any appropriate route which results in an effective treatment in the subject or a modified cell. As used herein, the terms "administering," and "introducing" are used interchangeably and refer to the placement of one or more modulating agents (i.e., inhibitor and/or activator), or a combination thereof, into a subject or cell by a method or route which results in at least partial localization of such agents at a desired site, such as a site of inflammation, or such as the cell surface or internally in the cell, such that a desired effect(s) is produced.

In some embodiments, the one or more modulators (i.e., inhibitor and/or activator) or combination thereof is administered to a subject having a chronic immune condition by any mode of administration that delivers the agent systemically or to a desired surface or target, and can include, but is not limited to, injection, infusion, instillation, and inhalation administration. To the extent that polypeptide agents can be protected from inactivation in the gut, oral administration forms are also contemplated. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the one or more modulating agents (i.e., inhibitors and/or activators) for use in the methods described herein are administered by intravenous infusion or injection.

The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of the one or more modulating agents (i.e., inhibitor or activator), or combination thereof, other than directly into a target site, tissue, or organ, such as a tumor site, such that it enters the subject's circulatory system and, thus, is subject to metabolism and other like processes.

For the clinical use of the methods described herein, administration of the one or more modulating agents (i.e., inhibitors or activators), or combinations thereof described herein, can include formulation into pharmaceutical compositions or pharmaceutical formulations for parenteral administration, e.g., intravenous; mucosal, e.g., intranasal; ocular, or other mode of administration. In some embodiments, the one or more modulating agents (i.e., inhibitors and/or activators), or combinations thereof described herein, can be administered along with any pharmaceutically acceptable carrier compound, material, or composition which results in an effective treatment in the subject. Thus, a pharmaceutical formulation for use in the methods described herein can contain one or more modulating agents (i.e., inhibitor and/or activator), or combination thereof, as described herein in combination with one or more pharmaceutically acceptable ingredients.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, one or more modulating agents (i.e., inhibitor and/or activator), or combination thereof. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) excipients, such as cocoa butter and suppository waxes; (8) oils, such as peanut oil, cottonseed oil, safflower oil, sesame oil, olive oil, corn oil and soybean oil; (9) glycols, such as propylene glycol; (10) polyols, such as glycerin, sorbitol, mannitol and polyethylene glycol (PEG); (11) esters, such as ethyl oleate and ethyl laurate; (12) agar; (13) buffering agents, such as magnesium hydroxide and aluminum hydroxide; (14) alginic acid; (15) pyrogen-free water; (16) isotonic saline; (17) Ringer's solution; (19) pH buffered solutions; (20) polyesters, polycarbonates and/or polyanhydrides; (21) bulking agents, such as polypeptides and amino acids (22) serum components, such as serum albumin, HDL and LDL; (23) C2-C12 alcohols, such as ethanol; and (24) other non-toxic compatible substances employed in pharmaceutical formulations. Release agents, coating agents, preservatives, and antioxidants can also be present in the formulation. The terms such as "excipient", "carrier", "pharmaceutically acceptable carrier" or the like are used interchangeably herein.

The one or more modulating agents (i.e., inhibitors and/or activators) or combinations thereof described herein can be specially formulated for administration of the compound to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (79) nasally. Additionally, a bispecific or multispecific polypeptide agent can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

Further embodiments of the formulations and modes of administration of the compositions comprising the one or more modulating agents (i.e., inhibitors and/or activators), or combinations thereof described herein, that can be used in the methods described herein are described below.

Parenteral Dosage Forms. Parenteral dosage forms of the one or more modulating agents (i.e., inhibitors or activators), or combinations thereof, can also be administered to a subject with a chronic immune condition by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms of the disclosure are well known to those skilled in the art. Examples include, without limitation: sterile water; water for injection USP; saline solution; glucose solution; aqueous vehicles such as but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Aerosol formulations. The one or more modulating agents (i.e., inhibitor or activator) described herein or combinations thereof can be packaged in a pressurized aerosol container together with suitable propellants, for example, hydrocarbon propellants like propane, butane, or isobutane with conventional adjuvants. An IL-27 or NFIL-3 modulator (i.e., inhibitor or activator), or combinations thereof described herein, can also be administered in a non-pressurized form such as in a nebulizer or atomizer. The one or more modulating agents (i.e., inhibitor and/or activator), or combinations thereof described herein, can also be administered directly to the airways in the form of a dry powder, for example, by use of an inhaler.

Suitable powder compositions include, by way of illustration, powdered preparations of the one or more modulating agents (i.e., inhibitor and/or activator), or combinations thereof described herein, thoroughly intermixed with lactose, or other inert powders acceptable for intrabronchial administration. The powder compositions can be administered via an aerosol dispenser or encased in a breakable capsule which can be inserted by the subject into a device that punctures the capsule and blows the powder out in a steady stream suitable for inhalation. The compositions can include propellants, surfactants, and co-solvents and can be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic and diagnostic agents to the respiratory tract," in Critical Reviews in Therapeutic Drug Carrier Systems, 6:273-313 (1990); Anderson et al., Am. Rev. Respir. Dis., 140: 1317-1324 (1989) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989); Rudt, S. and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 (1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

The formulations of the one or more modulating agents (i.e., inhibitors and/or activators), or combinations thereof described herein, further encompass anhydrous pharmaceutical compositions and dosage forms comprising the disclosed compounds as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

Controlled and Delayed Release Dosage Forms. In some embodiments of the aspects described herein, the one or more modulating agents (i.e., inhibitor and/or activator), or combinations thereof described herein, can be administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a compound of formula (I)'s onset of action, duration of action, plasma levels within the therapeutic window, and peak blood levels. In particular, controlled- or extended-release dosage forms or formulations can be used to ensure that the maximum effectiveness of a compound of formula (I) is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with the one or more modulating agents (i.e., inhibitors or activators), or combinations thereof described herein. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, DUOLITE® A568 and DUOLITE® AP143 (Rohm & Haas, Spring House, Pa. USA).

In some embodiments of the methods described herein, the one or more modulating agents (i.e., inhibitors and/or activators), or combinations thereof described herein, for use in the methods described herein is administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are particularly preferred when the disorder occurs continuously in the subject, for example where the subject has continuous or chronic symptoms of a viral infection. Each pulse dose can be reduced and the total amount of the one or more modulating agents (i.e., inhibitor or activator), or combinations thereof described herein, administered over the course of treatment to the subject or patient is minimized.

The interval between pulses, when necessary, can be determined by one of ordinary skill in the art. Often, the interval between pulses can be calculated by administering another dose of the composition when the composition or the active component of the composition is no longer detectable in the subject prior to delivery of the next pulse. Intervals can also be calculated from the in vivo half-life of the composition. Intervals can be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

In one embodiment, RNA interfering agents used in the methods described herein are taken up actively by cells in vivo following intravenous injection, e.g., hydrodynamic injection, without the use of a vector, illustrating efficient in vivo delivery of the RNA interfering agents, e.g., the siRNAs used in the methods of the invention. Exemplary delivery methods for RNA interfering agents may also be used to deliver any of CRISPR/Cas system, Zinc finger, or TALE.

Other strategies for delivery of the RNA interfering agents, e.g., the siRNAs or shRNAs, used in the methods of the invention, can also be employed, such as, for example, delivery by a vector, e.g., a plasmid or viral vector, e.g., a lentiviral vector. Such vectors can be used as described, for example, in Xiao-Feng Qin et al. Proc. Natl. Acad. Sci. U.S.A., 100: 183-188. Other delivery methods include delivery of the RNA interfering agents, e.g., the siRNAs or shRNAs of the invention, using a basic peptide by conjugating or mixing the RNA interfering agent with a basic peptide, e.g., a fragment of a TAT peptide, mixing with cationic lipids or formulating into particles.

As noted, the dsRNA, such as siRNA or shRNA can be delivered using an inducible vector, such as a tetracycline inducible vector. Methods described, for example, in Wang et al. Proc. Natl. Acad. Sci. 100: 5103-5106, using pTet-On vectors (BD Biosciences Clontech, Palo Alto, CA) can be used. In some embodiments, a vector can be a plasmid vector, a viral vector, or any other suitable vehicle adapted for the insertion and foreign sequence and for the introduction into eukaryotic cells. The vector can be an expression vector capable of directing the transcription of the DNA sequence of the agonist or antagonist nucleic acid molecules into RNA. Viral expression vectors can be selected from a group comprising, for example, reteroviruses, lentiviruses, Epstein Barr virus-, bovine papilloma virus, adenovirus- and adeno-associated-based vectors or hybrid virus of any of the above. In one embodiment, the vector is episomal. The use of a suitable episomal vector provides a means of maintaining the antagonist nucleic acid molecule in the subject in high copy number extra chromosomal DNA thereby eliminating potential effects of chromosomal integration.

Methods of delivering RNAi agents, e.g., an siRNA, or vectors containing an RNAi agent, to the target cells (e.g., basal cells or cells of the lung and/or respiratory system or other desired target cells) are well known to persons of ordinary skill in the art. In some embodiments, a RNAi agent can be administered to a subject via aerosol means, for example using a nebulizer and the like. In alternative embodiments, administration of a RNAi agent, e.g. can include, for example (i) injection of a composition containing the RNA interfering agent, e.g., an siRNA, or (ii) directly contacting the cell, e.g., a cell of the respiratory system, with a composition comprising an RNAi agent, e.g., an siRNA. In another embodiment, RNAi agents, e.g., an siRNA can be injected directly into any blood vessel, such as vein, artery, venule or arteriole, via, e.g., hydrodynamic injection or catheterization. In some embodiments an RNAi inhibitor can delivered to specific organs, for example the liver, bone marrow or systemic administration. Administration can be by a single injection or by two or more injections.

In some embodiments, a RNAi agent is delivered in a pharmaceutically acceptable carrier. One or more RNAi agents can be used simultaneously, e.g. one or more gene silencing RNAi agent inhibitors of target gene(s) can be together. The RNA interfering agents, can be delivered singly, or in combination with other RNA interfering agents, e.g., siRNAs, such as, for example siRNAs directed to other cellular genes. A gene silencing-RNAi agent inhibitor of target gene(s) can also be administered in combination with other pharmaceutical agents which are used to treat or prevent diseases or disorders.

In one embodiment, specific cells are targeted with RNA interference, limiting potential side effects of RNA interference caused by non-specific targeting of RNA interference. The method can use, for example, a complex or a fusion molecule comprising a cell targeting moiety and an RNA interference binding moiety that is used to deliver RNAi effectively into cells. For example, an antibody -protamine fusion protein when mixed with an siRNA, binds siRNA and selectively delivers the siRNA into cells expressing an antigen recognized by the antibody, resulting in silencing of gene expression only in those cells that express the antigen which is identified by the antibody. In some embodiments, the antibody can be any antibody which identifies an antigen expressed on cells expressing the target gene or gene product. In some embodiments, the antibody is an antibody which binds to the target gene product antigen, but where the antibody can or does not inhibit the target gene product function. In some embodiments, the siRNA can be conjugated to an antagonist of the target gene product, for example where the antagonist is a polypeptide, and where the conjugation with the RNAi does not interrupt the function of the antagonist.

In some embodiments, a siRNA or RNAi binding moiety is a protein or a nucleic acid binding domain or fragment of a protein, and the binding moiety is fused to a portion of the targeting moiety. The location of the targeting moiety can be either in the carboxyl-terminal or amino-terminal end of the construct or in the middle of the fusion protein.

In some embodiments, a viral-mediated delivery mechanism can also be employed to deliver siRNAs to cells in vitro and in vivo as described in Xia, H. et al. (2002) Nat Biotechnol 20(10): 1006. Plasmid- or viral-mediated delivery mechanisms of shRNA can also be employed to deliver shRNAs to cells in vitro and in vivo as described in Rubinson, D. A., et al. ((2003) Nat. Genet. 33:401-406) and Stewart, S. A., et al. ((2003) RNA 9:493-501). Alternatively, in other embodiments, a RNAi agent, e.g., a gene silencing-RNAi agent inhibitor of a target gene can also be introduced into cells via the vascular or extravascular circulation, the blood or lymph system, and the cerebrospinal fluid.

In general, any method of delivering a nucleic acid molecule can be adapted for use with an RNAi interference molecule (see e.g., Akhtar S. and Julian R L. (1992) Trends Cell. Biol. 2(5): 139-144; WO94/02595, which are incorporated herein by reference in their entirety). However, there are three factors that are important to consider in order to successfully deliver an RNAi molecule in vivo: (1) biological stability of the RNAi molecule, (2) preventing non-specific effects, and (3) accumulation of the RNAi molecule in the target tissue. The non-specific effects of an RNAi molecule can be minimized by local administration by e.g., direct injection into a tissue including, for example, a tumor or topically administering the molecule.

Local administration of an RNAi molecule to a treatment site limits the exposure of the e.g., siRNA to systemic tissues and permits a lower dose of the RNAi molecule to be administered. Several studies have shown successful knockdown of gene products when an RNAi molecule is administered locally. For example, intraocular delivery of a VEGF siRNA by intravitreal injection in cynomolgus monkeys (Tolentino, M J., et al (2004) Retina 24: 132-138) and subretinal injections in mice (Reich, S J., et al (2003) Mol. Vis. 9:210-216) were both shown to prevent neovascularization in an experimental model of age-related macular degeneration. In addition, direct intratumoral injection of an siRNA in mice reduces tumor volume (Pille, J., et al (2005) Mol. Ther.1 1:267-274) and can prolong survival of tumor-bearing mice (Kim, W J., et al (2006) Mol. Ther. 14:343-350; Li, S., et al (2007) Mol. Ther. 15:515-523). RNA interference has also shown success with local delivery to the CNS by direct injection (Dorn, G., et al (2004) Nucleic Acids 32:e49; Tan, P H., et al (2005) Gene Ther. 12:59-66; Makimura, H., et al (2002) BMC Neurosci. 3: 18; Shishkina, G T., et al (2004) Neuroscience 129:521-528; Thakker, E R., et al (2004) Proc. Natl. Acad. Sci. U.S.A. 101: 17270-17275; Akaneya,Y., et al (2005) J. Neurophysiol. 93:594-602) and to the lungs by intranasal administration (Howard, K A., et al (2006) Mol. Ther. 14:476-484; Zhang, X., et al (2004) J. Biol. Chem. 279: 10677-10684; Bitko, V., et al (2005) Nat. Med. 1 1:50-55).

For administering an RNAi molecule systemically for the treatment of a disease, the RNAi molecule can be either be modified or alternatively delivered using a drug delivery system; both methods act to prevent the rapid degradation of the RNAi molecule by endo- and exo-nucleases in vivo. Modification of the RNAi molecule or the pharmaceutical carrier can also permit targeting of the RNAi molecule to the target tissue and avoid undesirable off-target effects.

RNA interference molecules can be modified by chemical conjugation to lipophilic groups such as cholesterol to enhance cellular uptake and prevent degradation. For example, an siRNA directed against ApoB conjugated to a lipophilic cholesterol moiety was injected systemically into mice and resulted in knockdown of apoB mRNA in both the liver and jejunum (Soutschek, J., et al (2004) Nature 432: 173-178). Conjugation of an RNAi molecule to an aptamer has been shown to inhibit tumor growth and mediate tumor regression in a mouse model of prostate cancer (McNamara, J O., et al (2006) Nat. Biotechnol. 24: 1005-1015).

In an alternative embodiment, the RNAi molecules can be delivered using drug delivery systems such as e.g., a nanoparticle, a dendrimer, a polymer, liposomes, or a cationic delivery system. Positively charged cationic delivery systems facilitate binding of an RNA interference molecule (negatively charged) and also enhance interactions at the negatively charged cell membrane to permit efficient uptake of an siRNA by the cell. Cationic lipids, dendrimers, or polymers can either be bound to an RNA interference molecule, or induced to form a vesicle or micelle (see e.g., Kim S H., et al (2008) Journal of Controlled Release 129(2): 107-1 16) that encases an RNAi molecule. The formation of vesicles or micelles further prevents degradation of the RNAi molecule when administered systemically. Methods for making and administering cationic-RNAi complexes are well within the abilities of one skilled in the art (see e.g., Sorensen, D R., et al (2003) J. Mol. Biol 327:761-766; Verma, U N., et al (2003) Clin. Cancer Res. 9: 1291-1300; Arnold, A S et al (2007) J. Hypertens. 25: 197-205, which are incorporated herein by reference in their entirety).

Some non-limiting examples of drug delivery systems useful for systemic administration of RNAi include DOTAP (Sorensen, D R., et al (2003), supra; Verma, U N., et al (2003), supra), Oligofectamine, "solid nucleic acid lipid particles" (Zimmermann, T S., et al (2006) Nature 441:111-114), cardiolipin (Chien, P Y., et al (2005) Cancer Gene Ther. 12:321-328; Pal, A., et al (2005) Int J. Oncol. 26: 1087-1091), polyethyleneimine (Bonnet M E., et al (2008) Pharm. Res. August 16 Epub ahead of print; Aigner, A. (2006) J. Biomed. Biotechnol. 71659), Arg-Gly-Asp (RGD) peptides (Liu, S. (2006) Mol. Pharm. 3:472-487), and polyamidoamines (Tomalia, D A., et al (2007) Biochem. Soc. Trans. 35:61-67; Yoo, H., et al (1999) Pharm. Res. 16: 1799-1804). In some embodiments, an RNAi molecule forms a complex with cyclodextrin for systemic administration. Methods for administration and pharmaceutical compositions of RNAi molecules and cyclodextrins can be found in U.S. Pat. No. 7,427,605, which is herein incorporated by reference in its entirety. Specific methods for administering an RNAi molecule for the inhibition of angiogenesis can be found in e.g., U.S. Patent Application No. 20080152654, which is herein incorporated by reference in its entirety.

In some embodiments, the siRNA, dsRNA, or shRNA vector can be administered systemically, such as intravenously, e. g. via central venous catheter (CVC or central venous line or central venous access catheter) placed into a large vein in the neck (internal jugular vein), chest (subclavian vein) or groin (femoral vein). Methods of systemic delivery of siRNA, dsRNA, or shRNA vector are well known in the art, e. g. as described herein and in Gao and Huang, 2008, (Mol. Pharmaceutics, Web publication December 30) and review by Rossi, 2006, Gene Therapy, 13:583-584. The siRNA, dsRNA, or shRNA vector can be formulated in various ways, e. g. conjugation of a cholesterol moiety to one of the strands of the siRNA duplex for systemic delivery to the liver and jejunum (Soutschek J. et. al. 2004, Nature, 432: 173-178), complexing of siRNAs to protamine fused with an antibody fragment for receptor-mediated targeting of siRNAs (Song E, et al. 2005, Nat Biotechnol., 23: 709-717) and the use of a lipid bilayer system by Morrissey et al. 2005 (Nat Biotechnol., 23: 1002-1007). The lipid bilayer system produces biopolymers that are in the 120 nanometer diameter size range, and are labeled as SNALPs, for Stable-Nucleic-Acid-Lipid-Particles. The lipid combination protects the siRNAs from serum nucleases and allows cellular endosomal uptake and subsequent cytoplasmic release of the siRNAs (see WO/2006/007712). These references are incorporated by reference in their entirety.

The dose of the particular RNAi agent will be in an amount necessary to effect RNA interference, e.g., gene silencing of the target gene, thereby leading to a subsequent decrease in the target protein level.

In another embodiment of the invention, agents which are inhibitors of the target gene or protein are catalytic nucleic acid constructs, such as, for example ribozymes, which are capable of cleaving RNA transcripts and thereby preventing the production of wildtype protein. Ribozymes are targeted to and anneal with a particular sequence by virtue of two regions of sequence complementary to the target flanking the ribozyme catalytic site. After binding, the ribozyme cleaves the target in a site specific manner. The design and testing of ribozymes which specifically recognize and cleave sequences of the gene products described herein can be achieved by techniques well known to those skilled in the art (for example Lleber and Strauss, (1995) Mol Cell Biol 15:540.551, the disclosure of which is incorporated herein by reference).

The term "vectors" refers to a nucleic acid molecule capable of transporting another nucleic acid to which it has been linked; a plasmid is a species of the genus encompassed by "vector". The term "vector" typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA loops which, in their vector form are not bound to the chromosome, and typically comprise entities for stable or transient expression or the encoded DNA. Other expression vectors can be used in the methods as disclosed herein for example, but are not limited to, plasmids, episomes, bacterial artificial chromosomes, yeast artificial chromosomes, bacteriophages or viral vectors, and such vectors can integrate into the host's genome or replicate autonomously in the particular cell. A vector can be a DNA or RNA vector. Other forms of expression vectors known by those skilled in the art which serve the equivalent functions can also be used, for example self replicating extrachromosomal vectors or vectors which integrates into a host genome. Preferred vectors are those capable of autonomous replication and/or expression of nucleic acids to which they are linked. Vectors capable of directing the expression of genes to which they are operatively linked are referred to herein as "expression vectors".

The term "viral vectors" refers to the use as viruses, or virus-associated vectors as carriers of the nucleic acid construct into the cell. Constructs may be integrated and packaged into non-replicating, defective viral genomes like Adenovirus, Adeno-associated virus (AAV), or Herpes simplex virus (HSV) or others, including reteroviral and lentiviral vectors, for infection or transduction into cells. The vector may or may not be incorporated into the cells genome. The constructs may include viral sequences for transfection, if desired. Alternatively, the construct may be incorporated into vectors capable of episomal replication, e.g. EPV and EBV vectors.

As used herein, a "promoter" or "promoter region" or "promoter element" used interchangeably herein, refers to a segment of a nucleic acid sequence, typically but not limited to DNA or RNA or analogues thereof, that controls the transcription of the nucleic acid sequence to which it is operatively linked. The promoter region includes specific sequences that are sufficient for RNA polymerase recognition, binding and transcription initiation. This portion of the promoter region is referred to as the promoter. In addition, the promoter region includes sequences which modulate this recognition, binding and transcription initiation activity of RNA polymerase. These sequences may be cis-acting or may be responsive to trans-acting factors. Promoters, depending upon the nature of the regulation may be constitutive or regulated.

The term "regulatory sequences" is used interchangeably with "regulatory elements" herein refers element to a segment of nucleic acid, typically but not limited to DNA or RNA or analogues thereof, that modulates the transcription of the nucleic acid sequence to which it is operatively linked, and thus act as transcriptional modulators. Regulatory sequences modulate the expression of gene and/or nucleic acid sequence to which they are operatively linked. Regulatory sequence often comprise "regulatory elements" which are nucleic acid sequences that are transcription binding domains and are recognized by the nucleic acid-binding domains of transcriptional proteins and/or transcription factors, repressors or enhancers etc. Typical regulatory sequences include, but are not limited to, transcriptional promoters, inducible promoters and transcriptional elements, an optional operate sequence to control transcription, a sequence encoding suitable mRNA ribosomal binding sites, and sequences to control the termination of transcription and/or translation. Regulatory sequences can be a single regulatory sequence or multiple regulatory sequences, or modified regulatory sequences or fragments thereof. Modified regulatory sequences are regulatory sequences where the nucleic acid sequence has been changed or modified by some means, for example, but not limited to, mutation, methylation etc.

The term "operatively linked" as used herein refers to the functional relationship of the nucleic acid sequences with regulatory sequences of nucleotides, such as promoters, enhancers, transcriptional and translational stop sites, and other signal sequences. For example, operative linkage of nucleic acid sequences, typically DNA, to a regulatory sequence or promoter region refers to the physical and functional relationship between the DNA and the regulatory sequence or promoter such that the transcription of such DNA is initiated from the regulatory sequence or promoter, by an RNA polymerase that specifically recognizes, binds and transcribes the DNA. In order to optimize expression and/or in vitro transcription, it may be necessary to modify the regulatory sequence for the expression of the nucleic acid or DNA in the cell type for which it is expressed. The desirability of, or need of, such modification may be empirically determined. Enhancers need not be located in close proximity to the coding sequences whose transcription they enhance. Furthermore, a gene transcribed from a promoter regulated in trans by a factor transcribed by a second promoter may be said to be operatively linked to the second promoter. In such a case, transcription of the first gene is said to be operatively linked to the first promoter and is also said to be operatively linked to the second promoter.

Hence, in certain embodiments the invention involves vectors, e.g. for delivering or introducing in a cell the DNA targeting agent according to the invention as described herein, such as by means of example Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s) (e.g., sgRNAs); and, when a single vector provides for more than 16 RNA(s) (e.g., sgRNAs), one or more promoter(s) can drive expression of more than one of the RNA(s) (e.g., sgRNAs), e.g., when there are 32 RNA(s) (e.g., sgRNAs), each promoter can drive expression of two RNA(s) (e.g., sgRNAs), and when there are 48 RNA(s) (e.g., sgRNAs), each promoter can drive expression of three RNA(s) (e.g., sgRNAs). By simple arithmetic and well established cloning protocols and the teachings in this disclosure one skilled in the art can readily practice the invention as to the RNA(s) (e.g., sgRNA(s)), for a suitable exemplary vector such as AAV, and a suitable promoter such as the U6 promoter, e.g., U6-sgRNAs. For example, the packaging limit of AAV is ~4.7 kb. The length of a single U6-sgRNA (plus restriction sites for cloning) is 361 bp. Therefore, the skilled person can readily fit about 12-16, e.g., 13 U6-sgRNA cassettes in a single vector. This can be assembled by any suitable means, such as a golden gate strategy used for TALE assembly (http://www.genome-engineering.org/taleffectors/). The skilled person can also use a tandem guide strategy to increase the number of U6-sgRNAs by approximately 1.5 times, e.g., to increase from 12-16, e.g., 13 to approximately 18-24, e.g., about 19 U6-sgRNAs. Therefore, one skilled in the art can readily reach approximately 18-24, e.g., about 19 promoter-RNAs, e.g., U6-sgRNAs in a single vector, e.g., an AAV vector. A further means for increasing the number of promoters and RNAs, e.g., sgRNA(s) in a vector is to use a single promoter (e.g., U6) to express an array of RNAs, e.g., sgRNAs separated by cleavable sequences. And an even further means for increasing the number of promoter-RNAs, e.g., sgRNAs in a vector, is to express an array of promoter-RNAs, e.g., sgRNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals. org/content/34/7/e53.short,www.nature.com/mt/journal/v16/n9/abs/mt200 8144a.html). In an advantageous embodiment, AAV may package U6 tandem sgRNA targeting up to about 50 genes. Accordingly, from the knowledge in the art and the teachings in this disclosure the skilled person can readily make and use vector(s), e.g., a single vector, expressing multiple RNAs or guides or sgRNAs under the control or operatively or functionally linked to one or more promoters-especially as to the numbers of RNAs or guides or sgRNAs discussed herein, without any undue experimentation.

A poly nucleic acid sequence encoding the DNA targeting agent according to the invention as described herein, such as by means of example guide RNA(s), e.g., sgRNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the 3-actin promoter, the phosphoglycerol kinase (PGK) promoter, and the EF1α promoter. An advantageous promoter is the promoter is U6.

Through this disclosure and the knowledge in the art, the DNA targeting agent as described herein, such as, TALEs, CRISPR-Cas systems, etc., or components thereof or nucleic acid molecules thereof (including, for instance HDR template) or nucleic acid molecules encoding or providing components thereof may be delivered by a delivery system herein described both generally and in detail.

Vector delivery, e.g., plasmid, viral delivery: By means of example, the CRISPR enzyme, for instance a Cas9, and/or any of the present RNAs, for instance a guide RNA, can be delivered using any suitable vector, e.g., plasmid or viral vectors, such as adeno associated virus (AAV), lentivirus, adenovirus or other viral vector types, or combinations thereof. The DNA targeting agent as described herein, such as Cas9 and one or more guide RNAs can be packaged into one or more vectors, e.g., plasmid or viral vectors. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In an embodiment herein the delivery is via an adenovirus, which may be at a single booster dose containing at least $1\times10^5$ particles (also referred to as particle units, pu) of adenoviral vector. In an embodiment herein, the dose preferably is at least about $1\times10^6$ particles (for example, about $1\times10^6$-$1\times10^{12}$ particles), more preferably at least about $1\times10^7$ particles, more preferably at least about $1\times10^8$ particles (e.g., about $1\times10^8$-$1\times10^{11}$ particles or about $1\times10^8$-$1\times10^{12}$ particles), and most preferably at least about $1\times10^0$ particles (e.g., about $1\times10^9$-$1\times10^{10}$ particles or about $1\times10^9$-$1\times10^{12}$ particles), or even at least about $1\times10^{10}$ particles (e.g., about $1\times10^{10}$-$1\times10^{12}$ particles) of the adenoviral vector. Alternatively, the dose comprises no more than about $1\times10^{14}$ particles, preferably no more than about $1\times10^{13}$ particles, even more preferably no more than about $1\times10^{12}$ particles, even more preferably no more than about $1\times10^{11}$ particles, and most preferably no more than about $1\times10^{10}$ particles (e.g., no more than about $1\times10^9$ articles). Thus, the dose may contain a single dose of adenoviral vector with, for example, about $1\times10^6$ particle units (pu), about $2\times10^6$ pu, about $4\times10^6$ pu, about $1\times10^7$ pu, about $2\times10^7$ pu, about $4\times10^7$ pu, about $1\times10^8$ pu, about $2\times10^8$ pu, about $4\times10^8$ pu, about $1\times10^9$ pu, about $2\times10^9$ pu, about $4\times10^9$ pu, about $1\times10^{10}$ pu, about $2\times10^{10}$ pu, about $4\times10^{10}$ pu, about $1\times10^{11}$ pu, about $2\times10^{11}$ pu, about $4\times10^{11}$ pu, about $1\times10^{12}$ pu, about $2\times10^{12}$ pu, or about $4\times10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1\times10^{10}$ to about $1\times10^{10}$ functional AAV/ml solution. The dosage may be adjusted to balance the therapeutic benefit against any side effects. In an embodiment herein, the AAV dose is generally in the range of concentrations of from about $1\times10^5$ to $1\times10^{50}$ genomes AAV, from about $1\times10^8$ to $1\times10^{20}$ genomes AAV, from about $1\times10^{10}$ to about $1\times10^{16}$ genomes, or about $1\times10^{11}$ to about $1\times10^{16}$ genomes AAV. A human dosage may be about $1\times10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 g to about 10 g per 70 kg individual. Plasmids of the invention will generally comprise (i) a promoter; (ii) a sequence encoding a DNA targeting agent as described herein, such as a comprising a CRISPR enzyme, operably linked to said promoter; (iii) a selectable marker; (iv) an origin of replication; and (v) a transcription terminator downstream of and operably linked to (ii). The plasmid can also encode the RNA components of a CRISPR complex, but one or more of these may instead be encoded on a different vector.

The doses herein are based on an average 70 kg individual. The frequency of administration is within the ambit of the medical or veterinary practitioner (e.g., physician, veterinarian), or scientist skilled in the art. It is also noted that mice used in experiments are typically about 20 g and from mice experiments one can scale up to a 70 kg individual.

In some embodiments the RNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference. Delivery systems aimed specifically at the enhanced and improved delivery of siRNA into mammalian cells have been developed, (see, for example, Shen et al FEBS Let. 2003, 539: 111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen. 2002, 32: 107-108 and Simeoni et al., NAR 2003, 31, 11: 2717-2724) and may be applied to the present invention. siRNA has recently been successfully used for inhibition of gene expression in primates (see for example. Tolentino et al., Retina 24(4):660 which may also be applied to the present invention).

Indeed, RNA delivery is a useful method of in vivo delivery. It is possible to deliver the DNA targeting agent as described herein, such as Cas9 and gRNA (and, for instance, HR repair template) into cells using liposomes or particles. Thus delivery of the CRISPR enzyme, such as a Cas9 and/or delivery of the RNAs of the invention may be in RNA form and via microvesicles, liposomes or particles. For example, Cas9 mRNA and gRNA can be packaged into liposomal particles for delivery in vivo. Liposomal transfection reagents such as lipofectamine from Life Technologies and other reagents on the market can effectively deliver RNA molecules into the liver.

Means of delivery of RNA also preferred include delivery of RNA via nanoparticles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). Indeed, exosomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December;7(12):2112-26. doi: 10.1038/nprot.2012.131. Epub 2012 Nov. 15.) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purify and characterized from transfected cell supernatant, then RNA is loaded into the exosomes. Delivery or administration according to the invention can be performed with exosomes, in particular but not limited to the brain. Vitamin E ($\alpha$-tocopherol) may be conjugated with CRISPR Cas and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain. Mice were infused via Osmotic minipumps (model 1007D; Alzet, Cupertino, CA) filled with phosphate-buffered saline (PBS) or free Tocsi-BACE or Toc-siBACE/HDL and connected with Brain Infusion Kit 3 (Alzet). A brain-infusion cannula was placed about 0.5 mm posterior to the bregma at midline for infusion into the dorsal third ventricle. Uno et al. found that as little as 3 nmol of Toc-siRNA with HDL could induce a target reduction in comparable degree by the same ICV infusion method. A similar dosage of CRISPR Cas conjugated to α-tocopherol and co-administered with HDL targeted to the brain may be contemplated for humans in the present invention, for example, about 3 nmol to about 3 μmol of CRISPR Cas targeted to the brain may be contemplated. Zou et al. (HUMAN GENE THERAPY 22:465-475 (April 2011)) describes a method of lentiviral-mediated delivery of short-hairpin RNAs targeting PKCγ for in vivo gene silencing in the spinal cord of rats. Zou et al. administered about 10 μl of a recombinant lentivirus having a titer of $1\times10^9$ transducing units (TU)/ml by an intrathecal catheter. A similar dosage of CRISPR Cas expressed in a lentiviral vector targeted to the brain may be contemplated for humans in the present invention, for example, about 10-50 ml of CRISPR Cas targeted to the brain in a lentivirus having a titer of $1\times10^9$ transducing units (TU)/ml may be contemplated.

In terms of local delivery to the brain, this can be achieved in various ways. For instance, material can be delivered intrastriatally e.g. by injection. Injection can be performed stereotactically via a craniotomy.

Enhancing NHEJ or HR efficiency is also helpful for delivery. It is preferred that NHEJ efficiency is enhanced by co-expressing end-processing enzymes such as Trex2 (Dumitrache et al. Genetics. 2011 August; 188(4): 787-797). It is preferred that HR efficiency is increased by transiently inhibiting NHEJ machineries such as Ku70 and Ku86. HR efficiency can also be increased by co-expressing prokaryotic or eukaryotic homologous recombination enzymes such as RecBCD, RecA.

Packaging and Promoters Generally

Ways to package nucleic acid molecules, in particular the DNA targeting agent according to the invention as described herein, such as Cas9 coding nucleic acid molecules, e.g., DNA, into vectors, e.g., viral vectors, to mediate genome modification in vivo include:

To achieve NHEJ-mediated gene knockout:

- Single virus vector:
  - Vector containing two or more expression cassettes:
  - Promoter-Cas9 coding nucleic acid molecule-terminator
  - Promoter-gRNA1-terminator
  - Promoter-gRNA2-terminator
  - Promoter-gRNA(N)-terminator (up to size limit of vector)
- Double virus vector:
  - Vector 1 containing one expression cassette for driving the expression of Cas9
  - Promoter-Cas9 coding nucleic acid molecule-terminator
  - Vector 2 containing one more expression cassettes for driving the expression of one or more guide RNAs
  - Promoter-gRNA1-terminator
  - Promoter-gRNA(N)-terminator (up to size limit of vector)

To mediate homology-directed repair.

In addition to the single and double virus vector approaches described above, an additional vector is used to deliver a homology-direct repair template.

The promoter used to drive Cas9 coding nucleic acid molecule expression can include:

AAV ITR can serve as a promoter: this is advantageous for eliminating the need for an additional promoter element (which can take up space in the vector). The additional space freed up can be used to drive the expression of additional elements (gRNA, etc.). Also, ITR activity is relatively weaker, so can be used to reduce potential toxicity due to over expression of Cas9.

For ubiquitous expression, can use promoters: CMV, CAG, CBh, PGK, SV40, Ferritin heavy or light chains, etc.

For brain or other CNS expression, can use promoters: Synapsin I for all neurons, CaMKIIalpha for excitatory neurons, GAD67 or GAD65 or VGAT for GABAergic neurons, etc.

For liver expression, can use Albumin promoter.

For lung expression, can use SP-B.

For endothelial cells, can use ICAM.

For hematopoietic cells can use IFNbeta or CD45.

For Osteoblasts can use OG-2.

The promoter used to drive guide RNA can include:

Pol III promoters such as U6 or H1

Use of Pol II promoter and intronic cassettes to express gRNA

Adeno Associated Virus (AAV)

The DNA targeting agent according to the invention as described herein, such as by means of example Cas9 and one or more guide RNA can be delivered using adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual (e.g. a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into the tissue of interest. For cell-type specific genome modification, the expression of the DNA targeting agent according to the invention as described herein, such as by means of example Cas9 can be driven by a cell-type specific promoter. For example, liver-specific expression might use the Albumin promoter and neuron-specific expression (e.g. for targeting CNS disorders) might use the Synapsin I promoter.

In terms of in vivo delivery, AAV is advantageous over other viral vectors for a couple of reasons:

Low toxicity (this may be due to the purification method not requiring ultracentrifugation of cell particles that can activate the immune response)

Low probability of causing insertional mutagenesis because it doesn't integrate into the host genome.

AAV has a packaging limit of 4.5 or 4.75 Kb. This means that for instance Cas9 as well as a promoter and transcription terminator have to be all fit into the same viral vector. Constructs larger than 4.5 or 4.75 Kb will lead to significantly reduced virus production. SpCas9 is quite large, the gene itself is over 4.1 Kb, which makes it difficult for packing into AAV. Therefore embodiments of the invention include utilizing homologs of Cas9 that are shorter. For example:

| Species | Cas9 Size |
|---|---|
| *Corynebacter diphtheriae* | 3252 |
| *Eubacterium ventriosum* | 3321 |
| *Streptococcus pasteurianus* | 3390 |
| *Lactobacillus farciminis* | 3378 |
| *Sphaerochaeta globus* | 3537 |
| *Azospirillum* B510 | 3504 |
| *Gluconacetobacter diazotrophicus* | 3150 |
| *Neisseria cinerea* | 3246 |
| *Roseburia intestinalis* | 3420 |
| *Parvibaculum lavamentivorans* | 3111 |
| *Staphylococcus aureus* | 3159 |
| *Nitratifractor salsuginis* DSM 16511 | 3396 |
| *Campylobacter lari* CF89-12 | 3009 |
| *Streptococcus thermophilus* LMD-9 | 3396 |

These species are therefore, in general, preferred Cas9 species.

As to AAV, the AAV can be AAV1, AAV2, AAV5 or any combination thereof. One can select the AAV of the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The herein promoters and vectors are preferred individually. A tabulation of certain AAV serotypes as to these cells (see Grimm, D. et al, J. Virol. 82: 5887-5911 (2008)) is as follows:

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

Lentivirus

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows, by means of example for Cas delivery. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 μg of lentiviral transfer plasmid (pCasES10) and the following packaging plasmids: 5 μg of pMD2.G (VSV-g pseudotype), and 7.5 ug of psPAX2 (gag/pol/rev/tat). Transfection was done in 4 mL OptiMEM with a cationic lipid delivery agent (50 uL Lipofectamine 2000 and 100ul Plus reagent). After 6 hours, the media was changed to antibiotic-free DMEM with 10% fetal bovine serum. These methods use serum during cell culture, but serum-free methods are preferred.

Lentivirus may be purified as follows. Viral supernatants were harvested after 48 hours. Supernatants were first cleared of debris and filtered through a 0.45 um low protein binding (PVDF) filter. They were then spun in a ultracentrifuge for 2 hours at 24,000 rpm. Viral pellets were resuspended in 50 ul of DMEM overnight at 4° C. They were then aliquoted and immediately frozen at −80° C.

In another embodiment, minimal non-primate lentiviral vectors based on the equine infectious anemia virus (EIAV) are also contemplated, especially for ocular gene therapy (see, e.g., Balagan, J Gene Med 2006; 8: 275-285). In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) and this vector may be modified for the CRISPR-Cas system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used and/or adapted to the CRISPR-Cas system of the present invention. A minimum of $2.5\times10^6$ CD34+ cells per kilogram patient weight may be collected and prestimulated for 16 to 20 hours in X-VIVO 15 medium (Lonza) containing 2 μmol/L-glutamine, stem cell factor (100 ng/ml), Flt-3 ligand (Flt-3L) (100 ng/ml), and thrombopoietin (10 ng/ml) (CellGenix) at a density of $2\times10^6$ cells/ml. Prestimulated cells may be transduced with lentiviral at a multiplicity of infection of 5 for 16 to 24 hours in 75-$cm^2$ tissue culture flasks coated with fibronectin (25 mg/$cm^2$) (RetroNectin, Takara Bio Inc.).

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and U.S. Pat. No. 7,259,015.

RNA Delivery

RNA delivery: The DNA targeting agent according to the invention as described herein, such as the CRISPR enzyme, for instance a Cas9, and/or any of the present RNAs, for instance a guide RNA, can also be delivered in the form of RNA. Cas9 mRNA can be generated using in vitro transcription. For example, Cas9 mRNA can be synthesized using a PCR cassette containing the following elements: T7_promoter-kozak sequence (GCCACC)-Cas9-3' UTR from beta globin-polyA tail (a string of 120 or more adenines). The cassette can be used for transcription by T7 polymerase. Guide RNAs can also be transcribed using in vitro transcription from a cassette containing T7_promoter-GG-guide RNA sequence.

To enhance expression and reduce possible toxicity, the CRISPR enzyme-coding sequence and/or the guide RNA can be modified to include one or more modified nucleoside e.g. using pseudo-U or 5-Methyl-C.

mRNA delivery methods are especially promising for liver delivery currently.

Much clinical work on RNA delivery has focused on RNAi or antisense, but these systems can be adapted for delivery of RNA for implementing the present invention. References below to RNAi etc. should be read accordingly.

Particle Delivery Systems and/or Formulations:

Several types of particle delivery systems and/or formulations are known to be useful in a diverse spectrum of biomedical applications. In general, a particle is defined as a small object that behaves as a whole unit with respect to its transport and properties. Particles are further classified according to diameter Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation which includes a particle in accordance with the present invention. A particle in accordance with the present invention is any entity having a greatest dimension (e.g. diameter) of less than 100 microns (μm). In some embodiments, inventive particles have a greatest dimension of less than 10 μm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo (herein cargo refers to e.g., one or more components of for instance CRISPR-Cas system e.g., CRISPR enzyme or mRNA or guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Mention is made of U.S. Pat. Nos. 8,709,843; 6,007,845; 5,855,913; 5,985,309; 5,543,158; and the publication by James E. Dahlman and Carmen Barnes et al. Nature Nanotechnology (2014) published online 11 May 2014, doi:10.1038/nnano.2014.84, concerning particles, methods of making and using them and measurements thereof.

Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

Particles

The DNA targeting agent according to the invention as described herein, such as by means of example CRISPR enzyme mRNA and guide RNA may be delivered simultaneously using particles or lipid envelopes; for instance, CRISPR enzyme and RNA of the invention, e.g., as a complex, can be delivered via a particle as in Dahlman et al., WO2015089419 A2 and documents cited therein, such as 7C1 (see, e.g., James E. Dahlman and Carmen Barnes et al. Nature Nanotechnology (2014) published online 11 May 2014, doi:10.1038/nnano.2014.84), e.g., delivery particle comprising lipid or lipidoid and hydrophilic polymer, e.g., cationic lipid and hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5), wherein particles are formed using an efficient, multistep process wherein first, effector protein and RNA are mixed together, e.g., at a 1:1 molar ratio, e.g., at room temperature, e.g., for 30 minutes, e.g., in sterile, nuclease free 1× PBS; and separately, DOTAP, DMPC, PEG, and cholesterol as applicable for the formulation are dissolved in alcohol, e.g., 100% ethanol; and, the two solutions are mixed together to form particles containing the complexes.

For example, Su X, Fricke J, Kavanagh D G, Irvine D J ("In vitro and in vivo mRNA delivery using lipid-enveloped pH-responsive polymer nanoparticles" Mol Pharm. 2011 Jun. 6; 8(3):774-87. doi: 10.1021/mp100390w. Epub 2011 April 1) describes biodegradable core-shell structured particles with a poly(O-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

In one embodiment, particles based on self assembling bioadhesive polymers are contemplated, which may be applied to oral delivery of peptides, intravenous delivery of peptides and nasal delivery of peptides, all to the brain. Other embodiments, such as oral absorption and ocular delivery of hydrophobic drugs are also contemplated. The molecular envelope technology involves an engineered polymer envelope which is protected and delivered to the site of the disease (see, e.g., Mazza, M. et al. ACS Nano, 2013. 7(2): 1016-1026; Siew, A., et al. Mol Pharm, 2012. 9(1):14-28; Lalatsa, A., et al. J Contr Rel, 2012. 161(2):523-36; Lalatsa, A., et al., Mol Pharm, 2012. 9(6):1665-80; Lalatsa, A., et al. Mol Pharm, 2012. 9(6):1764-74; Garrett, N. L., et al. J Biophotonics, 2012. 5(5-6):458-68; Garrett, N. L., et al. J Raman Spect, 2012. 43(5):681-688; Ahmad, S., et al. J Royal Soc Interface 2010. 7:S423-33; Uchegbu, I.F. Expert Opin Drug Deliv, 2006. 3(5):629-40; Qu, X., et al. Biomacromolecules, 2006. 7(12):3452-9 and Uchegbu, I. F., et al. Int J Pharm, 2001. 224:185-199). Doses of about 5 mg/kg are contemplated, with single or multiple doses, depending on the target tissue.

In one embodiment, particles that can deliver DNA targeting agents according to the invention as described herein, such as RNA to a cancer cell to stop tumor growth developed by Dan Anderson's lab at MIT may be used and/or adapted to the CRISPR Cas system according to certain embodiments of the present invention. In particular, the Anderson lab developed fully automated, combinatorial systems for the synthesis, purification, characterization, and formulation of new biomaterials and nanoformulations. See, e.g., Alabi et al., Proc Natl Acad Sci USA. 2013 Aug. 6; 110(32):12881-6; Zhang et al., Adv Mater. 2013 Sep. 6; 25(33):4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93.

US patent application 20110293703 relates to lipidoid compounds are also particularly useful in the administration of polynucleotides, which may be applied to deliver the DNA targeting agent according to the invention, such as for instance the CRISPR Cas system according to certain embodiments of the present invention. In one aspect, the aminoalcohol lipidoid compounds are combined with an agent to be delivered to a cell or a subject to form microparticles, particles, liposomes, or micelles. The agent to be delivered by the particles, liposomes, or micelles may be in the form of a gas, liquid, or solid, and the agent may be a polynucleotide, protein, peptide, or small molecule. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Publication No. 20110293703 also provides methods of preparing the aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30-100° C., preferably at approximately 50-90° C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

US Patent Publication No. 20110293703 also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

US Patent Publication No. 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering. The teachings of US Patent Publication No. 20130302401 may be applied to the DNA targeting agent according to the invention, such as for instance the CRISPR Cas system according to certain embodiments of the present invention.

In another embodiment, lipid particles (LNPs) are contemplated. An antitransthyretin small interfering RNA has been encapsulated in lipid particles and delivered to humans (see, e.g., Coelho et al., N Engl J Med 2013; 369:819-29), and such a ssystem may be adapted and applied to the CRISPR Cas system of the present invention. Doses of about 0.01 to about 1 mg per kg of body weight administered intravenously are contemplated. Medications to reduce the risk of infusion-related reactions are contemplated, such as dexamethasone, acetaminophen, diphenhydramine or cetirizine, and ranitidine are contemplated. Multiple doses of about 0.3 mg per kilogram every 4 weeks for five doses are also contemplated.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding CRISPR Cas to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, December 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilinoleyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, December 2011). A dosage of 1 g/ml of LNP or by means of example CRISPR-Cas RNA in or associated with the LNP may be contemplated, especially for a formulation containing DLinKC2-DMA.

Preparation of LNPs and the DNA targeting agent according to the invention as described herein, such as by means of example CRISPR Cas encapsulation may be used and/or adapted from Rosin et al, Molecular Therapy, vol. 19, no. 12, pages 1286-2200, (December 2011). The cationic lipids 1,2-dilinoleyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG)), and R-3-[(o-methoxy-poly(ethylene glycol)2000) carbamoyl]-1,2-dimyristyloxlpropyl-3-amine (PEG-C-DOMG) may be provided by Tekmira Pharmaceuticals (Vancouver, Canada) or synthesized. Cholesterol may be purchased from Sigma (St Louis, MO). The specific CRISPR Cas RNA may be encapsulated in LNPs containing DLinDAP, DLinDMA, DLinK-DMA, and DLinKC2-DMA (cationic lipid:DSPC: CHOL: PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid:DSPC:cholesterol:PEG-c-DOMG (40:10:40:10 molar ratio) in ethanol to a final lipid concentration of 10 mmol/l. This ethanol solution of lipid may be added drop-wise to 50 mmol/l citrate, pH 4.0 to form multilamellar vesicles to produce a final concentration of 30% ethanol vol/vol. Large unilamellar vesicles may be formed following extrusion of multilamellar vesicles through two stacked 80 nm. Nuclepore polycarbonate filters using the Extruder (Northern Lipids, Vancouver, Canada). Encapsulation may be achieved by adding RNA dissolved at 2 mg/ml in 50 mmol/l citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Particle size distribution may be determined by dynamic light scattering using a NICOMP 370 particle sizer, the vesicle/intensity modes, and Gaussian fitting (Nicomp Particle Sizing, Santa Barbara, CA). The particle size for all three LNP systems may be −70 nm in diameter. RNA encapsulation efficiency may be determined by removal of free RNA using VivaPureD MiniH columns (Sartorius Stedim Biotech) from samples collected before and after dialysis. The encapsulated RNA may be extracted from the eluted particles and quantified at 260 nm. RNA to lipid ratio was determined by measurement of cholesterol content in vesicles using the Cholesterol E enzymatic assay from Wako Chemicals USA (Richmond, VA). In conjunction with the herein discussion of LNPs and PEG lipids, PEGylated liposomes or LNPs are likewise suitable for delivery of a CRISPR-Cas system or components thereof.

Preparation of large LNPs may be used and/or adapted from Rosin et al, Molecular Therapy, vol. 19, no. 12, pages 1286-2200, December 2011. A lipid premix solution (20.4 mg/ml total lipid concentration) may be prepared in ethanol containing DLinKC2-DMA, DSPC, and cholesterol at 50:10:38.5 molar ratios. Sodium acetate may be added to the lipid premix at a molar ratio of 0.75:1 (sodium acetate: DLinKC2-DMA). The lipids may be subsequently hydrated by combining the mixture with 1.85 volumes of citrate buffer (10 mmol/l, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano Z S, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at an RNA to total lipid ratio of approximately 1:10 (wt:wt), followed by incubation for 30 minutes at 37° C. to form loaded LNPs. The mixture may be subsequently dialyzed overnight in PBS and filtered with a 0.45-μm syringe filter.

Spherical Nucleic Acid (SNA™) constructs and other particles (particularly gold particles) are also contemplated as a means to deliver the DNA targeting agent according to the invention as described herein, such as by means of example CRISPR-Cas system to intended targets. Significant data show that AuraSense Therapeutics' Spherical Nucleic Acid (SNA™) constructs, based upon nucleic acid-functionalized gold particles, are useful.

Literature that may be employed in conjunction with herein teachings include: Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19):7625-7630, Jensen et al., Sci. Transl. Med. 5, 209ra152 (2013) and Mirkin, et al., Small, 10:186-192.

Self-assembling particles with RNA may be constructed with polyethyleneimine (PEI) that is PEGylated with an Arg-Gly-Asp (RGD) peptide ligand attached at the distal end of the polyethylene glycol (PEG). This system has been used, for example, as a means to target tumor neovasculature expressing integrins and deliver siRNA inhibiting vascular endothelial growth factor receptor-2 (VEGF R2) expression and thereby achieve tumor angiogenesis (see, e.g., Schiffelers et al., Nucleic Acids Research, 2004, Vol. 32, No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. A dosage of about 100 to 200 mg of CRISPR Cas is envisioned for delivery in the self-assembling particles of Schiffelers et al.

The nanoplexes of Bartlett et al. (PNAS, Sep. 25, 2007, vol. 104, no. 39) may also be applied to the present invention. The nanoplexes of Bartlett et al. are prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. The DOTA-siRNA of Bartlett et al. was synthesized as follows: 1,4,7,10-tetraazacyclododecane-1,4,7,10-tetraacetic acid mono(N-hydroxysuccinimide ester) (DOTA-NHSester) was ordered from Macrocyclics (Dallas, TX). The amine modified RNA sense strand with a 100-fold molar excess of DOTA-NHS-ester in carbonate buffer (pH 9) was added to a microcentrifuge tube. The contents were reacted by stirring for 4 h at room temperature. The DOTA-RNAsense conjugate was ethanol-precipitated, resuspended in water, and annealed to the unmodified antisense strand to yield DOTA-siRNA. All liquids were pretreated with Chelex-100 (Bio-Rad, Hercules, CA) to remove trace metal contaminants. Tf-targeted and nontargeted siRNA particles may be formed by using cyclodextrin-containing polycations. Typically, particles were formed in water at a charge ratio of 3 (+/−) and an siRNA concentration of 0.5 g/liter. One percent of the adamantane-PEG molecules on the surface of the targeted particles were modified with Tf (adamantane-PEG-Tf). The particles were suspended in a 5% (wt/vol) glucose carrier solution for injection.

Davis et al. (Nature, Vol 464, 15 Apr. 2010) conducts a RNA clinical trial that uses a targeted particle-delivery system (clinical trial registration number NCT00689065). Patients with solid cancers refractory to standard-of-care therapies are administered doses of targeted particles on days 1, 3, 8 and 10 of a 21-day cycle by a 30-min intravenous infusion. The particles consist of a synthetic delivery system containing: (1) a linear, cyclodextrin-based polymer (CDP), (2) a human transferrin protein (TF) targeting ligand displayed on the exterior of the particle to engage TF receptors (TFR) on the surface of the cancer cells, (3) a hydrophilic polymer (polyethylene glycol (PEG) used to promote particle stability in biological fluids), and (4) siRNA designed to reduce the expression of the RRM2 (sequence used in the clinic was previously denoted siR2B+5). The TFR has long been known to be upregulated in malignant cells, and RRM2 is an established anti-cancer target. These particles (clinical version denoted as CALAA-01) have been shown to be well tolerated in multi-dosing studies in non-human primates. Although a single patient with chronic myeloid leukaemia has been administered siRNAby liposomal delivery, Davis et al.'s clinical trial is the initial human trial to systemically deliver siRNA with a targeted delivery system and to treat patients with solid cancer. To ascertain whether the targeted delivery system can provide effective delivery of functional siRNA to human tumours, Davis et al. investigated biopsies from three patients from three different dosing cohorts; patients A, B and C, all of whom had metastatic melanoma and received CALAA-01 doses of 18, 24 and 30 mg $m^{-2}$ siRNA, respectively. Similar doses may also be contemplated for the CRISPR Cas system of the present invention. The delivery of the invention may be achieved with particles containing a linear, cyclodextrin-based polymer (CDP), a human transferrin protein (TF) targeting ligand displayed on the exterior of the particle to engage TF receptors (TFR) on the surface of the cancer cells and/or a hydrophilic polymer (for example, polyethylene glycol (PEG) used to promote particle stability in biological fluids).

In terms of this invention, it is preferred to have one or more components of the DNA targeting agent according to the invention as described herein, such as by means of example the CRISPR complex, e.g., CRISPR enzyme or mRNA or guide RNA delivered using particles or lipid envelopes. Other delivery systems or vectors are may be used in conjunction with the particle aspects of the invention.

In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, particles of the invention have a greatest dimension ranging between 35 nm and 60 nm. In other preferred embodiments, the particles of the invention are not nanoparticles.

Particles encompassed in the present invention may be provided in different forms, e.g., as solid particles (e.g., metal such as silver, gold, iron, titanium), non-metal, lipid-based solids, polymers, suspensions of particles, or combinations thereof. Metal, dielectric, and semiconductor particles may be prepared, as well as hybrid structures (e.g., core-shell particles). Particles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

Semi-solid and soft particles have been manufactured, and are within the scope of the present invention. A prototype particle of semi-solid nature is the liposome. Various types of liposome particles are currently used clinically as delivery systems for anticancer drugs and vaccines. Particles with one half hydrophilic and the other half hydrophobic are termed Janus particles and are particularly effective for stabilizing emulsions. They can self-assemble at water/oil interfaces and act as solid surfactants.

U.S. Pat. No. 8,709,843, incorporated herein by reference, provides a drug delivery system for targeted delivery of therapeutic agent-containing particles to tissues, cells, and intracellular compartments. The invention provides targeted particles comprising polymer conjugated to a surfactant, hydrophilic polymer or lipid. U.S. Pat. No. 6,007,845, incorporated herein by reference, provides particles which have a core of a multiblock copolymer formed by covalently linking a multifunctional compound with one or more hydrophobic polymers and one or more hydrophilic polymers, and contain a biologically active material. U.S. Pat. No. 5,855,913, incorporated herein by reference, provides a particulate composition having aerodynamically light particles having a tap density of less than 0.4 g/cm3 with a mean diameter of between 5 μm and 30 μm, incorporating a surfactant on the surface thereof for drug delivery to the pulmonary system. U.S. Pat. No. 5,985,309, incorporated herein by reference, provides particles incorporating a surfactant and/or a hydrophilic or hydrophobic complex of a positively or negatively charged therapeutic or diagnostic agent and a charged molecule of opposite charge for delivery to the pulmonary system. U.S. Pat. No. 5,543,158, incorporated herein by reference, provides biodegradable injectable particles having a biodegradable solid core containing a biologically active material and poly(alkylene glycol) moieties on the surface. WO2012135025 (also published as US20120251560), incorporated herein by reference, describes conjugated polyethyleneimine (PEI) polymers and conjugated aza-macrocycles (collectively referred to as "conjugated lipomer" or "lipomers"). In certain embodiments, it can envisioned that such conjugated lipomers can be used in the context of the CRISPR-Cas system to achieve in vitro, ex vivo and in vivo genomic perturbations to modify gene expression, including modulation of protein expression.

In one embodiment, the particle may be epoxide-modified lipid-polymer, advantageously 7C1 (see, e.g., James E. Dahlman and Carmen Barnes et al. Nature Nanotechnology (2014) published online 11 May 2014, doi:10.1038/nnano.2014.84). C71 was synthesized by reacting C15 epoxide-terminated lipids with PEI600 at a 14:1 molar ratio, and was formulated with C14PEG2000 to produce particles (diameter between 35 and 60 nm) that were stable in PBS solution for at least 40 days.

An epoxide-modified lipid-polymer may be utilized to deliver the CRISPR-Cas system of the present invention to pulmonary, cardiovascular or renal cells, however, one of skill in the art may adapt the system to deliver to other target organs. Dosage ranging from about 0.05 to about 0.6 mg/kg are envisioned. Dosages over several days or weeks are also envisioned, with a total dosage of about 2 mg/kg.

Exosomes

Exosomes are endogenous nano-vesicles that transport RNAs and proteins, and which can deliver RNA to the brain and other target organs. To reduce immunogenicity, Alvarez-Erviti et al. (2011, Nat Biotechnol 29: 341) used self-derived dendritic cells for exosome production. Targeting to the brain was achieved by engineering the dendritic cells to express Lamp2b, an exosomal membrane protein, fused to the neuron-specific RVG peptide. Purified exosomes were loaded with exogenous RNA by electroporation. Intravenously injected RVG-targeted exosomes delivered GAPDH siRNA specifically to neurons, microglia, oligodendrocytes in the brain, resulting in a specific gene knockdown. Pre-exposure to RVG exosomes did not attenuate knockdown, and non-specific uptake in other tissues was not observed. The therapeutic potential of exosome-mediated siRNA delivery was demonstrated by the strong mRNA (60%) and protein (62%) knockdown of BACE1, a therapeutic target in Alzheimer's disease.

To obtain a pool of immunologically inert exosomes, Alvarez-Erviti et al. harvested bone marrow from inbred C57BL/6 mice with a homogenous major histocompatibility complex (MHC) haplotype. As immature dendritic cells produce large quantities of exosomes devoid of T-cell activators such as MHC-II and CD86, Alvarez-Erviti et al. selected for dendritic cells with granulocyte/macrophage-colony stimulating factor (GM-CSF) for 7 d. Exosomes were purified from the culture supernatant the following day using well-established ultracentrifugation protocols. The exosomes produced were physically homogenous, with a size distribution peaking at 80 nm in diameter as determined by particle tracking analysis (NTA) and electron microscopy. Alvarez-Erviti et al. obtained 6-12 μg of exosomes (measured based on protein concentration) per $10^6$ cells.

Next, Alvarez-Erviti et al. investigated the possibility of loading modified exosomes with exogenous cargoes using electroporation protocols adapted for nanoscale applications. As electroporation for membrane particles at the nanometer scale is not well-characterized, nonspecific Cy5-labeled RNA was used for the empirical optimization of the electroporation protocol. The amount of encapsulated RNA was assayed after ultracentrifugation and lysis of exosomes.

Electroporation at 400 V and 125 μF resulted in the greatest retention of RNA and was used for all subsequent experiments.

Alvarez-Erviti et al. administered 150 μg of each BACE1 siRNA encapsulated in 150 μg of RVG exosomes to normal C57BL/6 mice and compared the knockdown efficiency to four controls: untreated mice, mice injected with RVG exosomes only, mice injected with BACE1 siRNA complexed to an in vivo cationic liposome reagent and mice injected with BACE1 siRNA complexed to RVG-9R, the RVG peptide conjugated to 9 D-arginines that electrostatically binds to the siRNA. Cortical tissue samples were analyzed 3 d after administration and a significant protein knockdown (45%, P<0.05, versus 62%, P<0.01) in both siRNA-RVG-9R-treated and siRNARVG exosome-treated mice was observed, resulting from a significant decrease in BACE1 mRNA levels (66% [+ or −]15%, P<0.001 and 61% [+ or −]13% respectively, P<0.01). Moreover, Applicants demonstrated a significant decrease (55%, P<0.05) in the total [beta]-amyloid 1-42 levels, a main component of the amyloid plaques in Alzheimer's pathology, in the RVG-exosome-treated animals. The decrease observed was greater than the β-amyloid 1-40 decrease demonstrated in normal mice after intraventricular injection of BACE1 inhibitors. Alvarez-Erviti et al. carried out 5'-rapid amplification of cDNA ends (RACE) on BACE1 cleavage product, which provided evidence of RNAi-mediated knockdown by the siRNA.

Finally, Alvarez-Erviti et al. investigated whether RNA-RVG exosomes induced immune responses in vivo by assessing IL-6, IP-10, TNFα and IFN-α serum concentrations. Following exosome treatment, nonsignificant changes in all cytokines were registered similar to siRNA-transfection reagent treatment in contrast to siRNA-RVG-9R, which potently stimulated IL-6 secretion, confirming the immunologically inert profile of the exosome treatment. Given that exosomes encapsulate only 20% of siRNA, delivery with RVG-exosome appears to be more efficient than RVG-9R delivery as comparable mRNA knockdown and greater protein knockdown was achieved with fivefold less siRNA without the corresponding level of immune stimulation. This experiment demonstrated the therapeutic potential of RVG-exosome technology, which is potentially suited for long-term silencing of genes related to neurodegenerative diseases. The exosome delivery system of Alvarez-Erviti et al. may be applied to deliver the DNA targeting agent according to the invention as described herein, such as by means of example the CRISPR-Cas system of the present invention to therapeutic targets, especially neurodegenerative diseases. A dosage of about 100 to 1000 mg of CRISPR Cas encapsulated in about 100 to 1000 mg of RVG exosomes may be contemplated for the present invention.

El-Andaloussi et al. (Nature Protocols 7,2112-2126 (2012)) discloses how exosomes derived from cultured cells can be harnessed for delivery of RNA in vitro and in vivo. This protocol first describes the generation of targeted exosomes through transfection of an expression vector, comprising an exosomal protein fused with a peptide ligand. Next, El-Andaloussi et al. explain how to purify and characterize exosomes from transfected cell supernatant. Next, El-Andaloussi et al. detail crucial steps for loading RNA into exosomes. Finally, El-Andaloussi et al. outline how to use exosomes to efficiently deliver RNA in vitro and in vivo in mouse brain. Examples of anticipated results in which exosome-mediated RNA delivery is evaluated by functional assays and imaging are also provided. The entire protocol takes ~3 weeks. Delivery or administration according to the invention may be performed using exosomes produced from self-derived dendritic cells. From the herein teachings, this can be employed in the practice of the invention.

In another embodiment, the plasma exosomes of Wahlgren et al. (Nucleic Acids Research, 2012, Vol. 40, No. 17 e130) are contemplated. Exosomes are nano-sized vesicles (30-90 nm in size) produced by many cell types, including dendritic cells (DC), B cells, T cells, mast cells, epithelial cells and tumor cells. These vesicles are formed by inward budding of late endosomes and are then released to the extracellular environment upon fusion with the plasma membrane. Because exosomes naturally carry RNA between cells, this property may be useful in gene therapy, and from this disclosure can be employed in the practice of the instant invention.

Exosomes from plasma can be prepared by centrifugation of buffy coat at 900 g for 20 min to isolate the plasma followed by harvesting cell supernatants, centrifuging at 300 g for 10 min to eliminate cells and at 16 500 g for 30 min followed by filtration through a 0.22 mm filter. Exosomes are pelleted by ultracentrifugation at 120000 g for70 min. Chemical transfection of siRNA into exosomes is carried out according to the manufacturer's instructions in RNAi Human/Mouse Starter Kit (Qiagen, Hilden, Germany). siRNA is added to 100 ml PBS at a final concentration of 2 mmol/ml. After adding HiPerFect transfection reagent, the mixture is incubated for 10 min at RT. In order to remove the excess of micelles, the exosomes are re-isolated using aldehyde/sulfate latex beads. The chemical transfection of CRISPR Cas into exosomes may be conducted similarly to siRNA. The exosomes may be co-cultured with monocytes and lymphocytes isolated from the peripheral blood of healthy donors. Therefore, it may be contemplated that exosomes containing the DNA targeting agent according to the invention as described herein, such as by means of example CRISPR Cas may be introduced to monocytes and lymphocytes of and autologously reintroduced into a human. Accordingly, delivery or administration according to the invention may beperformed using plasma exosomes.

Liposomes

Delivery or administration according to the invention can be performed with liposomes. Liposomes are spherical vesicle structures composed of a uni- or multilamellar lipid bilayer surrounding internal aqueous compartments and a relatively impermeable outer lipophilic phospholipid bilayer. Liposomes have gained considerable attention as drug delivery carriers because they are biocompatible, nontoxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review).

Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. Further, liposomes are prepared from hydrogenated egg phosphatidylcholine or egg phosphatidylcholine, cholesterol, and dicetyl phosphate, and their mean vesicle sizes were adjusted to about 50 and 100 nm. (see, e.g., Spuch and Navarro, Journal of Drug Delivery, vol. 2011, Article ID 469679, 12 pages, 2011. doi:10.1155/2011/469679 for review).

A liposome formulation may be mainly comprised of natural phospholipids and lipids such as 1,2-distearoyl-sn-glycero-3-phosphatidyl choline (DSPC), sphingomyelin, egg phosphatidylcholines and monosialoganglioside. Since this formulation is made up of phospholipids only, liposomal formulations have encountered many challenges, one of the ones being the instability in plasma. Several attempts to overcome these challenges have been made, specifically in the manipulation of the lipid membrane. One of these attempts focused on the manipulation of cholesterol. Addition of cholesterol to conventional formulations reduces rapid release of the encapsulated bioactive compound into the plasma or 1,2-dioleoyl-sn-glycero-3-phosphoethanolamine (DOPE) increases the stability (see, e.g., Spuch and Navarro, Journal of Drug Delivery, vol. 2011, Article ID 469679, 12 pages, 2011. doi:10.1155/2011/469679 for review).

In a particularly advantageous embodiment, Trojan Horse liposomes (also known as Molecular Trojan Horses) are desirable and protocols may be found at cshprotocols.cshlp.org/content/2010/4/pdb.prot5407.long. These particles allow delivery of a transgene to the entire brain after an intravascular injection. Without being bound by limitation, it is believed that neutral lipid particles with specific antibodies conjugated to surface allow crossing of the blood brain barrier via endocytosis. Applicant postulates utilizing Trojan Horse Liposomes to deliver the DNA targeting agent according to the invention as described herein, such as by means of example the CRISPR family of nucleases to the brain via an intravascular injection, which would allow whole brain transgenic animals without the need for embryonic manipulation. About 1-5 g of DNA or RNA may be contemplated for in vivo administration in liposomes.

In another embodiment, the DNA targeting agent according to the invention as described herein, such as by means of example the CRISPR Cas system may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of a specific CRISPR Cas targeted in a SNALP are contemplated. The daily treatment may be over about three days and then weekly for about five weeks. In another embodiment, a specific CRISPR Cas encapsulated (SNALP) administered by intravenous injection to at doses of about 1 or 2.5 mg/kg are also contemplated (see, e.g., Zimmerman et al., Nature Letters, Vol. 441, 4 May 2006). The SNALP formulation may contain the lipids 3-N-[(methoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio (see, e.g., Zimmerman et al., Nature Letters, Vol. 441, 4 May 2006).

In another embodiment, stable nucleic-acid-lipid particles (SNALPs) have proven to be effective delivery molecules to highly vascularized HepG2-derived liver tumors but not in poorly vascularized HCT-116 derived liver tumors (see, e.g., Li, Gene Therapy (2012) 19, 775-780). The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulted SNALP liposomes are about 80-100 nm in size.

In yet another embodiment, a SNALP may comprise synthetic cholesterol (Sigma-Aldrich, St Louis, MO, USA), dipalmitoylphosphatidylcholine (Avanti Polar Lipids, Alabaster, AL, USA), 3-N-[(w-methoxy poly(ethylene glycol) 2000)carbamoyl]-1,2-dimyristoyloxypropylamine, and cationic 1,2-dilinoleyloxy-3-N,N-dimethylaminopropane (see, e.g., Geisbert et al., Lancet 2010; 375: 1896-905). A dosage of about 2 mg/kg total CRISPR Cas per dose administered as, for example, a bolus intravenous infusion may be contemplated.

In yet another embodiment, a SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N,N-dimethyl)aminopropane (DLinDMA) (see, e.g., Judge, J. Clin. Invest. 119:661-673 (2009)). Formulations used for in vivo studies may comprise a final lipid/RNA mass ratio of about 9:1.

The safety profile of RNAi nanomedicines has been reviewed by Barros and Gollob of Alnylam Pharmaceuticals (see, e.g., Advanced Drug Delivery Reviews 64 (2012) 1730-1737). The stable nucleic acid lipid particle (SNALP) is comprised of four different lipids an ionizable lipid (DLinDMA) that is cationic at low pH, a neutral helper lipid, cholesterol, and a diffusible polyethylene glycol (PEG)-lipid. The particle is approximately 80 nm in diameter and is charge-neutral at physiologic pH. During formulation, the ionizable lipid serves to condense lipid with the anionic RNA during particle formation. When positively charged under increasingly acidic endosomal conditions, the ionizable lipid also mediates the fusion of SNALP with the endosomal membrane enabling release of RNA into the cytoplasm. The PEG-lipid stabilizes the particle and reduces aggregation during formulation, and subsequently provides a neutral hydrophilic exterior that improves pharmacokinetic properties.

To date, two clinical programs have been initiated using SNALP formulations with RNA. Tekmira Pharmaceuticals recently completed a phase I single-dose study of SNALP-ApoB in adult volunteers with elevated LDL cholesterol. ApoB is predominantly expressed in the liver and jejunum and is essential for the assembly and secretion of VLDL and LDL. Seventeen subjects received a single dose of SNALP-ApoB (dose escalation across 7 dose levels). There was no evidence of liver toxicity (anticipated as the potential dose-limiting toxicity based on preclinical studies). One (of two) subjects at the highest dose experienced flu-like symptoms consistent with immune system stimulation, and the decision was made to conclude the trial.

Alnylam Pharmaceuticals has similarly advanced ALN-TTR01, which employs the SNALP technology described above and targets hepatocyte production of both mutant and wild-type TTR to treat TTR amyloidosis (ATTR). Three ATTR syndromes have been described: familial amyloidotic polyneuropathy (FAP) and familial amyloidotic cardiomyopathy (FAC) both caused by autosomal dominant mutations in TTR; and senile systemic amyloidosis (SSA) cause by wildtype TTR. A placebo-controlled, single dose-escalation phase I trial of ALN-TTR01 was recently completed in patients with ATTR. ALN-TTR01 was administered as a 15-minute IV infusion to 31 patients (23 with study drug and 8 with placebo) within a dose range of 0.01 to 1.0 mg/kg (based on siRNA). Treatment was well tolerated with no significant increases in liver function tests. Infusion-related reactions were noted in 3 of 23 patients at >0.4 mg/kg; all responded to slowing of the infusion rate and all continued on study. Minimal and transient elevations of serum cytokines IL-6, IP-10 and IL-ira were noted in two patients at the highest dose of 1 mg/kg (as anticipated from preclinical and NHP studies). Lowering of serum TTR, the expected pharmacodynamics effect of ALN-TTR01, was observed at 1 mg/kg.

In yet another embodiment, a SNALP may be made by solubilizing a cationic lipid, DSPC, cholesterol and PEG-lipid e.g., in ethanol, e.g., at a molar ratio of 40:10:40:10, respectively (see, Semple et al., Nature Biotechnology, Volume 28 Number 2 Feb. 2010, pp. 172-177). The lipid mixture was added to an aqueous buffer (50 mM citrate, pH 4) with mixing to a final ethanol and lipid concentration of 30% (vol/vol) and 6.1 mg/ml, respectively, and allowed to equilibrate at 22° C. for 2 min before extrusion. The hydrated lipids were extruded through two stacked 80 nm pore-sized filters (Nuclepore) at 22° C. using a Lipex Extruder (Northern Lipids) until a vesicle diameter of 70-90 nm, as determined by dynamic light scattering analysis, was obtained. This generally required 1-3 passes. The siRNA (solubilized in a 50 mM citrate, pH 4 aqueous solution containing 30% ethanol) was added to the pre-equilibrated (35° C.) vesicles at a rate of −5 ml/min with mixing. After a final target siRNA/lipid ratio of 0.06 (wt/wt) was reached, the mixture was incubated for a further 30 min at 35° C. to allow vesicle reorganization and encapsulation of the siRNA. The ethanol was then removed and the external buffer replaced with PBS (155 mM NaCl, 3 mM $Na_2HPO_4$, 1 mM $KH_2PO_4$, pH 7.5) by either dialysis or tangential flow diafiltration. siRNA were encapsulated in SNALP using a controlled step-wise dilution method process. The lipid constituents of KC2-SNALP were DLin-KC2-DMA (cationic lipid), dipalmitoylphosphatidylcholine (DPPC; Avanti Polar Lipids), synthetic cholesterol (Sigma) and PEG-C-DMA used at a molar ratio of 57.1:7.1:34.3:1.4. Upon formation of the loaded particles, SNALP were dialyzed against PBS and filter sterilized through a 0.2 μm filter before use. Mean particle sizes were 75-85 nm and 90-95% of the siRNA was encapsulated within the lipid particles. The final siRNA/lipid ratio in formulations used for in vivo testing was −0.15 (wt/wt). LNP-siRNA systems containing Factor VII siRNA were diluted to the appropriate concentrations in sterile PBS immediately before use and the formulations were administered intravenously through the lateral tail vein in a total volume of 10 ml/kg. This method and these delivery systems may be extrapolated to the CRISPR Cas system of the present invention.

Other Lipids

Other cationic lipids, such as amino lipid 2,2-dilinoleyl-4-dimethylaminoethyl-[1,3]-dioxolane (DLin-KC2-DMA) may be utilized to encapsulate the DNA targeting agent according to the invention as described herein, such as by means of example CRISPR Cas or components thereof or nucleic acid molecule(s) coding therefor e.g., similar to SiRNA (see, e.g., Jayaraman, Angew. Chem. Int. Ed. 2012, 51, 8529-8533), and hence may be employed in the practice of the invention. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11+0.04 (n=56), the particles may be extruded up to three times through 80 nm membranes prior to adding the CRISPR Cas RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Michael S D Kormann et al. ("Expression of therapeutic proteins after delivery of chemically modified mRNA in mice: Nature Biotechnology, Volume:29, Pages: 154-157 (2011)) describes the use of lipid envelopes to deliver RNA. Use of lipid envelopes is also preferred in the present invention.

In another embodiment, lipids may be formulated with the CRISPR Cas system of the present invention to form lipid particles (LNPs). Lipids include, but are not limited to, DLin-KC2-DMA4, C12-200 and colipids distearoylphosphatidylcholine, cholesterol, and PEG-DMG may be formulated with CRISPR Cas instead of siRNA (see, e.g., Novobrantseva, Molecular Therapy-Nucleic Acids (2012) 1, e4; doi:10.1038/mtna.2011.3) using a spontaneous vesicle formation procedure. The component molar ratio may be about 50/10/38.5/1.5 (DLin-KC2-DMA or C12-200/distearoylphosphatidyl choline/cholesterol/PEG-DMG). The final lipid:siRNA weight ratio may be ~12:1 and 9:1 in the case of DLin-KC2-DMA and C12-200 lipid particles (LNPs), respectively. The formulations may have mean particle diameters of −80 nm with >90% entrapment efficiency. A 3 mg/kg dose may be contemplated.

Tekmira has a portfolio of approximately 95 patent families, in the U.S. and abroad, that are directed to various aspects of LNPs and LNP formulations (see, e.g., U.S. Pat. Nos. 7,982,027; 7,799,565; 8,058,069; 8,283,333; 7,901,708; 7,745,651; 7,803,397; 8,101,741; 8,188,263; 7,915,399; 8,236,943 and 7,838,658 and European Pat. Nos 1766035; 1519714; 1781593 and 1664316), all of which may be used and/or adapted to the present invention.

The DNA targeting agent according to the invention as described herein, such as by means of example CRISPR Cas system or components thereof or nucleic acid molecule(s) coding therefor may be delivered encapsulated in PLGA Microspheres such as that further described in US published applications 20130252281 and 20130245107 and 20130244279 (assigned to Moderna Therapeutics) which relate to aspects of formulation of compositions comprising modified nucleic acid molecules which may encode a protein, a protein precursor, or a partially or fully processed form of the protein or a protein precursor. The formulation may have a molar ratio 50:10:38.5:1.5-3.0 (cationic lipid: fusogenic lipid:cholesterol:PEG lipid). The PEG lipid may be selected from, but is not limited to PEG-c-DOMG, PEG-DMG. The fusogenic lipid may be DSPC. See also, Schrum et al., Delivery and Formulation of Engineered Nucleic Acids, US published application 20120251618.

Nanomerics' technology addresses bioavailability challenges for a broad range of therapeutics, including low molecular weight hydrophobic drugs, peptides, and nucleic acid based therapeutics (plasmid, siRNA, miRNA). Specific administration routes for which the technology has demonstrated clear advantages include the oral route, transport across the blood-brain-barrier, delivery to solid tumours, as well as to the eye. See, e.g., Mazza et al., 2013, ACS Nano. 2013 Feb. 26; 7(2):1016-26; Uchegbu and Siew, 2013, J Pharm Sci. 102(2):305-10 and Lalatsa et al., 2012, J Control Release. 2012 Jul. 20; 161(2):523-36.

US Patent Publication No. 20050019923 describes cationic dendrimers for delivering bioactive molecules, such as polynucleotide molecules, peptides and polypeptides and/or pharmaceutical agents, to a mammalian body. The dendrimers are suitable for targeting the delivery of the bioactive molecules to, for example, the liver, spleen, lung, kidney or heart (or even the brain). Dendrimers are synthetic 3-dimensional macromolecules that are prepared in a step-wise fashion from simple branched monomer units, the nature and functionality of which can be easily controlled and varied. Dendrimers are synthesised from the repeated addition of building blocks to a multifunctional core (divergent approach to synthesis), or towards a multifunctional core (convergent approach to synthesis) and each addition of a 3-dimensional shell of building blocks leads to the formation of a higher generation of the dendrimers. Polypropylenimine dendrimers start from a diaminobutane core to which is added twice the number of amino groups by a double Michael addition of acrylonitrile to the primary amines followed by the hydrogenation of the nitriles. This results in a doubling of the amino groups. Polypropylenimine dendrimers contain 100% protonable nitrogens and up to 64 terminal amino groups (generation 5, DAB 64). Protonable groups are usually amine groups which are able to accept protons at neutral pH. The use of dendrimers as gene delivery agents has largely focused on the use of the polyamidoamine. and phosphorous containing compounds with a mixture of amine/amide or N—P($O_2$)S as the conjugating units respectively with no work being reported on the use of the lower generation polypropylenimine dendrimers for gene delivery. Polypropylenimine dendrimers have also been studied as pH sensitive controlled release systems for drug delivery and for their encapsulation of guest molecules when chemically modified by peripheral amino acid groups. The cytotoxicity and interaction of polypropylenimine dendrimers with DNA as well as the transfection efficacy of DAB 64 has also been studied.

US Patent Publication No. 20050019923 is based upon the observation that, contrary to earlier reports, cationic dendrimers, such as polypropylenimine dendrimers, display suitable properties, such as specific targeting and low toxicity, for use in the targeted delivery of bioactive molecules, such as genetic material. In addition, derivatives of the cationic dendrimer also display suitable properties for the targeted delivery of bioactive molecules. See also, Bioactive Polymers, US published application 20080267903, which discloses "Various polymers, including cationic polyamine polymers and dendrimeric polymers, are shown to possess anti-proliferative activity, and may therefore be useful for treatment of disorders characterised by undesirable cellular proliferation such as neoplasms and tumours, inflammatory disorders (including autoimmune disorders), psoriasis and atherosclerosis. The polymers may be used alone as active agents, or as delivery vehicles for other therapeutic agents, such as drug molecules or nucleic acids for gene therapy. In such cases, the polymers' own intrinsic anti-tumour activity may complement the activity of the agent to be delivered." The disclosures of these patent publications may be employed in conjunction with herein teachings for delivery of CRISPR Cas system(s) or component(s) thereof or nucleic acid molecule(s) coding therefor.

Supercharged Proteins

Supercharged proteins are a class of engineered or naturally occurring proteins with unusually high positive or negative net theoretical charge and may be employed in delivery of the DNA targeting agent according to the invention as described herein, such as by means of example CRISPR Cas system(s) or component(s) thereof or nucleic acid molecule(s) coding therefor. Both supernegatively and superpositively charged proteins exhibit a remarkable ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo. David Liu's lab reported the creation and characterization of supercharged proteins in 2007 (Lawrence et al., 2007, Journal of the American Chemical Society 129, 10110-10112).

The nonviral delivery of RNA and plasmid DNA into mammalian cells are valuable both for research and therapeutic applications (Akinc et al., 2010, Nat. Biotech. 26, 561-569). Purified+36 GFP protein (or other superpositively charged protein) is mixed with RNAs in the appropriate serum-free media and allowed to complex prior addition to cells. Inclusion of serum at this stage inhibits formation of the supercharged protein-RNA complexes and reduces the effectiveness of the treatment. The following protocol has been found to be effective for a variety of cell lines (McNaughton et al., 2009, Proc. Natl. Acad. Sci. USA 106, 6111-6116) (However, pilot experiments varying the dose of protein and RNA should be performed to optimize the procedure for specific cell lines): (1) One day before treatment, plate $1\times10^5$ cells per well in a 48-well plate. (2) On the day of treatment, dilute purified+36 GFP protein in serumfree media to a final concentration 200 nM. Add RNA to a final concentration of 50 nM. Vortex to mix and incubate at room temperature for 10 min. (3) During incubation, aspirate media from cells and wash once with PBS. (4) Following incubation of +36 GFP and RNA, add the protein-RNA complexes to cells. (5) Incubate cells with complexes at 37° C. for 4 h. (6) Following incubation, aspirate the media and wash three times with 20 U/mL heparin PBS. Incubate cells with serum-containing media for a further 48 h or longer depending upon the assay for activity. (7) Analyze cells by immunoblot, qPCR, phenotypic assay, or other appropriate method.

David Liu's lab has further found+36 GFP to be an effective plasmid delivery reagent in a range of cells. As plasmid DNA is a larger cargo than siRNA, proportionately more +36 GFP protein is required to effectively complex plasmids. For effective plasmid delivery Applicants have developed a variant of +36 GFP bearing a C-terminal HA2 peptide tag, a known endosome-disrupting peptide derived from the influenza virus hemagglutinin protein. The following protocol has been effective in a variety of cells, but as above it is advised that plasmid DNA and supercharged protein doses be optimized for specific cell lines and delivery applications: (1) One day before treatment, plate $1\times10'$ per well in a 48-well plate. (2) On the day of treatment, dilute purified b36 GFP protein in serumfree media to a final concentration 2 mM. Add 1 mg of plasmid DNA. Vortex to mix and incubate at room temperature for 10 min. (3) During incubation, aspirate media from cells and wash once with PBS. (4) Following incubation of b36 GFP and plasmid DNA, gently add the protein-DNA complexes to cells. (5) Incubate cells with complexes at 37 C for 4 h. (6) Following incubation, aspirate the media and wash with PBS. Incubate cells in serum-containing media and incubate for a further 24-48 h. (7) Analyze plasmid delivery (e.g., by plasmid-driven gene expression) as appropriate. See also, e.g., McNaughton et al., Proc. Natl. Acad. Sci. USA 106, 6111-6116 (2009); Cronican et al., ACS Chemical Biology 5, 747-752 (2010); Cronican et al., Chemistry & Biology 18, 833-838 (2011); Thompson et al., Methods in Enzymology 503, 293-319 (2012); Thompson, D. B., et al., Chemistry &

Biology 19 (7), 831-843 (2012). The methods of the super charged proteins may be used and/or adapted for delivery of the CRISPR Cas system of the present invention. These systems of Dr. Lui and documents herein in inconjunction with herein teachints can be employed in the delivery of the DNA targeting agent according to the invention as described herein, such as by means of example CRISPR Cas system(s) or component(s) thereof or nucleic acid molecule(s) coding therefor.

Cell Penetrating Peptides (CPPs)

In yet another embodiment, cell penetrating peptides (CPPs) are contemplated for the delivery of the DNA targeting agent according to the invention as described herein, such as by means of example CRISPR Cas system. CPPs are short peptides that facilitate cellular uptake of various molecular cargo (from nanosize particles to small chemical molecules and large fragments of DNA). The term "cargo" as used herein includes but is not limited to the group consisting of therapeutic agents, diagnostic probes, peptides, nucleic acids, antisense oligonucleotides, plasmids, proteins, particles, liposomes, chromophores, small molecules and radioactive materials. In aspects of the invention, the cargo may also comprise any component of the DNA targeting agent according to the invention as described herein, such as by means of example CRISPR Cas system or the entire functional CRISPR Cas system. Aspects of the present invention further provide methods for delivering a desired cargo into a subject comprising: (a) preparing a complex comprising the cell penetrating peptide of the present invention and a desired cargo, and (b) orally, intraarticularly, intraperitoneally, intrathecally, intraarterially, intranasally, intraparenchymally, subcutaneously, intramuscularly, intravenously, dermally, intrarectally, or topically administering the complex to a subject. The cargo is associated with the peptides either through chemical linkage via covalent bonds or through non-covalent interactions.

The function of the CPPs are to deliver the cargo into cells, a process that commonly occurs through endocytosis with the cargo delivered to the endosomes of living mammalian cells. Cell-penetrating peptides are of different sizes, amino acid sequences, and charges but all CPPs have one distinct characteristic, which is the ability to translocate the plasma membrane and facilitate the delivery of various molecular cargoes to the cytoplasm or an organelle. CPP translocation may be classified into three main entry mechanisms: direct penetration in the membrane, endocytosis-mediated entry, and translocation through the formation of a transitory structure. CPPs have found numerous applications in medicine as drug delivery agents in the treatment of different diseases including cancer and virus inhibitors, as well as contrast agents for cell labeling. Examples of the latter include acting as a carrier for GFP, MRI contrast agents, or quantum dots. CPPs hold great potential as in vitro and in vivo delivery vectors for use in research and medicine. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. One of the initial CPPs discovered was the trans-activating transcriptional activator (Tat) from Human Immunodeficiency Virus 1 (HIV-1) which was found to be efficiently taken up from the surrounding media by numerous cell types in culture. Since then, the number of known CPPs has expanded considerably and small molecule synthetic analogues with more effective protein transduction properties have been generated. CPPs include but are not limited to Penetratin, Tat (48-60), Transportan, and (R-AhX-R)4 (Ahx=aminohexanoyl) SEQ ID NO: 165.

U.S. Pat. No. 8,372,951, provides a CPP derived from eosinophil cationic protein (ECP) which exhibits highly cell-penetrating efficiency and low toxicity. Aspects of delivering the CPP with its cargo into a vertebrate subject are also provided. Further aspects of CPPs and their delivery are described in U.S. Pat. Nos. 8,575,305; 8,614,194 and 8,044,019. CPPs can be used to deliver the CRISPR-Cas system or components thereof. That CPPs can be employed to deliver the CRISPR-Cas system or components thereof is also provided in the manuscript "Gene disruption by cell-penetrating peptide-mediated delivery of Cas9 protein and guide RNA", by Suresh Ramakrishna, Abu-Bonsrah Kwaku Dad, Jagadish Beloor, et al. Genome Res. 2014 Apr. 2. [Epub ahead of print], incorporated by reference in its entirety, wherein it is demonstrated that treatment with CPP-conjugated recombinant Cas9 protein and CPP-complexed guide RNAs lead to endogenous gene disruptions in human cell lines. In the paper the Cas9 protein was conjugated to CPP via a thioether bond, whereas the guide RNA was complexed with CPP, forming condensed, positively charged particles. It was shown that simultaneous and sequential treatment of human cells, including embryonic stem cells, dermal fibroblasts, HEK293T cells, HeLa cells, and embryonic carcinoma cells, with the modified Cas9 and guide RNA led to efficient gene disruptions with reduced off-target mutations relative to plasmid transfections.

Implantable Devices

In another embodiment, implantable devices are also contemplated for delivery of the DNA targeting agent according to the invention as described herein, such as by means of example the CRISPR Cas system or component(s) thereof or nucleic acid molecule(s) coding therefor. For example, US Patent Publication 20110195123 discloses an implantable medical device which elutes a drug locally and in prolonged period is provided, including several types of such a device, the treatment modes of implementation and methods of implantation. The device comprising of polymeric substrate, such as a matrix for example, that is used as the device body, and drugs, and in some cases additional scaffolding materials, such as metals or additional polymers, and materials to enhance visibility and imaging. An implantable delivery device can be advantageous in providing release locally and over a prolonged period, where drug is released directly to the extracellular matrix (ECM) of the diseased area such as tumor, inflammation, degeneration or for symptomatic objectives, or to injured smooth muscle cells, or for prevention. One kind of drug is RNA, as disclosed above, and this system may be used and/or adapted to the DNA targeting agent according to the invention as described herein, such as by means of example CRISPR Cas system of the present invention. The modes of implantation in some embodiments are existing implantation procedures that are developed and used today for other treatments, including brachytherapy and needle biopsy. In such cases the dimensions of the new implant described in this invention are similar to the original implant. Typically a few devices are implanted during the same treatment procedure.

As described in US Patent Publication 20110195123, there is provided a drug delivery implantable or insertable system, including systems applicable to a cavity such as the abdominal cavity and/or any other type of administration in which the drug delivery system is not anchored or attached, comprising a biostable and/or degradable and/or bioabsorbable polymeric substrate, which may for example optionally be a matrix. It should be noted that the term "insertion" also includes implantation. The drug delivery system is preferably implemented as a "Loder" as described in US Patent Publication 20110195123.

The polymer or plurality of polymers are biocompatible, incorporating an agent and/or plurality of agents, enabling the release of agent at a controlled rate, wherein the total volume of the polymeric substrate, such as a matrix for example, in some embodiments is optionally and preferably no greater than a maximum volume that permits a therapeutic level of the agent to be reached. As a non-limiting example, such a volume is preferably within the range of 0.1 $m^3$ to 1000 $mm^3$, as required by the volume for the agent load. The Loder may optionally be larger, for example when incorporated with a device whose size is determined by functionality, for example and without limitation, a knee joint, an intra-uterine or cervical ring and the like.

The drug delivery system (for delivering the composition) is designed in some embodiments to preferably employ degradable polymers, wherein the main release mechanism is bulk erosion; or in some embodiments, non degradable, or slowly degraded polymers are used, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the surface is preferably maintained effectively constant during a significant period of the total drug releasing period, and therefore the diffusion rate is effectively constant (termed "zero mode" diffusion). By the term "constant" it is meant a diffusion rate that is preferably maintained above the lower threshold of therapeutic effectiveness, but which may still optionally feature an initial burst and/or may fluctuate, for example increasing and decreasing to a certain degree. The diffusion rate is preferably so maintained for a prolonged period, and it can be considered constant to a certain level to optimize the therapeutically effective period, for example the effective silencing period.

The drug delivery system optionally and preferably is designed to shield the nucleotide based therapeutic agent from degradation, whether chemical in nature or due to attack from enzymes and other factors in the body of the subject.

The drug delivery system as described in US Patent Publication 20110195123 is optionally associated with sensing and/or activation appliances that are operated at and/or after implantation of the device, by non and/or minimally invasive methods of activation and/or acceleration/deceleration, for example optionally including but not limited to thermal heating and cooling, laser beams, and ultrasonic, including focused ultrasound and/or RF (radiofrequency) methods or devices.

According to some embodiments of US Patent Publication 20110195123, the site for local delivery may optionally include target sites characterized by high abnormal proliferation of cells, and suppressed apoptosis, including tumors, active and/or chronic inflammation and infection including autoimmune diseases states, degenerating tissue including muscle and nervous tissue, chronic pain, degenerative sites, and location of bone fractures and other wound locations for enhancement of regeneration of tissue, and injured cardiac, smooth and striated muscle.

The site for implantation of the composition, or target site, preferably features a radius, area and/or volume that is sufficiently small for targeted local delivery. For example, the target site optionally has a diameter in a range of from about 0.1 mm to about 5 cm.

The location of the target site is preferably selected for maximum therapeutic efficacy. For example, the composition of the drug delivery system (optionally with a device for implantation as described above) is optionally and preferably implanted within or in the proximity of a tumor environment, or the blood supply associated thereof.

For example the composition (optionally with the device) is optionally implanted within or in the proximity to pancreas, prostate, breast, liver, via the nipple, within the vascular system and so forth.

The target location is optionally selected from the group consisting of (as non-limiting examples only, as optionally any site within the body may be suitable for implanting a Loder): 1. brain at degenerative sites like in Parkinson or Alzheimer disease at the basal ganglia, white and gray matter; 2. spine as in the case of amyotrophic lateral sclerosis (ALS); 3. uterine cervix to prevent HPV infection; 4. active and chronic inflammatory joints; 5. dermis as in the case of psoriasis; 6. sympathetic and sensoric nervous sites for analgesic effect; 7. Intra osseous implantation; 8. acute and chronic infection sites; 9. Intra vaginal; 10. Inner ear—auditory system, labyrinth of the inner ear, vestibular system; 11. Intra tracheal; 12. Intra-cardiac; coronary, epicardiac; 13. urinary bladder; 14. biliary system; 15. parenchymal tissue including and not limited to the kidney, liver, spleen; 16. lymph nodes; 17. salivary glands; 18. dental gums; 19. Intra-articular (into joints); 20. Intra-ocular; 21. Brain tissue; 22. Brain ventricles; 23. Cavities, including abdominal cavity (for example but without limitation, for ovary cancer); 24. Intra esophageal and 25. Intra rectal.

Optionally insertion of the system (for example a device containing the composition) is associated with injection of material to the ECM at the target site and the vicinity of that site to affect local pH and/or temperature and/or other biological factors affecting the diffusion of the drug and/or drug kinetics in the ECM, of the target site and the vicinity of such a site.

Optionally, according to some embodiments, the release of said agent could be associated with sensing and/or activation appliances that are operated prior and/or at and/or after insertion, by non and/or minimally invasive and/or else methods of activation and/or acceleration/deceleration, including laser beam, radiation, thermal heating and cooling, and ultrasonic, including focused ultrasound and/or RF (radiofrequency) methods or devices, and chemical activators.

According to other embodiments of US Patent Publication 20110195123, the drug preferably comprises a RNA, for example for localized cancer cases in breast, pancreas, brain, kidney, bladder, lung, and prostate as described below. Although exemplified with RNAi, many drugs are applicable to be encapsulated in Loder, and can be used in association with this invention, as long as such drugs can be encapsulated with the Loder substrate, such as a matrix for example, and this system may be used and/or adapted to deliver the CRISPR Cas system of the present invention.

As another example of a specific application, neuro and muscular degenerative diseases develop due to abnormal gene expression. Local delivery of RNAs may have therapeutic properties for interfering with such abnormal gene expression. Local delivery of anti apoptotic, anti inflammatory and anti degenerative drugs including small drugs and macromolecules may also optionally be therapeutic. In such cases the Loder is applied for prolonged release at constant rate and/or through a dedicated device that is implanted separately. All of this may be used and/or adapted to the DNA targeting agent according to the invention as described herein, such as by means of example CRISPR Cas system of the present invention.

As yet another example of a specific application, psychiatric and cognitive disorders are treated with gene modifiers. Gene knockdown is a treatment option. Loders locally delivering agents to central nervous system sites are therapeutic options for psychiatric and cognitive disorders including but not limited to psychosis, bi-polar diseases, neurotic disorders and behavioral maladies. The Loders could also deliver locally drugs including small drugs and macromolecules upon implantation at specific brain sites. All of this may be used and/or adapted to the CRISPR Cas system of the present invention.

As another example of a specific application, silencing of innate and/or adaptive immune mediators at local sites enables the prevention of organ transplant rejection. Local delivery of RNAs and immunomodulating reagents with the Loder implanted into the transplanted organ and/or the implanted site renders local immune suppression by repelling immune cells such as CD8 activated against the transplanted organ. All of this may be used and/or adapted to the DNA targeting agent according to the invention as described herein, such as by means of example CRISPR Cas system of the present invention.

As another example of a specific application, vascular growth factors including VEGFs and angiogenin and others are essential for neovascularization. Local delivery of the factors, peptides, peptidomimetics, or suppressing their repressors is an important therapeutic modality; silencing the repressors and local delivery of the factors, peptides, macromolecules and small drugs stimulating angiogenesis with the Loder is therapeutic for peripheral, systemic and cardiac vascular disease.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as ERCP, stereotactic methods into the brain tissue, Laparoscopy, including implantation with a laparoscope into joints, abdominal organs, the bladder wall and body cavities.

Implantable device technology herein discussed can be employed with herein teachings and hence by this disclosure and the knowledge in the art, the DNA targeting agent according to the invention as described herein, such as by means of example CRISPR-Cas system or components thereof or nucleic acid molecules thereof or encoding or providing components may be delivered via an implantable device.

The present application also contemplates an inducible CRISPR Cas system. Reference is made to international patent application Serial No. PCT/US13/51418 filed Jul. 21, 2013, which published as WO2014/018423 on Jan. 30, 2014.

In one aspect the invention provides a DNA targeting agent according to the invention as described herein, such as by means of example a non-naturally occurring or engineered CRISPR Cas system which may comprise at least one switch wherein the activity of said CRISPR Cas system is controlled by contact with at least one inducer energy source as to the switch. In an embodiment of the invention the control as to the at least one switch or the activity of said CRISPR Cas system may be activated, enhanced, terminated or repressed. The contact with the at least one inducer energy source may result in a first effect and a second effect.

The first effect may be one or more of nuclear import, nuclear export, recruitment of a secondary component (such as an effector molecule), conformational change (of protein, DNA or RNA), cleavage, release of cargo (such as a caged molecule or a co-factor), association or dissociation. The second effect may be one or more of activation, enhancement, termination or repression of the control as to the at least one switch or the activity of said the DNA targeting agent according to the invention as described herein, such as by means of example CRISPR Cas system. In one embodiment the first effect and the second effect may occur in a cascade.

The invention comprehends that the inducer energy source may be heat, ultrasound, electromagnetic energy or chemical. In a preferred embodiment of the invention, the inducer energy source may be an antibiotic, a small molecule, a hormone, a hormone derivative, a steroid or a steroid derivative. In a more preferred embodiment, the inducer energy source maybe abscisic acid (ABA), doxycycline (DOX), cumate, rapamycin, 4-hydroxytamoxifen (4OHT), estrogen or ecdysone.

The invention provides that the at least one switch may be selected from the group consisting of antibiotic based inducible systems, electromagnetic energy based inducible systems, small molecule based inducible systems, nuclear receptor based inducible systems and hormone based inducible systems. In a more preferred embodiment the at least one switch may be selected from the group consisting of tetracycline (Tet)/DOX inducible systems, light inducible systems, ABA inducible systems, cumate repressor/operator systems, 4OHT/estrogen inducible systems, ecdysone-based inducible systems and FKBP12/FRAP (FKBP12-rapamycin complex) inducible systems.

In one aspect of the invention the inducer energy source is electromagnetic energy. The electromagnetic energy may be a component of visible light having a wavelength in the range of 450 nm-700 nm. In a preferred embodiment the component of visible light may have a wavelength in the range of 450 nm-500 nm and may be blue light. The blue light may have an intensity of at least 0.2 mW/cm2, or more preferably at least 4 mW/cm2. In another embodiment, the component of visible light may have a wavelength in the range of 620-700 nm and is red light.

In a further aspect, the invention provides a method of controlling the DNA targeting agent according to the invention as described herein, such as by means of example a non-naturally occurring or engineered CRISPR Cas system, comprising providing said CRISPR Cas system comprising at least one switch wherein the activity of said CRISPR Cas system is controlled by contact with at least one inducer energy source as to the switch.

In an embodiment of the invention, the invention provides methods wherein the control as to the at least one switch or the activity of said the DNA targeting agent according to the invention as described herein, such as by means of example CRISPR Cas system may be activated, enhanced, terminated or repressed. The contact with the at least one inducer energy source may result in a first effect and a second effect. The first effect may be one or more of nuclear import, nuclear export, recruitment of a secondary component (such as an effector molecule), conformational change (of protein, DNA or RNA), cleavage, release of cargo (such as a caged molecule or a co-factor), association or dissociation. The second effect may be one or more of activation, enhancement, termination or repression of the control as to the at least one switch or the activity of said CRISPR Cas system. In one embodiment the first effect and the second effect may occur in a cascade.

The invention comprehends that the inducer energy source may be heat, ultrasound, electromagnetic energy or chemical. In a preferred embodiment of the invention, the inducer energy source may be an antibiotic, a small molecule, a hormone, a hormone derivative, a steroid or a steroid derivative. In a more preferred embodiment, the inducer energy source maybe abscisic acid (ABA), doxycycline (DOX), cumate, rapamycin, 4-hydroxytamoxifen (4OHT), estrogen or ecdysone. The invention provides that the at least one switch may be selected from the group consisting of antibiotic based inducible systems, electromagnetic energy based inducible systems, small molecule based inducible systems, nuclear receptor based inducible systems and hormone based inducible systems. In a more preferred embodiment the at least one switch may be selected from the group consisting of tetracycline (Tet)/DOX inducible systems, light inducible systems, ABA inducible systems, cumate repressor/operator systems, 4OHT/estrogen inducible systems, ecdysone-based inducible systems and FKBP12/FRAP (FKBP12-rapamycin complex) inducible systems.

In one aspect of the methods of the invention the inducer energy source is electromagnetic energy. The electromagnetic energy may be a component of visible light having a wavelength in the range of 450 nm-700 nm. In a preferred embodiment the component of visible light may have a wavelength in the range of 450 nm-500 nm and may be blue light. The blue light may have an intensity of at least 0.2 mW/cm2, or more preferably at least 4 mW/cm2. In another embodiment, the component of visible light may have a wavelength in the range of 620-700 nm and is red light.

In another preferred embodiment of the invention, the inducible effector may be a Light Inducible Transcriptional Effector (LITE). The modularity of the LITE system allows for any number of effector domains to be employed for transcriptional modulation. In yet another preferred embodiment of the invention, the inducible effector may be a chemical. The invention also contemplates an inducible multiplex genome engineering using CRISPR (clustered regularly interspaced short palindromic repeats)/Cas systems.

Self-Inactivating Systems

Once all copies of a gene in the genome of a cell have been edited, continued CRISPR/Cas9 expression in that cell is no longer necessary. Indeed, sustained expression would be undesirable in case of off-target effects at unintended genomic sites, etc. Thus time-limited expression would be useful. Inducible expression offers one approach, but in addition Applicants have engineered a Self-Inactivating CRISPR-Cas9 system that relies on the use of a non-coding guide target sequence within the CRISPR vector itself. Thus, after expression begins, the CRISPR system will lead to its own destruction, but before destruction is complete it will have time to edit the genomic copies of the target gene (which, with a normal point mutation in a diploid cell, requires at most two edits). Simply, the self inactivating CRISPR-Cas system includes additional RNA (i.e., guide RNA) that targets the coding sequence for the CRISPR enzyme itself or that targets one or more non-coding guide target sequences complementary to unique sequences present in one or more of the following:

(a) within the promoter driving expression of the non-coding RNA elements, (b) within the promoter driving expression of the Cas9 gene, (c) within 100 bp of the ATG translational start codon in the Cas9 coding sequence, (d) within the inverted terminal repeat (iTR) of a viral delivery vector, e.g., in the AAV genome.

Furthermore, that RNA can be delivered via a vector, e.g., a separate vector or the same vector that is encoding the CRISPR complex. When provided by a separate vector, the CRISPR RNA that targets Cas expression can be administered sequentially or simultaneously. When administered sequentially, the CRISPR RNA that targets Cas expression is to be delivered after the CRISPR RNA that is intended for e.g. gene editing or gene engineering. This period may be a period of minutes (e.g. 5 minutes, 10 minutes, 20 minutes, 30 minutes, 45 minutes, 60 minutes). This period may be a period of hours (e.g. 2 hours, 4 hours, 6 hours, 8 hours, 12 hours, 24 hours). This period may be a period of days (e.g. 2 days, 3 days, 4 days, 7 days). This period may be a period of weeks (e.g. 2 weeks, 3 weeks, 4 weeks). This period may be a period of months (e.g. 2 months, 4 months, 8 months, 12 months). This period may be a period of years (2 years, 3 years, 4 years). In this fashion, the Cas enzyme associates with a first gRNA/chiRNA capable of hybridizing to a first target, such as a genomic locus or loci of interest and undertakes the function(s) desired of the CRISPR-Cas system (e.g., gene engineering); and subsequently the Cas enzyme may then associate with the second gRNA/chiRNA capable of hybridizing to the sequence comprising at least part of the Cas or CRISPR cassette. Where the gRNA/chiRNA targets the sequences encoding expression of the Cas protein, the enzyme becomes impeded and the system becomes self inactivating. In the same manner, CRISPR RNA that targets Cas expression applied via, for example liposome, lipofection, nanoparticles, microvesicles as explained herein, may be administered sequentially or simultaneously. Similarly, self-inactivation may be used for inactivation of one or more guide RNA used to target one or more targets.

In some aspects, a single gRNA is provided that is capable of hybridization to a sequence downstream of a CRISPR enzyme start codon, whereby after a period of time there is a loss of the CRISPR enzyme expression. In some aspects, one or more gRNA(s) are provided that are capable of hybridization to one or more coding or non-coding regions of the polynucleotide encoding the CRISPR-Cas system, whereby after a period of time there is a inactivation of one or more, or in some cases all, of the CRISPR-Cas system. In some aspects of the system, and not to be limited by theory, the cell may comprise a plurality of CRISPR-Cas complexes, wherein a first subset of CRISPR complexes comprise a first chiRNA capable of targeting a genomic locus or loci to be edited, and a second subset of CRISPR complexes comprise at least one second chiRNA capable of targeting the polynucleotide encoding the CRISPR-Cas system, wherein the first subset of CRISPR-Cas complexes mediate editing of the targeted genomic locus or loci and the second subset of CRISPR complexes eventually inactivate the CRISPR-Cas system, thereby inactivating further CRISPR-Cas expression in the cell.

Thus the invention provides a CRISPR-Cas system comprising one or more vectors for delivery to a eukaryotic cell, wherein the vector(s) encode(s): (i) a CRISPR enzyme; (ii) a first guide RNA capable of hybridizing to a target sequence in the cell; (iii) a second guide RNA capable of hybridizing to one or more target sequence(s) in the vector which encodes the CRISPR enzyme; (iv) at least one tracr mate sequence; and (v) at least one tracr sequence. The first and second complexes can use the same tracr and tracr mate, thus differing only by the guide sequence, wherein, when expressed within the cell: the first guide RNA directs sequence-specific binding of a first CRISPR complex to the target sequence in the cell; the second guide RNA directs sequence-specific binding of a second CRISPR complex to the target sequence in the vector which encodes the CRISPR enzyme; the CRISPR complexes comprise (a) a tracr mate sequence hybridised to a tracr sequence and (b) a CRISPR enzyme bound to a guide RNA, such that a guide RNA can hybridize to its target sequence; and the second CRISPR complex inactivates the CRISPR-Cas system to prevent continued expression of the CRISPR enzyme by the cell.

Further characteristics of the vector(s), the encoded enzyme, the guide sequences, etc. are disclosed elsewhere herein. For instance, one or both of the guide sequence(s) can be part of a chiRNA sequence which provides the guide, tracr mate and tracr sequences within a single RNA, such that the system can encode (i) a CRISPR enzyme; (ii) a first chiRNA comprising a sequence capable of hybridizing to a first target sequence in the cell, a first tracr mate sequence, and a first tracr sequence; (iii) a second guide RNA capable of hybridizing to the vector which encodes the CRISPR enzyme, a second tracr mate sequence, and a second tracr sequence. Similarly, the enzyme can include one or more NLS, etc.

The various coding sequences (CRISPR enzyme, guide RNAs, tracr and tracr mate) can be included on a single vector or on multiple vectors. For instance, it is possible to encode the enzyme on one vector and the various RNA sequences on another vector, or to encode the enzyme and one chiRNA on one vector, and the remaining chiRNA on another vector, or any other permutation. In general, a system using a total of one or two different vectors is preferred.

Where multiple vectors are used, it is possible to deliver them in unequal numbers, and ideally with an excess of a vector which encodes the first guide RNA relative to the second guide RNA, thereby assisting in delaying final inactivation of the CRISPR system until genome editing has had a chance to occur.

The first guide RNA can target any target sequence of interest within a genome, as described elsewhere herein. The second guide RNA targets a sequence within the vector which encodes the CRISPR Cas9 enzyme, and thereby inactivates the enzyme's expression from that vector. Thus the target sequence in the vector must be capable of inactivating expression. Suitable target sequences can be, for instance, near to or within the translational start codon for the Cas9 coding sequence, in a non-coding sequence in the promoter driving expression of the non-coding RNA elements, within the promoter driving expression of the Cas9 gene, within 100 bp of the ATG translational start codon in the Cas9 coding sequence, and/or within the inverted terminal repeat (iTR) of a viral delivery vector, e.g., in the AAV genome. A double stranded break near this region can induce a frame shift in the Cas9 coding sequence, causing a loss of protein expression. An alternative target sequence for the "self-inactivating" guide RNA would aim to edit/inactivate regulatory regions/sequences needed for the expression of the CRISPR-Cas9 system or for the stability of the vector. For instance, if the promoter for the Cas9 coding sequence is disrupted then transcription can be inhibited or prevented. Similarly, if a vector includes sequences for replication, maintenance or stability then it is possible to target these. For instance, in a AAV vector a useful target sequence is within the iTR. Other useful sequences to target can be promoter sequences, polyadenylation sites, etc.

Furthermore, if the guide RNAs are expressed in array format, the "self-inactivating" guide RNAs that target both promoters simultaneously will result in the excision of the intervening nucleotides from within the CRISPR-Cas expression construct, effectively leading to its complete inactivation. Similarly, excision of the intervening nucleotides will result where the guide RNAs target both ITRs, or targets two or more other CRISPR-Cas components simultaneously. Self-inactivation as explained herein is applicable, in general, with CRISPR-Cas9 systems in order to provide regulation of the CRISPR-Cas9. For example, self-inactivation as explained herein may be applied to the CRISPR repair of mutations, for example expansion disorders, as explained herein. As a result of this self-inactivation, CRISPR repair is only transiently active.

Addition of non-targeting nucleotides to the 5' end (e.g. 1-10 nucleotides, preferably 1-5 nucleotides) of the "self-inactivating" guide RNA can be used to delay its processing and/or modify its efficiency as a means of ensuring editing at the targeted genomic locus prior to CRISPR-Cas9 shutdown.

In one aspect of the self-inactivating AAV—CRISPR-Cas9 system, plasmids that co-express one or more sgRNA targeting genomic sequences of interest (e.g. 1-2, 1-5, 1-10, 1-15, 1-20, 1-30) may be established with "self-inactivating" sgRNAs that target an SpCas9 sequence at or near the engineered ATG start site (e.g. within 5 nucleotides, within 15 nucleotides, within 30 nucleotides, within 50 nucleotides, within 100 nucleotides). A regulatory sequence in the U6 promoter region can also be targeted with an sgRNA. The U6-driven sgRNAs may be designed in an array format such that multiple sgRNA sequences can be simultaneously released. When first delivered into target tissue/cells (left cell) sgRNAs begin to accumulate while Cas9 levels rise in the nucleus. Cas9 complexes with all of the sgRNAs to mediate genome editing and self-inactivation of the CRISPR-Cas9 plasmids.

One aspect of a self-inactivating CRISPR-Cas9 system is expression of singly or in tandem array format from 1 up to 4 or more different guide sequences; e.g. up to about 20 or about 30 guides sequences. Each individual self inactivating guide sequence may target a different target. Such may be processed from, e.g. one chimeric pol3 transcript. Pol3 promoters such as U6 or H1 promoters may be used. Pol2 promoters such as those mentioned throughout herein. Inverted terminal repeat (iTR) sequences may flank the Pol3 promoter-sgRNA(s)-Pol2 promoter-Cas9.

One aspect of a chimeric, tandem array transcript is that one or more guide(s) edit the one or more target(s) while one or more self inactivating guides inactivate the CRISPR/Cas9 system. Thus, for example, the described CRISPR-Cas9 system for repairing expansion disorders may be directly combined with the self-inactivating CRISPR-Cas9 system described herein. Such a system may, for example, have two guides directed to the target region for repair as well as at least a third guide directed to self-inactivation of the CRISPR-Cas9. Reference is made to Application Ser. No. PCT/US2014/069897, entitled "Compositions And Methods Of Use Of Crispr-Cas Systems In Nucleotide Repeat Disorders," published Dec. 12, 2014 as WO/2015/089351.

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include a T cell modulating agent, are used to treat or alleviate a symptom associated with an immune-related disorder or an aberrant immune response. The present invention also provides methods of treating or alleviating a symptom associated with an immune-related disorder or an aberrant immune response. A therapeutic regimen is carried out by identifying a subject, e.g., a human patient suffering from (or at risk of developing) an immune-related disorder or aberrant immune response, using standard methods. For example, T cell modulating agents are useful therapeutic tools in the treatment of cancers.

A therapeutically effective amount of a T cell modulating agent relates generally to the amount needed to achieve a therapeutic objective. The amount required to be administered will furthermore depend on the specificity of the T cell modulating agent for its specific target, and will also depend on the rate at which an administered T cell modulating agent is depleted from the free volume other subject to which it is administered. The T cell modulating agent may be administered in vivo or ex vivo as described herein.

T cell modulating agents can be administered for the treatment of a variety of diseases and disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where polypeptide-based T cell modulating agents are used, the smallest fragment that specifically binds to the target and retains therapeutic function is preferred. Such fragments can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

Therapy or treatment according to the invention may be performed alone or in conjunction with another therapy, and may be provided at home, the doctor's office, a clinic, a hospital's outpatient department, or a hospital. Treatment generally begins at a hospital so that the doctor can observe the therapy's effects closely and make any adjustments that are needed. The duration of the therapy depends on the age and condition of the patient, the stage of a cardiovascular disease, and how the patient responds to the treatment. Additionally, a person having a greater risk of developing a cardiovascular disease (e.g., a person who is genetically predisposed) may receive prophylactic treatment to inhibit or delay symptoms of the disease.

The medicaments of the invention are prepared in a manner known to those skilled in the art, for example, by means of conventional dissolving, lyophilizing, mixing, granulating or confectioning processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York.

Administration of medicaments of the invention may be by any suitable means that results in a compound concentration that is effective for treating or inhibiting (e.g., by delaying) the development of a cardiovascular disease. The compound is admixed with a suitable carrier substance, e.g., a pharmaceutically acceptable excipient that preserves the therapeutic properties of the compound with which it is administered. One exemplary pharmaceutically acceptable excipient is physiological saline. The suitable carrier substance is generally present in an amount of 1-95% by weight of the total weight of the medicament. The medicament may be provided in a dosage form that is suitable for oral, rectal, intravenous, intramuscular, subcutaneous, inhalation, nasal, topical or transdermal, vaginal, or ophthalmic administration. Thus, the medicament may be in form of, e.g., tablets, capsules, pills, powders, granulates, suspensions, emulsions, solutions, gels including hydrogels, pastes, ointments, creams, plasters, drenches, delivery devices, suppositories, enemas, injectables, implants, sprays, or aerosols.

The practice of the present invention employs, unless otherwise indicated, conventional techniques of immunology, biochemistry, chemistry, molecular biology, microbiology, cell biology, genomics and recombinant DNA, which are within the skill of the art. See MOLECULAR CLONING: A LABORATORY MANUAL, 2nd edition (1989) (Sambrook, Fritsch and Maniatis); MOLECULAR CLONING: A LABORATORY MANUAL, 4th edition (2012)

(Green and Sambrook); CURRENT PROTOCOLS IN MOLECULAR BIOLOGY (1987) (F. M. Ausubel, et al. eds.); the series METHODS IN ENZYMOLOGY (Academic Press, Inc.); PCR 2: A PRACTICAL APPROACH (1995) (M. J. MacPherson, B. D. Hames and G. R. Taylor eds.); ANTIBODIES, A LABORATORY MANUAL (1988) (Harlow and Lane, eds.); ANTIBODIES A LABORATORY MANUAL, 2nd edition (2013) (E. A. Greenfield ed.); and ANIMAL CELL CULTURE (1987) (R. I. Freshney, ed.).

The practice of the present invention employs, unless otherwise indicated, conventional techniques for generation of genetically modified mice. See Marten H. Hofker and Jan van Deursen, TRANSGENIC MOUSE METHODS AND PROTOCOLS, 2nd edition (2011).

This invention is further illustrated by the following examples which should not be construed as limiting. It is understood that the foregoing description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

IL-27 is a member of the IL-12 family of cytokines that is produced by antigen presenting cells. IL-27 was initially found to promote a Type I pro-inflammatory response; however, emerging evidence suggests that this cytokine plays an important role in the resolution of tissue inflammation (Yoshida, H. & Hunter, C. A. (2015) Annual review of immunology 33, 417-443). IL-27 administration in vivo suppresses the development of effector T cells and inhibits the development of autoimmunity. In contrast, IL-27ra (WSX-1) deficient mice exhibit increased inflammation during *Toxoplasma gondii* infection and exhibit exacerbated central nervous system autoimmunity (Awasthi, A. et al. 2007; Hirahara, K. et al. 2012; Villarino, A. et al. 2003). Indeed, it has been shown that IL-27 induces IL-10-secreting Type I regulatory (Tr1) cells that are immune suppressive (Awasthi, A. et al. 2007). Moreover, it has been shown that IL-27 induces Tim-3, which has been shown to cooperate with PD-1 in exhausted T cells (Zhu, C. et al. 2015; Sakuishi, et al., 2011). Together these observations raised the possibility that IL-27 may also induce the expression of additional co-inhibitory receptors that cooperate to promote T cell dysfunction.

Data provided herein shows that IL-27 signaling drives the expression of a gene module that includes not only Tim-3, but also LAG-3 and Tigit, molecules that have been previously associated with T cell dysfunction. The inventors identified a large overlap in the IL-27-induced transcriptome and the gene signatures that define dysfunctional T cells in chronic viral infection and cancer. Further, the inventors identified a panel of novel candidate molecules that are induced by IL-27, are associated with T-cell dysfunction, and can be modulated to improve effector T cell responses in vivo. These data define a new role for IL-27 signaling in an inhibitory gene module that sets the stage for the development of a dysfunctional phenotype in T cells and further provide a means by which to identify novel and potentially synergistic targets for therapeutic application in chronic disease settings.

The inventors further realised that modulation of genes or gene products comprised by the gene signatures as taught herein in isolated immune cells can modulate the properties of the cells and thereby provide for advantageous effects, such as increasing or decreasing dysfunctional phenotype of the immune cells, or rendering the immune cells more resistant or more sensitive to becoming dysfunctional, or increasing or decreasing activated phenotype of the immune cells, or rendering the immune cells more resistant or more sensitive to becoming activated. Such modulation can be of value inter alia in therapeutic applications, such as for example but without limitation in ex vivo or allogeneic therapies involving immune cells, such as T cells, such as CD8+ T cells, e.g., CAR-T therapies.

Example 1: Experimental Results

IL-27 Induces a Co-Expressed Set of Co-Inhibitory Receptors Associated with T Cell Dysfunction on CD4 and CD8 T Cells.

Recent studies have demonstrated that IL-27 induces the expression of co-inhibitory cell-surface receptors, such as Tim-3 and PD-L1, on CD4+ and CD8+ T cells (Hirahara et al., (2012) *Immunity* 36, 1017-30; Zhu et al., (2015) *Nature communications* 6, 6072). Together with evidence supporting a key role for IL-27 in driving resolution of tissue inflammation (e.g., Awasthi et al., (2007) *Nature immunology* 8, 1380-1389; Hirahara et al., (2012) *Immunity* 36, 1017-30; Stumhofer et al., (2007) *Nature immunology* 8, 1363-1371; Fitzgerald et al., (2007b) *Nature immunology* 8, 1372-1379), Applicants hypothesized that IL-27 might induce expression of additional co-inhibitory receptors in T cells. Accordingly, it was examined whether activation of naïve CD4 and CD8 T cells in the presence of IL-27 induced additional co-inhibitory molecules.

Indeed, Applicants found that besides Tim-3 (Havcr2) IL-27 induced at both the mRNA and protein level two additional co-inhibitory molecules associated with T cell dysfunction, Lag-3 and TIGIT (FIG. 1A, B), on CD4+ and CD8+ T cells. Expression of all three co-inhibitory molecules (Tim-3, Lag-3 and TIGIT) was reduced in IL-27R-deficient T cells, further confirming the importance of IL-27 in driving their expression. Interestingly, while the induction of Tim-3, Lag-3, and TIGIT in vitro was largely dependent on IL-27, PD-1 (Pdcd1) expression was not affected by IL-27 (FIG. 1A, B).

At a population level, co-inhibitory receptors are often co-expressed on dysfunctional T cells in vivo, where the accumulation of co-inhibitory receptor expression has been shown to correlate directly with the degree of dysfunction (Wherry, E. J. and Kurachi, M. (2015) *Nature Reviews Immunology* 15, 486-499). However, it has not been clear to what extent co-inhibitory receptors are co-expressed at the single cell level. Applicants recently showed with single cell RNA-Seq the co-expression of a module of co-inhibitory receptors (including Tim-3, TIGIT, PD1, Lag-3 and CTLA-4) in CD8+ TILs from human melanoma tumors (Tirosh et al., (2016) *Science* 352, 189-196); however, assessing the functional state of human cells in vivo is challenging. Applicants therefore analyzed single cell RNAseq profiles of 516 CD8 TILs from B16F10 melanoma (Singer et al., companion manuscript) and indeed found that PD-1, Lag3, Tim-3, CTLA-4, 41BB and TIGIT strongly co-vary across single cells, such that cells co-express their transcripts (FIG. 1C).

The observed induction of multiple known co-inhibitory receptors by IL-27 suggested the possibility of shared regulatory elements and co-variant expression on T cells. Indeed, co-inhibitory receptors are often co-expressed on dysfunctional T cells in vivo where the accumulation of co-inhibitory receptor expression has been shown to be proportional to the severity of dysfunctional phenotype. The co-expressed set of co-inhibitory genes is also apparent at the protein level in $CD4^+$ and $CD8^+$ TILs, as assessed by single-cell mass cytometry (CyTOF, Bendall et al., (2011) *Science* 332, 687-696; Newell et al., (2012) *Immunity* 36, 142-152). This technology allows for simultaneous analysis of the expression of up to 30 molecules on a single cell. Applicants developed a custom CyTOF panel that included 15 antibodies against known co-stimulatory and co-inhibitory cell-surface receptors, as well as lineage-defining cell surface markers (Table 15; FIG. 1D), and used it to analyze TILs isolated from B16F10 melanoma tumors from WT and IL-27R knockout mice.

TABLE 15

| Ab | Metal |
|---|---|
| PD-1 | 171Yb |
| Tim-3 | 141Pr |
| LAG-3 | 147Sm |
| TIGIT | 149Sm |
| CTLA4 | 176Yb |
| GITR | 174Yb |
| CD160 | 143Nd |
| BTLA | 153Eu |
| Lilrb4 | 152Sm |
| ICOS | 160Gd |
| 4-1BB | 169Tm |
| OX40 | 170Er |
| SLAMF6 | 167Er |
| CD226 | 168Er |
| HVEM | 175Lu |
| Thy1.2 | 156Gd |
| CD8a | 164Dy |
| CD4 | 145Nd |
| IFNg | 159Tb |
| TNFa | 148Nd |

Figure 1E:
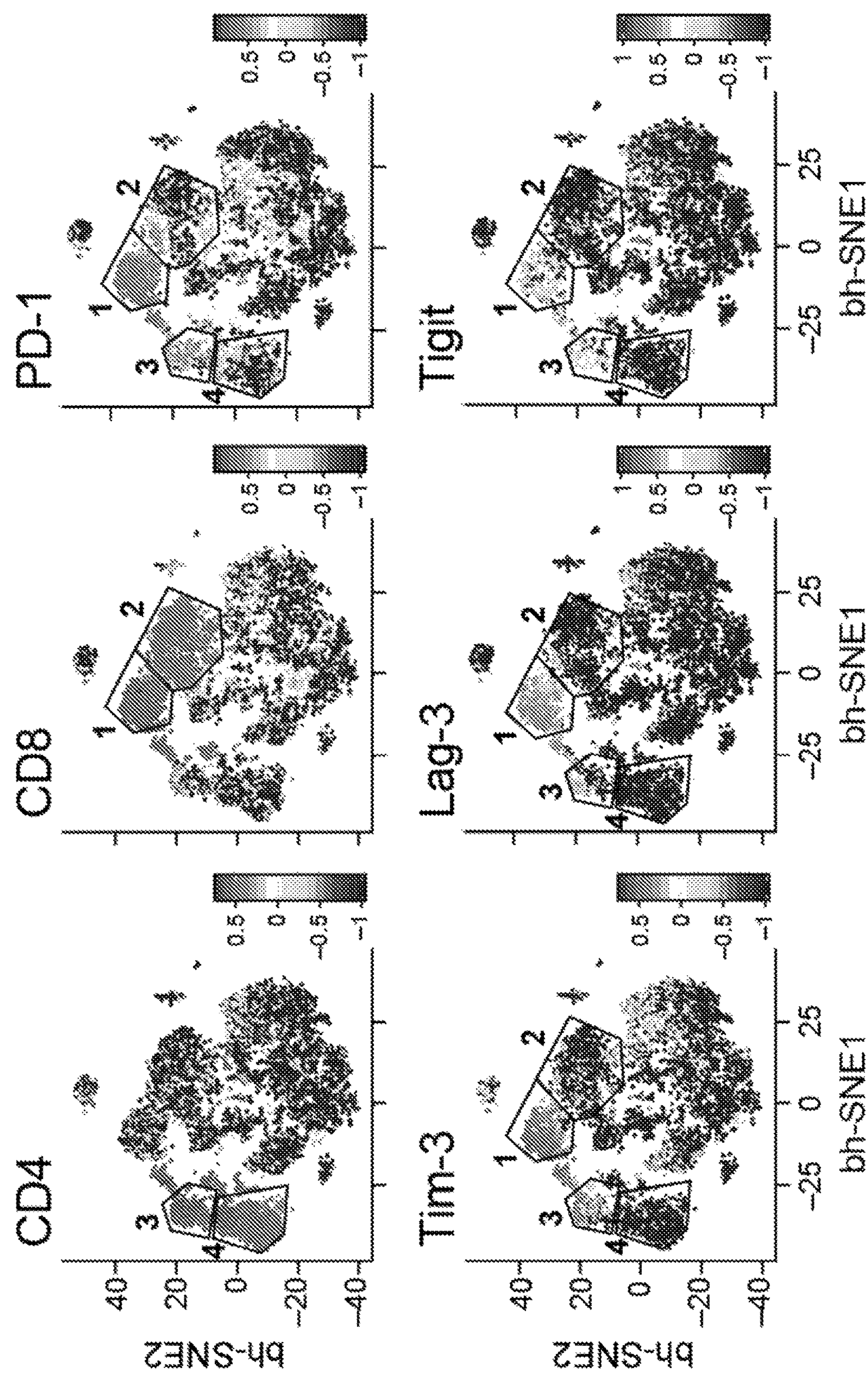
Figure 1H:
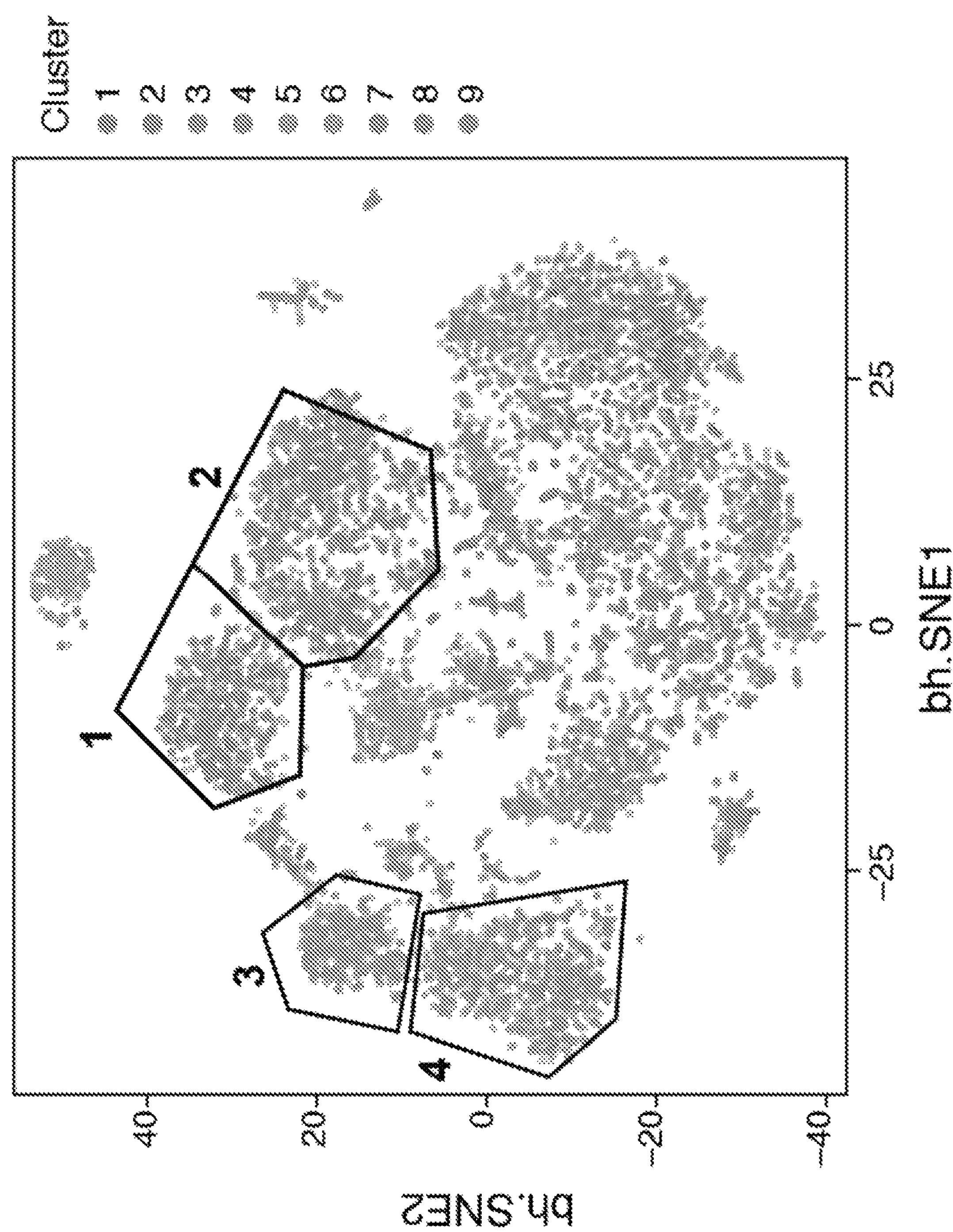
Figure 1I:
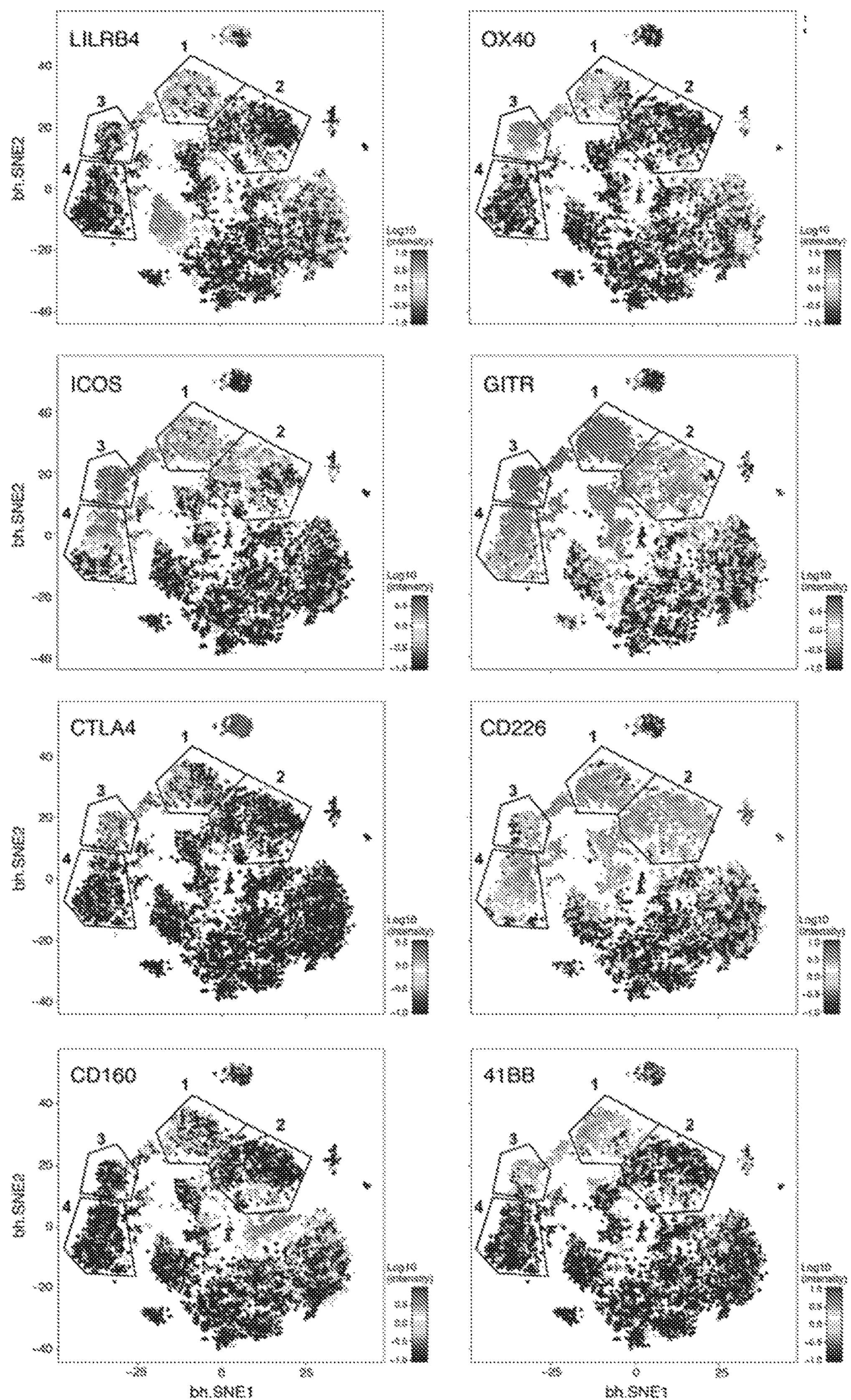

Four co-inhibitory receptors (PD-1, LAG3, TIM-3, and TIGIT) had tightly correlated expression on $CD8^+$ and $CD4^+$ TILs. PD-1, TIM-3, and LAG-3 showed the highest degree of correlation, particularly on $CD8^+$ TILs (FIG. 1C and FIG. 1D for $CD4^+$ TILs). K-means clustering of the cells following visualization with a non-linear embedding of the protein expression profiles using t-stochastic neighborhood embedding (t-SNE (Maaten L, (2008) *Journal of Machine Learning Research,* 2579-2605), Example 2: Methods) showed two discrete groups of $CD8^+$ TILs, described herein as clusters 1 and 2. The co-inhibitory receptor quartet (PD-1, LAG3, TIM-3, and TIGIT) was mainly expressed in cells in cluster 1 (FIG. 1E, FIG. 1F,G,H). Additional co-inhibitory receptors, including CD160, CTLA-4, and LILRB4 were expressed on smaller sub-sets of cells within cluster 1 (FIG. 1I). Some known co-stimulatory molecules, particularly those of the TNF-receptor family, such as 4-1BB, OX-40, and GITR, were also co-expressed with the co-inhibitory receptors on cells within cluster 1 (FIG. 1I). In contrast, other co-stimulatory molecules such as ICOS and CD226 were more comparably expressed on cells in both cluster 1 and cluster 2 (FIG. 1I). Thus, cluster 1 is highly enriched for $CD8^+$ T cells that express multiple co-inhibitory receptors together with co-stimulatory receptors of the TNF-receptor family.

Figure 1J:
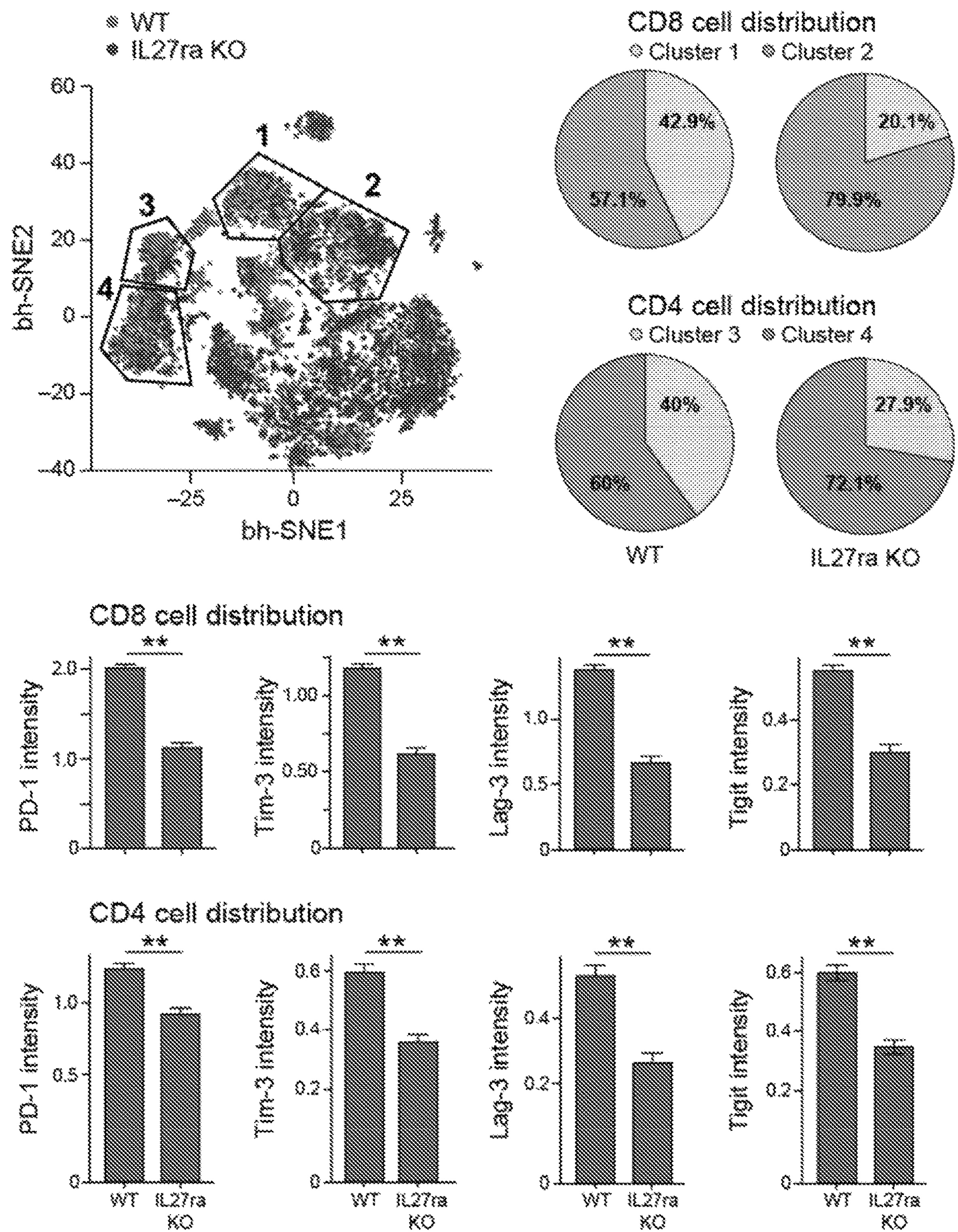
Figure 1K:
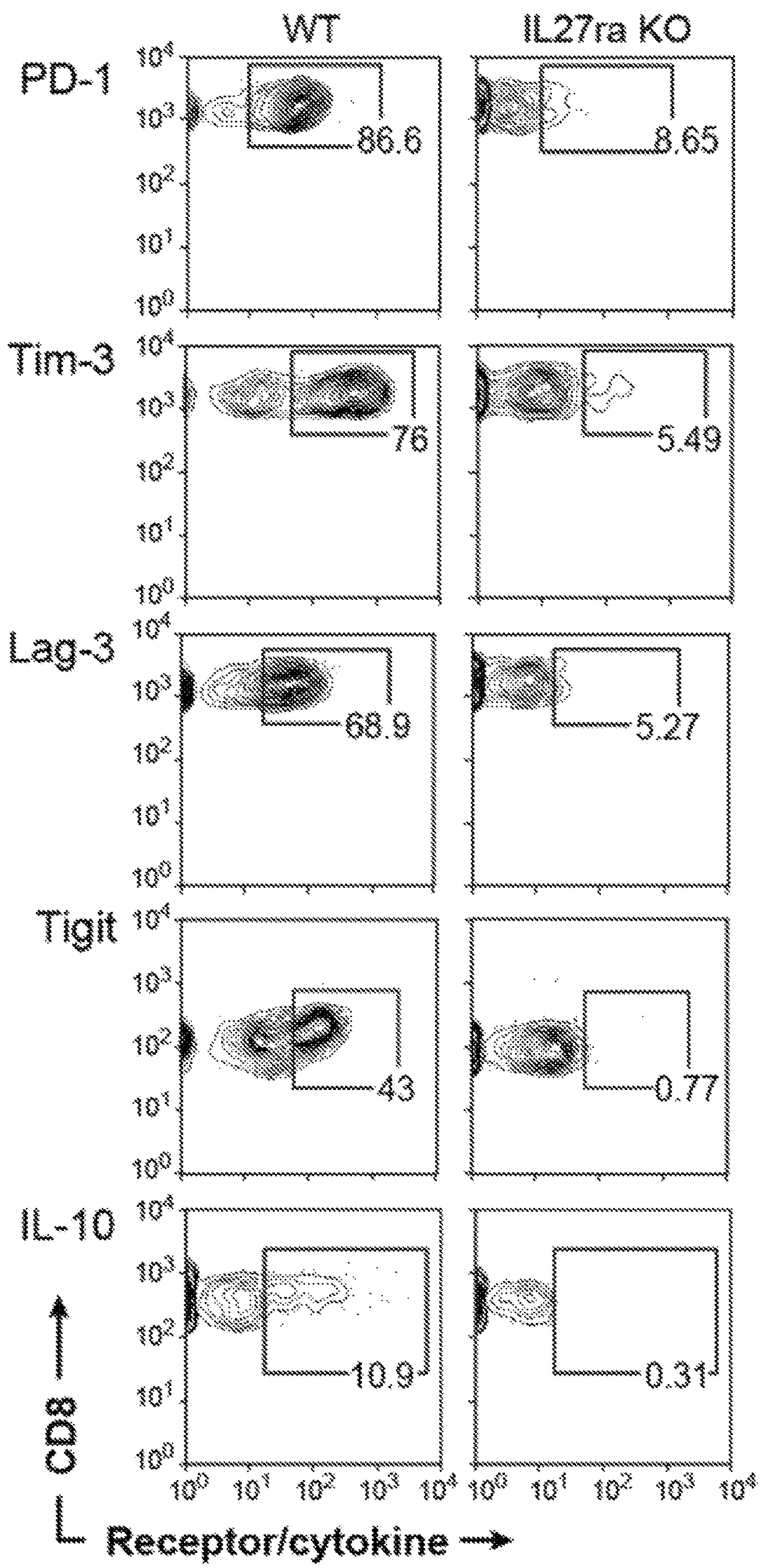
Figure 1L:
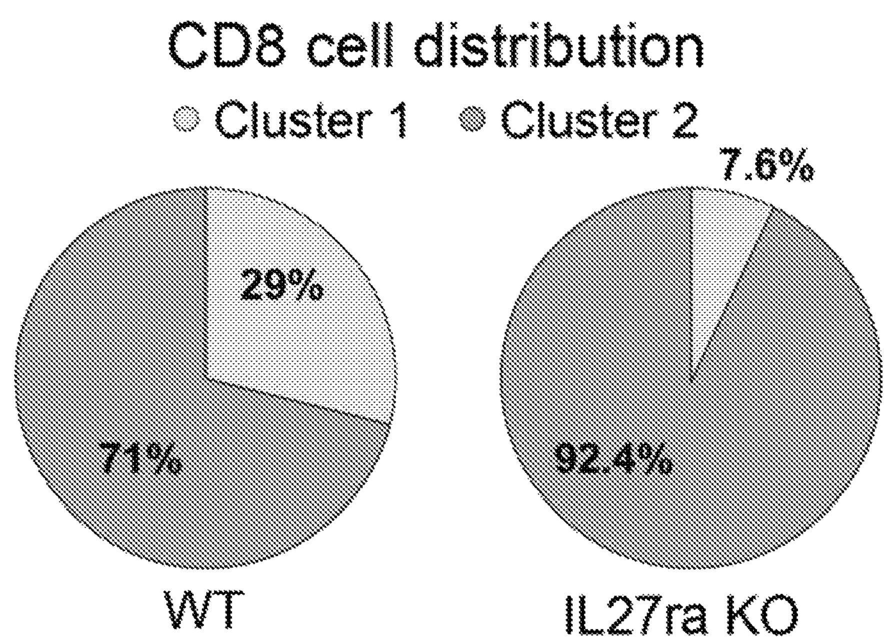
Figure 1M:
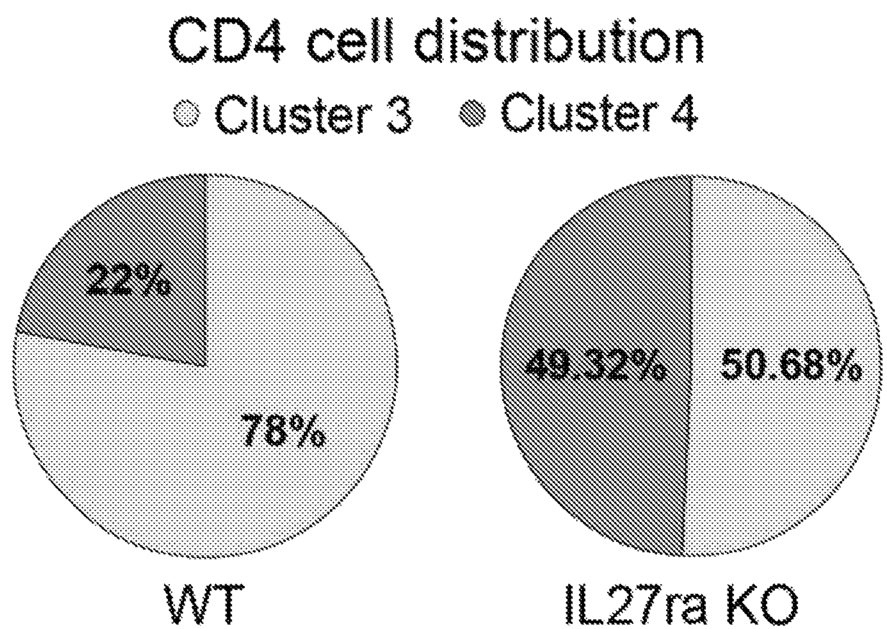
Figure 4:
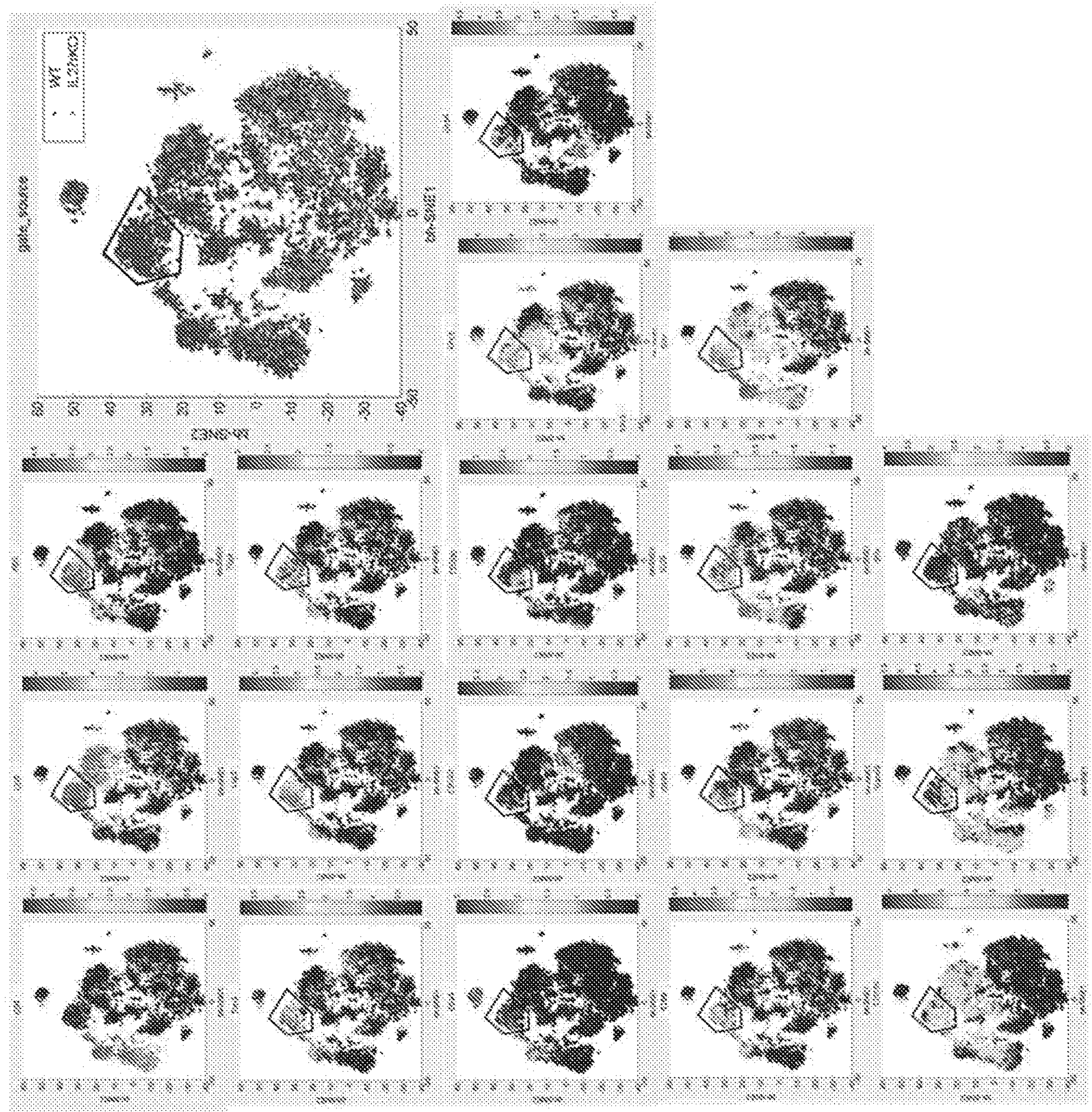
FIG. 4. TILs were harvested from WT and IL27ra deficient mice bearing B16F10 melanoma and analyzed using CyTOF. Right panel shows TILs from WT (blue) and IL27ra KO (red). All data were analyzed using vi-SNE. (Right top). Graphical representation of the distribution of CD8$^+$ TILs in cluster 1 and cluster 2 in WT and IL27ra KO CD8$^+$ TILs.
Figure 5:
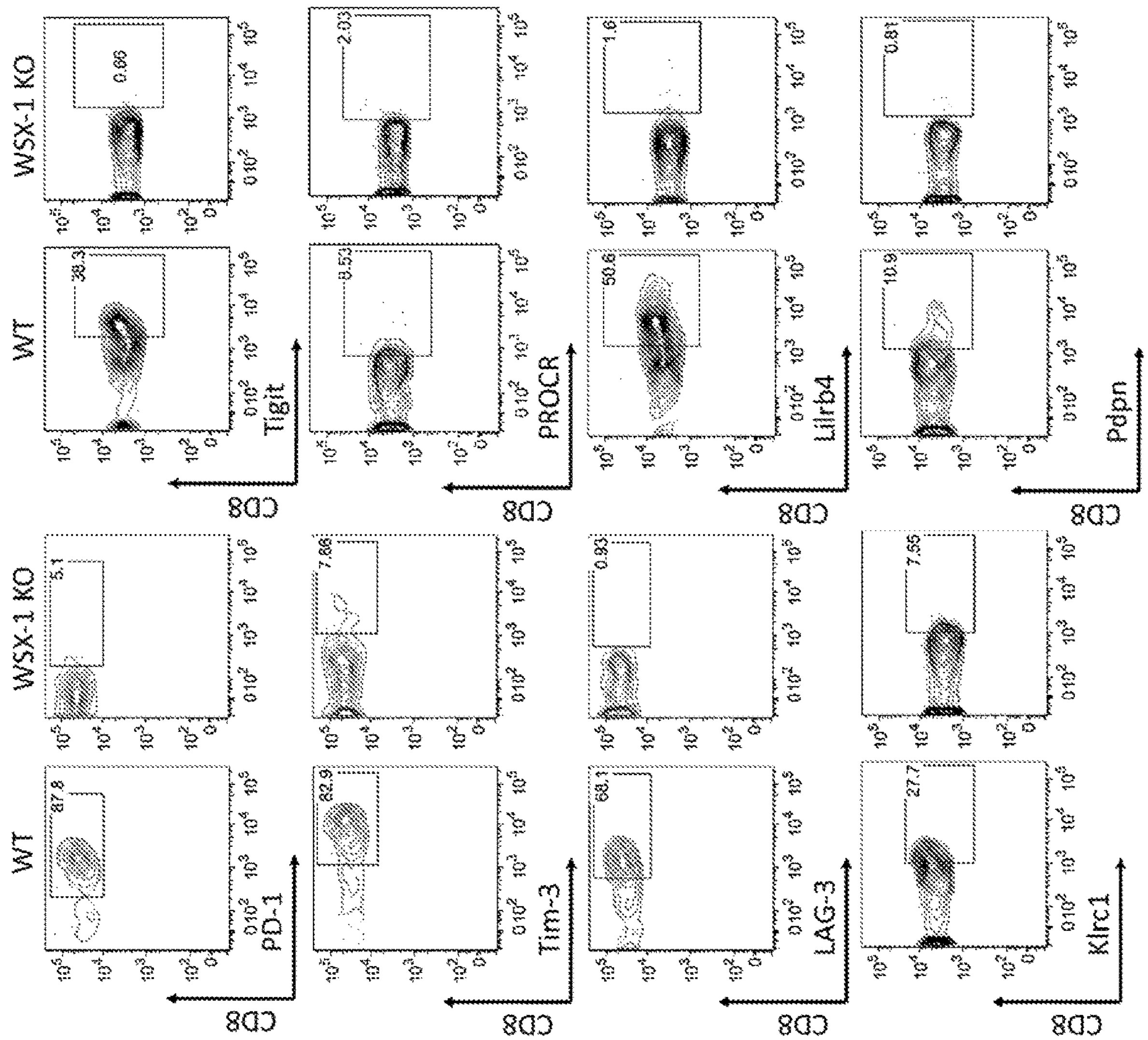
FIG. 5. IL-27 inducing inhibitory molecules and PD-1 expression in TILs. Surface molecule expression on TILs from WT and IL27ra$^{-/-}$. Surface molecules expression on CD8 TILs obtained from WT and WSX-1$^{-/-}$ mice bearing B16F10 melanoma was analyzed by FACS.

Notably, cluster 1 was relatively depleted of cells from IL-27ra KO CD8+ TILs compared to WT (FIG. 1J, hyperG p-value=5e-23), suggesting that in the absence of IL-27 signaling there are far fewer CD8+ TILs with co-expressed co-inhibitory receptors. Applicants further confirmed the reduced proportion of cells that express PD-1, TIM-3, LAG3, TIGIT, and IL-10 on CD8+ TILs isolated from IL-27ra KO mice by flow cytometry (FIG. 1K) and in several replicate CyTOF experiments (FIG. 1L). Thus, IL-27 signaling is a key driver of an inhibitory gene module that includes co-inhibitory receptors and IL-10 which are strongly co-expressed in vivo. Of note and in contrast to our in vitro data, Applicants saw that PD-1 expression is dependent on IL-27R signaling in vivo. Together, these data indicate that cluster 1 is highly enriched for cells that express co-inhibitory receptors and found that the TILS identified as cluster 1 is significantly decreased in the absence of IL-27 signaling. This significant reduction of CD8 T cells expressing PD-1, Tim-3, LAG-3, and TIGIT was confirmed in IL-27ra−/− mice using conventional flow cytometry. Together these data indicate that IL-27 signaling is a key driver of a module of co-inhibitory receptors that exhibit a high degree of co-variance in vivo.

IL-27 Driven Inhibitory Molecules Dissect Cluster1-CD8 TILs

The identification of additional co-inhibitory molecules dependent upon IL-27R signaling permitted the further dissection of the subpopulation of cluster1-CD8 TILs based on their function. IL-27R signaling dependent population was overlapped with PD-1 expressing cells. While PD-1 is important for exhaustion (Wherry, E. J., (2011) *Nature immunology* 12, 492-499), it is also expressed on activated T cells. IL-27 does not induce PD-1 directly. Each inhibitory molecule had a different pattern of expression within cluster1-CD8 T cells, for example PD-1 high CD8 cells produce more IFNg than PD-1 middle cells, but PD-1 high Tim-3 high CD8 T cells produce less TNFα than PD-1 high Tim-3 low cells do. This correlation is further emphasized for PD-1 high Tim-3 high Tigit+ cells. Thus, the accumulation of multiple inhibitory molecules rather than the intensity of a single one on the same cell leads to is a better predictor for stepwise decrease of effector cytokines from CD8 TILs. In general, cluster-2-CD8 TILs, which is enriched for IL27ra KO derived cells, showed a stronger effector function than cluster-1. However, the expression of some co-stimulatory molecules was observed, including 4-1BB co-expressed with several inhibitory molecules; PD-1, Tim-3, Tigit, and CD160 in a part of cluster-1-CD8 TILs where it might represent counter regulation of exhaustion pressures under tumor microenvironment. On the other hand, IL-10 producing cells are also higher in the exhausted phenotype of CD8 T cells in an IL-27R signal dependent manner. IL-10 has been reported to be immunosuppressive in the context of tumor immunity (Hisada, M. et al., (2004) *Cancer research* 64, 1152-1156). Within the tumor microenvironment, IL-27 signature drives inhibitory molecules that augment deficit of effector cytokines from CD8 T cells. At the same time they are producing IL-10 and further exacerbating the circumstance of immune suppressive environment. IL-27 induces a gene module that is present in other dysfunctional T cells and includes novel cell-surface molecules The importance of IL-27 signaling for driving known co-inhibitory receptors both in vitro and in vivo, prompted the inventors to examine whether IL-27 may drive additional and yet unknown molecules that have regulatory function. To examine whether IL-27 may also induce the expression of additional novel inhibitory molecules that could regulate anti-tumor immunity, Applicants used transcriptional profiling to identify a signature of IL-27 dependent genes in wild-type and IL-27ra−/− T cells after stimulation with or without IL-27 at time points selected for optimal expression of known co-inhibitory receptors (Tim-3, Lag-3, and Tigit) on CD4+ and CD8+ T cells. Applicants first measured a 445 gene transcriptional signature (measured by nCounter, Example 2: Methods, Table 16) in WT and IL-27ra KO CD4+ and CD8+ T cells at 6 times point along a 96 hour time course after activation in the presence or absence of IL-27.

TABLE 16

| Transcriptional Gene Signature | | | | | | | |
|---|---|---|---|---|---|---|---|
| 1700097N02Rik | Ccnl1 | Daxx | Hif1a | Irf5 | Ncoal | Rgs16 | Tap1 |
| 2310031A07Rik | Ccr1 | Ddr1 | Hip1r | Irf7 | Nfatc1 | Rgs8 | Tbx21 |
| 2900064A13Rik | Ccr2 | Dntt | Hlx | Irf8 | Nfatc2 | Rora | Tcf4 |
| 5830405N20Rik | Ccr4 | Dpp4 | Hprt | Irf9 | NFE2 | Rorc | Tcf7 |
| 6330442E10Rik | Ccr5 | Drd1 | Hsbp1 | Isg20 | Nfe2l2 | Rpp14 | Tgfb1 |
| Abcg2 | Ccr6 | dsc2 | Htr1a | Itch | Nfil3 | Runx1 | Tgfb3 |
| AchE | Ccr8 | EBi3 | Icos | Itga3 | Nfkbie | Runx2 | Tgfbr1 |
| Actin | Ccr9 | Egr2 | Id2 | Itgb1 | Nfkbiz | Runx3 | Tgfbr3 |
| Acvr1b | Cd160 | Eif3e | Id3 | Jak3 | Nkg7 | Rxra | Tgif1 |
| Acvr2a | Cd2 | Eif3h | Ier3 | Jun | Nmdar1 | Sap30 | Tgm2 |
| adam8 | Cd200 | Elk3 | Ifi35 | Jup | Notch1 | Sema4d | Tigit |
| Adrb2 | Cd226 | Emp1 | Ifih1 | Kat2b | Notch2 | Sema7a | Timp2 |
| Aes | Cd247 | Eomes | Ifit1 | Katna1 | Nr3c1 | Serpinb1a | TLE1 |
| Ahr | Cd24a | Ercc5 | Ifitm2 | Khdrbs1 | Nudt4 | Serpinb1b | TLE2 |
| Aim1 | Cd274 | Errfi1 | Ifng | Klf10 | Oas2 | serpinb9b | TLE3 |
| alox5 | Cd28 | ETS1 | Ifngr2 | Klf3 | p28 | Serpine1 | TLE4 |
| Anxa4 | Cd36 | Etv6 | Ifnra1 | Klf6 | Pbx3 | Serpine2 | Tmed7 |
| Api5 | Cd39 | Fas | Ifnra2 | Klf7 | Pcbp2 | Sertad1 | Tmem119 |
| Aqp3 | Cd4 | Fasl | Igfbp4 | Klf9 | Pdcd1 | Sesn3 | Tmem126a |
| Arg1 | Cd44 | Fasn | Ikzf3 | Klrd1 | Pdcdl1 | Sgk1 | TNFa |
| Arhgef3 | Cd51 | FGL2 | Ikzf4 | Klrg1 | Pdcdl1g2 | Sgta | Tnfrsf12a |
| Arid5a | Cd70 | Fip1l1 | Ill0 | L1CAM | Pdpn | SIM1 | Tnfrsf13b |
| Ar15a | Cd74 | Fli1 | Il3 | Lad1 | Peci | SIM2 | Tnfrsf25 |
| Armcx2 | Cd80 | Flna | Il6st | Lag3 | Peli2 | Skap2 | Tnfrsf4 |
| Arnt1 | Cd83 | Flot1 | Il10ra | Lamp2 | Phlda1 | Ski | Tnfsf11 |
| Arnt2 | Cd86 | Foxf1 | Il12rb1 | Lef1 | Plac8 | Slamf7 | Tnfsf8 |
| Arntl | Cd9 | Foxm1 | Il12rb2 | Lgals3bp | Plagl1 | Slc1a4 | Tnfsf9 |
| Atf4 | CEACAM1 | Foxo1 | Il15ra | Lif | Plek | Slc2a1 | Tnip2 |
| B4galt1 | Cebpb | Foxp1 | Il17a | Lilrb4 | Plekhf2 | Slc6a4 | Tob |
| Bat3 | Chat | Foxp3 | Il17f | Litaf | Pmepa1 | Slc6a6 | Toso |
| Batf | Chd7 | Frmd4b | Il17ra | Lmnb1 | Pml | Slc7a3 | Tox2 |
| Batf2 | ChRM1 | Fzd7 | Il1r1 | LPXN | Pomc | Smad2 | Tph1 |
| Batf3 | ChRM3 | GABRA1 | Il1r2 | LRMP | Pou2af1 | Smad3 | Traf3 |
| BC021614 | ChRM5 | Gad1 | Il1rl1 | Lrrfip1 | Prc1 | Smad4 | Trat1 |
| Bcl11b | ChRNA10 | Gap43 | Il1rn | Lsp1 | Prdm1 | Smad7 | Trim24 |
| Bc12 | ChRNA4 | Gapdh | Il21 | Ltf | Prf1 | Smarca4 | Trim25 |
| Bcl211 | ChRNA9 | Gata3 | Il21r | Ly6c2 | Prickle1 | Smox | Trim30 |
| Bcl2111 | ChRNB2 | Gem | Il22 | Maf | Prkca | socs2 | Trps1 |
| Bcl3 | ChRNB4 | Gfi1 | Il23 | Maff | Prkd3 | Socs3 | Tsc22d3 |
| Bcl6 | Clcf1 | GIMAP5 | Il23r | Maob | Prnp | Spp1 | Tubb5 |
| Beta Actin | Cmtm6 | Gjal | Il24 | Map3k5 | Procr | Spry 1 | Tyh |
| BHLHE40 | CMTM6 | Glipr1 | Il27ra | Max | Prrx1 | Srxn1 | Ube3a |
| Bmpr1a | Comt | GMFG | Il2ra | Mbnl3 | Psmb9 | Stard10 | Ubiad1 |
| Calca | CREBZF | gng11 | Il2rb | Med24 | Pstpip1 | Stat1 | Vav3 |
| Cand1 | Csf2 | Golga3 | Il3 | Mgll | Ptprj | Stat2 | Vax2 |
| Casp1 | Csnk1a1 | Gp130 | Il33 | Mina | Ptprk | Stat3 | Xbp1 |
| Casp3 | Ctla2A | Gpr56 | Il35 | Mkln1 | Pxf/Pex19 | Stat4 | Xrcc5 |
| Casp4 | Ctla2b | Gpr65 | Il4 | Mt1 | Pycrl | Stat5 | ZBTB32 |
| Casp6 | CTLA4 | Grail | Il4ra | Mt2 | Rab33a | Stat5a | Zeb1 |
| cbl-b | Ctsw | Grn | IL6 | Mta3 | rab37 | Stat5b | Zfp161 |
| ccdc64 | Cxcl10 | Gusb | Il6st | Mxil | Rad51ap1 | Stat6 | Zfp238 |
| Ccl1 | Cxcl3 | Gzma | Il7r | Mycl1 | Rasgrp1 | Sufu | Zfp281 |
| Ccl12 | Cxcr3 | Gzmd | Il9 | Myd88 | Rbpj | Sult2b1 | Zfp410 |
| Ccl20 | Cxcr4 | Gzmg | Inhba | Myst4 | Rel | Tac1 | |
| Ccl4 | Cxcr5 | H2-Q10 | Irf1 | Nampt | Rela | Tacr1 | |
| Ccl5 | Cxcr6 | Havcr2 | Irf4 | Ncf1 | Rfk | Tal2 | |

Optimal expression of these co-inhibitory receptors (Tim-3, Lag-3, and Tigit) was observed at 96 hours for $CD4^+$ and 72 hours for $CD8^+$ T cells (FIG. 6A,B). Applicants then undertook whole genome mRNA profiling of $CD4^+$ and $CD8^+$ T cells in the presence of IL-27 at these corresponding timepoints. Applicants identified 1,392 genes that were differentially expressed between WT $CD4^+$ T cells stimulated in the presence or absence of IL-27 (Fold change>2 and FDR<0.2) and depended on TL-27 signaling based on JL,-27ra KG $CD4^+$ T cells. A subset of 118 differentially expressed genes were annotated as cell surface receptors or cytokines. Importantly, several genes known to encode molecules that have been previously shown to have an inhibitory effect on T cells such as, Tim3, Lag3, Jnhba, Alcam, CTLA2A as well as, cytokines such as IL10 were among the 118 genes. The subset (FIG. 6C, FIG. 6D) of 118 genes that encode cell surface receptors or cytokines, also included Tim3, Lag3, TIGIT, and IL10. Importantly, $CD4^+$ and $CD8^+$ T cells showed a similar pattern of differential gene expression (FIG. 6C, E, F).

Strikingly, there is a highly significant overlap between the IL-27-driven gene signature and gene signatures for other T cell states associated with dysfunction, including cancer, chronic viral infection, anergy, and tolerance (FIG. 6G, H, I, J). Specifically, Applicants found a significant overlap with each of the following signatures: (1) a gene signature for dysfunctional T cells in cancer (Singer et al., companion manuscript) defined by comparing PD-$1^+$Tim-$3^+$ $CD8^+$ (DP) TILs (representative of cluster 1 in FIG. 1E), which contain $CD8^+$ T cells that exhibit a severe dysfunctional phenotype, to that of PD-$1^-$Tim3-$CD8^+$ (DN) TILs (representative of cluster 2 in FIG. 1E), which preferentially contain $CD8^+$ T cells that have preserved effector function (Sakuishi et al., (2010) *The Journal of experimental medicine* 207, 2187-2194); (2) a gene signature for dysfunctional T cells from chronic viral infection, from previously published profiles (Doering et al., (2012) *Immunity* 37, 1130-1144) from virus-specific $CD8^+$ T cells isolated from mice infected with either the chronic clone 13 strain or the acute Armstrong strain of LCMV; (3) T cell anergy (Safford et al, (2005) *Nature immunology* 6, 472-480); and (4) induced T cell tolerance with either antigen-specific (Burton et al., (2014) *Nature communications* 5, 4741) or non-specific (anti-CD3 antibody) (Mayo et al., (2016) Brain, *A journal of Neurology*, Advance Access doi:10.1093/brain/aww113, 1-19) stimulation. This overall significant overlap (FIG. 6G) suggests that IL-27 may impact T cell function through one gene module across multiple states of T cell non-responsiveness. In particular, the IL-27-induced co-inhibitory receptors Tim-3, TIGIT, and Lag-3 were shared across at least four of the 5 analyzed signatures. Indeed, blockade of each of these molecules has already been shown to inhibit T cell exhaustion and promote anti-tumor and anti-viral immunity (Johnston et al., (2014) *Cancer cell* 26, 923-937; Woo et al., (2012) *Cancer research* 72, 917-927; Sakuishi et al., (2010) *The Journal of experimental medicine* 207, 2187-2194; Jin et al., (2010) *Proc Natl Acad Sci U S A* 107, 14733-14738; and Blackburn et al., (2009) *Nature immunology* 10, 29-37).

More specifically, a gene signature for dysfunctional T cells in cancer was generated by comparing the gene expression of PD-$1^+$ Tim-$3^+$ $CD8^+$ TILs (representative of cluster 1), which contains CD8+ T cells with severe exhausted phenotype, to that of PD-1-Tim$3^-$ $CD8^+$ TILs (representative of cluster 2), which contains CD8+ T cells that retain good effector function (Sakuishi, et al., (2011) Trends in immunology 32, 345-349). Gene signatures for exhausted T cells were further generated in the chronic LCMV model from publically available gene expression data by comparing virus-specific $CD8^+$ T cells from clone13 LCMV infection to virus-specific $CD8_+$ T cells from Armstrong LCMV infection (Harker, J. A., et al., (2013) *Immunity* 39, 548-559). The IL-27-induced module of surface receptors/cytokines was then compared with the signatures for dysfunctional T cells from cancer and chronic viral infection and significant overlap was observed in the number of surface receptors/cytokines across the different data sets. Importantly, it was found that the IL-27 induced co-inhibitory receptors Tim-3 (HAVCR2), Tigit and Lag-3 were shared among the three data sets, supporting the association of IL-27-driven genes to dysfunctional T cell states in vivo. The entire IL-27-induced gene signature was further found to overlap significantly with the gene signatures for dysfunctional T cells from cancer and chronic virus infection as well as other states of T cell non-responsiveness such as anergy and tolerance (p-value<0.01). Of note, several survival factors including IL-21, IL-2Ra, I16st and IL-7R and activation markers were also found as shared genes, indicating that the IL-27-driven gene module is not merely a collection of co-inhibitory molecules that restrain activated T cells but also factors that regulate the survival of cells in tissue. Together these data strongly point to a key role for IL-27 in driving molecular programs that dampen effector T cell function.

Procr and Pdpn are Novel Co-Inhibitory Receptors Induced by IL-27

Figure 6M:
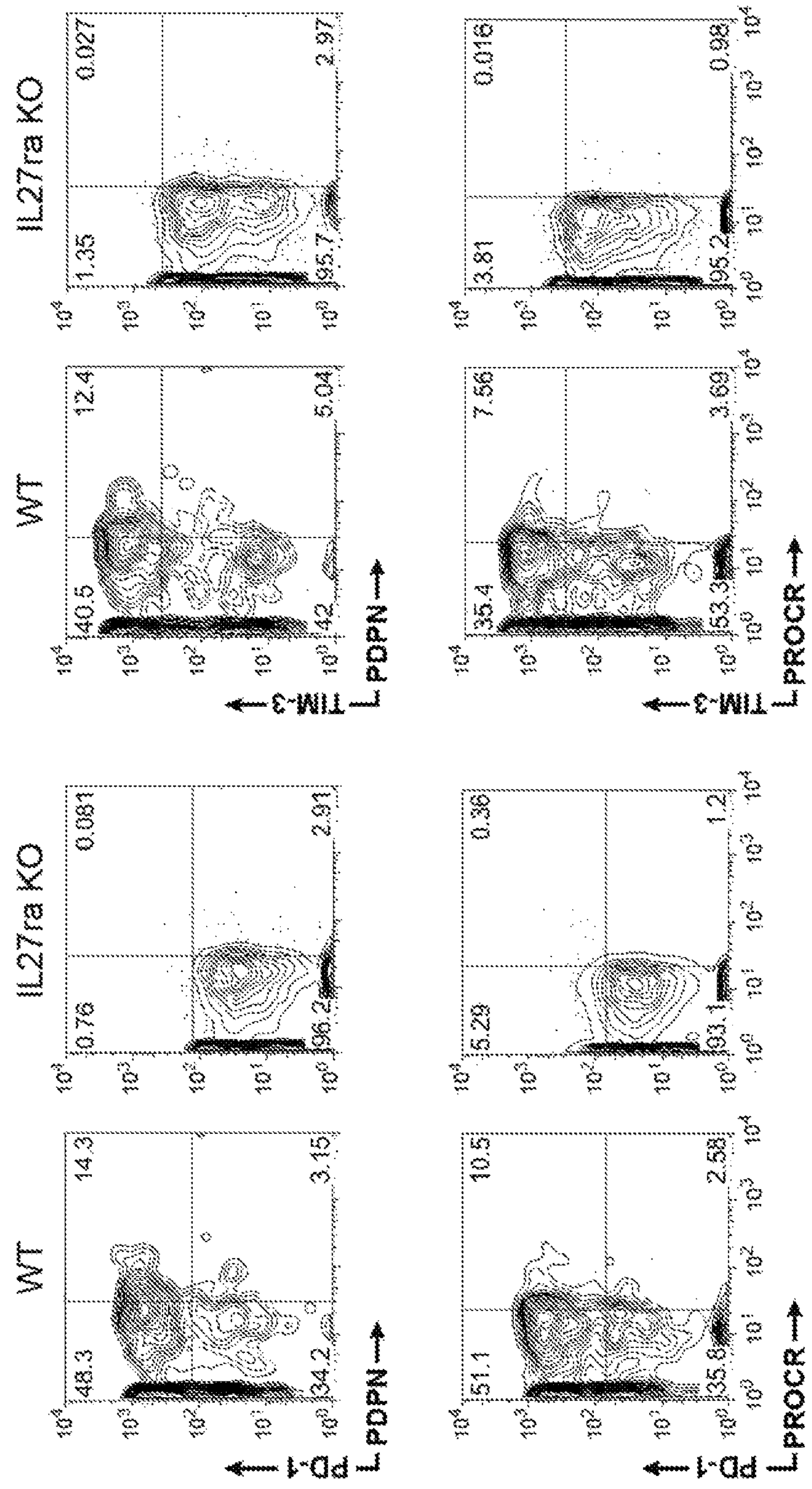

Among the 118 surface molecules and cytokines induced by IL-27 (FIG. 6C), some molecules were also highly expressed in specific settings (FIG. 6G), such as in cancer or in chronic viral infection (FIG. 6K), allowing stratification of molecules for additional investigation, based on their uniqueness to specific settings. In particular, two of the IL27-induced surface molecules, Procr (protein C receptor) and Pdpn (podoplanin) were highly expressed in the setting of cancer T cell dysfunction compared to other states of T cell non-responsiveness (FIG. 6K). Applicants confirmed that activation of naïve $CD4^+$ and $CD8^+$ T cells in vitro in the presence of IL-27 induced the expression of both Procr and Pdpn as determined by qPCR and flow cytometry (FIG. 6L). Furthermore, both Procr and Pdpn were co-expressed with PD-1 and Tim-3 on $CD8^+$ TILs and their expression was lost in the absence of IL-27 receptor signaling (FIG. 6M).

Figure 6N:
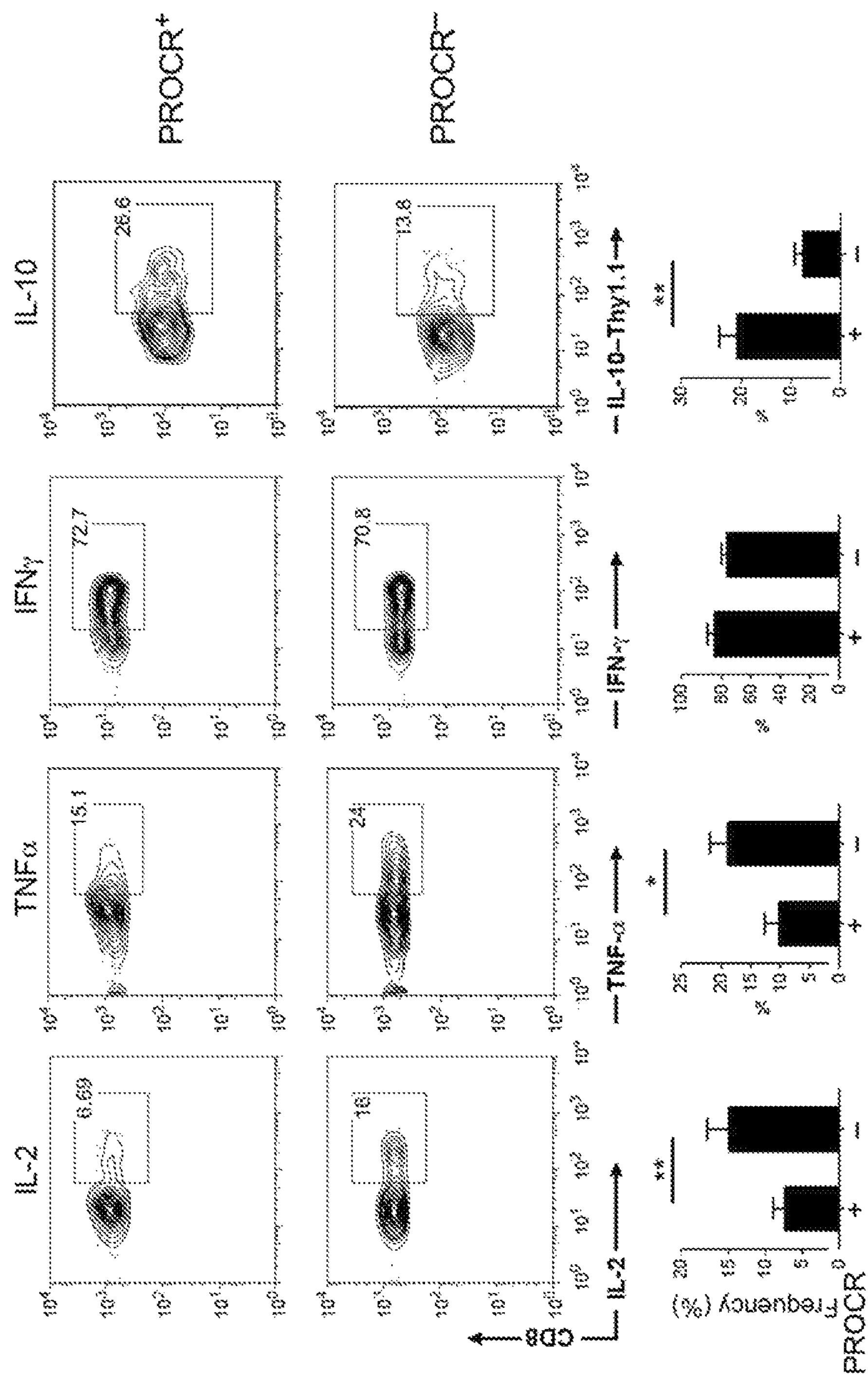
Figure 6O:
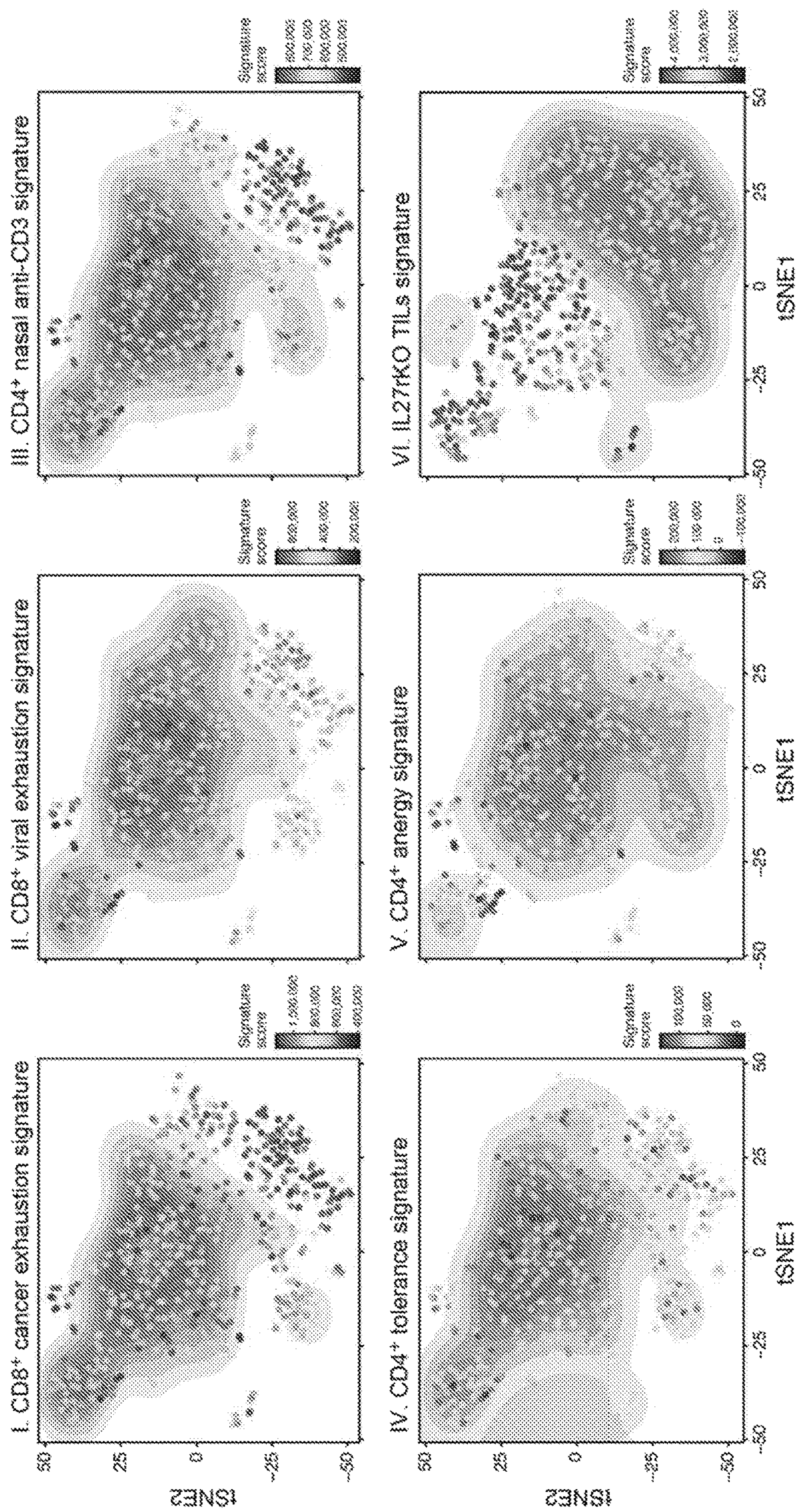

Procr is a cell surface receptor known to be expressed on both vascular endothelial cells and tumor cells, where it regulates endothelial cell function and tumor cell migration and invasion, respectively (Mohan Rao et al., (2014) Blood 124, 1553-1562). In the lymphocyte compartment, Procr is expressed on $CD4^+$ T cells, particularly Th17 cells (Yosef et al., (2013) *Nature* 496, 461-468), where it is in co-variance with the regulatory module (Gaublomme et al., (2015) *Cell* 163, 6, p1400-1412); however its function on $CD8^+$ T cells has not been previously explored. $Procr^+$ $CD8^+$ TILs exhibit a dysfunctional phenotype, producing less TNFα and IL-2 and more IL-10 than Procr-$CD8^+$ TILs (FIG. 6N).

Figure 7A:
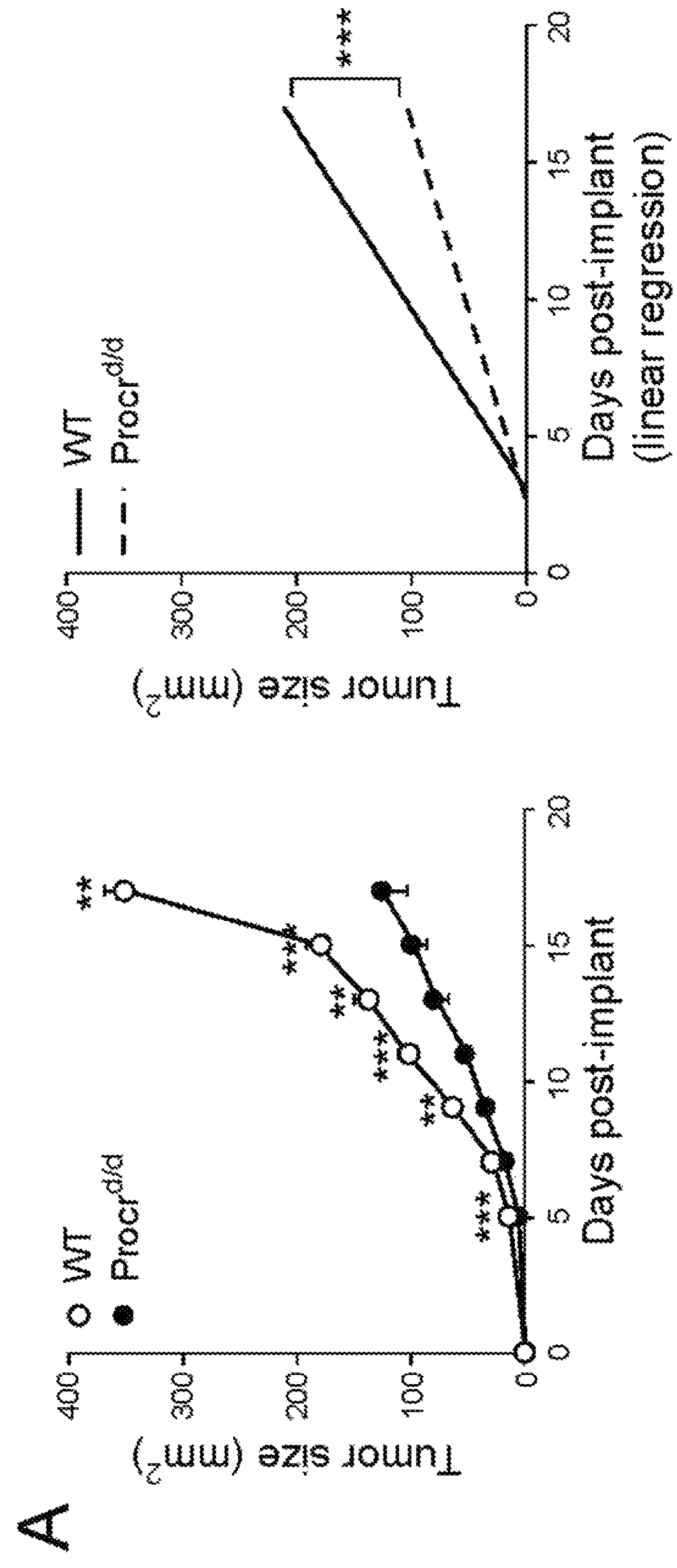
Figure 7B:
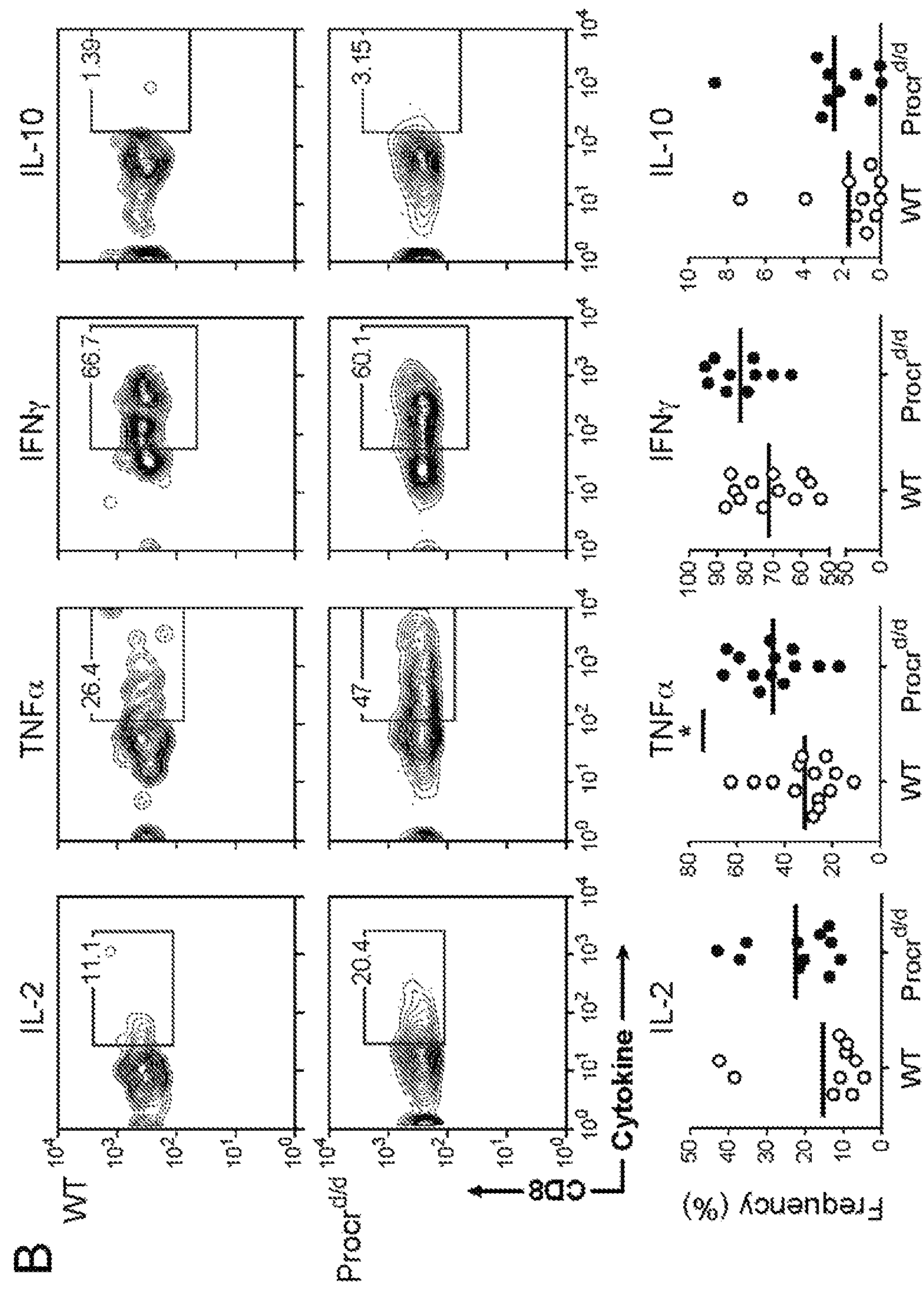
Figure 7C:
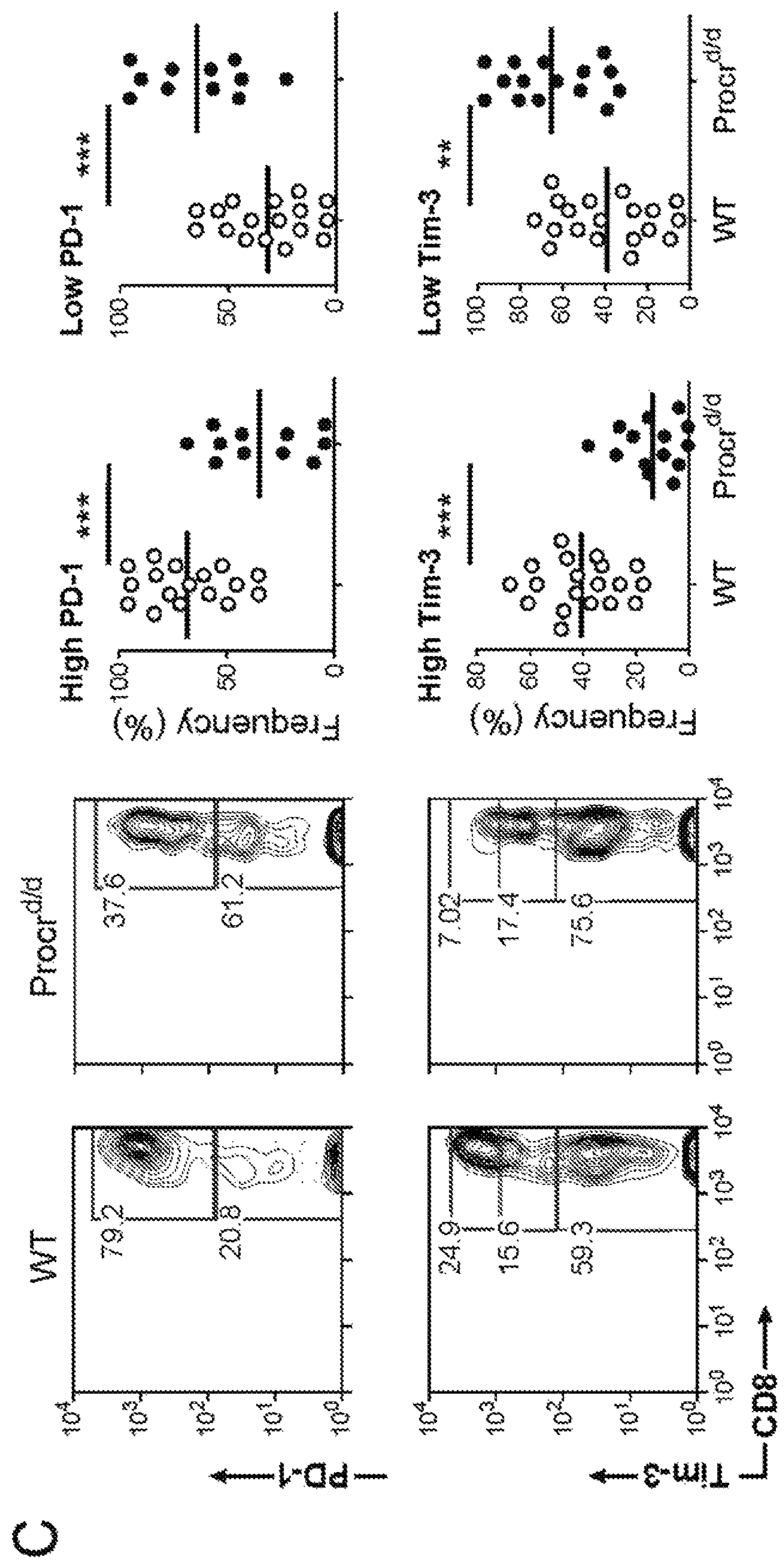
Figure 8:
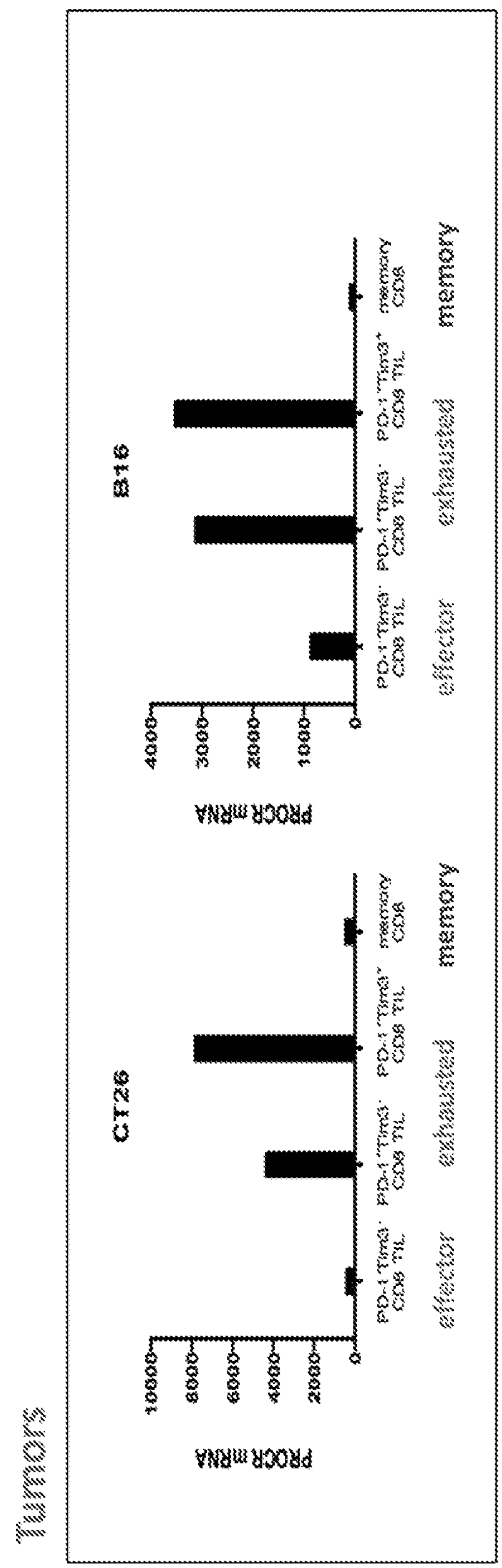
FIG. 8. Exemplary data indicating that PROCR is on exhausted CD8 T cells.
Figure 9:
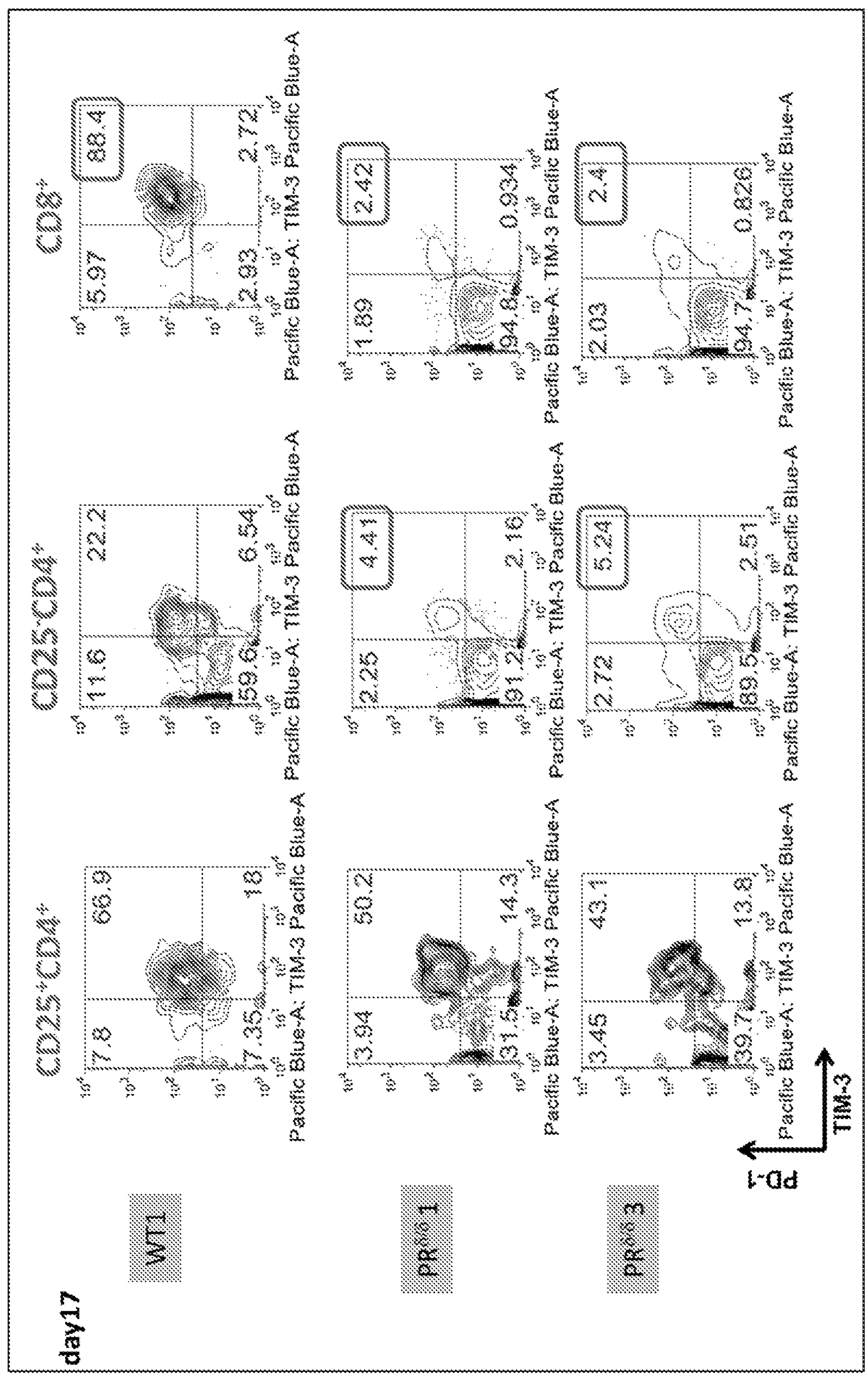
FIG. 9. Reduced accumulation of exhausted T cells in $PR^{d/d}$ mice.

To examine the role of Procr in regulating effector CD8+ T cell function, Applicants used a Procr hypomorph ($Procr^{d/d}$) mouse strain (Castellino et al., (2002) *Thrombosis and haemostasis* 88, 462-472). B16F10 melanoma cells were implanted into $Procr_{d/d}$ mice and striking inhibition of tumor growth was observed (FIG. 7A). Importantly, CD8+ TILs from $Procr^{d/d}$ mice exhibited enhanced TNFα production, corresponding to enhanced tumor immunity but did not show a significant difference in the expression of other cytokines, including IL-2, IFN-γ and IL-10 (FIG. 7B). Moreover, $Procr^{d/d}$ TILs exhibited a striking decrease in the frequency of $CD8^+$ T cells expressing high levels of Tim-3 and PD-1, suggesting that Procr signaling on $CD8^+$ T cells promotes severe dysfunctional phenotype and loss of Procr in the host partially reverses this (FIG. 7C).

Figure 10C:
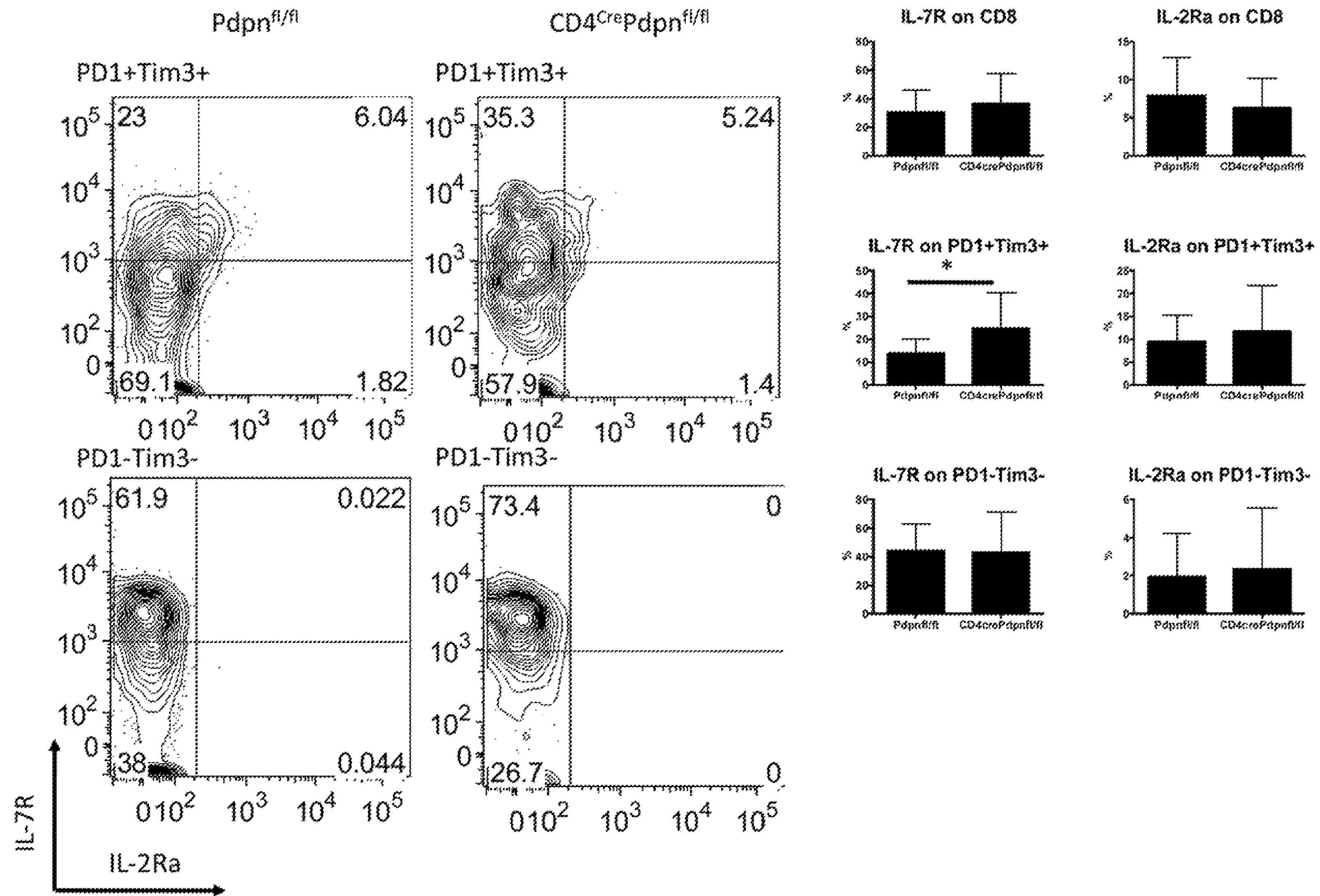

Another cell surface molecule Podoplanin (Pdpn) is expressed on several tumor types, in which it has a role in lymphovascular invasion and metastasis (Wicki et al., (2006) *Cancer cell* 9, 261-272). More recently, it was reported that Pdpn is expressed in effector $CD4^+$ T cells where it functions to limit T cell survival in inflamed tissues in an autoimmune setting (Peters et al., (2015) *The Journal of clinical investigation* 125, 129-140); however, whether Pdpn has a role in tumor-induced $CD8^+$ T cell dysfunction is not known. The current data indicate that Pdpn is specifically expressed on $CD8^+Tim\text{-}3_+PD\text{-}1^+$ TILs and marks a population which still has pro-inflammatory cytokine production, but already start producing IL-10. (FIG. 10A).

Figure 11A:
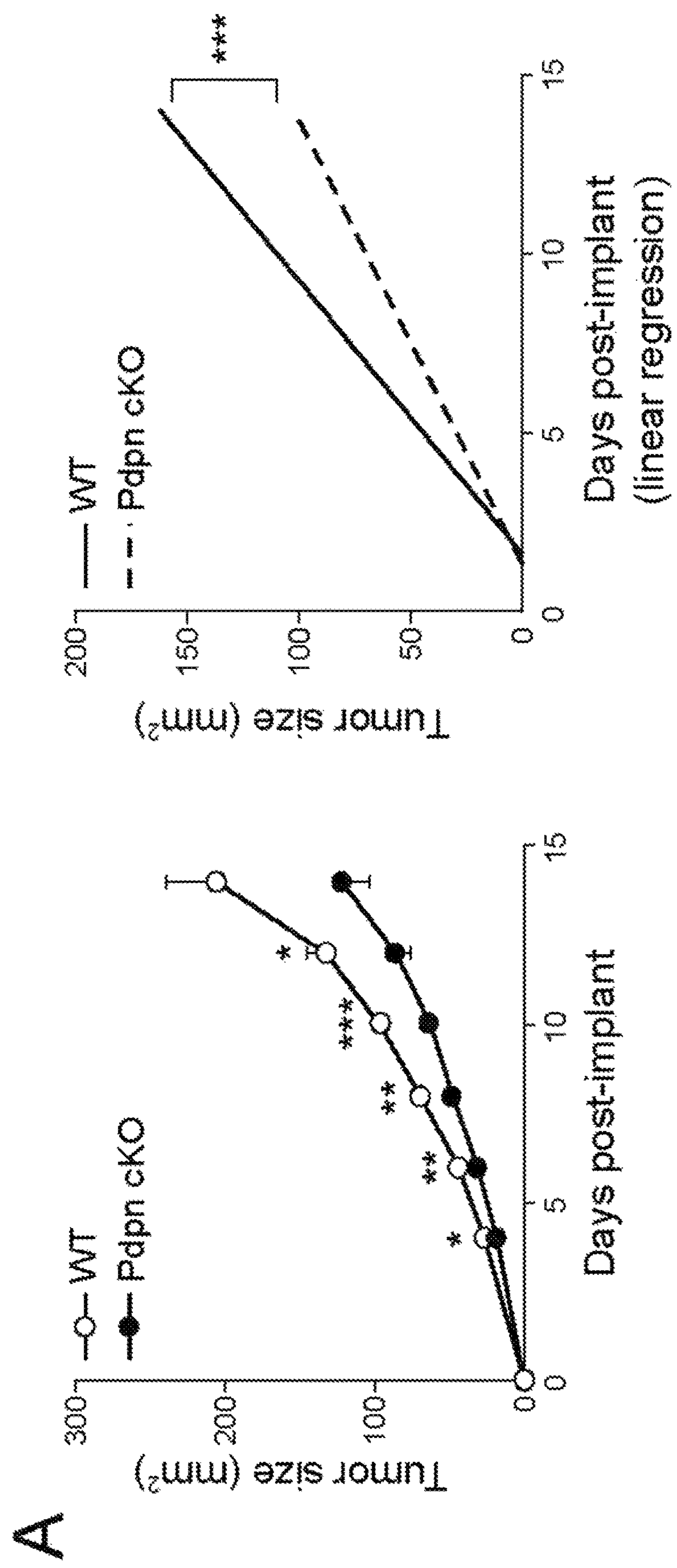
FIG. 11A-C. Role of Pdpn in T cell dysfunction and anti-tumor immunity. A) Pdpn fl/fl (WT, n=5) and CD4crePdpnfl/fl (Pdpn cKO, n=5) mice were implanted with B16F10 melanoma. Left panel, mean tumor size ±s.e.m. *p<0.05; p<0.01; *p<0.001, t-test. Right panel, linear regression p<0.001. Data shown are representative of 3 independent experiments. B) Top panels, representative flow cytometry data showing cytokine production of $CD8^+$ TILs from WT and Pdpn cKO bearing B16F10 melanoma. Bottom panels, summary data. *p<0.05; ***p<0.001, t-test. C) Pdpn deficient CD8 T cells lose PD-$1^+$ $Tim3^{high}$ subpopulation. Lack of Pdpn lost Tim-$3^{high}$ population of CD8 TILs. Left panels, representative flow cytometry data showing Tim-3 and PD-1 expression on $CD8^+$ TILs from WT and Pdpn cKO bearing B16F10 melanoma. Right panels, summary data. *p<0.05, t-test.
Figure 11B:
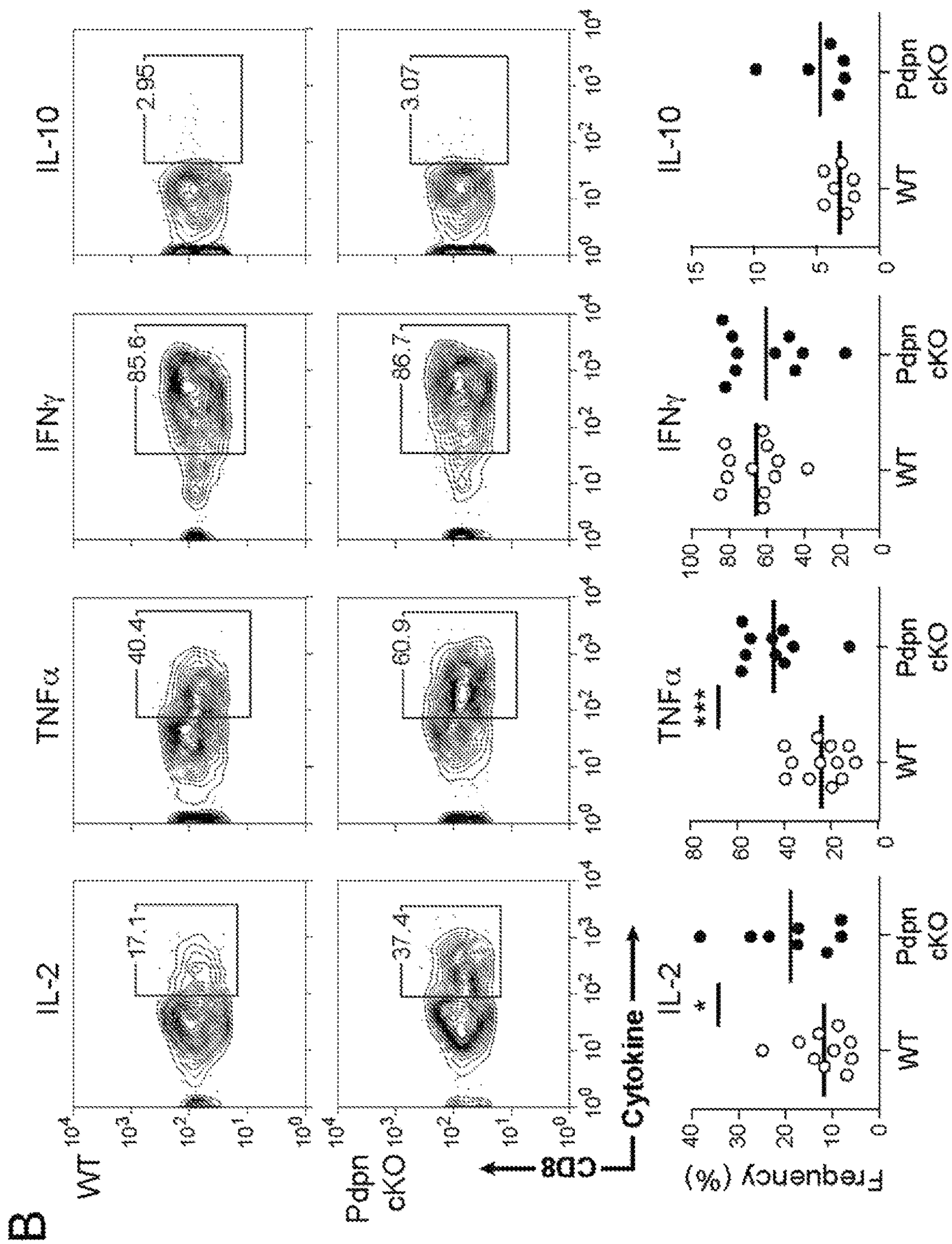
Figure 11C:
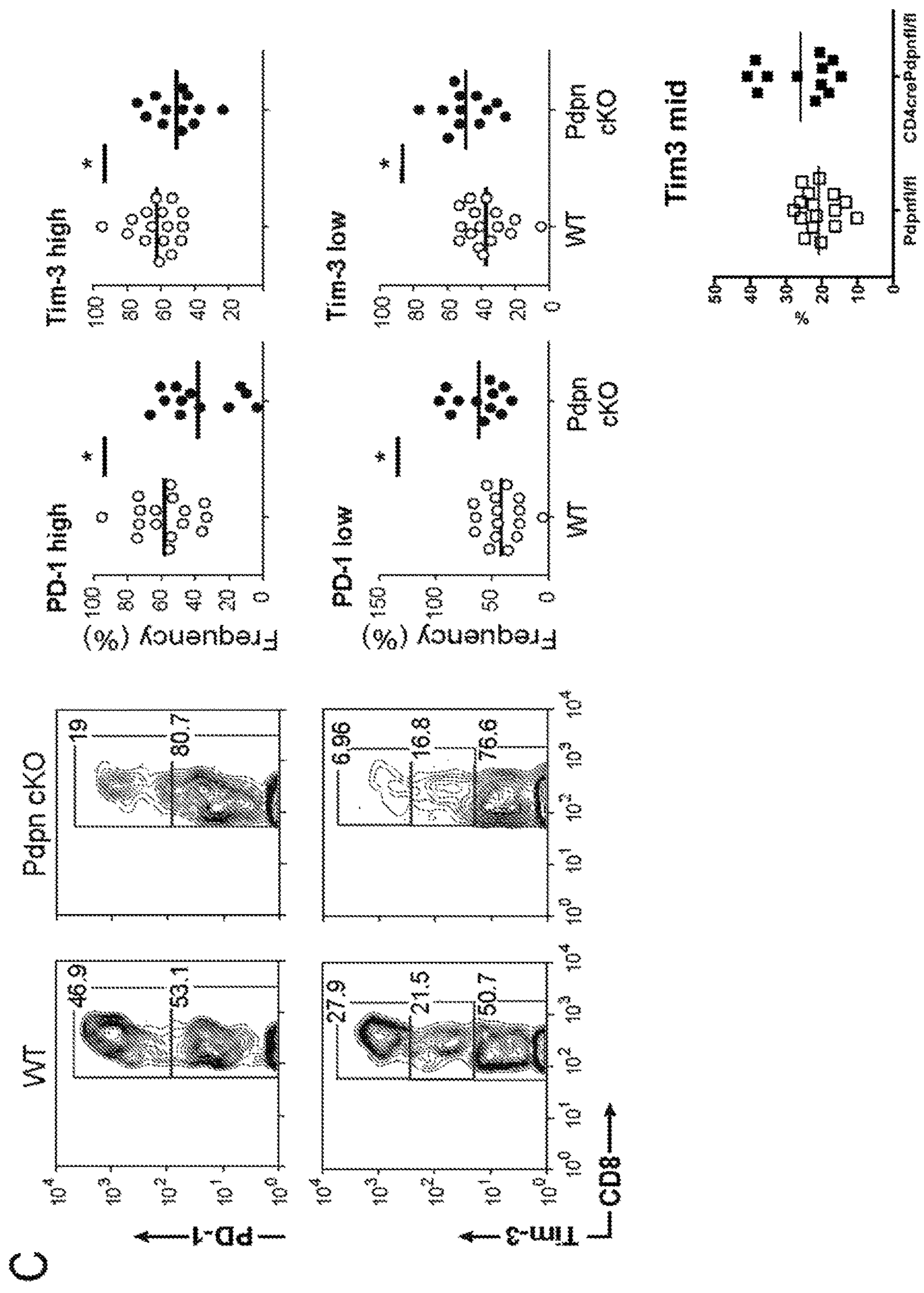

To analyze the functional role of Pdpn in anti-tumor immunity, Applicants used T-cell specific Pdpn conditional knock-out mice (Pdpn cKO). Mice with Pdpn-deficient T cells showed a significant delay in growth of B16F10 melanoma compared to control mice (FIG. 11A) and Pdpn-deficient $CD8^+$ TILs exhibited enhanced IL-2 and TNFα production but no significant difference in IFN-γ and IL-10 production (FIG. 11B). Consistent with these data, lack of Pdpn on T cells was also associated with a decrease in the frequency of $CD8^+$ TILs expressing high levels of Tim-3 and PD-1, indicating reduced accumulation of T cells with a severe dysfunctional T cell phenotype (Sakuishi et al., (2010) *The Journal of experimental medicine* 207, 2187-2194) (FIG. 11C). Moreover, Pdpn-deficient $PD\text{-}1^+$ $Tim\text{-}3^+$ $CD8^+$ TILs had higher expression of IL-7Ra when compared to wild type, as was previously shown (Peters et al., (2015) *The Journal of clinical investigation* 125, 129-140), indicating that Pdpn may contribute to T cell dysfunction by limiting the survival of $CD8^+$ TILs in the tumor microenvironment (FIG. 10B).

$CD8^+$ T cells exhibit an exhausted phenotype within the tumor microenvironment, and express multiple co-inhibitory receptors on their surface. Here it is shown that the IL-27 signaling pathway induces multiple known, as well as several heretofore unknown receptors with co-inhibitory function on naïve $CD8^+$ T cells. By using global gene expression data and computational approaches to compare the IL-27-driven gene signature to the gene signature of dysfunctional T cells in two chronic disease states, Applicants identified an "inhibitory module" induced by IL-27 that includes known co-inhibitory receptors (Tim-3, Lag-3, TIGIT), along with 37 novel cell-surface molecules and cytokines. It is shown herein that two of these novel molecules have co-inhibitory function in vivo. These data indicate that IL-27 signaling induces a complex repertoire of inhibitory receptors, each of which can contribute to the exhausted state, thus setting the stage for the development of a dysfunctional effector T cell phenotype.

The inventors further applied this computational approach including gene signatures from several T cell impairment states, such as anergic CD4 T cells, tolerized CD4 T cells following chronic stimulation with subcutaneous antigen, and anti-CD3 stimulated IL-10 producing Foxp3-CD4 T (Tr1) cells compared with to IL-10 non-producing Foxp3-CD4 T cells following nasal tolerance. This approach increased the number of candidates represent regulatory state of IL-27 signature to a total of 57 molecules. Of note, known co-inhibitory molecules; LAG-3, Tim-3, and Tigit were still highly shared genes among data sets, indicating that the IL-27 signature has the potential to introduce general gene module of T cell impairment states.

The inventors identified 2 of the molecules, Pdpn and Procr, as co-inhibitory receptors that suppress tumor immunity and promote a dysfunctional phenotype in TILs cells. It was previously reported that Pdpn regulates IL-7R expression on T cells, which is important for long-term T cell survival (Peters et al., 2015). Studies suggested that exhausted CD8 T cells have a defect in their survival and IL-7R expression, whereas IL-7 antagonized inhibitory networks and promote survival of CD8 T cells (Lang, K. S. et al. (2005) European journal of immunology 35, 738-745; Pellegrini, M. et al. (2009) Nature medicine 15, 528-536). In the current tumor model, loss of Pdpn resulted in recovery of IL-7R expression on PD-1+ Tim-3+CD8 T cells. This indicates that there may be antagonism between PDPN and I1-7R expression and therefore affecting IL-7 responsiveness and survival of exhausted T cells.

Lack of Procr signaling had strong impact on losing $PD\text{-}1^{30}$ $Tim\text{-}3^{high}$ CD8 TILs and facilitating tumor immunity. Although the role of Procr on CD8 T cells still needs further analysis, the inventors also found that with mutations of Procr resulted in a loss of the exhausted CD8 T cell phenotype in the chronic model of LCMV infection mice.

The strategy of global screening analysis of IL-27R signaling identified novel biomerkers in the field of T cell exhaustion that facilitated dissection of this functional state and can also be useful for prognosis prediction before and after check-point therapy. Thus, targeting Pdpn and Procr for enhanced tumor immunity has been validated as a potential new check-point therapy.

Prdm1 partially regulates the IL-27-driven gene module

Given the observation that individual cells co-express multiple co-inhibitory molecules, many of which are induced by a common stimulus, IL-27, Applicants hypothesized that a common regulator downstream of IL-27 signaling controls this module. Several lines of evidence supported a role for the transcription factor Prdm1 as a common regulator. First, Prdm1 can be induced by IL-27 and is known to regulate IL-10 production in T cells (Newmann et al., (2014) *The Journal of experimental medicine* 211, 1807-1819). Second, 80% of the genes within the IL-27-driven inhibitory gene module have evidence for binding by Prdm1 in their promoter regions based on ChIP-Seq data from CD8+ T cells (Shin et al., (2013) *Immunity* 39, 661-675) (Example 2: Methods and Resources). Third, the ChIP-Seq evidence was further extended into a validated network model by in vitro functional testing based on gene expression profiles from naïve CD8+ T cells from WT and Prdm1-deficient mice stimulated with IL-27. Thus, Prdm1 binds and functionally regulates multiple cell surface molecules and cytokines in the IL-27 driven inhibitory gene module including Tim-3, Tigit, and Lag3 (FIG. 12A). Finally, Prdm1 was not only induced by IL-27 in $CD8^+$ cells in vitro but also expressed at higher levels by dysfunctional $Tim\text{-}3^-PD\text{-}1^+$ (SP) and $Tim\text{-}3^+PD\text{-}1^+$ (DP) $CD8^+$ TTLs compared to $Tim\text{-}3^-PD\text{-}1^-$ $CD8^+$ (DN) TTLs that maintain effector function (FIG. 12B).

Figure 12C:
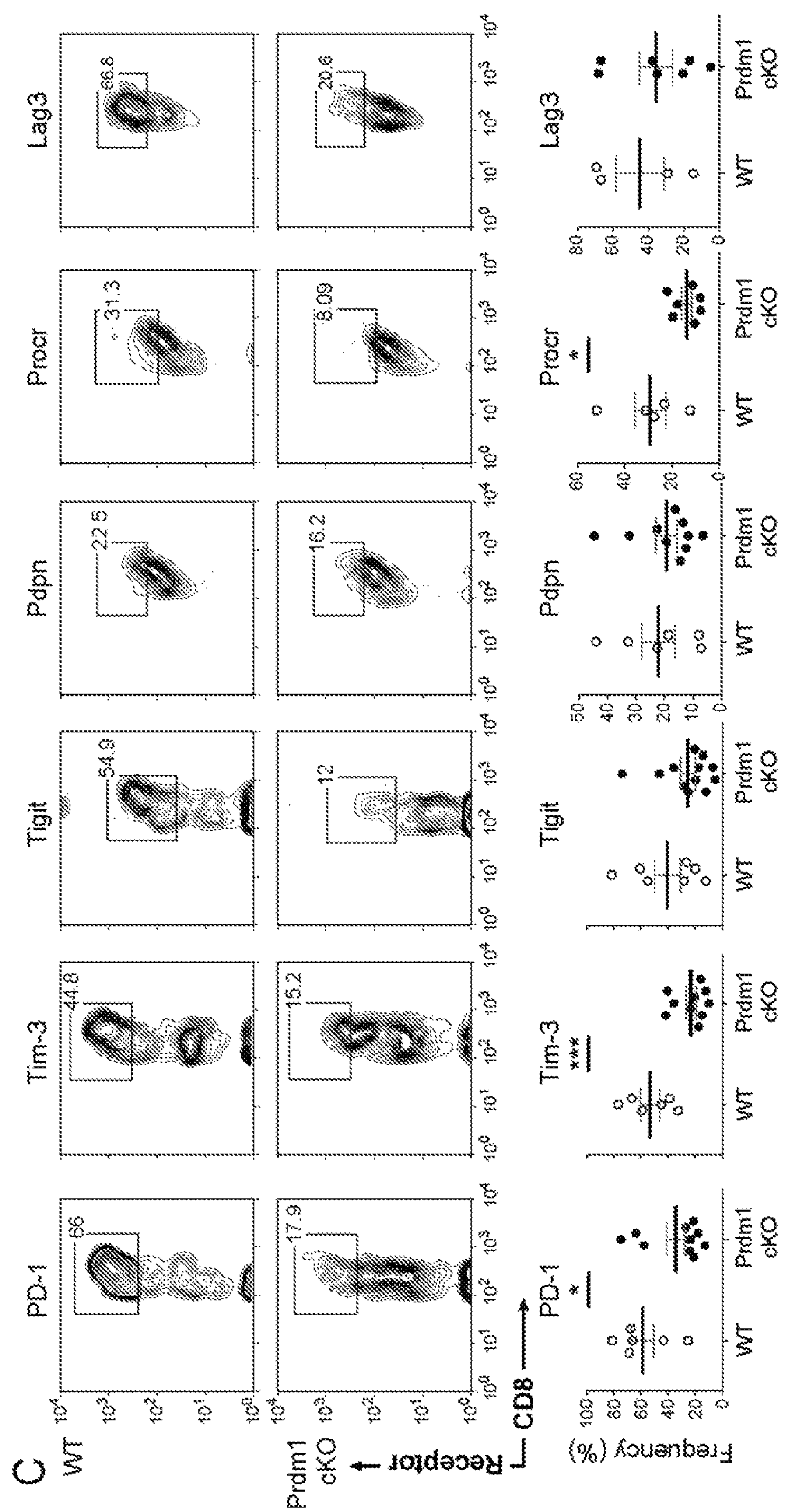
Figure 12D:
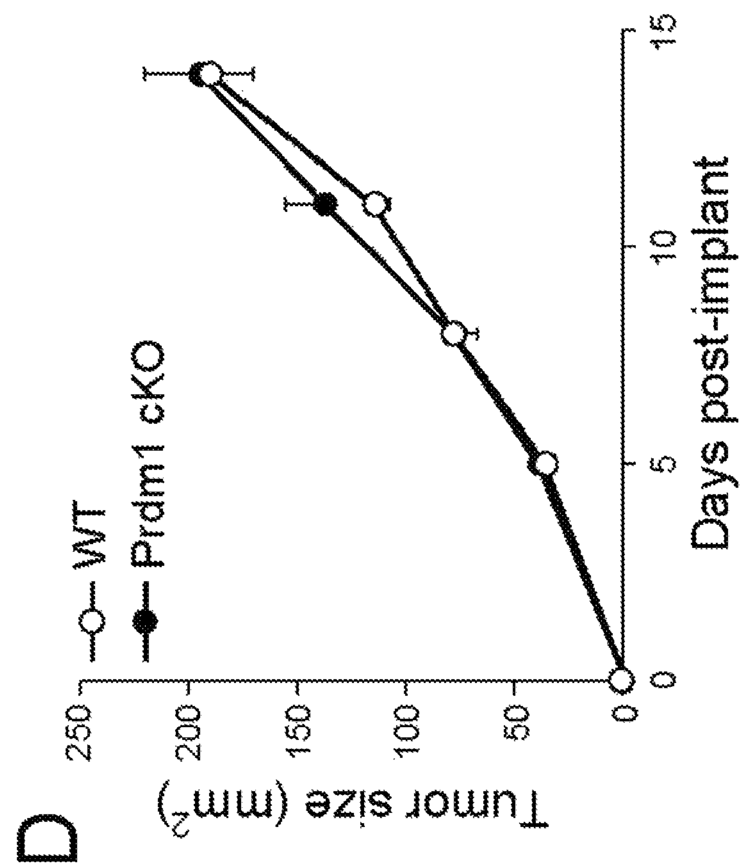

Applicants thus hypothesized that Prdm1 plays a role in CD8+ T cells in vivo in regulating the expression of members of the co-inhibitory gene module and in anti-tumor immunity. To test this, Applicants examined mice with a T cell specific deletion of Prdm1 (Prdm1 cKO) and found that Prdm1-deficient $CD8^+$ TILs expressed lower levels of multiple co-inhibitory receptors including Tim-3, PD-1, TIGIT, Lag3, and Procr, but not Pdpn (FIG. 12C). However, despite the overall decreased expression of co-inhibitory receptors in Prdm1 cKO mice, there was no difference in the growth of B16F10 melanoma as compared to wild type controls (FIG. 12D). Thus, the reduction of co-inhibitory receptor expression in Prdm1 cKO mice was not sufficient to completely reverse the dysfunctional phenotype and recover effector T cell responses to promote anti-tumor immunity.

c-Maf Plays an Alternate Role for Regulating Co-Inhibitory Molecules

Since regulatory networks are often dense and interconnected across multiple, partially redundant regulators (Novershterm et al., (2011) *Cell* 144, 296-309; Yosef et al., (2013) Nature 496, 461-468), Applicants explored whether other transcriptional regulator(s) may also mediate expression of the co-inhibitory receptor module and could compensate in vivo for the lack of Prdm1. Applicants analyzed gene expression in CD8$^+$ TILs from Prdm1 cKO mice using a custom code set of 397 genes representing both the IL-27-driven gene signature (245 genes) and the dysfunctional CD8$^+$ TIL gene signature (245 genes) (Example 2: Methods, Table 17). In addition to the expected reduction in the expression of multiple co-inhibitory, including PD-1, Tim-3, Lag3, and Tigit in Prdm1 deficient CD8+ TILs relative to wild type T cells (FIG. 13A), only a few genes were consistently induced, including one transcription factor, c-Maf.

TABLE 17

| Tr1 and Cancer | | Tr1 not in cancer | | Cancer not in Tr1 | | Other | House keeping |
|---|---|---|---|---|---|---|---|
| SPP1 | KLHL6 | CEBPB | GATM | EPAS1 | ZFP362 | CD94 | Tubb5 |
| GZME | ST6GAL1 | JUN | P4HA1 | PBX3 | RAI1 | RankL | hprt |
| KLRE1 | PARP9 | HLX | ACADL | ARNT2 | SLC39A8 | CD160 | actin |
| GZMD | CXCR4 | FOSL2 | SLC7A3 | MDFIC | HEMGN | CD200 | gapdh |
| IL1R2 | CXCL10 | IRF8 | FZD7 | UHRF2 | TNFSF8 | CD152 | |
| GSTM5 | SOCS1 | STAT1 | IER3 | CDKN2B | PKD1 | CD226 | |
| CALCB | EPCAM | KLF7 | IL12RB2 | TRPS1 | WDR59 | CD279 (PD-1) | |
| GZMC | SOCS3 | ATF6 | LGALS3 | ETV5 | STIM2 | ICOS | |
| MT2 | GATSL3 | GTF3C5 | NFIL3 | PABPCIL | GSTK1 | TNFRSF14 | |
| MT1 | IGTP | NFE2L2 | PSTPIP1 | NCOR2 | GYPC | TNFRSF18 | |
| MYO10 | CDK5R1 | NFYB | ALCAM | GZMD | MAPK1IP1 | TNFRSF9 | |
| PENK | DAXX | TLE6 | LILRB4 | GZMF | TOX | BTLA | |
| SPATS2 | IFI47 | ZKSCAN6 | BCL2L11 | GLDC | SPRY2 | NR3C1 | |
| SERPINE2 | IRF6 | MAFF | GZMA | SERPINB9B | REM2 | TIGIT | |
| SRXN1 | TOP1MT | STAT3 | IL10RA | SPIN4 | NR4A2 | FoxP3 | |
| SDCBP2 | DHCR24 | BATF | IL2RB | OSGIN1 | ELK3 | KLRa3 | |
| PRF1 | STAT5A | HIF1A | KLRC1 | TMPRSS6 | BHLHE40 | IFNg | |
| ENO3 | BC006779 | IRF4 | PTPN1 | IGSF5.PCP4 | NFATC1 | TNFa | |
| SYTL3 | MTAP | STAT4 | IL12RB1 | TMEM171 | PDCD1 | IL2 | |
| FILIP1 | EGR3 | FLI1 | SIGIRR | GABRR1 | PKD2 | WSX1 | |
| AKRIB8 | FAM26F | RUNX1 | BCL2 | OSBPL3 | NRN1 | IL23R | |
| OCIAD2 | STYK1 | GATA3 | IL21R | CD244 | DUSP4 | CCR4 | |
| RBPJ | DUSP16 | IRF1 | SEMA7A | CCRL2 | PLSCR1 | CCR5 | |
| ADAM9 | SEMA4C | IRF9 | IL21 | LTF | SLC16A11 | CCR8 | |
| BNIP3 | C1QL3 | BCL3 | CCR5 | NSL1 | SLC22A15 | CCR7 | |
| EMILIN2 | ITIH5 | ETV6 | CTLA2A | GZMG | RAPH1 | CXCR3 | |
| GEM | PHACTR2 | ID2 | CTLA2B | GPR56 | GPD2 | CCL4 | |
| CDK6 | TG | AHR | IL10 | RASD2 | ATP2B2 | CCL5 | |
| ANXA2 | CSF1 | ARID5A | SERPINF1 | RIPPLY3 | NCAM1 | Runx2 | |
| CCNB1 | PADI2 | BATF3 | DDR1 | TMEM119 | SLC16A4 | eomes | |
| PRDM1 | CREB3L2 | CHD7 | SEMA4D | DEPDC1A | SERPINB6A | rorc | |
| LITAF | TWSG1 | MYST4 | SERPINB1A | ALOX5 | FASL | rora | |
| ABCB9 | SERPINA3G | SAP30 | IFITM3 | MSRB3 | UBASH3B | Foxo3a | |
| SLC39A14 | PTER | CREM | MYD88 | MGAT3 | TNFRSF4 | Tcf4 | |
| ZBTB32 | COPZ2 | PML | IL17RA | ARF2 | DUSP3 | Tcfe2a | |
| BC068157 | SERPINB9 | ATF3 | IL6ST | KLHL30 | AFF3 | Tcf7L1 | |
| GALC | SERPINB6B | ETS1 | SGK1 | RXRA | LEF1 | Tcf7L2 | |
| AA467197 | TBX21 | NOTCH1 | LAMP2 | TCF7 | IL1RL2 | axin2 | |
| EXO1 | CASP4 | SERTAD1 | | RERE | | cysltr1 | |
| DENND3 | IL2RA | GFI1 | | SSBP2 | | cysltr2 | |
| SLC2A3 | NDRG1 | JUNB | | PPP1R13B | | cysltr3 | |
| LPXN | TMCC3 | KLF6 | | ZSCAN12 | | IL33 | |
| MXI1 | TRPC1 | MLLT6 | | IKBKB | | bcl6 | |
| WDFY1 | LANCL3 | SP4 | | TCF12 | | bcl6b | |
| KLF10 | GSTT3 | TULP4 | | FOXP1 | | | |
| PLEKHF1 | SRGAP3 | IRF7 | | FOXO1 | | | |
| PPP1R3B | FAM176B | ZFP281 | | YEATS2 | | | |
| CTSD | SH3BGRL | SELP | | TLE4 | | | |
| PKP2 | TMEM49 | SERPINB5 | | ZEB1 | | | |
| HAVCR2 | KLRD1 | TMEM35 | | PHC2 | | | |
| ADAM8 | LPAR3 | CH25H | | ZFP1 | | | |
| IGF2BP2 | CIAPIN1 | RAB33A | | RGS10 | | | |
| PIWIL2 | PMEPA1 | TGM1 | | LOC100048338.PDLIM1 | | | |
| DAPL1 | ST3GAL6 | LAG3 | | PIK3R5 | | | |
| EMB | SELL | ERO1L | | TLR1 | | | |
| PDE4B | GBP2 | GBE1 | | FGF13 | | | |
| ID3 | PLTP | GSN | | IL6RA | | | |
| AB124611 | SEMA4F | H2-Q10 | | ARHGEF3 | | | |
| IL7R | CAMKK2 | HOPX | | RECK | | | |
| SLAMF6 | THA1 | PYGL | | PRICKLE1 | | | |

TABLE 17-continued

| Tr1 and Cancer | | Tr1 not in cancer | Cancer not in Tr1 | Other | House keeping |
|---|---|---|---|---|---|
| SEMA4B | FAM65B | SELENBP1 | ITGB7 | | |
| SMAD3 | GPR114 | GZMB | RASA3 | | |
| GPR18 | SH3BP5 | IMPA2 | CD7 | | |
| ENC1 | AQP9 | KLRK1 | IFIT1 | | |
| KBTBD8 | SATB1 | NKG7 | IFIT3 | | |
| AS3MT | LPINI | PLAC8 | PIM2 | | |
| PGS1 | SNHG7 | ACVRL1 | ARHGEF18 | | |
| EGLN3 | PDPN | DNTT | CHD3 | | |
| RTP4 | PROCR | TGFB3 | DGKA | | |

c-Maf is a transcription factor, which regulates IL-10 expression (Apetoh et al., 2010), is induced by IL-27 (Awasthi et atl., (2007) Nature immunology 8, 1380-1389), and was reported to drive expression of co-inhibitory molecules (Giordano et al., (2015) *EMBO J* 34, 2042-2058). Since Prdm1 is also reported to regulate IL-10 expression, Applicants hypothesized that compensatory up-regulation of c-Maf could explain the lack of anti-tumor immunity observed in Prdm1 cKO mice. Supporting this hypothesis, many of the genes in the IL-27-driven inhibitory gene module have a binding motif and a reported binding event for c-Maf within their promoter regions (Ciofani et al., (2012) *Cell* 151, 289-303).

Figure 13B:
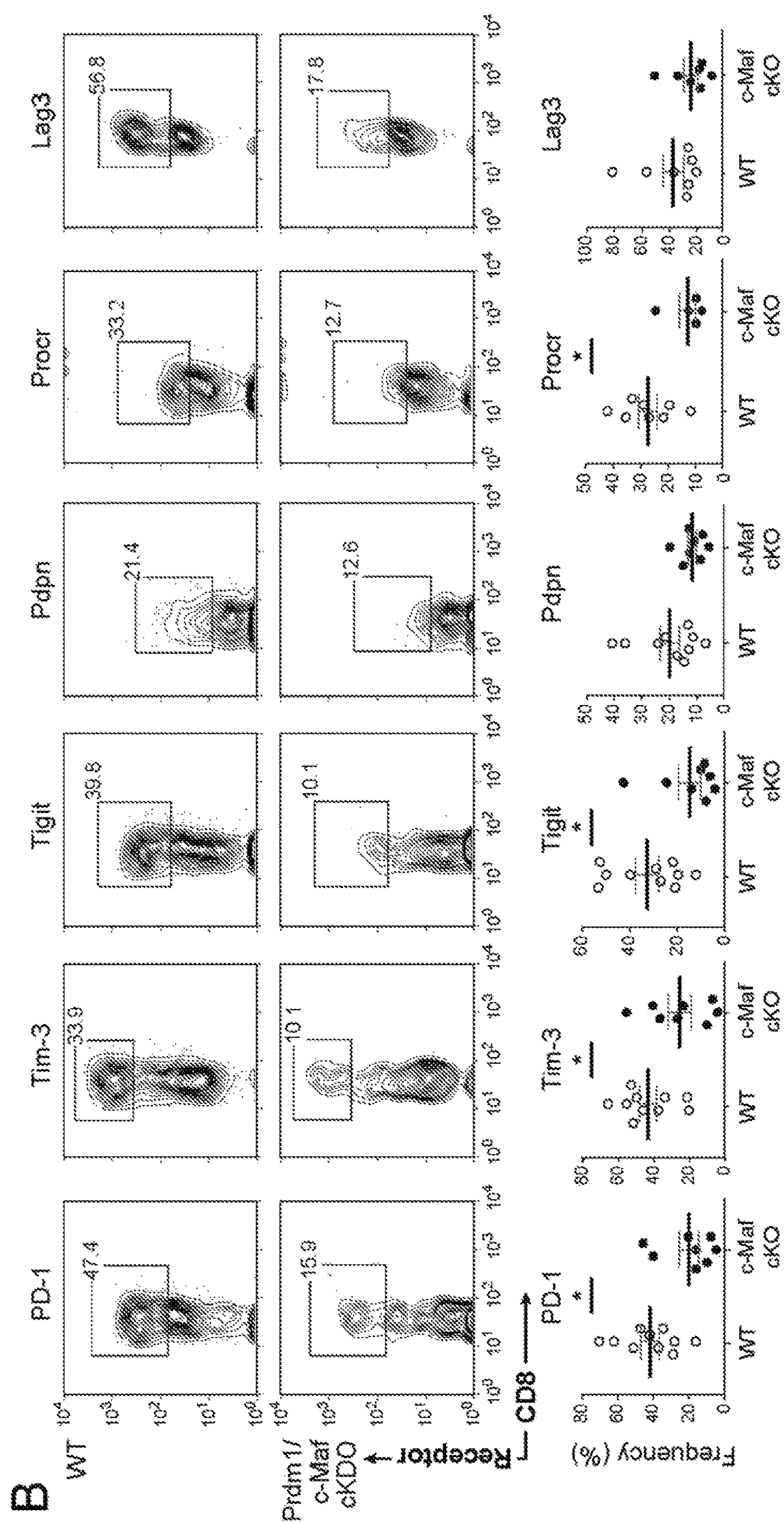

Indeed, similar to $CD8^+$ TILs from Prdm1 cKO mice, $CD8^+$ TILs from c-Maf cKO exhibited a decrease in the expression of multiple co-inhibitory receptors, including PD-1, Tim-3, Lag3, and Tigit (FIG. 13B). However, each of the two transcription factors impacted the expression of the various co-inhibitory receptors only partially (FIG. 13C). As in the Prdm1 cKO mice, c-Maf cKO mice did not show any significant difference in growth of B16F10 melanoma as compared to controls (FIG. 13D). Notably, Prdm1 expression in c-Maf cKO derived TILs cells was similar to that in wild type TILs. Thus, Prdm1 is available to drive expression of the inhibitory gene module in the absence of c-Maf.

Figure 14A:
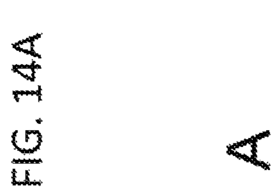
Figure 14B:
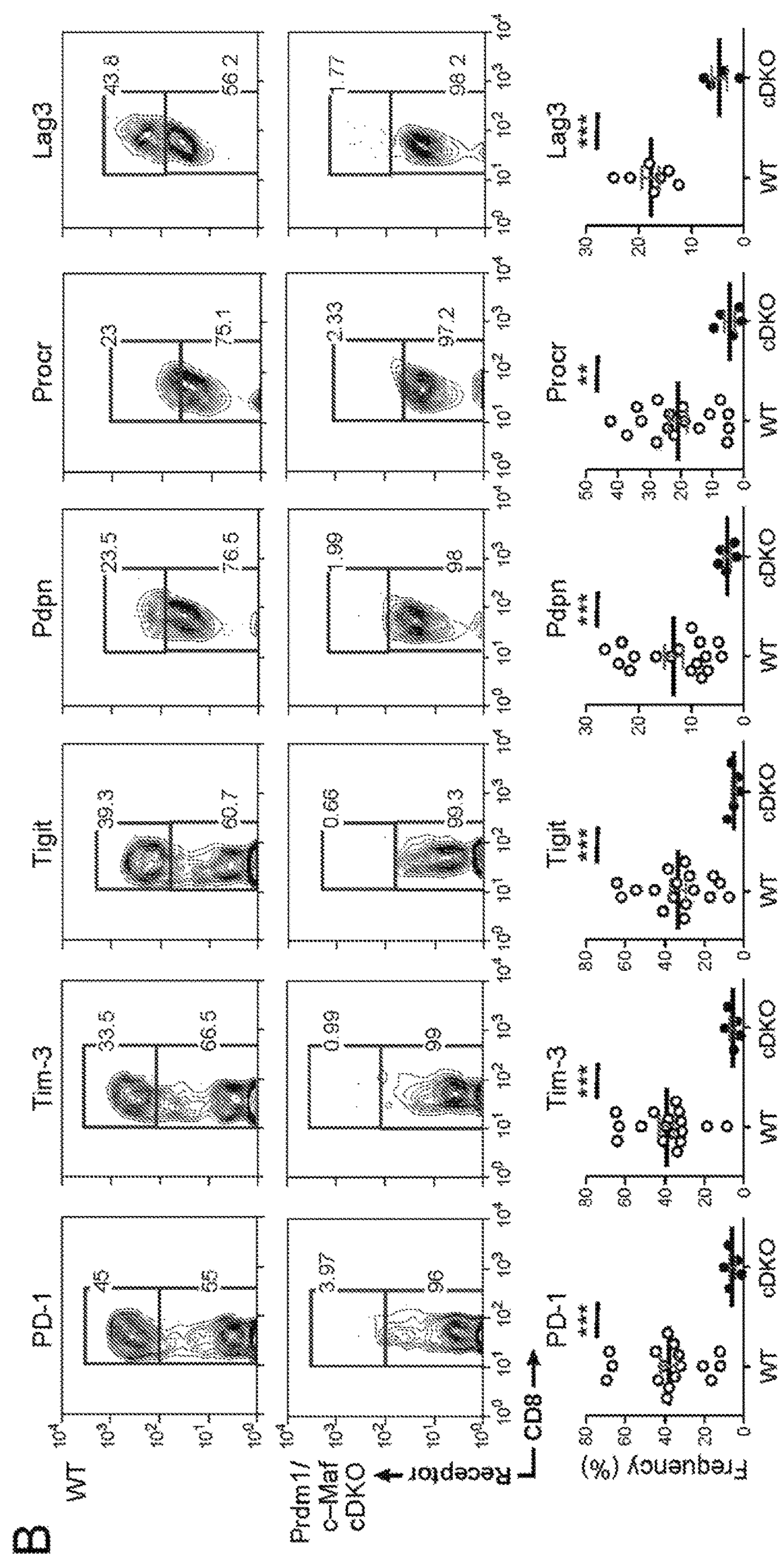

Prdm1 Together with c-Maf Regulates Co-Inhibitory Receptor Expression and Anti-Tumor Immunity The analysis indicated that each of Prdm1 and c-Maf contributes to the regulation of co-inhibitory receptor expression. To address the possibility that the two factors act cooperatively to regulate co-inhibitory receptor expression, Applicants generated a new network model for both factors (FIG. 14A). Applicants revised the model originally developed for Prdm1 (FIG. 12A) to incorporate regulation by c-Maf based on previously published c-Maf ChIP data (Ciofani et al., (2012) *Cell* 151, 289-303) and c-Maf functional targets defined as genes differentially expressed in wild type versus c-Maf cKO $CD8^+$ T cell activated in vitro in the presence of IL-27. The expanded network model suggested that Prdm1 and c-Maf bind a large number of shared targets (FIG. 14A, grey arrows), but those shared bound genes are not affected in either individual (single) knockout. This is consistent, among other possibilities, with cooperative ("AND") regulation (Capaldi et al., (2008) *Nat Genet* 40, 1300-1306). Furthermore, except for Procr and Tim3, other key module genes (TIGIT, LAG3, IL10, PDPN) are affected only by one of the two factors, even though they are bound by the other, further supporting a non-linear interaction between the two factors.

To test this, Applicants generated mice with a T cell specific deletion in both Prdm1 and c-Maf (Prdm1/c-Maf cDKO). Applicants implanted B16F10 melanoma in Prdm1/c-Maf cDKO mice and examined the expression of the co-inhibitory gene module and effector cytokine production in $CD8^+$ TILs. $CD8^+$ TILs from Prdm1/c-Maf cDKO mice exhibited a near absence of PD-1, Tim-3, Lag3, Tigit, Pdpn, and Procr expression (FIG. 14B), indicating that Prdm1 and c-Maf functionally co-operate to regulate the expression of co-inhibitory molecules in $CD8^+$ TILs. Importantly, Prdm1/c-Maf-deficient CD8+ TILs had enhanced IL-2 and TNFα production and markedly reduced IL-10 production (FIG. 14C). Finally, in striking contrast to each single knockout strain, Prdm1/c-Maf cDKO mice showed a significant delay in the growth of B16F10 melanoma as compared to controls (FIG. 14D). Collectively, the data show Prdm1/c-Maf cDKO CD8+ TILs exhibit loss of co-inhibitory receptor expression and retain effector function.

Figure 14E:
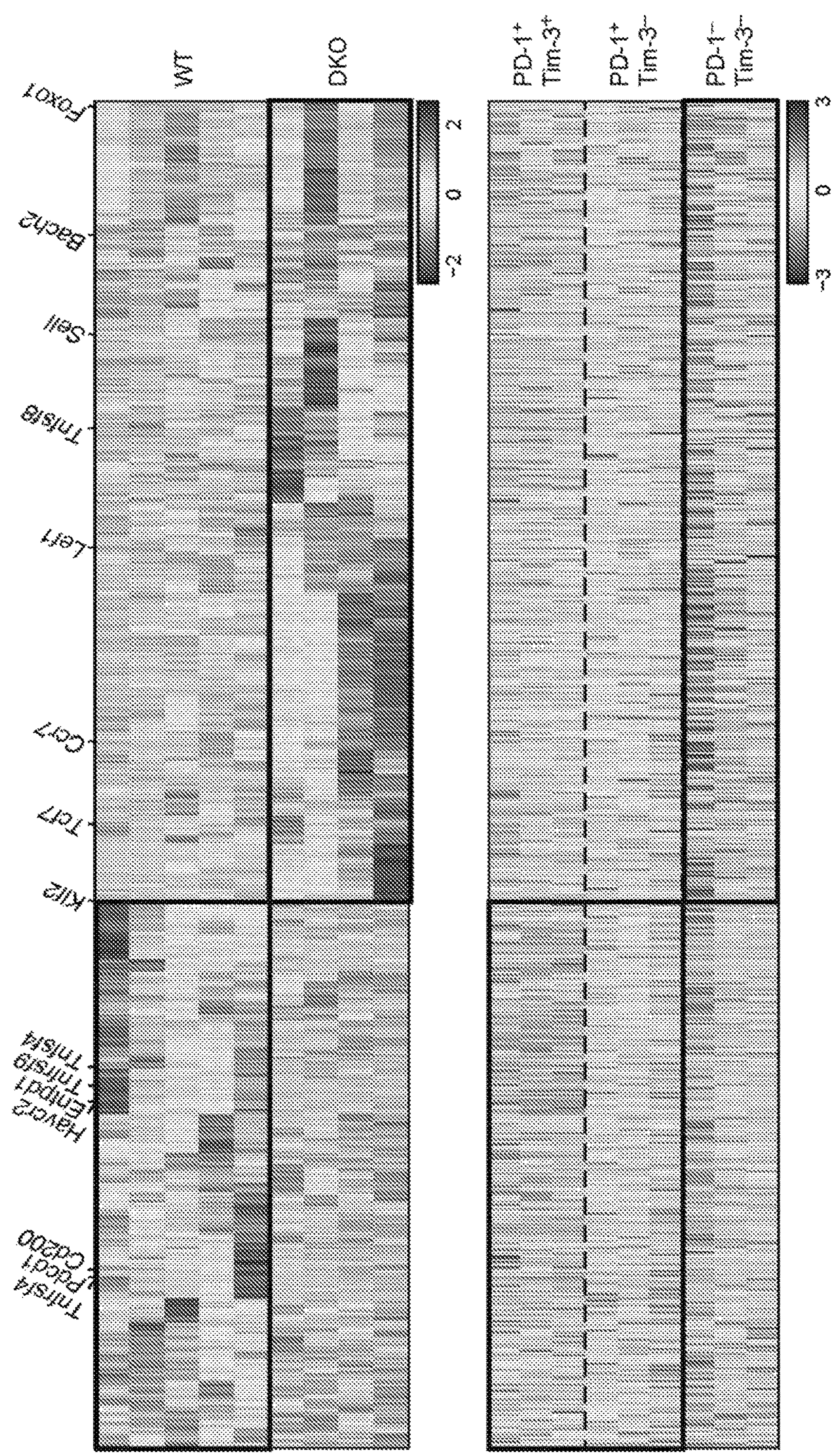
Figure 14F:
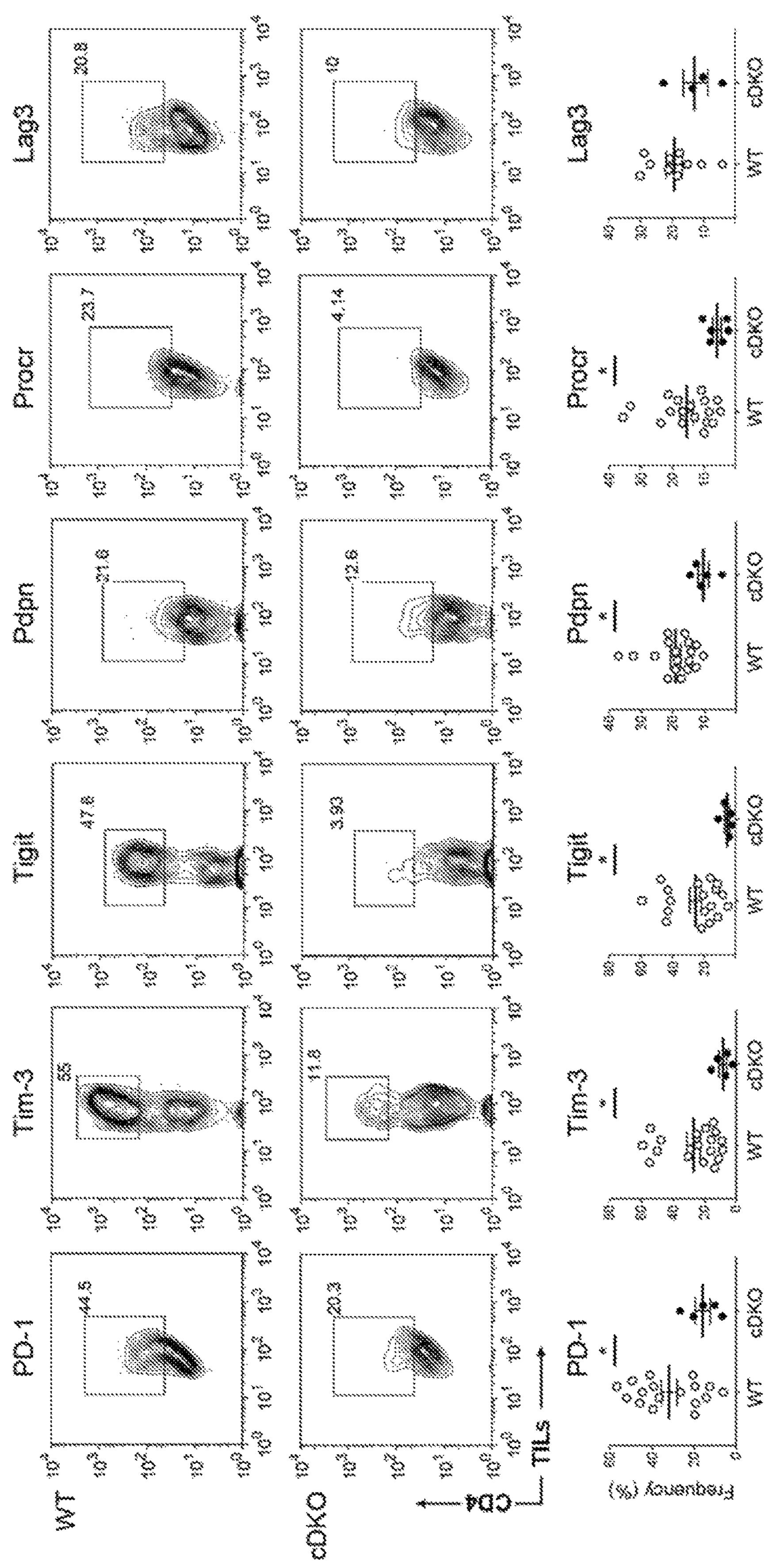
Figure 15A:
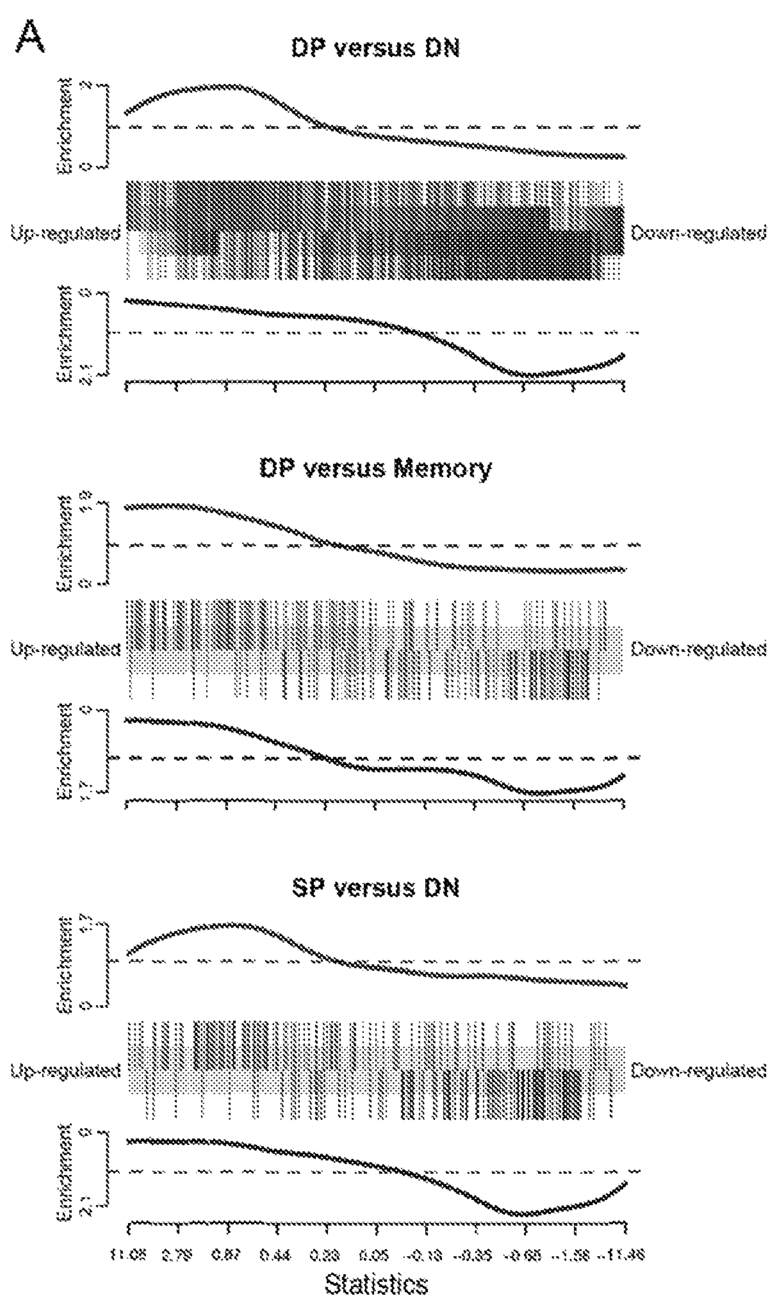
Figure 16:
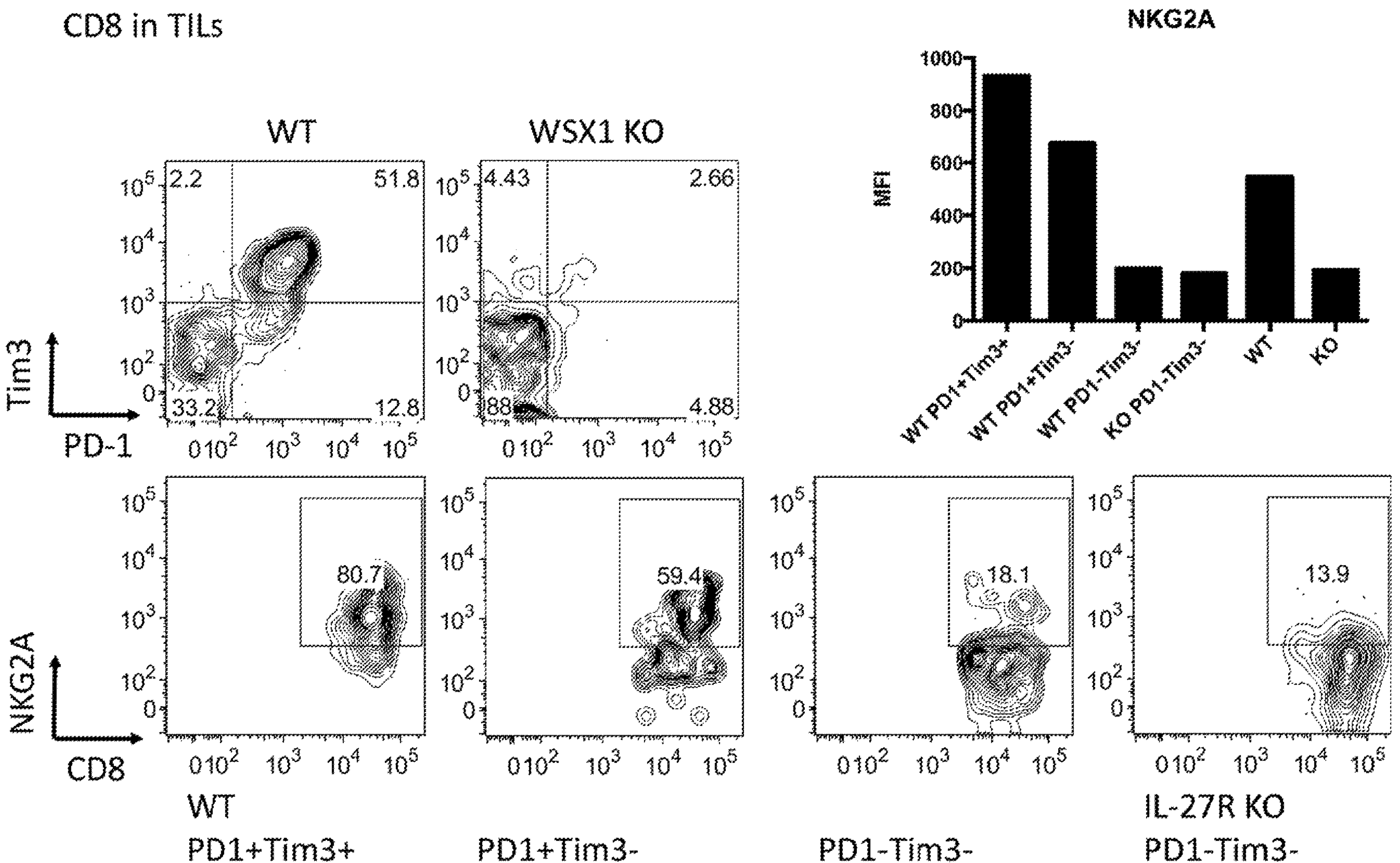
FIG. 16. NKG2A is co-expressed with $PD\text{-}1^+$ Tim3+ CD8 T cells.

Applicant also assessed the functional state of the Prdm1/c-Maf cDKO CD8+ TILs, in the context of gene expression signatures developed for T cell dysfunction (Singer et al., companion manuscript) for dysfunction and effector-like states. Applicants performed RNA-seq on $CD8^+$ TILs from Prdm1/c-Maf cDKO and CD8+ TILs from wild type mice and identified 940 differentially expressed (adj. P. value<0.05, likelihood ratio test and FDR correction). The gene expression pattern of cDKO CD8+ TILs strongly overlapped with that of CD8+ $Tim\text{-}3^-PD\text{-}1^-$ TILs as well as effector/memory cells from naïve tumor-free mice (p-value=2.834e-07 and 0.008, respectively, one-sample Kolmogorov-Smirnov test; FIG. 14E and FIG. 15A,B). There was strong evidence for activity of the Foxol transcription factor in the cDKO cells including enrichment of genes with Foxol binding events (Liao et al., (2014) *Bioinformatics* 26, 2347-2348). Among the genes up-regulated in cDKO compared to WT (P=1.486e-100, Fisher exact test), induction of the Foxol transcript itself, and induction of multiple Foxol downstream targets (Ness Michelini et al., (2013) *The Journal of experimental medicine* 210, 1189-1200), including the transcription factors Lefl, Bach2, Klf2 and Tcf7, as well as downstream targets of Tcf7 (e.g., Ccr7, Sell, and Tnfsf8 (CD30)) (Zhou et al., (2010) *Immunity* 33, 229-240) were upregulated in cDKO. The up-regulated genes were also enriched for targets of Myc (Kidder et al., (2008) PLoS One 3, e3932) and Stat3 (Kwon et al., (2009) *Immunity* 31, 941-952), although only Myc was also transcriptionally up-regulated. Importantly, Foxol, Tcf7, and Myc are also up-regulated in $CD8^+$ $Tim\text{-}3^-PD^-1$ (DN) TILs compared to dysfunctional $PD1^+$ $Tim3^+$ TILs (DP) (FIG. 15C). Overall, loss of c-Maf and Prdm-1 preferentially induces a population akin to the DN population, which shares features with both activated effector CD8+ and memory T cells (FIG. 14E).

Discussion

I1-27 signaling on naïve T cells induces I1-10, and blocks Th1, Th2 and Th17 differentiation. In an immune suppressive environment, IL-27 up-regulates inhibitory receptors and therefore marks them as dysfunctional.Co-inhibitory receptors play a crucial role in immune regulation and their dysregulated expression contributes to the dysfunctional T cell state in chronic disease conditions. Here, Applicants identify that the immunoregulatory cytokine IL-27 drives a co-inhibitory gene module that includes several known co-inhibitory receptors, including Tim-3, Lag-3, and TIGIT, in addition to the anti-inflammatory cytokine IL-10, and that this gene module strongly overlaps with multiple signatures of dysfunctional or tolerant T cell states. The module includes additional surface receptors that are co-regulated with known co-inhibitory receptors, including Procr and Pdpn, which Applicants show act as novel co-inhibitory receptors that cooperate with other inhibitory receptors to induce T cell dysfunction in the tumor microenvironment. Applicants further identified c-Maf and Prdm1 as key transcriptional regulators downstream of IL-27 that drive the inhibitory gene module. Our data thus provide a framework for understanding the underlying organizational principles by which co-inhibitory molecules are co-expressed and co-regulated in dysfunctional T cells.

Although IL-27 was initially described to have pro-inflammatory properties, its role as a potent immunoregulatory cytokine has come to the forefront in recent years (Awasthi et al., 2007; Fitzgerald et al., 2007b; Hirahara et al., 2012; Stumhofer et al., 2007). IL-27 has been shown to block the differentiation of Th17 cells (Fitzgerald et al., 2007a), and to promote the differentiation of both natural Tregs that specifically suppress Type 1 immunity (Hall et al., 2012) and IL-10 producing regulatory Tr cells (Awasthi et al., 2007). Our studies uncover a new mechanism, by which IL-27 inhibits effector T cells through the up-regulation of multiple co-inhibitory receptors on effector T cells, thereby priming them for the development of dysfunctional phenotype.

The IL-27 induced gene module not only includes co-inhibitory receptors but also several co-stimulatory molecules from the TNF-receptor family (4-1BB, OX-40 and GITR). The co-membership of co-inhibitory and co-stimulatory receptors in the IL-27 module provides a rationale for considering the combination of checkpoint receptor blockade with agonists that target TNF-receptor family co-stimulatory receptors. Such a combination could function synergistically by abrogating inhibitory signals (e.g., via blockade of PD-1 signaling), while enhancing co-stimulatory signals (e.g., via activating OX-40) to expand clonotypes that are otherwise inhibited in the tumor microenvironment.

It was recently shown that IL-35, which shares the Ebi3 chain with IL-27, is produced by intratumoral $CD4^+$ $Foxp3^+$ Tregs and that IL-35 promotes co-inhibitory receptor expression on CD8+ T cells (Turnis et al., 2016). Treg-specific deletion of Ebi3 resulted in a reduction in tumor growth and a loss of dysfunctional $CD8^+$ T cell phenotype. It is possible that IL-35 and IL-27 may synergize to dampen anti-tumor immunity by promotion of co-inhibitory receptor expression and T cell dysfunction in the tumor microenvironment.

The induction of multiple co-inhibitory receptors on the same cell suggests that individual molecules could either potentially regulate distinct aspects of T cell dysfunction, or that signals from multiple molecules could combine additively or non-linearly to enhance the response. Similar to our previous results for $CD4^+$ T cells (Peters et al., 2015), Pdpn may regulate T cell survival through inhibition of IL-7Ra expression on $CD8^+$ T cells. Indeed, previous studies have shown that dysfunctional $CD8^+$ T cells have defects in their survival and IL-7Ra expression (Lang et al., 2005; Pellegrini et al., 2009). In contrast, Procr may preferentially modulate proinflammatory cytokine production. In fact, this property underlies the therapeutic use of Activated protein C, a Procr ligand, to induce protease activated receptor-I driven NF-kB suppression in acute and chronic inflammatory conditions (Mohan Rao et al., 2014).

Applicants identified two transcription factors, Prdm1 and c-Maf, which co-regulate the expression of the IL-27 module. Prdm1 and c-Maf expression is increased by IL-27R signaling and both are implicated in IL-10 production. $CD8^+$ T cells deficient in either transcription factor exhibited decreased expression of multiple co-inhibitory receptors in the IL-27R dependent gene expression module, but for effective anti-tumor immunity, both had to be deleted together from $CD8^+$ TILs. Thus, a partial down-regulation of co-inhibitory receptors is not always sufficient to restore effective T cell responses, due to alternative compensatory mechanisms. This has been borne out in a recent study where anti-PD-I non-responsiveness was due to increased expression of Tim-3 in $CD8^+$ TILs (Koyama et al., 2016). Interestingly, the transcriptional signature of TILs from mice deficient for both Prdm1 and c-Maf significantly overlapped that of Tim-3-PD-1-DN TILs, suggesting that Prdm1 and c-Maf DKO cells resemble cells that normally exist in vivo.

The in vitro defined IL-27 module did not include PD-1; however PD-1 expression was dependent on IL-27R signaling in vivo. PD-1 expression was partially reduced in both Prdm1 cKO and c-Maf cKO $CD8^+$ TILs, and nearly lost in Prdm1/c-Maf cDKO, further supporting the dependence of PD-1 expression on IL-27R signaling in vivo. Further analysis for the upstream transcriptional network of Prdm1 and c-Maf may provide additional clues as to why PD-1 expression depends on IL-27R induction in vivo but not in vitro. More generally, the presence of multiple, complex and possibly synergistic inputs into infiltrating T cells in the tumor microenvironment could explain why Applicants cannot fully replicate in vitro the IL-27 circuit that is present in vivo.

In conclusion, the data adds to the mechanisms by which IL-27 signaling can suppress immune responses. IL-27 acts on naïve T cells to induce IL-10 producing Tr cells (Awasthi et al., 2007; Stumhofer et al., 2007) and inhibit Th17 differentiation (Batten et al., 2008; Murugaiyan et al., 2009). It acts on Treg to specialize them for suppression of Type 1 immunity. Applicants now show that IL-27 can promote co-inhibitory receptor expression on effector T cells and target them for T cell dysfunction. Our identification of the IL-27-driven gene module further provides a tool with which to identify novel molecules that may play an important role in promoting T cell dysfunction and uncover co-stimulatory molecules that might work together with the co-inhibitory molecules to antagonize T cell dysfunction. The elucidation of the IL-27 driven inhibitory gene module broadens the potential repertoire of therapeutic targets and a molecular basis for understanding the pathways that lead to the dysfunctional T cell state that could constitute mechanisms of resistance to current checkpoint blockade therapies.

Example 2: Methods

Mice: C57BL/6 wild-type (WT), IL-27ra KO (WSX-1−/−), and Prdm1 fl/fl mice were obtained from the Jackson Laboratory (Bar Harbor, ME). c-Maf fl/fl, Pdpn fl/fl mice and Procr delta/delta mice were previously described (Castellino et al., 2002; Peters et al., 2015; Wende et al., 2012). Pdpn fl/fl mice were initially obtained from Christopher Buckley (University of Birmihngham, Birmingham, UK) and crossed to CD4Cre mice to obtain conditional CD4 and CD8 T cell gene knock-out mice. CD4Cre mice were purchased from Taconic (Hudson, NY). Prdm1 fl/fl and c-Maf fl/fl mice were crossed to CD4Cre mice to generate doubly deficient T cell conditional knockout mice. All experiments were performed in accordance to the guidelines outlined by the Harvard Medical Area Standing Committee on Animals (Boston, MA).

Flow cytometry: Single cell suspensions were stained with antibodies against CD4 (RM4-5), CD8 (53-6.7), PD-1 (RMP1-30), Lag-3 (C9B7W), TIGIT (GIGD7), and Tim-3 (5D12), Procr (eBiol560), and Pdpn (8.1.1.) and were obtained from BioLegend (San Diego, CA). Fixable viability dye eF506 (eBioscience) was used to exclude dead cells. For intra-cytoplasmic cytokine staining, cells were stimulated with (PMA) (50 ng/ml, Sigma-Aldrich, MO), ionomycin (1 μg/ml, Sigma-Aldrich, MO). Permeabilized cells were then stained with antibodies against IL-2, TNF-α, IFN-γ or IL-10. All data were collected on a BD LSR II (BD Biosciences) and analyzed with FlowJo software (Tree Star).

In vitro T-cell differentiation: $CD4^+$ and $CD8^+$ T cells were purified from spleen and lymph nodes using anti-CD4 microbeads (Miltenyi Biotec) then stained in PBS with 0.5% BSA for 15 min on ice with anti-CD4, anti-CD8, anti-CD62L, and anti-CD44 antibodies (all from Biolegend, CA). Naïve $CD4^+$ or $CD8^+$ $CD62L^{high}CD441^{low}$ T cells were sorted using the BD FACSAria cell sorter. Sorted cells were activated with plate bound anti-CD3 (2 μg/ml for CD4 and 1 μg/ml for CD8) and anti-CD28 (2 g/ml) in the presence of mIL-27 (25 ng/ml) (eBioscience). Cells were harvested at various time points for RNA, intracellular cytokine staining, and flow cytometry.

Real-time PCR: Total RNA was extracted using RNeasy columns (Qiagen). Reverse transcription of mRNA was performed in a thermal cycler (Bio-Rad) using iScript™ cDNA Synthesis Kit (Bio-Rad). Real-time PCR was performed in the Vii7™ Real-Time PCR system (Applied Biosystems) using the primers for Taqman gene expression (Applied Biosystems). Data was normalized to the expression of ACTB.

Nanostring RNA Analysis:

Expression profiling along a time course in vitro. Naïve $CD4^+$ and $CD8^+$ T cells isolated from WT and IL-27ra KO mice were activated in vitro with IL-27 stimulation. Cells were collected at 0, 12, 24, 48, 72 and 96 hours and analyzed in 3 replicates, using a custom nanostring code-set containing probes for regulatory genes on T cells (TableS2). Expression values were normalized by first adjusting each sample based on its relative value to all samples. This was followed by subtracting the calculated background (mean.2sd) from each sample with additional normalization by housekeeping geometric mean, where housekeeping genes were defined as: Hprt, Gapdh, Actin and Tubb5.

Expression profiling of TILs. Applicants analyzed gene expression in $CD8^+$ TILs from Prdm1 or c-Maf cKO mice bearing B16F10 melanoma collected on day 14 after tumor implantation, using a custom code set of 397 genes representing both the IL-27-driven gene signature (245 genes) and the dysfunctional $CD8^+$ TIL gene signature (245 genes) (Table 17). Expression values were normalized as described above. Differentially expressed genes were defined using the function that fits multiple linear models from the Bioconductor package limma in R (Smyth, 2004) with p-value<0.05.

Microarray and data analysis: Naïve $CD4^+$ and $CD8^+$ T cells were isolated from WT or IL-27ra KO mice, and differentiated in vitro with or without IL-27. Cells were collected at 72 hours for $CD8^+$ and 96 hours for $CD4^+$ and Affymetrix GeneChip Mouse Genome 430 2.0 Arrays were used to measure the resulting mRNA levels at these time points. Individual CEL files were RMA normalized and merged to an expression matrix using the ExpressionFileCreator of GenePattern with default parameters (Reich et al., 2006). Gene-specific intensities were then computed by taking for each gene j and sample i the maximal probe value observed for that gene. Samples were then transferred to log-space by taking log 2(intensity).

Differentially expressed genes were annotated as genes with fold-change>2 and FDR-corrected ANOVA <0.2 computed between the CD4 with or without IL-27 stimulation ($CD4^+$ IL27 and Th0) subpopulations. A list of 972 cell surface/cytokines genes of interest that include: cytokines, adhesion, aggregation, chemotaxis and other cell surface molecules (Table 18) was composed using GO annotation in Biomart.

TABLE 18

| | | | | | | | |
|---|---|---|---|---|---|---|---|
| DDR1 | PAM | BMP10 | EGFR | HYAL5 | THBS1 | IL9 | CKLF |
| CX3CL1 | CXCL10 | FCER1A | EMR4 | UMODL1 | ARSA | RPL13A | GRAMD2 |
| PLAT | CORIN | KLRC3 | KLRC1 | CD40 | ADAM2 | IL25 | CXCL5 |
| LAMP1 | MPP3 | EFNA5 | SCNN1A | RTN4RL2 | ENTPD6 | CMTM5 | PPBP |
| KIT | SCNN1G | LDLR | ACE2 | ADAM6A | CD164 | TNFSF14 | PF4 |
| LPL | FGFBP1 | BACE1 | FCGR4 | ITGA1 | CD320 | CLCF1 | CXCL3 |
| SDC1 | HCST | ABCA1 | PEAR1 | LY6E | ENTPD5 | IL31 | CXCL15 |
| PEBP1 | PDGFC | FGFR3 | CR2 | HEG1 | CD248 | TNFSF13B | CXCL1 |
| SLC2A4 | ITGAX | ADAM17 | CD8A | FZD10 | CAP1 | CER1 | CXCL2 |
| VCAM1 | TLR2 | NR3C1 | H2-K1 | GPR116 | AMN | FAM3B | CXCL11 |
| FGG | ACVR2B | PDGFRA | GREM1 | UNC5D | SIVA1 | BMP8B | CCL26 |
| CD24A | CD163 | EPHA4 | ITGAL | CHRNA7 | TRAF3 | BMP8A | TRPM4 |
| SCARB1 | CD3G | ICOS | WNT1 | GPR174 | MS4A6B | IL1F8 | ARHGEF5 |
| HSPA5 | CD37 | TGFA | AQP4 | WNT4 | CD47 | IL1F9 | RETNLG |
| CD9 | ICOSL | L1CAM | KLRA8 | KCNH5 | ABCB1A | IL1F6 | RPS19 |
| CD34 | TNFRSF11A | NCAM1 | H2-AB1 | TNN | IGLL1 | IL1F5 | FLT1 |
| ADAM9 | CD96 | ITGA3 | BMPR1A | LAYN | CD160 | IL1F10 | MYO9B |
| CD83 | ENPP1 | CRHR2 | CD74 | DLK1 | IDO1 | CCL17 | CALCA |
| HMGB1 | FZD4 | TGFBR2 | H2-D1 | LRP1 | PROCR | NAMPT | PTPRO |
| USP14 | TNFRSF13C | TNFRSF22 | ANXA5 | TRPV1 | CD2AP | IL12B | RAC1 |
| IL2RG | PDPN | SEMA7A | SLAMF1 | NTRK1 | IL18R1 | IL22 | CXADR |
| CD81 | CTLA4 | ITGAM | PTPRJ | CD226 | TNFRSF8 | ILTIFB | PRKCA |
| MIF | STAB2 | CDH5 | AIPL1 | GHSR | IL8RB | IL11 | SYK |
| LAMP2 | SPAM1 | GABBR1 | TGFBR3 | LBP | CXCR5 | GRN | SLC37A4 |
| MCAM | CLEC2D | MSR1 | CEP290 | ITGAE | TNFRSF10B | IFNB1 | AMICA1 |

TABLE 18-continued

| | | | | | | | |
|---|---|---|---|---|---|---|---|
| HSP90AB1 | SELL | WNT3A | KLHL20 | IFNGR1 | ABCG2 | GM12597 | NCKAP1L |
| M6PR | C3AR1 | ACVR1B | NFAM1 | CDH1 | ICAM4 | IFNA14 | TGFB2 |
| CD82 | IL1R2 | TNFRSF23 | HMMR | C1QBP | ENTPD1 | IFNA9 | EDN3 |
| BGN | FLT3 | CD3E | PSEN2 | ADAM3 | GYPC | IFNA12 | EDN2 |
| GABARAPL1 | ISG20 | FLT3L | AMOT | THBD | CD99L2 | IFNA13 | S100A8 |
| CRYAB | LGALS1 | FCER2A | IFNG | IL7R | PRR3 | GM13280 | S100A9 |
| AIMP1 | CD93 | PTPRC | KLRB1F | CD53 | SLC3A2 | IFNA2 | CSF3R |
| PDIA4 | TNF | SPN | PTPRR | FCGR3 | CAST | IFNAB | CXCR2 |
| EPCAM | CCR1 | PLAU | CD72 | ENPEP | NT5E | GM13271 | ITGA9 |
| SFRP1 | BMPR2 | CLEC2I | CD209B | HYAL2 | PGP | GM13283 | PDE4B |
| PLA2G1B | CD4 | C5AR1 | CD8B1 | CXCR4 | CCND2 | GM13290 | PDE4D |
| AMBP | PROM1 | CD200R1 | KLRA7 | ICAM2 | CD3EAP | TNFSF11 | CORO1A |
| SERPINE2 | WNT6 | SCN5A | CD209A | OCLN | SCO1 | GM13289 | LYST |
| BACE2 | CD7 | CCR5 | ROBO4 | NCOR2 | DARC | GM13272 | SBDS |
| PTPRU | CD274 | IL6RA | ALCAM | IL1R1 | SLC44A1 | IFNZ | CCR2 |
| APOH | RTN4R | GLRA1 | SLC1A3 | CD1D1 | PTGFRN | GM13276 | GAS6 |
| DPP4 | CD22 | TACR1 | HSPD1 | LY9 | NRP | GM13277 | HRH1 |
| PLG | GAB2 | CD40LG | RYK | CD68 | LSM1 | GM13278 | NUP85 |
| ATP5B | TREML2 | CCR8 | GPM6A | GPR65 | CTSD | GM13275 | EDNRB |
| ADAM8 | P2RX7 | TNFRSF18 | HSP90AA1 | MUC1 | PRNP | GM13279 | ROCK1 |
| CLPTM1 | CSF1R | GP1BA | AGRN | NDP | GSS | GM13285 | MSN |
| LY6D | TMX3 | IL1RL1 | LRPAP1 | B2M | PTPRCAP | GM13287 | EZR |
| TRPV2 | RC3H2 | ART1 | GPR125 | PTGER2 | CD2BP2 | GM13288 | OLR1 |
| HSPA2 | PSEN1 | IL15RA | BOC | LY75 | PVRL3 | IFNA7 | FERMT3 |
| LPAR1 | TNFRSF4 | ITGA6 | ITGB1 | RAPSN | CD200 | IFNA11 | TNIP1 |
| PDGFRB | CD86 | GLRB | PCSK6 | KDR | CD302 | IFNA6 | GCNT1 |
| LY6A | KLRB1B | CR1L | ACE | AOC3 | IFNAR1 | IFNA5 | PODXL2 |
| TMEM123 | DCBLD2 | WNT5B | ENOX2 | KCNE2 | TLR1 | IFNA4 | LEP |
| CD14 | EPHA5 | ACHE | ROBO1 | IL27RA | CD5L | IFNA1 | SELPLG |
| ENG | SELP | ADIPOQ | CD48 | KLRB1C | CCR6 | IFNE | GOLPH3 |
| H13 | LPAR2 | EBAG9 | MUC3 | PDCD1 | PEMT | CMTM2A | CHST4 |
| TNFRSF1A | CFTR | IRAK1BP1 | ITGB4 | EPHB4 | LAP3 | CMTM6 | STK10 |
| CAV2 | GPR84 | TLR3 | DSCAML1 | SCUBE1 | PLXNC1 | CMTM7 | FN1 |
| F3 | APP | CNTNAP2 | FZD9 | IL4 | SCARB2 | CMTM2B | IGHG2C |
| TGFB3 | HSPA8 | CXCR6 | SHH | VPREB1 | IL13RA1 | CMTM8 | PLA2G2A |
| RAMP1 | TGFB1 | EPS8 | GHRHR | CASR | SP1 | CMTM3 | REG4 |
| SERPINF2 | ARNT2 | CD3D | CD80 | LAG3 | CD151 | CMTM4 | F11 |
| FLOT2 | KCNE1 | KCND2 | CCRL2 | CXCR3 | TNFSF10 | C1QTNF4 | PTGDS |
| TRPV4 | IL17RB | CD84 | TNFRSF9 | CD70 | IGSF8 | SCGB3A1 | KLKB1 |
| IL2RB | IL2RA | TNFSF9 | GPRC6A | CD244 | TIGIT | IL16 | OLFM4 |
| CXCL12 | CLEC7A | FZD5 | KLRA1 | CX3CR1 | LILRB4 | IL17D | BGLAP2 |
| SLC11A2 | HPN | HSPB1 | FGB | PLA2R1 | Gene | SCG2 | SPOCK3 |
| CD28 | CD247 | FPR2 | ADAM10 | FGF22 | PDCD1LG2 | GDF10 | C8G |
| CD276 | CHRNB2 | AGTRAP | NRXN1 | KLRB1A | CTLA2B | GDF2 | SERPINC1 |
| CALR | KLRA5 | TFRC | REEP4 | IL6 | CTLA2A | PGLYRP1 | OLFM1 |
| CD79B | ART2B | MME | CD69 | GABRR1 | IL12A | CCL20 | CTRB1 |
| SDC4 | IL13 | FZD1 | XPOT | KLRC2 | SPP1 | INHBA | OGN |
| PVRL2 | GDI2 | GFRA2 | RPS6KB1 | PDGFB | TNFSF18 | IL34 | C1QTNF7 |
| TJP1 | SEMA4D | GYPA | CD99 | MRC1 | OSM | AREG | GPLD1 |
| ITGA2B | NTRK2 | IL1RN | ADCYAP1R1 | IL21R | LIF | TNFSF12 | EGF |
| APOA4 | FGFR2 | HNRNPU | PAQR3 | KISS1R | BMP3 | BC096441 | IL18BP |
| PLA2G5 | WNT7B | PAQR4 | HFE2 | KLRK1 | WNT2 | TNFSF13 | UCMA |
| SYNJ2BP | IL17RA | IDE | AQP11 | ITGA2 | SLURP1 | GDF9 | CFI |
| FCGR1 | VEGFA | THY1 | HYAL4 | CD33 | PRL7D1 | IL5 | MMP1A |
| GPR97 | MFGE8 | RALA | RSPO2 | LY6F | GDF1 | THPO | MMP8 |
| VLDLR | TIMP2 | CD36 | CNRIP1 | CD19 | CRLF1 | CSF2 | APOC2 |
| GHR | IL4RA | TNFRSF13B | GUCY2G | ITGB2 | IL17F | IL3 | IAPP |
| ADA | MRC2 | MS4A1 | SULF2 | FSHR | GDF15 | BMP4 | PTPRG |
| B4GALT1 | GPC4 | ERP44 | CD200R3 | FUT4 | IL17C | CCL24 | C8B |
| EPHB6 | TRPC1 | ITGA5 | ULBP1 | TDGF1 | GDF7 | IL2 | GIF |
| NRP1 | GPR56 | PTPRK | SCARA5 | FOLR1 | GDF6 | IL21 | COL6A2 |
| TRIP10 | ITGA4 | SLC34A1 | ANXA9 | LRP6 | GDF5 | FGF2 | C8A |
| CAR4 | PTPN11 | SORT1 | P2RY12 | SFRP4 | TSLP | CSF3 | SERPINE3 |
| TLR4 | ITGAV | WNT7A | MUC16 | EMR1 | GDF3 | IL24 | MYOC |
| STX2 | CHRNA4 | CLIC4 | APOE | CTSL | IFNL2 | IL20 | ADAMTS20 |
| IL12RB1 | CIITA | ADRB1 | INTU | STX4A | IFNL3 | IL19 | F7 |
| RAMP2 | TREM2 | PDIA3 | NR4A2 | HAVCR2 | IL23A | IL10 | FGF10 |
| THSD1 | PTPRT | PGRMC1 | CD38 | AMELX | CCL1 | BMP5 | CTS7 |
| IL15 | IL6ST | CCR7 | ECE1 | FOLR2 | GREM2 | | SERPINB10 |
| FCER1G | PECAM1 | 2-Sep | FERMT2 | FGF8 | IL1A | CCL21C | CTSB |
| HBEGF | IL18RAP | SLC46A2 | ATPIF1 | NOTCH2 | BMP15 | CCL27A | WNT9A |
| CD5 | KLRA2 | JAM3 | ISLR2 | CD6 | IL1B | CXCL13 | NEPN |
| GPR124 | H2-M3 | NID2 | CNTN2 | SLC6A1 | IFNK | GM21541 | POMC |
| ITGA7 | CLEC5A | CDH13 | P2RX2 | ADAMTS7 | IL27 | GM13304 | APOD |
| CD97 | ANPEP | ABCG1 | GRIA1 | CD27 | BMP7 | GM13306 | PRL3D1 |
| TSPAN32 | HHIP | S1PR1 | H2-AA | TNFRSF14 | GDF11 | CCL28 | CEL |
| CAV3 | CDON | TRPC4 | CD200R4 | PLAUR | EBI3 | CCL21B | COL25A1 |
| SCNN1B | KCNJ3 | AXL | VWF | TREML1 | GPI1 | GM10591 | PRL3B1 |
| HSPA9 | MS4A2 | BMP2 | FCGR2B | GPIHBP1 | IL7 | GM2564 | BCHE |
| FURIN | ITGB3 | ATP6AP2 | ACVRL1 | GPR160 | TNFSF15 | CCL27B | CNTF |

TABLE 18-continued

| | | | | | | | |
|---|---|---|---|---|---|---|---|
| TNFRSF12A | CD46 | IFITM3 | SCUBE3 | TMEM102 | LEFTY2 | CCL19 | CEACAM10 |
| GPR162 | CEACAM2 | CD44 | TLN1 | SLAMF7 | LEFTY1 | CCL21A | SMPD1 |
| ASTN1 | GRIN2A | PVR | TNR | ERP29 | TNFSF8 | XCL1 | HPX |
| NOTCH1 | TRPM8 | 1600029D21RIK | SULF1 | AAMP | CTF1 | CXCL16 | WFDC1 |
| CXCL9 | IL5RA | PDLIM2 | IRAK2 | NLGN2 | CTF2 | CCL2 | TFF2 |
| CAPN5 | IL12RB2 | ICAM1 | GRK5 | PTPN3 | CSF1 | CCL7 | FBLN1 |
| TIRAP | TMC1 | IGF2R | WNT5A | BTLA | IL18 | CCL11 | SERPINI2 |
| CD59A | SLC6A2 | IFITM1 | RTN4RL1 | BSG | BMP6 | CCL12 | TFF1 |
| PDGFA | CYSLTR2 | FGA | NOTCH4 | PPFIA2 | IL17B | CCL8 | SEZ6 |
| LPAR3 | CD1D2 | REEP2 | F2R | PKD2L1 | KITL | CCL5 | FBLN5 |
| ITGB7 | NLGN1 | CST8 | ACVR2A | VTCN1 | LTB | CCL9 | ADCYAP1 |
| CD55 | CCR4 | ANGPTL3 | PCSK9 | ROBO2 | IL33 | CCL6 | F5 |
| CD2 | IL17A | PSTPIP1 | P4HB | KLRE1 | LTA | CCL3 | CNP |
| TEK | GPR98 | SLIT2 | IL10RA | CD52 | MSTN | CCL4 | |
| FASL | STRC | BCAM | GRIN1 | MSLN | BMP1 | CXCL14 | |
| SERPINA5 | SELE | KCNMA1 | RGMA | KLRD1 | EDN1 | CCL25 | |
| CHRNA1 | TNFSF4 | BST2 | 5830411N06RIK | FAS | NODAL | CCL22 | |

Signature analysis of other dysfunctional states: For viral exhaustion: Microarray dataset (Doering et al., 2012) was downloaded, followed by RMA. A signature of viral exhaustion was defined as the genes that are differentially expressed between chronic and acute viral infection on day 15 and day 30. Genes were ranked based on a t-test statistic and fold change, each gene rank was then adjusted for multiple hypotheses testing using false discovery rate (FDR). A threshold of fold change>1.1 and FDR<0.2 was applied.

For anergy: Data ((Safford et al., 2005), Table 1) were downloaded. 90 genes were reported as upregulated in T cells stimulated in conditions that promote versus inhibit anergy.

For antigen-specific tolerance: Data (Burton et al., 2014) were downloaded. Two groups were defined, group 1 that includes the PBS and 0.008 μg treated samples (treatment number 1) versus group 2-80 μg (treatment number 5 and 6). After Log2 transformation and quantile normalization, the Limma package was used to estimate the fold changes and standard errors by fitting a linear model for each gene for the assessment of differential expression. Genes with p value <0.05 were selected: 1,845 genes were upregulated of which 88 were defined as cytokine and cell surface molecules (Davis and Meltzer, 2007; Smyth, 2004, 2005).

For antigen non-specific tolerance: Data was downloaded from (Mayo et al., 2016). Robust Multi-array Average (RMA) and quantile normalization were applied for background correction and normalization using the Expression-FileCreator module of GenePatterns. Differentially expressed genes were defined using signal-to-noise ratio (SNR), following FDR correction. Differentially expressed genes were identified as genes having a FDR<0.2 between mRNA expression profiles of naïve $CD4^+$ or $CD4^+$ GFP/IL-$10^+$ T-cells isolated from the spleen or cLNs of B6NODF1$^{IL10:GFP}$ mice following nasal treatment with anti-CD3 which attenuates the progressive phase of EAE.

For cancer: Data was obtained from (Singer et al., companion manuscript). Briefly, mRNA samples from $CD8^+$ $Tim3^-PD1^-$ (DN) TILs, $CD8^+Tim3^-PD1^+$(SP), and $CD8^+$ $Tim3^+PD1^+$ (DP) TILs were measured using Affymetrix GeneChip Mouse Genome 430 2.0 Arrays, expression values were RMA normalized, corrected for batch effects using COMBAT (Johnson et al., 2007) and gene-specific intensities were then computed by using the maximal prob intensity per gene, values were transferred to log-space by taking log 2(intensity). Differentially expressed genes were defined as genes with either an FDR-corrected t-test p-value smaller or equal to 0.2 computed between the DN and DP subpopulations and a fold-change of at least 1.5 between the two subpopulations.

RNA expression profiling of tumor infiltrating cells: Tumor infiltrating $CD8^+$ T cells were isolated from WT or IL-27ra KO tumor bearing mice via FACS sorting on a FACSAria (BD Biosciences). Tumor infiltrating $CD8^+$ T cells were processed using an adaptation of the SMART-Seq 2 protocol (Tirosh et al., 2016) (Shekhar et al. 2016 in press), using 5 μL of lysate from bulk $CD8^+$ T cells as the input for each sample during RNA cleanup via SPRI beads (~2,000 cells lysed on average in RLT).

RNAseq reads were aligned using Tophat (Trapnell et al., 2009) (mm9) and RSEM-based quantification (Li and Dewey, 2011) using known transcripts (mm9), followed by further processing using the Bioconductor package DESeq in R (Anders and Huber, 2010). The data was normalized using TMM normalization. The TMM method estimates scale factors between samples that can be incorporated into currently used statistical methods for DE analysis. Post-processing and statistical analysis was carried out in R (Li and Dewey, 2011). Differentially expressed genes were defined using the differential expression pipeline on the raw counts with a single call to the function DESeq (adjusted p value<0.1). Heatmap figures were generated using pheatmap package (Kolde, 2015).

Network construction: Networks were generated using Cytoscape version 3.2.1 (Lopes et al., 2010). The network model is based on coupling in vitro gene expression data of naïve $CD8^+$ T cells from KO (Prdm1 or c-Maf) and WT controls stimulated in the presence of IL-27 and previously published ChTPseq data for that specific regulator. More specifically, samples were analyzed using a custom code set of 397 genes representing both the IL-27-driven gene signature (245 genes) and the dysfunctional $CD8^+$ TIL gene signature (245 genes) (Table 17). Differentially expressed genes between WT control and KO were defined using the function that fits multiple linear models from the Bioconductor package limma in R (Smyth, 2004) with p-value<0.05. For the ChIP-Seq evidence Applicants used published Prdm1 (Shin et al., 2013) and c-Maf (Ciofani et al., 2012) published binding events dataset. In the network presentation, Applicants selected the 61 genes that are part of the IL-27 inhibitory module (FIG. 6G).

Single-cell RNA-Seq: Briefly, tumor infiltrating lymphocytes from B16 melanomas were sorted into 96-well plates with 5 μl lysis buffer comprised of Buffer TCL (Qiagen) plus 1% 2-mercaptoethanol (Sigma). Plates were then spun down for one minute at 3000 rpm and immediately frozen at −80°

C. Cells were thawed and RNA was isolated with 2.2× RNAClean SPRI beads (Beckman Coulter Genomics) without final elution (Shalek et al., 2013). The beads were then air-dried and processed immediately for cDNA synthesis. Samples were then processed using the Smart-seq2 protocol (Picelli et al., 2014), with minor modifications applied to the reverse transcription (RT) step. This was followed by making 25 μl reaction mix for each PCR and performed 21 cycles for cDNA amplification. Then, using 0.25 ng cDNA of each cell and ¼ of the standard Illumina Nextera XT reaction volume in both the tagmentation and final PCR amplification steps. Finally, plates were pooled to 384 single-cell libraries, and sequenced 50×25 paired-end reads using a single kit on the NextSeq500 5 instrument.

Single-cell analysis: Briefly, paired reads were mapped to mouse annotation mm10 using Bowtie (Langmead et al., 2009) (allowing a maximum of one mismatch in seed alignment, and suppressing reads that had more than 10 valid alignments) and TPMs were computed using RSEM (Li and Dewey, 2011), and log 2(TPM+1) values were used for subsequent analyses.

Tumor Experiments: $5\times10^5$ B16F10 melanoma cells (ATCC) were implanted into the right flank of C57BL/6 mice. Tumor size was measured in two dimensions using a caliper. TILs were isolated by dissociating tumor tissue in the presence of 2.5 mg/ml collagenase D for 20 min before centrifugation on a discontinuous Percoll gradient (GE Healthcare). Isolated cells were then used in various assays of T cell function.

CyTOF analysis: Antibodies were labeled using MaxPar® Metal Labeling Kits (DVS) by The Longwood Medical Area CyTOF Antibody Resource and Core. In some experiments, TILs were enriched using Dynabeads FlowComp Mouse Pan T (CD90.2) Kit (Invitrogen). Cells were washed and resuspended in CyTOF PBS (PBS+0.05% sodium azide+ 0.5% BSA) and stained with the cocktail of antibodies against cell-surface molecules for 30 min. Cells were washed again and resuspended in CyTOF PBS with 4% paraformaldehyde. After 10 min fixation, cells were washed and stained with Cell-ID intercalators (DVS) overnight. Before analysis, cells were resuspended in water with beads and loaded to the CyTOF® Mass Cytometer (DVS). CyTOF data were recorded in dual-count according to Fluidigm's recommended settings and the analysis was done on the fly.

To obtain clusters of cells similar in their protein expression patterns, cells were clustered using k-means algorithm. Optimal cluster number was estimated using the within groups sum of squared error (SSE) plot followed by gap statistics with bootstrapping and first SE max method. These methods suggested 9 clusters as optimal in the multidimensional space. Applying k-means clustering with (k=9) on our CyTOF data, resulted in clear distinction between cluster 1 and cluster 2 of the $CD8^+$ cells. This separation could be further visualized by two-dimensional non-linear embedding of the protein expression profiles using t-stochastic neighborhood embedding (t-SNE (Maaten L, 2008)). The t-SNE plot can then be overlaid by k-means clustering results to reflect a non-biased approach to the clusters or with intensity of the different markers.

Example 3: CD39 Regulates Dysfunction in $CD8^+$ TILs and Marks a Novel Population with an Altered Functional Phenotype CD39 (also known as ectonucleoside triphosphate diphosphohydrolase-1) is encoded by the gene ENTPDL. It is a cell surface ptorien with an extracellular catalytic site that catalyzes the hydrolysis of various P2 receptor ligands, including ATP, ADP, UTP and other phosphate containing molecules. The enzymatic activities of CD39, in conjunction with CD73, play a role in calibrating the duration, magnitude, and chemical nature of purinergic signals delivered to immune cells. As disclosed herein, CD39 and up-regulation of ENTPD1 is associated with several dysfunctional T cell states.

Applicants postulated that CD39 (i.e. ENTPD1) may be involved in regulating $CD8^+$ T cell dysfunction. Applicants can validate that CD39 performs important functions for inducing T cell dysfunction, and more specifically, can determine whether modulating CD39 in T cells provides an enhanced immune response in cancer.

In a certain example, Applicants characterize CD39 expression and its associated function in $CD8^+$ WT tumor-bearing mice. TILs (tumor infiltrating lymphocytes) are isolated from the mice and expression is determined. Cells may be sorted and sequenced in bulk or single cells may be sequenced. CD39 may be expressed on a subpopulation of CD8 T cells having a signature of dysfunction as described herein or a signature of dysfunction previously described (Singer et al., Cell, Vol 166, Issue 6, p1500-1511.e9, 8 Sep. 2016). The dysfunctional subpopulation may be found in TILs, but not in tumor draining lymph node.

In a certain example, cytokine expression in CD39-expressing $CD8^+$ TILs is examined to determine whether the CD39 expression correlates with $CD8^+$ T cell function. This result may determine whether CD39 CD8 TILs are not only poorly functional as measured by a dysfunctional signature, but they may also actively produce suppressive cytokines and contribute to suppression locally in the tumor microenvironment. Suppressive cytokines may include, but are not limited to IL-10.

Applicants can determine whether CD39 is a regulator of the suppressive function of dysfunctional $CD8^+$ T cells in cancer. In a certain example, CD39 WT or knockout $CD8^+$ T cells are assessed for their ability to influence effector T cell proliferation using a suppression assay, such that $CD39^{-/-}$ TILs fail to suppress effector T cell proliferation compared to WT dysfunctional TILs.

In a certain example, to directly analyze the functional role of CD39 in regulating $CD8^+$ T cell dysfunction, a lentiviral CRISPR/cas9 targeting approach is used to knockout CD39 in T cells. In a certain example, naïve transgenic pmel $CD8^+$ T cells are used. Control or CD39 CRISPR lentiviruses are transduced into $CD8^+$ T cells isolated from PMEL transgenic mice in which all T cells have a single tumor antigen specific TCR with specificity for the mouse homologue of the human premelanosome protein. PMEL $CD8^+$ T cells are normally ineffective at controlling growth of B16F10 melanoma tumors, such that perturbations that promote tumor clearance can be readily discerned. Control or CD39-targeted (deleted, i.e., $CD39^{-/-}$) pmel $CD8^+$ T cells are activated and equal numbers of cells are transferred into WT mice with established B16F10 melanoma tumor. Mice are then followed for tumor growth. Efficiency of CD39 deletion may be determined by quantitative real time PCR. The transfer of $CD39^{-/-}$ pmel $CD8^+$ T cells is expected to significantly delay tumor growth in WT mice.

Upon transfer into WT hosts, $CD39^{-/-}$ pmel $CD8^+$ T cells may produce a higher percent of poly-functional IL-2 and IFNg-producing cells, consistent with a less dysfunctional phenotype compared to control WT pmel $CD8^+$ T cells. Accordingly, the transfer of $CD39^{-/-}$ pmel $CD8^+$ T cells may delay tumor growth in WT mice. These data may support a role for CD39 as a regulator of the $CD8^+$ T cell dysfunction program that contributes to poor tumor control.

In a certain example, Applicants can further demonstrate that tumor growth is significantly reduced or abolished in $CD39^{-/-}$ KO mice, and that splenic $CD39^{-/-}$ $CD8^+$ T cells from $CD39^{-/-}$ KO mice harboring a tumor has a reduction in tumor size when transferred into tumor harboring wild type animals. In particular, WT or $CD39^{-/-}$ mice are implanted with B16-F10 tumor subcutaneously. At day 18, CD8 and CD4 T cells are isolated from the spleens of WT and $CD39^{-/-}$ mice and transferred into WT host mice which are subsequently injected with B16-F10 tumor subcutaneously. Tumor growth is then followed.

A CRISPR/cas9 targeting approach is also used to knockout CD39 followed by RNA-seq to determine gene networks regulated by CD39.

Figure 17:
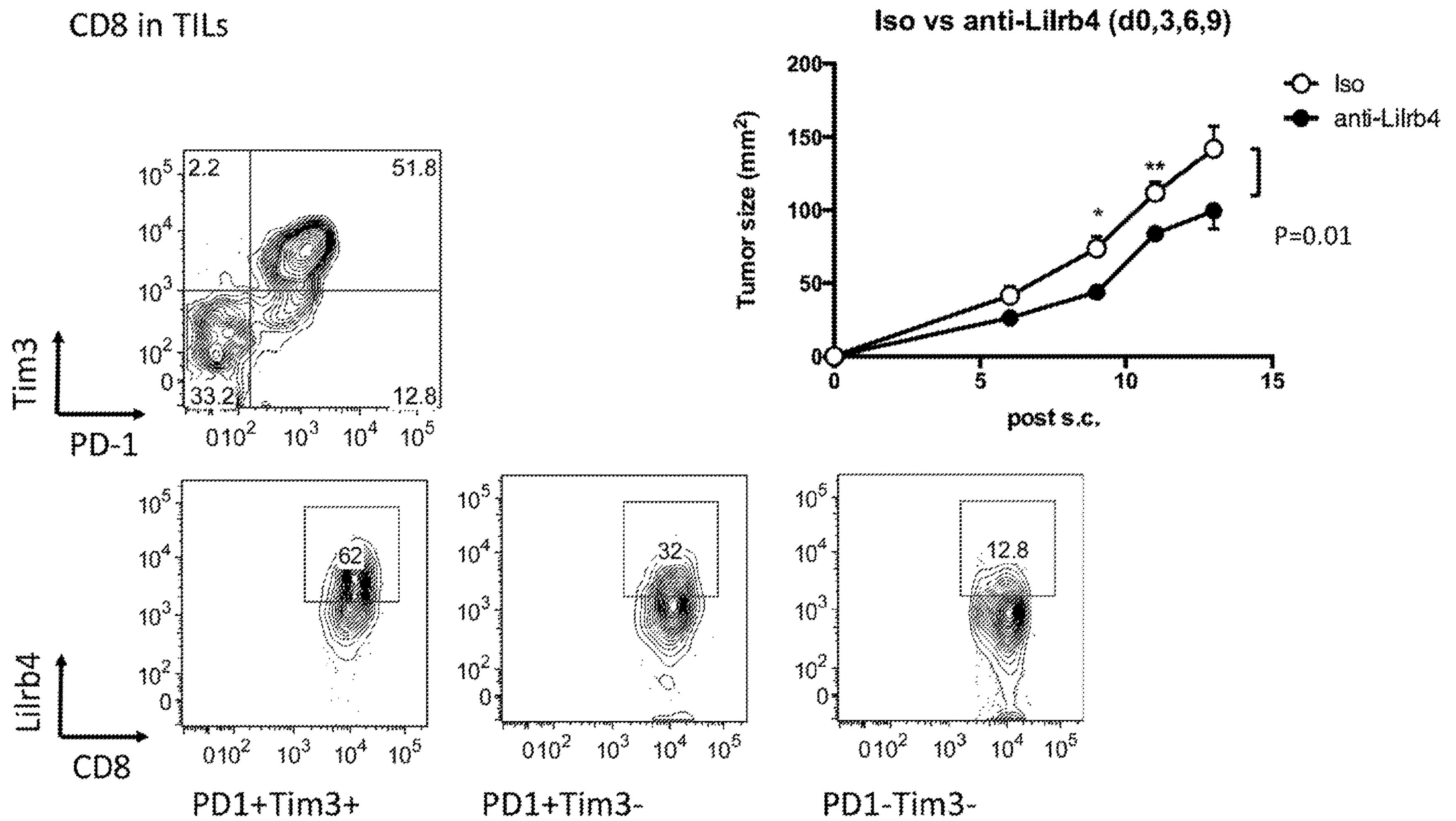
FIG. 17. Lilrb4 is co-expressed with $PD\text{-}1^+$ Tim3+ CD8 T cells and blocking antibody slightly suppress tumor growth (B16 melanoma).
Figure 18:
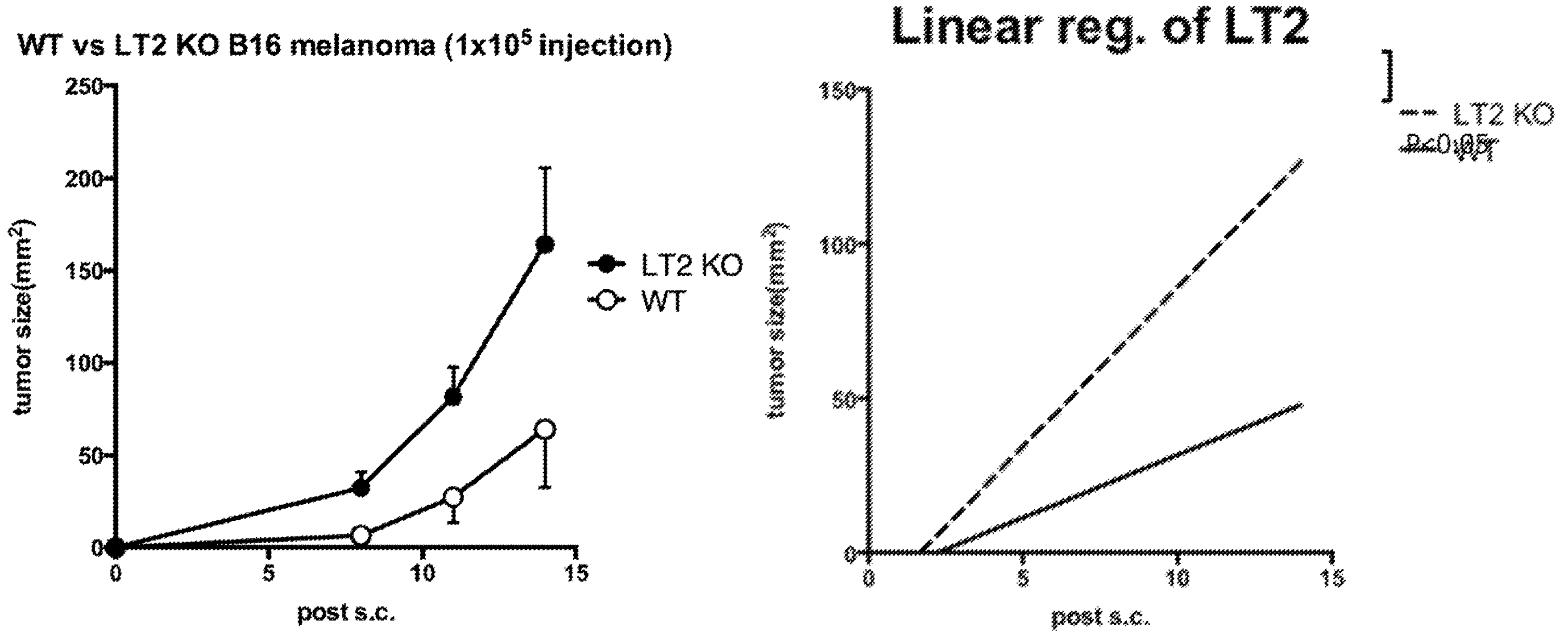
FIG. 18. Cysltr2 (LT2) deficiency enhances tumor growth. WT and LT2 KO mice were injected with B16F10 melanoma cells on day 0 and the change in tumor size was plotted (WT: N=5, LT2 KO: N=5). Linear regression following ANOVA was performed between the groups.
Figure 19:
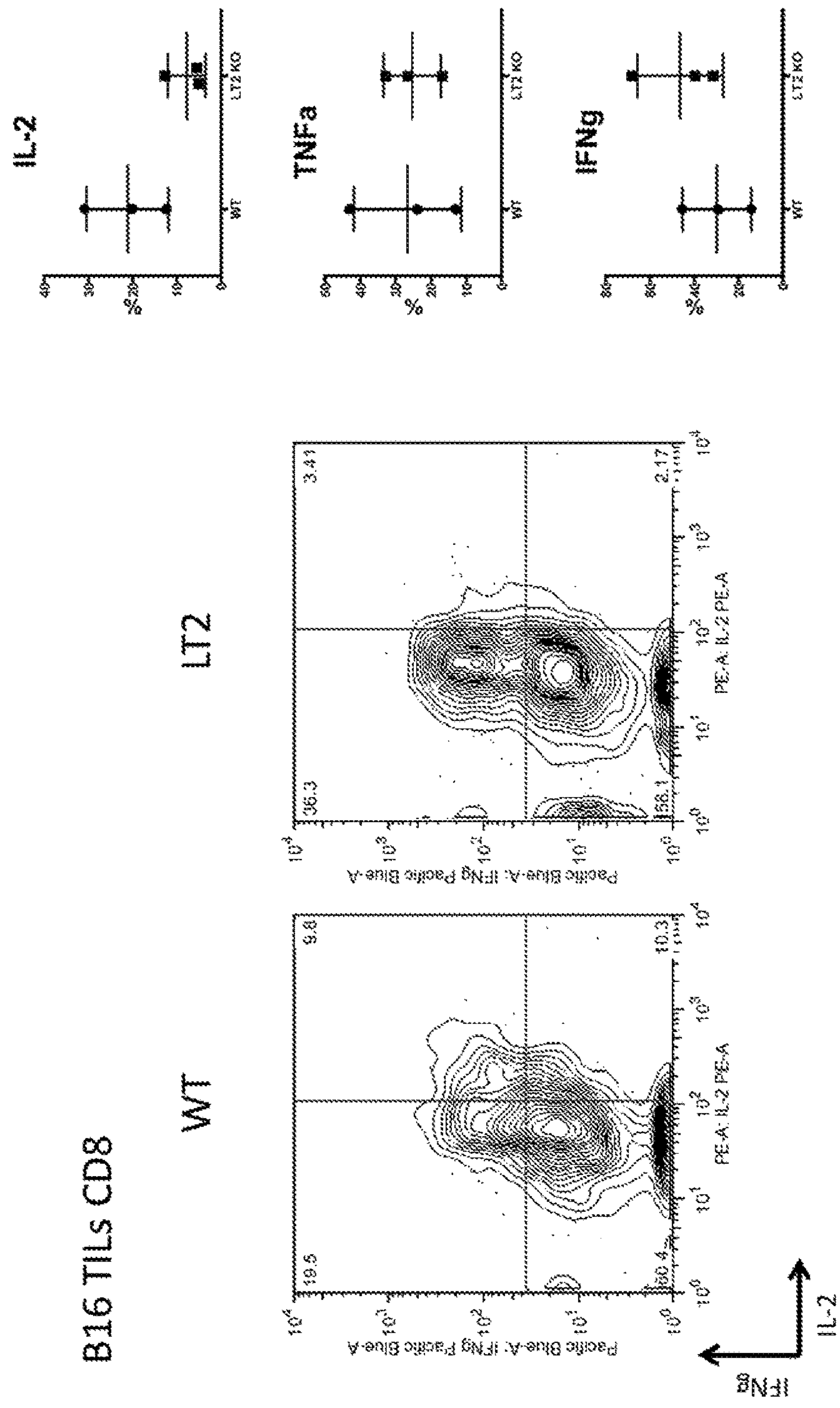
FIG. 19. Cysltr2 (LT2) deficiency reduces IL-2 production by CD8 TILs. Cytokine production from CD8 TILs was analyzed by intracellular cytokine staining using FACS. Representative data are shown as flow-cytometric schemes and the data from multiple experiments are combined and shown as plots.
Figure 20:
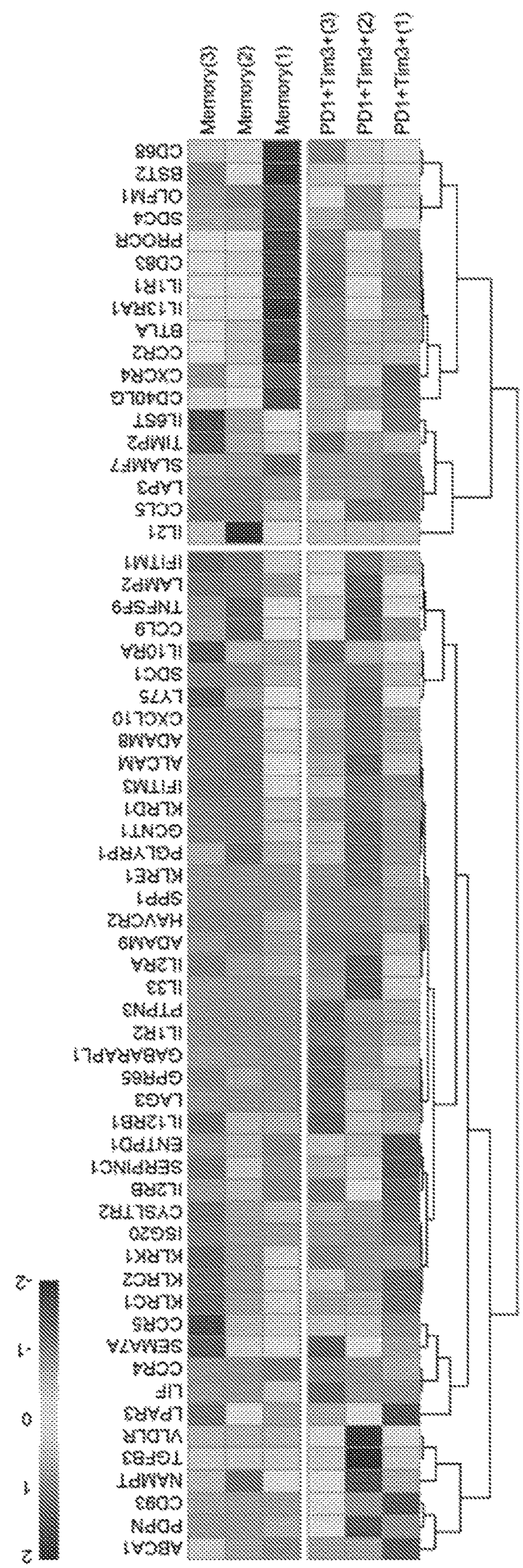
FIG. 20. Comparison of expression levels between exhausted CD8 cells and memory cells for the target genes. Those genes that were up-regulated in the memory cells can be associated with survival/stimulatory/inhibitory-of-inhibitory effects.

Turning to FIG. 17, Applicants show that CD39 is co-expressed with PD-1+ Tim3+CD8 T cells and blocking antibody slightly suppress tumor growth (B16 melanoma).

Example 4: Therapeutic Modulation of CD39

In a certain example, modulation of CD39 is used in the treatment of cancer in a patient in need thereof. In a certain example, Applicants modulate expression or activity of CD39 in autologous T cells obtained from a patient in need thereof to perform adoptive cell transfer. The autologous T cells may be made resistant to exhaustion or exhausted T cells are activated by knockdown or knockout of expression or activity of CD39. Additionally, activity or expression of CD39 is modulated in CAR T cells. T cells may be modulated ex vivo and transferred to a patient by any method described herein.

In a certain example, Applicants target dysfunctional $CD8^+$ T cells in vivo in a patient in need thereof suffering from cancer, such that T cells expressing CD39 are targeted with a therapeutic composition with specific affinity for CD39. The therapeutic composition may be an antibody, such as but not limited to an antibody drug conjugate. Effective tumor control may be provided by removing dysfunctional T cells in the tumor microenvironment, thus enhancing immunity and decreasing suppression.

Example 5: Experimental Procedures for Verifying Activity of CD39

Mice 6-8 week old female Balb/c, C57BL/6, pmel transgenic, and OTI transgenic mice are purchased from the Jackson Laboratory.

Tumor Experiments

B16F10 ($5\times10^5$) are implanted subcutaneously into the right flank. Tumor size was measured in two dimensions by caliper and is expressed as the product of two perpendicular diameters. For adoptive transfer tumor experiments, tumor cells are implanted five days prior to intravenous injection of T cells. Naïve ($CD8^+$ CD62L+$CD441^{lo}$) T cells from PMEL (for crispr/cas9 targeting experiments) are isolated by cell sorting (BD FACS Aria) and activated by 2 μg/ml each of plate-bound anti-CD3 and anti-CD28 antibodies for 48 hours, rested for 3 days, and then reactivated with 1 ug/ml of anti-CD3 and anti-CD28 antibodies for 2 days prior to transfer into recipient mice. Retroviral and lentiviral infections of primary T cells are optimized and experiments are performed as described herein. Briefly, retrovirus is used to spin-infect T cells one day after activation and lentivirus is used to infect T cells twice, at 16 hours prior to activation and at 4 hours post activation. Targeting efficiency of retrovirus is determined by measuring GFP expression; whereas effective CRISPR/cas9-mediated deletion of the target gene using lentivirus is determined by qPCR.

Isolation of Tumor Infiltrating Lymphocytes.

Tumor infiltrating lymphocytes are isolated by dissociating tumor tissue in the presence of collagenase D (2.5 mg/ml) for 20 min prior to centrifugation on a discontinuous Percoll gradient (GE Healthcare). Isolated cells are then used in various assays of T cell function. Cells are cultured in DMEM supplemented with 10% (vol/vol) FCS, 50 μM 2-mercaptoethanol, 1 mM sodium pyruvate, nonessential amino acids, L-glutamine and 100 U/ml penicillin and 100 g/ml streptomycin.

Flow Cytometry

Single cell suspensions are stained with antibodies against surface molecules. CD4 (RM4-5), CD8 (53-6.7), and PD-1 (RMP1-30) antibodies are purchased from BioLegend. Tim-3 (5D12) antibody is generated in house. Fixable viability dye eF506 (eBioscience) is used to exclude dead cells. For intra-cytoplasmic cytokine staining, cells are stimulated with 12-myristate 13-acetate (PMA) (50 ng/ml, Sigma-Aldrich, MO), ionomycin (1 μg/ml, Sigma-Aldrich, MO) in the presence of Brefeldin A (Golgiplug, BD Bioscience) for four hours prior to staining with antibodies against surface proteins followed by fixation and permeabilization and staining with antibodies against IL-2 (JES6-5H4), TNF-α (MP6-XT22), IFN-γ (XMG-1.2) (eBioscience), and Granzyme B (GB11) (Biolegend). For measurement of intracellular zinc, cells are stained with 1 μM Zinpyr-1 (Sigma) in PBS for 20 min at 37deg, washed with media, followed by regular surface staining. All data are collected on a BD LsrII (BD Biosciences) and analyzed with FlowJo software (Tree Star).

Generation of Lentiviral Constructs Using CRISPR/CAS9 Targeting.

The initial guide sequences are selected based on the exon structure of target genes (i.e. ENTPD1) and ranked by the repertoire of potential off-target sites to select designs that minimize the possibility of off-target cleavage. The guides are then cloned into CRISPR-Cas9 vectors via golden-gate cloning as described previously (Cong et al., 2013, Science 339, 819-823). The vector used is a lenti-viral vector, pCKO_2, bearing mammalian-codon-optimized SaCas9 linked to puromycin selection cassette (Ran et al., 2015, Nature 520, 186-191; Shalem et al., 2014, Science 343, 84-87), and an sgRNA-expression cassette that is modified to enhance RNA expression. The constructs are sequence verified and tested to screen for the efficiency against ENTPD1 using a mouse T-lymphocyte cell line, EL4 (ATCC) before moving on to lentiviral production. To quantify the genomic modification induced by the CRISPR-Cas9 system, genomic DNA is extracted using QuickExtract Solution (Epicentre), as described previously (Cong et al., 2013, supra). Indel formation is measured by either SURVEYOR nuclease assay (IDT DNA) or targeted deep sequencing as described previously (Cong et al., 2013, supra). Briefly, the genomic region around the CRISPR-Cas9 targeting site (i.e. ENTPD1) is amplified, and then subject to either SURVEYOR nuclease digestion following re-annealing or re-amplified to add on Illumina P5/P7 adapters with barcodes for deep-sequencing analysis using the MiSeq sequencing system (Illumina).

After screening of guides in cell lines, the top-ranked guides based on their targeting efficiency for ENTPD1 are used for viral production. 293FT cells (Thermo Fisher) are maintained as recommended by the manufacturer in 150 mm plates. For each transfection, 10 μg of pVSVG envelope plasmid, 15 μg of pDelta packaging plasmids, and 20 μg of pCKO_2 vector carrying the construct of interest are used. The transfection is either carried out using lipofectamine 2000 (Thermo Fisher) following the manufacturer's recommendations, or with PEI, where 5:1 ratio of PEI solution is added to the DNA mixture, and incubated for 5 minutes before adding the final complex onto cells. After incubation for 16 hours, 20 mL of fresh warm media is applied to replace the old growth media. Virus is harvested between 48 h and 72 h post transfection by taking the supernatant and pelleting cell debris via centrifugation. The viral particles are then filtered through a 0.45 μm filtration system (Millipore), and then either directly used as purified supernatant, or concentrated further with 15-mL Amicon concentrator (Millipore). Lentiviral vectors are titered by real-time qPCR using a customized probe against the transgene.

For all primary T-cell experiments, the efficacy of the CRISPR-Cas9 lentiviral vectors is first tested by transducing in vitro primary mouse T-cell culture, followed by cleavage measurement and qPCR detection of target gene knockdown. The most efficient viral constructs are then used for downstream experiments.

The invention is further described by the following numbered paragraphs:

1. A method of modulating T-cell dysfunction, the method comprising contacting a dysfunctional T-cell with a modulating agent or agents that modulate the expression, activity and/or function of one or more target genes or gene products thereof selected from the target genes listed in Table 1, Table 2, or any combination thereof.
2. The method of paragraph 1, wherein the T-cell dysfunction is T-cell exhaustion.
3. The method of paragraph 2, wherein the modulation of T-cell exhaustion comprises a decrease in the exhausted T-cell phenotype, such that functional T-cell activity is increased.
4. The method of paragraph 1, wherein the selected target gene or gene product or a combination thereof is/are identified as participating in the inhibition of functional T-cell activity.
5. The method of paragraph 4, wherein the modulating agent inhibits the expression, activity and/or function of the selected target gene or gene product or combination thereof.
6. The method of paragraph 1, wherein the selected target gene or combination of target genes is/are identified as participating in the promotion of functional T-cell activity.
7. The method of paragraph 6, wherein the modulating agent promotes or activates the expression, activity and/or function of the selected target gene or gene product or combination thereof.
8. The method of paragraph 1, comprising contacting the dysfunctional T-cell with modulating agents that modulate the expression, activity and/or function of at least two target genes or gene products selected from the target genes listed in Table 1, Table 2, or any combination thereof.
9. The method of paragraph 1, wherein the modulating agent comprises a peptide agent, polypeptide agent, a soluble variant of a membrane-associated polypeptide, antibody agent, a nucleic acid agent, a nucleic acid ligand, or a small molecule agent.
10. The method of paragraph 1, further comprising contacting the dysfunctional T-cell with an agent or treatment selected from the group consisting of a PD-1 inhibitor, a CTLA4 inhibitor, chemotherapy, radiation therapy, a Braf inhibitor, a MEK inhibitor, a Sting agonist, a TLR agonist, an IDO inhibitor, and an agonist for OX-40, 4-1BB, GITR, CD226, KLRC2, KLRE1, KLRK1, IL12RB1, IL1R1, and/or SLAMF7.
11. A method of treating a condition involving or characterized by the presence of T cells exhibiting a dysfunctional or exhausted phenotype, the method comprising administering an amount of a modulating agent effective to modulate the expression, activity and/or function of one or more target genes or gene products thereof selected from the target genes listed in Table 1, Table 2, or any combination thereof.
12. The method of paragraph 11, wherein the condition is cancer or a persistent infection.
13. The method of paragraph 11, wherein the selected target gene or combination of target genes is/are identified as participating in the inhibition of T cell activation.
14. The method of paragraph 13, wherein the modulating agent inhibits the expression, activity and/or function of the target gene or gene product or combination thereof.
15. The method of paragraph 11 wherein a selected target gene or combination of target genes is/are identified as participating in the promotion of T cell activation.
16. The method of paragraph 15, wherein the modulating agent promotes or activates the expression, activity and/or function of the target gene or gene product or combination thereof.
17. The method of paragraph 11, wherein the modulating agent comprises a peptide agent, polypeptide agent, a soluble variant of a membrane-associated polypeptide, antibody agent, a nucleic acid agent, a nucleic acid ligand, or a small molecule agent.
18. A pharmaceutical composition for modulating T cell dysfunction, the composition comprising a first modulating agent and a second modulating agent that modulate the expression, activity and/or function of two or more target genes or gene products thereof selected from the target genes listed in Table 1, Table 2, or any combination thereof.
19. A pharmaceutical composition for modulating T cell dysfunction, the composition comprising a first modulating agent that inhibits the expression, activity and/or function of one or more target genes or gene products thereof selected from the target genes listed in Table 1, Table 2, or any combination thereof and a second modulating agent that promotes the expression, activity and/or function of one or more target genes or gene products thereof selected from the target genes listed in Table 1, Table 2, or any combination thereof.
20. A pharmaceutical composition for modulating T cell dysfunction, the composition comprising a modulating agent that modulates the expression, activity and/or function of one or more target genes or gene products thereof selected from the target genes listed in Table 1, Table 2, or any combination thereof and an agent selected from the group consisting of a PD-1 inhibitor, a CTLA4 inhibitor, chemotherapy, a Braf inhibitor, a MEK inhibitor, a Sting agonist, a TLR agonist, an IDO inhibitor, and an agonist for OX-40, 4-1BB, GITR, CD226, KLRC2, KLRE1, KLRK1, IL12RB1, IL1R1, and/or SLAMF7.

21. The composition of any one of paragraphs 18-20 wherein the T cell dysfunction comprises T cell exhaustion.
22. The composition of any one of paragraphs 18-21 wherein the T cell exhaustion occurs in an individual with cancer or a persistent infection.
23. A pharmaceutical composition for modulating T cell dysfunction, the composition comprising an inhibitor of the expression and/or activity of PDPN and an inhibitor of the expression and/or activity of PROCR.
24. A pharmaceutical composition for modulating T cell dysfunction comprising:
   (a) an inhibitor of the expression and/or activity of PDPN and an inhibitor of the expression and/or activity of PROCR; and
   (b) an inhibitor of the expression and/or activity of at least one of the molecules selected from the group consisting of TIGIT, LAG3, LILRB4, and KLRC1; and/or an activator of the expression and/or activity of at least one of the molecules selected from the group consisting of CD226, OX-40, GITR, TNFSF9 (4-1BB), KLRC2, KLRE1, KLRK1, IL12RB1, IL1R1, and SLAMF7.
25. A pharmaceutical composition for modulating an IL-27-regulated co-inhibitory module comprising:
   (a) an inhibitor of the expression and/or activity of at least one of the molecules selected from the group consisting of PDPN, PROCR, TIGIT, LAG3, LILRB4, ALCAM and KLRC1; and
   (b) an activator of the expression and/or activity of at least one of the molecules selected from the group consisting of CD226, OX-40, GITR, TNFSF9 (4-1BB), KLRC2, KLRE1, KLRK1, IL12RB1, ILiR1, and SLAMF7.
26. The pharmaceutical composition of any one of paragraphs 23-25, further comprising an inhibitor of the expression and/or activity of TIM-3.
27. The pharmaceutical composition of any one of paragraphs 23-25, further comprising an inhibitor of the expression and/or activity of PD-1.
28. The pharmaceutical composition of any one of paragraphs 23-25, further comprising an inhibitor of the expression and/or activity of CTLA4.
29. The pharmaceutical composition of any one of paragraphs 23-25, further comprising an inhibitor of the expression and/or activity of TIM-3 and an inhibitor of the expression and/or activity of PD-1.
30. The pharmaceutical composition of any one of paragraphs 23-25, further comprising an inhibitor of the expression and/or activity of TIM-3 and an inhibitor of the expression and/or activity of CTLA4.
31. The pharmaceutical composition of any one of paragraphs 23-25, further comprising an inhibitor of the expression and/or activity of CTLA4 and an inhibitor of the expression and/or activity of PD-1.
32. The pharmaceutical composition of any one of paragraphs 23-25, further comprising an inhibitor of the expression and/or activity of TIM-3, an inhibitor of the expression and/or activity of CTLA4 and an inhibitor of the expression and/or activity of PD-1.
33. The pharmaceutical composition of any one of paragraphs 23-32, wherein the inhibitors and activators are selected from an antibody or antigen binding fragment thereof, a small molecule compound, a protein or peptide molecule, a DNA or RNA aptamer, an antisense or siRNA molecule, and a structural analog.
34. The pharmaceutical composition of paragraph 33, wherein the antibody or antigen binding fragment thereof, a small molecule compound, a protein or peptide molecule, a DNA or RNA aptamer, an antisense or siRNA molecule, and a structural analog is selected from the group consisting of: an anti-CTLA4 antibody, an anti-PD-1 antibody, or aPDL-1 antagonist.
35. A method of modulating an IL-27-regulated co-inhibitory module in a subject in need thereof, the method comprising administering a pharmaceutical composition comprising an inhibitor of the expression and/or activity of PDPN and an inhibitor of the expression and/or activity of PROCR.
36. A method of modulating an IL-27-regulated co-inhibitory module in a subject in need thereof, the method comprising:
   (a) administering a pharmaceutical composition comprising an inhibitor of the expression and/or activity of PDPN, and an inhibitor of the expression and/or activity of PROCR; and
   (b) administering a pharmaceutical composition comprising an inhibitor of the expression and/or activity of at least one of the molecules selected from the group consisting of an inhibitor of the expression and/or activity of TIGIT, LAG3, LILRB4, and KLRC1; and/or an activator of the expression and/or activity of at least one of the molecules selected from the group consisting of CD226, OX-40, GITR, TNFSF9 (4-1BB), KLRC2, KLRE1, KLRK1, IL12RB1, IL1R1, and SLAMF7.
37. A method of modulating an IL-27-regulated co-inhibitory module in a subject in need thereof, the method comprising:
   (a) administering a pharmaceutical composition comprising an inhibitor of the expression and/or activity of at least one of the molecules selected from the group consisting of PDPN, PROCR, TIGIT, LAG3, LILRB4, ALCAM, and KLRC1; and
   (b) administering a pharmaceutical composition comprising an activator the expression and/or activity of at least one of the molecules selected from the group consisting of CD226, OX-40, GITR, TNFSF9 (4-1BB), KLRC2, KLRE1, KLRK1, IL12RB1, IL1R1, and SLAMF7.
38. The method of any one of paragraphs 35-37, further comprising an inhibitor of the expression and/or activity of TIM-3.
39. The method of any one of paragraphs 35-37, further comprising an inhibitor of the expression and/or activity of PD-1.
40. The method of any one of paragraphs 35-37, further comprising an inhibitor of the expression and/or activity of CTLA4.
41. The method of any one of paragraphs 35-37, further comprising an inhibitor of the expression and/or activity of TIM-3 and an inhibitor of the expression and/or activity of PD-1.
42. The method of any one of paragraphs 35-37, further comprising an inhibitor of the expression and/or activity of TIM-3 and an inhibitor of the expression and/or activity of CTLA4.
43. The method of any one of paragraphs 35-37, further comprising an inhibitor of the expression and/or activity of CTLA4 and an inhibitor of the expression and/or activity of PD-1.
44. The method of any one of paragraphs 35-37, further comprising an inhibitor of the expression and/or activity of TIM-3, an inhibitor of the expression and/or activity of PD-1, and an inhibitor of the expression and/or activity of CTLA4.

45. The method of any one of paragraphs 35-44, wherein the inhibitors and activators are selected from an antibody or antigen binding fragment thereof, a small molecule compound, a protein or peptide molecule, a DNA or RNA aptamer, an antisense or siRNA molecule, and a structural analog.

46. The method of paragraph 45, wherein the antibody or antigen binding fragment thereof, a small molecule compound, a protein or peptide molecule, a DNA or RNA aptamer, an antisense or siRNA molecule, and a structural analog is selected from the group consisting of: an anti-CTLA4 antibody, an anti-PD-1 antibody, and a PDL-1 antagonist.

47. The method of any one of paragraphs 35-46, wherein the subject in need thereof has a disease or disorder characterized by T-cell exhaustion.

48. The method of any one of paragraphs 35-46, wherein the subject in need thereof is diagnosed as having a cancer or tumor.

49. The method of any one of paragraphs 35-46, wherein the subject in need thereof is diagnosed as having a persistent infection.

50. A method of modulating T cell dysfunction, the method comprising contacting a dysfunctional T cell with a modulating agent or agents that modulate the expression, activity and/or function of one or more target genes or gene products thereof selected from the group consisting of: BTLA, TIGIT, HAVCR2 (TIM-3), LAG3, PDPN, ILIORA, IL1R2, PROCR, LILRB4, KLRC1, KLRC2, KLRE1, TNFSF9 (4-1BB), KLRK1, IL12RB1, ILiR1, AND SLAMF7.

51. The method of paragraph 50, wherein the T cell dysfunction is T cell exhaustion.

52. The method of paragraph 51, wherein the modulation of T cell exhaustion comprises a decrease in the exhausted T cell phenotype, such that T cell activation is increased.

53. The method of paragraph 51, wherein the selected target gene or combination of target genes is/are identified as participating in the inhibition of T cell activation.

54. The method of paragraph 53, wherein the modulating agent promotes the expression, activity and/or function of the target gene or gene product or combination thereof.

55. The method of paragraph 51, wherein the selected target gene or combination of target genes is/are identified as participating in the promotion of T cell activation.

56. The method of paragraph 55, wherein the modulating agent inhibits the expression, activity and/or function of the target gene or gene product or combination thereof.

57. The method of paragraph 50, wherein the modulating agent comprises a peptide agent, polypeptide agent, a soluble variant of a membrane-associated polypeptide, antibody agent, a nucleic acid agent, a nucleic acid ligand, or a small molecule agent.

58. A method of treating a condition involving or characterized by the presence of T cells exhibiting an exhausted phenotype, the method comprising administering an amount of a modulating agent effective to modulate the expression, activity and/or function of one or more target genes or gene products thereof selected from the group consisting of: BTLA, TIGIT, HAVCR2 (TIM-3), LAG3, PDPN, IL10RA, IL1R2, PROCR, LILRB4, KLRC1, KLRC2, KLRE1, TNFSF9 (4-1BB), KLRK1, IL12RB1, IL1R1, AND SLAMF7.

59. The method of paragraph 58 wherein the condition is cancer or a persistent infection.

60. The method of paragraph 58 wherein the selected target gene or combination of target genes is/are identified as participating in the inhibition of T cell activation.

61. The method of paragraph 60 wherein the modulating agent inhibits the expression, activity and/or function of the target gene or gene product or combination thereof.

62. The method of paragraph 58 wherein the selected target gene or combination of target genes is/are identified as participating in the promotion of T cell activation.

63. The method of paragraph 62 wherein the modulating agent promotes or activates the expression, activity and/or function of the target gene or gene product or combination thereof.

64. The method of paragraph 58 wherein the agent comprises a peptide agent, polypeptide agent, a soluble variant of a membrane-associated polypeptide, antibody agent, a nucleic acid agent, a nucleic acid ligand, or a small molecule agent.

65. A method of determining the presence of T cells exhibiting an exhausted phenotype, the method comprising detecting, in a sample comprising T cells, a level of expression, activity and/or function of one or more genes or expression products thereof selected from the target genes listed in Table 1, Table 2 or any combination thereof, and comparing the detected level to a reference, wherein a difference in the detected level relative to the reference indicates the presence of T cells exhibiting an exhausted phenotype.

66. The method of paragraph 65 wherein the sample is from an individual with cancer or a persistent infection.

67. A method of treating a disease or disorder characterized by aberrant or unwanted T-cell functional activity in a subject in need thereof, the method comprising administering a therapeutically effective amount of a modulating agent effective to modulate the expression, activity and/or function of one or more target genes or gene products thereof selected from the target genes listed in Table 1, Table 2, or any combination thereof.

68. The method of paragraph 67, wherein the disease or disorder is an autoimmune disease or graft vs. host disease.

69. The method of paragraph 67, wherein the selected target gene or combination of target genes is/are identified as participating in the inhibition of T cell activation.

70. The method of paragraph 69, wherein the modulating agent promotes the expression, activity and/or function of the target gene or gene product or combination thereof.

71. The method of paragraph 67, wherein the modulating agent promotes or activates the expression, activity and/or function of the target gene or gene product or combination thereof.

72. The method of paragraph 67, wherein the modulating agent comprises a peptide agent, polypeptide agent, a soluble variant of a membrane-associated polypeptide, antibody agent, a nucleic acid agent, a nucleic acid ligand, or a small molecule agent.

73. A method of modulating T-cell dysfunction, the method comprising contacting a dysfunctional T-cell with a modulating agent or agents that modulate the expression, activity and/or function of two or more target genes or gene products thereof selected from the target genes listed in Table 5.
74. A method of modulating T-cell dysfunction, the method comprising contacting a dysfunctional T-cell with a modulating agent or agents that modulate the expression, activity and/or function of two or more target genes or gene products thereof selected from the target genes listed in Table 6.
75. A method of modulating T-cell dysfunction, the method comprising contacting a dysfunctional T-cell with a modulating agent or agents that modulate the expression, activity and/or function of two or more target genes or gene products thereof selected from the target genes listed in Table 7.
76. A method of modulating T-cell dysfunction, the method comprising contacting a dysfunctional T-cell with a modulating agent or agents that modulate the expression, activity and/or function of two or more target genes or gene products thereof selected from the target genes listed in Table 8.
77. A method of modulating T-cell dysfunction, the method comprising contacting a dysfunctional T-cell with a modulating agent or agents that modulate the expression, activity and/or function of two or more target genes or gene products thereof selected from the target genes listed in Table 9.
78. The method of any one of paragraphs 73-77, wherein the T-cell dysfunction is T-cell exhaustion.
79. The method of paragraph 78, wherein the modulation of T-cell exhaustion comprises a decrease in the exhausted T-cell phenotype, such that functional T-cell activity is increased.
80. The method of any one of paragraphs 73-77, wherein the selected target gene or gene product or a combination thereof is/are identified as participating in the inhibition of functional T-cell activity.
81. The method of paragraph 80, wherein the modulating agent inhibits the expression, activity and/or function of the selected target gene or gene product or combination thereof.
82. The method of any one of paragraphs 73-77, wherein the selected target gene or combination of target genes is/are identified as participating in the promotion of functional T-cell activity.
83. The method of paragraph 82, wherein the modulating agent promotes or activates the expression, activity and/or function of the selected target gene or gene product or combination thereof.
84. The method of any one of paragraphs 73-77, wherein the modulating agent comprises a peptide agent, polypeptide agent, a soluble variant of a membrane-associated polypeptide, antibody agent, a nucleic acid agent, a nucleic acid ligand, or a small molecule agent.
85. The method of any one of paragraphs 73-77, further comprising contacting the dysfunctional T-cell with an agent or treatment selected from the group consisting of a PD-1 inhibitor, a CTLA4 inhibitor, chemotherapy, radiation therapy, a Braf inhibitor, a MEK inhibitor, a Sting agonist, a TLR agonist, an IDO inhibitor, and an agonist for OX-40, 4-1BB, GITR, CD226, KLRC2, KLRE1, KLRK1, IL12RB1, IL1R1, and/or SLAMF7.
86. A method of treating a condition involving or characterized by the presence of T cells exhibiting a dysfunctional or exhausted phenotype, the method comprising administering an amount of a modulating agent effective to modulate the expression, activity and/or function of two or more target genes or gene products thereof selected from the target genes listed in Table 5, Table 6, Table 7, Table 8, or Table 9.
87. The method of paragraph 86, wherein the condition is cancer or a persistent infection.
88. The method of paragraph 87, wherein the selected target gene or combination of target genes is/are identified as participating in the inhibition of T cell activation.
89. The method of paragraph 88, wherein the modulating agent inhibits the expression, activity and/or function of the target gene or gene product or combination thereof.
90. The method of paragraph 86, wherein a selected target gene or combination of target genes is/are identified as participating in the promotion of T cell activation.
91. The method of paragraph 90, wherein the modulating agent promotes or activates the expression, activity and/or function of the target gene or gene product or combination thereof.
92. The method of paragraph 86, wherein the modulating agent comprises a peptide agent, polypeptide agent, a soluble variant of a membrane-associated polypeptide, antibody agent, a nucleic acid agent, a nucleic acid ligand, or a small molecule agent.
93. A pharmaceutical composition for modulating T cell dysfunction, the composition comprising at least one modulating agent that modulates the expression, activity and/or function of one or more target genes or gene products thereof selected from the target genes listed in Table 5, Table 6, Table 7, Table 8, Table 9, Table 10, Table 11, Table 12, or Table 13.
94. A pharmaceutical composition for modulating T cell dysfunction, the composition comprising a first modulating agent that inhibits the expression, activity and/or function of one or more target genes or gene products thereof selected from the target genes listed in Table 5, Table 6, Table 7, Table 8, Table 9, Table 10, Table 11, Table 12, or Table 13 and a second modulating agent that promotes the expression, activity and/or function of one or more target genes or gene products thereof selected from the target genes listed in Table 5, Table 6, Table 7, Table 8, Table 9, Table 10, Table 11, Table 12, or Table 13.

REFERENCES

Anders, S., and Huber, W. (2010). Differential expression analysis for sequence count data. Genome Biol 11, R106.

Anderson, A. C., Joller, N., and Kuchroo, V. K. (2016). Lag-3, Tim-3, and TIGIT: Co-inhibitory Receptors with Specialized Functions in Immune Regulation. Immunity 44, 989-1004.

Apetoh, L., Quintana, F. J., Pot, C., Joller, N., Xiao, S., Kumar, D., Burns, E. J., Sherr, D. H., Weiner, H. L., and Kuchroo, V. K. (2010). The aryl hydrocarbon receptor interacts with c-Maf to promote the differentiation of type 1 regulatory T cells induced by IL-27. Nature immunology 11, 854-861.

Awasthi, A., Carrier, Y., Peron, J. P., Bettelli, E., Kamanaka, M., Flavell, R. A., Kuchroo, V. K., Oukka, M., and Weiner, H. L. (2007). A dominant function for interleukin 27 in generating interleukin 10-producing anti-inflammatory T cells. Nature immunology 8, 1380-1389.

Batten, M., Kljavin, N. M., Li, J., Walter, M. J., de Sauvage, F. J., and Ghilardi, N. (2008). Cutting edge: IL-27 is a potent inducer of IL-10 but not FoxP3 in murine T cells. Journal of immunology 180, 2752-2756.

Bendall, S. C., Simonds, E. F., Qiu, P., Amir el, A. D., Krutzik, P. O., Finck, R., Bruggner, R. V., Melamed, R., Trejo, A., Ornatsky, O. I., et al. (2011). Single-cell mass cytometry of differential immune and drug responses across a human hematopoietic continuum. Science 332, 687-696.

Blackburn, S. D., Shin, H., Haining, W. N., Zou, T., Workman, C. J., Polley, A., Betts, M. R., Freeman, G. J., Vignali, D. A., and Wherry, E. J. (2009). Coregulation of CD8+ T cell exhaustion by multiple inhibitory receptors during chronic viral infection. Nature immunology 10, 29-37.

Burton, B. R., Britton, G. J., Fang, H., Verhagen, J., Smithers, B., Sabatos-Peyton, C. A., Carney, L. J., Gough, J., Strobel, S., and Wraith, D. C. (2014). Sequential transcriptional changes dictate safe and effective antigen-specific immunotherapy. Nature communications 5, 4741.

Capaldi, A. P., Kaplan, T., Liu, Y., Habib, N., Regev, A., Friedman, N., and O'Shea, E. K. (2008). Structure and function of a transcriptional network activated by the MAPK Hog1. Nat Genet 40, 1300-1306.

Castellino, F. J., Liang, Z., Volkir, S. P., Haalboom, E., Martin, J. A., Sandoval-Cooper, M. J., and Rosen, E. D. (2002). Mice with a severe deficiency of the endothelial protein C receptor gene develop, survive, and reproduce normally, and do not present with enhanced arterial thrombosis after challenge. Thrombosis and haemostasis 88, 462-472.

Ciofani, M., Madar, A., Galan, C., Sellars, M., Mace, K., Pauli, F., Agarwal, A., Huang, W., Parkurst, C. N., Muratet, M., et al. (2012). A validated regulatory network for Th17 cell specification. Cell 151, 289-303.

Davis, S., and Meltzer, P. S. (2007). GEOquery: a bridge between the Gene Expression Omnibus (GEO) and BioConductor. Bioinformatics 23, 1846-1847.

Doering, T. A., Crawford, A., Angelosanto, J. M., Paley, M. A., Ziegler, C. G., and Wherry, E. J. (2012). Network analysis reveals centrally connected genes and pathways involved in CD8+ T cell exhaustion versus memory. Immunity 37, 1130-1144.

Fitzgerald, D. C., Ciric, B., Touil, T., Harle, H., Grammatikopolou, J., Das Sarma, J., Gran, B., Zhang, G. X., and Rostami, A. (2007a). Suppressive effect of IL-27 on encephalitogenic Th17 cells and the effector phase of experimental autoimmune encephalomyelitis. Journal of immunology 179, 3268-3275.

Fitzgerald, D. C., Zhang, G. X., El-Behi, M., Fonseca-Kelly, Z., Li, H., Yu, S., Saris, C. J., Gran, B., Ciric, B., and Rostami, A. (2007b). Suppression of autoimmune inflammation of the central nervous system by interleukin 10 secreted by interleukin 27-stimulated T cells. Nature immunology 8, 1372-1379.

Fourcade, J., Sun, Z., Pagliano, O., Chauvin, J. M., Sander, C., Janjic, B., Tarhini, A. A., Tawbi, H. A., Kirkwood, J. M., Moschos, S., et al. (2014). PD-1 and Tim-3 regulate the expansion of tumor antigen-specific CD8(+) T cells induced by melanoma vaccines. Cancer research 74, 1045-1055.

Giordano, M., Henin, C., Maurizio, J., Imbratta, C., Bourdely, P., Buferne, M., Baitsch, L., Vanhille, L., Sieweke, M. H., Speiser, D. E., et al. (2015). Molecular profiling of CD8 T cells in autochthonous melanoma identifies Maf as driver of exhaustion. EMBO J 34, 2042-2058.

Hall, A. O., Beiting, D. P., Tato, C., John, B., Oldenhove, G., Lombana, C. G., Pritchard, G. H., Silver, J. S., Bouladoux, N., Stumhofer, J. S., et al. (2012). The cytokines interleukin 27 and interferon-gamma promote distinct Treg cell populations required to limit infection-induced pathology. Immunity 37, 5I1-523.

Hamid, O., Robert, C., Daud, A., Hodi, F. S., Hwu, W. J., Kefford, R., Wolchok, J. D., Hersey, P., Joseph, R. W., Weber, J. S., et al. (2013). Safety and tumor responses with lambrolizumab (anti-PD-1) in melanoma. The New England journal of medicine 369, 134-144.

Hess Michelini, R., Doedens, A. L., Goldrath, A. W., and Hedrick, S. M. (2013). Differentiation of CD8 memory T cells depends on Foxol. The Journal of experimental medicine 210, 1189-1200.

Hirahara, K., Ghoreschi, K., Yang, X. P., Takahashi, H., Laurence, A., Vahedi, G., Sciume, G., Hall, A. O., Dupont, C. D., Francisco, L. M., et al. (2012). Interleukin-27 priming of T cells controls IL-17 production in trans via induction of the ligand PD-L1. Immunity 36, 1017-1030.

Hodi, F. S., O'Day, S. J., McDermott, D. F., Weber, R. W., Sosman, J. A., Haanen, J. B., Gonzalez, R., Robert, C., Schadendorf, D., Hassel, J. C., et al. (2010). Improved survival with ipilimumab in patients with metastatic melanoma. The New England journal of medicine 363, 7I1-723.

Jin, H. T., Anderson, A. C., Tan, W. G., West, E. E., Ha, S. J., Araki, K., Freeman, G. J., Kuchroo, V. K., and Ahmed, R. (2010). Cooperation of Tim-3 and PD-1 in CD8 T-cell exhaustion during chronic viral infection. Proc Natl Acad Sci USA 107, 14733-14738.

Johnson, W. E., Li, C., and Rabinovic, A. (2007). Adjusting batch effects in microarray expression data using empirical Bayes methods. Biostatistics 8, 118-127.

Johnston, R. J., Comps-Agrar, L., Hackney, J., Yu, X., Huseni, M., Yang, Y., Park, S., Javinal, V., Chiu, H., Irving, B., et al. (2014). The immunoreceptor TIGIT regulates antitumor and antiviral CD8(+) T cell effector function. Cancer cell 26, 923-937.

Kidder, B. L., Yang, J., and Palmer, S. (2008). Stat3 and c-Myc genome-wide promoter occupancy in embryonic stem cells. PLoS One 3, e3932.

Kolde, R. (2015). pheatmap: Pretty Heatmaps (R package version 1.0.2).

Koyama, S., Akbay, E. A., Li, Y. Y., Herter-Sprie, G. S., Buczkowski, K. A., Richards, W. G., Gandhi, L., Redig, A. J., Rodig, S. J., Asahina, H., et al. (2016). Adaptive resistance to therapeutic PD-1 blockade is associated with upregulation of alternative immune checkpoints. Nature communications 7, 10501.

Kwon, H., Thierry-Mieg, D., Thierry-Mieg, J., Kim, H. P., Oh, J., Tunyaplin, C., Carotta, S., Donovan, C. E., Goldman, M. L., Tailor, P., et al. (2009). Analysis of interleukin-21-induced Prdm1 gene regulation reveals functional cooperation of STAT3 and IRF4 transcription factors. Immunity 31, 941-952.

Lang, K. S., Recher, M., Navarini, A. A., Harris, N. L., Lohning, M., Junt, T., Probst, H. C., Hengartner, H., and Zinkernagel, R. M. (2005). Inverse correlation between IL-7 receptor expression and CD8 T cell exhaustion during persistent antigen stimulation. European journal of immunology 35, 738-745.

Langmead, B., Trapnell, C., Pop, M., and Salzberg, S. L. (2009). Ultrafast and memory-efficient alignment of short DNA sequences to the human genome. Genome Biol 10, R25.

Li, B., and Dewey, C. N. (2011). RSEM: accurate transcript quantification from RNA-Seq data with or without a reference genome. BMC Bioinformatics 12, 323.

Liao, W., Ouyang, W., Zhang, M. Q., and Li, M. O. (2014). Genome Wide Mapping of Foxol Binding-sites in Murine T Lymphocytes. Genome Data 2, 280-281.

Lopes, C. T., Franz, M., Kazi, F., Donaldson, S. L., Morris, Q., and Bader, G. D. (2010). Cytoscape Web: an interactive web-based network browser. Bioinformatics 26, 2347-2348.

Maaten L, H. G. (2008). Visualizing Data using t-SNE. Journal of Machine Learning Research, 2579-2605.

Mahoney, K. M., Rennert, P. D., and Freeman, G. J. (2015). Combination cancer immunotherapy and new immunomodulatory targets. Nature reviews Drug discovery 14, 561-584.

Mayo, L., Cunha, A. P., Madi, A., Beynon, V., Yang, Z., Alvarez, J. I., Prat, A., Sobel, R. A., Kobzik, L., Lassmann, H., et al. (2016). IL-10-dependent Tr cells attenuate astrocyte activation and ameliorate chronic central nervous system inflammation. Brain.

Mohan Rao, L. V., Esmon, C. T., and Pendurthi, U. R. (2014). Endothelial cell protein C receptor: a multiliganded and multifunctional receptor. Blood 124, 1553-1562.

Murugaiyan, G., Mittal, A., Lopez-Diego, R., Maier, L. M., Anderson, D. E., and Weiner, H. L. (2009). IL-27 is a key regulator of IL-10 and IL-17 production by human CD4+ T cells. Journal of immunology 183, 2435-2443.

Neumann, C., Heinrich, F., Neumann, K., Junghans, V., Mashreghi, M. F., Ahlers, J., Janke, M., Rudolph, C., Mockel-Tenbrinck, N., Kuhl, A. A., et al. (2014). Role of Blimp-1 in programing Th effector cells into IL-10 producers. The Journal of experimental medicine 211, 1807-1819.

Newell, E. W., Sigal, N., Bendall, S. C., Nolan, G. P., and Davis, M. M. (2012). Cytometry by time-of-flight shows combinatorial cytokine expression and virus-specific cell niches within a continuum of CD8+ T cell phenotypes. Immunity 36, 142-152.

Novershtern, N., Subramanian, A., Lawton, L. N., Mak, R. H., Haining, W. N., McConkey, M. E., Habib, N., Yosef, N., Chang, C. Y., Shay, T., et al. (2011). Densely interconnected transcriptional circuits control cell states in human hematopoiesis. Cell 144, 296-309.

Pellegrini, M., Calzascia, T., Elford, A. R., Shahinian, A., Lin, A. E., Dissanayake, D., Dhanji, S., Nguyen, L. T., Gronski, M. A., Morre, M., et al. (2009). Adjuvant IL-7 antagonizes multiple cellular and molecular inhibitory networks to enhance immunotherapies. Nature medicine 15, 528-536.

Peters, A., Burkett, P. R., Sobel, R. A., Buckley, C. D., Watson, S. P., Bettelli, E., and Kuchroo, V. K. (2015). Podoplanin negatively regulates CD4+ effector T cell responses. The Journal of clinical investigation 125, 129-140.

Reich, M., Liefeld, T., Gould, J., Lerner, J., Tamayo, P., and Mesirov, J. P. (2006). GenePattern 2.0. Nat Genet 38, 500-501.

Safford, M., Collins, S., Lutz, M. A., Allen, A., Huang, C. T., Kowalski, J., Blackford, A., Horton, M. R., Drake, C., Schwartz, R. H., et al. (2005). Egr-2 and Egr-3 are negative regulators of T cell activation. Nature immunology 6, 472-480.

Sakuishi, K., Apetoh, L., Sullivan, J. M., Blazar, B. R., Kuchroo, V. K., and Anderson, A. C. (2010). Targeting Tim-3 and PD-1 pathways to reverse T cell exhaustion and restore anti-tumor immunity. The Journal of experimental medicine 207, 2187-2194.

Shin, H. M., Kapoor, V. N., Guan, T., Kaech, S. M., Welsh, R. M., and Berg, L. J. (2013). Epigenetic modifications induced by Blimp-1 Regulate CD8(+) T cell memory progression during acute virus infection. Immunity 39, 661-675.

Smyth, G. K. (2004). Linear models and empirical bayes methods for assessing differential expression in microarray experiments. Statistical applications in genetics and molecular biology 3, Article3.

Smyth, G. K. (2005). Limma: linear models for microarray data. (New York: Springer).

Stumhofer, J. S., Silver, J. S., Laurence, A., Porrett, P. M., Harris, T. H., Turka, L. A., Ernst, M., Saris, C. J., O'Shea, J. J., and Hunter, C. A. (2007). Interleukins 27 and 6 induce STAT3-mediated T cell production of interleukin 10. Nature immunology 8, 1363-1371.

Tirosh, I., Izar, B., Prakadan, S. M., Wadsworth, M. H., 2nd, Treacy, D., Trombetta, J. J., Rotem, A., Rodman, C., Lian, C., Murphy, G., et al. (2016). Dissecting the multicellular ecosystem of metastatic melanoma by single-cell RNA-seq. Science 352, 189-196.

Topalian, S. L., Hodi, F. S., Brahmer, J. R., Gettinger, S. N., Smith, D. C., McDermott, D. F., Powderly, J. D., Carvajal, R. D., Sosman, J. A., Atkins, M. B., et al. (2012). Safety, activity, and immune correlates of anti-PD-1 antibody in cancer. The New England journal of medicine 366, 2443-2454.

Trapnell, C., Pachter, L., and Salzberg, S. L. (2009). TopHat: discovering splice junctions with RNA-Seq. Bioinformatics 25, 1105-1111.

Turnis, M. E., Sawant, D. V., Szymczak-Workman, A. L., Andrews, L. P., Delgoffe, G. M., Yano, H., Beres, A. J., Vogel, P., Workman, C. J., and Vignali, D. A. (2016). Interleukin-35 Limits Anti-Tumor Immunity. Immunity 44, 316-329.

Villarino, A., Hibbert, L., Lieberman, L., Wilson, E., Mak, T., Yoshida, H., Kastelein, R. A., Saris, C., and Hunter, C. A. (2003). The IL-27R (WSX-1) is required to suppress T cell hyperactivity during infection. Immunity 19, 645-655.

Wende, H., Lechner, S. G., Cheret, C., Bourane, S., Kolanczyk, M. E., Pattyn, A., Reuter, K., Munier, F. L., Carroll, P., Lewin, G. R., et al. (2012). The transcription factor c-Maf controls touch receptor development and function. Science 335, 1373-1376.

Wherry, E. J., and Kurachi, M. (2015). Molecular and cellular insights into T cell exhaustion. Nature reviews Immunology 15, 486-499.

Wicki, A., Lehembre, F., Wick, N., Hantusch, B., Kerjaschki, D., and Christofori, G. (2006). Tumor invasion in the absence of epithelial-mesenchymal transition: podoplanin-mediated remodeling of the actin cytoskeleton. Cancer cell 9, 261-272.

Wolchok, J. D., Kluger, H., Callahan, M. K., Postow, M. A., Rizvi, N. A., Lesokhin, A. M., Segal, N. H., Ariyan, C. E., Gordon, R. A., Reed, K., et al. (2013). Nivolumab plus ipilimumab in advanced melanoma. The New England journal of medicine 369, 122-133.

Woo, S. R., Turnis, M. E., Goldberg, M. V., Bankoti, J., Selby, M., Nirschl, C. J., Bettini, M. L., Gravano, D. M., Vogel, P., Liu, C. L., et al. (2012). Immune inhibitory molecules LAG-3 and PD-1 synergistically regulate T-cell function to promote tumoral immune escape. Cancer research 72, 917-927.

Yosef, N., Shalek, A. K., Gaublomme, J. T., Jin, H., Lee, Y., Awasthi, A., Wu, C., Karwacz, K., Xiao, S., Jorgolli, M., et al. (2013). Dynamic regulatory network controlling TH17 cell differentiation. Nature 496, 461-468.

Yoshida, H., and Hunter, C. A. (2015). The immunobiology of interleukin-27. Annual review of immunology 33, 417-443.

Zhou, X., Yu, S., Zhao, D. M., Harty, J. T., Badovinac, V. P., and Xue, H. H. (2010). Differentiation and persistence of memory CD8(+) T cells depend on T cell factor 1. Immunity 33, 229-240.

Zhu, C., Sakuishi, K., Xiao, S., Sun, Z., Zaghouani, S., Gu, G., Wang, C., Tan, D. J., Wu, C., Rangachari, M., et al. (2015). An IL-27/NFIL3 signalling axis drives Tim-3 and IL-10 expression and T-cell dysfunction. Nature communications 6, 6072.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An isolated immune cell genetically modified to (a) downregulate or abolish expression or activity of a gene encoding protein C receptor (PROCR) and one or more genes selected from the group consisting of genes encoding PRDMI, c-MAF, and Podoplanin (PDPN); or (b) comprise an agent capable of inducibly downregulating expression or activity of a gene encoding PROCR and one or more genes encoding PRDMI, c-MAF, and PDPN.

2. The isolated immune cell according to claim 1, wherein the isolated immune cell is a CD8+ T cell that displays tumor specificity.

3. The isolated immune cell according to claim 1, wherein the PROCR gene, and one or more of the PRDMI, c-MAF, or PDPN genes are genetically modified using a protein comprising (i) a DNA-binding portion configured to specifically bind to the PROCR gene, and one or more of the PRDMI, c-MAF, or PDPN genes and (ii) a DNA cleavage portion that comprises:

a zinc finger protein or DNA-binding domain thereof, a transcription activator-like effector (TALE) protein or DNA-binding domain thereof, or an RNA-guided protein or DNA-binding domain thereof;

a Cas protein modified to eliminate its nuclease activity; or a DNA-binding domain of a Cas protein;

wherein the protein is a nuclease or a heterologous repressor protein capable of repressing the transcription of the PROCR, PRDM1, c-MAF, or PDPN genes.

4. The isolated immune cell according to claim 1, wherein the isolated immune cell is genetically modified to down-regulate or abolish expression or activity of genes encoding PDPN, PRDM1, c-MAF, and PROCR.

5. A cell population of immune cells as defined in claim 1.

6. A method for generating the isolated immune cell as defined in claim 1, the method comprising (i) providing an isolated immune cell, and (ii) genetically modifying said isolated immune cell to comprise an altered expression or activity of a gene encoding PROCR and genes encoding one or more of PDPN, PRDMI and c-MAF.

7. A pharmaceutical composition comprising the isolated immune cell according to claim 1.

8. The isolated immune cell according to claim 1, wherein the isolated immune cell is further genetically modified to alter expression or activity of one or more genes encoding PD1, CTLA4, TIGIT, TIM3, LAG3, and PDL1.

9. The isolated immune cell according to claim 1, wherein the isolated immune cell is further genetically modified to alter expression or activity of one or more genes encoding TIGIT, LAG3, LILRB4, and KLRC1.

10. The isolated immune cell according to claim 1, wherein the isolated immune cell is further genetically modified to alter expression or activity of one or more genes encoding CD226, OX-40, GITR, TNFSF9 (4-1BB), KLRC2, KLRE1, KLRK1, IL12RB1, IL1R1, and SLAMF7.

11. The isolated immune cell according to claim 1, wherein the isolated immune cell is further genetically modified to alter expression or activity of one or more genes encoding TIGIT, LAG3, LILRB4, ALCAM, and KLRC1.

12. The isolated immune cell according to claim 1, wherein the isolated immune cell is further genetically modified to alter expression or activity of one or more genes encoding BTLA, TIGIT, HAVCR2 (TIM-3), LAG3, IL10RA, IL1R2, LILRB4, KLRC1, KLRC2, KLRE1, TNFSF9 (4-1BB), KLRK1, IL12RB1, IL1R1, and SLAMF7.

13. The isolated immune cell according to claim 1, wherein the isolated immune cell is further genetically modified to comprise an agent capable of inducibly altering expression or activity of one or more genes encoding PD1, CTLA4, TIGIT, TIM3, LAG3, PDL1, LILRB4, KLRC1, CD226, OX-40, GITR, TNFSF9 (4-IBB), KLRC2, KLRE1, KLRK1, IL12RB1, IL1R1, and SLAMF7.

14. The isolated immune cell according to claim 1, wherein the isolated immune cell is genetically modified to decrease expression or activity of genes encoding PROCR and PRDMI; genes encoding PROCR and c-MAF; or genes encoding PROCR and PDPN.

15. The isolated immune cell according to claim 1, wherein the isolated immune cell is genetically modified to decrease expression or activity of genes encoding PROCR, PRDM1 and c-MAF; or genes encoding PROCR, PRDM1 and PDPN.

16. The isolated immune cell according to claim 1, wherein the isolated immune cell is genetically modified to decrease expression or activity of genes encoding PROCR, c-MAF and PDPN.

17. The isolated immune cell according to claim 1, wherein the isolated immune cell is genetically modified to decrease expression or activity of genes encoding PROCR, PRDM1, c-MAF, and PDPN.

* * * * *